United States Patent
Murata et al.

(10) Patent No.: US 8,410,141 B2
(45) Date of Patent: Apr. 2, 2013

(54) INSECTICIDAL ARYLPYRROLINES

(75) Inventors: Tetsuya Murata, Osaka (JP); Yasushi Yoneta, Saitama (JP); Hidetoshi Kishikawa, Shiga (JP); Jun Mihara, Osaka (JP); Daiei Yamazaki, Yamaguchi (JP); Mamoru Hatazawa, Ibaraki (JP); Norio Sasaki, Ibaraki (JP); Kei Domon, Shizuoka (JP); Eiichi Shimojo, Tochigi (JP); Teruyuki Ichihara, Tochigi (JP); Katsuhiko Shibuya, Tochigi (JP); Masashi Ataka, Saitama (JP); Ulrich Görgens, Ratingen (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/319,287

(22) PCT Filed: May 18, 2010

(86) PCT No.: PCT/EP2010/003019
§ 371 (c)(1),
(2), (4) Date: Jan. 18, 2012

(87) PCT Pub. No.: WO2010/133336
PCT Pub. Date: Nov. 25, 2010

(65) Prior Publication Data
US 2012/0108635 A1    May 3, 2012

(30) Foreign Application Priority Data

May 19, 2009  (JP) .................................. 2009-121267

(51) Int. Cl.
| A61K 31/4427 | (2006.01) |
| A61K 31/41 | (2006.01) |
| A61K 31/415 | (2006.01) |
| A61K 31/4164 | (2006.01) |
| A61K 31/4192 | (2006.01) |
| A61K 31/4196 | (2006.01) |
| C07D 401/14 | (2006.01) |
| C07D 257/02 | (2006.01) |
| C07D 249/04 | (2006.01) |
| C07D 249/08 | (2006.01) |
| C07D 233/00 | (2006.01) |
| C07D 231/00 | (2006.01) |
| C07D 207/00 | (2006.01) |

(52) U.S. Cl. ........ 514/333; 514/341; 514/343; 514/381; 514/383; 514/385; 514/403; 514/406; 546/256; 546/268.4; 546/272.4; 546/272.7; 546/275.4; 546/276.4; 548/250; 548/255; 548/262.2; 548/300.1; 548/356.1; 548/518

(58) Field of Classification Search .................. 514/333, 514/341, 343, 381, 383, 385, 403, 406; 546/256, 546/268.4, 272.4, 272.7, 275.4, 276.4; 548/250, 548/255, 262.2, 300.1, 356.1, 518
See application file for complete search history.

(56) References Cited

U.S. PATENT DOCUMENTS

| 7,951,828 B1 | 5/2011 | Mita et al. |
| 2007/0066617 A1 | 3/2007 | Mita et al. |
| 2007/0111984 A1 | 5/2007 | Naidu et al. |
| 2009/0023923 A1 | 1/2009 | Mizukoshi et al. |
| 2009/0156643 A1 | 6/2009 | Mita et al. |
| 2010/0298558 A1 | 11/2010 | Mita et al. |
| 2011/0124858 A1 | 5/2011 | Iwata et al. |

FOREIGN PATENT DOCUMENTS

| EP | 1 538 138 A1 | 6/2005 |
| JP | 2007-016017 A | 1/2007 |
| JP | 2007-091708 A | 4/2007 |
| JP | 2007-106756 A | 4/2007 |
| JP | 2008-133273 A | 6/2008 |
| WO | WO 2007/070606 A2 | 6/2007 |
| WO | WO 2007/075459 A2 | 7/2007 |
| WO | WO 2007/079162 A1 | 7/2007 |
| WO | WO 2007/123853 A2 | 11/2007 |
| WO | WO 2007/123855 A2 | 11/2007 |
| WO | WO 2007/125984 A1 | 11/2007 |
| WO | WO 2008/122375 A2 | 10/2008 |
| WO | WO 2009/072621 A1 | 6/2009 |
| WO | WO 2009/097992 A1 | 8/2009 |

OTHER PUBLICATIONS

Echigo, Y., et al., "A Convenient Method for the Preparation of Isocyanides," *Chemistry Letters* 697-698, Chemical Society of Japan, Japan (1977).

Padwa, A., et al., "Silyl-Substituted Thioimidates as Nitrile Ylide Equivalents," *J. Org. Chem.* 52(6):1027-1035, American Chemical Society, United States (1987).

Tsuge, O., et al., "Cycloadditions of N-Benzylideneaminoacetonitrile as a Synthetic Equivalent of Methanenitrile Benzylide," *Chemistry Letters* 1601-1604, The Chemical Society of Japan, Japan (1985).

(Continued)

*Primary Examiner* — Rebecca Anderson
*Assistant Examiner* — Samantha Shterengarts
(74) *Attorney, Agent, or Firm* — Sterne, Kessler, Goldstein & Fox P.L.L.C.

(57) ABSTRACT

The invention relates to novel arylpyrroline compounds of formula (I) which have excellent insecticidal activity and which can thus be used as an insecticide.

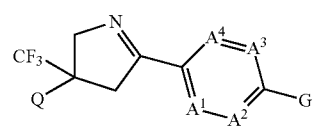

(I)

5 Claims, No Drawings

OTHER PUBLICATIONS

English Language Abstract of Japanese Patent Publication No. JP 2007-16017 A, Japanese Patent Office, Patent & Utility Model Gazette DB, Patent Abstracts of Japan, (2007).

STN CA Caesar Accession No. 1066, English Language Abstract of Japanese Patent Publication No. JP 2007-91708 A, Mita, et al., CAPLUS database, Apr. 12, 2007.

English Language Abstract of Japanese Patent Publication No. JP 2007-106756 A, Japanese Patent Office, Patent & Utility Model Gazette DB, Patent Abstracts of Japan, (2007).

English Language Abstract of WIPO Patent Publication No. WO 2007/125984 A1, European Patent Office, espacenet database—(2007).

English Language Abstract of Japanese Patent Publication No. JP 2008-133273 A, Japanese Patent Office, Patent & Utility Model Gazette DB, Patent Abstracts of Japan, (2008).

International Search Report with Written Opinion of the International Searching Authority for International Application No. PCT/EP2010/003019, European Patent Office, The Hague, Netherlands, mailed on Jul. 19, 2010.

INSECTICIDAL ARYLPYRROLINES

The present invention relates to novel arylpyrrolines and their use as insecticides, as well as to processes for the preparation of the arylpyrrolines.

Certain arylpyrroline compounds are described in WO 2009/072621, Japanese Patent Application Laid-Open No. 2009-32354 and WO2009/000559. It is described therein that some of these compounds have insecticidal activity.

Since ecological and economic demands on modern plant treatment agents are continually increasing, particularly in respect to the amount applied, residue formation, selectivity, toxicity and favourable production methodology, and also because, for example, resistance problems can occur, there is the on-going task to develop new plant treatment agents that at least in certain areas are able to demonstrate advantages over known agents.

The inventors of the present invention devotedly conducted research to create novel compounds exhibiting higher effects and having a wide spectrum as an insecticide. As a result, they found novel arylpyrroline compounds, which exhibit high biological activity, a wide spectrum and safety.

Thus, this invention is directed to arylpyrroline compounds of formula (I)

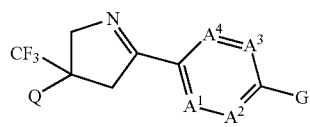

wherein

Q stands for a pyridyl group or phenyl group, each group may be substituted with at least one substituent X or $X^1$;

X and $X^1$ each independently stand for fluorine, chlorine, bromine, iodine, $C_{1-12}$haloalkyl, nitro, $C_{1-12}$alkyl, or $C_{1-12}$alkoxyl, cyano, $C_{1-12}$haloalkoxyl, $C_{1-12}$alkylsulfenyl, $C_{1-12}$alkylsulfinyl, $C_{1-12}$alkylsulfonyl, $C_{1-12}$haloalkylsulfenyl, $C_{1-12}$haloalkylsulfinyl, or $C_{1-12}$haloalkylsulfonyl, hydroxyl, thiol, amino, $C_{1-12}$acylamino, $C_{1-12}$alkoxycarbonylamino, $C_{1-12}$haloalkoxycarbonylamino, $C_{1-12}$alkoxyimino, $C_{1-12}$haloalkoxyimino, or $C_{1-12}$alkylsulfonylamino, or sulfur pentafluoride, preferably stand for fluorine, chlorine, bromine, $C_{1-6}$haloalkyl $C_{1-6}$haloalkoxyl and cyano, and more preferably stand for fluorine, chlorine, bromine, $CF_3$ and $OCF_3$;

$A^1$, $A^2$, $A^3$ and $A^4$ each independently stand for a carbon atom which may be substituted by a substituent Y, and whereas two adjacent substituents Y together with the carbon atoms to which they are attached may form a 5- or 6-membered aromatic ring, or $A^1$, $A^2$, $A^3$ and $A^4$ each independently stand for a nitrogen atom, under the proviso that only 2 of the chemical groups $A^1$, $A^2$, $A^3$ and $A^4$ stand at the same time for nitrogen;

Y stands for fluorine, chlorine, bromine, iodine, $C_{1-12}$haloalkyl, nitro, $C_{1-12}$alkyl, $C_{3-8}$cycloalkyl, $C_{3-8}$cycloaloalkyl, cyano, $C_{1-12}$haloalkoxyl, $C_{1-12}$alkylsulfenyl, $C_{1-12}$alkylsulfonyl, $C_{1-12}$haloalkylsulfenyl, $C_{1-12}$haloalkylsulfinyl, $C_{1-12}$haloalkylsulfonyl, $C_{1-12}$alkylsulfonyloxy, $C_{1-12}$haloalkylsulfonyloxy, $C_{1-12}$alkylaminosulfonyl, $C_{1-12}$haloalkylaminosulfonyl, di($C_{1-12}$)alkylaminosulfonyl, or di(($C_{1-12}$)haloalkyl)aminosulfonyl, hydroxyl, thiol, amino, $C_{1-12}$alkylamino, di($C_{1-12}$)alkylamino, $C_{1-12}$acylamino, $C_{1-12}$alkoxycarbonylamino, $C_{1-12}$haloalkoxycarbonylamino, $C_{1-12}$alkylsulfonylamino, $C_{1-12}$haloalkylsulfonylamino, $C_{1-12}$alkoxyimino, $C_{1-12}$haloalkoxyimino, $C_{1-12}$alkoxyiminoalkyl, $C_{1-12}$haloalkoxyimino($C_{1-12}$)alkyl, $C_{1-12}$alkylsulfinylimino($C_{1-12}$)alkyl, $C_{1-12}$alkylsulfinylimino($C_{1-12}$)alkylcarbonyl, $C_{1-12}$alkylsulfoxyimino, $C_{1-12}$alkylsulfoxyimino($C_{1-12}$)alkyl, $C_{1-12}$alkoxycarbonyl, $C_{1-12}$alkylcarbonyl, aminocarbonyl, $C_{1-12}$alkylaminocarbonyl, aminothiocarbonyl, $C_{1-12}$alkylaminothiocarbonyl, di($C_{1-12}$)alkylaminocarbonyl, or di($C_{1-12}$)alkylaminothiocarbonyl, preferably stands for fluorine, chlorine, bromine, iodine, $C_{1-6}$haloalkyl, nitro, $C_{1-6}$alkyl, $C_{1-6}$haloalkoxyl and cyano, and more preferably stands for fluorine, chlorine, bromine, cyano, nitro, methyl, $CF_3$ and $OCF_3$; and G stands for a heterocyclic group G1 to G9 having the following formula

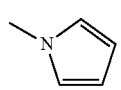
G1

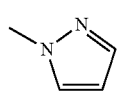
G2

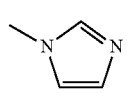
G3

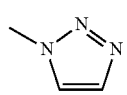
G4

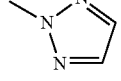
G5

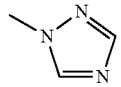
G6

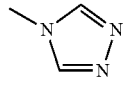
G7

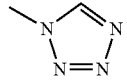
G8

G9 which may be substituted by a substituent Z which is selected among fluorine, chlorine, bromine, iodine, $C_{1-6}$ haloalkyl, nitro, $C_{1-6}$alkoxy, cyano, $C_{1-6}$haloalkoxy, $C_{1-6}$alkylsulfenyl, $C_{1-6}$alkylsulfinyl, $C_{1-6}$alkylsulfonyl, $C_{1-6}$haloalkylsulfenyl, $C_{1-6}$haloalkylsulfinyl, $C_{1-6}$haloalkylsulfonyl, hydroxyl and thiol, or represents a chemical group G10 characterized by the following formula:

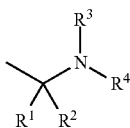
G10 wherein $R^1$ and $R^2$ each independently stand for hydrogen, $C_{1-12}$alkyl, $C_{3-8}$cycloalkyl, $C_{1-12}$haloalkyl, $C_{3-8}$cyclohaloalkyl, $C_{2-12}$alkenyl, $C_{2-12}$alkynyl, $C_{2-12}$haloalkenyl, $C_{2-12}$haloalkynyl, cyano, $C_{1-12}$alkoxycarbonyl, or $C_{1-12}$ alkoxythiocarbonyl, or $R^1$ and $R^2$, together with the carbon atom to which they are attached, form a 3 to 6-membered carbocyclic ring, preferably at least one of $R^1$ or $R^2$ stands for hydrogen or one of $R^1$ or $R^2$ stands for hydrogen while the other stands for $C_{1-6}$alkyl;

$R^3$ represents hydrogen, amino, hydroxyl, $C_{1-12}$alkoxy, $C_{1-12}$alkylcarbonylamino, $C_{1-12}$alkylimino, $C_{1-12}$alkyl, $C_{3-8}$cycloalkyl, or $C_{1-12}$haloalkyl, cyano, $C_{2-12}$alkenyl, $C_{2-12}$alkynyl, or $C_{1-12}$alkylcarbonyl, or is selected from the following groups $CH_2$—$R^5$, $C(=O)R^5$, $C(=S)R^5$, $R^4$ represents a chemical group selected among hydrogen, cyano, carbonyl, thiocarbonyl, $C_{1-12}$alkylcarbonyl, $C_{1-12}$alkylthiocarbonyl, $C_{1-12}$haloalkylcarbonyl, $C_{1-12}$haloalkylthiocarbonyl, $C_{1-12}$ alkylaminocarbonyl, $C_{1-12}$alkylaminothiocarbonyl, di$(C_{1-12})$alkylaminocarbonyl, di$(C_{1-12})$alkylaminothiocarbonyl, $C_{1-12}$alkoxyaminocarbonyl, $C_{1-12}$alkoxyaminothiocarbonyl, $C_{1-12}$alkoxycarbonyl, $C_{1-12}$alkoxythiocarbonyl, $C_{1-12}$thioalkoxycarbonyl, $C_{1-12}$thioalkoxythiocarbonyl, $C_{1-12}$alkylsulfonyl, $C_{1-12}$haloalkylsulfonyl, $C_{3-8}$cycloalkylcarbonyl, $C_{2-12}$alkenylcarbonyl, $C_{2-12}$alkynylcarbonyl, $C_{3-8}$cycloalkyl-$(C_{1-12})$alkylcarbonyl, $C_{1-12}$alkylsulfenyl$(C_{1-12})$alkylcarbonyl, $C_{1-12}$alkylsulfinyl$(C_{1-12})$alkylcarbonyl, $C_{1-12}$alkylsulfonyl$(C_{1-12})$alkylcarbonyl, $C_{1-12}$alkylcarbonyl$(C_{1-12})$alkylcarbonyl, $C_{3-8}$cyclalkylaminocarbonyl, $C_{2-12}$ alkenylaminocarbonyl, $C_{2-12}$alkynylaminocarbonyl, $C_{1-12}$alkoxy$(C_{1-12})$alkyl, or is selected from the groups $C(=O)R^5$ and $C(=S)R^5$, or $R^3$ and $R^4$, together with the nitrogen atom to which they are bound, form a 3- to 6-membered heterocyclic ring which may be substituted with a substituent X or $X^1$, or may be substituted with a keto, thioketo or nitroimino group;

$R^5$ represents optionally substituted phenyl, or an optionally substituted heterocyclic ring.

Compounds are preferred wherein in formula (I) the grouping

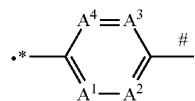

stands for a grouping selected among P1 to P4

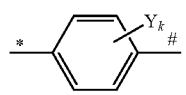
P1

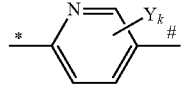
P2

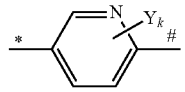
P3

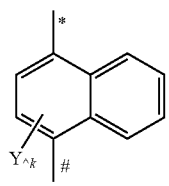
P4 wherein Y is as defined herein, and k stands for 0, 1, 2, 3 or 4; and/or wherein Q stands for a 2-pyridyl group, a 3-pyridyl group, or a 4-pyridyl group which may be substituted by at least one substituent X or $X^1$.

The present invention does not include the following compounds which are known from Japanese Patent Application Laid-Open No. 2009-32354:

Compounds of formula (I), wherein $A^1$, $A^2$, $A^4$ stand for a unsubstituted carbon atom while $A^3$ stand for a carbon atom substituted by Y, wherein G stands for a group G10 in which $R^1$ and $R^2$ represent hydrogen, and one of $R^3$ or $R^4$ represents hydrogen while the other represents ethylcarbonyl, and (i) wherein Q stands for a 4-pyrimidyl group which is substituted at the 2-position with $CF_3$ and Y is chlorine, or (ii) Q stands for a 4-pyridyl group which is substituted at the 2- and 6-positions with chlorine and Y is chlorine, or (iii) Q stands for a 3-pyridyl group which is substituted at the 6-position with $CF_3$ and Y is $CF_3$ or chlorine, (iv) Q stands for a 2-pyridyl group which is substituted at the 4- and 6-positions with $CF_3$ and Y is chlorine, (v) Q stands for a 3-pyridyl group which is substituted at the 6-position with chlorine and Y is chlorine, (vi) Q stands for a 3-pyridyl group which is substituted at the 6-position with methyl and Y is $CF_3$, or (vii) Q stands for a 2-pyridyl group which is substituted at the 5-position with $CF_3$ and Y is chlorine, and a compound of formula (I), wherein $A^1$, $A^2$, $A^4$ stand for a unsubstituted carbon atom while $A^3$ stand for a carbon atom substituted by Y, wherein G stands for a group G10 in which $R^1$ and $R^2$ represent hydrogen, and one of $R^3$ or $R^4$ represents acetyl while the other represents ethylcarbonyl, and Q stands for a 4-pyrimidyl group which is substituted at the 2-position with $CF_3$ and Y is $OCF_3$, and a compound of formula (I), wherein $A^1$, $A^2$, $A^4$ stand for a unsubstituted carbon atom while $A^3$ stand for a carbon atom substituted by Y, wherein G stands for a group G10 in which $R^1$ and $R^2$ represent methyl, and one of $R^3$ or $R^4$ represents hydrogen while the other represents i-propylcarbonyl, and Q stands for a 2-pyridyl group which is substituted at the 5-position with $CF_3$ and Y is chlorine, and a compound of formula (I), wherein $A^1$, $A^2$, $A^4$ stand for a unsubstituted carbon atom while $A^3$ stand for a carbon atom substituted by Y, wherein G stands for a group G10 in which one of $R^1$ or $R^2$ represents chlorine while the other represents methyl, and one of $R^3$ or $R^4$ represents hydrogen while the other represents tert-butylcarbonyl, and Q stands for a 2-pyridyl group which is substituted at the 4- and 6-position with $CF_3$ and Y is chlorine, and a compound of formula (I), wherein $A^1$, $A^2$, $A^4$ stand for a unsubstituted carbon atom while $A^3$ stand for a carbon atom substituted by Y, wherein G stands for a group G10 in which one of $R^1$ or $R^2$ represents hydrogen while the other represents hydroxyl, and one of $R^3$ or $R^4$ represents hydrogen while the other represents n-butylcarbonyl, and Q stands for a 3-pyridyl group which is substituted at the 6-position with chlorine and Y is $CF_3$, and a compound of formula (I), wherein $A^1$, $A^2$, $A^4$ stand for a unsubstituted carbon atom while $A^3$ stand for a carbon atom substituted by Y, wherein G stands for a group G10 in which one of $R^1$ or $R^2$ represents hydrogen while the other represents dimethylamino, and one of $R^3$ or $R^4$ represents hydrogen while the other represents iso-butylcarbonyl, and Q stands for a 3-pyridyl group which is substituted at the 6-position with methyl and Y is chlorine.

The compounds according to the invention have asymmetric carbons, and thus the compounds also include optically active species. Moreover, the present invention also salts of the compounds according to the invention.

The compounds according to the present invention exhibit a potent insecticidal action.

If not defined otherwise, the term "alkyl" used either alone or contained in other terms such as "aminoalkyl" or "haloalkyl" includes straight-chained or branched alkyl having 1 to 12 carbon atoms, such as methyl, ethyl, n- or iso-propyl; n-, iso-, secondary- or tertiary-butyl; n-pentyl, n-hexyl, n-heptyl, n-octyl, n-nonyl, n-decyl, n-undecyl or n-dodecyl, and preferably represents alkyl having 1 to 6 carbon atoms, the alkyl group may be optionally substituted by a substituent "J".

If not defined otherwise, the term "halogen" or "halo" used either alone or contained in other terms such as "haloalkyl" includes fluorine, chlorine, bromine or iodine.

If not defined otherwise, the term "haloalkyl" used either alone or combined with other terms refers to alkyl groups which are partially or fully substituted with halogen atoms which may be the same or different. Examples of "haloalkyl" include $CF_3$, $CH_2F$, $CHF_2$, $CH_2CHF_2$, $CCl_3$, $CH_2Cl$, $CHCl_2$, $CF_2CF_3$, $CH_2CF_3$, $CH_2CH_2Cl$, $CH_2CH_2F$, $CHClCH_3$, $CHFCH_3$, $CH_2CHFCl$, $CHCl_2$, $CF_2CF_2H$, $CH_2CF_3$ If not defined otherwise, the term "cycloalkyl" used either alone or combined with other terms preferably stands for cycloalkyl groups having 3 to 8 carbon atoms, such as cyclopropyl, cyclobutyl, cyclopentyl, cyclohexyl, cycloheptyl or cyclooctyl, and preferably represents cycloalkyl having 3 to 7 carbon atoms. The cycloalkyl group may be optionally substituted by a substituent "J".

If not defined otherwise, the term "alkenyl" used either alone or combined with other terms preferably stands for alkenyl having 2 to 12 carbon atoms, preferably 2 to 5 carbon atoms. Examples thereof include vinyl, allyl, 1-propenyl, 1-, 2-, or 3-butenyl or 1-pentenyl. More preferred it stands for alkenyl having 2 to 4 carbon atoms. The alkenyl group may be optionally substituted by a substituent "J".

If not defined otherwise, the term "alkynyl" used either alone or combined with other terms preferably stands for alkynyl having 2 to 12 carbon atoms, preferably 2 to 5 carbon atoms. Examples thereof include ethynyl, propargyl, 1-propynyl, but-3-ynyl or pent-4-ynyl. More preferred it stands for alkynyl having 2 to 4 carbon atoms. The alkynyl group may be optionally substituted by a substituent "J".

If not defined otherwise, the term "heterocyclic group" "heterocyclic ring" or "heterocycle" used either alone or combined with other terms preferably stands for a 5- or 6-membered heterocyclic group containing at least one of N, O and S as a heteroatom. Typically a heterocyclic group contains no more than 4 nitrogen atoms, no more than 2 oxygen atoms and/or no more than 2 sulfur atoms. The cyclic group, or the ring can be saturated, unsaturated or partially saturated. If not mentioned otherwise, a heterocyclic group can be attached to a main part through any available carbon or heteroatom of the heterocyclic group. The term additionally includes fused heterocyclic group which may be benzo-condensed. The heterocyclic group includes, for example, furyl, thienyl, pyrrolyl, isoxazolyl, pyrazolyl, oxazolyl, oxathiazolyl, imidazolyl, triazolyl, oxadiazolyl, thiadiazolyl, tetrazolyl, pyridyl, pyrimidinyl, pyridazinyl, pyrazinyl, triazinyl, indolyl, benzoxazolyl or quinolyl. The heterocyclic group may be optionally substituted by a substituent "J".

If not defined otherwise, the term "carbocyclic ring" preferably stands for a 3- to 6-membered carbocycles which can be saturated, unsaturated or partially saturated. Examples of a carbocyclic ring include cyclopropyl, cyclobutyl, cyclopentyl and cyclohexyl. The carbocyclic group may be optionally substituted by a substituent "J".

If not defined otherwise, the term "acylamino" includes groups like alkylcarbonylamino, cycloalkylcarbonylamino or benzoylamino.

If not defined otherwise, the term "optionally substituted by a substituent J" means being unsubstituted, or substituted with at least one substituent "J", which is selected among $C_{1-6}$Alkyl, $C_{2-6}$Alkenyl, $C_{2-6}$Alkynyl, $C_{3-6}$Cycloalkyl, chlorine, fluorine, bromine, iodine, $NO_2$, $NR_xR_y$, $N_3$, CN, SCN, $OR_x$, SH, $SF_5$, $COOR_x$, $C(O)R_x$, $CONR_xR_y$, $N=C(R_x)OR_y$, $SO_2NR_xR_y$, Phenyl, 5 or 6-membered heterocycles, whereas $R_x$ and $R_y$ each independently stand for H, $C_{1-6}$alkyl or $C_{1-6}$haloalkyl. The substituent J preferably stands for methyl, ethyl, iso-propyl, $C_3$-Cycloalkyl, chlorine, fluorine, bromine, iodine, $NO_2$, $NH_2$, $NMe_2$, $NHMe$, CN, SCN, OH, OMe, SH, $SF_5$, COOH, COOMe, C(O)H, COMe, $CONH_2COMe_2$, N=CHOH. N=CHOMe, N=CMeOH, $SO_2NHMe$, $SO_2NH_2$, $SO_2NMe_2$, Phenyl, a group G1 to G9 as defined herein, or pyridine.

If not defined otherwise, the term "fluorine reagents" means "fluorine-containing reagents". Such reagents are known in the art and include, for example, HF as well as potassium fluoride, tetramethylammonium fluoride, tetraethylammonium fluoride or tetrabutylammonium fluoride.

If not defined otherwise, the term "alkyl halide" stands for haloalkanes, such as fluoroalkanes, chloroalkanes, bromoalkanes and iodoalkanes, having from 1 to 6 carbon atoms.

In an aspect of the invention, compounds of formula (A-1) to (A-9) are preferred having the following formulae

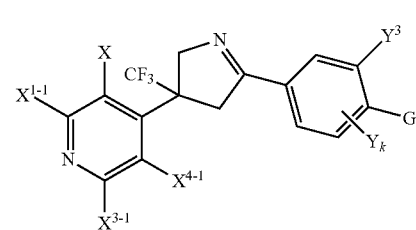

A-1

A-2 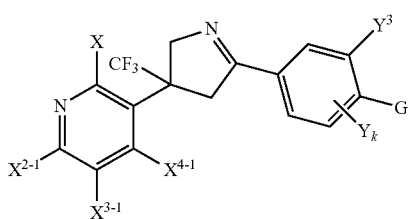

A-3 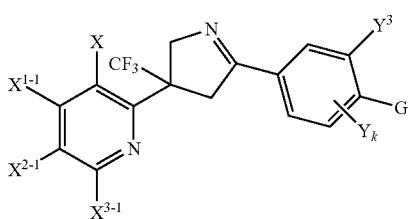

A-4 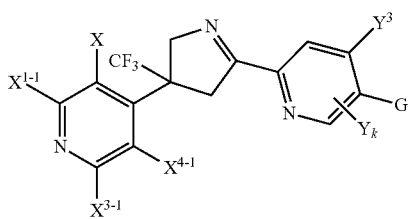

A-5 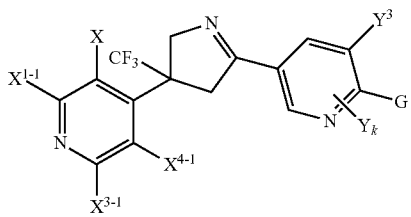

A-6 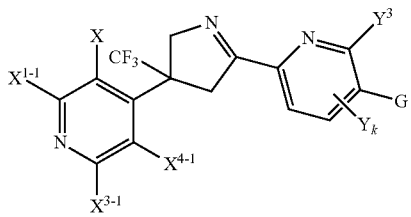

A-7 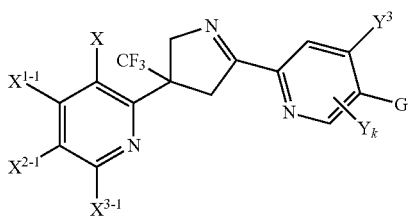

A-8 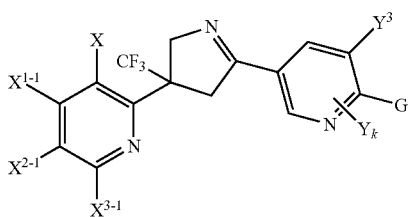

A-9 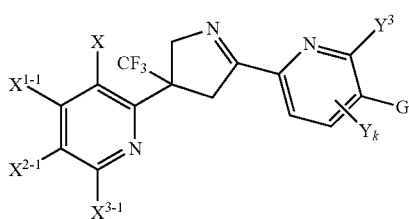

wherein X, Y and k are as defined herein, $X^{1-1}$, $X^{2-1}$, $X^{3-1}$ and $X^{4-1}$ are as defined herein for $X^1$, $Y^3$ is as defined herein for Y and wherein G stands for a group as defined herein, preferably is selected among the groups G1 to G9.

In another aspect of the invention, compounds of formula (B-1) are preferred having the following formula B-1 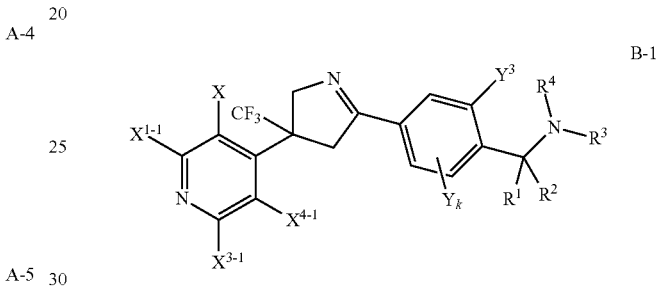

wherein X, Y, k, $R^1$, $R^2$, $R^3$ and $R^4$ are as defined herein, $Y^3$ is defined herein for Y, $X^{4-1}$ is as defined herein for $X^1$ and wherein one of either $X^{1-1}$ or $X^{3-1}$ stands for $C_{1-4}$haloalkyl while the other stand for halogen or $C_{1-4}$haloalkyl.

In another aspect of the invention compounds of formula (C-1) to (C-6) are preferred having the following formula C-1 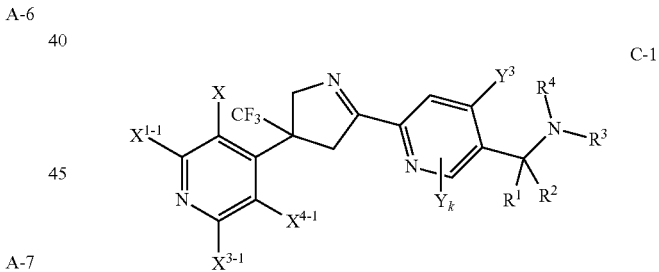

C-2 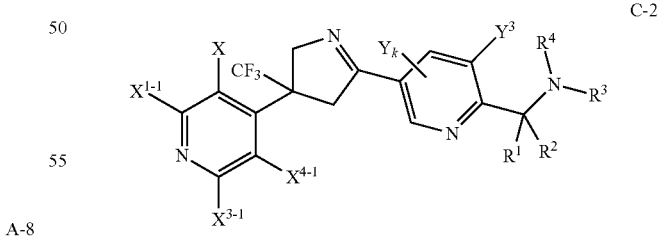

C-3 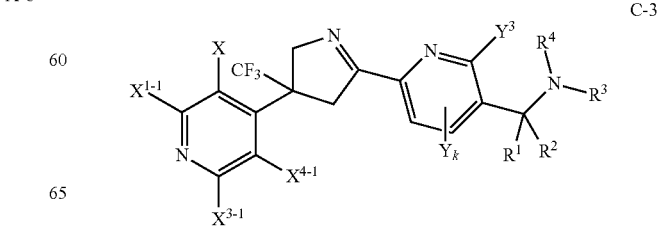

-continued

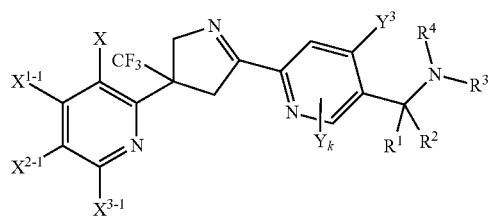
C-4

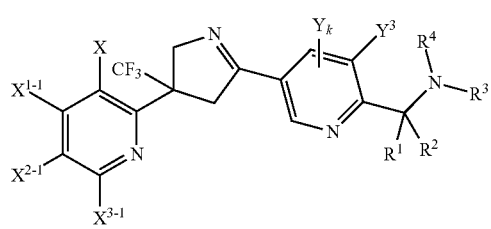
C-5

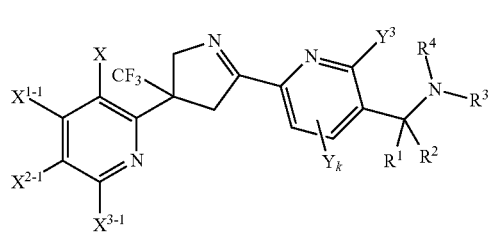
C-6 and wherein X, Y, k, $R^1$, $R^2$, $R^3$ and $R^4$ are as defined herein, wherein $X^{1-1}$, $X^{2-1}$, $X^{3-1}$ and $X^{4-1}$ are as defined herein for $X^1$ and $Y^3$ is defined herein for Y.

In another aspect of the invention compounds of formula (D-1) to (D-3) are preferred having the following formula

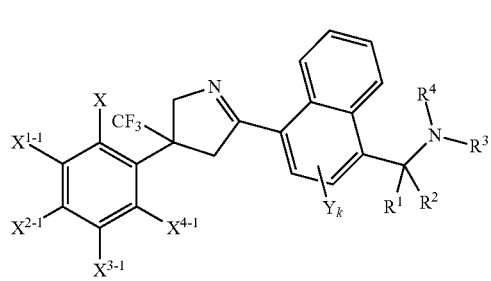
D-1

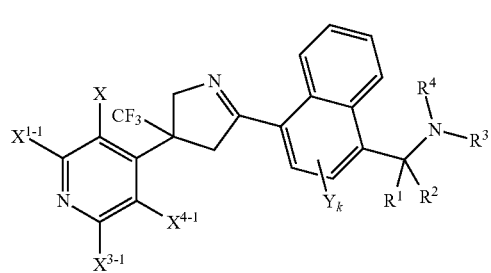
D-2

-continued

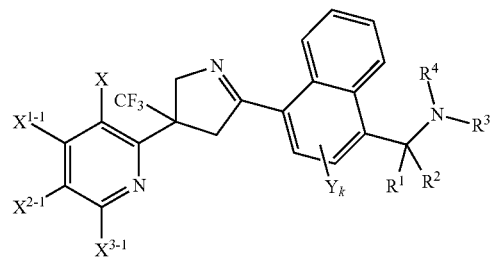
D-3 and wherein X, Y, k, $R^1$, $R^2$, $R^3$ and $R^4$ are as defined herein and wherein $X^{1-1}$, $X^{2-1}$, $X^{3-1}$ and $X^{4-1}$ are as defined herein for $X^1$.

The compounds according to the invention can be obtained by the preparation methods described in WO 2009/000559 and, thus, the methods described in WO2009/000559, particularly preparation methods (a) to (g) and (p) are herewith incorporated by reference; and which are illustrated by the following reaction schemes:

Thus, the invention is also directed to a preparation method (a) for the preparation of compounds according to the invention, comprising the step of shifting an imino double bond in compounds of the formula (II):

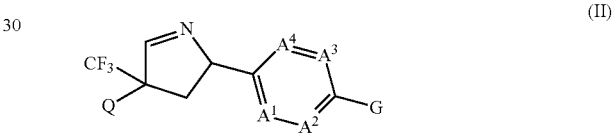
(II)

wherein $A^1$ to $A^4$, Q and G have the same meanings as defined herein, in the presence of a base.

The invention is moreover directed to a preparation method (b) for the preparation of compounds according to the invention wherein G stands for G1, G6 or G8, comprising reacting compounds of the formula (III):

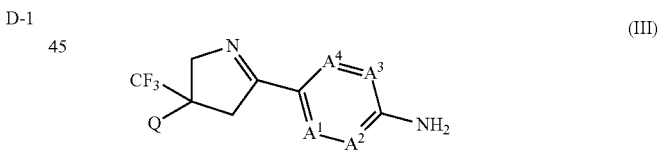
(III)

wherein $A^1$ to $A^4$ and q have the same meanings as defined herein, with either dialkoxytetrahydrofuran (e.g., dimethoxytetrahydrofuran), 1,2-diformylhydrazine, or sodium azide and trialkyl orthoformate.

The invention is also directed to a preparation method (c) for the preparation of compounds according to the invention, wherein G stands for G2, comprising reacting compounds of the formula (IV):

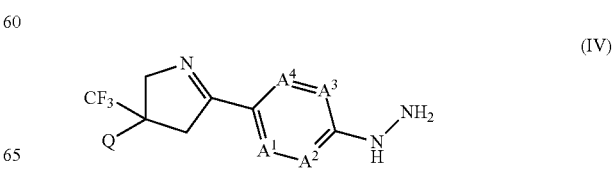
(IV)

$A^1$ to $A^4$, Q and R have the same meanings as defined herein, with 1,1,3,3-tetraalkoxypropane (e.g., 1,1,3,3-tetraethoxypropane).

The invention is also directed to a preparation method (d) for the preparation of compounds according to the invention, wherein G stands for G2, G3, G4, G5, G6, G8 or G9, comprising reacting compounds of the formula (V):

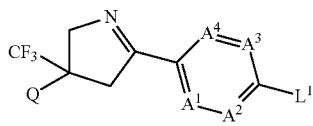
(V)

wherein $A^1$ to $A^4$ and G have the same meanings as defined herein, and wherein $L^1$ represents halogen, or a haloalkylsulfonyloxy group having 1 to 4 carbon atoms, with a chemical group G2-H, G3-H, G4-H, G5-H, G6-H, G8-H or G9-H.

The invention is also directed to a preparation method (e) for the preparation of compounds according to the invention, comprising reacting compounds of the formula (VI):

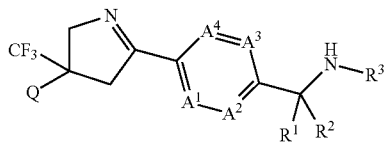
(VI)

wherein $A^1$ to $A^4$, Q, and $R^1$ to $R^3$ have the same meanings as defined herein, with compounds of the formula (VII):

 (VII)

wherein $R^4$ has the same meaning as defined herein; and L represents halogen, alkylsulfonyloxy, arylsulfonyloxy or alkylcarbonyloxy.

The invention is also directed to a preparation method (f) for the preparation of compounds according to the invention, comprising reacting compounds of the formula (VIII):

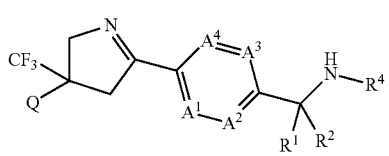
(VIII)

wherein $A^1$ to $A^4$, Q, and $R^1$, $R^2$, $R^4$ have the same meanings as defined herein, with compounds of the formula (IX):

 (IX)

wherein $R^3$ has the same meaning as defined herein; and L represents halogen, alkylsulfonyloxy, arylsulfonyloxy or alkylcarbonyloxy.

The invention is also directed to a preparation method (g) for the preparation of compounds according to the invention, comprising reacting compounds of the formula (X):

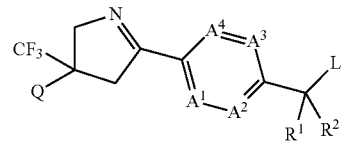
(X)

wherein $A^1$ to $A^4$, Q, $R^1$, $R^2$ and L have the same meanings as defined herein, with compounds of the formula (XI):

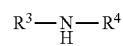 (XI)

$$R^3-\underset{H}{N}-R^4$$

wherein $R^3$ and $R^4$ have the same meanings as defined herein.

The invention is moreover directed to a preparation method (p) for the preparation of compounds according to the invention, comprising reacting compounds of the formula (XII):

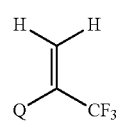
(XII)

wherein Q has the same meanings as defined herein, with compounds of the formula (XXXVI):

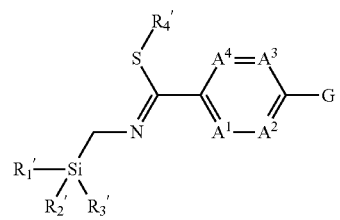
(XXXVI)

wherein $R_1'$, $R_2'$ and $R_3'$ each independently represent optionally substituted alkyl, preferably $C_{1-12}$ alkyl, or optionally substituted phenyl; and $R_4'$ represents hydrogen; or is selected among optionally substituted alkyl, preferably $C_{1-12}$ alkyl, optionally substituted alkenyl, preferably $C_{2-12}$ alkenyl, optionally substituted alkynyl, preferably $C_{2-12}$ alkynyl or optionally substituted benzyl; and $A^1$ to $A^4$ and G have the same meanings as defined herein, if appropriate, in the presence of a fluoride reagent and an alkylating reagent (preferably methyl iodide when $R_4'$ represents hydrogen).

The invention is also directed to a preparation method (h) for the preparation of compounds according to the invention, comprising reacting compounds of the formula (XX):

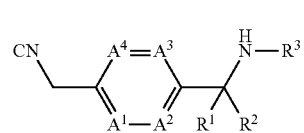
(XX)

with compounds of the formula (XII), to obtain compounds of the formula (XXI):

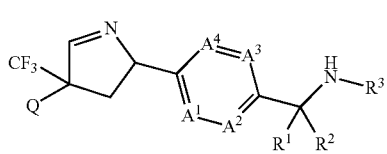
(XXI)

wherein $A^1$ to $A^4$, Q, and $R^1$ to $R^3$ have the same meanings as defined herein, followed by the step of shifting an imino double bond under basic conditions as described for example for preparation method (a).

The invention is also directed to a preparation method (i) for the preparation of compounds according to the invention, comprising reacting compounds of the formula (XXII):

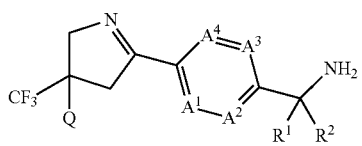
(XXII)

wherein $A^1$ to $A^4$, Q, and $R^1$ and $R^2$ have the same meanings as defined herein, with compounds of the formula (IX).

The invention is moreover directed to a preparation method (j) for the preparation of compounds according to the invention, comprising reacting compounds of the formula (X) with compounds of the formula (XXIII):

$R^3$—$NH_2$            (XXIII)

wherein $R^3$ is as defined herein.

The production methods (a) to (g) and (p) are illustrated by the following reaction schemes Reaction scheme 1 - Production method (a):

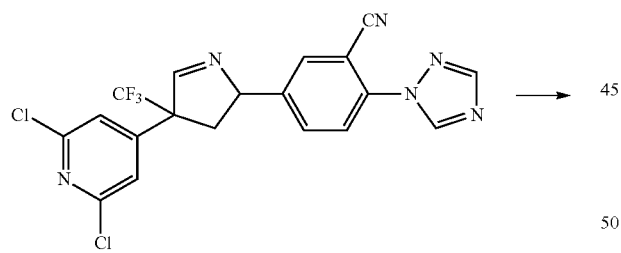

Here, 5-[4-(2,6-dichloropyridin-4-yl)-4-(trifluoromethyl)-3,4-dihydro-2H-pyrrol-2-yl]-2-(1H-1,2,4-triazol-1-yl)benzonitrile is used as starting material.

Reaction scheme 2 - Production method (b):

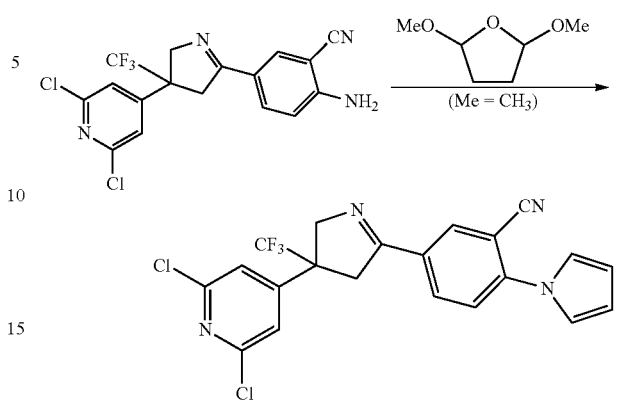

Here, 2-amino-5-[3-(2,6-dichloropyridin-4-yl)-3-(trifluoromethyl)-3,4-dihydro-2H-pyrrol-5-yl]benzonitrile and 2,5-dimethoxytetrahydrofuran are used as starting materials.

Reaction scheme 3 - Production method (c):

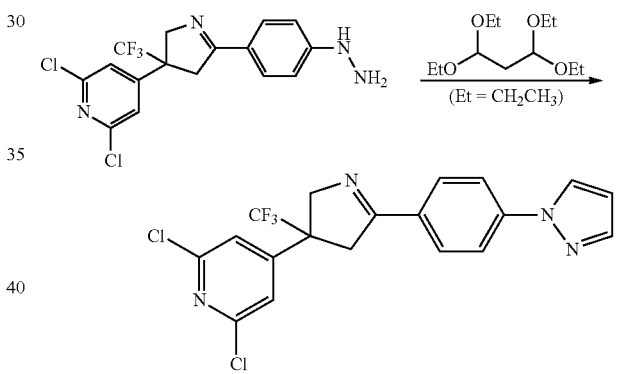

Here, 2,6-dichloro-4-[5-(4-hydrazinophenyl)-3-(trifluoromethyl)-3,4-dihydro-2H-pyrrol-3-yl]pyridine and 1,1,3,3-tetraethoxypropane are used as starting materials.

Reaction scheme 4 - Production method (d):

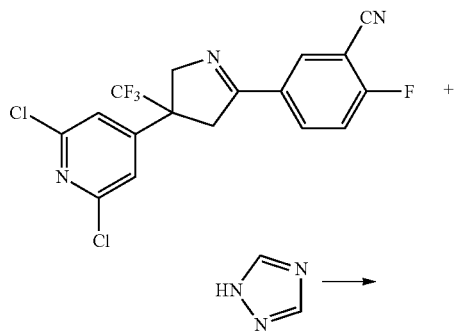

-continued

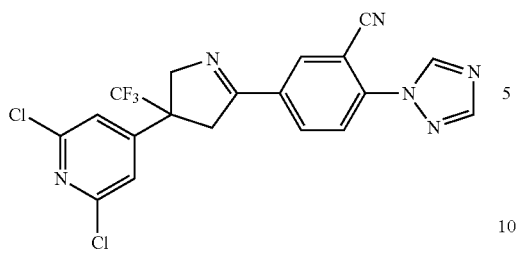

Here, 5-[3-(2,6-dichloropyridin-4-yl)-3-(trifluoromethyl)-3,4-dihydro-2H-pyrrol-5-yl]-2-fluorobenzonitrile and 1H-1,2,4-triazole are used as starting materials.

Reaction scheme 5 - Production method (e):

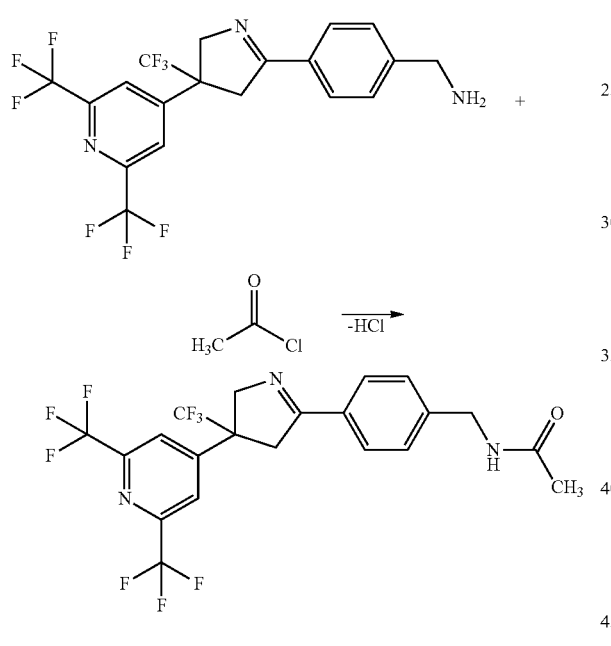

Here, 1-(4-{3-[2,6-bis(trifluoromethyl)pyridin-4-yl]-3-(trifluoromethyl)-3,4-dihydro-2H-pyrrol-5-yl}phenyl)methanamine and acetyl chloride are used as starting materials.

Reaction scheme 6 - Production method (f):

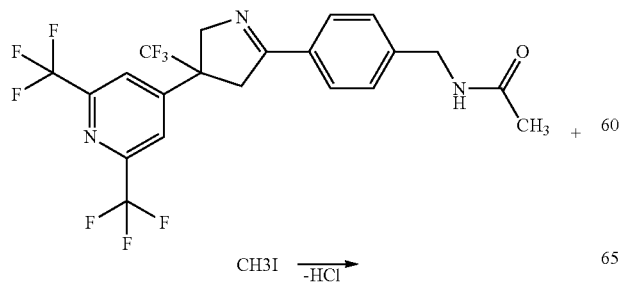

CH3I  $\xrightarrow{\text{-HCl}}$

-continued

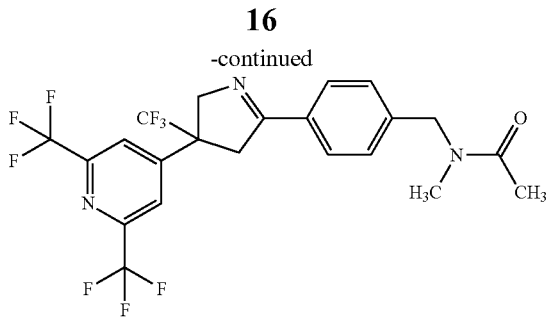

Here, N-(4-{3-[2,6-bis(trifluoromethyl)pyridin-4-yl]-3-(trifluoromethyl)-3,4-dihydro-2H-pyrrol-5-yl}benzyl)acetamide and iodomethane are used as starting materials.

Reaction scheme 7 - Production method (g):

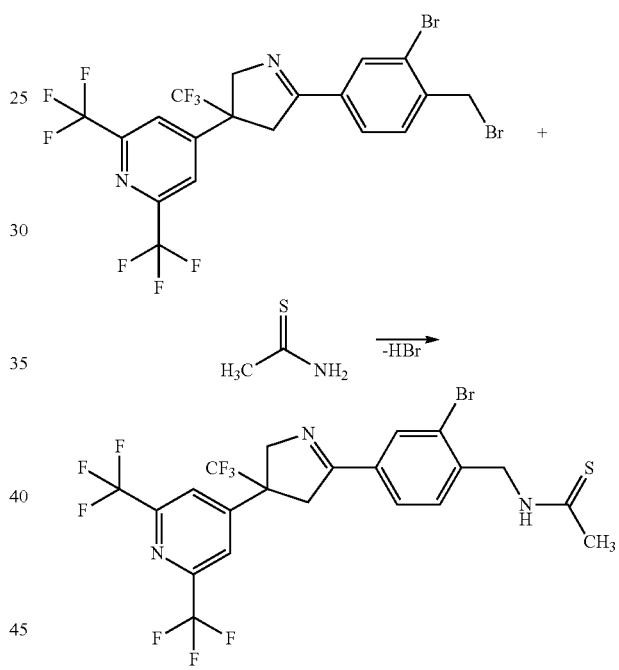

Here, 4-{5-[3-bromo-4-(bromomethyl)phenyl]-3-(trifluoromethyl)-3,4-dihydro-2H-pyrrol-3-yl}-2,6-bis(trifluoromethyl)pyridine and thioacetamide are used as starting materials.

Reaction scheme 8 - Production method (p):

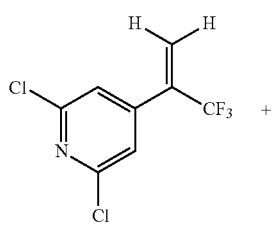

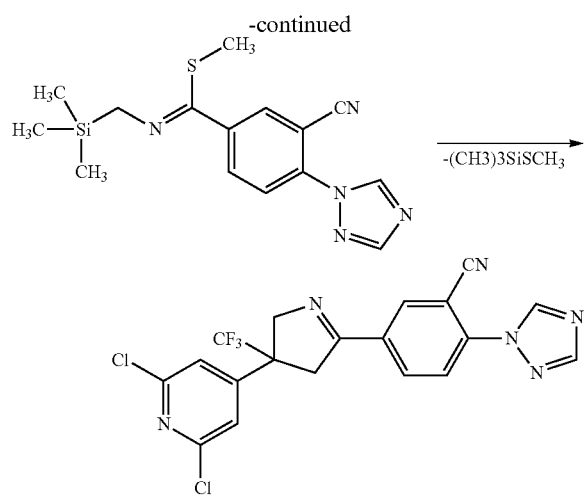

Here, 2,6-dichloro-4-(3,3,3-trifluoroprop-1-en-2-yl)pyridine and methyl 3-cyano-4-(1H-1,2,4-triazol-1-yl)-N-[(trimethylsilyl)methyl]benzenecarbimidothioate are used as starting materials.

Compounds of formula (II), which can be used as starting materials in the production method (a), are novel compounds, and can be synthesized using similar or the same methods as described in EP-A-1538138.

Compounds of formula (II) can be prepared by reacting compounds of the formula (XII) with compounds of the formula (XIII):

(XIII)

wherein $A^1$ to $A^4$ and G have the same meanings as defined herein, preferably, in the presence of a metal catalyst.

Compounds of formula (II) are, for example, 5-[4-(2,6-dichloropyridin-4-yl)-4-(trifluoromethyl)-3,4-dihydro-2H-pyrrol-2-yl]-2-(1H-1,2,4-triazol-1-yl)benzonitrile, 5-{4-[6-chloro-4-(trifluoromethyl)pyridin-2-yl]-4-(trifluoromethyl)-3,4-dihydro-2H-pyrrol-2-yl}-2-(1H-1,2,4-triazol-1-yl)benzonitrile, 544-(pyrimidin-5-yl)-4-(trifluoromethyl)-3,4-dihydro-2H-pyrrol-2-yl]-2-(1H-1,2,4-triazol-1-yl)benzonitrile, 6-[4-(2,6-dichloropyridin-4-yl)-4-(trifluoromethyl)-3,4-dihydro-2H-pyrrol-2-yl]-3-(1H-1,2,4-triazol-1-yl)pyridine-2-carbonitrile, 5-[4-(2,6-dichloropyridin-4-yl)-4-(trifluoromethyl)-3,4-dihydro-2H-pyrrol-2-yl]-2-(1H-1,2,4-triazol-1-yl)nicotinonitrile, 2-[4-(2,6-dichloropyridin-4-yl)-4-(trifluoromethyl)-3,4-dihydro-2H-pyrrol-2-yl]-5-(1H-1,2,4-triazol-1-yl)isonicotinonitrile, 2-{4-[2,6-bis(trifluoromethyl)pyridin-4-yl]-4-(trifluoromethyl)-3,4-dihydro-2H-pyrrol-2-yl}-5-(1H-1,2,4-triazol-1-yl)isonicotinonitrile, 5-{4-[4,6-bis(trifluoromethyl)pyridin-2-yl]-4-(trifluoromethyl)-3,4-dihydro-2H-pyrrol-2-yl}-2-(1H-1,2,4-triazol-1-yl)nicotinonitrile, 2-{4-[4,6-bis(trifluoromethyl)pyridin-2-yl]-4-(trifluoromethyl)-3,4-dihydro-2H-pyrrol-2-yl}-5-(1H-1,2,4-triazol-1-yl)isonicotinonitrile, 2-(1H-1,2,4-triazol-1-yl)-5-{4-(trifluoromethyl)-4-[5-(trifluoromethyl)pyridin-3-yl]-3,4-dihydro-2H-pyrrol-2-yl}benzonitrile, 5-{4-[2-chloro-6-(trifluoromethyl)pyridin-4-yl]-4-(trifluoromethyl)-3,4-dihydro-2H-pyrrol-2-yl}-2-(1H-1,2,4-triazol-1-yl)benzonitrile, 4-{2-[3-bromo-4-(1H-1,2,4-triazol-1-yl)phenyl]-4-(trifluoromethyl)-3,4-dihydro-2H-pyrrol-4-yl}-2,6-bis(trifluoromethyl)pyridine, 5-{4-[2,6-bis(trifluoromethyl)pyridin-4-yl]-4-(trifluoromethyl)-3,4-dihydro-2H-pyrrol-2-yl}-2-(1H-1,2,4-triazol-1-yl)benzonitrile, 3-chloro-5-[4-(2,6-dichloropyridin-4-yl)-4-(trifluoromethyl)-3,4-dihydro-2H-pyrrol-2-yl]-2-(1H-1,2,4-triazol-1-yl)pyridine, N44-{4-[2,6-bis(trifluoromethyl)pyridin-4-yl]-4-(trifluoromethyl)-3,4-dihydro-2H-pyrrol-2-yl}-2-(trifluoromethyl)benzyl]acetamide, N-(4-{4-[2,6-bis(trifluoromethyl)pyridin-4-yl]-4-(trifluoromethyl)-3,4-dihydro-2H-pyrrol-2-yl}-2-chlorobenzyl)-2-(methylsulfonyl)acetamide, N-[1-(4-{4-[2,6-bis(trifluoromethyl)pyridin-4-yl]-4-(trifluoromethyl)-3,4-dihydro-2H-pyrrol-2-yl}phenyl)ethyl]propanamide, 5-[4-(7-chloro-2,2-difluoro-1,3-benzodioxol-5-yl)-4-(trifluoromethyl)-3,4-dihydro-2H-pyrrol-2-yl]-2-(1H-1,2,4-triazol-1-yl)benzonitrile, N-[(6-{4-[2,6-bis(trifluoromethyl)pyridin-4-yl]-4-(trifluoromethyl)-3,4-dihydro-2H-pyrrol-2-yl}-4-chloropyridin-3-yl)methyl]propanamide, N-[(4-{4-[2,6-bis(trifluoromethyl)pyridin-4-yl]-4-(trifluoromethyl)-3,4-dihydro-2H-pyrrol-2-yl}-1-naphthyl)methyl]propanamide and N-{[6-{4-[2,6-bis(trifluoromethyl)pyridin-4-yl]-4-(trifluoromethyl)-3,4-dihydro-2H-pyrrol-2-yl]-2-(trifluoromethyl)pyridin-3-yl]methyl}propanamide.

Compounds of formula (XII) are described in The Journal of Organic Chemistry, Vol. 56, p. 7336-7340 (1991); ibid. Vol. 59, p. 2898-2901 (1994); Journal of Fluorine Chemistry, Vol. 95, p. 167-170 (1999) or WO 2005/5085216. Such compounds are, for example, [1-(trifluoromethyl)vinyl]benzene, 1,3-Difluoro-5-[1-(trifluoromethyl)vinyl]benzene, 1-chloro-3-[1-(trifluoromethyl)vinyl]benzene, 1,3-Dichloro-5-[1-(trifluoromethyl)vinyl]benzene, 1-trifluoromethyl-3-[1-(trifluoromethyl)vinyl]benzene, 1-Trifluoromethyl-4-[1-(trifluoromethyl) vinyl]benzene, 1,3-bis(trifluoromethyl)-5-[1-(trifluoromethyl)vinyl]benzene, 1,3-dibromo-5-[1-(trifluoromethyl)vinyl]benzene, 1,2,3-Trichloro-5-[1-(trifluoromethyl)vinyl]benzene, 1-fluoro-2-(trifluoromethyl)-4-[1-(trifluoromethyl)vinyl]benzene, 2,6-dichloro-4-(3,3,3-trifluoroprop-1-en-2-yl)pyridine, 4-chloro-2,2-difluoro-6-(3,3,3-trifluoroprop-1-en-2-yl)-1,3-benzodioxole, 2-chloro-6-(trifluoromethyl)-4-(3,3,3-trifluoroprop-1-en-2-yl)pyridine, 2-bromo-6-(trifluoromethyl)-4-(3,3,3-trifluoroprop-1-en-2-yl)pyridine, 2,4-bis(trifluoromethyl)-6-(3,3,3-trifluoroprop-1-en-2-yl)pyridine and 2,6-bis(trifluoromethyl)-4-(3,3,3-trifluoroprop-1-en-2-yl)pyridine.

Compounds of formula (XIII) can be synthesized by the methods described in Chem. Lett., p. 697-698 (1977) and/or can be obtained by reacting compounds of the formula (XIV) with ethyl formate

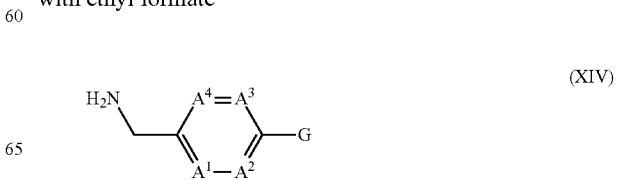

(XIV)

to obtain compounds of the formula (XV):

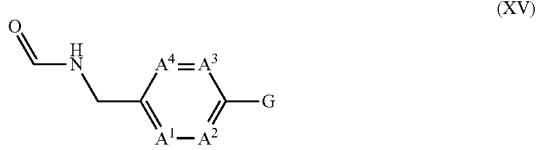

wherein $A^1$ to $A^4$ and G have the same meanings as defined herein, followed by the steps of halogenation, dehalogenation and hydrogenation.

Compounds of the formula (XIV), wherein G is as defined herein may be prepared by the method described in WO2009/097992.

Compounds of the formula (XV) are, for example, N-[3-bromo-4-(1H-1,2,4-triazol-1-yl)benzyl]formamide, N-{2-bromo-4-[(formylamino)methyl]benzyl}acetamide, tert-butyl ([4-(formamidomethyl)-1-naphthyl]methyl}carbamate and N-{[4-(formamidomethyl)-1-naphthyl]methyl}cyclopropanecarboxamide.

Additionally, the production method (a) can be carried out as described in Japanese Patent Application Laid-Open No. 2007-91708 and Chem. Lett., p. 1601-1604 (1985).

The reaction of the production method (a) can be performed in an appropriate diluent by using an alkali metal base such as sodium carbonate, potassium carbonate, sodium hydrogen carbonate, potassium hydrogen carbonate, sodium acetate, potassium acetate, sodium methoxide, sodium ethoxide or potassium tert-butoxide; an organic base such as triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane or imidazole; as the base; at temperatures from about −78 to about 200° C., preferably from −10 to about 100° C. Furthermore, the reaction can be performed at different pressures, such as normal pressure, i.e. 1013 mbar, or under reduced pressure, i.e. below 1013 mbar. The reaction time may vary and is from 0.1 to 72 hours, preferably from 1 to 24 hours.

Appropriate diluents for production method (a) include, for example, aliphatic, cycloaliphatic and aromatic hydrocarbons (optionally, may be chlorinated), for example, pentane, hexane, cyclohexane, petroleum ether, ligroin, benzene, toluene, xylene, dichloromethane, chloroform, carbon tetrachloride, 1,2-dichloroethane, chlorobenzene, dichlorobenzene and the like; ethers, for example, ethyl ether, methyl ethyl ether, isopropyl ether, butyl ether, dioxane, dimethoxyethane (DME), tetrahydrofuran (THF), diethylene glycol dimethyl ether (DGM) and the like; ketones, for example, acetone, methyl ethyl ketone (MEK), methyl isopropyl ketone, methyl isobutyl ketone (MIBK) and the like; nitriles, for example, acetonitrile, propionitrile, acrylonitrile and the like; alcohols, for example, methanol, ethanol, isopropanol, butanol, ethylene glycol and the like; esters, for example, ethyl acetate, amyl acetate and the like; acid amides, for example, dimethylformamide (DMF), dimethylacetamide (MDA), N-methylpyrrolidone, 1,3-dimethyl-2-imidazolidinone, hexamethylphosphoric triamide (RMPA) and the like; sulfones and sulfoxides, for example, dimethylsulfoxide (DMSO), sulfolane and the like; and bases, for example, pyridine and the like.

In carrying out the production method (a), for example, when 1 mole of the compounds of formula (II) is reacted with a base in an amount of 1 mole or in a slightly excess amount, in a diluent such as THF, compounds according to the invention can be obtained.

The compounds of formula (III), which can be used as starting materials, in the production method (b), are novel compounds, and can be synthesized according to the following preparation methods and reaction schemes. Compounds of formula (III) can be prepared by reacting compounds of the formula (XII) with compounds of the formula (XVI):

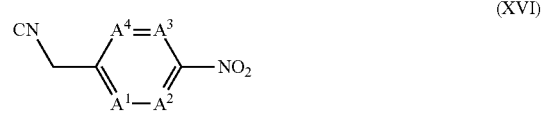

to obtain compounds of the formula (XVII):

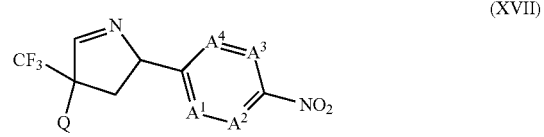

wherein $A^1$ to $A^4$ have the same meanings as the defined herein, followed by the step of shifting an imino double bond under basic conditions (e.g. in the presence of an alkali metal base) and reducing the —$NO_2$ group.

Compounds of the formula (XVI) are, for example, 2-fluoro-4-isocyanatomethyl-1-nitrobenzene, 2-Bromo-4-isocyanatomethyl-1-nitrobenzene, 2-Iodo-4-isocyanatomethyl-1-nitrobenzene, 2-Methyl-4-isocyanatomethyl-1-nitrobenzene and 2-Cyano-4-isocyanatomethyl-1-nitrobenzene.

Representative Compounds of formula (III) are, for example, 443-(3,5-dichlorophenyl)-3-(trifluoromethyl)-3,4-dihydro-2H-pyrrol-5-yl]aniline, 2-Bromo-4-[3-(3,5-dichlorophenyl)-3-(trifluoromethyl)-3,4-dihydro-2H-pyrrol-5-yl]aniline, 2-amino-5-[3-(2,6-dichloropyridin-4-yl)-3-(trifluoromethyl)-3,4-dihydro-2H-pyrrol-5-yl]benzonitrile, 2-bromo-4-[3-(3,4,5-trichlorophenyl)-3-(trifluoromethyl)-3,4-dihydro-2H-pyrrol-5-yl]aniline, 4-{3-[3,5-bis(trifluoromethyl)phenyl]-3-(trifluoromethyl)-3,4-dihydro-2H-pyrrol-5-yl}-2-(trifluoromethyl)aniline, 2-bromo-4-[3-(2,6-dichloropyridin-4-yl)-3-(trifluoromethyl)-3,4-dihydro-2H-pyrrol-5-yl]aniline and 4-{3-[2,6-bis(trifluoromethyl)pyridin-4-yl]-3-(trifluoromethyl)-3,4-dihydro-2H-pyrrol-5-yl}-2-bromoaniline.

Dialkoxytetrahydrofuran is, for example, 2,5-Dimethoxytetrahydrofuran, and 2,5-Diethoxytetrahydrofuran.

The reaction of the production method (b) can be performed in an appropriate diluent at temperatures from 0 to about 200° C., and preferably from room temperature i.e. about 20° C. to about 150° C. Furthermore, the reaction can be performed at different pressures, such as normal pressure, i.e. 1013 mbar, or under a pressure over or under normal pressure (reduced pressure). The reaction time may vary from 0.1 to 72 hours, preferably from 1 to 24 hours.

Appropriate diluents in production method (b) include, for example, aliphatic hydrocarbons (hexane, cyclohexane, benzene, toluene, xylene and others), acids (acetic acid, propionic acid), aromatic hydrocarbons (benzene, toluene, xylene, chlorobenzene and others), ethers (diethyl ether, dibutyl ether, dimethoxyethane (DME), tetrahydrofuran, dioxane and others), acid amides (dimethylformamide (DMF), dimethylacetamide (DME), N-methylpyrrolidone and others), acids (acetic acid, propionic acid), nitriles (acetonitrile, propionitrile and others), dimethylsulfoxide (DMSO), and solvent mixtures thereof.

In carrying out the production method (b), for example, when 1 mole of the compounds of formula (III) is reacted with 1 mole to 5 moles of 2,5-dimethoxytetrahydrofuran in a diluent such as acetic acid, compounds, according to the invention can be obtained.

In the case where a reaction with 1,2-diformylhydrazine is carried out in the production method (b), the reaction can be performed in the presence of a base, such as organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole, and trialkylhalosilane) and trialkylhalosilane, such as Trimethylchlorosilane, Triethylchlorosilane and Trimethylbromosilane.

In carrying out the production method, when 1 mole of the compounds of formula (III) is reacted with 1 to 5 moles of 1,2-diformylhydrazine, 1 to 10 moles of the base, and 1 to 25 moles of trialkylhalosilane, in a large excess of pyridine, compounds according to the invention can be obtained.

In the case that in production method (b), sodium azide is reacted with trialkyl orthoformate, examples of the trialkyl orthoformate include trimethyl orthoformate and triethyl orthoformate.

In carrying out the production method, when 1 mole of the compounds of formula (III) is reacted with 1 to 3 moles of sodium azide and 1 to 10 moles of trialkyl orthoformate in an appropriate diluent such as acetic acid, the compounds, according to the invention can be obtained.

The compounds of formula (N), which can be used as starting material in the production method (c), are novel compounds, and can be synthesized by subjecting compounds of formula (III) to the well known "Sandmeyer" reaction, and followed by a reduction reaction.

Representative compounds of formula (N) are, for example, 3-(3,5-dichlorophenyl)-1-(4-hydrazinophenyl)-3-(trifluoromethyl)-3,4-dihydro-2H-pyrrole, 3-(3,5-dichlorophenyl)-1-(4-hydrazino-3-methylphenyl)-3-(trifluoromethyl)-3,4-dihydro-2H-pyrrole, 2,6-dichloro-4-[5-(4-hydrazinophenyl)-3-(trifluoromethyl)-3,4-dihydro-2H-pyrrol-3-yl]pyridine, 5-(4-hydrazinophenyl)-3-(3,4,5-trichlorophenyl)-3-(trifluoromethyl)-3,4-dihydro-2H-pyrrole, 3-[3,5-bis(trifluoromethyl)phenyl]-5-[4-hydrazino-3-(trifluoromethyl)phenyl]-3-(trifluoromethyl)-3,4-dihydro-2H-pyrrole, 4-[5-(3-bromo-4-hydrazinophenyl)-3-(trifluoromethyl)-3,4-dihydro-2H-pyrrol-3-yl]-2-chloro-6-(trifluoromethyl)pyridine and 4-[5-(3-bromo-4-hydrazinophenyl)-3-(trifluoromethyl)-3,4-dihydro-2H-pyrrol-3-yl]-2,6-bis(trifluoromethyl)pyridine.

Suitable 1,1,3,3-tetraalkoxypropanes are, for example, 1,1,3,3-tetramethoxypropane and 1,1,3,3-Tetraethoxypropane, The reaction of the production method (c) can be performed in an appropriate diluent at temperatures and pressure as described for production method (b).

In carrying out the production method (c), for example, when 1 mole of the compounds of formula (IV) is reacted with 1 mole to 5 moles of 1,1,3,3-tetraalkoxypropane in a diluent such as ethanol, and if necessary, in the presence of a catalytic amount of an acid such as sulfuric acid, the compounds according to the invention can be obtained.

The compounds of formula (V), which can be used as starting materials in the production method (d), are known compounds, and can be synthesized by reacting the compounds of the formula (XII) with compounds of the formula (XVIII):

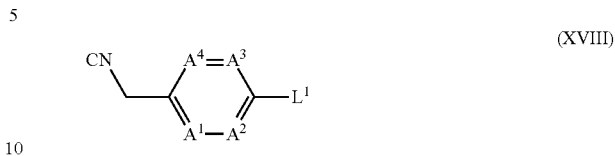

to obtain compounds of the following formula:

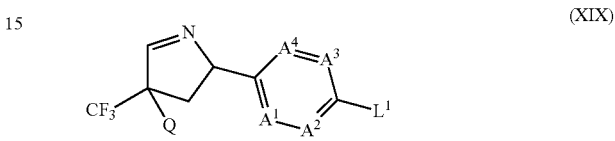

wherein $A^1$ to $A^4$, and $L^1$ have the same meanings as defined herein, followed by the step of shifting an imino double under basic conditions.

The compounds of the formula (XVIII) can be synthesized according to the method for producing the compounds of the formula (XIII). Specific compounds of the formula (XVIII) are, for example, 2-Fluoro-5-isocyanatomethyl-nitrobenzene and 2-Fluoro-5-isocyanatomethyl-benzonitrile.

Representative compounds of the formula (V) used in the production method (d) are, for example, 5-[3-(3,5-dichlorophenyl)-3-(trifluoromethyl)-3,4-dihydro-2H-pyrrol-5-yl]-2-fluorobenzonitrile and 5-{3-[3,5-bis(trifluoromethyl)phenyl]-3-(trifluoromethyl)-3,4-dihydro-2H-pyrrol-5-yl}-2-fluorobenzonitrile, 5-[3-(2,6-dichloropyridin-4-yl)-3-(trifluoromethyl)-3,4-dihydro-2H-pyrrol-5-yl]-2-fluorobenzonitrile, 2-fluoro-5-[3-(3,4,5-trichlorophenyl)-3-(trifluoromethyl)-3,4-dihydro-2H-pyrrol-5-yl]benzonitrile, 3-[3,5-bis(trifluoromethyl)phenyl]-5-[4-fluoro-3-(trifluoromethyl)phenyl]-3-(trifluoromethyl)-3,4-dihydro-2H-pyrrole, 5-[3-(7-chloro-2,2-difluoro-1,3-benzodioxol-5-yl)-3-(trifluoromethyl)-3,4-dihydro-2H-pyrrol-5-yl]-2-fluorobenzonitrile, 5-{3-[2-chloro-6-(trifluoromethyl)pyridin-4-yl]-3-(trifluoromethyl)-3,4-dihydro-2H-pyrrol-5-yl}-2-fluorobenzonitrile, 5-{3-[2,6-bis(trifluoromethyl)pyridin-4-yl]-3-(trifluoromethyl)-3,4-dihydro-2H-pyrrol-5-yl}-2-fluorobenzonitrile, 4-[5-(3-bromo-4-fluorophenyl)-3-(trifluoromethyl)-3,4-dihydro-2H-pyrrol-3-yl]-2,6-dichloropyridine, 4-[5-(3-bromo-4-fluorophenyl)-3-(trifluoromethyl)-3,4-dihydro-2H-pyrrol-3-yl]-2-chloro-6-(trifluoromethyl)pyridine, 4-[5-(3-bromo-4-fluorophenyl)-3-(trifluoromethyl)-3,4-dihydro-2H-pyrrol-3-yl]-2,6-bis(trifluoromethyl)pyridine, 5-(3-bromo-4-fluorophenyl)-3-(7-chloro-2,2-difluoro-1,3-benzodioxol-5-yl)-3-(trifluoromethyl)-3,4-dihydro-2H-pyrrole, 2-chloro-5-[3-(2,6-dichloropyridin-4-yl)-3-(trifluoromethyl)-3,4-dihydro-2H-pyrrol-5-yl]nicotinonitrile, 5-{3-[2,6-bis(trifluoromethyl)pyridin-4-yl]-3-(trifluoromethyl)-3,4-dihydro-2H-pyrrol-5-yl}-2-chloronicotinonitrile, 6-{3-[2,6-bis(trifluoromethyl)pyridin-4-yl]-3-(trifluoromethyl)-3,4-dihydro-2H-pyrrol-5-yl}-3-chloropyridine-2-carbonitrile, 3-chloro-6-[3-(2,6-dichloropyridin-4-yl)-3-(trifluoromethyl)-3,4-dihydro-2H-pyrrol-5-yl]pyridine-2-carbonitrile, 6-{3-[4,6-bis(trifluoromethyl)pyridin-2-yl]-3-(trifluoromethyl)-3,4-dihydro-2H-pyrrol-5-yl}-3-chloropyridine-2-carbonitrile and 5-{3-[4,6-bis(trifluoromethyl)pyridin-2-yl]-3-(trifluoromethyl)-3,4-dihydro-2H-pyrrol-5-yl}-2-chloronicotinonitrile.

Many of the compounds represented by the formulas G2-H, G3-H, G4-H, G5-H, G6-H, G8-H and G9-H, which are the starting material in the production method (d), are known compounds, and specific examples thereof include 1H-imidazole, 1H-pyrazole, 4-methyl-1H-pyrazole, 4-Fluoro-1H-pyrazole, 4-chloro-1H-pyrazole, 4-bromo-1H-pyrazole, 4-iodo-1H-pyrazole, 4-Nitro-1H-pyrazole, 3-trifluoromethyl-1H-pyrazole, 4-trifluoromethyl-1H-pyrazole, 4-cyano-1H-pyrazole, 1H-1,2,3-triazole, 1H-1,2,4-triazole, 1H-tetrazole, 5-methyl-1H-tetrazole, and 5-(methylthio)-1H-tetrazole.

The reaction of the production method (d) can be performed in an appropriate diluent by using an alkali metal base as exemplified at the reaction method (a) at reaction conditions (temperatures, pressure, reaction time) as described for production method (a).

In carrying out the production method (d), for example, when 1 mole of the compounds of formula (V) is reacted with 1 mole to 3 moles of G6-H in a diluent such as DMF, in the presence of 1 mole to 3 moles of a base, the compounds according to the invention can be obtained.

The compounds of formula (VI), which can be used as starting materials in the production method (e) can be obtained by the methods (g) and (h) to (j) as described herein.

The compounds of formula (XX) used in the production method (h) can be synthesized according to the procedure described for the preparation of compounds of formula (XIII), and are, for example, 1-[2-bromo-4-(isocyanomethyl) phenyl]-N-methylmethanamine, N-benzyl-1-[2-bromo-4-(isocyanomethyl)phenyl]methanamine.

The compounds of formula (XXI) can be synthesized according to the procedure described for the preparation of compounds of formula (II). Compounds of formula (XXI) are, for example, 1-{2-bromo-4-[4-(3,5-dichlorophenyl)-4-(trifluoromethyl)-3,4-dihydro-2H-pyrrol-2-yl]phenyl}-N-methylmethanamine, N-benzyl-1-{2-bromo-4-[4-(3,5-dichlorophenyl)-4-(trifluoromethyl)-3,4-dihydro-2H-pyrrol-2-yl]phenyl}methanamine, 1-(4-{4-[2,6-bis(trifluoromethyl)pyridin-4-yl]-4-(trifluoromethyl)-3,4-dihydro-2H-pyrrol-2-yl}-2-chlorophenyl)methanamine, 1-[4-{4-[2,6-bis(trifluoromethyl)pyridin-4-yl]-4-(trifluoromethyl)-3,4-dihydro-2H-pyrrol-2-yl}-2-(trifluoromethyl) phenyl]methanamine, 1-(4-{4-[2,6-bis(trifluoromethyl)pyridin-4-yl]-4-(trifluoromethyl)-3,4-dihydro-2H-pyrrol-2-yl}phenyl)ethanamine and 1-(4-{-4-[2-chloro-6-(trifluoromethyl)pyridin-4-yl]-4-(trifluoromethyl)-3,4-dihydro-2H-pyrrol-2-yl}phenyl)ethanamine, 1-{4-[4-(2,6-dichloropyridin-4-yl)-4-(trifluoromethyl)-3,4-dihydro-2H-pyrrol-2-yl]-1-naphthyl}methanamine and 1-(4-{4-[2,6-bis(trifluoromethyl)pyridin-4-yl]-4-(trifluoromethyl)-3,4-dihydro-2H-pyrrol-2-yl}-1-naphthyl)methanamine.

The compounds of the formula (XXII) can be synthesized according to the procedure described for the preparation of compounds of formula (I). Compounds of formula (XXII) are, for example, 1-{2-bromo-4-[3-(3,5-dichlorophenyl)-3-(trifluoromethyl)-3,4-dihydro-2H-pyrrol-5-yl] phenyl}methan-amine, 1-(4-{3-[2,6-bis(trifluoromethyl)pyridin-4-yl]-3-(trifluoromethyl)-3,4-dihydro-2H-pyrrol-5-yl}-2-chlorophenyl)methanamine, 1-(4-{3-[2,6-bis(trifluoromethyl)pyridin-4-yl]-3-(trifluoromethyl)-3,4-dihydro-2H-pyrrol-5-yl}-2-methylphenyl)methanamine, 1-(4-{3-[2,6-bis(trifluoromethyl)pyridin-4-yl]-3-(trifluoromethyl)-3,4-dihydro-2H-pyrrol-5-yl}-2-(trifluoromethyl) phenyl]methanamine, 1-(4-{3-[2,6-bis(trifluoromethyl)pyridin-4-yl]-3-(trifluoromethyl)-3,4-dihydro-2H-pyrrol-5-yl) phenyl)ethanamine, 1-(4-{3-[2,6-bis(trifluoromethyl) pyridin-4-yl]-3-(trifluoromethyl)-3,4-dihydro-2H-pyrrol-5-yl}-1-naphthyl)methanamine, 1-{4-[3-(2,6-dichloropyridin-4-yl)-3-(trifluoromethyl)-3,4-dihydro-2H-pyrrol-5-yl]-1-naphthyl}methanamine and 2-(aminomethyl)-5-[3-(3,5-dichlorophenyl)-3-(trifluoromethyl)-3,4-dihydro-2H-pyrrol-5-yl]benzonitrile.

Suitable compounds of the formula (VII) for use in the preparation method are, for example, acetyl chloride, propionyl chloride, pivaloyl chloride, acryloyl chloride, methyl chloroformate, N,N-dimethylcarbamoyl chloride, cyclopropylcarbonyl chloride, N,N-dimethylthiocarbamoyl chloride, benzoyl chloride, nicotinyl chloride, anhydrous acetic acid, anhydrous trifluoroacetic acid or methanesulfonyl chloride.

The reaction of the production method (e) can be performed in an appropriate diluent by using a base as exemplified at the production method (a) at conditions (temperature, pressure, reaction time) as described for production method (a).

In carrying out the production method (e), for example, when 1 mole of the compounds of formula (VI) is reacted with 1 mole to 3 moles of the compounds of formula (VII) in a diluent such as DMF, in the presence of 1 mole to 3 moles of a base, the compound according to the present invention can be obtained.

Suitable compounds of the formula (VIII) for the use in the production method (f), can be obtained by the production methods (g) and (k) to (m).

Production Method (k)

A method for the preparation of compounds of formula (VIII) comprising a step (a) of reacting compounds of the formula (XXIV) with the compounds of the formula (XII),

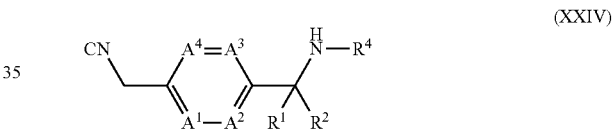

to obtain compounds of the formula (XXV):

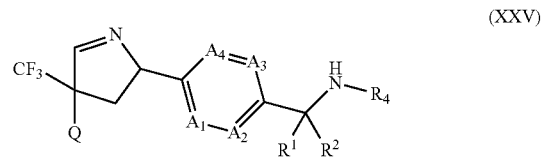

wherein $A^1$ to $A^4$, Q, $R^1$, $R^2$, and $R^4$ have the same meanings as defined herein; and a step (b) of shifting an imino double bond under basic conditions.

Production Method (l)

A method of reacting the compounds of the formula (XXII) with the compounds of the formula (VII).

Production Method (m)

A method of reacting the compounds of the formula (X) with compounds of the following formula:

$R^4$—$NH_2$         (XXVI)

wherein $R^4$ has the same meaning as defined herein.

Compounds of the formula (XXIV) can be synthesized according to the procedure described for the preparation of compounds of formula (XIII). Representative compounds of formula (XXIV) are, for example, N-[2-fluoro-4-(isocyanatomethyl)benzyl]acetamide, N-[2-bromo-4-(isocyanatomethyl)benzyl]acetamide, N-[2-iodo-4-(isocyanatomethyl)benzyl]acetamide, N-[2-methyl-4-(isocyanatomethyl)benzyl]acetamide N-[2-cyano-4-(isocyanatomethyl)benzyl]acetamide and 1-[4-(isocyanomethyl)-1-naphthyl]methanamine.

The compounds of the formula (XXV) can be synthesized according to the procedure described for the preparation of compounds of formula (II). Representative examples thereof are, for example, N-{2-bromo-4-[4-(3,5-dichlorophenyl)-4-(trifluoromethyl)-3,4-dihydro-2H-pyrrol-2-yl]benzyl}acetamide, N-{2-bromo-4-[4-(3,5-dichlorophenyl)-4-(trifluoromethyl)-3,4-dihydro-2H-pyrrol-2-yl]benzyl}benzamide, N-(4-{4-[2,6-bis(trifluoromethyl)pyridin-4-yl]-4-(trifluoromethyl)-3,4-dihydro-2H-pyrrol-2-yl}-2-bromobenzyl)acetamide, N-(4-{4-[2,6-bis(trifluoromethyl)pyridin-4-yl]-4-(trifluoromethyl)-3,4-dihydro-2H-pyrrol-2-yl}-2-chlorobenzyl)propanamide, N-[4-{4-[2,6-bis(trifluoromethyl)pyridin-4-yl]-4-(trifluoromethyl)-3,4-dihydro-2H-pyrrol-2-yl}-2-(trifluoromethyl)benzyl]-2-(methylsulfonyl)acetamide and N-[1-(4-{4-[2,6-bis(trifluoromethyl)pyridin-4-yl]-4-(trifluoromethyl)-3,4-dihydro-2H-pyrrol-2-yl}phenyl)ethyl]propanamide.

The compounds of the formula (XXII) in the aforementioned production method (l) correspond to compounds of the formula (VI) wherein $R^3$ stands for hydrogen.

Suitable compounds of the formula (XXVI) for the use in the production method (m) are, for example, formamide, acetamide, propionamide, 2,2,2-trifluoroacetamide, benzamide, ethyl carbamate or ethanethioamide.

Production method (l) can be performed under the same conditions as those described for production method (e).

Suitable compounds of formula (X) for the use in the production method (g) can be obtained by the production method (n) or (o).

Production Method (n)

A method of reacting compounds of the following formula:

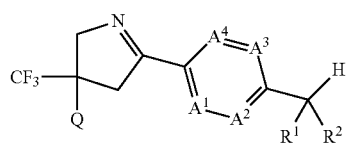

(XXVII)

wherein $A^1$ to $A^4$, Q, $R^1$, and $R^2$ have the same meanings as defined herein, with a halogenating agent.

Production Method (o)

A method for the preparation of compounds to the invention, comprising reducing compounds of the formula (XXVIII):

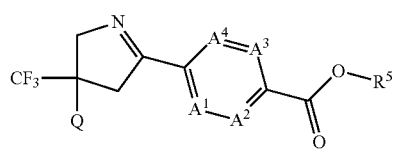

(XXVIII)

wherein $A^1$ to $A^4$ have the same meanings as defined herein; and wherein $R^5$ stands for an alkyl group, to obtain compounds of the formula (XXIX):

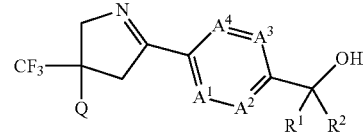

(XXIX)

wherein $A^1$ to $A^4$, Q, $R^1$, and $R^2$ have the same meanings as defined herein, and then reacting the compound (XXIX) with methanesulfonyl chloride or a halogenating agent.

The compounds of the formula (XXVII) can be obtained, for example, by reacting compounds of the formula (XXX):

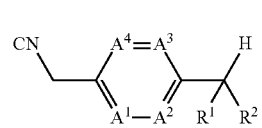

(XXX)

wherein $A^1$ to $A^4$, $R^1$, and $R^2$ have the same meanings as defined herein, with compounds of the formula (XII) to obtain compounds of the following formula (XXXI):

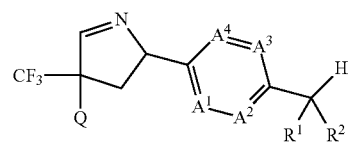

(XXXI)

wherein $A^1$ to $A^4$, Q, $R^1$ and $R^2$ have the same meanings as defined herein, followed by the step of shifting an imino double bond under basic conditions.

The compounds of the formula (XXVIII) can be obtained, by reacting compounds of the formula (XXXII):

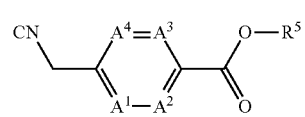

(XXXII)

wherein $A^1$ to $A^4$, and $R^5$ have the same meanings as defined herein, with the compounds of the formula (XII) to obtain compounds of the formula (XXXIII):

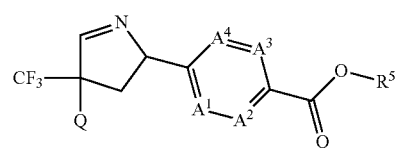

(XXXIII)

wherein $A^1$ to $A^4$, Q, and $R^5$ have the same meanings as defined herein, followed by the step of shifting an imino double bond under basic conditions.

Representative compounds of the formula (XXX) are, for example, 2-bromo-4-(isocyanomethyl)-1-methylbenzene, 2-Cyano-4-(isocyanomethyl)-1-methylbenzene, 2-bromo-4-

(isocyanomethyl)-1-ethylbenzene, (4-methyl-1-naphthyl) methyl isocyanide, 4-[2-(4-methyl-1-naphthyl)-4-(trifluoromethyl)-3,4-dihydro-2H-pyrrol-4-yl]-2,6-bis (trifluoromethyl)pyridine and 1-ethyl-4-(isocyanomethyl) benzene.

Moreover, compounds of the formula (XXXVIII)

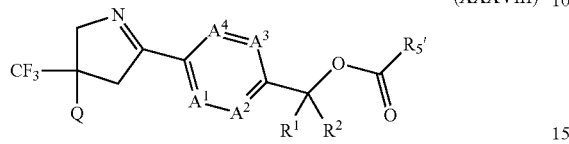

(XXXVIII)

wherein $A^1$ to $A^4$, Q, $R^1$, $R^2$ and $R_5'$ have the same meanings as defined herein, can also be synthesized by reacting compounds of the formula (XXXVII)

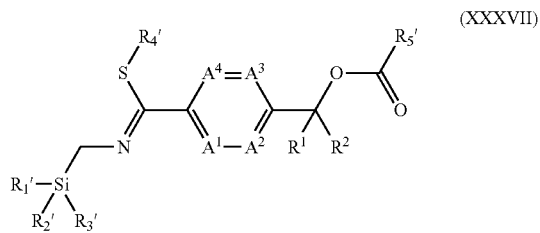

(XXXVII)

wherein $R^1$, $R^2$, and $A^1$ to $A^4$ have the same meanings as defined herein, and wherein $R_1'$, $R_2'$ and $R_3'$ each independently represent optionally substituted alkyl or optionally substituted phenyl; and $R_4'$ represents hydrogen; or a chemical group selected among optionally substituted alkyl, alkenyl, or alkynyl; or optionally substituted benzyl; and $R_5'$ represents hydrogen, optionally substituted alkyl or optionally substituted phenyl; with compounds of formula (XII), if appropriate, in the presence of a fluorine reagent and an alkylating reagent (preferably methyl iodide when $R_4'$ represents hydrogen).

Compounds of formula (XXIX) can be synthesized by subjecting the compounds of formula (XXXVIII) to a hydrolysis using known procedures.

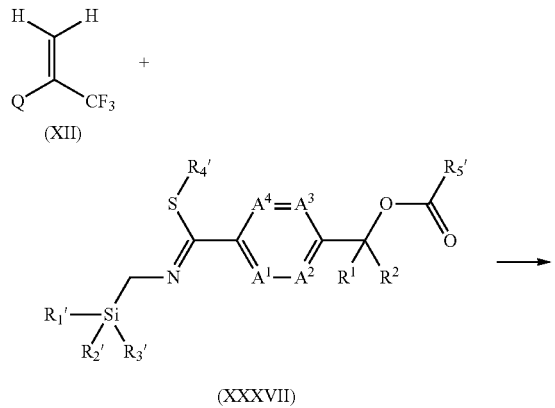

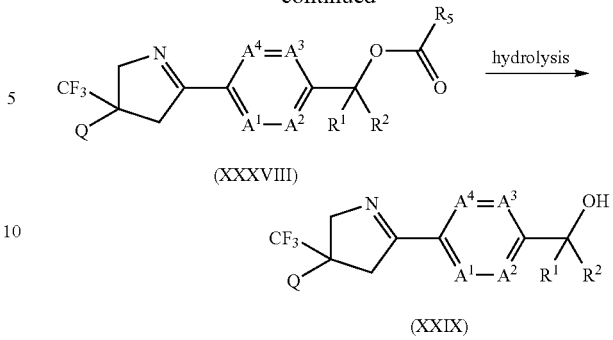

Compounds of formula (XXIX) are then reacted with methanesulfonyl chloride or a halogenating agent to yield compounds according to the invention.

Compounds of the formula (XXXVII) can be synthesized according to reaction process described in WO2009/097992.

Compounds of the formula (XXXVII) are, for example, 2-bromo-4-[(methylsulfanyl){[(trimethylsilyl)methyl] imino}methyl]benzyl acetate, 2-chloro-4-[(methyl sulfanyl)-{[(trimethylsilyl)methyl]imino}methyl]benzyl acetate, 2-trifluoromethyl-4-[(methyl sulfanyl)-{[(trimethylsilyl)methyl) imino]methyl]benzyl acetate, {6-[(methylsulfanyl){ [(trimethylsilyl)-methyl]imino}methyl]-2-(trifluoromethyl) pyridin-3-yl}methyl acetate, {6-[(methylsulfanyl)-{ [(trimethylsilyl)methyl]imino}methyl]-4-(trifluoromethyl) pyridin-3-yl}methyl acetate, 4-[5-(4-methyl-1-naphthyl)-3-(trifluoromethyl)-3,4-dihydro-2H-pyrrol-3-yl]-2,6-bis (trifluoromethyl)pyridine and 1-{4-[(methylsulfanyl){ [(trimethylsilyl)methyl]imino}methyl]phenyl}ethyl acetate.

Additionally, the production method for the preparation of compounds of the formula (XXXVIII) can be carried out according to the methods described in The Journal of Organic Chemistry, Vol. 52, p. 1027-1035 (1987).

The production method for the preparation of compounds of the formula (XXXVIII) can be performed in an appropriate diluent, by using a fluorine reagent such as potassium fluoride, or tetramethylammonium fluoride, tetraethylammonium fluoride or tetrabutylammonium fluoride if $R_4'$ dose not stands for hydrogen. In the case that $R_4'$ stands for hydrogen, the reaction can be carried out in a one pot reaction by firstly adding an alkylating reagent, such as methyl iodide, to the reaction system and then adding an appropriate fluorine reagent. The reaction can be performed at temperatures from about −78 to about 100° C., preferably −10 to about 50° C. Furthermore, it is desirable to perform the reaction at normal pressure, i.e. 1013 mbar but the reaction can also be operated under pressure i.e. above 1013 mbar or under reduced pressure i.e. under 1013 mbar. The reaction time is from 0.1 to 10 hours, preferably from 1 to 5 hours.

In carrying out the production method of the compounds of the formula (XXXVIII), for example, when 1 mole of the compounds of formula (XXXVII) is reacted with 1 mole of the compounds of formula (XII) in a diluent such as THF, in the presence of 0.1 mole of fluorination agent, such as tetrabutylammonium fluoride, the compound of formula (XXXVIII) can be obtained.

Compounds of the formula (XXXVIII) are, for example, 2-Bromo-4-[3-(3,5-dichlorophenyl)-3-(trifluoromethyl)-3, 4-dihydro-2H-pyrrol-5-yl]benzyl acetate, 2-Chloro-4-[3-(3, 5-dichlorophenyl)-3-(trifluoromethyl)-3,4-dihydro-2H-pyrrol-5-yl]benzyl acetate, 2-Cyano-4-[3-(3,5-dichlorophenyl)-3-(trifluoromethyl)-3,4-dihydro-2H-pyrrol-5-yl]benzyl acetate, 2-Trifluoromethyl-4-[3-(3,5-dichlorophenyl)-3-(trifluoromethyl)-3,4-dihydro-2H-pyrrol-5-yl]benzyl acetate, 2-Bromo-4-[3-(3,5-dibromophenyl)-3-(trifluoromethyl)-3,4-dihydro-2H-pyrrol-5-yl]benzyl acetate, 2-Chloro-4-[3-(3,5-dibromophenyl)-3-(trifluoromethyl)-3,4-dihydro-2,1-pyrrol-5-yl]benzyl acetate, 2-Cyano-4-[3-(3,5-dibromophenyl)-3-(trifluoromethyl)-3,4-d hydro-2H-pyrrol-5-yl]benzyl acetate, 2-Trifluoromethyl-4-[3-(3,5-d bromophenyl)-3-(trifluoromethyl)-3,4-dihydro-2H-pyrrol-5-yl]benzyl acetate, 2-Bromo-4-[3-(3,5-bistrifluoromethylphenyl)-3-(trifluoromethyl)-3,4-dihydro-2H-pyrrol-5-yl]benzyl acetate, 2-Chloro-4-[3-(3,5-bistrifluoromethylphenyl)-3-(trifluoromethyl)-3,4-dihydro-2H-pyrrol-5-yl]benzyl acetate, 2-Cyano-4-[3-(3,5-bistrifluoromethylphenyl)-3-(trifluoromethyl)-3,4-dihydro-2H-pyrrol-5-yl]benzyl acetate, 2-Trifluoromethyl-4-[3-(3,5-bistrifluoromethylphenyl)-3-(trifluoromethyl)-3,4-dihydro-2H-pyrrol-5-yl]benzyl acetate, 2-Bromo-4-[3-(3,4,5-trichlorophenyl)-3-(trifluoromethyl)-3,4-dihydro-2H-pyrrol-5-yl]benzyl acetate, 2-Chloro-4-[3-(3,4,5-trichlorophenyl)-3-(trifluoromethyl)-3,4-dihydro-2H-pyrrol-5-yl]benzyl acetate, 2-Cyano-4-[3-(3,4,5-trichlorophenyl)-3-(trifluoromethyl)-3,4-dihydro-2H-pyrrol-5-yl]benzyl acetate, 2-Trifluoromethyl-4-[3-(3,4,5-trichlorophenyl)-3-(trifluoromethyl)-3,4-dihydro-2H-pyrrol-5-yl]benzyl acetate, {6-[3-(3,5-dichlorophenyl)-3-(trifluoromethyl)-3,4-dihydro-2H-pyrrol-5-yl]-2-(trifluoromethyl)pyridin-3-yl}methyl acetate, {6-[3-(3,5-dichlorophenyl)-3-(trifluoromethyl)-3,4-dihydro-2H-pyrrol-5-yl]-4-(trifluoromethyl)pyridin-3-yl}methyl acetate, 4-[3-(2,6-dichloropyridin-4-yl)-3-(trifluoromethyl)-3,4-dihydro-2H-pyrrol-5-yl]-2-(trifluoromethyl)benzyl acetate, 2-(trifluoromethyl)-4-{3-(trifluoromethyl)-3-[2-(trifluoromethyl)pyridin-4-yl]-3,4-dihydro-2H-pyrrol-5-yl}benzyl acetate, 4-{3-[2,6-bis(trifluoromethyl)pyridin-4-yl]-3-(trifluoromethyl)-3,4-dihydro-2H-pyrrol-5-yl}-2-(trifluoromethyl)benzyl acetate, 2-(trifluoromethyl)-4-{3-(trifluoromethyl)-3-[6-(trifluoromethyl)pyridin-2-yl]-3,4-dihydro-2H-pyrrol-5-yl}benzyl acetate, 4-{3-[4,6-bis(trifluoromethyl)pyridin-2-yl]-3-(trifluoromethyl)-3,4-dihydro-2H-pyrrol-5-yl}-2-(trifluoromethyl)benzyl acetate, 2-bromo-4-[3-(2,6-dichloropyridin-4-yl)-3-(trifluoromethyl)-3,4-dihydro-2H-pyrrol-5-yl]benzyl acetate, 2-cyano-4-[3-(2,6-dichloropyridin-4-yl)-3-(trifluoromethyl)-3,4-dihydro-2H-pyrrol-5-yl]benzyl acetate, 2-chloro-4,3-(2,6-dichloropyridin-4-yl)-3-(trifluoromethyl)-3,4-dihydro-2H-pyrrol-5-yl]benzyl acetate, 2-chloro-4-{3-(trifluoromethyl)-3-[2-(trifluoromethyl)pyridin-4-yl]-3,4-dihydro-2H-pyrrol-5-yl}benzyl acetate, 4-{3-[2,6-bis(trifluoromethyl)pyridin-4-yl]-3-(trifluoromethyl)-3,4-dihydro-2H-pyrrol-5-yl}-2-chlorobenzyl acetate, 2-chloro-4-{3-(trifluoromethyl)-3-[6-(trifluoromethyl)pyridin-2-yl]-3,4-dihydro-2H-pyrrol-5-yl}benzyl acetate, 4-{3-[4,6-bis(trifluoromethyl)pyridin-2-yl]-3-(trifluoromethyl)-3,4-dihydro-2H-pyrrol-5-yl}-2-chlorobenzyl acetate, 4-{3-[2,6-bis(trifluoromethyl)pyridin-4-yl]-3-(trifluoromethyl)-3,4-dihydro-2H-pyrrol-5-yl}-2-chlorobenzyl acetate, 4-{3-[2,6-bis(trifluoromethyl)pyridin-4-yl]-3-(trifluoromethyl)-3,4-dihydro-2H-pyrrol-5-yl}-2-bromobenzyl acetate, 4-{3-[2,6-bis(trifluoromethyl)pyridin-4-yl]-3-(trifluoromethyl)-3,4-dihydro-2H-pyrrol-5-yl}-2-(trifluoromethyl)benzyl acetate, methyl 4-{3-[2,6-bis(trifluoromethyl)pyridin-4-yl]-3-(trifluoromethyl)-3,4-dihydro-2H-pyrrol-5-yl}-1-naphthoate and 1-(4-{3-[2,6-bis(trifluoromethyl)pyridin-4-yl]-3-(trifluoromethyl)-3,4-dihydro-2H-pyrrol-5-yl}phenyl)ethyl acetate.

Suitable amide compounds of the formula (XI) in the production method (g) are, for example, acetamide, 2,2,2-trifluoroacetamide, 2,2,2-trifluoro-N-methylacetamide, pyrrolidin-2-one, piperidin-2-one and N-(pyridin-2-ylmethyl)acetamide.

The production method (g) can be performed under the same conditions as those described for production method (e).

Reaction scheme 13 shows a synthesis method for the preparation of compounds of the formula (XXXVI), wherein G stand for G10.

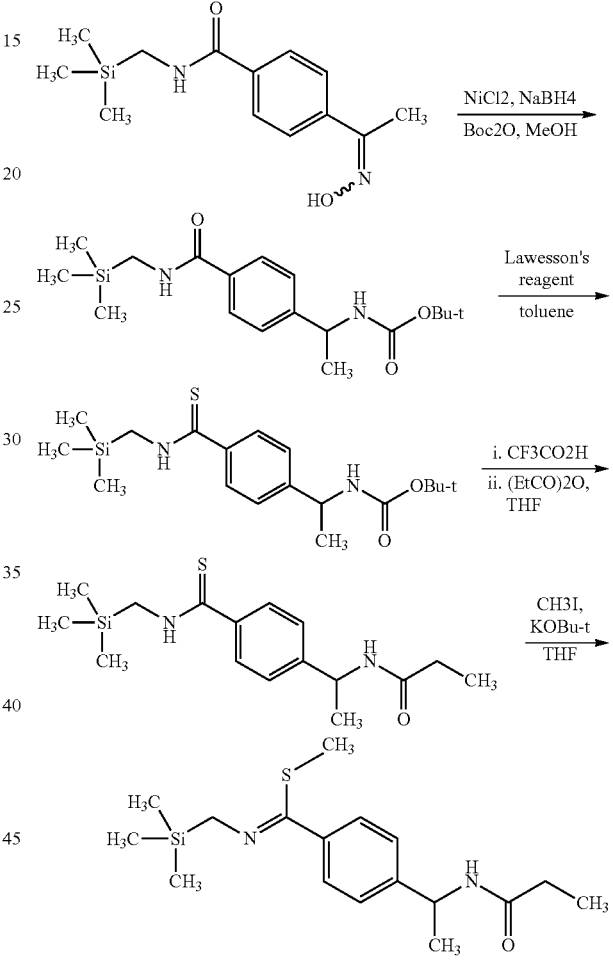

Reaction scheme 13 wherein Boc2O represents Di-tert-butyl dicarbonate, Bu-t represents tert-butyl, THF represents tetrahydrofuran and Lawesson's reagent represents 2,4-bis(4-methoxyphenyl)-1,3-dithia-2,4-diphosphetane-2,4-disulfide.

Compounds of the formula (XXXVI) can be synthesized according to reaction process described in WO2009/097992

Compounds of the formula (XXXVI) are, for example, methyl 3-bromo-4-(1H-1,2,4-triazol-1-yl)-N-[(trimethylsilyl)methyl]benzenecarbimidothioate, methyl 3-chloro-4-(1H-1,2,4-triazol-1-yl)-N-[(trimethylsilyl)methyl]benzenecarbimidothioate, methyl 3-trifluoromethyl-4-(1H-1,2,4-triazol-1-yl)-N-[(trimethylsilyl)methyl] benzenecarbimidothioate, methyl 3-cyano-4-(1H-1,2,4-triazol-1-yl)-N-[(trimethylsilyl)methyl] benzenecarbimidothioate, ethyl 3-bromo-4-(1H-1,2,4-triazol-1-yl)-N-[(trimethylsilyl)methyl]

benzenecarbimidothioate, methyl 3-bromo-4-(1H-1,2,4-triazol-1-yl)-N-[(triethylsilyl)methyl]benzenecarbimidothioate, methyl 3-bromo-4-(1H-1,2,4-triazol-1-yl)-N-[(t-butyldimethylsilyl)methyl]benzenecarbimidothioate, methyl 4-{[(tert-butoxycarbonyl)amino]-methyl}-3-(trifluoromethyl)-N-[(trimethylsilyl)methyl]benzenecarbimidothioate, methyl 4-{[(tert-butoxycarbonyl)amino]methyl}-3-chloro-N-[(trimethylsilyl)methyl]benzenecarbimidothioate, methyl 4-{[(tert-butoxycarbonyl)amino]methyl}-3-methyl-N-[(trimethylsilyl)methyl]benzene-carbimidothioate, methyl 4-{[(tert-butoxycarbonyl)amino]methyl)-N-[(trimethylsilyl)methyl]-benzenecarbimidothioate, methyl 4-{1-[(tert-butoxycarbonyl)amino]ethyl}-N-[(trimethylsilyl)methyl]benzenecarbimidothioate, methyl 4-(1-acetamidoethyl)-N-[(trimethylsilyl)methyl]benzenecarbimidothioate, methyl 4-[1-(propionylamino)ethyl]-N-[(trimethylsilyl)methyl]benzenecarbimidothioate, methyl 4-{1-[(cyclopropylcarbonyl)amino]ethyl}-N-[(trimethylsilyl)methyl]benzenecarbimidothioate and methyl 4-(1-{[(methyl sulfanyl)acetyl]amino}ethyl)-N-[(trimethylsilyl)methyl] benzenecarbimidothioate.

The production method (p) can be performed under the same conditions as those described for the production method of compounds of the formula (XXXVIII).

The compounds of the formulae (XXXVI) and (XXXVII) are represented by the general formula (XXXIX).

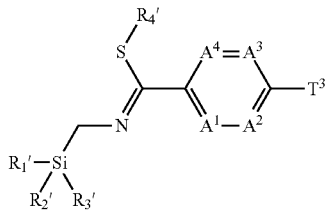

(XXXIX)

wherein $T^3$ stands for a halogen, such as fluorine, chlorine, bromine or iodine, or one of the chemical groups G1 to G9 or represents one of the following chemical group:

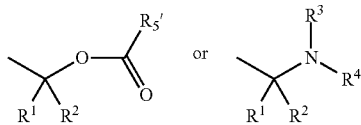

wherein $R^1$, $R^2$, $R^3$, $R^4$, and $R_5'$ have the same meanings as the aforementioned, and $R_1'$, $R_2'$, $R_3'$, $R_4'$ and $A^1$ to $A^4$ have the same meanings as the defined herein.

Compounds of the general formula (XXXIX) are useful intermediates for the preparation of compounds according to the invention. Namely, as compounds according to the invention can be prepared by reacting a compound of formula (XII) with a compound of formula (XXXIX) in the presence of a fluorine reagent if $R_4'$ does not stand for H. In case that $R_4'$ stands for H, the reaction can be carried out in a one pot reaction by firstly adding an alkylating reagent, such as methyl iodide, to the reaction system and then adding a fluorine reagent.

Compounds of the formula (XXXIX) are, for example, those mentioned in tables described later as well as methyl 3-cyano-4-fluoro-N-[(trimethylsilyl)methyl]benzenecarbimidothioate.

The active compounds according to the invention may be used in combination with suitable synergists or other active compounds, such as for example insecticides, acaricides, nematicides, fungicides, biological control agents, and bactericides. Such combinations can also result in a synergistic effect, i.e. the biological activity of such a combination is synergistically increased. Examples of such combination partners are the following insecticides, acaricides, nematicides The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, and xylylcarb; or organophosphates, e.g. acephate, azamethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl)salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon, and vamidothion.

(2) GABA-gated chloride channel antagonists, for example organochlorines, e.g. chlordane, endosulfan (alpha-); or fiproles (phenylpyrazoles), e.g. ethiprole, fipronil, pyrafluprole, and pyriprole.

(3) Sodium channel modulators/voltage-dependent sodium channel blockers, for example pyrethroids, e.g. acrinathrin, allethrin (d-cis-trans, d-trans), bifenthrin, bioallethrin, bioallethrin S-cyclopentenyl, bioresmethrin, cyloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers), esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer), prallethrin, profluthrin, pyrethrin (pyrethrum), resmethrin, RU 15525, silafluofen, tefluthrin, tetramethrin[(1R)-isomers)], tralomethrin, transfluthrin and ZXI 8901; or DDT; or methoxychlor.

(4) Nicotinergic acetylcholine receptor agonists, for example chloronicotinyls, e.g. acetamiprid, clothianidin, dinotefuran, imidacloprid, nitenpyram, thiacloprid, thiamethoxam; or nicotine.

(5) Allosteric acetylcholine receptor modulators (agonists), for example spinosyns, e.g. spinetoram and spinosad.

(6) Chloride channel activators, for example avermectins/milbemycins, e.g. abamectin, emamectin benzoate, lepimectin, and milbemectin.

(7) Juvenile hormone mimics, e.g. hydroprene, kinoprene, methoprene; or fenoxycarb; pyriproxyfen.

(8) Miscellaneous non-specific (multi-site) inhibitors, for example gassing agents, e.g. methyl bromide and other alkyl halides; or chloropicrin; sulfuryl fluoride; borax; tartar emetic.
(9) Selective homopteran feeding blockers, e.g. pymetrozine or flonicamid.
(10) Mite growth inhibitors, e.g. clofentezine, diflovidazin, hexythiazox, etoxazole.
(11) Microbial disruptors of insect midgut membranes, e.g. *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.
(12) Inhibitors of mitochondrial ATP synthase, for example diafenthiuron; or organotin miticides, e.g. azocyclotin, cyhexatin, and fenbutatin oxide; or propargite; tetradifon.
(13) Uncouplers of oxidative phosphorylation via disruption of the proton gradient, for example chlorfenapyr, and DNOC.
(14) Nicotinic acetylcholine receptor channel blockers, for example bensultap, cartap hydrochloride, thiocyclam, and thiosultap-sodium.
(15) Inhibitors of chitin biosynthesis, type 0, for example benzoylureas, e.g. bistrifluoron, chlorfluazuron, diflubenzuron, flucycloxuron, flufenoxuron, hexaflumuron, lufenuron, novaluron, noviflumuron, penfluoron, teflubenzuron, and triflumuron.
(16) Inhibitors of chitin biosynthesis, type 1, for example buprofezin.
(17) Moulting disruptors, for example cyromazine.
(18) Ecdysone receptor agonists/disruptors, for example diacylhydrazines, e.g. chromafenozide, halofenozide, methoxyfenozide, and tebufenozide.
(19) Octopamine receptor agonists, for example amitraz.
(20) Mitochondrial complex III electron transport inhibitors, for example hydramethylnon; acequinocyl or fluacrypyrim.
(21) Mitochondrial complex I electron transport inhibitors, for example METI acaricides, e.g. fenazaquin, fenpyroximate, pyrimidifen, pyridaben, tebufenpyrad, tolfenpyrad or rotenone. (Derris).
(22) Voltage-dependent sodium channel blockers, e.g. indoxacarb; metaflumizone.
(23) Inhibitors of acetyl CoA carboxylase, for example tetronic acid derivatives, e.g. spirodiclofen and spiromesifen; or tetramic acid derivatives, e.g. spirotetramat.
(24) Mitochondrial complex IV electron inhibitors, for example phosphines, e.g. aluminium phosphide, calcium phosphide, phosphine, and zinc phosphide or cyanide.
(25) Mitochondrial complex II electron transport inhibitors, for example cyenopyrafen.
(28) Ryanodine receptor modulators, for example diamides, e.g. chlorantraniliprole (Rynaxypyr), Cyantraniliprole (Cyazypyr), and flubendiamide.

Further active ingredients with unknown or uncertain mode of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulfonyl]-1,3-thiazole), flufenerim, pyridalyl, and pyrifluquinazon; furthermore products based on *Bacillus firmus* (I-1582, BioNeem, Votivo) or one of the following known active compounds:
4-{[(6-brompyrid-3-yl)methyl] (2-fluorethyl)amino}furan-2 (5H)-on (known from WO 2007/115644), 4-{[(6-fluoropyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)—on (known from WO 2007/115644), 4-{[(6-chlorpyrid-3-yl)methyl](2,2-difluorethyl)amino}furan-2(5H)-on known from WO 2007/115644), 4-{[(6-chlor-5-fluorpyrid-3-yl)methyl](methyl)amino}furan-2(5H)-on (known from WO 2007/115643), 4-{[(5,6-dichlorpyrid-3-yl)methyl](2-fluorethyl) amino}furan-2(5H)-on (known from WO 2007/115646), 4-{[(6-chlor-5-fluorpyrid-3-yl)methyl](cyclopropyl) amino}furan-2(5H)-on (known from WO 2007/115643), 4-{[(6-chlorpyrid-3-yl)methyl](cyclopropyl) amino}furan-2(5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl)oxido-λ4-sulfanylidencyanamid (known from WO 2007/149134), [1-(6-chlorpyridin-3-yl)ethyl](methyl)oxido-λ4-sulfanylidencyanamid (known from WO 2007/149134) and its diastereomeres (A) and (B)

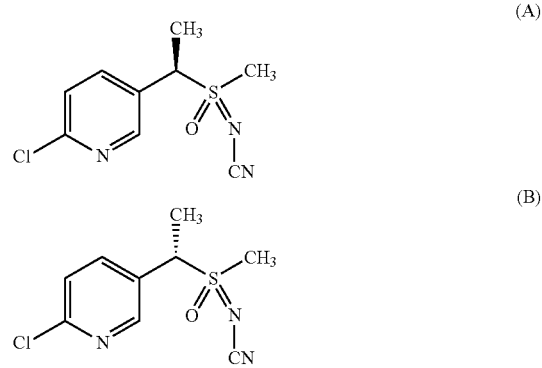

(also known from WO 2007/149134), [(6-trifluormethylpyridin-3-yl)methyl](methyl)oxido-λ4-sulfanylidencyanamid (known from WO 2007/095229), or sulfoxaflor (also known from WO 2007/149134), 11-(4-chloro-2,6-dimethylphenyl)-12-hydroxy-1,4-dioxa-9-azadispiro[4.2.4.2]tetra-dec-11-en-10-one (known from WO 2006/089633), 3-(4'-fluoro-2,4-dimethylbiphenyl-3-yl)-4-hydroxy-8-oxa-1-azaspiro[4.5] dec-3-en-2-one (known from WO 2008/067911), and 1-[2-fluoro-4-methyl-5-[(2,2,2-trifluoroethyl)sulfinyl]phenyl]-3-(trifluoromethyl)-1H-1,2,4-Triazol-5-amine (known from WO 2006/043635).

Examples of further combination partners are the following fungicides:
(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazolep, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) inhibitors of the respiratory chain at complex I or II, for example bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and salts thereof.

(3) inhibitors of the respiratory chain at complex III, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}-phenyl)ethanamide, (2E)-2-(methoxyimino)-N-methyl-2-{2-[(E)-({1-[3-(trifluoromethyl)phenyl]-ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)-methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[((1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethylphenoxy)methyl]phenyl}-2-methoxy-N-methylacetamide and salts thereof.

(4) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine, 3-chloro-5-(6-chloropyridin-3-yl)-6-methyl-4-(2,4,6-trifluorophenyl)pyridazine and salts thereof.

(5) Compounds capable to have a multisite action, like for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb, ziram and salts thereof.

(6) Compounds capable to induce a host defence, like for example acibenzolar-S-methyl, isotianil, probenazole, tiadinil and salts thereof.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and salts thereof.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon and tricyclazole.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, like for example binapacryl, dinocap, ferimzone, fluazinam and meptyldinocap.

(15) Further compounds, like for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminium, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorous acid and its salts, propamocarb-fosetylate, propanosine-sodium, proquinazid, pyrrolnitrine, tebufloquin, tecloftalam, tolnifanide, triazoxide, trichlamide, zarilamid, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-

(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl) pyridine, 2,3-dibutyl-6-chlorothieno[2,3-d]pyrimidin-4 (3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulfate (2:1).

(16) Further compounds like for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methyl but-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N-2-(methylsulfonyl)valinamide.

The compounds according to the present invention show a potent insecticidal action and can, therefore, be used as an insecticide. Furthermore, the compounds according to the present invention exhibit a strong control effect against harmful animal pests, in particular arthropods and/or insects, particularly to agricultural pests, without imposing any harmful side effects of drug to the animal or the cultivated plants. The compounds of the present invention can thus be used for the control of a wide range of pest species, for example, harmful sucking insects, chewing insects, as well as other plant parasitic pests, storage insects, hygiene pests and the like, and can be applied for the purpose of disinfestations and extermination thereof.

The active compounds and active compound combinations according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development. The abovementioned pests include:

Order: Arthropoda:

From the class of the Arachnida, for example *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Centruroides* spp., *Chorioptes* spp., *Dermanyssus gallinae*, *Dermatophagoides pteronyssius*, *Dermatophagoides farinae*, *Dermacentor* spp., *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes spp., *Scorpio maurus, Stenotarsonemus* spp., *Tarsonemus* spp., *Tetranychus* spp., *Vaejovis* spp., *Vasates lycopersici*.

From the order of the Anoplura (Phthiraptera), for example, *Damalinia* spp., *Haematopinus* spp., *Linognathus* spp., *Pediculus* spp., *Ptirus pubis, Trichodectes* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp, *Stomoxys* spp., *Tabanus* spp., *Tannia* spp., *Tetanops* spp., *Tipula* spp.

From the order of the Heteroptera, for example, *Anasa tristis, Antestiopsis* spp., *Boisea* spp., *Blissus* spp., *Calocoris* spp., *Campylomma livida, Cavelerius* spp., *Cimex* spp., *Cimex lectularius, Cimex hemipterus, Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

From the order of the Isopoda, for example, *Armadillidium vulgare, Oniscus asellus, Porcellio scaber*.

From the order of the Isoptera, for example, *Coptotermes* spp., *Cornitermes cumulans, Cryptotermes* spp., *Incisitermes* spp., *Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitclla, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., Pectinophora spp., *Perileucoptera* spp., *Phthorimaea* spp., *Phyllocnistis citrella*, *Phyllonorycter* spp., *Pieris* spp., *Platynota stultana*, *Plodia interpunctella*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichophaga tapetzella*, *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta* spp., *Pulex irritans*, *Schistocerca gregaria*, *Supella longipalpa*.

From the order of the Siphonaptera, for example, *Ceratophyllus* spp., *Ctenocephalides* spp., *Tunga penetrans*, *Xenopsylla cheopis*.

From the order of the Symphyla, for example, *Scutigerella* spp.

From the order of the Thysanoptera, for example, *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Zygentoma (=Thysanura), for example, *Lepisma saccharina*, *Thermobia domestica*.

Order: Mollusca:

From the class of the Bivalvia, for example, *Dreissena* spp.

From the class of the Gastropoda, for example, *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

Order: Plathelminthes, Nematodes (animal parasites)

From the class of the Helminths, for example, *Ancylostoma duodenale*, *Ancylostoma ceylanicum*, *Acylostoma braziliensis*, *Ancylostoma* spp., *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp, *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

Order: Nematodes (plant parasites, phytoparasites)

From the group of the phytoparasitic nematodes, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

Subphylum: Protozoa:

It is furthermore possible to control protozoa, such as *Eimeria*.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and genetic engineering methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seed, also by applying one or more coats.

The compounds according to the present invention show a systemic action which means that the compounds can permeate plants body and translocate from the underground part of plants to the aerial part of plants.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof, are treated. The terms "parts", "parts of plants" and "plant parts" have been explained above.

Particularly preferably, plants of the plant cultivars which are in each case commercially available or in use are treated according to the invention. Plant cultivars are understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive "synergistic" effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The preferred transgenic plants or plant cultivars (obtained by genetic engineering) which are to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are the increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and Cry1F and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds according to the invention at a suitable concentration.

Furthermore, in the field of veterinary medicine, the novel compounds of the present invention can be effectively used against various harmful animal parasitic pests (endoparasites and ectoparasites), for example, insects and helminthes. Examples of such animal parasitic pests include the pests as described below. Examples of the insects include *Gasterophilus* spp., *Stomoxys* spp., *Trichodectes* spp., *Rhodnius* spp., *Ctenocephalides canis*, *Cimx lecturius*, *Ctenocephalides felis*, *Lucilia cuprina*, and the like. Examples of acari include *Ornithodoros* spp., *Ixodes* spp., *Boophilus* spp., and the like.

In the veterinary fields, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;* from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi;* from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypo-*

*derma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorrhoidalis, Gasterophilus inermis, Gasterophilus nasalis, Gasterophilus nigricornis, Gasterophilus pecorum, Braula coeca;* from the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis;* from the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus (Boophilus)* spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni;* from the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psorergates ovis, Pneumonyssoidic mange, Pneumonyssoides caninum, Acarapis woodi.*

The active compounds according to the invention are also suitable for controlling arthropods, helminths and protozoae, which attack animals. Animals include agricultural livestock such as, cattle, sheep, goats, horses, pigs, donkeys, camels, buffaloes, rabbits, chickens, turkeys, ducks, geese, cultured fish, honeybees. Moreover, animals include domestic animals—also referred to as companion animals—such as dogs, cats, cage birds, aquarium fish and what are known as experimental animals such as hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the hosts (when applicable). Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Generally, when used for the treatment of animals, the active compounds according to the invention can be applied directly. Preferably, they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, or suppositories; or by parenteral administration, such as injections (intramuscular, subcutaneous, intravenous, intraperitoneal and the like), implants, nasal application, or dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, or unpressurized sprays, for example, pump sprays and atomizer sprays.

When used for livestock, poultry, domestic animals and the like, the active compounds according to the invention can be applied as formulations (for example, powders, wettable powders ["WP"], emulsions, emulsifiable concentrates ["EC"], flowables, homogeneous solutions, and suspension concentrates ["SC"]) which comprise the active compounds in an amount of from 1 to 80% by weight, either directly or after dilution (e.g. 100- to 10 000-fold dilution), or else as a chemical bath.

When used in the veterinary field, the active compounds according to the invention may be used in combination with suitable synergists or other active compounds, such as acaricides, insecticides, anthelmintics, or anti-protozoal drugs.

In the present invention, a substance having an insecticidal action against pests including all of these is referred to as an insecticide.

An active compound of the present invention can be prepared in conventional formulation forms, when used as an insecticide. Examples of the formulation forms include solutions, emulsions, wettable powders, water dispersible granules, suspensions, powders, foams, pastes, tablets, granules, aerosols, active compound-infiltrated natural and synthetic materials, microcapsules, seed coating agents, formulations used with a combustion apparatus (for example, fumigation and smoking cartridges, cans, coils or the like as the combustion apparatus), or ULV (cold mist, warm mist), and the like.

These formulations can be produced by methods that are known per se. For example, a formulation can be produced by mixing the active compound with a developer, that is, a liquid diluent or carrier; a liquefied gas diluent or carrier; or a solid diluent or carrier, and optionally with a surfactant, that is, an emulsifier and/or dispersant and/or foaming agent.

In the case where water is used as the developer, for example, an organic solvent can also be used as an auxiliary solvent.

Examples of the liquid diluent or carrier include aromatic hydrocarbons (for example, xylene, toluene, alkylnaphthalene and the like), chlorinated aromatic or chlorinated aliphatic hydrocarbons (for example, chlorobenzenes, ethylene chlorides, methylene chlorides), aliphatic hydrocarbons (for example, cyclohexanes), paraffins (for example, mineral oil fractions), alcohols (for example, butanol, glycols and their ethers, esters and the like), ketones (for example, acetone, methyl ethyl ketone, methyl isobutyl ketone, cyclohexanone and the like), strongly polar solvents (for example, dimethylformamide, dimethylsulfoxide and the like), water and the like.

The liquefied gas diluent or carrier may be those which are gaseous at normal temperature and normal pressure, for example, aerosol propellants such as butane, propane, nitrogen gas, carbon dioxide and halogenated hydrocarbons.

Examples of the solid diluent include pulverized natural minerals (for example, kaolin, clay, talc, chalk, quartz, attapulgite, montmorillonite, diatomaceous earth, and the like), pulverized synthetic minerals (for example, highly dispersed silicic acid, alumina, silicates and the like), and the like.

Examples of the solid carrier for granules include pulverized and screened rocks (for example, calcite, marble, pumice, sepiolite, dolomite and the like), synthetic granules of inorganic and organic powder, fine particles of organic materials (for example, sawdust, coconut shells, maize cobs, tobacco stalk and the like), and the like.

Examples of the emulsifier and/or foaming agent include nonionic and anionic emulsifiers [for example, polyoxyethylene fatty acid esters, polyoxyethylene fatty acid alcohol ethers (for example, alkylaryl polyglycol ether), alkylsulfonates, alkylsulfates, arylsulfonates and the like], albumin hydrolyzate, and the like.

Examples of the dispersant include lignin sulfite waste liquor and methylcellulose.

Fixing agents can also be used in the formulations (powders, granules, or emulsions), and examples of the fixing agent include carboxymethylcellulose, natural and synthetic polymers (for example, gum arabic, polyvinyl alcohol, polyvinyl acetate, and the like) and the like.

Colorants can also be used, and examples of the colorants include inorganic pigments (for example, iron oxide, titanium oxide, Prussian Blue and the like), organic dyes such as alizarin dyes, azo dyes or metal phthalocyanine dyes, and in addition, trace elements such as the salts of iron, manganese, boron, copper, cobalt, molybdenum and zinc.

The formulations in general can contain the active ingredient in an amount ranging from 0.1 to 95% by weight, and preferably 0.5 to 90% by weight.

The compound according to the present invention can also exist as an admixture with other active compounds, for example, insecticides, poisonous baits, bactericides, miticides, nematicides, fungicides, growth regulators, herbicides and the like, in the form of their commercially useful formulation forms and in the application forms prepared from those formulations.

The content of the compound according to the present invention in a commercially useful application form can be varied within a wide range.

The concentration of the active compound according to the present invention in actual usage can be, for example, in the range of 0.0000001 to 100% by weight, and preferably 0.00001 to 1% by weight.

The compounds according to the present invention can be used through conventional methods that are appropriate for the usage form.

The active compound of the present invention have, when used against hygiene pests and pests associated with stored products, stability effective against alkali on lime materials, and also shows excellent residual effectiveness on wood and soil.

Next, the present invention is exemplified by way of the following examples, but the invention is not intended to be limited thereto.

In addition, Me stands for Methyl, Ac stands for acetyl and Ms stands for methanesulfonyl in the examples. References to room temperature means temperatures of about 18 to about 30° C.

EXAMPLE A

Synthesis of 5-[3-(2,6-dichloropyridin-4-yl)-3-(trifluoromethyl)-3,4-dihydro-2H-pyrrol-5-yl]-2-(1H-1,2,4-triazol-1-yl)benzonitrile (No. 1-1)

Step 1. Synthesis of 2,6-dichloro-4-(3,3,3-trifluoroprop-1-en-2-yl)pyridine

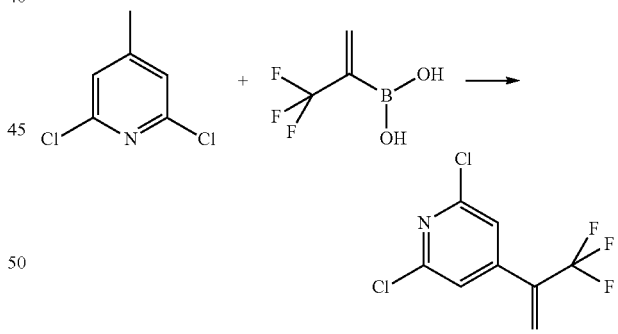

2,6-dichloro-4-iodopyridine (0.87 g), (3,3,3-trifluoroprop-1-en-2-yl)boronic acid (purity: 65%, 0.75 g) and potassium carbonate (0.96 g) were dissolved in the mixed solvent of THF and water, which was then degassed three times. To the solution was added dichlorobis(triphenylphosphine) palladium (II) (0.04 g), and the mixture was heated to reflux for 3 hours under argon atmosphere. The mixture was cooled to room temperature and then poured into water, which was then extracted twice with hexane. The organic layer was combined, which was then washed with water and dried over anhydrous magnesium sulfate. After the drying agent was filtered off, the solvent was distilled away under reduced pressure, and the residue was then purified by silica gel chromatography to obtain 2,6-dichloro-4-(3,3,3-trifluoroprop-1-en-2-yl)pyridine (0.70 g) at a yield of 82%.

1H-NMR (CDCl3) δ: 6.03 (1H, s), 6.21 (1H, s), 7.34 (2H, s)

Step 2. Synthesis of 5-[3-(2,6-dichloropyridin-4-yl)-3-(trifluoromethyl)-3,4-dihydro-2H-pyrrol-5-yl]-2-(1H-1,2,4-triazol-1-yl)benzonitrile

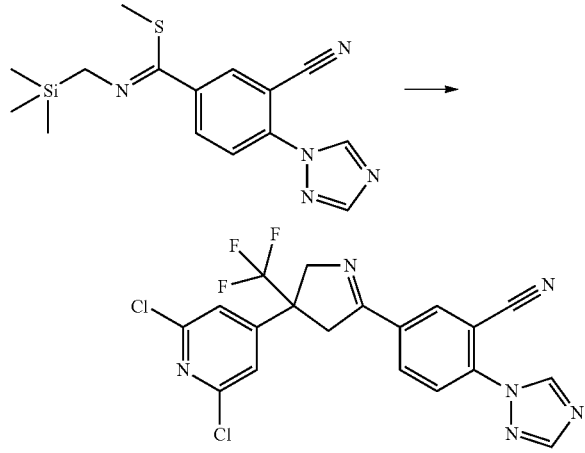

To the crude solution of methyl 3-cyano-4-(1H-1,2,4-triazol-1-yl)-N-[(trimethylsilyl)methyl]benzenecarbimidothioate (Japanese patent application JP2008-143120) was added 2,6-dichloro-4-(3,3,3-trifluoroprop-1-en-2-yl)pyridine (0.15 g) and the resultant mixture was cooled to −10° C. Additionally, a solution of tetrabutylammonium fluoride (0.70 mL of 1.0 M in THF) in THF was added over 10 minutes under argon atmosphere. The reaction mixture was stirred for 30 minutes at the same temperature and returned to room temperature gradually, and then stirred 3 hours. Water was added to the reaction liquor, and aqueous layer was extracted with ethyl acetate. The combined organic layers were washed with a saturated aqueous brine, and subsequently dried over magnesium sulfate. After filtering the reaction mixture, the solvent was distilled off under reduced pressure, and the resulting mixture was purified by silica gel chromatography, to obtain 5-[3-(2,6-dichloropyridin-4-yl)-3-(trifluoromethyl)-3,4-dihydro-2H-pyrrol-5-yl]-2-(1H-1,2,4-triazol-1-yl)benzonitrile (0.14 g) at a yield of 46%.

1H-NMR (CDCl3) δ: 3.47 (1H, d), 3.83 (1H, d), 4.49 (1H, d), 4.96 (1H, d), 7.25 (2H, s), 7.95 (1H, d), 8.23-8.31 (3H, m), 8.91 (1H, s).

EXAMPLE B

Synthesis of N-(4-{3-[2,6-bis(trifluoromethyl)pyridin-4-yl]-3-(trifluoromethyl)-3,4-dihydro-2H-pyrrol-5-yl}-2-bromobenzyl)propanamide (No. 2-2733)

Step 1. Synthesis of 2,6-bis(trifluoromethyl)-4-(3,3,3-trifluoroprop-1-en-2-yl)pyridine

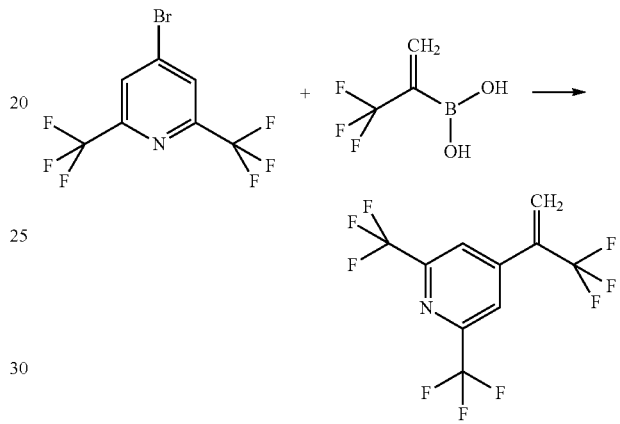

4-bromo-2,6-bis(trifluoromethyl)pyridine (1.53 g), (3,3,3-trifluoroprop-1-en-2-yl)boronic acid (purity: 40%, 2.00 g) and potassium carbonate (1.58 g) were dissolved in the mixed solvent of THF and water, which was then degassed three times. To the solution was added dichlorobis(triphenylphosphine) palladium (II) (0.07 g), and the mixture was heated to reflux for 3 hours under argon atmosphere. The mixture was cooled to room temperature and then poured into water, which was then extracted twice with pentane. The organic layer was combined, which was then washed with water and dried over anhydrous magnesium sulfate. After the drying agent was filtered off, the solvent was distilled away under reduced pressure, and the residue was then purified by silica gel chromatography to obtain 2,6-bis(trifluoromethyl)-4-(3,3,3-trifluoroprop-1-en-2-yl)pyridine (1.59 g) at a yield of 98%.

1H-NMR (CDCl3) δ: 6.17 (1H, s), 6.35 (1H, s), 7.92 (2H, s)

Step 2. Synthesis of 4-{3-[2,6-bis(trifluoromethyl)pyridin-4-yl]-3-(trifluoromethyl)-3,4-dihydro-2H-pyrrol-5-yl}-2-bromobenzyl acetate

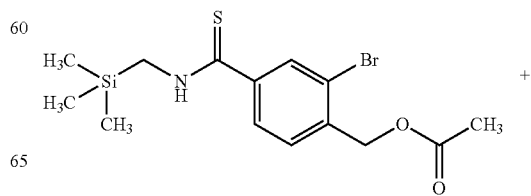

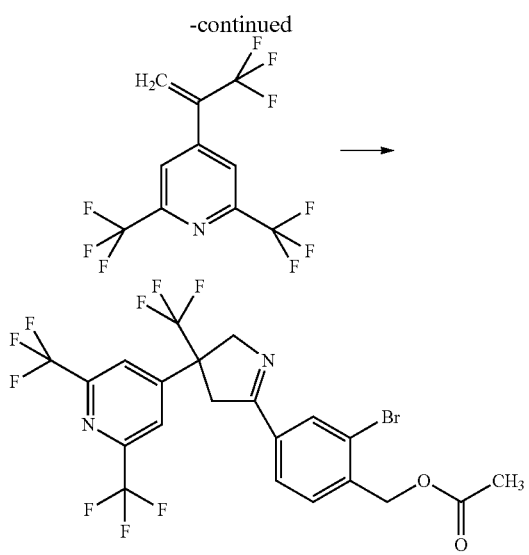

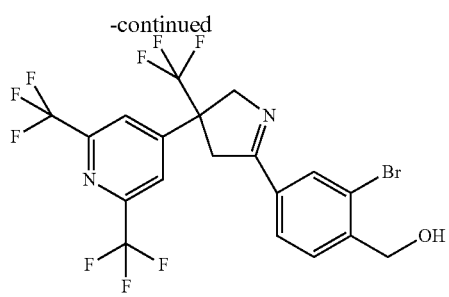

Under argon atmosphere, t-BuOK (0.36 g) was slowly added to 2-bromo-4-{[(trimethylsilyl)methyl]carbamothioyl}benzyl acetate (1.0 g) and iodomethane (0.45 g) in THF at −10° C., and the resultant mixture was stirred for 30 minutes at the same temperature. 2,6-bis(trifluoromethyl)-4-(3,3,3-trifluoroprop-1-en-2-yl)pyridine (1.1 g) was added to the reaction mixture, and then n-Bu4NF in TI-IF (0.25 ml, 1M solution) was slowly added to the mixture at −10° C. under argon atmosphere. After stirring the resultant blend for 30 minutes at the same temperature, the blend was allowed to slowly warm to room temperature. The blend was stirred at room temperature overnight. The blend was diluted with t-BuOMe, and washed with 1N HCl and brine. The organic layer was dried over MgSO₄. The solvent was evaporated under reduced pressure and the residue was purified by column chromatography to get the targeted product (0.58 g).

1H-NMR (CDCl3) δ: 2.18 (3H, s), 3.47 (1H, d), 3.90 (1H, dd), 4.51 (111, d), 5.01 (1H, dd), 5.23 (2H, s), 7.51 (1H, d), 7.80 (1H, dd), 7.85 (2H, s), 8.09 (1H, d)

Step 3. Synthesis of (4-{3-[2,6-bis(trifluoromethyl)pyridin-4-yl]-3-(trifluoromethyl)-3,4-dihydro-2H-pyrrol-5-yl}-2-bromophenyl)methanol

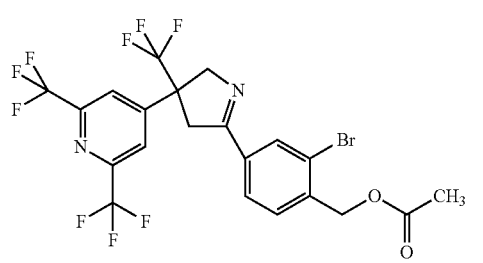

4-{3-[2,6-bis(trifluoromethyl)pyridin-4-yl]-3-(trifluoromethyl)-3,4-dihydro-2H-pyrrol-5-yl}-2-bromobenzyl acetate (0.5 g) and Sodium methoxide (0.005 g) in MeOH (10 ml) were stirred at room temperature for 30 minutes. The mixture was diluted with t-BuOMe, and washed with brine, and the organic layer was dried over MgSO₄. After the solvent was evaporated under reduced pressure, the targeted product was obtained (0.4 g).

1H-NMR (CDCl3) δ: 2.07 (1H, t), 3.48 (1H, d), 3.91 (1H, dd), 4.51 (1H, d), 4.81 (2H, d), 5.01 (1H, dd), 7.63 (1H, d), 7.81 (1H, dd), 7.85 (2H, s), 8.07 (1H, d)

Step 4. Synthesis of 1-(4-{3-[2,6-bis(trifluoromethyl)pyridin-4-yl]-3-(trifluoromethyl)-3,4-dihydro-2H-pyrrol-5-yl}-2-bromophenyl)methanamine

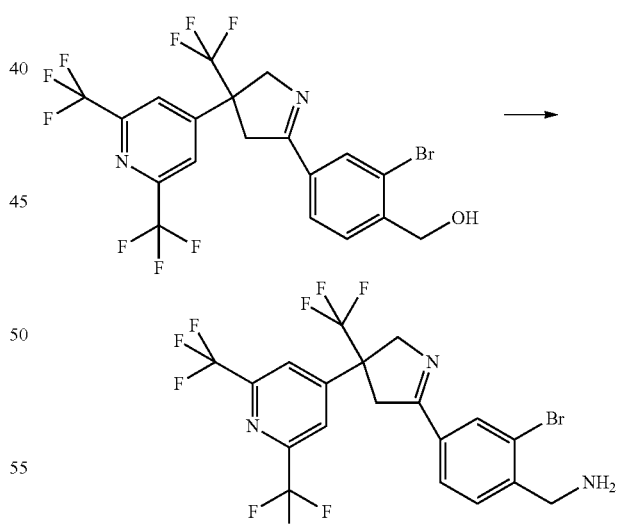

Methanesulfonyl chloride (0.17 g) was added to (4-{3-[2,6-bis(trifluoromethyl)pyridin-4-yl]-3-(trifluoromethyl)-3,4-dihydro-2H-pyrrol-5-yl}-2-bromophenyl)methanol (0.46 g) and triethylamine (0.26 g) in THF at −10° C. and the resultant mixture was stirred for 30 min. The mixture was poured into ammonia (10 ml), THF (10 ml) and MeOH (10 ml), and the resultant was stirred at room temperature overnight. After the solvents were evaporated under reduced pressure, the residue was diluted with t-BuOMe and H₂O, and the organic layer was dried over MgSO₄. After the solvents were evaporated under reduced pressure, the residue was purified with column chromatography to get the targeted product (0.4 g).

1H-NMR (CDCl3) δ: 3.47 (1H, d), 3.90 (1H, dd), 3.98 (2H, s), 4.51 (1H, d), 5.00 (1H, dd), 7.53 (1H, d), 7.79 (1H, dd), 7.85 (2H, s), 8.06 (1H, d)

Step 5. Synthesis of N-(4-{3-[2,6-bis(trifluoromethyl)pyridin-4-yl]-3-(trifluoromethyl)-3,4-dihydro-2H-pyrrol-5-yl}-2-bromobenzyl)propanamide

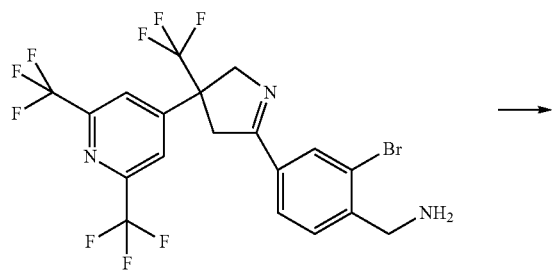

→

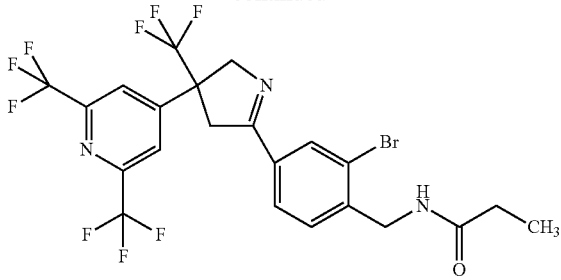

1-(4-{3-[2,6-bis(trifluoromethyl)pyridin-4-yl]-3-(trifluoromethyl)-3,4-dihydro-2H-pyrrol-5-yl}-2-bromophenyl)methanamine (0.1 g), pyridine (0.15 g) and propionic anhydride (0.029 g) in THF (5 ml) were stirred at room temperature for 1 hour. After the solvent was evaporated under reduced pressure, the residue was purified with column chromatography to get the targeted product (0.06 g).

1H-NMR (CDCl3) δ: 1.18 (3H, t), 2.27 (2H, q), 3.46 (1H, d), 3.88 (1H, d), 4.47-4.56 (3H, m), 5.00 d), 5.97 (1H, br s), 7.50 (1H, d), 7.74 (1H, dd), 7.84 (2H, s), 8.08 (1H, d)

The compounds of the present invention obtained according to the above synthesis examples A and B and the production methods (a) to (g) and (p) and intermediates are presented in the following tables.

In the tables, the abbreviations are as follows. Me: methyl, Et: ethyl, Pr: propyl, Bu: butyl, Ph: phenyl, py: pyridyl, n-Pr: normal-propyl, iso-Pr: isopropyl, tert-Bu: tertiary-butyl, cyc-Pr: cyclopropyl.

TABLE 1-1

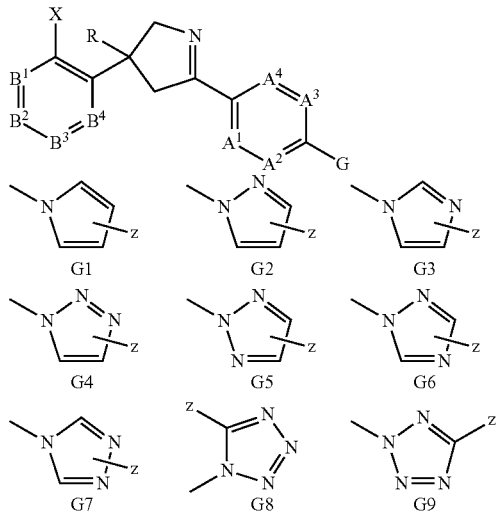

| Example No. | X | B¹ | B² | B³ | B⁴ | R | A1 | A² | A³ | A⁴ | G | Z |
|---|---|---|---|---|---|---|---|---|---|---|---|---|
| 1-3 | H | C—Cl | C—N(CH3)2 | C—Cl | C—H | CF3 | C—H | C—H | C—CN | C—H | G6 | H |
| 1-4 | H | C—CF3 | C—F | C—H | C—H | CF3 | C—H | C—H | C—CN | C—H | G6 | H |
| 1-5 | H | C—CF3 | C—F | C—H | C—H | CF3 | C—H | C—H | C—H | C—H | G6 | H |
| 1-6 | H | C—CF3 | C—F | C—H | C—H | CF3 | C—H | N | C—CN | C—H | G6 | H |
| 1-7 | H | C—CF3 | C—F | C—H | C—H | CF3 | C—H | C—H | C—CN | N | G6 | H |
| 1-8 | H | C—CF3 | C—F | C—H | C—H | CF3 | C—H | N | C—H | C—H | G6 | H |
| 1-9 | H | C—CF3 | C—F | C—H | C—H | CF3 | C—H | C—H | C—H | N | G6 | H |
| 1-10 | H | C—CF3 | C—H | C—Cl | C—H | CF3 | C—H | C—H | C—CN | C—H | G6 | H |
| 1-11 | H | C—Cl | C—CF3 | C—H | C—H | CF3 | C—H | C—H | C—CN | C—H | G6 | H |
| 1-12 | H | C—Cl | C—CF3 | C—Cl | C—H | CF3 | C—H | C—H | C—CN | C—H | G6 | H |
| 1-13 | H | C—Cl | C—F | C—Cl | C—H | CF3 | C—H | C—H | C—CN | C—H | G6 | H |
| 1-14 | H | C—Cl | C—F | C—Cl | C—H | CF3 | C—H | C—H | C—H | C—H | G6 | H |
| 1-15 | H | C—Cl | C—Br | C—Cl | C—H | CF3 | C—H | C—H | C—CN | C—H | G6 | H |

TABLE 1-1-continued

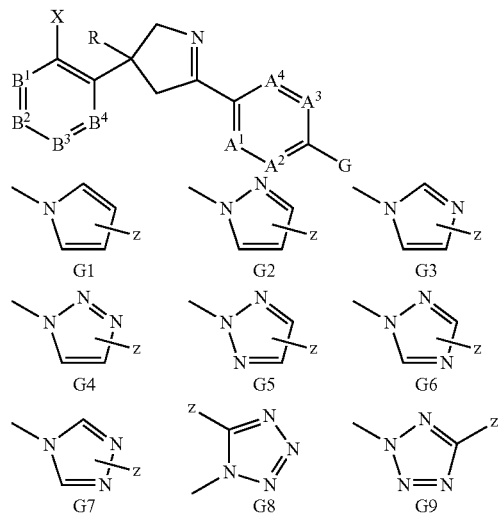

| Example No. | X | B¹ | B² | B³ | B⁴ | R | A1 | A² | A³ | A⁴ | G | Z |
|---|---|---|---|---|---|---|---|---|---|---|---|---|
| 1-16 | H | C—Cl | C—Br | C—Cl | C—H | CF3 | C—H | C—H | C—H | C—H | G6 | H |
| 1-17 | H | C—Br | C—Cl | C—Br | C—H | CF3 | C—H | C—H | C—CN | C—H | G6 | H |
| 1-18 | H | C—Br | C—Cl | C—Cl | C—H | CF3 | C—H | C—H | C—CN | C—H | G6 | H |
| 1-19 | F | C—CF3 | C—H | C—H | C—H | CF3 | C—H | C—H | C—CN | C—H | G6 | H |
| 1-20 | F | C—Cl | C—F | C—Cl | C—H | CF3 | C—H | C—H | C—CN | C—H | G6 | H |
| 1-23 | H | C—CN | C—H | C—CF3 | C—H | CF3 | C—H | C—H | C—CN | C—H | G6 | H |
| 1-24 | H | C—Cl | —OCH2O— | | C—H | CF3 | C—H | C—H | C—CN | C—H | G6 | H |
| 1-25 | H | C—Cl | —OCF2O— | | C—H | CF3 | C—H | C—H | C—CN | C—H | G6 | H |
| 1-26 | H | C—Cl | —O(CH3)2O— | | C—H | CF3 | C—H | C—H | C—CN | C—H | G6 | H |
| 1-27 | H | C—Cl | C—Cl | C—Cl | C—H | CF3 | C—H | C—H | C—H | C—H | G6 | H |
| 1-28 | H | C—Cl | C—Cl | C—CF3 | C—H | CF3 | C—H | C—H | C—H | C—H | G6 | H |
| 1-29 | H | C—Cl | C—Cl | C—Cl | C—H | CF3 | C—H | C—H | C—F | C—H | G6 | H |
| 1-30 | H | C—Cl | C—Cl | C—Cl | C—H | CF3 | C—H | C—H | C—Cl | C—H | G6 | H |
| 1-31 | H | C—Cl | C—Cl | C—Cl | C—H | CF3 | C—H | C—H | C—Br | C—H | G6 | H |
| 1-32 | H | C—Cl | C—Cl | C—Cl | C—H | CF3 | C—H | C—H | C-I | C—H | G6 | H |
| 1-33 | H | C—Cl | C—Cl | C—Cl | C—H | CF3 | C—H | C—H | C—CH3 | C—H | G6 | H |
| 1-34 | H | C—Cl | C—Cl | C—Cl | C—H | CF3 | C—H | C—H | C—CF3 | C—H | G6 | H |
| 1-35 | H | C—Cl | C—Cl | C—Cl | C—H | CF3 | C—H | C—H | C—NO2 | C—H | G6 | H |
| 1-36 | H | C—Cl | C—Cl | C—Cl | C—H | CF3 | C—H | C—H | C—NH2 | C—H | G6 | H |
| 1-37 | H | C—Cl | C—Cl | C—Cl | C—H | CF3 | C—H | C—H | C—NHC(=O)CH3 | C—H | G6 | H |
| 1-38 | H | C—Cl | C—Cl | C—Cl | C—H | CF3 | C—H | C—H | C—NHC(=O)CF3 | C—H | G6 | H |
| 1-39 | H | C—Cl | C—Cl | C—Cl | C—H | CF3 | C—H | C—H | C—CH2OC(=O)CH3 | C—H | G6 | H |
| 1-40 | H | C—Cl | C—Cl | C—Cl | C—H | CF3 | C—H | C—H | C—CH2SCH2CF3 | C—H | G6 | H |
| 1-41 | H | C—Cl | C—Cl | C—Cl | C—H | CF3 | C—H | C—H | C—CH2SOCH2CF3 | C—H | G6 | H |
| 1-42 | H | C—Cl | C—Cl | C—Cl | C—H | CF3 | C—H | C—H | C—CH2SO2CH2CF3 | C—H | G6 | H |
| 1-43 | H | C—Cl | C—Cl | C—Cl | C—H | CF3 | C—H | C—H | C—SCH3 | C—H | G6 | H |
| 1-44 | H | C—Cl | C—Cl | C—Cl | C—H | CF3 | C—H | C—H | C—SOCH3 | C—H | G6 | H |
| 1-45 | H | C—Cl | C—Cl | C—Cl | C—H | CF3 | C—H | C—H | C—SO2CH3 | C—H | G6 | H |
| 1-46 | H | C—Cl | C—Cl | C—Cl | C—H | CF3 | C—H | C—H | C—SCF3 | C—H | G6 | H |
| 1-47 | H | C—Cl | C—Cl | C—Cl | C—H | CF3 | C—H | C—H | C—SOCF3 | C—H | G6 | H |
| 1-48 | H | C—Cl | C—Cl | C—Cl | C—H | CF3 | C—H | C—H | C—SO2CF3 | C—H | G6 | H |
| 1-49 | H | C—Cl | C—Cl | C—Cl | C—H | CF3 | C—H | C—H | C—SCH2CF3 | C—H | G6 | H |
| 1-50 | H | C—Cl | C—Cl | C—Cl | C—H | CF3 | C—H | C—H | C—SOCH2CF3 | C—H | G6 | H |
| 1-51 | H | C—Cl | C—Cl | C—Cl | C—H | CF3 | C—H | C—H | C—SO2CH2CF3 | C—H | G6 | H |
| 1-52 | H | C—Cl | C—Cl | C—Cl | C—H | CF3 | C—H | N | C—CN | C—H | G6 | H |
| 1-53 | H | C—Cl | C—F | C—Cl | C—H | CF3 | C—H | N | C—CN | C—H | G6 | H |
| 1-54 | H | C—Cl | C—F | C—Cl | C—H | CF3 | C—H | C—H | C—CN | N | G6 | H |
| 1-55 | H | C—Cl | C—F | C—Cl | C—H | CF3 | C—H | N | C—H | C—H | G6 | H |
| 1-56 | H | C—Cl | C—F | C—Cl | C—H | CF3 | C—H | C—H | C—H | N | G6 | H |
| 1-57 | H | C—Cl | C—Br | C—Cl | C—H | CF3 | C—H | N | C—CN | C—H | G6 | H |
| 1-58 | H | C—Cl | C—Br | C—Cl | C—H | CF3 | C—H | C—H | C—CN | N | G6 | H |
| 1-59 | H | C—Cl | C—Br | C—Cl | C—H | CF3 | C—H | N | C—H | C—H | G6 | H |
| 1-60 | H | C—Cl | C—Br | C—Cl | C—H | CF3 | C—H | C—H | C—H | N | G6 | H |
| 1-61 | H | C—Cl | C—Cl | C—CF3 | C—H | CF3 | C—H | N | C—CN | C—H | G6 | H |
| 1-62 | H | C—CF3 | C—H | C—CF3 | C—H | CF3 | C—H | C—H | C—H | C—H | G6 | H |
| 1-63 | H | C—CF3 | C—H | C—CF3 | C—H | CF3 | C—H | N | C—CN | C—H | G6 | H |
| 1-64 | H | C—CF3 | C—H | C—Cl | C—H | CF3 | C—H | N | C—CN | C—H | G6 | H |
| 1-65 | H | C—CF3 | C—H | C—H | C—H | CF3 | C—H | N | C—CN | C—H | G6 | H |
| 1-70 | H | C—Cl | C—Cl | C—Cl | C—H | CF3 | C—H | C—H | C—CN | N | G6 | H |
| 1-71 | H | C—Cl | C—Cl | C—F | C—H | CF3 | C—H | C—H | C—CN | N | G6 | H |
| 1-72 | H | C—Cl | C—Cl | C—Br | C—H | CF3 | C—H | C—H | C—CN | N | G6 | H |
| 1-73 | H | C—Cl | C—Cl | C—CF3 | C—H | CF3 | C—H | C—H | C—CN | N | G6 | H |

TABLE 1-1-continued

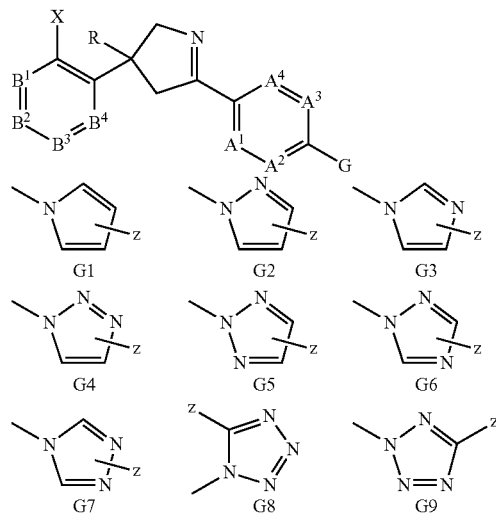

| Example No. | X | B¹ | B² | B³ | B⁴ | R | A1 | A² | A³ | A⁴ | G | Z |
|---|---|---|---|---|---|---|---|---|---|---|---|---|
| 1-74 | H | C—CF3 | C—H | C—CF3 | C—H | CF₃ | C—H | C—H | C—CN | N | G6 | H |
| 1-75 | H | C—CF3 | C—H | C—Cl | C—H | CF₃ | C—H | C—H | C—CN | N | G6 | H |
| 1-76 | H | C—CF3 | C—H | C—H | C—H | CF₃ | C—H | C—H | C—CN | N | G6 | H |
| 1-94 | H | C—Cl | C—Cl | C—Cl | C—H | CF₃ | C—H | C—H | C—H | N | G6 | H |
| 1-95 | H | C—Cl | C—Cl | C—F | C—H | CF₃ | C—H | C—H | C—H | N | G6 | H |
| 1-96 | H | C—Cl | C—Cl | C—Br | C—H | CF₃ | C—H | C—H | C—CN | N | G6 | H |
| 1-97 | H | C—Cl | C—Cl | C—CF3 | C—H | CF₃ | C—H | C—H | C—H | N | G6 | H |
| 1-98 | H | C—CF3 | C—H | C—CF3 | C—H | CF₃ | C—H | C—H | C—H | N | G6 | H |
| 1-99 | H | C—CF3 | C—H | C—Cl | C—H | CF₃ | C—H | C—H | C—H | N | G6 | H |
| 1-100 | H | C—CF3 | C—H | C—H | C—H | CF₃ | C—H | C—H | C—H | N | G6 | H |
| 1-108 | F | C—CF3 | C—H | C—H | C—H | CF₃ | C—H | C—H | C—H | N | G6 | H |
| 1-109 | F | C—CF3 | C—H | C—H | C—H | CF₃ | C—H | C—H | C—CN | N | G6 | H |
| 1-110 | H | C—Cl | C—Cl | C—Cl | C—H | CF₃ | C—H | N | C—H | C—H | G6 | H |
| 1-111 | H | C—Cl | C—Cl | C—F | C—H | CF₃ | C—H | N | C—H | C—H | G6 | H |
| 1-112 | H | C—Cl | C—Cl | C—Br | C—H | CF₃ | C—H | N | C—CN | C—H | G6 | H |
| 1-113 | H | C—Cl | C—Cl | C—CF3 | C—H | CF₃ | C—H | N | C—H | C—H | G6 | H |
| 1-114 | H | C—CF3 | C—H | C—CF3 | C—H | CF₃ | C—H | N | C—H | C—H | G6 | H |
| 1-115 | H | C—CF3 | C—H | C—Cl | C—H | CF₃ | C—H | N | C—H | C—H | G6 | H |
| 1-116 | H | C—CF3 | C—H | C—H | C—H | CF₃ | C—H | N | C—H | C—H | G6 | H |
| 1-124 | F | C—CF3 | C—H | C—H | C—H | CF₃ | C—H | N | C—H | C—H | G6 | H |
| 1-125 | F | C—CF3 | C—H | C—H | C—H | CF₃ | C—H | N | C—CN | C—H | G6 | H |
| 1-138 | H | C—Br | C—H | C—Br | C—H | CF3 | C—H | C—H | C—H | C—H | G6 | H |
| 1-139 | H | C—Br | C—H | C—Br | C—H | CF3 | C—H | N | C—CN | C—H | G6 | H |
| 1-140 | H | C—Br | C—H | C—Br | C—H | CF3 | C—H | C—H | C—CN | N | G6 | H |
| 1-141 | H | C—Br | C—H | C—Br | C—H | CF3 | C—H | N | C—H | C—H | G6 | H |
| 1-142 | H | C—Br | C—H | C—Br | C—H | CF3 | C—H | C—H | C—H | N | G6 | H |
| 1-143 | H | C—CF3 | C—H | C—F | C—H | CF3 | C—H | C—H | C—CN | C—H | G6 | H |
| 1-144 | H | C—CF3 | C—H | C—F | C—H | CF3 | C—H | C—H | C—CN | C—H | G6 | H |
| 1-145 | F | C—CF3 | C—H | C—F | C—H | CF3 | C—H | C—H | C—CN | C—H | G6 | H |
| 1-146 | H | C—CF3 | C—H | C—F | C—H | CF₃ | C—H | N | C—CN | C—H | G6 | H |
| 1-147 | H | C—CF3 | C—H | C—F | C—H | CF₃ | C—H | C—H | C—CN | N | G6 | H |
| 1-148 | H | C—CF3 | C—H | C—F | C—H | CF₃ | C—H | N | C—H | C—H | G6 | H |
| 1-149 | H | C—CF3 | C—H | C—F | C—H | CF₃ | C—H | C—H | C—H | N | G6 | H |
| 1-162 | H | C—Br | C—H | C—F | C—H | CF₃ | C—H | C—H | C—CN | C—H | G6 | H |
| 1-163 | H | C—Br | C—H | C—F | C—H | CF₃ | C—H | C—H | C—H | C—H | G6 | H |
| 1-164 | H | C—Br | C—H | C—F | C—H | CF₃ | C—H | N | C—CN | C—H | G6 | H |
| 1-165 | H | C—Br | C—H | C—F | C—H | CF₃ | C—H | C—H | C—CN | N | G6 | H |
| 1-166 | H | C—Br | C—H | C—F | C—H | CF₃ | C—H | C—H | C—H | N | G6 | H |
| 1-167 | H | C—Br | C—H | C—F | C—H | CF₃ | C—H | N | C—H | C—H | G6 | H |
| 1-168 | H | C—CF3 | C—F | C—Br | C—H | CF3 | C—H | C—H | C—CN | C—H | G6 | H |
| 1-169 | H | C—CF3 | C—F | C—Br | C—H | CF3 | C—H | C—H | C—H | C—H | G6 | H |
| 1-170 | H | C—CF3 | C—F | C—Br | C—H | CF3 | C—H | N | C—CN | C—H | G6 | H |
| 1-171 | H | C—CF3 | C—F | C—Br | C—H | CF3 | C—H | C—H | C—CN | N | G6 | H |
| 1-172 | H | C—CF3 | C—F | C—Br | C—H | CF3 | C—H | C—H | C—H | N | G6 | H |
| 1-173 | H | C—CF3 | C—F | C—Br | C—H | CF3 | C—H | N | C—H | C—H | G6 | H |
| 1-174 | H | C—NO2 | C—CH3 | C—H | C—H | CF3 | C—H | C—H | C—CN | C—H | G6 | H |
| 1-175 | H | C—NO2 | C—CH3 | C—H | C—H | CF3 | C—H | C—H | C—H | C—H | G6 | H |
| 1-176 | H | C—NO2 | C—CH3 | C—H | C—H | CF3 | C—H | N | C—CN | C—H | G6 | H |
| 1-177 | H | C—NO2 | C—CH3 | C—H | C—H | CF3 | C—H | C—H | C—CN | N | G6 | H |
| 1-178 | H | C—NO2 | C—CH3 | C—H | C—H | CF3 | C—H | C—H | C—H | N | G6 | H |
| 1-179 | H | C—NO2 | C—CH3 | C—H | C—H | CF3 | C—H | N | C—H | C—H | G6 | H |
| 1-180 | H | C—NO2 | C—H | C—CH3 | C—H | CF3 | C—H | C—H | C—CN | C—H | G6 | H |

TABLE 1-1-continued

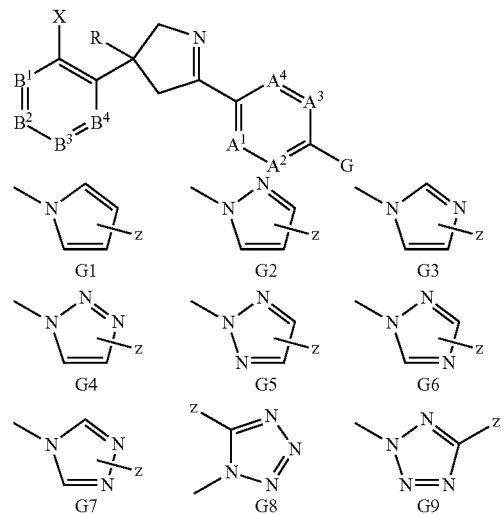

| Example No. | X | B¹ | B² | B³ | B⁴ | R | A1 | A² | A³ | A⁴ | G | Z |
|---|---|---|---|---|---|---|---|---|---|---|---|---|
| 1-181 | H | C—NO2 | C—H | C—CH3 | C—H | CF₃ | C—H | C—H | C—H | C—H | G6 | H |
| 1-182 | H | C—NO2 | C—H | C—CH3 | C—H | CF₃ | C—H | N | C—CN | C—H | G6 | H |
| 1-183 | H | C—NO2 | C—H | C—CH3 | C—H | CF₃ | C—H | C—H | C—CN | N | G6 | H |
| 1-184 | H | C—NO2 | C—H | C—CH3 | C—H | CF₃ | C—H | C—H | C—H | N | G6 | H |
| 1-185 | H | C—NO2 | C—H | C—CH3 | C—H | CF₃ | C—H | N | C—H | C—H | G6 | H |
| 1-186 | H | C—Br | C—H | C—H | C—H | CF₃ | C—H | C—H | C—CN | C—H | G6 | H |
| 1-187 | H | C—Br | C—H | C—H | C—H | CF₃ | C—H | C—H | C—H | C—H | G6 | H |
| 1-188 | H | C—Br | C—H | C—H | C—H | CF₃ | C—H | N | C—CN | C—H | G6 | H |
| 1-189 | H | C—Br | C—H | C—H | C—H | CF₃ | C—H | C—H | C—CN | N | G6 | H |
| 1-190 | H | C—Br | C—H | C—H | C—H | CF₃ | C—H | C—H | C—H | N | G6 | H |
| 1-191 | H | C—Br | C—H | C—H | C—H | CF₃ | C—H | N | C—H | C—H | G6 | H |
| 1-192 | H | C—Cl | C—Cl | C—Cl | C—H | CF3 | C—H | C—H | C—CN | C—H | G1 | H |
| 1-193 | H | C—Cl | C—Cl | C—Cl | C—H | CF3 | C—H | N | C—CN | C—H | G1 | H |
| 1-194 | H | C—Cl | C—Cl | C—Cl | C—H | CF3 | C—H | C—H | C—CN | N | G1 | H |
| 1-195 | H | C—Cl | C—Cl | C—Cl | C—H | CF3 | C—H | C—H | C—CN | C—H | G2 | H |
| 1-196 | H | C—Cl | C—Cl | C—Cl | C—H | CF3 | C—H | N | C—CN | C—H | G2 | H |
| 1-197 | H | C—Cl | C—Cl | C—Cl | C—H | CF3 | C—H | C—H | C—CN | N | G2 | H |
| 1-198 | H | C—Cl | C—Cl | C—Cl | C—H | CF3 | C—H | C—H | C—CN | C—H | G2 | 4-F |
| 1-199 | H | C—Cl | C—Cl | C—Cl | C—H | CF3 | C—H | C—H | C—CN | C—H | G2 | 4-Cl |
| 1-200 | H | C—Cl | C—Cl | C—Cl | C—H | CF3 | C—H | C—H | C—CN | C—H | G2 | 4-Br |
| 1-201 | H | C—Cl | C—Cl | C—Cl | C—H | CF3 | C—H | C—H | C—CN | C—H | G2 | 4-I |
| 1-202 | H | C—Cl | C—Cl | C—Cl | C—H | CF3 | C—H | C—H | C—CN | C—H | G2 | 4-CN |
| 1-203 | H | C—Cl | C—Cl | C—Cl | C—H | CF3 | C—H | C—H | C—CN | C—H | G2 | 4-NO2 |
| 1-204 | H | C—Cl | C—Cl | C—Cl | C—H | CF3 | C—H | C—H | C—CN | C—H | G2 | 4-NH2 |
| 1-205 | H | C—Cl | C—Cl | C—Cl | C—H | CF3 | C—H | C—H | C—CN | C—H | G3 | H |
| 1-206 | H | C—Cl | C—Cl | C—Cl | C—H | CF3 | C—H | N | C—CN | C—H | G3 | H |
| 1-207 | H | C—Cl | C—Cl | C—Cl | C—H | CF3 | C—H | C—H | C—CN | N | G3 | H |
| 1-208 | H | C—Cl | C—Cl | C—Cl | C—H | CF3 | C—H | C—H | C—CN | C—H | G4 | H |
| 1-209 | H | C—Cl | C—Cl | C—Cl | C—H | CF3 | C—H | N | C—CN | C—H | G4 | H |
| 1-210 | H | C—Cl | C—Cl | C—Cl | C—H | CF3 | C—H | C—H | C—CN | N | G4 | H |
| 1-211 | H | C—Cl | C—Cl | C—Cl | C—H | CF3 | C—H | C—H | C—CN | C—H | G5 | H |
| 1-212 | H | C—Cl | C—Cl | C—Cl | C—H | CF3 | C—H | N | C—CN | C—H | G5 | H |
| 1-213 | H | C—Cl | C—Cl | C—Cl | C—H | CF3 | C—H | C—H | C—CN | N | G5 | H |
| 1-214 | H | C—Cl | C—Cl | C—Cl | C—H | CF3 | C—H | C—H | C—CN | C—H | G7 | H |
| 1-215 | H | C—Cl | C—Cl | C—Cl | C—H | CF3 | C—H | N | C—CN | C—H | G7 | H |
| 1-216 | H | C—Cl | C—Cl | C—Cl | C—H | CF3 | C—H | C—H | C—CN | N | G7 | H |
| 1-217 | H | C—Cl | C—Cl | C—Cl | C—H | CF3 | C—H | N | C—CN | C—H | G8 | H |
| 1-218 | H | C—Cl | C—Cl | C—Cl | C—H | CF3 | C—H | C—H | C—CN | N | G8 | H |
| 1-219 | H | C—Cl | C—Cl | C—Cl | C—H | CF3 | C—H | C—H | C—CN | C—H | G9 | H |
| 1-220 | H | C—Cl | C—Cl | C—Cl | C—H | CF3 | C—H | N | C—CN | C—H | G9 | H |
| 1-221 | H | C—Cl | C—Cl | C—Cl | C—H | CF3 | C—H | C—H | C—CN | N | G9 | H |
| 1-434 | H | C—F | C—F | C—F | C—H | CF3 | C—H | C—H | C—CN | C—H | G6 | H |
| 1-435 | H | C—F | C—F | C—F | C—H | CF3 | C—H | C—H | C—H | C—H | G6 | H |
| 1-436 | F | C—F | C—F | C—F | C—H | CF3 | C—H | C—H | C—CN | C—H | G6 | H |
| 1-437 | H | C—F | C—F | C—F | C—H | CF₃ | C—H | N | C—CN | C—H | G6 | H |
| 1-438 | H | C—F | C—F | C—F | C—H | CF₃ | C—H | C—H | C—CN | N | G6 | H |
| 1-439 | H | C—F | C—F | C—F | C—H | CF₃ | C—H | N | C—H | C—H | G6 | H |
| 1-440 | H | C—F | C—F | C—F | C—H | CF₃ | C—H | C—H | C—H | N | G6 | H |
| 1-441 | F | C—F | C—F | C—F | C—F | CF₃ | C—H | C—H | C—CN | C—H | G6 | H |
| 1-442 | F | C—F | C—F | C—F | C—F | CF₃ | C—H | C—H | C—H | C—H | G6 | H |
| 1-443 | F | C—F | C—F | C—F | C—F | CF₃ | C—H | C—H | C—CN | C—H | G6 | H |
| 1-444 | F | C—F | C—F | C—F | C—F | CF₃ | C—H | N | C—CN | C—H | G6 | H |

TABLE 1-1-continued

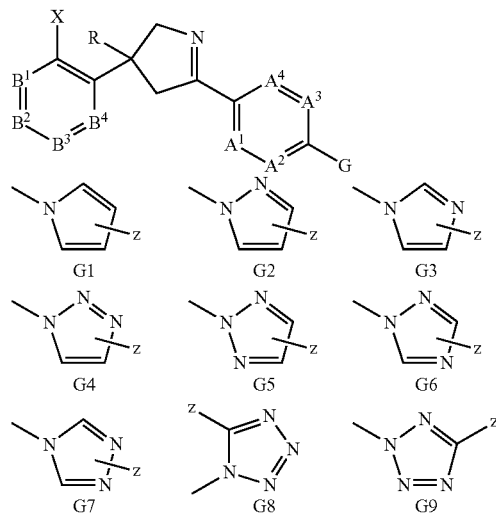

| Example No. | X | B¹ | B² | B³ | B⁴ | R | A1 | A2 | A3 | A⁴ | G | Z |
|---|---|---|---|---|---|---|---|---|---|---|---|---|
| 1-445 | F | C—F | C—F | C—F | C—F | CF₃ | C—H | C—H | C—CN | N | G6 | H |
| 1-446 | F | C—F | C—F | C—F | C—F | CF₃ | C—H | N | C—H | C—H | G6 | H |
| 1-447 | F | C—F | C—F | C—F | C—F | CF₃ | C—H | C—H | C—H | N | G6 | H |
| 1-448 | H | C—Cl | C—H | C—Cl | C—H | CF₃ | N | C—H | C—H | C—H | G6 | H |
| 1-449 | H | C—Cl | C—H | C—Cl | C—H | CF₃ | N | C—H | C—CN | C—H | G6 | H |
| 1-450 | H | C—Cl | C—Cl | C—Cl | C—H | CF₃ | N | C—H | C—H | C—H | G6 | H |
| 1-451 | H | C—Cl | C—Cl | C—Cl | C—H | CF₃ | N | C—H | C—CN | C—H | G6 | H |
| 1-456 | H | C—CF3 | C—H | C—CF3 | C—H | CF₃ | N | C—H | C—H | C—H | G6 | H |
| 1-457 | H | C—CF3 | C—H | C—CF3 | C—H | CF₃ | N | C—H | C—CN | C—H | G6 | H |
| 1-458 | H | C—CF3 | C—H | C—Cl | C—H | CF₃ | N | C—H | C—H | C—H | G6 | H |
| 1-459 | H | C—CF3 | C—H | C—Cl | C—H | CF₃ | N | C—H | C—CN | C—H | G6 | H |
| 1-460 | H | C—CF3 | C—F | C—H | C—H | CF₃ | N | C—H | C—H | C—H | G6 | H |
| 1-461 | H | C—CF3 | C—F | C—H | C—H | CF₃ | N | C—H | C—CN | C—H | G6 | H |
| 1-462 | H | C—CF3 | C—H | C—H | C—H | CF₃ | N | C—H | C—H | C—H | G6 | H |
| 1-463 | H | C—CF3 | C—H | C—H | C—H | CF₃ | N | C—H | C—CN | C—H | G6 | H |
| 1-464 | F | C—CF3 | C—H | C—H | C—H | CF₃ | N | C—H | C—H | C—H | G6 | H |
| 1-465 | F | C—CF3 | C—H | C—H | C—H | CF₃ | N | C—H | C—CN | C—H | G6 | H |
| 1-466 | H | C—CF3 | C—H | C—F | C—H | CF₃ | N | C—H | C—H | C—H | G6 | H |
| 1-467 | H | C—CF3 | C—H | C—F | C—H | CF₃ | N | C—H | C—CN | C—H | G6 | H |
| 1-472 | H | C—Cl | C—F | C—Cl | C—H | CF₃ | N | C—H | C—H | C—H | G6 | H |
| 1-473 | H | C—Cl | C—F | C—Cl | C—H | CF₃ | N | C—H | C—CN | C—H | G6 | H |
| 1-474 | H | C—Cl | C—Br | C—Cl | C—H | CF₃ | N | C—H | C—H | C—H | G6 | H |
| 1-475 | H | C—Cl | C—Br | C—Cl | C—H | CF₃ | N | C—H | C—CN | C—H | G6 | H |
| 1-476 | H | C—Br | C—H | C—Br | C—H | CF₃ | N | C—H | C—H | C—H | G6 | H |
| 1-477 | H | C—Br | C—H | C—Br | C—H | CF₃ | N | C—H | C—CN | C—H | G6 | H |
| 1-478 | H | C—Cl | C—Cl | C—CF3 | C—H | CF₃ | N | C—H | C—H | C—H | G6 | H |
| 1-479 | H | C—Cl | C—Cl | C—CF3 | C—H | CF₃ | N | C—H | C—CN | C—H | G6 | H |
| 1-482 | H | C—CF3 | C—H | C—H | C—F | CF₃ | C—H | C—H | C—CN | C—H | G6 | H |
| 1-483 | H | C—OCHF2 | C—H | C—H | C—H | CF₃ | C—H | C—H | C—CN | C—H | G6 | H |
| 1-485 | H | C—OCHF2 | C—H | C—OCHF2 | C—H | CF₃ | C—H | C—H | C—CN | C—H | G6 | H |
| 1-488 | H | C—Cl | C—H | C—Cl | C—Cl | CF₃ | C—H | C—H | C—CN | C—H | G6 | H |
| 1-489 | H | C—Cl | C—NO2 | C—Cl | C—H | CF₃ | C—H | C—H | C—CN | C—H | G6 | H |
| 1-491 | H | C—CF3 | C—H | C—CF3 | C—H | CF₃ | C—H | N | C—Cl | C—H | G6 | H |
| 1-494 | H | C—CF3 | C—H | C—CF3 | C—H | CF₃ | C—H | N | C—CN | C—H | G6 | H |
| 1-495 | H | C—Cl | —OCF2O— | | C—H | CF₃ | C—H | C—H | C—CN | C—H | G6 | H |
| 1-496 | H | C—Br | —OCF2O— | | C—H | CF₃ | C—H | C—H | C—CN | C—H | G6 | H |
| 1-497 | H | C—OCHF2 | C—H | C—CF3 | C—H | CF₃ | C—H | C—H | C—CN | C—H | G6 | H |
| 1-501 | H | C—Cl | C—H | C—Cl | C—H | CF2Cl | C—H | C—H | C—CN | C—H | G1 | H |
| 1-502 | H | C—Cl | C—H | C—Cl | C—H | CF2Cl | C—H | C—H | C—CN | C—H | G2 | H |
| 1-503 | H | C—Cl | C—H | C—Cl | C—H | CF2Cl | C—H | C—H | C—CN | C—H | G3 | H |
| 1-504 | H | C—Cl | C—H | C—Cl | C—H | CF2Cl | C—H | C—H | C—CN | C—H | G4 | H |
| 1-505 | H | C—Cl | C—H | C—Cl | C—H | CF2Cl | C—H | C—H | C—CN | C—H | G5 | H |
| 1-506 | H | C—Cl | C—H | C—Cl | C—H | CF2Cl | C—H | C—H | C—CN | C—H | G6 | H |
| 1-507 | H | C—Cl | C—H | C—Cl | C—H | CF2Cl | C—H | C—H | C—CN | C—H | G7 | H |
| 1-508 | H | C—Cl | C—H | C—Cl | C—H | CF2Cl | C—H | C—H | C—CN | C—H | G8 | H |
| 1-509 | H | C—Cl | C—H | C—Cl | C—H | CF2Cl | C—H | C—H | C—CN | C—H | G9 | H |
| 1-510 | H | C—Cl | C—Cl | C—Cl | C—H | CF2Cl | C—H | C—H | C—CN | C—H | G1 | H |
| 1-511 | H | C—Cl | C—Cl | C—Cl | C—H | CF2Cl | C—H | C—H | C—CN | C—H | G2 | H |
| 1-512 | H | C—Cl | C—Cl | C—Cl | C—H | CF2Cl | C—H | C—H | C—CN | C—H | G3 | H |
| 1-513 | H | C—Cl | C—Cl | C—Cl | C—H | CF2Cl | C—H | C—H | C—CN | C—H | G4 | H |
| 1-514 | H | C—Cl | C—Cl | C—Cl | C—H | CF2Cl | C—H | C—H | C—CN | C—H | G5 | H |
| 1-515 | H | C—Cl | C—Cl | C—Cl | C—H | CF2Cl | C—H | C—H | C—CN | C—H | G6 | H |

TABLE 1-1-continued

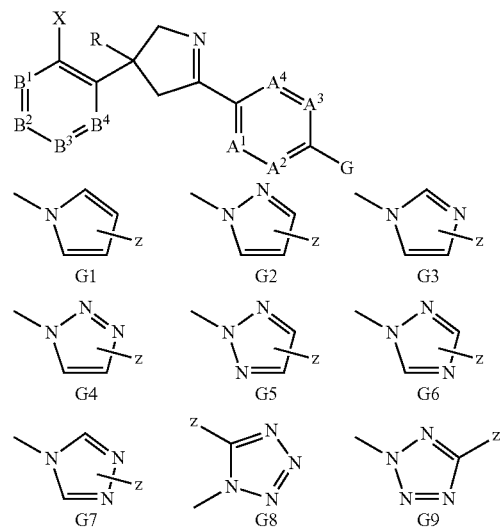

| Example No. | X | B¹ | B² | B³ | B⁴ | R | A1 | A² | A³ | A⁴ | G | Z |
|---|---|---|---|---|---|---|---|---|---|---|---|---|
| 1-516 | H | C—Cl | C—Cl | C—Cl | C—H | CF2Cl | C—H | C—H | C—CN | C—H | G7 | H |
| 1-517 | H | C—Cl | C—Cl | C—Cl | C—H | CF2Cl | C—H | C—H | C—CN | C—H | G8 | H |
| 1-518 | H | C—Cl | C—Cl | C—Cl | C—H | CF2Cl | C—H | C—H | C—CN | C—H | G9 | H |
| 1-519 | H | C—CF3 | C—H | C—CF3 | C—H | CF2Cl | C—H | C—H | C—CN | C—H | G1 | H |
| 1-520 | H | C—CF3 | C—H | C—CF3 | C—H | CF2Cl | C—H | C—H | C—CN | C—H | G2 | H |
| 1-521 | H | C—CF3 | C—H | C—CF3 | C—H | CF2Cl | C—H | C—H | C—CN | C—H | G3 | H |
| 1-522 | H | C—CF3 | C—H | C—CF3 | C—H | CF2Cl | C—H | C—H | C—CN | C—H | G4 | H |
| 1-523 | H | C—CF3 | C—H | C—CF3 | C—H | CF2Cl | C—H | C—H | C—CN | C—H | G5 | H |
| 1-524 | H | C—CF3 | C—H | C—CF3 | C—H | CF2Cl | C—H | C—H | C—CN | C—H | G6 | H |
| 1-525 | H | C—CF3 | C—H | C—CF3 | C—H | CF2Cl | C—H | C—H | C—CN | C—H | G7 | H |
| 1-526 | H | C—CF3 | C—H | C—CF3 | C—H | CF2Cl | C—H | C—H | C—CN | C—H | G8 | H |
| 1-527 | H | C—CF3 | C—H | C—CF3 | C—H | CF2Cl | C—H | C—H | C—CN | C—H | G9 | H |
| 1-555 | H | C—Cl | C—H | C—Cl | C—H | CF2H | C—H | C—H | C—CN | C—H | G1 | H |
| 1-556 | H | C—Cl | C—H | C—Cl | C—H | CF2H | C—H | C—H | C—CN | C—H | G2 | H |
| 1-557 | H | C—Cl | C—H | C—Cl | C—H | CF2H | C—H | C—H | C—CN | C—H | G3 | H |
| 1-558 | H | C—Cl | C—H | C—Cl | C—H | CF2H | C—H | C—H | C—CN | C—H | G4 | H |
| 1-559 | H | C—Cl | C—H | C—Cl | C—H | CF2H | C—H | C—H | C—CN | C—H | G5 | H |
| 1-560 | H | C—Cl | C—H | C—Cl | C—H | CF2H | C—H | C—H | C—CN | C—H | G6 | H |
| 1-561 | H | C—Cl | C—H | C—Cl | C—H | CF2H | C—H | C—H | C—CN | C—H | G7 | H |
| 1-562 | H | C—Cl | C—H | C—Cl | C—H | CF2H | C—H | C—H | C—CN | C—H | G8 | H |
| 1-563 | H | C—Cl | C—H | C—Cl | C—H | CF2H | C—H | C—H | C—CN | C—H | G9 | H |
| 1-564 | H | C—Cl | C—Cl | C—Cl | C—H | CF2H | C—H | C—H | C—CN | C—H | G1 | H |
| 1-565 | H | C—Cl | C—Cl | C—Cl | C—H | CF2H | C—H | C—H | C—CN | C—H | G2 | H |
| 1-566 | H | C—Cl | C—Cl | C—Cl | C—H | CF2H | C—H | C—H | C—CN | C—H | G3 | H |
| 1-567 | H | C—Cl | C—Cl | C—Cl | C—H | CF2H | C—H | C—H | C—CN | C—H | G4 | H |
| 1-568 | H | C—Cl | C—Cl | C—Cl | C—H | CF2H | C—H | C—H | C—CN | C—H | G5 | H |
| 1-569 | H | C—Cl | C—Cl | C—Cl | C—H | CF2H | C—H | C—H | C—CN | C—H | G6 | H |
| 1-570 | H | C—Cl | C—Cl | C—Cl | C—H | CF2H | C—H | C—H | C—CN | C—H | G7 | H |
| 1-571 | H | C—Cl | C—Cl | C—Cl | C—H | CF2H | C—H | C—H | C—CN | C—H | G8 | H |
| 1-572 | H | C—Cl | C—Cl | C—Cl | C—H | CF2H | C—H | C—H | C—CN | C—H | G9 | H |
| 1-573 | H | C—CF3 | C—H | C—CF3 | C—H | CF2H | C—H | C—H | C—CN | C—H | G1 | H |
| 1-574 | H | C—CF3 | C—H | C—CF3 | C—H | CF2H | C—H | C—H | C—CN | C—H | G2 | H |
| 1-575 | H | C—CF3 | C—H | C—CF3 | C—H | CF2H | C—H | C—H | C—CN | C—H | G3 | H |
| 1-576 | H | C—CF3 | C—H | C—CF3 | C—H | CF2H | C—H | C—H | C—CN | C—H | G4 | H |
| 1-577 | H | C—CF3 | C—H | C—CF3 | C—H | CF2H | C—H | C—H | C—CN | C—H | G5 | H |
| 1-578 | H | C—CF3 | C—H | C—CF3 | C—H | CF2H | C—H | C—H | C—CN | C—H | G6 | H |
| 1-579 | H | C—CF3 | C—H | C—CF3 | C—H | CF2H | C—H | C—H | C—CN | C—H | G7 | H |
| 1-580 | H | C—CF3 | C—H | C—CF3 | C—H | CF2H | C—H | C—H | C—CN | C—H | G8 | H |
| 1-581 | H | C—CF3 | C—H | C—CF3 | C—H | CF2H | C—H | C—H | C—CN | C—H | G9 | H |
| 1-609 | H | C—H | —OCF2CF2O— | | C—H | CF3 | C—H | C—H | C—CN | C—H | G6 | H |
| 1-610 | H | C—Cl | —OCF2CF2O— | | C—H | CF3 | C—H | C—H | C—CN | C—H | G6 | H |
| 1-611 | H | C—Br | —OCF2CF2O— | | C—H | CF3 | C—H | C—H | C—CN | C—H | G6 | H |

TABLE 1-2

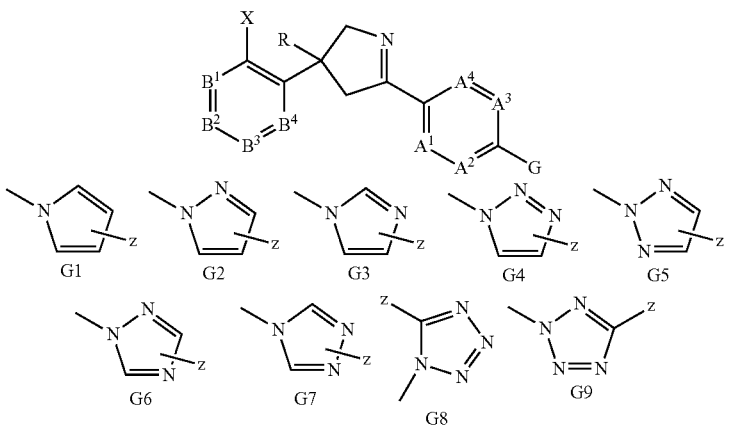

| Example No. | X | B¹ | B² | B³ | B⁴ | R | A1 | A² | A³ | A⁴ | G | Z |
|---|---|---|---|---|---|---|---|---|---|---|---|---|
| 1-1 | H | C—Cl | N | C—Cl | C—H | CF3 | C—H | C—H | C—CN | C—H | G6 | H |
| 1-2 | H | C—Cl | N | C—Cl | C—H | CF3 | C—H | C—H | C—H | C—H | G6 | H |
| 1-21 | H | C—CF3 | N | C—H | C—H | CF3 | C—H | C—H | C—CN | C—H | G6 | H |
| 1-22 | H | C—CF3 | N | C—CF3 | C—H | CF3 | C—H | C—H | C—CN | C—H | G6 | H |
| 1-66 | H | C—Cl | N | C—Cl | C—H | CF₃ | C—H | N | C—CN | C—H | G6 | H |
| 1-67 | H | C—CF3 | N | C—H | C—H | CF₃ | C—H | C—H | C—H | C—H | G6 | H |
| 1-68 | H | C—CF3 | N | C—H | C—H | CF₃ | C—H | N | C—CN | C—H | G6 | H |
| 1-69 | H | C—CF3 | N | C—CF3 | C—H | CF₃ | C—H | N | C—CN | C—H | G6 | H |
| 1-77 | H | C—Cl | N | C—Cl | C—H | CF₃ | C—H | C—H | C—CN | N | G6 | H |
| 1-78 | H | C—CF3 | N | C—H | C—H | CF₃ | C—H | C—H | C—CN | N | G6 | H |
| 1-79 | H | C—CF3 | N | C—CF3 | C—H | CF₃ | C—H | C—H | C—CN | N | G6 | H |
| 1-80 | H | C—CF3 | C—H | C—CF3 | N | CF₃ | C—H | C—H | C—CN | C—H | G6 | H |
| 1-81 | H | C—CF3 | C—H | C—CF3 | N | CF₃ | C—H | C—H | C—H | C—H | G6 | H |
| 1-82 | H | C—CF3 | C—H | C—CF3 | N | CF₃ | C—H | N | C—CN | C—H | G6 | H |
| 1-83 | H | C—CF3 | C—H | C—CF3 | N | CF₃ | C—H | C—H | C—CN | N | G6 | H |
| 1-84 | H | C—CF3 | C—H | C—Cl | N | CF₃ | C—H | C—H | C—CN | C—H | G6 | H |
| 1-85 | H | C—CF3 | C—H | C—Cl | N | CF₃ | C—H | N | C—CN | C—H | G6 | H |
| 1-86 | H | C—CF3 | C—H | C—Cl | N | CF₃ | C—H | C—H | C—CN | N | G6 | H |
| 1-87 | H | C—CF3 | C—H | C—Br | N | CF₃ | C—H | C—H | C—CN | C—H | G6 | H |
| 1-88 | H | C—CF3 | C—H | C—Br | N | CF₃ | C—H | N | C—CN | C—H | G6 | H |
| 1-89 | H | C—CF3 | C—H | C—Br | N | CF₃ | C—H | C—H | C—CN | N | G6 | H |
| 1-90 | H | C—CF3 | C—H | C—H | N | CF₃ | C—H | C—H | C—CN | C—H | G6 | H |
| 1-91 | H | C—CF3 | C—H | C—H | N | CF₃ | C—H | C—H | C—H | C—H | G6 | H |
| 1-92 | H | C—CF3 | C—H | C—H | N | CF₃ | C—H | N | C—CN | C—H | G6 | H |
| 1-93 | H | C—CF3 | C—H | C—H | N | CF₃ | C—H | C—H | C—CN | N | G6 | H |
| 1-101 | H | C—Cl | N | C—Cl | C—H | CF3 | C—H | C—H | C—H | N | G6 | H |
| 1-102 | H | C—CF3 | N | C—H | C—H | CF₃ | C—H | C—H | C—H | N | G6 | H |
| 1-103 | H | C—CF3 | N | C—CF3 | C—H | CF₃ | C—H | C—H | C—H | N | G6 | H |
| 1-104 | H | C—CF3 | C—H | C—CF3 | N | CF₃ | C—H | C—H | C—H | N | G6 | H |
| 1-105 | H | C—CF3 | C—H | C—Cl | N | CF₃ | C—H | C—H | C—H | N | G6 | H |
| 1-106 | H | C—CF3 | C—H | C—Br | N | CF₃ | C—H | C—H | C—H | N | G6 | H |
| 1-107 | H | C—CF3 | C—H | C—H | N | CF₃ | C—H | C—H | C—H | N | G6 | H |
| 1-117 | H | C—Cl | N | C—Cl | C—H | CF3 | C—H | N | C—H | C—H | G6 | H |
| 1-118 | H | C—CF3 | N | C—H | C—H | CF3 | C—H | N | C—H | C—H | G6 | H |
| 1-119 | H | C—CF3 | N | C—CF3 | C—H | CF3 | C—H | N | C—H | C—H | G6 | H |
| 1-120 | H | C—CF3 | C—H | C—CF3 | N | CF₃ | C—H | N | C—H | C—H | G6 | H |
| 1-121 | H | C—CF3 | C—H | C—Cl | N | CF₃ | C—H | N | C—H | C—H | G6 | H |
| 1-122 | H | C—CF3 | C—H | C—Br | N | CF₃ | C—H | N | C—H | C—H | G6 | H |
| 1-123 | H | C—CF3 | C—H | C—H | N | CF₃ | C—H | N | C—H | C—H | G6 | H |
| 1-126 | H | C—H | C—H | C—CF3 | N | CF₃ | C—H | C—H | C—CN | C—H | G6 | H |
| 1-127 | H | C—H | C—H | C—CF3 | N | CF₃ | C—H | C—H | C—H | C—H | G6 | H |
| 1-128 | H | C—H | C—H | C—CF3 | N | CF₃ | C—H | N | C—CN | C—H | G6 | H |
| 1-129 | H | C—H | C—H | C—CF3 | N | CF₃ | C—H | C—H | C—CN | N | G6 | H |
| 1-130 | H | C—H | C—H | C—H | N | CF₃ | C—H | C—H | C—CN | N | G6 | H |
| 1-131 | H | C—H | C—H | C—CF3 | N | CF₃ | C—H | N | C—H | C—H | G6 | H |
| 1-132 | H | C—Cl | C—H | C—Cl | N | CF₃ | C—H | C—H | C—CN | C—H | G6 | H |
| 1-133 | H | C—Cl | C—H | C—Cl | N | CF₃ | C—H | C—H | C—H | C—H | G6 | H |
| 1-134 | H | C—Cl | C—H | C—Cl | N | CF₃ | C—H | N | C—CN | C—H | G6 | H |
| 1-135 | H | C—Cl | C—H | C—Cl | N | CF₃ | C—H | C—H | C—CN | N | G6 | H |
| 1-136 | H | C—Cl | C—H | C—Cl | N | CF₃ | C—H | C—H | C—H | N | G6 | H |
| 1-137 | H | C—Cl | C—H | C—Cl | N | CF₃ | C—H | N | C—H | C—H | G6 | H |
| 1-150 | H | C—Cl | C—CH3 | C—Cl | N | CF₃ | C—H | C—H | C—CN | C—H | G6 | H |
| 1-151 | H | C—Cl | C—CH3 | C—Cl | N | CF₃ | C—H | C—H | C—H | C—H | G6 | H |
| 1-152 | H | C—Cl | C—CH3 | C—Cl | N | CF₃ | C—H | N | C—CN | C—H | G6 | H |
| 1-153 | H | C—Cl | C—CH3 | C—Cl | N | CF₃ | C—H | C—H | C—CN | N | G6 | H |
| 1-154 | H | C—Cl | C—CH3 | C—Cl | N | CF₃ | C—H | C—H | C—H | N | G6 | H |
| 1-155 | H | C—Cl | C—CH3 | C—Cl | N | CF₃ | C—H | N | C—H | C—H | G6 | H |

TABLE 1-2-continued

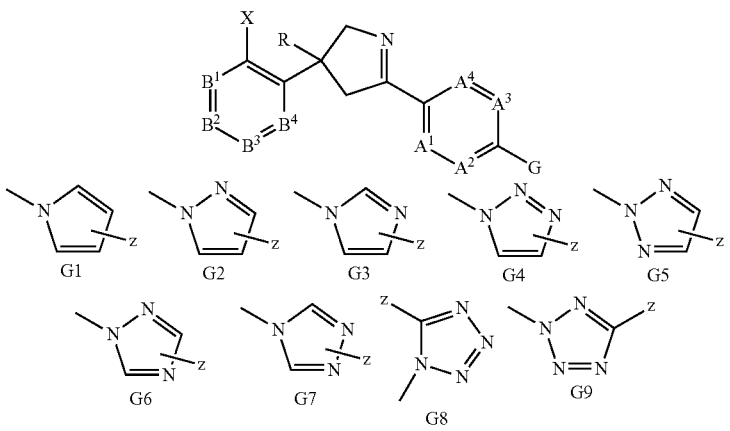

| Example No. | X | B$^1$ | B$^2$ | B$^3$ | B$^4$ | R | A1 | A$^2$ | A$^3$ | A$^4$ | G | Z |
|---|---|---|---|---|---|---|---|---|---|---|---|---|
| 1-156 | H | C—C2F5 | N | C—H | C—H | CF3 | C—H | C—H | C—CN | C—H | G6 | H |
| 1-157 | H | C—C2F5 | N | C—H | C—H | CF$_3$ | C—H | C—H | C—H | C—H | G6 | H |
| 1-158 | H | C—C2F5 | N | C—H | C—H | CF$_3$ | C—H | N | C—CN | C—H | G6 | H |
| 1-159 | H | C—C2F5 | N | C—H | C—H | CF$_3$ | C—H | C—H | C—CN | N | G6 | H |
| 1-160 | H | C—C2F5 | N | C—H | C—H | CF$_3$ | C—H | C—H | C—H | N | G6 | H |
| 1-161 | H | C—C2F5 | N | C—H | C—H | CF$_3$ | C—H | C—H | C—H | C—H | G6 | H |
| 1-222 | H | C—Cl | N | C—H | C—H | CF3 | C—H | C—H | C—H | C—H | G6 | H |
| 1-223 | H | C—Cl | N | C—Cl | C—H | CF3 | C—H | C—H | C—F | C—H | G6 | H |
| 1-224 | H | C—Cl | N | C—Cl | C—H | CF3 | C—H | C—H | C—Cl | C—H | G6 | H |
| 1-225 | H | C—Cl | N | C—Cl | C—H | CF3 | C—H | C—H | C—Br | C—H | G6 | H |
| 1-226 | H | C—Cl | N | C—Cl | C—H | CF3 | C—H | C—H | C—I | C—H | G6 | H |
| 1-227 | H | C—Cl | N | C—Cl | C—H | CF3 | C—H | C—H | C—CH3 | C—H | G6 | H |
| 1-228 | H | C—Cl | N | C—Cl | C—H | CF3 | C—H | C—H | C—CF3 | C—H | G6 | H |
| 1-229 | H | C—Cl | N | C—Cl | C—H | CF3 | C—H | C—H | C—NO2 | C—H | G6 | H |
| 1-230 | H | C—Cl | N | C—Cl | C—H | CF3 | C—H | C—H | C—NH2 | C—H | G6 | H |
| 1-231 | H | C—Cl | N | C—Cl | C—H | CF3 | C—H | C—H | C—NHC(=O)CH3 | C—H | G6 | H |
| 1-232 | H | C—Cl | N | C—Cl | C—H | CF3 | C—H | C—H | C—NHC(=O)CF3 | C—H | G6 | H |
| 1-233 | H | C—Cl | N | C—Cl | C—H | CF3 | C—H | C—H | C—CH2OC(=O)CH3 | C—H | G6 | H |
| 1-234 | H | C—Cl | N | C—Cl | C—H | CF3 | C—H | C—H | C—CH2SCH2CF3 | C—H | G6 | H |
| 1-235 | H | C—Cl | N | C—Cl | C—H | CF3 | C—H | C—H | C—CH2SOCH2CF3 | C—H | G6 | H |
| 1-236 | H | C—Cl | N | C—Cl | C—H | CF3 | C—H | C—H | C—CH2SO2CH2CF3 | C—H | G6 | H |
| 1-237 | H | C—Cl | N | C—Cl | C—H | CF3 | C—H | C—H | C—SCH3 | C—H | G6 | H |
| 1-238 | H | C—Cl | N | C—Cl | C—H | CF3 | C—H | C—H | C—SOCH3 | C—H | G6 | H |
| 1-239 | H | C—Cl | N | C—Cl | C—H | CF3 | C—H | C—H | C—SO2CH3 | C—H | G6 | H |
| 1-240 | H | C—Cl | N | C—Cl | C—H | CF3 | C—H | C—H | C—SCF3 | C—H | G6 | H |
| 1-241 | H | C—Cl | N | C—Cl | C—H | CF3 | C—H | C—H | C—SOCF3 | C—H | G6 | H |
| 1-242 | H | C—Cl | N | C—Cl | C—H | CF3 | C—H | C—H | C—SO2CF3 | C—H | G6 | H |
| 1-243 | H | C—Cl | N | C—Cl | C—H | CF3 | C—H | C—H | C—SCH2CF3 | C—H | G6 | H |
| 1-244 | H | C—Cl | N | C—Cl | C—H | CF3 | C—H | C—H | C—SOCH2CF3 | C—H | G6 | H |
| 1-245 | H | C—Cl | N | C—Cl | C—H | CF3 | C—H | C—H | C—SO2CH2CF3 | C—H | G6 | H |
| 1-246 | H | C—Cl | N | C—Cl | C—H | CF$_3$ | C—H | C—H | C—H | N | G6 | H |
| 1-247 | H | C—Cl | N | C—Cl | C—H | CF$_3$ | C—H | N | C—H | C—H | G6 | H |
| 1-248 | H | C—Cl | N | C—Cl | C—H | CF3 | C—H | C—H | C—CN | C—H | G1 | H |
| 1-249 | H | C—Cl | N | C—Cl | C—H | CF3 | C—H | N | C—CN | C—H | G1 | H |
| 1-250 | H | C—Cl | N | C—Cl | C—H | CF3 | C—H | C—H | C—CN | N | G1 | H |
| 1-251 | H | C—Cl | N | C—Cl | C—H | CF3 | C—H | C—H | C—CN | C—H | G2 | H |
| 1-252 | H | C—Cl | N | C—Cl | C—H | CF3 | C—H | N | C—CN | C—H | G2 | H |
| 1-253 | H | C—Cl | N | C—Cl | C—H | CF3 | C—H | C—H | C—CN | N | G2 | H |
| 1-254 | H | C—Cl | N | C—Cl | C—H | CF3 | C—H | C—H | C—CN | C—H | G2 | 4-F |
| 1-255 | H | C—Cl | N | C—Cl | C—H | CF3 | C—H | C—H | C—CN | C—H | G2 | 4-Cl |
| 1-256 | H | C—Cl | N | C—Cl | C—H | CF3 | C—H | C—H | C—CN | C—H | G2 | 4-Br |
| 1-257 | H | C—Cl | N | C—Cl | C—H | CF3 | C—H | C—H | C—CN | C—H | G2 | 4-I |
| 1-258 | H | C—Cl | N | C—Cl | C—H | CF3 | C—H | C—H | C—CN | C—H | G2 | 4-CN |
| 1-259 | H | C—Cl | N | C—Cl | C—H | CF3 | C—H | C—H | C—CN | C—H | G2 | 4-NO2 |
| 1-260 | H | C—Cl | N | C—Cl | C—H | CF3 | C—H | C—H | C—CN | C—H | G2 | 4-NH2 |
| 1-261 | H | C—Cl | N | C—Cl | C—H | CF3 | C—H | C—H | C—CN | C—H | G3 | H |
| 1-262 | H | C—Cl | N | C—Cl | C—H | CF3 | C—H | N | C—CN | C—H | G3 | H |
| 1-263 | H | C—Cl | N | C—Cl | C—H | CF3 | C—H | C—H | C—CN | N | G3 | H |
| 1-264 | H | C—Cl | N | C—Cl | C—H | CF3 | C—H | C—H | C—CN | C—H | G4 | H |
| 1-265 | H | C—Cl | N | C—Cl | C—H | CF3 | C—H | N | C—CN | C—H | G4 | H |
| 1-266 | H | C—Cl | N | C—Cl | C—H | CF3 | C—H | C—H | C—CN | N | G4 | H |
| 1-267 | H | C—Cl | N | C—Cl | C—H | CF3 | C—H | C—H | C—CN | C—H | G5 | H |
| 1-268 | H | C—Cl | N | C—Cl | C—H | CF3 | C—H | N | C—CN | C—H | G5 | H |
| 1-269 | H | C—Cl | N | C—Cl | C—H | CF3 | C—H | C—H | C—CN | N | G5 | H |
| 1-270 | H | C—Cl | N | C—Cl | C—H | CF3 | C—H | C—H | C—CN | C—H | G7 | H |
| 1-271 | H | C—Cl | N | C—Cl | C—H | CF3 | C—H | N | C—CN | C—H | G7 | H |
| 1-272 | H | C—Cl | N | C—Cl | C—H | CF3 | C—H | C—H | C—CN | N | G7 | H |

TABLE 1-2-continued

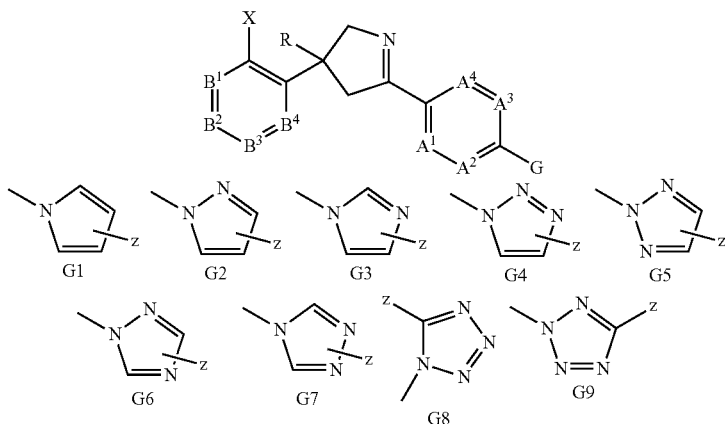

| Example No. | X | B¹ | B² | B³ | B⁴ | R | A1 | A² | A³ | A⁴ | G | Z |
|---|---|---|---|---|---|---|---|---|---|---|---|---|
| 1-273 | H | C—Cl | N | C—Cl | C—H | CF3 | C—H | C—H | C—CN | C—H | G8 | H |
| 1-274 | H | C—Cl | N | C—Cl | C—H | CF3 | C—H | N | C—CN | C—H | G8 | H |
| 1-275 | H | C—Cl | N | C—Cl | C—H | CF3 | C—H | C—H | C—CN | N | G8 | H |
| 1-276 | H | C—Cl | N | C—Cl | C—H | CF3 | C—H | C—H | C—CN | C—H | G9 | H |
| 1-277 | H | C—Cl | N | C—Cl | C—H | CF3 | C—H | N | C—CN | C—H | G9 | H |
| 1-278 | H | C—Cl | N | C—Cl | C—H | CF3 | C—H | C—H | C—CN | N | G9 | H |
| 1-279 | H | C—CF3 | N | C—H | C—H | CF3 | C—H | C—H | C—CN | C—H | G1 | H |
| 1-280 | H | C—CF3 | N | C—H | C—H | CF3 | C—H | N | C—CN | C—H | G1 | H |
| 1-281 | H | C—CF3 | N | C—H | C—H | CF3 | C—H | C—H | C—CN | N | G1 | H |
| 1-282 | H | C—CF3 | N | C—H | C—H | CF3 | C—H | C—H | C—CN | C—H | G2 | H |
| 1-283 | H | C—CF3 | N | C—H | C—H | CF3 | C—H | N | C—CN | C—H | G2 | H |
| 1-284 | H | C—CF3 | N | C—H | C—H | CF3 | C—H | C—H | C—CN | N | G2 | H |
| 1-285 | H | C—CF3 | N | C—H | C—H | CF3 | C—H | C—H | C—CN | C—H | G2 | 4-F |
| 1-286 | H | C—CF3 | N | C—H | C—H | CF3 | C—H | C—H | C—CN | C—H | G2 | 4-Cl |
| 1-287 | H | C—CF3 | N | C—H | C—H | CF3 | C—H | C—H | C—CN | C—H | G2 | 4-Br |
| 1-288 | H | C—CF3 | N | C—H | C—H | CF3 | C—H | C—H | C—CN | C—H | G2 | 4-I |
| 1-289 | H | C—CF3 | N | C—H | C—H | CF3 | C—H | C—H | C—CN | C—H | G2 | 4-CN |
| 1-290 | H | C—CF3 | N | C—H | C—H | CF3 | C—H | C—H | C—CN | C—H | G2 | 4-NO2 |
| 1-291 | H | C—CF3 | N | C—H | C—H | CF3 | C—H | C—H | C—CN | C—H | G2 | 4-NH2 |
| 1-292 | H | C—CF3 | N | C—H | C—H | CF3 | C—H | C—H | C—CN | C—H | G3 | H |
| 1-293 | H | C—CF3 | N | C—H | C—H | CF3 | C—H | N | C—CN | C—H | G3 | H |
| 1-294 | H | C—CF3 | N | C—H | C—H | CF3 | C—H | C—H | C—CN | N | G3 | H |
| 1-295 | H | C—CF3 | N | C—H | C—H | CF3 | C—H | C—H | C—CN | C—H | G4 | H |
| 1-296 | H | C—CF3 | N | C—H | C—H | CF3 | C—H | N | C—CN | C—H | G4 | H |
| 1-297 | H | C—CF3 | N | C—H | C—H | CF3 | C—H | C—H | C—CN | N | G4 | H |
| 1-298 | H | C—CF3 | N | C—H | C—H | CF3 | C—H | C—H | C—CN | C—H | G5 | H |
| 1-299 | H | C—CF3 | N | C—H | C—H | CF3 | C—H | N | C—CN | C—H | G5 | H |
| 1-300 | H | C—CF3 | N | C—H | C—H | CF3 | C—H | C—H | C—CN | N | G5 | H |
| 1-301 | H | C—CF3 | N | C—H | C—H | CF3 | C—H | C—H | C—CN | C—H | G7 | H |
| 1-302 | H | C—CF3 | N | C—H | C—H | CF3 | C—H | N | C—CN | C—H | G7 | H |
| 1-303 | H | C—CF3 | N | C—H | C—H | CF3 | C—H | C—H | C—CN | N | G7 | H |
| 1-304 | H | C—CF3 | N | C—H | C—H | CF3 | C—H | C—H | C—CN | C—H | G8 | H |
| 1-305 | H | C—CF3 | N | C—H | C—H | CF3 | C—H | N | C—CN | C—H | G8 | H |
| 1-306 | H | C—CF3 | N | C—H | C—H | CF3 | C—H | C—H | C—CN | N | G8 | H |
| 1-307 | H | C—CF3 | N | C—H | C—H | CF3 | C—H | C—H | C—CN | C—H | G9 | H |
| 1-308 | H | C—CF3 | N | C—H | C—H | CF3 | C—H | N | C—CN | C—H | G9 | H |
| 1-309 | H | C—CF3 | N | C—H | C—H | CF3 | C—H | C—H | C—CN | N | G9 | H |
| 1-310 | H | C—CF3 | N | C—CF3 | C—H | CF3 | C—H | C—H | C—CN | C—H | G1 | H |
| 1-311 | H | C—CF3 | N | C—CF3 | C—H | CF3 | C—H | N | C—CN | C—H | G1 | H |
| 1-312 | H | C—CF3 | N | C—CF3 | C—H | CF3 | C—H | C—H | C—CN | N | G1 | H |
| 1-313 | H | C—CF3 | N | C—CF3 | C—H | CF3 | C—H | C—H | C—CN | C—H | G2 | H |
| 1-314 | H | C—CF3 | N | C—CF3 | C—H | CF3 | C—H | N | C—CN | C—H | G2 | H |
| 1-315 | H | C—CF3 | N | C—CF3 | C—H | CF3 | C—H | C—H | C—CN | N | G2 | H |
| 1-316 | H | C—CF3 | N | C—CF3 | C—H | CF3 | C—H | C—H | C—CN | C—H | G2 | 4-F |
| 1-317 | H | C—CF3 | N | C—CF3 | C—H | CF3 | C—H | C—H | C—CN | C—H | G2 | 4-Cl |
| 1-318 | H | C—CF3 | N | C—CF3 | C—H | CF3 | C—H | C—H | C—CN | C—H | G2 | 4-Br |
| 1-319 | H | C—CF3 | N | C—CF3 | C—H | CF3 | C—H | C—H | C—CN | C—H | G2 | 4-I |
| 1-320 | H | C—CF3 | N | C—CF3 | C—H | CF3 | C—H | C—H | C—CN | C—H | G2 | 4-CN |
| 1-321 | H | C—CF3 | N | C—CF3 | C—H | CF3 | C—H | C—H | C—CN | C—H | G2 | 4-NO2 |
| 1-322 | H | C—CF3 | N | C—CF3 | C—H | CF3 | C—H | C—H | C—CN | C—H | G2 | 4-NH2 |
| 1-323 | H | C—CF3 | N | C—CF3 | C—H | CF3 | C—H | C—H | C—CN | C—H | G3 | H |
| 1-324 | H | C—CF3 | N | C—CF3 | C—H | CF3 | C—H | N | C—CN | C—H | G3 | H |
| 1-325 | H | C—CF3 | N | C—CF3 | C—H | CF3 | C—H | C—H | C—CN | N | G3 | H |
| 1-326 | H | C—CF3 | N | C—CF3 | C—H | CF3 | C—H | C—H | C—CN | C—H | G4 | H |
| 1-327 | H | C—CF3 | N | C—CF3 | C—H | CF3 | C—H | N | C—CN | C—H | G4 | H |
| 1-328 | H | C—CF3 | N | C—CF3 | C—H | CF3 | C—H | C—H | C—CN | N | G4 | H |
| 1-329 | H | C—CF3 | N | C—CF3 | C—H | CF3 | C—H | C—H | C—CN | C—H | G5 | H |

TABLE 1-2-continued

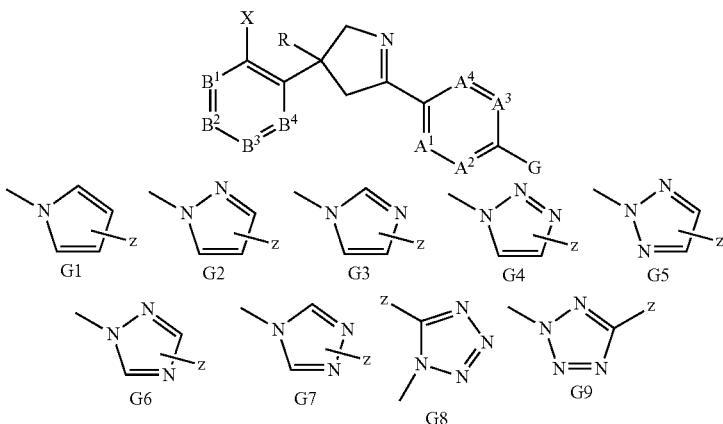

| Example No. | X | B¹ | B² | B³ | B⁴ | R | A1 | A² | A³ | A⁴ | G | Z |
|---|---|---|---|---|---|---|---|---|---|---|---|---|
| 1-330 | H | C—CF3 | N | C—CF3 | C—H | CF3 | C—H | N | C—CN | C—H | G5 | H |
| 1-331 | H | C—CF3 | N | C—CF3 | C—H | CF3 | C—H | C—H | C—CN | N | G5 | H |
| 1-332 | H | C—CF3 | N | C—CF3 | C—H | CF3 | C—H | C—H | C—CN | C—H | G7 | H |
| 1-333 | H | C—CF3 | N | C—CF3 | C—H | CF3 | C—H | N | C—CN | C—H | G7 | H |
| 1-334 | H | C—CF3 | N | C—CF3 | C—H | CF3 | C—H | C—H | C—CN | N | G7 | H |
| 1-335 | H | C—CF3 | N | C—CF3 | C—H | CF3 | C—H | C—H | C—CN | C—H | G8 | H |
| 1-336 | H | C—CF3 | N | C—CF3 | C—H | CF3 | C—H | N | C—CN | C—H | G8 | H |
| 1-337 | H | C—CF3 | N | C—CF3 | C—H | CF3 | C—H | C—H | C—CN | N | G8 | H |
| 1-338 | H | C—CF3 | N | C—CF3 | C—H | CF3 | C—H | C—H | C—CN | C—H | G9 | H |
| 1-339 | H | C—CF3 | N | C—CF3 | C—H | CF3 | C—H | N | C—CN | C—H | G9 | H |
| 1-340 | H | C—CF3 | N | C—CF3 | C—H | CF3 | C—H | C—H | C—CN | N | G9 | H |
| 1-341 | H | C—CF3 | C—H | C—H | N | CF3 | C—H | C—H | C—CN | C—H | G1 | H |
| 1-342 | H | C—CF3 | C—H | C—H | N | CF3 | C—H | N | C—CN | C—H | G1 | H |
| 1-343 | H | C—CF3 | C—H | C—H | N | CF3 | C—H | C—H | C—CN | N | G1 | H |
| 1-344 | H | C—CF3 | C—H | C—H | N | CF3 | C—H | C—H | C—CN | C—H | G2 | H |
| 1-345 | H | C—CF3 | C—H | C—H | N | CF3 | C—H | N | C—CN | C—H | G2 | H |
| 1-346 | H | C—CF3 | C—H | C—H | N | CF3 | C—H | C—H | C—CN | N | G2 | H |
| 1-347 | H | C—CF3 | C—H | C—H | N | CF3 | C—H | C—H | C—CN | C—H | G2 | 4-F |
| 1-348 | H | C—CF3 | C—H | C—H | N | CF3 | C—H | C—H | C—CN | C—H | G2 | 4-Cl |
| 1-349 | H | C—CF3 | C—H | C—H | N | CF3 | C—H | C—H | C—CN | C—H | G2 | 4-Br |
| 1-350 | H | C—CF3 | C—H | C—H | N | CF3 | C—H | C—H | C—CN | C—H | G2 | 4-I |
| 1-351 | H | C—CF3 | C—H | C—H | N | CF3 | C—H | C—H | C—CN | C—H | G2 | 4-CN |
| 1-352 | H | C—CF3 | C—H | C—H | N | CF3 | C—H | C—H | C—CN | C—H | G2 | 4-NO2 |
| 1-353 | H | C—CF3 | C—H | C—H | N | CF3 | C—H | C—H | C—CN | C—H | G2 | 4-NH2 |
| 1-354 | H | C—CF3 | C—H | C—H | N | CF3 | C—H | C—H | C—CN | C—H | G3 | H |
| 1-355 | H | C—CF3 | C—H | C—H | N | CF3 | C—H | N | C—CN | C—H | G3 | H |
| 1-356 | H | C—CF3 | C—H | C—H | N | CF3 | C—H | C—H | C—CN | N | G3 | H |
| 1-357 | H | C—CF3 | C—H | C—H | N | CF3 | C—H | C—H | C—CN | C—H | G4 | H |
| 1-358 | H | C—CF3 | C—H | C—H | N | CF3 | C—H | N | C—CN | C—H | G4 | H |
| 1-359 | H | C—CF3 | C—H | C—H | N | CF3 | C—H | C—H | C—CN | N | G4 | H |
| 1-360 | H | C—CF3 | C—H | C—H | N | CF3 | C—H | C—H | C—CN | C—H | G5 | H |
| 1-361 | H | C—CF3 | C—H | C—H | N | CF3 | C—H | N | C—CN | C—H | G5 | H |
| 1-362 | H | C—CF3 | C—H | C—H | N | CF3 | C—H | C—H | C—CN | N | G5 | H |
| 1-363 | H | C—CF3 | C—H | C—H | N | CF3 | C—H | C—H | C—CN | C—H | G7 | H |
| 1-364 | H | C—CF3 | C—H | C—H | N | CF3 | C—H | N | C—CN | C—H | G7 | H |
| 1-365 | H | C—CF3 | C—H | C—H | N | CF3 | C—H | C—H | C—CN | N | G7 | H |
| 1-366 | H | C—CF3 | C—H | C—H | N | CF3 | C—H | C—H | C—CN | C—H | G8 | H |
| 1-367 | H | C—CF3 | C—H | C—H | N | CF3 | C—H | N | C—CN | C—H | G8 | H |
| 1-368 | H | C—CF3 | C—H | C—H | N | CF3 | C—H | C—H | C—CN | N | G8 | H |
| 1-369 | H | C—CF3 | C—H | C—H | N | CF3 | C—H | C—H | C—CN | C—H | G9 | H |
| 1-370 | H | C—CF3 | C—H | C—H | N | CF3 | C—H | N | C—CN | C—H | G9 | H |
| 1-371 | H | C—CF3 | C—H | C—H | N | CF3 | C—H | C—H | C—CN | N | G9 | H |
| 1-372 | H | C—H | C—H | C—CF3 | N | CF3 | C—H | C—H | C—CN | C—H | G1 | H |
| 1-373 | H | C—H | C—H | C—CF3 | N | CF3 | C—H | N | C—CN | C—H | G1 | H |
| 1-374 | H | C—H | C—H | C—CF3 | N | CF3 | C—H | C—H | C—CN | N | G1 | H |
| 1-375 | H | C—H | C—H | C—CF3 | N | CF3 | C—H | C—H | C—CN | C—H | G2 | H |
| 1-376 | H | C—H | C—H | C—CF3 | N | CF3 | C—H | N | C—CN | C—H | G2 | H |
| 1-377 | H | C—H | C—H | C—CF3 | N | CF3 | C—H | C—H | C—CN | N | G2 | H |
| 1-378 | H | C—H | C—H | C—CF3 | N | CF3 | C—H | C—H | C—CN | C—H | G2 | 4-F |
| 1-379 | H | C—H | C—H | C—CF3 | N | CF3 | C—H | C—H | C—CN | C—H | G2 | 4-Cl |
| 1-380 | H | C—H | C—H | C—CF3 | N | CF3 | C—H | C—H | C—CN | C—H | G2 | 4-Br |
| 1-381 | H | C—H | C—H | C—CF3 | N | CF3 | C—H | C—H | C—CN | C—H | G2 | 4-I |
| 1-382 | H | C—H | C—H | C—CF3 | N | CF3 | C—H | C—H | C—CN | C—H | G2 | 4-CN |
| 1-383 | H | C—H | C—H | C—CF3 | N | CF3 | C—H | C—H | C—CN | C—H | G2 | 4-NO2 |
| 1-384 | H | C—H | C—H | C—CF3 | N | CF3 | C—H | C—H | C—CN | C—H | G2 | 4-NH2 |
| 1-385 | H | C—H | C—H | C—CF3 | N | CF3 | C—H | C—H | C—CN | C—H | G3 | H |
| 1-386 | H | C—H | C—H | C—CF3 | N | CF3 | C—H | N | C—CN | C—H | G3 | H |

TABLE 1-2-continued

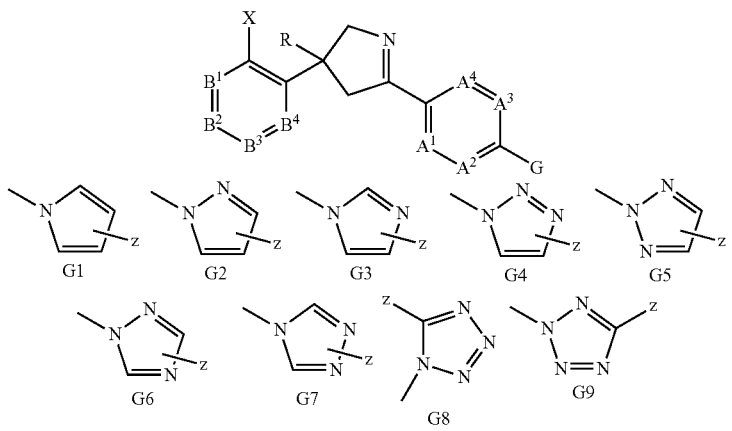

| Example No. | X | B¹ | B² | B³ | B⁴ | R | A1 | A² | A³ | A⁴ | G | Z |
|---|---|---|---|---|---|---|---|---|---|---|---|---|
| 1-387 | H | C—H | C—H | C—CF3 | N | CF3 | C—H | C—H | C—CN | N | G3 | H |
| 1-388 | H | C—H | C—H | C—CF3 | N | CF3 | C—H | C—H | C—CN | C—H | G4 | H |
| 1-389 | H | C—H | C—H | C—CF3 | N | CF3 | C—H | N | C—CN | C—H | G4 | H |
| 1-390 | H | C—H | C—H | C—CF3 | N | CF3 | C—H | C—H | C—CN | N | G4 | H |
| 1-391 | H | C—H | C—H | C—CF3 | N | CF3 | C—H | C—H | C—CN | C—H | G5 | H |
| 1-392 | H | C—H | C—H | C—CF3 | N | CF3 | C—H | N | C—CN | C—H | G5 | H |
| 1-393 | H | C—H | C—H | C—CF3 | N | CF3 | C—H | C—H | C—CN | N | G5 | H |
| 1-394 | H | C—H | C—H | C—CF3 | N | CF3 | C—H | C—H | C—CN | C—H | G7 | H |
| 1-395 | H | C—H | C—H | C—CF3 | N | CF3 | C—H | N | C—CN | C—H | G7 | H |
| 1-396 | H | C—H | C—H | C—CF3 | N | CF3 | C—H | C—H | C—CN | N | G7 | H |
| 1-397 | H | C—H | C—H | C—CF3 | N | CF3 | C—H | C—H | C—CN | C—H | G8 | H |
| 1-398 | H | C—H | C—H | C—CF3 | N | CF3 | C—H | N | C—CN | C—H | G8 | H |
| 1-399 | H | C—H | C—H | C—CF3 | N | CF3 | C—H | C—H | C—CN | N | G8 | H |
| 1-400 | H | C—H | C—H | C—CF3 | N | CF3 | C—H | C—H | C—CN | C—H | G9 | H |
| 1-401 | H | C—H | C—H | C—CF3 | N | CF3 | C—H | N | C—CN | C—H | G9 | H |
| 1-402 | H | C—H | C—H | C—CF3 | N | CF3 | C—H | C—H | C—CN | N | G9 | H |
| 1-403 | H | C—CF3 | C—H | C—CF3 | N | CF3 | C—H | C—H | C—CN | C—H | G1 | H |
| 1-404 | H | C—CF3 | C—H | C—CF3 | N | CF3 | C—H | N | C—CN | C—H | G1 | H |
| 1-405 | H | C—CF3 | C—H | C—CF3 | N | CF3 | C—H | C—H | C—CN | N | G1 | H |
| 1-406 | H | C—CF3 | C—H | C—CF3 | N | CF3 | C—H | C—H | C—CN | C—H | G2 | H |
| 1-407 | H | C—CF3 | C—H | C—CF3 | N | CF3 | C—H | N | C—CN | C—H | G2 | H |
| 1-408 | H | C—CF3 | C—H | C—CF3 | N | CF3 | C—H | C—H | C—CN | N | G2 | H |
| 1-409 | H | C—CF3 | C—H | C—CF3 | N | CF3 | C—H | C—H | C—CN | C—H | G2 | 4-F |
| 1-410 | H | C—CF3 | C—H | C—CF3 | N | CF3 | C—H | C—H | C—CN | C—H | G2 | 4-Cl |
| 1-411 | H | C—CF3 | C—H | C—CF3 | N | CF3 | C—H | C—H | C—CN | C—H | G2 | 4-Br |
| 1-412 | H | C—CF3 | C—H | C—CF3 | N | CF3 | C—H | C—H | C—CN | C—H | G2 | 4-I |
| 1-413 | H | C—CF3 | C—H | C—CF3 | N | CF3 | C—H | C—H | C—CN | C—H | G2 | 4-CN |
| 1-414 | H | C—CF3 | C—H | C—CF3 | N | CF3 | C—H | C—H | C—CN | C—H | G2 | 4-NO2 |
| 1-415 | H | C—CF3 | C—H | C—CF3 | N | CF3 | C—H | C—H | C—CN | C—H | G2 | 4-NH2 |
| 1-416 | H | C—CF3 | C—H | C—CF3 | N | CF3 | C—H | C—H | C—CN | C—H | G3 | H |
| 1-417 | H | C—CF3 | C—H | C—CF3 | N | CF3 | C—H | N | C—CN | C—H | G3 | H |
| 1-418 | H | C—CF3 | C—H | C—CF3 | N | CF3 | C—H | C—H | C—CN | N | G3 | H |
| 1-419 | H | C—CF3 | C—H | C—CF3 | N | CF3 | C—H | C—H | C—CN | C—H | G4 | H |
| 1-420 | H | C—CF3 | C—H | C—CF3 | N | CF3 | C—H | N | C—CN | C—H | G4 | H |
| 1-421 | H | C—CF3 | C—H | C—CF3 | N | CF3 | C—H | C—H | C—CN | N | G4 | H |
| 1-422 | H | C—CF3 | C—H | C—CF3 | N | CF3 | C—H | C—H | C—CN | C—H | G5 | H |
| 1-423 | H | C—CF3 | C—H | C—CF3 | N | CF3 | C—H | N | C—CN | C—H | G5 | H |
| 1-424 | H | C—CF3 | C—H | C—CF3 | N | CF3 | C—H | C—H | C—CN | N | G5 | H |
| 1-425 | H | C—CF3 | C—H | C—CF3 | N | CF3 | C—H | C—H | C—CN | C—H | G7 | H |
| 1-426 | H | C—CF3 | C—H | C—CF3 | N | CF3 | C—H | N | C—CN | C—H | G7 | H |
| 1-427 | H | C—CF3 | C—H | C—CF3 | N | CF3 | C—H | C—H | C—CN | N | G7 | H |
| 1-428 | H | C—CF3 | C—H | C—CF3 | N | CF3 | C—H | C—H | C—CN | C—H | G8 | H |
| 1-429 | H | C—CF3 | C—H | C—CF3 | N | CF3 | C—H | N | C—CN | C—H | G8 | H |
| 1-430 | H | C—CF3 | C—H | C—CF3 | N | CF3 | C—H | C—H | C—CN | N | G8 | H |
| 1-431 | H | C—CF3 | C—H | C—CF3 | N | CF3 | C—H | C—H | C—CN | C—H | G9 | H |
| 1-432 | H | C—CF3 | C—H | C—CF3 | N | CF3 | C—H | N | C—CN | C—H | G9 | H |
| 1-433 | H | C—CF3 | C—H | C—CF3 | N | CF3 | C—H | C—H | C—CN | N | G9 | H |
| 1-452 | H | C—Cl | N | C—Cl | C—H | CF₃ | N | C—H | C—H | C—H | G6 | H |
| 1-453 | H | C—Cl | N | C—Cl | C—H | CF₃ | N | C—H | C—CN | C—H | G6 | H |
| 1-454 | H | C—CF3 | N | C—CF3 | C—H | CF₃ | N | C—H | C—H | C—H | G6 | H |
| 1-455 | H | C—CF3 | N | C—CF3 | C—H | CF₃ | N | C—H | C—CN | C—H | G6 | H |
| 1-468 | H | C—CF3 | N | C—H | C—H | CF₃ | N | C—H | C—H | C—H | G6 | H |
| 1-469 | H | C—CF3 | N | C—H | C—H | CF₃ | N | C—H | C—CN | C—H | G6 | H |
| 1-470 | H | C—CF3 | C—H | C—CF3 | N | CF₃ | N | C—H | C—H | C—H | G6 | H |
| 1-471 | H | C—CF3 | C—H | C—CF3 | N | CF₃ | N | C—H | C—CN | C—H | G6 | H |
| 1-480 | H | N | C—H | C—Cl | C—H | CF₃ | C—H | C—H | C—CN | C—H | G6 | H |
| 1-481 | H | N | C—H | C—CF3 | C—H | CF₃ | C—H | C—H | C—CN | C—H | G6 | H |

TABLE 1-2-continued

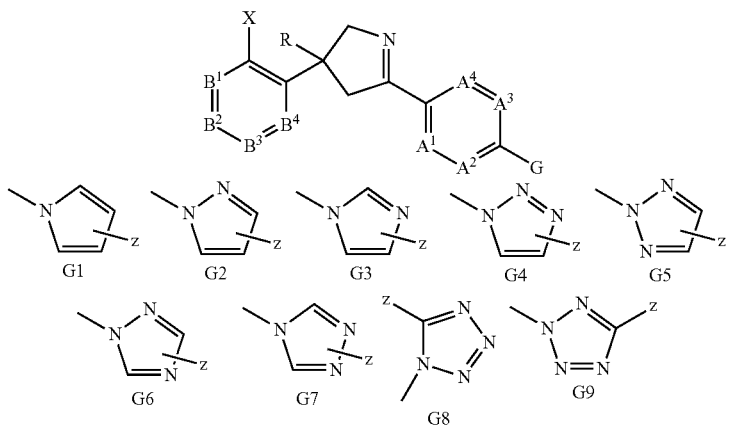

| Example No. | X | B¹ | B² | B³ | B⁴ | R | A1 | A² | A³ | A⁴ | G | Z |
|---|---|---|---|---|---|---|---|---|---|---|---|---|
| 1-484 | H | C—Cl | N | C—H | C—H | CF₃ | C—H | C—H | C—CN | C—H | G6 | H |
| 1-486 | H | C—C3F7-n | N | C—H | C—H | CF₃ | C—H | C—H | C—CN | C—H | G6 | H |
| 1-487 | H | N | C—H | N | C—H | CF₃ | C—H | C—H | C—CN | C—H | G6 | H |
| 1-490 | H | C—Cl | N | C—Cl | C—H | CF₃ | C—H | N | C—Cl | C—H | G6 | H |
| 1-492 | H | C—Cl | N | C—CF3 | C—H | CF₃ | C—H | C—H | C—CN | C—H | G6 | H |
| 1-493 | H | C—CN | N | C—CF3 | C—H | CF₃ | C—H | C—H | C—CN | C—H | G6 | H |
| 1-528 | H | C—Cl | N | C—Cl | C—H | CF2Cl | C—H | C—H | C—CN | C—H | G1 | H |
| 1-529 | H | C—Cl | N | C—Cl | C—H | CF2Cl | C—H | C—H | C—CN | C—H | G2 | H |
| 1-530 | H | C—Cl | N | C—Cl | C—H | CF2Cl | C—H | C—H | C—CN | C—H | G3 | H |
| 1-531 | H | C—Cl | N | C—Cl | C—H | CF2Cl | C—H | C—H | C—CN | C—H | G4 | H |
| 1-532 | H | C—Cl | N | C—Cl | C—H | CF2Cl | C—H | C—H | C—CN | C—H | G5 | H |
| 1-533 | H | C—Cl | N | C—Cl | C—H | CF2Cl | C—H | C—H | C—CN | C—H | G6 | H |
| 1-534 | H | C—Cl | N | C—Cl | C—H | CF2Cl | C—H | C—H | C—CN | C—H | G7 | H |
| 1-535 | H | C—Cl | N | C—Cl | C—H | CF2Cl | C—H | C—H | C—CN | C—H | G8 | H |
| 1-536 | H | C—Cl | N | C—Cl | C—H | CF2Cl | C—H | C—H | C—CN | C—H | G9 | H |
| 1-537 | H | C—Cl | N | C—CF3 | C—H | CF2Cl | C—H | C—H | C—CN | C—H | G1 | H |
| 1-538 | H | C—Cl | N | C—CF3 | C—H | CF2Cl | C—H | C—H | C—CN | C—H | G2 | H |
| 1-539 | H | C—Cl | N | C—CF3 | C—H | CF2Cl | C—H | C—H | C—CN | C—H | G3 | H |
| 1-540 | H | C—Cl | N | C—CF3 | C—H | CF2Cl | C—H | C—H | C—CN | C—H | G4 | H |
| 1-541 | H | C—Cl | N | C—CF3 | C—H | CF2Cl | C—H | C—H | C—CN | C—H | G5 | H |
| 1-542 | H | C—Cl | N | C—CF3 | C—H | CF2Cl | C—H | C—H | C—CN | C—H | G6 | H |
| 1-543 | H | C—Cl | N | C—CF3 | C—H | CF2Cl | C—H | C—H | C—CN | C—H | G7 | H |
| 1-544 | H | C—Cl | N | C—CF3 | C—H | CF2Cl | C—H | C—H | C—CN | C—H | G8 | H |
| 1-545 | H | C—Cl | N | C—CF3 | C—H | CF2Cl | C—H | C—H | C—CN | C—H | G9 | H |
| 1-546 | H | C—CF3 | N | C—CF3 | C—H | CF2Cl | C—H | C—H | C—CN | C—H | G1 | H |
| 1-547 | H | C—CF3 | N | C—CF3 | C—H | CF2Cl | C—H | C—H | C—CN | C—H | G2 | H |
| 1-548 | H | C—CF3 | N | C—CF3 | C—H | CF2Cl | C—H | C—H | C—CN | C—H | G3 | H |
| 1-549 | H | C—CF3 | N | C—CF3 | C—H | CF2Cl | C—H | C—H | C—CN | C—H | G4 | H |
| 1-550 | H | C—CF3 | N | C—CF3 | C—H | CF2Cl | C—H | C—H | C—CN | C—H | G5 | H |
| 1-551 | H | C—CF3 | N | C—CF3 | C—H | CF2Cl | C—H | C—H | C—CN | C—H | G6 | H |
| 1-552 | H | C—CF3 | N | C—CF3 | C—H | CF2Cl | C—H | C—H | C—CN | C—H | G7 | H |
| 1-553 | H | C—CF3 | N | C—CF3 | C—H | CF2Cl | C—H | C—H | C—CN | C—H | G8 | H |
| 1-554 | H | C—CF3 | N | C—CF3 | C—H | CF2Cl | C—H | C—H | C—CN | C—H | G9 | H |
| 1-582 | H | C—Cl | N | C—Cl | C—H | CF2H | C—H | C—H | C—CN | C—H | G1 | H |
| 1-583 | H | C—Cl | N | C—Cl | C—H | CF2H | C—H | C—H | C—CN | C—H | G2 | H |
| 1-584 | H | C—Cl | N | C—Cl | C—H | CF2H | C—H | C—H | C—CN | C—H | G3 | H |
| 1-585 | H | C—Cl | N | C—Cl | C—H | CF2H | C—H | C—H | C—CN | C—H | G4 | H |
| 1-586 | H | C—Cl | N | C—Cl | C—H | CF2H | C—H | C—H | C—CN | C—H | G5 | H |
| 1-587 | H | C—Cl | N | C—Cl | C—H | CF2H | C—H | C—H | C—CN | C—H | G6 | H |
| 1-588 | H | C—Cl | N | C—Cl | C—H | CF2H | C—H | C—H | C—CN | C—H | G7 | H |
| 1-589 | H | C—Cl | N | C—Cl | C—H | CF2H | C—H | C—H | C—CN | C—H | G8 | H |
| 1-590 | H | C—Cl | N | C—Cl | C—H | CF2H | C—H | C—H | C—CN | C—H | G9 | H |
| 1-591 | H | C—Cl | N | C—CF3 | C—H | CF2H | C—H | C—H | C—CN | C—H | G1 | H |
| 1-592 | H | C—Cl | N | C—CF3 | C—H | CF2H | C—H | C—H | C—CN | C—H | G2 | H |
| 1-593 | H | C—Cl | N | C—CF3 | C—H | CF2H | C—H | C—H | C—CN | C—H | G3 | H |
| 1-594 | H | C—Cl | N | C—CF3 | C—H | CF2H | C—H | C—H | C—CN | C—H | G4 | H |
| 1-595 | H | C—Cl | N | C—CF3 | C—H | CF2H | C—H | C—H | C—CN | C—H | G5 | H |
| 1-596 | H | C—Cl | N | C—CF3 | C—H | CF2H | C—H | C—H | C—CN | C—H | G6 | H |
| 1-597 | H | C—Cl | N | C—CF3 | C—H | CF2H | C—H | C—H | C—CN | C—H | G7 | H |
| 1-598 | H | C—Cl | N | C—CF3 | C—H | CF2H | C—H | C—H | C—CN | C—H | G8 | H |
| 1-599 | H | C—Cl | N | C—CF3 | C—H | CF2H | C—H | C—H | C—CN | C—H | G9 | H |
| 1-600 | H | C—CF3 | N | C—CF3 | C—H | CF2H | C—H | C—H | C—CN | C—H | G1 | H |
| 1-601 | H | C—CF3 | N | C—CF3 | C—H | CF2H | C—H | C—H | C—CN | C—H | G2 | H |
| 1-602 | H | C—CF3 | N | C—CF3 | C—H | CF2H | C—H | C—H | C—CN | C—H | G3 | H |
| 1-603 | H | C—CF3 | N | C—CF3 | C—H | CF2H | C—H | C—H | C—CN | C—H | G4 | H |
| 1-604 | H | C—CF3 | N | C—CF3 | C—H | CF2H | C—H | C—H | C—CN | C—H | G5 | H |
| 1-605 | H | C—CF3 | N | C—CF3 | C—H | CF2H | C—H | C—H | C—CN | C—H | G6 | H |

TABLE 1-2-continued

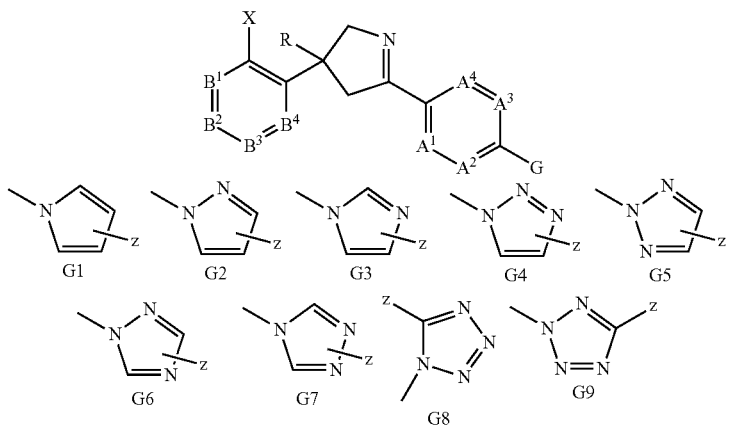

| Example No. | X | $B^1$ | $B^2$ | $B^3$ | $B^4$ | R | A1 | $A^2$ | $A^3$ | $A^4$ | G | Z |
|---|---|---|---|---|---|---|---|---|---|---|---|---|
| 1-606 | H | C—CF3 | N | C—CF3 | C—H | CF2H | C—H | C—H | C—CN | C—H | G7 | H |
| 1-607 | H | C—CF3 | N | C—CF3 | C—H | CF2H | C—H | C—H | C—CN | C—H | G8 | H |
| 1-608 | H | C—CF3 | N | C—CF3 | C—H | CF2H | C—H | C—H | C—CN | C—H | G9 | H |
| 1-612 | H | C—CF3 | N | N | C—H | CF3 | C—H | C—H | C—CN | C—H | G6 | H |
| 1-613 | H | C—CF3 | N | C—CF3 | C—H | CF3 | C—H | C—H | C—Br | C—H | G1 | H |
| 1-614 | H | C—CF3 | N | C—CF3 | C—H | CF3 | C—H | C—H | C—Br | C—H | G2 | H |
| 1-615 | H | C—CF3 | N | C—CF3 | C—H | CF3 | C—H | C—H | C—Br | C—H | G2 | 4-F |
| 1-616 | H | C—CF3 | N | C—CF3 | C—H | CF3 | C—H | C—H | C—Br | C—H | G2 | 4-Cl |
| 1-617 | H | C—CF3 | N | C—CF3 | C—H | CF3 | C—H | C—H | C—Br | C—H | G2 | 4-Br |
| 1-618 | H | C—CF3 | N | C—CF3 | C—H | CF3 | C—H | C—H | C—Br | C—H | G2 | 4-I |
| 1-619 | H | C—CF3 | N | C—CF3 | C—H | CF3 | C—H | C—H | C—Br | C—H | G2 | 4-CN |
| 1-620 | H | C—CF3 | N | C—CF3 | C—H | CF3 | C—H | C—H | C—Br | C—H | G2 | 4-NO2 |
| 1-621 | H | C—CF3 | N | C—CF3 | C—H | CF3 | C—H | C—H | C—Br | C—H | G2 | 4-NH2 |
| 1-622 | H | C—CF3 | N | C—CF3 | C—H | CF3 | C—H | C—H | C—Br | C—H | G3 | H |
| 1-623 | H | C—CF3 | N | C—CF3 | C—H | CF3 | C—H | C—H | C—Br | C—H | G4 | H |
| 1-624 | H | C—CF3 | N | C—CF3 | C—H | CF3 | C—H | C—H | C—Br | C—H | G5 | H |
| 1-625 | H | C—CF3 | N | C—CF3 | C—H | CF3 | C—H | C—H | C—Br | C—H | G6 | H |
| 1-626 | H | C—CF3 | N | C—CF3 | C—H | CF3 | C—H | C—H | C—Br | C—H | G7 | H |
| 1-627 | H | C—CF3 | N | C—CF3 | C—H | CF3 | C—H | C—H | C—Br | C—H | G8 | H |
| 1-628 | H | C—CF3 | N | C—CF3 | C—H | CF3 | C—H | C—H | C—Br | C—H | G9 | H |
| 1-629 | H | C—CF3 | N | C—CF3 | C—H | CF3 | C—H | C—H | C—CH3 | C—H | G1 | H |
| 1-630 | H | C—CF3 | N | C—CF3 | C—H | CF3 | C—H | C—H | C—CH3 | C—H | G2 | H |
| 1-631 | H | C—CF3 | N | C—CF3 | C—H | CF3 | C—H | C—H | C—CH3 | C—H | G2 | 4-F |
| 1-632 | H | C—CF3 | N | C—CF3 | C—H | CF3 | C—H | C—H | C—CH3 | C—H | G2 | 4-Cl |
| 1-633 | H | C—CF3 | N | C—CF3 | C—H | CF3 | C—H | C—H | C—CH3 | C—H | G2 | 4-Br |
| 1-634 | H | C—CF3 | N | C—CF3 | C—H | CF3 | C—H | C—H | C—CH3 | C—H | G2 | 4-I |
| 1-635 | H | C—CF3 | N | C—CF3 | C—H | CF3 | C—H | C—H | C—CH3 | C—H | G2 | 4-CN |
| 1-636 | H | C—CF3 | N | C—CF3 | C—H | CF3 | C—H | C—H | C—CH3 | C—H | G2 | 4-NO2 |
| 1-637 | H | C—CF3 | N | C—CF3 | C—H | CF3 | C—H | C—H | C—CH3 | C—H | G2 | 4-NH2 |
| 1-638 | H | C—CF3 | N | C—CF3 | C—H | CF3 | C—H | C—H | C—CH3 | C—H | G3 | H |
| 1-639 | H | C—CF3 | N | C—CF3 | C—H | CF3 | C—H | C—H | C—CH3 | C—H | G4 | H |
| 1-640 | H | C—CF3 | N | C—CF3 | C—H | CF3 | C—H | C—H | C—CH3 | C—H | G5 | H |
| 1-641 | H | C—CF3 | N | C—CF3 | C—H | CF3 | C—H | C—H | C—CH3 | C—H | G6 | H |
| 1-642 | H | C—CF3 | N | C—CF3 | C—H | CF3 | C—H | C—H | C—CH3 | C—H | G7 | H |
| 1-643 | H | C—CF3 | N | C—CF3 | C—H | CF3 | C—H | C—H | C—CH3 | C—H | G8 | H |
| 1-644 | H | C—CF3 | N | C—CF3 | C—H | CF3 | C—H | C—H | C—CH3 | C—H | G9 | H |
| 1-645 | H | C—CF3 | N | C—CF3 | C—H | CF3 | C—H | C—H | C—NO2 | C—H | G1 | H |
| 1-646 | H | C—CF3 | N | C—CF3 | C—H | CF3 | C—H | C—H | C—NO2 | C—H | G2 | H |
| 1-647 | H | C—CF3 | N | C—CF3 | C—H | CF3 | C—H | C—H | C—NO2 | C—H | G2 | 4-F |
| 1-648 | H | C—CF3 | N | C—CF3 | C—H | CF3 | C—H | C—H | C—NO2 | C—H | G2 | 4-Cl |
| 1-649 | H | C—CF3 | N | C—CF3 | C—H | CF3 | C—H | C—H | C—NO2 | C—H | G2 | 4-Br |
| 1-650 | H | C—CF3 | N | C—CF3 | C—H | CF3 | C—H | C—H | C—NO2 | C—H | G2 | 4-I |
| 1-651 | H | C—CF3 | N | C—CF3 | C—H | CF3 | C—H | C—H | C—NO2 | C—H | G2 | 4-CN |
| 1-652 | H | C—CF3 | N | C—CF3 | C—H | CF3 | C—H | C—H | C—NO2 | C—H | G2 | 4-NO2 |
| 1-653 | H | C—CF3 | N | C—CF3 | C—H | CF3 | C—H | C—H | C—NO2 | C—H | G2 | 4-NH2 |
| 1-654 | H | C—CF3 | N | C—CF3 | C—H | CF3 | C—H | C—H | C—NO2 | C—H | G3 | H |
| 1-655 | H | C—CF3 | N | C—CF3 | C—H | CF3 | C—H | C—H | C—NO2 | C—H | G4 | H |
| 1-656 | H | C—CF3 | N | C—CF3 | C—H | CF3 | C—H | C—H | C—NO2 | C—H | G5 | H |
| 1-657 | H | C—CF3 | N | C—CF3 | C—H | CF3 | C—H | C—H | C—NO2 | C—H | G6 | H |
| 1-658 | H | C—CF3 | N | C—CF3 | C—H | CF3 | C—H | C—H | C—NO2 | C—H | G7 | H |
| 1-659 | H | C—CF3 | N | C—CF3 | C—H | CF3 | C—H | C—H | C—NO2 | C—H | G8 | H |
| 1-660 | H | C—CF3 | N | C—CF3 | C—H | CF3 | C—H | C—H | C—NO2 | C—H | G9 | H |
| 1-661 | H | C—CF3 | N | C—CF3 | C—H | CF3 | C—H | C—H | C—F | C—H | G2 | H |
| 1-662 | H | C—CF3 | N | C—CF3 | C—H | CF3 | C—H | C—H | C—F | C—H | G2 | 4-F |
| 1-663 | H | C—CF3 | N | C—CF3 | C—H | CF3 | C—H | C—H | C—F | C—H | G2 | 4-Cl |
| 1-664 | H | C—CF3 | N | C—CF3 | C—H | CF3 | C—H | C—H | C—F | C—H | G2 | 4-Br |
| 1-665 | H | C—CF3 | N | C—CF3 | C—H | CF3 | C—H | C—H | C—F | C—H | G2 | 4-CN |

TABLE 1-2-continued

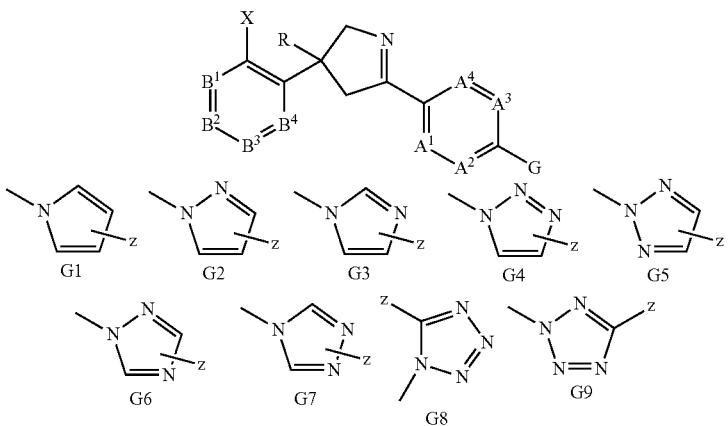

| Example No. | X | B¹ | B² | B³ | B⁴ | R | A1 | A² | A³ | A⁴ | G | Z |
|---|---|---|---|---|---|---|---|---|---|---|---|---|
| 1-666 | H | C—CF3 | N | C—CF3 | C—H | CF3 | C—H | C—H | C—F | C—H | G2 | 4-NO2 |
| 1-667 | H | C—CF3 | N | C—CF3 | C—H | CF3 | C—H | C—H | C—F | C—H | G6 | H |
| 1-668 | H | C—CF3 | N | C—CF3 | C—H | CF3 | C—H | C—H | C—F | C—H | G8 | H |
| 1-669 | H | C—CF3 | N | C—CF3 | C—H | CF3 | C—H | C—H | C—F | C—H | G9 | H |
| 1-670 | H | C—CF3 | N | C—CF3 | C—H | CF3 | C—H | C—H | C—Cl | C—H | G2 | H |
| 1-671 | H | C—CF3 | N | C—CF3 | C—H | CF3 | C—H | C—H | C—Cl | C—H | G2 | 4-F |
| 1-672 | H | C—CF3 | N | C—CF3 | C—H | CF3 | C—H | C—H | C—Cl | C—H | G2 | 4-Cl |
| 1-673 | H | C—CF3 | N | C—CF3 | C—H | CF3 | C—H | C—H | C—Cl | C—H | G2 | 4-Br |
| 1-674 | H | C—CF3 | N | C—CF3 | C—H | CF3 | C—H | C—H | C—Cl | C—H | G2 | 4-CN |
| 1-675 | H | C—CF3 | N | C—CF3 | C—H | CF3 | C—H | C—H | C—Cl | C—H | G2 | 4-NO2 |
| 1-676 | H | C—CF3 | N | C—CF3 | C—H | CF3 | C—H | C—H | C—Cl | C—H | G6 | H |
| 1-677 | H | C—CF3 | N | C—CF3 | C—H | CF3 | C—H | C—H | C—Cl | C—H | G8 | H |
| 1-678 | H | C—CF3 | N | C—CF3 | C—H | CF3 | C—H | C—H | C—Cl | C—H | G9 | H |
| 1-679 | H | C—CF3 | N | C—CF3 | C—H | CF3 | C—H | C—H | C—CF3 | C—H | G2 | H |
| 1-680 | H | C—CF3 | N | C—CF3 | C—H | CF3 | C—H | C—H | C—CF3 | C—H | G2 | 4-F |
| 1-681 | H | C—CF3 | N | C—CF3 | C—H | CF3 | C—H | C—H | C—CF3 | C—H | G2 | 4-Cl |
| 1-682 | H | C—CF3 | N | C—CF3 | C—H | CF3 | C—H | C—H | C—CF3 | C—H | G2 | 4-Br |
| 1-683 | H | C—CF3 | N | C—CF3 | C—H | CF3 | C—H | C—H | C—CF3 | C—H | G2 | 4-CN |
| 1-684 | H | C—CF3 | N | C—CF3 | C—H | CF3 | C—H | C—H | C—CF3 | C—H | G2 | 4-NO2 |
| 1-685 | H | C—CF3 | N | C—CF3 | C—H | CF3 | C—H | C—H | C—CF3 | C—H | G6 | H |
| 1-686 | H | C—CF3 | N | C—CF3 | C—H | CF3 | C—H | C—H | C—CF3 | C—H | G8 | H |
| 1-687 | H | C—CF3 | N | C—CF3 | C—H | CF3 | C—H | C—H | C—CF3 | C—H | G9 | H |
| 1-688 | H | C—CF3 | N | C—F | C—H | CF3 | C—H | C—H | C—CN | C—H | G1 | H |
| 1-689 | H | C—CF3 | N | C—F | C—H | CF3 | C—H | C—H | C—CN | C—H | G2 | H |
| 1-690 | H | C—CF3 | N | C—F | C—H | CF3 | C—H | C—H | C—CN | C—H | G2 | 4-F |
| 1-691 | H | C—CF3 | N | C—F | C—H | CF3 | C—H | C—H | C—CN | C—H | G2 | 4-Cl |
| 1-692 | H | C—CF3 | N | C—F | C—H | CF3 | C—H | C—H | C—CN | C—H | G2 | 4-Br |
| 1-693 | H | C—CF3 | N | C—F | C—H | CF3 | C—H | C—H | C—CN | C—H | G2 | 4-CN |
| 1-694 | H | C—CF3 | N | C—F | C—H | CF3 | C—H | C—H | C—CN | C—H | G2 | 4-NO2 |
| 1-695 | H | C—CF3 | N | C—F | C—H | CF3 | C—H | C—H | C—CN | C—H | G3 | H |
| 1-696 | H | C—CF3 | N | C—F | C—H | CF3 | C—H | C—H | C—CN | C—H | G4 | H |
| 1-697 | H | C—CF3 | N | C—F | C—H | CF3 | C—H | C—H | C—CN | C—H | G5 | H |
| 1-698 | H | C—CF3 | N | C—F | C—H | CF3 | C—H | C—H | C—CN | C—H | G6 | H |
| 1-699 | H | C—CF3 | N | C—F | C—H | CF3 | C—H | C—H | C—CN | C—H | G7 | H |
| 1-700 | H | C—CF3 | N | C—F | C—H | CF3 | C—H | C—H | C—CN | C—H | G8 | H |
| 1-701 | H | C—CF3 | N | C—F | C—H | CF3 | C—H | C—H | C—CN | C—H | G9 | H |
| 1-702 | H | C—CN | N | C—CF3 | C—H | CF3 | C—H | C—H | C—CN | C—H | G1 | H |
| 1-703 | H | C—CN | N | C—CF3 | C—H | CF3 | C—H | C—H | C—CN | C—H | G2 | H |
| 1-704 | H | C—CN | N | C—CF3 | C—H | CF3 | C—H | C—H | C—CN | C—H | G2 | 4-F |
| 1-705 | H | C—CN | N | C—CF3 | C—H | CF3 | C—H | C—H | C—CN | C—H | G2 | 4-Cl |
| 1-706 | H | C—CN | N | C—CF3 | C—H | CF3 | C—H | C—H | C—CN | C—H | G2 | 4-Br |
| 1-707 | H | C—CN | N | C—CF3 | C—H | CF3 | C—H | C—H | C—CN | C—H | G2 | 4-CN |
| 1-708 | H | C—CN | N | C—CF3 | C—H | CF3 | C—H | C—H | C—CN | C—H | G2 | 4-NO2 |
| 1-709 | H | C—CN | N | C—CF3 | C—H | CF3 | C—H | C—H | C—CN | C—H | G8 | H |
| 1-710 | H | C—CN | N | C—CF3 | C—H | CF3 | C—H | C—H | C—CN | C—H | G9 | H |
| 1-711 | H | C—Br | N | C—Br | C—H | CF3 | C—H | C—H | C—CN | C—H | G1 | H |
| 1-712 | H | C—Br | N | C—Br | C—H | CF3 | C—H | C—H | C—CN | C—H | G2 | H |
| 1-713 | H | C—Br | N | C—Br | C—H | CF3 | C—H | C—H | C—CN | C—H | G2 | 4-F |
| 1-714 | H | C—Br | N | C—Br | C—H | CF3 | C—H | C—H | C—CN | C—H | G2 | 4-Cl |
| 1-715 | H | C—Br | N | C—Br | C—H | CF3 | C—H | C—H | C—CN | C—H | G2 | 4-Br |
| 1-716 | H | C—Br | N | C—Br | C—H | CF3 | C—H | C—H | C—CN | C—H | G2 | 4-CN |
| 1-717 | H | C—Br | N | C—Br | C—H | CF3 | C—H | C—H | C—CN | C—H | G2 | 4-NO2 |
| 1-718 | H | C—Br | N | C—Br | C—H | CF3 | C—H | C—H | C—CN | C—H | G6 | H |
| 1-719 | H | C—Br | N | C—Br | C—H | CF3 | C—H | C—H | C—CN | C—H | G8 | H |
| 1-720 | H | C—Br | N | C—Br | C—H | CF3 | C—H | C—H | C—CN | C—H | G9 | H |
| 1-721 | H | C—F | N | C—F | C—H | CF3 | C—H | C—H | C—CN | C—H | G2 | H |
| 1-722 | H | C—F | N | C—F | C—H | CF3 | C—H | C—H | C—CN | C—H | G2 | 4-CN |

TABLE 1-2-continued

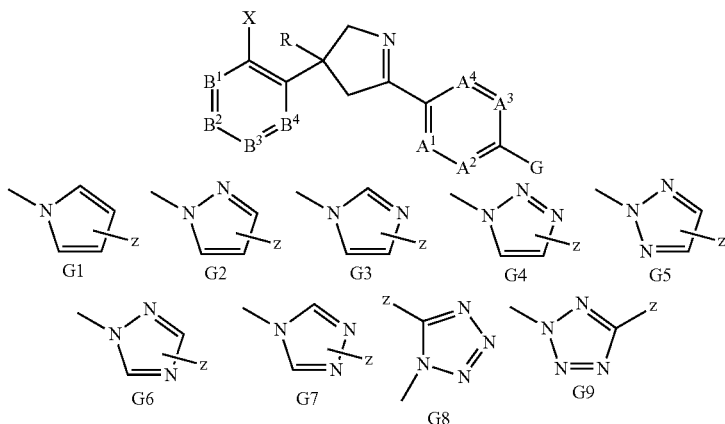

| Example No. | X | B¹ | B² | B³ | B⁴ | R | A1 | A² | A³ | A⁴ | G | Z |
|---|---|---|---|---|---|---|---|---|---|---|---|---|
| 1-723 | H | C—F | N | C—F | C—H | CF3 | C—H | C—H | C—CN | C—H | G2 | 4-NO2 |
| 1-724 | H | C—F | N | C—F | C—H | CF3 | C—H | C—H | C—CN | C—H | G6 | H |
| 1-725 | H | C—F | N | C—F | C—H | CF3 | C—H | C—H | C—CN | C—H | G8 | H |
| 1-726 | H | C—F | N | C—F | C—H | CF3 | C—H | C—H | C—CN | C—H | G9 | H |
| 1-727 | H | C—CHF2 | N | C—CHF2 | C—H | CF3 | C—H | C—H | C—CN | C—H | G1 | H |
| 1-728 | H | C—CHF2 | N | C—CHF2 | C—H | CF3 | C—H | C—H | C—CN | C—H | G2 | H |
| 1-729 | H | C—CHF2 | N | C—CHF2 | C—H | CF3 | C—H | C—H | C—CN | C—H | G2 | 4-F |
| 1-730 | H | C—CHF2 | N | C—CHF2 | C—H | CF3 | C—H | C—H | C—CN | C—H | G2 | 4-Cl |
| 1-731 | H | C—CHF2 | N | C—CHF2 | C—H | CF3 | C—H | C—H | C—CN | C—H | G2 | 4-Br |
| 1-732 | H | C—CHF2 | N | C—CHF2 | C—H | CF3 | C—H | C—H | C—CN | C—H | G2 | 4-CN |
| 1-733 | H | C—CHF2 | N | C—CHF2 | C—H | CF3 | C—H | C—H | C—CN | C—H | G2 | 4-NO2 |
| 1-734 | H | C—CHF2 | N | C—CHF2 | C—H | CF3 | C—H | C—H | C—CN | C—H | G6 | H |
| 1-735 | H | C—CHF2 | N | C—CHF2 | C—H | CF3 | C—H | C—H | C—CN | C—H | G8 | H |
| 1-736 | H | C—CHF2 | N | C—CHF2 | C—H | CF3 | C—H | C—H | C—CN | C—H | G9 | H |
| 1-737 | H | C—Cl | C—Cl | N | C—H | CF3 | C—H | C—H | C—CN | C—H | G1 | H |
| 1-738 | H | C—Cl | C—Cl | N | C—H | CF3 | C—H | C—H | C—CN | C—H | G2 | H |
| 1-739 | H | C—Cl | C—Cl | N | C—H | CF3 | C—H | C—H | C—CN | C—H | G2 | 4-F |
| 1-740 | H | C—Cl | C—Cl | N | C—H | CF3 | C—H | C—H | C—CN | C—H | G2 | 4-Cl |
| 1-741 | H | C—Cl | C—Cl | N | C—H | CF3 | C—H | C—H | C—CN | C—H | G2 | 4-Br |
| 1-742 | H | C—Cl | C—Cl | N | C—H | CF3 | C—H | C—H | C—CN | C—H | G2 | 4-CN |
| 1-743 | H | C—Cl | C—Cl | N | C—H | CF3 | C—H | C—H | C—CN | C—H | G2 | 4-NO2 |
| 1-744 | H | C—Cl | C—Cl | N | C—H | CF3 | C—H | C—H | C—CN | C—H | G6 | H |
| 1-745 | H | C—Cl | C—Cl | N | C—H | CF3 | C—H | C—H | C—CN | C—H | G8 | H |
| 1-746 | H | C—Cl | C—Cl | N | C—H | CF3 | C—H | C—H | C—CN | C—H | G9 | H |
| 1-747 | H | C—CF3 | C—Cl | N | C—H | CF3 | C—H | C—H | C—CN | C—H | G1 | H |
| 1-748 | H | C—CF3 | C—Cl | N | C—H | CF3 | C—H | C—H | C—CN | C—H | G2 | H |
| 1-749 | H | C—CF3 | C—Cl | N | C—H | CF3 | C—H | C—H | C—CN | C—H | G2 | 4-F |
| 1-750 | H | C—CF3 | C—Cl | N | C—H | CF3 | C—H | C—H | C—CN | C—H | G2 | 4-Cl |
| 1-751 | H | C—CF3 | C—Cl | N | C—H | CF3 | C—H | C—H | C—CN | C—H | G2 | 4-Br |
| 1-752 | H | C—CF3 | C—Cl | N | C—H | CF3 | C—H | C—H | C—CN | C—H | G2 | 4-CN |
| 1-753 | H | C—CF3 | C—Cl | N | C—H | CF3 | C—H | C—H | C—CN | C—H | G2 | 4-NO2 |
| 1-754 | H | C—CF3 | C—Cl | N | C—H | CF3 | C—H | C—H | C—CN | C—H | G6 | H |
| 1-755 | H | C—CF3 | C—Cl | N | C—H | CF3 | C—H | C—H | C—CN | C—H | G8 | H |
| 1-756 | H | C—CF3 | C—Cl | N | C—H | CF3 | C—H | C—H | C—CN | C—H | G9 | H |

TABLE 2-1

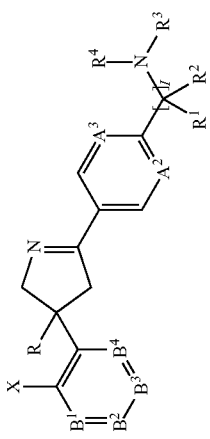

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-1 | H | C—Cl | C—Cl | C—Cl | C—H | CF3 | C—H | C—CF3 | H | H | H | H | 1 |
| 2-2 | H | C—Cl | C—Cl | C—Cl | C—H | CF3 | C—H | C—CF3 | H | H | CH3OCH2CH2CO | H | 1 |
| 2-3 | H | C—Cl | C—Cl | C—Cl | C—H | CF3 | C—H | C—CF3 | H | H | CH3OCH(Me)CH2CO | H | 1 |
| 2-4 | H | C—Cl | C—Cl | C—Cl | C—H | CF3 | C—H | C—CF3 | H | H | n-PrCO | H | 1 |
| 2-5 | H | C—Cl | C—Cl | C—Cl | C—H | CF3 | C—H | C—CF3 | H | H | cyclo-PrCH2CO | H | 1 |
| 2-6 | H | C—Cl | C—Cl | C—Cl | C—H | CF3 | N | C—CF3 | H | H | H | H | 1 |
| 2-7 | H | C—Cl | C—Cl | C—Cl | C—H | CF3 | N | C—CF3 | H | H | MeCO | H | 1 |
| 2-8 | H | C—Cl | C—Cl | C—Cl | C—H | CF3 | N | C—CF3 | H | H | EtCO | H | 1 |
| 2-9 | H | C—Cl | C—Cl | C—Cl | C—H | CF3 | N | C—CF3 | H | H | cyclo-PrCO | H | 1 |
| 2-10 | H | C—Cl | C—Cl | C—Cl | C—H | CF3 | N | C—CF3 | H | H | cyclo-PrCH2CO | H | 1 |
| 2-11 | H | C—Cl | C—Cl | C—Cl | C—H | CF3 | N | C—CF3 | H | H | CF3CH2CO | H | 1 |
| 2-12 | H | C—Cl | C—Cl | C—Cl | C—H | CF3 | N | C—CF3 | H | H | CH3SCH2CO | H | 1 |
| 2-13 | H | C—Cl | C—Cl | C—Cl | C—H | CF3 | N | C—CF3 | H | H | CH3SOCH2CO | H | 1 |
| 2-14 | H | C—Cl | C—Cl | C—Cl | C—H | CF3 | N | C—CF3 | H | H | CH3SO2CH2CO | H | 1 |
| 2-15 | H | C—Cl | C—Cl | C—Cl | C—H | CF3 | N | C—CF3 | H | H | EtNHCO | H | 1 |
| 2-16 | H | C—Cl | C—Cl | C—Cl | C—H | CF3 | C—H | C—CF3 | —CH2CH2— | | H | H | 1 |
| 2-17 | H | C—Cl | C—Cl | C—Cl | C—H | CF3 | C—H | C—CF3 | —CH2CH2— | | MeCO | H | 1 |
| 2-18 | H | C—Cl | C—Cl | C—Cl | C—H | CF3 | C—H | C—CF3 | —CH2CH2— | | EtCO | H | 1 |
| 2-19 | H | C—Cl | C—Cl | C—Cl | C—H | CF3 | C—H | C—CF3 | —CH2CH2— | | CF3CH2CO | H | 1 |
| 2-20 | H | C—Cl | C—Cl | C—Cl | C—H | CF3 | C—H | C—CF3 | —CH2CH2— | | cyclo-PrCO | H | 1 |
| 2-21 | H | C—Cl | C—Cl | C—Cl | C—H | CF3 | C—H | C—CF3 | —CH2CH2— | | EtNHCO | H | 1 |
| 2-22 | H | C—Cl | C—Cl | C—Cl | C—H | CF3 | N | C—CF3 | —CH2CH2— | | CH3SCH2CO | H | 1 |
| 2-23 | H | C—Cl | C—Cl | C—Cl | C—H | CF3 | N | C—CF3 | —CH2CH2— | | CH3SOCH2CO | H | 1 |
| 2-24 | H | C—Cl | C—Cl | C—Cl | C—H | CF3 | N | C—CF3 | —CH2CH2— | | CH3SO2CH2CO | H | 1 |
| 2-25 | H | C—Cl | C—Cl | C—Cl | C—H | CF3 | C—H | C—Cl | H | H | H | H | 1 |
| 2-26 | H | C—Cl | C—Cl | C—Cl | C—H | CF3 | C—H | C—Cl | H | H | n-PrCO | H | 1 |
| 2-27 | H | C—Cl | C—Cl | C—Cl | C—H | CF3 | C—H | C—Cl | H | H | cyclo-PrCH2CO | H | 1 |
| 2-28 | H | C—Cl | C—Cl | C—Cl | C—H | CF3 | C—H | C—Cl | H | H | CH3OCH2CH2CO | H | 1 |
| 2-29 | H | C—Cl | C—Cl | C—Cl | C—H | CF3 | C—H | C—Cl | H | H | CH3OCH(Me)CH2CO | H | 1 |
| 2-30 | H | C—Cl | C—Cl | C—Cl | C—H | CF3 | C—H | C—Cl | H | H | tert-ButOC(=O) | H | 1 |
| 2-31 | H | C—Cl | C—Cl | C—Cl | C—H | CF3 | N | C—Cl | H | H | H | H | 1 |
| 2-32 | H | C—Cl | C—Cl | C—Cl | C—H | CF3 | N | C—Cl | H | H | MeCO | H | 1 |
| 2-33 | H | C—Cl | C—Cl | C—Cl | C—H | CF3 | N | C—Cl | H | H | EtCO | H | 1 |
| 2-34 | H | C—Cl | C—Cl | C—Cl | C—H | CF3 | N | C—Cl | H | H | cyclo-PrCO | H | 1 |
| 2-35 | H | C—Cl | C—Cl | C—Cl | C—H | CF3 | N | C—Cl | H | H | cyclo-PrCH2CO | H | 1 |
| 2-36 | H | C—Cl | C—Cl | C—Cl | C—H | CF3 | N | C—Cl | H | H | CF3CH2CO | H | 1 |
| 2-37 | H | C—Cl | C—Cl | C—Cl | C—H | CF3 | N | C—Cl | H | H | CH3SCH2CO | H | 1 |
| 2-38 | H | C—Cl | C—Cl | C—Cl | C—H | CF3 | N | C—Cl | H | H | CH3SOCH2CO | H | 1 |

TABLE 2-1-continued

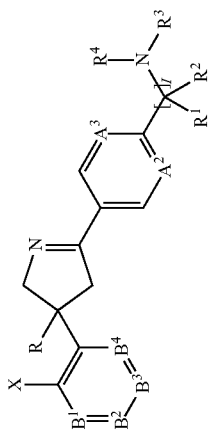

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-39 | H | C-Cl | C-Cl | C-Cl | C-H | CF3 | N | C-Cl | H | H | CH3SO2CH2CO | H | 1 |
| 2-40 | H | C-Cl | C-Cl | C-Cl | C-H | CF3 | N | C-Cl | H | H | EtNHCO | H | 1 |
| 2-41 | H | C-Cl | C-Cl | C-Cl | C-H | CF3 | C-H | C-Cl | Me | H | H | H | 1 |
| 2-42 | H | C-Cl | C-Cl | C-Cl | C-H | CF3 | C-H | C-Cl | Me | H | MeCO | H | 1 |
| 2-43 | H | C-Cl | C-Cl | C-Cl | C-H | CF3 | C-H | C-Cl | Me | H | EtCO | H | 1 |
| 2-44 | H | C-Cl | C-Cl | C-Cl | C-H | CF3 | C-H | C-Cl | Me | H | cyclo-PrCO | H | 1 |
| 2-45 | H | C-Cl | C-Cl | C-Cl | C-H | CF3 | C-H | C-Cl | Me | H | cyclo-PrCH2CO | H | 1 |
| 2-46 | H | C-Cl | C-Cl | C-Cl | C-H | CF3 | C-H | C-Cl | Me | H | CF3CH2CO | H | 1 |
| 2-47 | H | C-Cl | C-Cl | C-Cl | C-H | CF3 | C-H | C-Cl | Me | H | CH3SCH2CO | H | 1 |
| 2-48 | H | C-Cl | C-Cl | C-Cl | C-H | CF3 | C-H | C-Cl | Me | H | CH3SOCH2CO | H | 1 |
| 2-49 | H | C-Cl | C-Cl | C-Cl | C-H | CF3 | C-H | C-Cl | Me | H | CH3SO2CH2CO | H | 1 |
| 2-50 | H | C-Cl | C-Cl | C-Cl | C-H | CF3 | C-H | C-Cl | Me | H | EtNHCO | H | 1 |
| 2-51 | H | C-Cl | C-Cl | C-Cl | C-H | CF3 | C-H | C-Cl | —CH2CH2— | | H | H | 1 |
| 2-52 | H | C-Cl | C-Cl | C-Cl | C-H | CF3 | C-H | C-Cl | —CH2CH2— | | MeCO | H | 1 |
| 2-53 | H | C-Cl | C-Cl | C-Cl | C-H | CF3 | C-H | C-Cl | —CH2CH2— | | EtCO | H | 1 |
| 2-54 | H | C-Cl | C-Cl | C-Cl | C-H | CF3 | C-H | C-Cl | —CH2CH2— | | cyclo-PrCO | H | 1 |
| 2-55 | H | C-Cl | C-Cl | C-Cl | C-H | CF3 | C-H | C-Cl | —CH2CH2— | | CF3CH2CO | H | 1 |
| 2-56 | H | C-Cl | C-Cl | C-Cl | C-H | CF3 | C-H | C-Cl | —CH2CH2— | | CH3SCH2CO | H | 1 |
| 2-57 | H | C-Cl | C-Cl | C-Cl | C-H | CF3 | C-H | C-Cl | —CH2CH2— | | CH3SOCH2CO | H | 1 |
| 2-58 | H | C-Cl | C-Cl | C-Cl | C-H | CF3 | C-H | C-Cl | —CH2CH2— | | CH3SO2CH2CO | H | 1 |
| 2-59 | H | C-Cl | C-Cl | C-Cl | C-H | CF3 | C-H | C-Cl | —CH2CH2— | | EtNHCO | H | 1 |
| 2-60 | H | C-Cl | C-Cl | C-Cl | C-H | CF3 | C-H | C-Br | H | H | n-PrCO | H | 1 |
| 2-61 | H | C-Cl | C-Cl | C-Cl | C-H | CF3 | C-H | C-Br | H | H | cyclo-PrCH2CO | H | 1 |
| 2-62 | H | C-Cl | C-Cl | C-Cl | C-H | CF3 | C-H | C-Br | H | H | CH3OCH2CH2CO | H | 1 |
| 2-63 | H | C-Cl | C-Cl | C-Cl | C-H | CF3 | C-H | C-Br | H | H | CH3OCH(Me)CH2CO | H | 1 |
| 2-64 | H | C-Cl | C-Cl | C-Cl | C-H | CF3 | C-H | C-Br | H | H | CH3SCH2CO | H | 1 |
| 2-65 | H | C-Cl | C-Cl | C-Cl | C-H | CF3 | C-H | C-Br | H | H | CH3SOCH2CO | H | 1 |
| 2-66 | H | C-Cl | C-Cl | C-Cl | C-H | CF3 | C-H | C-Br | H | H | CH3SO2CH2CO | H | 1 |
| 2-67 | H | C-Cl | C-Cl | C-Cl | C-H | CF3 | C-H | C-Br | H | H | cyclo-PrCH2CO | H | 1 |
| 2-68 | H | C-Cl | C-Cl | C-Cl | C-H | CF3 | C-H | C-CN | H | H | n-PrCO | H | 1 |
| 2-69 | H | C-Cl | C-Cl | C-Cl | C-H | CF3 | C-H | C-CN | H | H | CH3SCH2CO | H | 1 |
| 2-70 | H | C-Cl | C-Cl | C-Cl | C-H | CF3 | C-H | C-CN | H | H | CH3SOCH2CO | H | 1 |
| 2-71 | H | C-Cl | C-Cl | C-Cl | C-H | CF3 | C-H | C-CN | H | H | CH3SO2CH2CO | H | 1 |
| 2-72 | H | C-Cl | C-Cl | C-Cl | C-H | CF3 | C-H | C-CN | H | H | EtNHCO | H | 1 |
| 2-73 | H | C-Cl | C-Cl | C-Cl | C-H | CF3 | C-H | C-CN | H | H | EtCO | H | 1 |
| 2-74 | H | C-Cl | C-Cl | C-Cl | C-H | CF3 | C-H | C-CN | H | H | CF3CH2CO | H | 1 |
| 2-75 | H | C-Cl | C-Cl | C-Cl | C-H | CF3 | N | C-CN | H | H | H | H | 1 |
| 2-76 | H | C-Cl | C-Cl | C-Cl | C-H | CF3 | C-H | C-Me | H | H | tert-ButOC(=O) | H | 1 |
| 2-77 | H | C-Cl | C-Cl | C-Cl | C-H | CF3 | C-H | C-Me | H | H | cyclo-PrCH2CO | H | 1 |
| 2-78 | H | C-Cl | C-Cl | C-Cl | C-H | CF3 | C-H | C-Me | H | H | n-PrCO | H | 1 |
| 2-79 | H | C-Cl | C-Cl | C-Cl | C-H | CF3 | C-H | C-Me | H | H | n-PrCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-80 | H | C—Cl | C—Cl | C—Cl | C—H | CF₃ | C—H | C—Me | H | H | CH3SO2CH2CO | H | 1 |
| 2-81 | H | C—Cl | C—Cl | C—Cl | C—H | CF₃ | C—H | C—Me | H | H | CH3OCH2CH2CO | H | 1 |
| 2-82 | H | C—Cl | C—Cl | C—Cl | C—H | CF₃ | C—H | C—Me | H | H | CH3OCH(Me)CH2CO | H | 1 |
| 2-83 | H | C—Cl | C—Cl | C—Cl | C—H | CF₃ | C—H | C—Me | Me | H | EtCO | H | 1 |
| 2-84 | H | C—Cl | C—Cl | C—Cl | C—H | CF₃ | C—H | C—Me | Me | H | CF3CH2CO | H | 1 |
| 2-85 | H | C—Cl | C—Cl | C—Cl | C—H | CF₃ | N | C—Me | H | H | EtCO | H | 1 |
| 2-86 | H | C—Cl | C—Cl | C—Cl | C—H | CF₃ | N | C—Me | H | H | CF3CH2CO | H | 1 |
| 2-87 | H | C—Cl | C—Cl | C—Cl | C—H | CF₃ | C—H | C—NO₂ | H | H | H | H | 1 |
| 2-88 | H | C—Cl | C—Cl | C—Cl | C—H | CF₃ | C—H | C—NO₂ | H | H | CH3OCH2CH2CO | H | 1 |
| 2-89 | H | C—Cl | C—Cl | C—Cl | C—H | CF₃ | C—H | C—NO₂ | H | H | CH3OCH(Me)CH2CO | H | 1 |
| 2-90 | H | C—Cl | C—Cl | C—Cl | C—H | CF₃ | C—H | C—NO₂ | H | H | cyclo-PCH2rCO | H | 1 |
| 2-91 | H | C—Cl | C—Cl | C—Cl | C—H | CF₃ | C—H | C—NO₂ | H | H | CH3SO2CH2CO | H | 1 |
| 2-92 | H | C—Cl | C—Cl | C—Cl | C—H | CF₃ | C—H | C—NO₂ | Me | H | EtCO | H | 1 |
| 2-93 | H | C—Cl | C—Cl | C—Cl | C—H | CF₃ | C—H | C—NO₂ | Me | H | CF3CH2CO | H | 1 |
| 2-94 | H | C—Cl | C—Cl | C—Cl | C—H | CF₃ | N | C—NO₂ | H | H | EtCO | H | 1 |
| 2-95 | H | C—Cl | C—Cl | C—Cl | C—H | CF₃ | N | C—NO₂ | H | H | CF3CH2CO | H | 1 |
| 2-96 | H | C—Cl | C—Cl | C—Cl | C—H | CF₃ | C—H | C—SMe | H | H | H | H | 1 |
| 2-97 | H | C—Cl | C—Cl | C—Cl | C—H | CF₃ | C—H | C—SMe | H | H | CH3OCH2CH2CO | H | 1 |
| 2-98 | H | C—Cl | C—Cl | C—Cl | C—H | CF₃ | C—H | C—SMe | H | H | CH3OCH(Me)CH2CO | H | 1 |
| 2-99 | H | C—Cl | C—Cl | C—Cl | C—H | CF₃ | C—H | C—SMe | H | H | cyclo-PrCH2CO | H | 1 |
| 2-100 | H | C—Cl | C—Cl | C—Cl | C—H | CF₃ | C—H | C—SMe | Me | H | EtCO | H | 1 |
| 2-101 | H | C—Cl | C—Cl | C—Cl | C—H | CF₃ | C—H | C—SMe | Me | H | CF3CH2CO | H | 1 |
| 2-102 | H | C—Cl | C—Cl | C—Cl | C—H | CF₃ | N | C—SMe | H | H | EtCO | H | 1 |
| 2-103 | H | C—Cl | C—Cl | C—Cl | C—H | CF₃ | N | C—SMe | H | H | CF3CH2CO | H | 1 |
| 2-104 | H | C—Cl | C—Cl | C—Cl | C—H | CF₃ | C—H | C—SOMe | H | H | H | H | 1 |
| 2-105 | H | C—Cl | C—Cl | C—Cl | C—H | CF₃ | C—H | C—SOMe | H | H | MeCO | H | 1 |
| 2-106 | H | C—Cl | C—Cl | C—Cl | C—H | CF₃ | C—H | C—SOMe | H | H | EtCO | H | 1 |
| 2-107 | H | C—Cl | C—Cl | C—Cl | C—H | CF₃ | C—H | C—SOMe | H | H | cyclo-PrCH2CO | H | 1 |
| 2-108 | H | C—Cl | C—Cl | C—Cl | C—H | CF₃ | C—H | C—SOMe | H | H | cyclo-PrCO | H | 1 |
| 2-109 | H | C—Cl | C—Cl | C—Cl | C—H | CF₃ | C—H | C—SOMe | H | H | CH3SCH2CO | H | 1 |
| 2-110 | H | C—Cl | C—Cl | C—Cl | C—H | CF₃ | C—H | C—SOMe | H | H | CH3SOCH2CO | H | 1 |
| 2-111 | H | C—Cl | C—Cl | C—Cl | C—H | CF₃ | C—H | C—SOMe | H | H | CH3SO2CH2CO | H | 1 |
| 2-112 | H | C—Cl | C—Cl | C—Cl | C—H | CF₃ | C—H | C—SOMe | Me | H | EtNHCO | H | 1 |
| 2-113 | H | C—Cl | C—Cl | C—Cl | C—H | CF₃ | C—H | C—SOMe | Me | H | EtCO | H | 1 |
| 2-114 | H | C—Cl | C—Cl | C—Cl | C—H | CF₃ | C—H | C—SOMe | H | H | CF3CH2CO | H | 1 |
| 2-115 | H | C—Cl | C—Cl | C—Cl | C—H | CF₃ | N | C—SOMe | H | H | EtCO | H | 1 |
| 2-116 | H | C—Cl | C—Cl | C—Cl | C—H | CF₃ | N | C—SOMe | H | H | CF3CH2CO | H | 1 |
| 2-117 | H | C—Cl | C—Cl | C—Cl | C—H | CF₃ | C—H | C—SO2Me | H | H | H | H | 1 |
| 2-118 | H | C—Cl | C—Cl | C—Cl | C—H | CF₃ | C—H | C—SO2Me | H | H | MeCO | H | 1 |
| 2-119 | H | C—Cl | C—Cl | C—Cl | C—H | CF₃ | C—H | C—SO2Me | H | H | EtCO | H | 1 |
| 2-120 | H | C—Cl | C—Cl | C—Cl | C—H | CF₃ | C—H | C—SO2Me | H | H | CF3CH2CO | H | 1 |

TABLE 2-1-continued

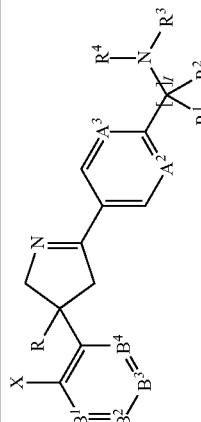

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-121 | H | C-Cl | C-Cl | C-Cl | C-H | CF3 | C-H | C-SO2Me | H | H | CF3CH2CO | H | 1 |
| 2-122 | H | C-Cl | C-Cl | C-Cl | C-H | CF3 | C-H | C-SO2Me | H | H | cyclo-PrCO | H | 1 |
| 2-123 | H | C-Cl | C-Cl | C-Cl | C-H | CF3 | C-H | C-SO2Me | H | H | cyclo-PrCH2CO | H | 1 |
| 2-124 | H | C-Cl | C-Cl | C-Cl | C-H | CF3 | C-H | C-SO2Me | H | H | CH3SCH2CO | H | 1 |
| 2-125 | H | C-Cl | C-Cl | C-Cl | C-H | CF3 | C-H | C-SO2Me | H | H | CH3SOCH2CO | H | 1 |
| 2-126 | H | C-Cl | C-Cl | C-Cl | C-H | CF3 | C-H | C-SO2Me | H | H | CH3SO2CH2CO | H | 1 |
| 2-127 | H | C-Cl | C-Cl | C-Cl | C-H | CF3 | C-H | C-SO2Me | H | H | EtNHCO | H | 1 |
| 2-128 | H | C-Cl | C-Cl | C-Cl | C-H | CF3 | C-H | C-SO2Me | Me | H | EtCO | H | 1 |
| 2-129 | H | C-Cl | C-Cl | C-Cl | C-H | CF3 | C-H | C-SO2Me | Me | H | CF3CH2CO | H | 1 |
| 2-130 | H | C-Cl | C-Cl | C-Cl | C-H | CF3 | N | C-SO2Me | H | H | EtCO | H | 1 |
| 2-131 | H | C-Cl | C-Cl | C-Cl | C-H | CF3 | N | C-SO2Me | H | H | CF3CH2CO | H | 1 |
| 2-132 | H | C-Cl | C-Cl | C-Cl | C-H | CF3 | C-H | C-SCF3 | H | H | H | H | 1 |
| 2-133 | H | C-Cl | C-Cl | C-Cl | C-H | CF3 | C-H | C-SCF3 | H | H | cyclo-PrCH2CO | H | 1 |
| 2-134 | H | C-Cl | C-Cl | C-Cl | C-H | CF3 | C-H | C-SCF3 | H | H | CH3SOCH2CO | H | 1 |
| 2-135 | H | C-Cl | C-Cl | C-Cl | C-H | CF3 | C-H | C-SCF3 | Me | H | EtCO | H | 1 |
| 2-136 | H | C-Cl | C-Cl | C-Cl | C-H | CF3 | C-H | C-SCF3 | Me | H | CF3CH2CO | H | 1 |
| 2-137 | H | C-Cl | C-Cl | C-Cl | C-H | CF3 | N | C-SCF3 | H | H | EtCO | H | 1 |
| 2-138 | H | C-Cl | C-Cl | C-Cl | C-H | CF3 | N | C-SCF3 | H | H | CF3CH2CO | H | 1 |
| 2-139 | H | C-Cl | C-Cl | C-Cl | C-H | CF3 | C-H | C-SOCF3 | H | H | H | H | 1 |
| 2-140 | H | C-Cl | C-Cl | C-Cl | C-H | CF3 | C-H | C-SOCF3 | H | H | MeCO | H | 1 |
| 2-141 | H | C-Cl | C-Cl | C-Cl | C-H | CF3 | C-H | C-SOCF3 | H | H | EtCO | H | 1 |
| 2-142 | H | C-Cl | C-Cl | C-Cl | C-H | CF3 | C-H | C-SOCF3 | H | H | CF3CH2CO | H | 1 |
| 2-143 | H | C-Cl | C-Cl | C-Cl | C-H | CF3 | C-H | C-SOCF3 | H | H | cyclo-PrCO | H | 1 |
| 2-144 | H | C-Cl | C-Cl | C-Cl | C-H | CF3 | C-H | C-SOCF3 | H | H | cyclo-PrCH2CO | H | 1 |
| 2-145 | H | C-Cl | C-Cl | C-Cl | C-H | CF3 | C-H | C-SOCF3 | H | H | CH3SCH2CO | H | 1 |
| 2-146 | H | C-Cl | C-Cl | C-Cl | C-H | CF3 | C-H | C-SOCF3 | H | H | CH3SOCH2CO | H | 1 |
| 2-147 | H | C-Cl | C-Cl | C-Cl | C-H | CF3 | C-H | C-SOCF3 | H | H | CH3SO2CH2CO | H | 1 |
| 2-148 | H | C-Cl | C-Cl | C-Cl | C-H | CF3 | C-H | C-SOCF3 | H | H | EtNHCO | H | 1 |
| 2-149 | H | C-Cl | C-Cl | C-Cl | C-H | CF3 | C-H | C-SOCF3 | Me | H | EtCO | H | 1 |
| 2-150 | H | C-Cl | C-Cl | C-Cl | C-H | CF3 | C-H | C-SOCF3 | Me | H | CF3CH2CO | H | 1 |
| 2-151 | H | C-Cl | C-Cl | C-Cl | C-H | CF3 | N | C-SOCF3 | H | H | EtCO | H | 1 |
| 2-152 | H | C-Cl | C-Cl | C-Cl | C-H | CF3 | N | C-SOCF3 | H | H | CF3CH2CO | H | 1 |
| 2-153 | H | C-Cl | C-Cl | C-Cl | C-H | CF3 | C-H | C-SO2CF3 | H | H | H | H | 1 |
| 2-154 | H | C-Cl | C-Cl | C-Cl | C-H | CF3 | C-H | C-SO2CF3 | H | H | MeCO | H | 1 |
| 2-155 | H | C-Cl | C-Cl | C-Cl | C-H | CF3 | C-H | C-SO2CF3 | H | H | EtCO | H | 1 |
| 2-156 | H | C-Cl | C-Cl | C-Cl | C-H | CF3 | C-H | C-SO2CF3 | H | H | CF3CH2CO | H | 1 |
| 2-157 | H | C-Cl | C-Cl | C-Cl | C-H | CF3 | C-H | C-SO2CF3 | H | H | cyclo-PrCO | H | 1 |
| 2-158 | H | C-Cl | C-Cl | C-Cl | C-H | CF3 | C-H | C-SO2CF3 | H | H | cyclo-PrCH2CO | H | 1 |
| 2-159 | H | C-Cl | C-Cl | C-Cl | C-H | CF3 | C-H | C-SO2CF3 | H | H | CH3SCH2CO | H | 1 |
| 2-160 | H | C-Cl | C-Cl | C-Cl | C-H | CF3 | C-H | C-SO2CF3 | H | H | CH3SOCH2CO | H | 1 |
| 2-161 | H | C-Cl | C-Cl | C-Cl | C-H | CF3 | C-H | C-SO2CF3 | H | H | CH3SO2CH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-162 | H | C—Cl | C—Cl | C—Cl | C—H | CF3 | C—H | C—SO2CF3 | H | H | EtNHCO | H | 1 |
| 2-163 | H | C—Cl | C—Cl | C—Cl | C—H | CF3 | C—H | C—SO2CF3 | Me | H | EtCO | H | 1 |
| 2-164 | H | C—Cl | C—Cl | C—Cl | C—H | CF3 | C—H | C—SO2CF3 | Me | H | CF3CH2CO | H | 1 |
| 2-165 | H | C—Cl | C—Cl | C—Cl | C—H | CF3 | N | C—SO2CF3 | H | H | EtCO | H | 1 |
| 2-166 | H | C—Cl | C—Cl | C—Cl | C—H | CF3 | C—H | C—SO2CF3 | H | H | CF3CH2CO | H | 1 |
| 2-167 | H | C—Cl | C—Cl | C—Cl | C—H | CF3 | C—H | C—H | H | H | H | H | 1 |
| 2-168 | H | C—Cl | C—Cl | C—Cl | C—H | CF3 | C—H | C—H | H | H | MeCO | H | 1 |
| 2-169 | H | C—Cl | C—Cl | C—Cl | C—H | CF3 | C—H | C—H | H | H | EtCO | H | 1 |
| 2-170 | H | C—Cl | C—Cl | C—Cl | C—H | CF3 | C—H | C—H | H | H | CF3CH2CO | H | 1 |
| 2-171 | H | C—Cl | C—Cl | C—Cl | C—H | CF3 | C—H | C—H | H | H | n-PrCO | H | 1 |
| 2-172 | H | C—Cl | C—Cl | C—Cl | C—H | CF3 | C—H | C—H | H | H | cyclo-PrCO | H | 1 |
| 2-173 | H | C—Cl | C—Cl | C—Cl | C—H | CF3 | C—H | C—H | H | H | cyclo-PrCH2CO | H | 1 |
| 2-174 | H | C—Cl | C—Cl | C—Cl | C—H | CF3 | C—H | C—H | H | H | CH3SCH2CO | H | 1 |
| 2-175 | H | C—Cl | C—Cl | C—Cl | C—H | CF3 | C—H | C—H | H | H | CH3SOCH2CO | H | 1 |
| 2-176 | H | C—Cl | C—Cl | C—Cl | C—H | CF3 | C—H | C—H | H | H | CH3SO2CH2CO | H | 1 |
| 2-177 | H | C—Cl | C—Cl | C—Cl | C—H | CF3 | C—H | C—H | H | H | EtNHCO | H | 1 |
| 2-178 | H | C—Cl | C—Cl | C—Cl | C—H | CF3 | C—H | C—H | Me | H | MeCO | H | 1 |
| 2-179 | H | C—Cl | C—Cl | C—Cl | C—H | CF3 | C—H | C—H | Me | H | EtCO | H | 1 |
| 2-180 | H | C—Cl | C—Cl | C—Cl | C—H | CF3 | C—H | C—H | Me | H | CF3CH2CO | H | 1 |
| 2-181 | H | C—Cl | C—Cl | C—Cl | C—H | CF3 | C—H | C—H | Me | H | CH3SCH2CO | H | 1 |
| 2-182 | H | C—Cl | C—Cl | C—Cl | C—H | CF3 | C—H | C—H | H | H | MeCO | H | 1 |
| 2-183 | H | C—Cl | C—Cl | C—Cl | C—H | CF3 | N | C—H | H | H | EtCO | H | 1 |
| 2-184 | H | C—Cl | C—Cl | C—Cl | C—H | CF3 | N | C—H | H | H | CF3CH2CO | H | 1 |
| 2-185 | H | C—Cl | C—Cl | C—Cl | C—H | CF3 | N | C—H | H | H | CH3SCH2CO | H | 1 |
| 2-186 | H | C—Cl | C—Cl | C—Cl | C—H | CF3 | C—H | C—F | H | H | H | H | 1 |
| 2-187 | H | C—Cl | C—Cl | C—Cl | C—H | CF3 | C—H | C—F | H | H | cyclo-PrCH2CO | H | 1 |
| 2-188 | H | C—Cl | C—Cl | C—Cl | C—H | CF3 | C—H | C—F | H | H | CH3SO2CH2CO | H | 1 |
| 2-189 | H | C—Cl | C—Cl | C—Cl | C—H | CF3 | C—H | C—F | H | H | EtCO | H | 1 |
| 2-190 | H | C—Cl | C—Cl | C—Cl | C—H | CF3 | C—H | C—F | Me | H | EtCO | H | 1 |
| 2-191 | H | C—Cl | C—Cl | C—Cl | C—H | CF3 | N | C—F | H | H | CF3CH2CO | H | 1 |
| 2-192 | H | C—Cl | C—Cl | C—Cl | C—H | CF3 | C—H | C—F | H | H | CF3CH2CO | H | 1 |
| 2-193 | H | C—Cl | C—Cl | C—Cl | C—H | CF3 | C—H | C—I | H | H | EtCO | H | 1 |
| 2-194 | H | C—Cl | C—Cl | C—Cl | C—H | CF3 | C—H | C—I | H | H | cyclo-PrCH2CO | H | 1 |
| 2-195 | H | C—Cl | C—Cl | C—Cl | C—H | CF3 | C—H | C—I | H | H | CH3SO2CH2CO | H | 1 |
| 2-196 | H | C—Cl | C—Cl | C—Cl | C—H | CF3 | C—H | C—I | Me | H | EtCO | H | 1 |
| 2-197 | H | C—Cl | C—Cl | C—Cl | C—H | CF3 | N | C—I | Me | H | EtCO | H | 1 |
| 2-198 | H | C—Cl | C—Cl | C—Cl | C—H | CF3 | N | C—I | H | H | CF3CH2CO | H | 1 |
| 2-199 | H | C—Cl | C—Cl | C—Cl | C—H | CF3 | C—H | C—I | H | H | EtCO | H | 1 |
| 2-200 | H | C—Cl | C—Cl | C—Cl | C—H | CF3 | C—H | C—NH2 | H | H | CF3CH2CO | H | 1 |
| 2-201 | H | C—Cl | C—Cl | C—Cl | C—H | CF3 | C—H | C—NH2 | H | H | MeCO | H | 1 |
| 2-202 | H | C—Cl | C—Cl | C—Cl | C—H | CF3 | C—H | C—NH2 | H | H | EtCO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-203 | H | C—Cl | C—Cl | C—Cl | C—H | CF3 | C—H | C—NH2 | H | H | CF3CH2CO | H | 1 |
| 2-204 | H | C—Cl | C—Cl | C—Cl | C—H | CF3 | C—H | C—NH2 | H | H | cyclo-PrCO | H | 1 |
| 2-205 | H | C—Cl | C—Cl | C—Cl | C—H | CF3 | C—H | C—NH2 | H | H | cyclo-PrCH2CO | H | 1 |
| 2-206 | H | C—Cl | C—Cl | C—Cl | C—H | CF3 | C—H | C—NH2 | H | H | CH3SCH2CO | H | 1 |
| 2-207 | H | C—Cl | C—Cl | C—Cl | C—H | CF3 | C—H | C—NH2 | H | H | CH3SOCH2CO | H | 1 |
| 2-208 | H | C—Cl | C—Cl | C—Cl | C—H | CF3 | C—H | C—NH2 | H | H | CH3SO2CH2CO | H | 1 |
| 2-209 | H | C—Cl | C—Cl | C—Cl | C—H | CF3 | C—H | C—NH2 | H | H | EtNHCO | H | 1 |
| 2-210 | H | C—Cl | C—Cl | C—Cl | C—H | CF3 | C—H | C—NH2 | Me | H | EtCO | H | 1 |
| 2-211 | H | C—Cl | C—Cl | C—Cl | C—H | CF3 | C—H | C—NH2 | Me | H | CF3CH2CO | H | 1 |
| 2-212 | H | C—Cl | C—Cl | C—Cl | C—H | CF3 | N | C—NH2 | H | H | EtCO | H | 1 |
| 2-213 | H | C—Cl | C—Cl | C—Cl | C—H | CF3 | N | C—NH2 | H | H | CF3CH2CO | H | 1 |
| 2-214 | H | C—Cl | C—Cl | C—Cl | C—H | CF3 | C—H | C—NHAc | H | H | H | H | 1 |
| 2-215 | H | C—Cl | C—Cl | C—Cl | C—H | CF3 | C—H | C—NHAc | H | H | MeCO | H | 1 |
| 2-216 | H | C—Cl | C—Cl | C—Cl | C—H | CF3 | C—H | C—NHAc | H | H | EtCO | H | 1 |
| 2-217 | H | C—Cl | C—Cl | C—Cl | C—H | CF3 | C—H | C—NHAc | H | H | CF3CH2CO | H | 1 |
| 2-218 | H | C—Cl | C—Cl | C—Cl | C—H | CF3 | C—H | C—NHAc | H | H | cyclo-PrCO | H | 1 |
| 2-219 | H | C—Cl | C—Cl | C—Cl | C—H | CF3 | C—H | C—NHAc | H | H | cyclo-PrCH2CO | H | 1 |
| 2-220 | H | C—Cl | C—Cl | C—Cl | C—H | CF3 | C—H | C—NHAc | H | H | CH3SCH2CO | H | 1 |
| 2-221 | H | C—Cl | C—Cl | C—Cl | C—H | CF3 | C—H | C—NHAc | H | H | CH3SOCH2CO | H | 1 |
| 2-222 | H | C—Cl | C—Cl | C—Cl | C—H | CF3 | C—H | C—NHAc | H | H | CH3SO2CH2CO | H | 1 |
| 2-223 | H | C—Cl | C—Cl | C—Cl | C—H | CF3 | C—H | C—NHAc | H | H | EtNHCO | H | 1 |
| 2-224 | H | C—Cl | C—Cl | C—Cl | C—H | CF3 | C—H | C—NHAc | Me | H | EtCO | H | 1 |
| 2-225 | H | C—Cl | C—Cl | C—Cl | C—H | CF3 | C—H | C—NHAc | Me | H | CF3CH2CO | H | 1 |
| 2-226 | H | C—Cl | C—Cl | C—Cl | C—H | CF3 | N | C—NHAc | H | H | EtCO | H | 1 |
| 2-227 | H | C—Cl | C—Cl | C—Cl | C—H | CF3 | N | C—NHAc | H | H | CF3CH2CO | H | 1 |
| 2-228 | H | C—Cl | C—Cl | C—Cl | C—H | CF3 | C—H | C—NHCOCF3 | H | H | H | H | 1 |
| 2-229 | H | C—Cl | C—Cl | C—Cl | C—H | CF3 | C—H | C—NHCOCF3 | H | H | MeCO | H | 1 |
| 2-230 | H | C—Cl | C—Cl | C—Cl | C—H | CF3 | C—H | C—NHCOCF3 | H | H | EtCO | H | 1 |
| 2-231 | H | C—Cl | C—Cl | C—Cl | C—H | CF3 | C—H | C—NHCOCF3 | H | H | CF3CH2CO | H | 1 |
| 2-232 | H | C—Cl | C—Cl | C—Cl | C—H | CF3 | C—H | C—NHCOCF3 | H | H | cyclo-PrCO | H | 1 |
| 2-233 | H | C—Cl | C—Cl | C—Cl | C—H | CF3 | C—H | C—NHCOCF3 | H | H | cyclo-PrCH2CO | H | 1 |
| 2-234 | H | C—Cl | C—Cl | C—Cl | C—H | CF3 | C—H | C—NHCOCF3 | H | H | CH3SCH2CO | H | 1 |
| 2-235 | H | C—Cl | C—Cl | C—Cl | C—H | CF3 | C—H | C—NHCOCF3 | H | H | CH3SOCH2CO | H | 1 |
| 2-236 | H | C—Cl | C—Cl | C—Cl | C—H | CF3 | C—H | C—NHCOCF3 | H | H | CH3SO2CH2CO | H | 1 |
| 2-237 | H | C—Cl | C—Cl | C—Cl | C—H | CF3 | C—H | C—NHCOCF3 | H | H | EtNHCO | H | 1 |
| 2-238 | H | C—Cl | C—Cl | C—Cl | C—H | CF3 | C—H | C—NHCOCF3 | Me | H | EtCO | H | 1 |
| 2-239 | H | C—Cl | C—Cl | C—Cl | C—H | CF3 | C—H | C—NHCOCF3 | Me | H | CF3CH2CO | H | 1 |
| 2-240 | H | C—Cl | C—Cl | C—Cl | C—H | CF3 | N | C—NHCOCF3 | H | H | EtCO | H | 1 |
| 2-241 | H | C—Cl | C—Cl | C—Cl | C—H | CF3 | N | C—NHCOCF3 | H | H | CF3CH2CO | H | 1 |
| 2-242 | H | C—Cl | C—Cl | C—Cl | C—H | CF3 | C—H | C—CH2OAc | H | H | H | H | 1 |
| 2-243 | H | C—Cl | C—Cl | C—Cl | C—H | CF3 | C—H | C—CH2OAc | H | H | MeCO | H | 1 |

TABLE 2-1-continued

| Example No. | X | B¹ | B² | B³ | B⁴ | R | A² | A³ | | R¹ | R² | R⁴ | R³ | I |
|---|---|---|---|---|---|---|---|---|---|---|---|---|---|---|
| 2-244 | H | C—Cl | C—Cl | C—Cl | C—H | CF3 | C—H | C—CH2OAc | | H | H | EtCO | H | 1 |
| 2-245 | H | C—Cl | C—Cl | C—Cl | C—H | CF3 | C—H | C—CH2OAc | | H | H | CF3CH2CO | H | 1 |
| 2-246 | H | C—Cl | C—Cl | C—Cl | C—H | CF3 | C—H | C—CH2OAc | | H | H | cyclo-PrCO | H | 1 |
| 2-247 | H | C—Cl | C—Cl | C—Cl | C—H | CF3 | C—H | C—CH2OAc | | H | H | cyclo-PrCH2CO | H | 1 |
| 2-248 | H | C—Cl | C—Cl | C—Cl | C—H | CF3 | C—H | C—CH2OAc | | H | H | CH3SCH2CO | H | 1 |
| 2-249 | H | C—Cl | C—Cl | C—Cl | C—H | CF3 | C—H | C—CH2OAc | | H | H | CH3SOCH2CO | H | 1 |
| 2-250 | H | C—Cl | C—Cl | C—Cl | C—H | CF3 | C—H | C—CH2OAc | | H | H | CH3SO2CH2CO | H | 1 |
| 2-251 | H | C—Cl | C—Cl | C—Cl | C—H | CF3 | C—H | C—CH2OAc | | H | H | CH3OCH2CO | H | 1 |
| 2-252 | H | C—Cl | C—Cl | C—Cl | C—H | CF3 | C—H | C—CH2OAc | | H | H | CH3OCH(Me)CH2CO | H | 1 |
| 2-253 | H | C—Cl | C—Cl | C—Cl | C—H | CF3 | C—H | C—CH2OAc | | H | H | EtNHCO | H | 1 |
| 2-254 | H | C—Cl | C—Cl | C—Cl | C—H | CF3 | C—H | C—CH2OAc | | Me | H | EtCO | H | 1 |
| 2-255 | H | C—Cl | C—Cl | C—Cl | C—H | CF3 | C—H | C—CH2OAc | | Me | H | CF3CH2CO | H | 1 |
| 2-256 | H | C—Cl | C—Cl | C—Cl | C—H | CF3 | N | C—CH2OAc | | H | H | EtCO | H | 1 |
| 2-257 | H | C—Cl | C—Cl | C—Cl | C—H | CF3 | N | C—CH2OAc | | H | H | CF3CH2CO | H | 1 |
| 2-258 | H | C—Cl | C—Cl | C—Cl | C—H | CF3 | C—H | C—CF3 | | H | H | H | H | 1 |
| 2-259 | H | C—Cl | C—Cl | C—Cl | C—H | CF3 | C—H | C—CF3 | | Me | H | EtCO | H | 1 |
| 2-260 | H | C—Cl | C—Cl | C—Cl | C—H | CF3 | C—H | C—CF3 | | Me | H | CF3CH2CO | H | 1 |
| 2-261 | H | C—Cl | C—Cl | C—Cl | C—H | CF3 | C—H | C—CF3 | | Me | H | CH3SCH2CO | H | 1 |
| 2-262 | H | C—Cl | C—Cl | C—Cl | C—H | CF3 | N | C—CF3 | | H | H | H | H | 1 |
| 2-263 | H | C—Cl | C—Cl | C—Cl | C—H | CF3 | N | C—CF3 | | H | H | CF3CH2CO | H | 1 |
| 2-264 | H | C—Cl | C—Cl | C—Cl | C—H | CF3 | N | C—CF3 | | H | H | CH3SCH2CO | H | 1 |
| 2-265 | H | C—Cl | C—Cl | C—Cl | C—H | CF3 | C—H | C—Cl | | H | H | H | H | 1 |
| 2-266 | H | C—Cl | C—Cl | C—Cl | C—H | CF3 | C—H | C—Cl | | H | H | CF3CH2CO | H | 1 |
| 2-267 | H | C—Cl | C—Cl | C—Cl | C—H | CF3 | C—H | C—Cl | | H | H | n-PrCO | H | 1 |
| 2-268 | H | C—Cl | C—Cl | C—Cl | C—H | CF3 | C—H | C—Cl | | H | H | cyclo-PrCO | H | 1 |
| 2-269 | H | C—Cl | C—Cl | C—Cl | C—H | CF3 | C—H | C—Cl | | H | H | CH3SOCH2CO | H | 1 |
| 2-270 | H | C—Cl | C—Cl | C—Cl | C—H | CF3 | C—H | C—Cl | | Me | H | EtCO | H | 1 |
| 2-271 | H | C—Cl | C—Cl | C—Cl | C—H | CF3 | C—H | C—Cl | | Me | H | CF3CH2CO | H | 1 |
| 2-272 | H | C—Cl | C—Cl | C—Cl | C—H | CF3 | C—H | C—Cl | | Me | H | CH3SCH2CO | H | 1 |
| 2-273 | H | C—Cl | C—Cl | C—Cl | C—H | CF3 | N | C—Cl | | H | H | H | H | 1 |
| 2-274 | H | C—Cl | C—Cl | C—Cl | C—H | CF3 | N | C—Cl | | H | H | CF3CH2CO | H | 1 |
| 2-275 | H | C—Cl | C—Cl | C—Cl | C—H | CF3 | N | C—Cl | | H | H | CH3SCH2CO | H | 1 |
| 2-276 | H | C—Cl | C—Cl | C—Cl | C—H | CF3 | C—H | C—Br | | H | H | H | H | 1 |
| 2-277 | H | C—Cl | C—Cl | C—Cl | C—H | CF3 | C—H | C—Br | | H | H | CF3CH2CO | H | 1 |
| 2-278 | H | C—Cl | C—Cl | C—Cl | C—H | CF3 | C—H | C—Br | | H | H | cyclo-PrCH2CO | H | 1 |
| 2-279 | H | C—Cl | C—Cl | C—Cl | C—H | CF3 | C—H | C—Br | | H | H | CH3SCH2CO | H | 1 |
| 2-280 | H | C—Cl | C—Cl | C—Cl | C—H | CF3 | C—H | C—Br | | H | H | CH3SOCH2CO | H | 1 |
| 2-281 | H | C—Cl | C—Cl | C—Cl | C—H | CF3 | C—H | C—Br | | H | H | CH3SO2CH2CO | H | 1 |
| 2-282 | H | C—Cl | C—Cl | C—Cl | C—H | CF3 | C—H | C—Br | | H | H | EtNHCO | H | 1 |
| 2-283 | H | C—Cl | C—Cl | C—Cl | C—H | CF3 | C—H | C—Br | | Me | H | H | H | 1 |
| 2-284 | H | C—Cl | C—Cl | C—Cl | C—H | CF3 | C—H | C—Br | | Me | H | H | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-285 | H | C—Cl | C—H | C—Cl | C—H | CF3 | C—H | C—Br | Me | H | EtCO | H | 1 |
| 2-286 | H | C—Cl | C—H | C—Cl | C—H | CF3 | C—H | C—Br | Me | H | CF3CH2CO | H | 1 |
| 2-287 | H | C—Cl | C—H | C—Cl | C—H | CF3 | C—H | C—Br | Me | H | CH3SCH2CO | H | 1 |
| 2-288 | H | C—Cl | C—H | C—Cl | C—H | CF3 | N | C—Br | H | H | H | H | 1 |
| 2-289 | H | C—Cl | C—H | C—Cl | C—H | CF3 | N | C—Br | H | H | EtCO | H | 1 |
| 2-290 | H | C—Cl | C—H | C—Cl | C—H | CF3 | N | C—Br | H | H | CF3CH2CO | H | 1 |
| 2-291 | H | C—Cl | C—H | C—Cl | C—H | CF3 | N | C—Br | H | H | CH3SCH2CO | H | 1 |
| 2-292 | H | C—Cl | C—H | C—Cl | C—H | CF3 | C—H | C—CN | H | H | H | H | 1 |
| 2-293 | H | C—Cl | C—H | C—Cl | C—H | CF3 | C—H | C—CN | H | H | cyclo-PrCH2CO | H | 1 |
| 2-294 | H | C—Cl | C—H | C—Cl | C—H | CF3 | C—H | C—CN | H | H | CH3SCH2CO | H | 1 |
| 2-295 | H | C—Cl | C—H | C—Cl | C—H | CF3 | C—H | C—CN | H | H | CH3SOCH2CO | H | 1 |
| 2-296 | H | C—Cl | C—H | C—Cl | C—H | CF3 | C—H | C—CN | H | H | CH3SO2CH2CO | H | 1 |
| 2-297 | H | C—Cl | C—H | C—Cl | C—H | CF3 | C—H | C—CN | H | H | EtNHCO | H | 1 |
| 2-298 | H | C—Cl | C—H | C—Cl | C—H | CF3 | C—H | C—CN | Me | H | EtCO | H | 1 |
| 2-299 | H | C—Cl | C—H | C—Cl | C—H | CF3 | C—H | C—CN | Me | H | CF3CH2CO | H | 1 |
| 2-300 | H | C—Cl | C—H | C—Cl | C—H | CF3 | N | C—CN | H | H | CF3CH2CO | H | 1 |
| 2-301 | H | C—Cl | C—H | C—Cl | C—H | CF3 | C—H | C—Me | H | H | H | H | 1 |
| 2-302 | H | C—Cl | C—H | C—Cl | C—H | CF3 | C—H | C—Me | H | H | EtCO | H | 1 |
| 2-303 | H | C—Cl | C—H | C—Cl | C—H | CF3 | C—H | C—Me | H | H | CF3CH2CO | H | 1 |
| 2-304 | H | C—Cl | C—H | C—Cl | C—H | CF3 | C—H | C—Me | H | H | cyclo-PrCO | H | 1 |
| 2-305 | H | C—Cl | C—H | C—Cl | C—H | CF3 | C—H | C—Me | H | H | cyclo-PrCH2CO | H | 1 |
| 2-306 | H | C—Cl | C—H | C—Cl | C—H | CF3 | C—H | C—Me | H | H | CH3SCH2CO | H | 1 |
| 2-307 | H | C—Cl | C—H | C—Cl | C—H | CF3 | C—H | C—Me | H | H | CH3SOCH2CO | H | 1 |
| 2-308 | H | C—Cl | C—H | C—Cl | C—H | CF3 | C—H | C—Me | H | H | CH3SO2CH2CO | H | 1 |
| 2-309 | H | C—Cl | C—H | C—Cl | C—H | CF3 | C—H | C—Me | H | H | EtNHCO | H | 1 |
| 2-310 | H | C—Cl | C—H | C—Cl | C—H | CF3 | C—H | C—Me | Me | H | EtCO | H | 1 |
| 2-311 | H | C—Cl | C—H | C—Cl | C—H | CF3 | C—H | C—Me | Me | H | CF3CH2CO | H | 1 |
| 2-312 | H | C—Cl | C—H | C—Cl | C—H | CF3 | N | C—Me | H | H | EtCO | H | 1 |
| 2-313 | H | C—Cl | C—H | C—Cl | C—H | CF3 | N | C—Me | H | H | CF3CH2CO | H | 1 |
| 2-314 | H | C—Cl | C—H | C—Cl | C—H | CF3 | C—H | C—NO2 | H | H | H | H | 1 |
| 2-315 | H | C—Cl | C—H | C—Cl | C—H | CF3 | C—H | C—NO2 | H | H | EtCO | H | 1 |
| 2-316 | H | C—Cl | C—H | C—Cl | C—H | CF3 | C—H | C—NO2 | H | H | CF3CH2CO | H | 1 |
| 2-317 | H | C—Cl | C—H | C—Cl | C—H | CF3 | C—H | C—NO2 | H | H | cyclo-PrCO | H | 1 |
| 2-318 | H | C—Cl | C—H | C—Cl | C—H | CF3 | C—H | C—NO2 | H | H | cyclo-PrCH2CO | H | 1 |
| 2-319 | H | C—Cl | C—H | C—Cl | C—H | CF3 | C—H | C—NO2 | H | H | CH3SCH2CO | H | 1 |
| 2-320 | H | C—Cl | C—H | C—Cl | C—H | CF3 | C—H | C—NO2 | H | H | CH3SOCH2CO | H | 1 |
| 2-321 | H | C—Cl | C—H | C—Cl | C—H | CF3 | C—H | C—NO2 | H | H | CH3SO2CH2CO | H | 1 |
| 2-322 | H | C—Cl | C—H | C—Cl | C—H | CF3 | C—H | C—NO2 | H | H | EtNHCO | H | 1 |
| 2-323 | H | C—Cl | C—H | C—Cl | C—H | CF3 | C—H | C—NO2 | Me | H | EtCO | H | 1 |
| 2-324 | H | C—Cl | C—H | C—Cl | C—H | CF3 | C—H | C—NO2 | Me | H | CF3CH2CO | H | 1 |
| 2-325 | H | C—Cl | C—H | C—Cl | C—H | CF3 | N | C—NO2 | H | H | EtCO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-326 | H | C-Cl | C-H | C-Cl | C-H | CF3 | N | C-NO2 | H | H | CF3CH2CO | H | 1 |
| 2-327 | H | C-Cl | C-H | C-Cl | C-H | CF3 | C-H | C-SMe | H | H | H | H | 1 |
| 2-328 | H | C-Cl | C-H | C-Cl | C-H | CF3 | C-H | C-SMe | H | H | CF3CH2CO | H | 1 |
| 2-329 | H | C-Cl | C-H | C-Cl | C-H | CF3 | C-H | C-SMe | H | H | cyclo-PrCO | H | 1 |
| 2-330 | H | C-Cl | C-H | C-Cl | C-H | CF3 | C-H | C-SMe | H | H | cyclo-PrCH2CO | H | 1 |
| 2-331 | H | C-Cl | C-H | C-Cl | C-H | CF3 | C-H | C-SMe | H | H | CH3SCH2CO | H | 1 |
| 2-332 | H | C-Cl | C-H | C-Cl | C-H | CF3 | C-H | C-SMe | H | H | CH3SOCH2CO | H | 1 |
| 2-333 | H | C-Cl | C-H | C-Cl | C-H | CF3 | C-H | C-SMe | H | H | CH3SO2CH2CO | H | 1 |
| 2-334 | H | C-Cl | C-H | C-Cl | C-H | CF3 | C-H | C-SMe | H | H | EtNHCO | H | 1 |
| 2-335 | H | C-Cl | C-H | C-Cl | C-H | CF3 | C-H | C-SMe | Me | H | EtCO | H | 1 |
| 2-336 | H | C-Cl | C-H | C-Cl | C-H | CF3 | C-H | C-SMe | Me | H | CF3CH2CO | H | 1 |
| 2-337 | H | C-Cl | C-H | C-Cl | C-H | CF3 | N | C-SMe | H | H | EtCO | H | 1 |
| 2-338 | H | C-Cl | C-H | C-Cl | C-H | CF3 | C-H | C-SMe | H | H | CF3CH2CO | H | 1 |
| 2-339 | H | C-Cl | C-H | C-Cl | C-H | CF3 | C-H | C-SOMe | H | H | H | H | 1 |
| 2-340 | H | C-Cl | C-H | C-Cl | C-H | CF3 | C-H | C-SOMe | H | H | CF3CH2CO | H | 1 |
| 2-341 | H | C-Cl | C-H | C-Cl | C-H | CF3 | C-H | C-SOMe | H | H | cyclo-PrCO | H | 1 |
| 2-342 | H | C-Cl | C-H | C-Cl | C-H | CF3 | C-H | C-SOMe | H | H | cyclo-PrCH2CO | H | 1 |
| 2-343 | H | C-Cl | C-H | C-Cl | C-H | CF3 | C-H | C-SOMe | H | H | CH3SCH2CO | H | 1 |
| 2-344 | H | C-Cl | C-H | C-Cl | C-H | CF3 | C-H | C-SOMe | H | H | CH3SOCH2CO | H | 1 |
| 2-345 | H | C-Cl | C-H | C-Cl | C-H | CF3 | C-H | C-SOMe | H | H | CH3SO2CH2CO | H | 1 |
| 2-346 | H | C-Cl | C-H | C-Cl | C-H | CF3 | C-H | C-SOMe | H | H | EtNHCO | H | 1 |
| 2-347 | H | C-Cl | C-H | C-Cl | C-H | CF3 | C-H | C-SOMe | Me | H | EtCO | H | 1 |
| 2-348 | H | C-Cl | C-H | C-Cl | C-H | CF3 | C-H | C-SOMe | Me | H | CF3CH2CO | H | 1 |
| 2-349 | H | C-Cl | C-H | C-Cl | C-H | CF3 | N | C-SOMe | H | H | EtCO | H | 1 |
| 2-350 | H | C-Cl | C-H | C-Cl | C-H | CF3 | C-H | C-SOMe | H | H | CF3CH2CO | H | 1 |
| 2-351 | H | C-Cl | C-H | C-Cl | C-H | CF3 | C-H | C-SO2Me | H | H | H | H | 1 |
| 2-352 | H | C-Cl | C-H | C-Cl | C-H | CF3 | C-H | C-SO2Me | H | H | CF3CH2CO | H | 1 |
| 2-353 | H | C-Cl | C-H | C-Cl | C-H | CF3 | C-H | C-SO2Me | H | H | cyclo-PrCO | H | 1 |
| 2-354 | H | C-Cl | C-H | C-Cl | C-H | CF3 | C-H | C-SO2Me | H | H | cyclo-PrCH2CO | H | 1 |
| 2-355 | H | C-Cl | C-H | C-Cl | C-H | CF3 | C-H | C-SO2Me | H | H | CH3SCH2CO | H | 1 |
| 2-356 | H | C-Cl | C-H | C-Cl | C-H | CF3 | C-H | C-SO2Me | H | H | CH3SOCH2CO | H | 1 |
| 2-357 | H | C-Cl | C-H | C-Cl | C-H | CF3 | C-H | C-SO2Me | H | H | CH3SO2CH2CO | H | 1 |
| 2-358 | H | C-Cl | C-H | C-Cl | C-H | CF3 | C-H | C-SO2Me | H | H | EtNHCO | H | 1 |
| 2-359 | H | C-Cl | C-H | C-Cl | C-H | CF3 | C-H | C-SO2Me | Me | H | EtCO | H | 1 |
| 2-360 | H | C-Cl | C-H | C-Cl | C-H | CF3 | C-H | C-SO2Me | Me | H | CF3CH2CO | H | 1 |
| 2-361 | H | C-Cl | C-H | C-Cl | C-H | CF3 | N | C-SO2Me | H | H | EtCO | H | 1 |
| 2-362 | H | C-Cl | C-H | C-Cl | C-H | CF3 | C-H | C-SO2Me | H | H | CF3CH2CO | H | 1 |
| 2-363 | H | C-Cl | C-H | C-Cl | C-H | CF3 | C-H | C-SCF3 | H | H | H | H | 1 |
| 2-364 | H | C-Cl | C-H | C-Cl | C-H | CF3 | C-H | C-SCF3 | H | H | cyclo-PrCO | H | 1 |
| 2-365 | H | C-Cl | C-H | C-Cl | C-H | CF3 | C-H | C-SCF3 | H | H | cyclo-PrCH2CO | H | 1 |
| 2-366 | H | C-Cl | C-H | C-Cl | C-H | CF3 | C-H | C-SCF3 | H | H | CH3SCH2CO | H | 1 |

TABLE 2-1-continued

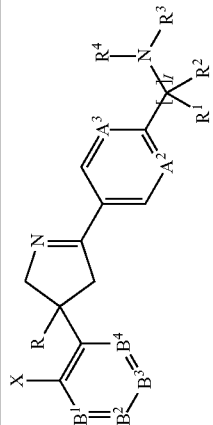

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-367 | H | C—Cl | C—H | C—Cl | C—H | CF3 | C—H | C—SCF3 | H | H | CH3SOCH2CO | H | 1 |
| 2-368 | H | C—Cl | C—H | C—Cl | C—H | CF3 | C—H | C—SCF3 | H | H | CH3SO2CH2CO | H | 1 |
| 2-369 | H | C—Cl | C—H | C—Cl | C—H | CF3 | C—H | C—SCF3 | H | H | EtNHCO | H | 1 |
| 2-370 | H | C—Cl | C—H | C—Cl | C—H | CF3 | C—H | C—SCF3 | Me | H | EtCO | H | 1 |
| 2-371 | H | C—Cl | C—H | C—Cl | C—H | CF3 | C—H | C—SCF3 | Me | H | CF3CH2CO | H | 1 |
| 2-372 | H | C—Cl | C—H | C—Cl | C—H | CF3 | N | C—SCF3 | H | H | EtCO | H | 1 |
| 2-373 | H | C—Cl | C—H | C—Cl | C—H | CF3 | N | C—SCF3 | H | H | CF3CH2CO | H | 1 |
| 2-374 | H | C—Cl | C—H | C—Cl | C—H | CF3 | C—H | C—SOCF3 | H | H | H | H | 1 |
| 2-375 | H | C—Cl | C—H | C—Cl | C—H | CF3 | C—H | C—SOCF3 | H | H | EtCO | H | 1 |
| 2-376 | H | C—Cl | C—H | C—Cl | C—H | CF3 | C—H | C—SOCF3 | H | H | CF3CH2CO | H | 1 |
| 2-377 | H | C—Cl | C—H | C—Cl | C—H | CF3 | C—H | C—SOCF3 | H | H | cyclo-PrCO | H | 1 |
| 2-378 | H | C—Cl | C—H | C—Cl | C—H | CF3 | C—H | C—SOCF3 | H | H | cyclo-PrCH2CO | H | 1 |
| 2-379 | H | C—Cl | C—H | C—Cl | C—H | CF3 | C—H | C—SOCF3 | H | H | CH3SOCH2CO | H | 1 |
| 2-380 | H | C—Cl | C—H | C—Cl | C—H | CF3 | C—H | C—SOCF3 | H | H | CH3SO2CH2CO | H | 1 |
| 2-381 | H | C—Cl | C—H | C—Cl | C—H | CF3 | C—H | C—SOCF3 | H | H | EtNHCO | H | 1 |
| 2-382 | H | C—Cl | C—H | C—Cl | C—H | CF3 | C—H | C—SOCF3 | Me | H | EtCO | H | 1 |
| 2-383 | H | C—Cl | C—H | C—Cl | C—H | CF3 | C—H | C—SOCF3 | Me | H | CF3CH2CO | H | 1 |
| 2-384 | H | C—Cl | C—H | C—Cl | C—H | CF3 | N | C—SOCF3 | H | H | EtCO | H | 1 |
| 2-385 | H | C—Cl | C—H | C—Cl | C—H | CF3 | N | C—SOCF3 | H | H | CF3CH2CO | H | 1 |
| 2-386 | H | C—Cl | C—H | C—Cl | C—H | CF3 | C—H | C—SO2CF3 | H | H | EtCO | H | 1 |
| 2-387 | H | C—Cl | C—H | C—Cl | C—H | CF3 | C—H | C—SO2CF3 | H | H | H | H | 1 |
| 2-388 | H | C—Cl | C—H | C—Cl | C—H | CF3 | C—H | C—SO2CF3 | H | H | EtCO | H | 1 |
| 2-389 | H | C—Cl | C—H | C—Cl | C—H | CF3 | C—H | C—SO2CF3 | H | H | CF3CH2CO | H | 1 |
| 2-390 | H | C—Cl | C—H | C—Cl | C—H | CF3 | C—H | C—SO2CF3 | H | H | cyclo-PrCO | H | 1 |
| 2-391 | H | C—Cl | C—H | C—Cl | C—H | CF3 | C—H | C—SO2CF3 | H | H | cyclo-PrCH2CO | H | 1 |
| 2-392 | H | C—Cl | C—H | C—Cl | C—H | CF3 | C—H | C—SO2CF3 | H | H | CH3SOCH2CO | H | 1 |
| 2-393 | H | C—Cl | C—H | C—Cl | C—H | CF3 | C—H | C—SO2CF3 | H | H | CH3SO2CH2CO | H | 1 |
| 2-394 | H | C—Cl | C—H | C—Cl | C—H | CF3 | C—H | C—SO2CF3 | H | H | EtNHCO | H | 1 |
| 2-395 | H | C—Cl | C—H | C—Cl | C—H | CF3 | C—H | C—SO2CF3 | Me | H | EtCO | H | 1 |
| 2-396 | H | C—Cl | C—H | C—Cl | C—H | CF3 | C—H | C—SO2CF3 | Me | H | CF3CH2CO | H | 1 |
| 2-397 | H | C—Cl | C—H | C—Cl | C—H | CF3 | N | C—SO2CF3 | H | H | EtCO | H | 1 |
| 2-398 | H | C—Cl | C—H | C—Cl | C—H | CF3 | C—H | C—SO2CF3 | H | H | CF3CH2CO | H | 1 |
| 2-399 | H | C—Cl | C—H | C—Cl | C—H | CF3 | C—H | C—SO2CF3 | H | H | EtCO | H | 1 |
| 2-400 | H | C—Cl | C—H | C—Cl | C—H | CF3 | C—H | C—H | H | H | CF3CH2CO | H | 1 |
| 2-401 | H | C—Cl | C—H | C—Cl | C—H | CF3 | C—H | C—H | H | H | H | H | 1 |
| 2-402 | H | C—Cl | C—H | C—Cl | C—H | CF3 | C—H | C—H | H | H | cyclo-PrCO | H | 1 |
| 2-403 | H | C—Cl | C—H | C—Cl | C—H | CF3 | C—H | C—H | H | H | cyclo-PrCH2CO | H | 1 |
| 2-404 | H | C—Cl | C—H | C—Cl | C—H | CF3 | C—H | C—H | H | H | CH3SOCH2CO | H | 1 |
| 2-405 | H | C—Cl | C—H | C—Cl | C—H | CF3 | C—H | C—H | H | H | CH3SO2CH2CO | H | 1 |
| 2-406 | H | C—Cl | C—H | C—Cl | C—H | CF3 | C—H | C—H | H | H | CH3SO2CH2CO | H | 1 |
| 2-407 | H | C—Cl | C—H | C—Cl | C—H | CF3 | C—H | C—H | H | H | EtNHCO | H | 1 |

TABLE 2-1-continued

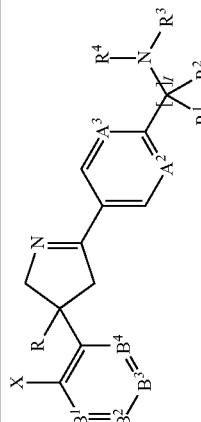

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-408 | H | C—Cl | C—H | C—Cl | C—H | CF3 | C—H | C—H | Me | H | EtCO | H | 1 |
| 2-409 | H | C—Cl | C—H | C—Cl | C—H | CF3 | C—H | C—H | Me | H | CF3CH2CO | H | 1 |
| 2-410 | H | C—Cl | C—H | C—Cl | C—H | CF3 | N | C—H | H | H | EtCO | H | 1 |
| 2-411 | H | C—Cl | C—H | C—Cl | C—H | CF3 | C—H | C—H | H | H | CF3CH2CO | H | 1 |
| 2-412 | H | C—Cl | C—H | C—Cl | C—H | CF3 | C—H | C—F | H | H | H | H | 1 |
| 2-413 | H | C—Cl | C—H | C—Cl | C—H | CF3 | C—H | C—F | H | H | EtCO | H | 1 |
| 2-414 | H | C—Cl | C—H | C—Cl | C—H | CF3 | C—H | C—F | H | H | CF3CH2CO | H | 1 |
| 2-415 | H | C—Cl | C—H | C—Cl | C—H | CF3 | C—H | C—F | H | H | cyclo-PrCO | H | 1 |
| 2-416 | H | C—Cl | C—H | C—Cl | C—H | CF3 | C—H | C—F | H | H | cyclo-PrCH2CO | H | 1 |
| 2-417 | H | C—Cl | C—H | C—Cl | C—H | CF3 | C—H | C—F | H | H | CH3SCH2CO | H | 1 |
| 2-418 | H | C—Cl | C—H | C—Cl | C—H | CF3 | C—H | C—F | H | H | CH3SOCH2CO | H | 1 |
| 2-419 | H | C—Cl | C—H | C—Cl | C—H | CF3 | C—H | C—F | H | H | CH3SO2CH2CO | H | 1 |
| 2-420 | H | C—Cl | C—H | C—Cl | C—H | CF3 | C—H | C—F | H | H | EtNHCO | H | 1 |
| 2-421 | H | C—Cl | C—H | C—Cl | C—H | CF3 | C—H | C—F | Me | H | EtCO | H | 1 |
| 2-422 | H | C—Cl | C—H | C—Cl | C—H | CF3 | C—H | C—F | Me | H | CF3CH2CO | H | 1 |
| 2-423 | H | C—Cl | C—H | C—Cl | C—H | CF3 | N | C—H | H | H | EtCO | H | 1 |
| 2-424 | H | C—Cl | C—H | C—Cl | C—H | CF3 | C—H | C—F | H | H | CF3CH2CO | H | 1 |
| 2-425 | H | C—Cl | C—H | C—Cl | C—H | CF3 | C—H | C—I | H | H | H | H | 1 |
| 2-426 | H | C—Cl | C—H | C—Cl | C—H | CF3 | C—H | C—I | H | H | EtCO | H | 1 |
| 2-427 | H | C—Cl | C—H | C—Cl | C—H | CF3 | C—H | C—I | H | H | CF3CH2CO | H | 1 |
| 2-428 | H | C—Cl | C—H | C—Cl | C—H | CF3 | C—H | C—I | H | H | cyclo-PrCO | H | 1 |
| 2-429 | H | C—Cl | C—H | C—Cl | C—H | CF3 | C—H | C—I | H | H | cyclo-PrCH2CO | H | 1 |
| 2-430 | H | C—Cl | C—H | C—Cl | C—H | CF3 | C—H | C—I | H | H | CH3SCH2CO | H | 1 |
| 2-431 | H | C—Cl | C—H | C—Cl | C—H | CF3 | C—H | C—I | H | H | CH3SOCH2CO | H | 1 |
| 2-432 | H | C—Cl | C—H | C—Cl | C—H | CF3 | C—H | C—I | H | H | CH3SO2CH2CO | H | 1 |
| 2-433 | H | C—Cl | C—H | C—Cl | C—H | CF3 | C—H | C—I | H | H | EtNHCO | H | 1 |
| 2-434 | H | C—Cl | C—H | C—Cl | C—H | CF3 | C—H | C—I | Me | H | EtCO | H | 1 |
| 2-435 | H | C—Cl | C—H | C—Cl | C—H | CF3 | C—H | C—I | Me | H | CF3CH2CO | H | 1 |
| 2-436 | H | C—Cl | C—H | C—Cl | C—H | CF3 | N | C—H | H | H | EtCO | H | 1 |
| 2-437 | H | C—Cl | C—H | C—Cl | C—H | CF3 | C—H | C—I | H | H | CF3CH2CO | H | 1 |
| 2-438 | H | C—Cl | C—H | C—Cl | C—H | CF3 | C—H | C—NH2 | H | H | H | H | 1 |
| 2-439 | H | C—Cl | C—H | C—Cl | C—H | CF3 | C—H | C—NH2 | H | H | EtCO | H | 1 |
| 2-440 | H | C—Cl | C—H | C—Cl | C—H | CF3 | C—H | C—NH2 | H | H | CF3CH2CO | H | 1 |
| 2-441 | H | C—Cl | C—H | C—Cl | C—H | CF3 | C—H | C—NH2 | H | H | cyclo-PrCO | H | 1 |
| 2-442 | H | C—Cl | C—H | C—Cl | C—H | CF3 | C—H | C—NH2 | H | H | cyclo-PrCH2CO | H | 1 |
| 2-443 | H | C—Cl | C—H | C—Cl | C—H | CF3 | C—H | C—NH2 | H | H | CH3SCH2CO | H | 1 |
| 2-444 | H | C—Cl | C—H | C—Cl | C—H | CF3 | C—H | C—NH2 | H | H | CH3SOCH2CO | H | 1 |
| 2-445 | H | C—Cl | C—H | C—Cl | C—H | CF3 | C—H | C—NH2 | H | H | CH3SO2CH2CO | H | 1 |
| 2-446 | H | C—Cl | C—H | C—Cl | C—H | CF3 | C—H | C—NH2 | H | H | EtNHCO | H | 1 |
| 2-447 | H | C—Cl | C—H | C—Cl | C—H | CF3 | C—H | C—NH2 | Me | H | EtCO | H | 1 |
| 2-448 | H | C—Cl | C—H | C—Cl | C—H | CF3 | N | C—NH2 | Me | H | CF3CH2CO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-449 | H | C—Cl | C—H | C—Cl | C—H | CF3 | N | C—NH2 | H | H | CF3CH2CO | H | 1 |
| 2-450 | H | C—Cl | C—H | C—Cl | C—H | CF3 | C—H | C—NHAc | H | H | H | H | 1 |
| 2-451 | H | C—Cl | C—H | C—Cl | C—H | CF3 | C—H | C—NHAc | H | H | CF3CH2CO | H | 1 |
| 2-452 | H | C—Cl | C—H | C—Cl | C—H | CF3 | C—H | C—NHAc | H | H | cyclo-PrCO | H | 1 |
| 2-453 | H | C—Cl | C—H | C—Cl | C—H | CF3 | C—H | C—NHAc | H | H | cyclo-PrCH2CO | H | 1 |
| 2-454 | H | C—Cl | C—H | C—Cl | C—H | CF3 | C—H | C—NHAc | H | H | CH3SCH2CO | H | 1 |
| 2-455 | H | C—Cl | C—H | C—Cl | C—H | CF3 | C—H | C—NHAc | H | H | CH3SOCH2CO | H | 1 |
| 2-456 | H | C—Cl | C—H | C—Cl | C—H | CF3 | C—H | C—NHAc | H | H | CH3SO2CH2CO | H | 1 |
| 2-457 | H | C—Cl | C—H | C—Cl | C—H | CF3 | C—H | C—NHAc | H | H | EtNHCO | H | 1 |
| 2-458 | H | C—Cl | C—H | C—Cl | C—H | CF3 | C—H | C—NHAc | Me | H | EtCO | H | 1 |
| 2-459 | H | C—Cl | C—H | C—Cl | C—H | CF3 | C—H | C—NHAc | Me | H | CF3CH2CO | H | 1 |
| 2-460 | H | C—Cl | C—H | C—Cl | C—H | CF3 | N | C—NHAc | H | H | EtCO | H | 1 |
| 2-461 | H | C—Cl | C—H | C—Cl | C—H | CF3 | N | C—NHAc | H | H | CF3CH2CO | H | 1 |
| 2-462 | H | C—Cl | C—H | C—Cl | C—H | CF3 | C—H | C—NHCOCF3 | H | H | H | H | 1 |
| 2-463 | H | C—Cl | C—H | C—Cl | C—H | CF3 | C—H | C—NHCOCF3 | H | H | MeCO | H | 1 |
| 2-464 | H | C—Cl | C—H | C—Cl | C—H | CF3 | C—H | C—NHCOCF3 | H | H | EtCO | H | 1 |
| 2-465 | H | C—Cl | C—H | C—Cl | C—H | CF3 | C—H | C—NHCOCF3 | H | H | CF3CH2CO | H | 1 |
| 2-466 | H | C—Cl | C—H | C—Cl | C—H | CF3 | C—H | C—NHCOCF3 | H | H | cyclo-PrCO | H | 1 |
| 2-467 | H | C—Cl | C—H | C—Cl | C—H | CF3 | C—H | C—NHCOCF3 | H | H | cyclo-PrCH2CO | H | 1 |
| 2-468 | H | C—Cl | C—H | C—Cl | C—H | CF3 | C—H | C—NHCOCF3 | H | H | CH3SCH2CO | H | 1 |
| 2-469 | H | C—Cl | C—H | C—Cl | C—H | CF3 | C—H | C—NHCOCF3 | H | H | CH3SOCH2CO | H | 1 |
| 2-470 | H | C—Cl | C—H | C—Cl | C—H | CF3 | C—H | C—NHCOCF3 | H | H | CH3SO2CH2CO | H | 1 |
| 2-471 | H | C—Cl | C—H | C—Cl | C—H | CF3 | C—H | C—NHCOCF3 | H | H | EtNHCO | H | 1 |
| 2-472 | H | C—Cl | C—H | C—Cl | C—H | CF3 | C—H | C—NHCOCF3 | Me | H | EtCO | H | 1 |
| 2-473 | H | C—Cl | C—H | C—Cl | C—H | CF3 | C—H | C—NHCOCF3 | Me | H | CF3CH2CO | H | 1 |
| 2-474 | H | C—Cl | C—H | C—Cl | C—H | CF3 | N | C—NHCOCF3 | H | H | EtCO | H | 1 |
| 2-475 | H | C—Cl | C—H | C—Cl | C—H | CF3 | N | C—NHCOCF3 | H | H | CF3CH2CO | H | 1 |
| 2-476 | H | C—Cl | C—H | C—Cl | C—H | CF3 | C—H | C—CH2OAc | H | H | H | H | 1 |
| 2-477 | H | C—Cl | C—H | C—Cl | C—H | CF3 | C—H | C—CH2OAc | H | H | MeCO | H | 1 |
| 2-478 | H | C—Cl | C—H | C—Cl | C—H | CF3 | C—H | C—CH2OAc | H | H | EtCO | H | 1 |
| 2-479 | H | C—Cl | C—H | C—Cl | C—H | CF3 | C—H | C—CH2OAc | H | H | CF3CH2CO | H | 1 |
| 2-480 | H | C—Cl | C—H | C—Cl | C—H | CF3 | C—H | C—CH2OAc | H | H | cyclo-PrCO | H | 1 |
| 2-481 | H | C—Cl | C—H | C—Cl | C—H | CF3 | C—H | C—CH2OAc | H | H | cyclo-PrCH2CO | H | 1 |
| 2-482 | H | C—Cl | C—H | C—Cl | C—H | CF3 | C—H | C—CH2OAc | H | H | CH3SCH2CO | H | 1 |
| 2-483 | H | C—Cl | C—H | C—Cl | C—H | CF3 | C—H | C—CH2OAc | H | H | CH3SOCH2CO | H | 1 |
| 2-484 | H | C—Cl | C—H | C—Cl | C—H | CF3 | C—H | C—CH2OAc | H | H | CH3SO2CH2CO | H | 1 |
| 2-485 | H | C—Cl | C—H | C—Cl | C—H | CF3 | C—H | C—CH2OAc | H | H | EtNHCO | H | 1 |
| 2-486 | H | C—Cl | C—H | C—Cl | C—H | CF3 | C—H | C—CH2OAc | Me | H | EtCO | H | 1 |
| 2-487 | H | C—Cl | C—H | C—Cl | C—H | CF3 | C—H | C—CH2OAc | Me | H | CF3CH2CO | H | 1 |
| 2-488 | H | C—Cl | C—H | C—Cl | C—H | CF3 | N | C—CH2OAc | H | H | EtCO | H | 1 |
| 2-489 | H | C—Cl | C—H | C—Cl | C—H | CF3 | N | C—CH2OAc | H | H | CF3CH2CO | H | 1 |

TABLE 2-1-continued

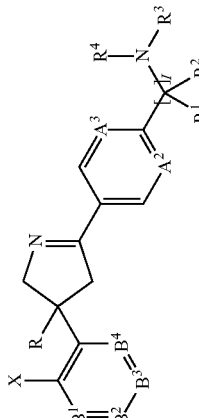

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-490 | H | C—Cl | C—H | C—Cl | C—H | CF3 | C—H | C—CF3 | H | H | H | H | 1 |
| 2-491 | H | C—Cl | C—H | C—Cl | C—H | CF3 | C—H | C—CF3 | H | H | cyclo-PrCH2CO | H | 1 |
| 2-492 | H | C—Cl | C—H | C—Cl | C—H | CF3 | C—H | C—CF3 | H | H | CH3SCH2CO | H | 1 |
| 2-493 | H | C—Cl | C—H | C—Cl | C—H | CF3 | C—H | C—CF3 | H | H | CH3SOCH2CO | H | 1 |
| 2-494 | H | C—Cl | C—H | C—Cl | C—H | CF3 | C—H | C—CF3 | H | H | CH3SO2CH2CO | H | 1 |
| 2-495 | H | C—Cl | C—H | C—Cl | C—H | CF3 | C—H | C—CF3 | Me | H | H | H | 1 |
| 2-496 | H | C—Cl | C—H | C—Cl | C—H | CF3 | C—H | C—CF3 | Me | H | CH3SCH2CO | H | 1 |
| 2-497 | H | C—Cl | C—H | C—Cl | C—H | CF3 | N | C—CF3 | H | H | H | H | 1 |
| 2-498 | H | C—Cl | C—H | C—Cl | C—H | CF3 | N | C—CF3 | H | H | EtCO | H | 1 |
| 2-499 | H | C—Cl | C—H | C—Cl | C—H | CF3 | N | C—CF3 | H | H | CF3CH2CO | H | 1 |
| 2-500 | H | C—Cl | C—H | C—Cl | C—H | CF3 | N | C—CF3 | H | H | CH3SCH2CO | H | 1 |
| 2-501 | H | C—CF3 | C—H | C—CF3 | C—H | CF3 | C—H | C—CF3 | H | H | H | H | 1 |
| 2-502 | H | C—CF3 | C—H | C—CF3 | C—H | CF3 | C—H | C—CF3 | H | H | CH3OCH2CH2CO | H | 1 |
| 2-503 | H | C—CF3 | C—H | C—CF3 | C—H | CF3 | C—H | C—CF3 | H | H | CH3OCH(MeCH2CO | H | 1 |
| 2-504 | H | C—CF3 | C—H | C—CF3 | C—H | CF3 | C—H | C—CF3 | H | H | cyclo-PrCH2CO | H | 1 |
| 2-505 | H | C—CF3 | C—H | C—CF3 | C—H | CF3 | C—H | C—CF3 | Me | H | H | H | 1 |
| 2-506 | H | C—CF3 | C—H | C—CF3 | C—H | CF3 | C—H | C—CF3 | Me | H | EtCO | H | 1 |
| 2-507 | H | C—CF3 | C—H | C—CF3 | C—H | CF3 | C—H | C—CF3 | Me | H | CF3CH2CO | H | 1 |
| 2-508 | H | C—CF3 | C—H | C—CF3 | C—H | CF3 | C—H | C—CF3 | Me | H | CH3SCH2CO | H | 1 |
| 2-509 | H | C—CF3 | C—H | C—CF3 | C—H | CF3 | N | C—CF3 | H | H | H | H | 1 |
| 2-510 | H | C—CF3 | C—H | C—CF3 | C—H | CF3 | N | C—CF3 | H | H | EtCO | H | 1 |
| 2-511 | H | C—CF3 | C—H | C—CF3 | C—H | CF3 | N | C—CF3 | H | H | CF3CH2CO | H | 1 |
| 2-512 | H | C—CF3 | C—H | C—CF3 | C—H | CF3 | N | C—CF3 | H | H | CH3SCH2CO | H | 1 |
| 2-513 | H | C—CF3 | C—H | C—CF3 | C—H | CF3 | C—H | C—Cl | H | H | H | H | 1 |
| 2-514 | H | C—CF3 | C—H | C—CF3 | C—H | CF3 | C—H | C—Cl | H | H | CH3OCH2CH2CO | H | 1 |
| 2-515 | H | C—CF3 | C—H | C—CF3 | C—H | CF3 | C—H | C—Cl | H | H | CH3OCH(MeCH2CO | H | 1 |
| 2-516 | H | C—CF3 | C—H | C—CF3 | C—H | CF3 | C—H | C—Cl | H | H | cyclo-PrCH2CO | H | 1 |
| 2-517 | H | C—CF3 | C—H | C—CF3 | C—H | CF3 | C—H | C—Cl | Me | H | H | H | 1 |
| 2-518 | H | C—CF3 | C—H | C—CF3 | C—H | CF3 | C—H | C—Cl | Me | H | EtCO | H | 1 |
| 2-519 | H | C—CF3 | C—H | C—CF3 | C—H | CF3 | C—H | C—Cl | Me | H | CF3CH2CO | H | 1 |
| 2-520 | H | C—CF3 | C—H | C—CF3 | C—H | CF3 | C—H | C—Cl | Me | H | CH3SCH2CO | H | 1 |
| 2-521 | H | C—CF3 | C—H | C—CF3 | C—H | CF3 | N | C—Cl | H | H | H | H | 1 |
| 2-522 | H | C—CF3 | C—H | C—CF3 | C—H | CF3 | N | C—Cl | H | H | EtCO | H | 1 |
| 2-523 | H | C—CF3 | C—H | C—CF3 | C—H | CF3 | N | C—Cl | H | H | CF3CH2CO | H | 1 |
| 2-524 | H | C—CF3 | C—H | C—CF3 | C—H | CF3 | N | C—Cl | H | H | CH3SCH2CO | H | 1 |
| 2-525 | H | C—CF3 | C—H | C—CF3 | C—H | CF3 | C—H | C—Br | H | H | H | H | 1 |
| 2-526 | H | C—CF3 | C—H | C—CF3 | C—H | CF3 | C—H | C—Br | H | H | CH3OCH2CH2CO | H | 1 |
| 2-527 | H | C—CF3 | C—H | C—CF3 | C—H | CF3 | C—H | C—Br | H | H | CH3OCH(MeCH2CO | H | 1 |
| 2-528 | H | C—CF3 | C—H | C—CF3 | C—H | CF3 | C—H | C—Br | H | H | cyclo-PrCH2CO | H | 1 |
| 2-529 | H | C—CF3 | C—H | C—CF3 | C—H | CF3 | C—H | C—Br | Me | H | H | H | 1 |
| 2-530 | H | C—CF3 | C—H | C—CF3 | C—H | CF3 | C—H | C—Br | Me | H | EtCO | H | 1 |

TABLE 2-1-continued

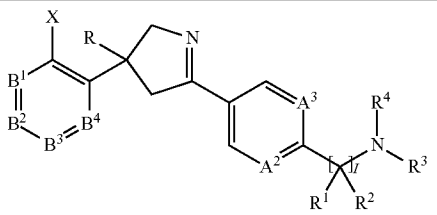

| Example No. | X | B¹ | B² | B³ | B⁴ | R | A² | A³ | R¹ | R² | R⁴ | | R³ | I |
|---|---|---|---|---|---|---|---|---|---|---|---|---|---|---|
| 2-531 | H | C—CF3 | C—H | C—CF3 | C—H | CF3 | C—H | C—Br | Me | H | CF3CH2CO | | H | 1 |
| 2-532 | H | C—CF3 | C—H | C—CF3 | C—H | CF3 | C—H | C—Br | Me | H | CH3SCH2CO | | H | 1 |
| 2-533 | H | C—CF3 | C—H | C—CF3 | C—H | CF3 | N | C—Br | H | H | H | | H | 1 |
| 2-534 | H | C—CF3 | C—H | C—CF3 | C—H | CF3 | N | C—Br | H | H | EtCO | | H | 1 |
| 2-535 | H | C—CF3 | C—H | C—CF3 | C—H | CF3 | N | C—Br | H | H | CF3CH2CO | | H | 1 |
| 2-536 | H | C—CF3 | C—H | C—CF3 | C—H | CF3 | C—H | C—Br | H | H | CH3SCH2CO | | H | 1 |
| 2-537 | H | C—CF3 | C—H | C—CF3 | C—H | CF3 | C—H | C—CN | H | H | H | | H | 1 |
| 2-538 | H | C—CF3 | C—H | C—CF3 | C—H | CF3 | C—H | C—CN | H | H | cyclo-PrCH2CO | | H | 1 |
| 2-539 | H | C—CF3 | C—H | C—CF3 | C—H | CF3 | C—H | C—CN | H | H | CH3SCH2CO | | H | 1 |
| 2-540 | H | C—CF3 | C—H | C—CF3 | C—H | CF3 | C—H | C—CN | H | H | CH3SOCH2CO | | H | 1 |
| 2-541 | H | C—CF3 | C—H | C—CF3 | C—H | CF3 | C—H | C—CN | H | H | CH3SO2CH2CO | | H | 1 |
| 2-542 | H | C—CF3 | C—H | C—CF3 | C—H | CF3 | C—H | C—CN | H | H | EtNHCO | | H | 1 |
| 2-543 | H | C—CF3 | C—H | C—CF3 | C—H | CF3 | C—H | C—CN | Me | H | EtCO | | H | 1 |
| 2-544 | H | C—CF3 | C—H | C—CF3 | C—H | CF3 | C—H | C—CN | Me | H | CF3CH2CO | | H | 1 |
| 2-545 | H | C—CF3 | C—H | C—CF3 | C—H | CF3 | N | C—CN | H | H | EtCO | | H | 1 |
| 2-546 | H | C—CF3 | C—H | C—CF3 | C—H | CF3 | C—H | C—CN | H | H | EtCO | | H | 1 |
| 2-547 | H | C—CF3 | C—H | C—CF3 | C—H | CF3 | C—H | C—Me | H | H | H | | H | 1 |
| 2-548 | H | C—CF3 | C—H | C—CF3 | C—H | CF3 | C—H | C—Me | H | H | tert-ButOC(=O) | | H | 1 |
| 2-549 | H | C—CF3 | C—H | C—CF3 | C—H | CF3 | C—H | C—Me | H | H | CH3OCH2CO | | H | 1 |
| 2-550 | H | C—CF3 | C—H | C—CF3 | C—H | CF3 | C—H | C—Me | H | H | CH3OCH(Me)CH2CO | | H | 1 |
| 2-551 | H | C—CF3 | C—H | C—CF3 | C—H | CF3 | C—H | C—Me | H | H | cyclo-PrCH2CO | | H | 1 |
| 2-552 | H | C—CF3 | C—H | C—CF3 | C—H | CF3 | N | C—Me | H | H | H | | H | 1 |
| 2-553 | H | C—CF3 | C—H | C—CF3 | C—H | CF3 | N | C—Me | Me | H | EtCO | | H | 1 |
| 2-554 | H | C—CF3 | C—H | C—CF3 | C—H | CF3 | C—H | C—Me | Me | H | CF3CH2CO | | H | 1 |
| 2-555 | H | C—CF3 | C—H | C—CF3 | C—H | CF3 | C—H | C—Me | Me | H | CH3SCH2CO | | H | 1 |
| 2-556 | H | C—CF3 | C—H | C—CF3 | C—H | CF3 | C—H | C—Me | H | H | H | | H | 1 |
| 2-557 | H | C—CF3 | C—H | C—CF3 | C—H | CF3 | C—H | C—Me | H | H | EtCO | | H | 1 |
| 2-558 | H | C—CF3 | C—H | C—CF3 | C—H | CF3 | C—H | C—Me | H | H | CF3CH2CO | | H | 1 |
| 2-559 | H | C—CF3 | C—H | C—CF3 | C—H | CF3 | C—H | C—Me | H | H | CH3SCH2CO | | H | 1 |
| 2-560 | H | C—CF3 | C—H | C—CF3 | C—H | CF3 | C—H | C—Me | H | H | H | | H | 1 |
| 2-561 | H | C—CF3 | C—H | C—CF3 | C—H | CF3 | C—H | C—NO2 | H | H | CH3OCH2CO | | H | 1 |
| 2-562 | H | C—CF3 | C—H | C—CF3 | C—H | CF3 | C—H | C—NO2 | H | H | CH3OCH(Me)CH2CO | | H | 1 |
| 2-563 | H | C—CF3 | C—H | C—CF3 | C—H | CF3 | C—H | C—NO2 | H | H | cyclo-PrCH2CO | | H | 1 |
| 2-564 | H | C—CF3 | C—H | C—CF3 | C—H | CF3 | N | C—NO2 | H | H | EtCO | | H | 1 |
| 2-565 | H | C—CF3 | C—H | C—CF3 | C—H | CF3 | C—H | C—NO2 | Me | H | CF3CH2CO | | H | 1 |
| 2-566 | H | C—CF3 | C—H | C—CF3 | C—H | CF3 | N | C—NO2 | Me | H | EtCO | | H | 1 |
| 2-567 | H | C—CF3 | C—H | C—CF3 | C—H | CF3 | N | C—NO2 | Me | H | CF3CH2CO | | H | 1 |
| 2-568 | H | C—CF3 | C—H | C—CF3 | C—H | CF3 | N | C—NO2 | H | H | CH3SCH2CO | | H | 1 |
| 2-569 | H | C—CF3 | C—H | C—CF3 | C—H | CF3 | C—H | C—NO2 | H | H | CF3CH2CO | | H | 1 |
| 2-570 | H | C—CF3 | C—H | C—CF3 | C—H | CF3 | C—H | C—SMe | H | H | CH3SCH2CO | | H | 1 |
| 2-571 | H | C—CF3 | C—H | C—CF3 | C—H | CF3 | C—H | C—SMe | H | H | CH3OCH2CH2CO | | H | 1 |

TABLE 2-1-continued

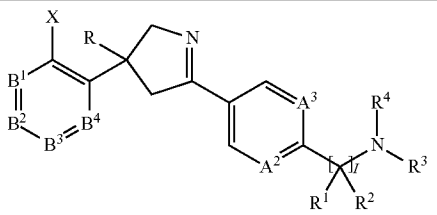

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-572 | H | C—CF3 | C—H | C—CF3 | C—H | CF3 | C—H | C—SMe | H | H | CH3OCH(Me)CH2CO | H | 1 |
| 2-573 | H | C—CF3 | C—H | C—CF3 | C—H | CF3 | C—H | C—SMe | H | H | cyclo-PrCH2CO | H | 1 |
| 2-574 | H | C—CF3 | C—H | C—CF3 | C—H | CF3 | C—H | C—SMe | Me | H | EtCO | H | 1 |
| 2-575 | H | C—CF3 | C—H | C—CF3 | C—H | CF3 | C—H | C—SMe | Me | H | EtCO | H | 1 |
| 2-576 | H | C—CF3 | C—H | C—CF3 | C—H | CF3 | N | C—SMe | H | H | EtCO | H | 1 |
| 2-577 | H | C—CF3 | C—H | C—CF3 | C—H | CF3 | N | C—SMe | H | H | CF3CH2CO | H | 1 |
| 2-578 | H | C—CF3 | C—H | C—CF3 | C—H | CF3 | C—H | C—SMe | H | H | CF3CH2CO | H | 1 |
| 2-579 | H | C—CF3 | C—H | C—CF3 | C—H | CF3 | C—H | C—SOMe | H | H | H | H | 1 |
| 2-580 | H | C—CF3 | C—H | C—CF3 | C—H | CF3 | C—H | C—SOMe | H | H | MeCO | H | 1 |
| 2-581 | H | C—CF3 | C—H | C—CF3 | C—H | CF3 | C—H | C—SOMe | H | H | EtCO | H | 1 |
| 2-582 | H | C—CF3 | C—H | C—CF3 | C—H | CF3 | C—H | C—SOMe | H | H | CF3CH2CO | H | 1 |
| 2-583 | H | C—CF3 | C—H | C—CF3 | C—H | CF3 | C—H | C—SOMe | H | H | cyclo-PrCO | H | 1 |
| 2-584 | H | C—CF3 | C—H | C—CF3 | C—H | CF3 | C—H | C—SOMe | H | H | cyclo-PrCH2CO | H | 1 |
| 2-585 | H | C—CF3 | C—H | C—CF3 | C—H | CF3 | C—H | C—SOMe | H | H | CH3SCH2CO | H | 1 |
| 2-586 | H | C—CF3 | C—H | C—CF3 | C—H | CF3 | C—H | C—SOMe | H | H | CH3SOCH2CO | H | 1 |
| 2-587 | H | C—CF3 | C—H | C—CF3 | C—H | CF3 | C—H | C—SOMe | H | H | CH3SO2CH2CO | H | 1 |
| 2-588 | H | C—CF3 | C—H | C—CF3 | C—H | CF3 | C—H | C—SOMe | H | H | EtNHCO | H | 1 |
| 2-589 | H | C—CF3 | C—H | C—CF3 | C—H | CF3 | C—H | C—SOMe | Me | H | EtCO | H | 1 |
| 2-590 | H | C—CF3 | C—H | C—CF3 | C—H | CF3 | C—H | C—SOMe | Me | H | CF3CH2CO | H | 1 |
| 2-591 | H | C—CF3 | C—H | C—CF3 | C—H | CF3 | N | C—SOMe | H | H | EtCO | H | 1 |
| 2-592 | H | C—CF3 | C—H | C—CF3 | C—H | CF3 | C—H | C—SO2Me | H | H | CF3CH2CO | H | 1 |
| 2-593 | H | C—CF3 | C—H | C—CF3 | C—H | CF3 | C—H | C—SO2Me | H | H | H | H | 1 |
| 2-594 | H | C—CF3 | C—H | C—CF3 | C—H | CF3 | C—H | C—SO2Me | H | H | MeCO | H | 1 |
| 2-595 | H | C—CF3 | C—H | C—CF3 | C—H | CF3 | C—H | C—SO2Me | H | H | EtCO | H | 1 |
| 2-596 | H | C—CF3 | C—H | C—CF3 | C—H | CF3 | C—H | C—SO2Me | H | H | cyclo-PrCO | H | 1 |
| 2-597 | H | C—CF3 | C—H | C—CF3 | C—H | CF3 | C—H | C—SO2Me | H | H | cyclo-PrCH2CO | H | 1 |
| 2-598 | H | C—CF3 | C—H | C—CF3 | C—H | CF3 | C—H | C—SO2Me | H | H | CH3SCH2CO | H | 1 |
| 2-599 | H | C—CF3 | C—H | C—CF3 | C—H | CF3 | C—H | C—SO2Me | H | H | CH3SOCH2CO | H | 1 |
| 2-600 | H | C—CF3 | C—H | C—CF3 | C—H | CF3 | C—H | C—SO2Me | H | H | CH3SO2CH2CO | H | 1 |
| 2-601 | H | C—CF3 | C—H | C—CF3 | C—H | CF3 | C—H | C—SO2Me | H | H | EtNHCO | H | 1 |
| 2-602 | H | C—CF3 | C—H | C—CF3 | C—H | CF3 | C—H | C—SO2Me | Me | H | EtCO | H | 1 |
| 2-603 | H | C—CF3 | C—H | C—CF3 | C—H | CF3 | C—H | C—SO2Me | Me | H | CF3CH2CO | H | 1 |
| 2-604 | H | C—CF3 | C—H | C—CF3 | C—H | CF3 | N | C—SO2Me | H | H | EtCO | H | 1 |
| 2-605 | H | C—CF3 | C—H | C—CF3 | C—H | CF3 | C—H | C—SCF3 | H | H | CF3CH2CO | H | 1 |
| 2-606 | H | C—CF3 | C—H | C—CF3 | C—H | CF3 | C—H | C—SCF3 | H | H | H | H | 1 |
| 2-607 | H | C—CF3 | C—H | C—CF3 | C—H | CF3 | C—H | C—SCF3 | H | H | cyclo-PrCO | H | 1 |
| 2-608 | H | C—CF3 | C—H | C—CF3 | C—H | CF3 | C—H | C—SCF3 | H | H | cyclo-PrCH2CO | H | 1 |
| 2-609 | H | C—CF3 | C—H | C—CF3 | C—H | CF3 | C—H | C—SCF3 | H | H | CH3SCH2CO | H | 1 |
| 2-610 | H | C—CF3 | C—H | C—CF3 | C—H | CF3 | C—H | C—SCF3 | H | H | CH3SOCH2CO | H | 1 |
| 2-611 | H | C—CF3 | C—H | C—CF3 | C—H | CF3 | C—H | C—SCF3 | H | H | CH3SO2CH2CO | H | 1 |
| 2-612 | H | C—CF3 | C—H | C—CF3 | C—H | CF3 | C—H | C—SCF3 | H | H | EtNHCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-613 | H | C—CF3 | C—H | C—CF3 | C—H | CF3 | C—H | C—SCF3 | Me | H | EtCO | H | 1 |
| 2-614 | H | C—CF3 | C—H | C—CF3 | C—H | CF3 | C—H | C—SCF3 | Me | H | CF3CH2CO | H | 1 |
| 2-615 | H | C—CF3 | C—H | C—CF3 | C—H | CF3 | N | C—SCF3 | H | H | EtCO | H | 1 |
| 2-616 | H | C—CF3 | C—H | C—CF3 | C—H | CF3 | N | C—SCF3 | H | H | CF3CH2CO | H | 1 |
| 2-617 | H | C—CF3 | C—H | C—CF3 | C—H | CF3 | C—H | C—SCF3 | H | H | H | H | 1 |
| 2-618 | H | C—CF3 | C—H | C—CF3 | C—H | CF3 | C—H | C—SOCF3 | H | H | MeCO | H | 1 |
| 2-619 | H | C—CF3 | C—H | C—CF3 | C—H | CF3 | C—H | C—SOCF3 | H | H | EtCO | H | 1 |
| 2-620 | H | C—CF3 | C—H | C—CF3 | C—H | CF3 | C—H | C—SOCF3 | H | H | CF3CH2CO | H | 1 |
| 2-621 | H | C—CF3 | C—H | C—CF3 | C—H | CF3 | C—H | C—SOCF3 | H | H | cyclo-PrCO | H | 1 |
| 2-622 | H | C—CF3 | C—H | C—CF3 | C—H | CF3 | C—H | C—SOCF3 | H | H | cyclo-PrCH2CO | H | 1 |
| 2-623 | H | C—CF3 | C—H | C—CF3 | C—H | CF3 | C—H | C—SOCF3 | H | H | CH3SCH2CO | H | 1 |
| 2-624 | H | C—CF3 | C—H | C—CF3 | C—H | CF3 | C—H | C—SOCF3 | H | H | CH3SOCH2CO | H | 1 |
| 2-625 | H | C—CF3 | C—H | C—CF3 | C—H | CF3 | C—H | C—SOCF3 | H | H | CH3SO2CH2CO | H | 1 |
| 2-626 | H | C—CF3 | C—H | C—CF3 | C—H | CF3 | C—H | C—SOCF3 | H | H | EtNHCO | H | 1 |
| 2-627 | H | C—CF3 | C—H | C—CF3 | C—H | CF3 | C—H | C—SOCF3 | Me | H | EtCO | H | 1 |
| 2-628 | H | C—CF3 | C—H | C—CF3 | C—H | CF3 | C—H | C—SOCF3 | Me | H | CF3CH2CO | H | 1 |
| 2-629 | H | C—CF3 | C—H | C—CF3 | C—H | CF3 | N | C—SOCF3 | H | H | EtCO | H | 1 |
| 2-630 | H | C—CF3 | C—H | C—CF3 | C—H | CF3 | N | C—SOCF3 | H | H | CF3CH2CO | H | 1 |
| 2-631 | H | C—CF3 | C—H | C—CF3 | C—H | CF3 | C—H | C—SOCF3 | H | H | H | H | 1 |
| 2-632 | H | C—CF3 | C—H | C—CF3 | C—H | CF3 | C—H | C—SO2CF3 | H | H | MeCO | H | 1 |
| 2-633 | H | C—CF3 | C—H | C—CF3 | C—H | CF3 | C—H | C—SO2CF3 | H | H | EtCO | H | 1 |
| 2-634 | H | C—CF3 | C—H | C—CF3 | C—H | CF3 | C—H | C—SO2CF3 | H | H | CF3CH2CO | H | 1 |
| 2-635 | H | C—CF3 | C—H | C—CF3 | C—H | CF3 | C—H | C—SO2CF3 | H | H | cyclo-PrCO | H | 1 |
| 2-636 | H | C—CF3 | C—H | C—CF3 | C—H | CF3 | C—H | C—SO2CF3 | H | H | cyclo-PrCH2CO | H | 1 |
| 2-637 | H | C—CF3 | C—H | C—CF3 | C—H | CF3 | C—H | C—SO2CF3 | H | H | CH3SCH2CO | H | 1 |
| 2-638 | H | C—CF3 | C—H | C—CF3 | C—H | CF3 | C—H | C—SO2CF3 | H | H | CH3SOCH2CO | H | 1 |
| 2-639 | H | C—CF3 | C—H | C—CF3 | C—H | CF3 | C—H | C—SO2CF3 | H | H | CH3SO2CH2CO | H | 1 |
| 2-640 | H | C—CF3 | C—H | C—CF3 | C—H | CF3 | C—H | C—SO2CF3 | H | H | EtNHCO | H | 1 |
| 2-641 | H | C—CF3 | C—H | C—CF3 | C—H | CF3 | C—H | C—SO2CF3 | Me | H | EtCO | H | 1 |
| 2-642 | H | C—CF3 | C—H | C—CF3 | C—H | CF3 | C—H | C—SO2CF3 | Me | H | CF3CH2CO | H | 1 |
| 2-643 | H | C—CF3 | C—H | C—CF3 | C—H | CF3 | N | C—SO2CF3 | H | H | EtCO | H | 1 |
| 2-644 | H | C—CF3 | C—H | C—CF3 | C—H | CF3 | N | C—SO2CF3 | H | H | CF3CH2CO | H | 1 |
| 2-645 | H | C—CF3 | C—H | C—CF3 | C—H | CF3 | C—H | C—SO2CF3 | H | H | H | H | 1 |
| 2-646 | H | C—CF3 | C—H | C—CF3 | C—H | CF3 | C—H | C—H | H | H | MeCO | H | 1 |
| 2-647 | H | C—CF3 | C—H | C—CF3 | C—H | CF3 | C—H | C—H | H | H | EtCO | H | 1 |
| 2-648 | H | C—CF3 | C—H | C—CF3 | C—H | CF3 | C—H | C—H | H | H | CF3CH2CO | H | 1 |
| 2-649 | H | C—CF3 | C—H | C—CF3 | C—H | CF3 | C—H | C—H | H | H | cyclo-PrCO | H | 1 |
| 2-650 | H | C—CF3 | C—H | C—CF3 | C—H | CF3 | C—H | C—H | H | H | cyclo-PrCH2CO | H | 1 |
| 2-651 | H | C—CF3 | C—H | C—CF3 | C—H | CF3 | C—H | C—H | H | H | CH3SCH2CO | H | 1 |
| 2-652 | H | C—CF3 | C—H | C—CF3 | C—H | CF3 | C—H | C—H | H | H | CH3SOCH2CO | H | 1 |
| 2-653 | H | C—CF3 | C—H | C—CF3 | C—H | CF3 | C—H | C—H | H | H | CH3SO2CH2CO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-654 | H | C—CF3 | C—H | C—CF3 | C—H | CF3 | C—H | C—H | H | H | EtNHCO | H | 1 |
| 2-655 | H | C—CF3 | C—H | C—CF3 | C—H | CF3 | C—H | C—H | Me | H | EtCO | H | 1 |
| 2-656 | H | C—CF3 | C—H | C—CF3 | C—H | CF3 | C—H | C—H | Me | H | CF3CH2CO | H | 1 |
| 2-657 | H | C—CF3 | C—H | C—CF3 | C—H | CF3 | N | C—H | H | H | EtCO | H | 1 |
| 2-658 | H | C—CF3 | C—H | C—CF3 | C—H | CF3 | C—H | C—H | H | H | CF3CH2CO | H | 1 |
| 2-659 | H | C—CF3 | C—H | C—CF3 | C—H | CF3 | C—H | C—F | H | H | EtCO | H | 1 |
| 2-660 | H | C—CF3 | C—H | C—CF3 | C—H | CF3 | C—H | C—F | H | H | H | H | 1 |
| 2-661 | H | C—CF3 | C—H | C—CF3 | C—H | CF3 | C—H | C—F | Me | H | cyclo-PrCH2CO | H | 1 |
| 2-662 | H | C—CF3 | C—H | C—CF3 | C—H | CF3 | C—H | C—F | Me | H | EtCO | H | 1 |
| 2-663 | H | C—CF3 | C—H | C—CF3 | C—H | CF3 | N | C—H | H | H | CF3CH2CO | H | 1 |
| 2-664 | H | C—CF3 | C—H | C—CF3 | C—H | CF3 | C—H | C—I | H | H | EtCO | H | 1 |
| 2-665 | H | C—CF3 | C—H | C—CF3 | C—H | CF3 | C—H | C—I | H | H | H | H | 1 |
| 2-666 | H | C—CF3 | C—H | C—CF3 | C—H | CF3 | C—H | C—I | Me | H | cyclo-PrCH2CO | H | 1 |
| 2-667 | H | C—CF3 | C—H | C—CF3 | C—H | CF3 | C—H | C—I | Me | H | EtCO | H | 1 |
| 2-668 | H | C—CF3 | C—H | C—CF3 | C—H | CF3 | C—H | C—I | H | H | CF3CH2CO | H | 1 |
| 2-669 | H | C—CF3 | C—H | C—CF3 | C—H | CF3 | N | C—I | H | H | EtCO | H | 1 |
| 2-670 | H | C—CF3 | C—H | C—CF3 | C—H | CF3 | C—H | C—I | H | H | CF3CH2CO | H | 1 |
| 2-671 | H | C—CF3 | C—H | C—CF3 | C—H | CF3 | C—H | C—NH2 | H | H | H | H | 1 |
| 2-672 | H | C—CF3 | C—H | C—CF3 | C—H | CF3 | C—H | C—NH2 | H | H | MeCO | H | 1 |
| 2-673 | H | C—CF3 | C—H | C—CF3 | C—H | CF3 | C—H | C—NH2 | H | H | EtCO | H | 1 |
| 2-674 | H | C—CF3 | C—H | C—CF3 | C—H | CF3 | C—H | C—NH2 | H | H | CF3CH2CO | H | 1 |
| 2-675 | H | C—CF3 | C—H | C—CF3 | C—H | CF3 | C—H | C—NH2 | H | H | cyclo-PrCO | H | 1 |
| 2-676 | H | C—CF3 | C—H | C—CF3 | C—H | CF3 | C—H | C—NH2 | H | H | cyclo-PrCH2CO | H | 1 |
| 2-677 | H | C—CF3 | C—H | C—CF3 | C—H | CF3 | C—H | C—NH2 | H | H | CH3SOCH2CO | H | 1 |
| 2-678 | H | C—CF3 | C—H | C—CF3 | C—H | CF3 | C—H | C—NH2 | H | H | CH3SCH2CO | H | 1 |
| 2-679 | H | C—CF3 | C—H | C—CF3 | C—H | CF3 | C—H | C—NH2 | H | H | CH3SO2CH2CO | H | 1 |
| 2-680 | H | C—CF3 | C—H | C—CF3 | C—H | CF3 | C—H | C—NH2 | H | H | EtNHCO | H | 1 |
| 2-681 | H | C—CF3 | C—H | C—CF3 | C—H | CF3 | C—H | C—NH2 | Me | H | EtCO | H | 1 |
| 2-682 | H | C—CF3 | C—H | C—CF3 | C—H | CF3 | N | C—NH2 | H | H | CF3CH2CO | H | 1 |
| 2-683 | H | C—CF3 | C—H | C—CF3 | C—H | CF3 | N | C—NH2 | H | H | EtCO | H | 1 |
| 2-684 | H | C—CF3 | C—H | C—CF3 | C—H | CF3 | N | C—NH2 | H | H | CF3CH2CO | H | 1 |
| 2-685 | H | C—CF3 | C—H | C—CF3 | C—H | CF3 | C—H | C—NHAc | H | H | H | H | 1 |
| 2-686 | H | C—CF3 | C—H | C—CF3 | C—H | CF3 | C—H | C—NHAc | H | H | MeCO | H | 1 |
| 2-687 | H | C—CF3 | C—H | C—CF3 | C—H | CF3 | C—H | C—NHAc | H | H | EtCO | H | 1 |
| 2-688 | H | C—CF3 | C—H | C—CF3 | C—H | CF3 | C—H | C—NHAc | H | H | CF3CH2CO | H | 1 |
| 2-689 | H | C—CF3 | C—H | C—CF3 | C—H | CF3 | C—H | C—NHAc | H | H | cyclo-PrCO | H | 1 |
| 2-690 | H | C—CF3 | C—H | C—CF3 | C—H | CF3 | C—H | C—NHAc | H | H | cyclo-PrCH2CO | H | 1 |
| 2-691 | H | C—CF3 | C—H | C—CF3 | C—H | CF3 | C—H | C—NHAc | H | H | CH3SCH2CO | H | 1 |
| 2-692 | H | C—CF3 | C—H | C—CF3 | C—H | CF3 | C—H | C—NHAc | H | H | CH3SOCH2CO | H | 1 |
| 2-693 | H | C—CF3 | C—H | C—CF3 | C—H | CF3 | C—H | C—NHAc | H | H | CH3SO2CH2CO | H | 1 |
| 2-694 | H | C—CF3 | C—H | C—CF3 | C—H | CF3 | C—H | C—NHAc | H | H | EtNHCO | H | 1 |

TABLE 2-1-continued

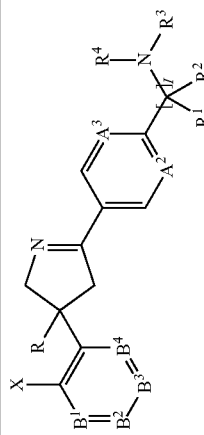

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-695 | H | C—CF3 | C—H | C—CF3 | C—H | CF3 | C—H | C—NHAc | Me | H | EtCO | H | 1 |
| 2-696 | H | C—CF3 | C—H | C—CF3 | C—H | CF3 | C—H | C—NHAc | Me | H | CF3CH2CO | H | 1 |
| 2-697 | H | C—CF3 | C—H | C—CF3 | C—H | CF3 | N | C—NHAc | H | H | EtCO | H | 1 |
| 2-698 | H | C—CF3 | C—H | C—CF3 | C—H | CF3 | C—H | C—NHAc | H | H | CF3CH2CO | H | 1 |
| 2-699 | H | C—CF3 | C—H | C—CF3 | C—H | CF3 | C—H | C—NHCOCF3 | H | H | H | H | 1 |
| 2-700 | H | C—CF3 | C—H | C—CF3 | C—H | CF3 | C—H | C—NHCOCF3 | H | H | MeCO | H | 1 |
| 2-701 | H | C—CF3 | C—H | C—CF3 | C—H | CF3 | C—H | C—NHCOCF3 | H | H | EtCO | H | 1 |
| 2-702 | H | C—CF3 | C—H | C—CF3 | C—H | CF3 | C—H | C—NHCOCF3 | H | H | CF3CH2CO | H | 1 |
| 2-703 | H | C—CF3 | C—H | C—CF3 | C—H | CF3 | C—H | C—NHCOCF3 | H | H | cyclo-PrCO | H | 1 |
| 2-704 | H | C—CF3 | C—H | C—CF3 | C—H | CF3 | C—H | C—NHCOCF3 | H | H | cyclo-PrCH2CO | H | 1 |
| 2-705 | H | C—CF3 | C—H | C—CF3 | C—H | CF3 | C—H | C—NHCOCF3 | H | H | CH3SCH2CO | H | 1 |
| 2-706 | H | C—CF3 | C—H | C—CF3 | C—H | CF3 | C—H | C—NHCOCF3 | H | H | CH3SOCH2CO | H | 1 |
| 2-707 | H | C—CF3 | C—H | C—CF3 | C—H | CF3 | C—H | C—NHCOCF3 | H | H | CH3SO2CH2CO | H | 1 |
| 2-708 | H | C—CF3 | C—H | C—CF3 | C—H | CF3 | C—H | C—NHCOCF3 | H | H | EtNHCO | H | 1 |
| 2-709 | H | C—CF3 | C—H | C—CF3 | C—H | CF3 | C—H | C—NHCOCF3 | Me | H | EtCO | H | 1 |
| 2-710 | H | C—CF3 | C—H | C—CF3 | C—H | CF3 | C—H | C—NHCOCF3 | Me | H | CF3CH2CO | H | 1 |
| 2-711 | H | C—CF3 | C—H | C—CF3 | C—H | CF3 | N | C—NHCOCF3 | H | H | EtCO | H | 1 |
| 2-712 | H | C—CF3 | C—H | C—CF3 | C—H | CF3 | C—H | C—NHCOCF3 | H | H | CF3CH2CO | H | 1 |
| 2-713 | H | C—CF3 | C—H | C—CF3 | C—H | CF3 | C—H | C—CH2OAc | H | H | H | H | 1 |
| 2-714 | H | C—CF3 | C—H | C—CF3 | C—H | CF3 | C—H | C—CH2OAc | H | H | MeCO | H | 1 |
| 2-715 | H | C—CF3 | C—H | C—CF3 | C—H | CF3 | C—H | C—CH2OAc | H | H | EtCO | H | 1 |
| 2-716 | H | C—CF3 | C—H | C—CF3 | C—H | CF3 | C—H | C—CH2OAc | H | H | CF3CH2CO | H | 1 |
| 2-717 | H | C—CF3 | C—H | C—CF3 | C—H | CF3 | C—H | C—CH2OAc | H | H | cyclo-PrCO | H | 1 |
| 2-718 | H | C—CF3 | C—H | C—CF3 | C—H | CF3 | C—H | C—CH2OAc | H | H | cyclo-PrCH2CO | H | 1 |
| 2-719 | H | C—CF3 | C—H | C—CF3 | C—H | CF3 | C—H | C—CH2OAc | H | H | CH3SCH2CO | H | 1 |
| 2-720 | H | C—CF3 | C—H | C—CF3 | C—H | CF3 | C—H | C—CH2OAc | H | H | CH3SOCH2CO | H | 1 |
| 2-721 | H | C—CF3 | C—H | C—CF3 | C—H | CF3 | C—H | C—CH2OAc | H | H | CH3SO2CH2CO | H | 1 |
| 2-722 | H | C—CF3 | C—H | C—CF3 | C—H | CF3 | C—H | C—CH2OAc | H | H | EtNHCO | H | 1 |
| 2-723 | H | C—CF3 | C—H | C—CF3 | C—H | CF3 | C—H | C—CH2OAc | Me | H | EtCO | H | 1 |
| 2-724 | H | C—CF3 | C—H | C—CF3 | C—H | CF3 | C—H | C—CH2OAc | Me | H | CF3CH2CO | H | 1 |
| 2-725 | H | C—CF3 | C—H | C—CF3 | C—H | CF3 | N | C—CH2OAc | H | H | EtCO | H | 1 |
| 2-726 | H | C—CF3 | C—H | C—Cl | C—H | CF3 | C—H | C—CH2OAc | H | H | CF3CH2CO | H | 1 |
| 2-727 | H | C—CF3 | C—H | C—Cl | C—H | CF3 | C—H | C—CF3 | H | H | H | H | 1 |
| 2-728 | H | C—CF3 | C—H | C—Cl | C—H | CF3 | C—H | C—CF3 | H | H | CF3CH2CO | H | 1 |
| 2-729 | H | C—CF3 | C—H | C—Cl | C—H | CF3 | C—H | C—CF3 | H | H | cyclo-PrCO | H | 1 |
| 2-730 | H | C—CF3 | C—H | C—Cl | C—H | CF3 | C—H | C—CF3 | H | H | cyclo-PrCH2CO | H | 1 |
| 2-731 | H | C—CF3 | C—H | C—Cl | C—H | CF3 | C—H | C—CF3 | H | H | CH3SCH2CO | H | 1 |
| 2-732 | H | C—CF3 | C—H | C—Cl | C—H | CF3 | C—H | C—CF3 | H | H | CH3SOCH2CO | H | 1 |
| 2-733 | H | C—CF3 | C—H | C—Cl | C—H | CF3 | C—H | C—CF3 | H | H | CH3SO2CH2CO | H | 1 |
| 2-734 | H | C—CF3 | C—H | C—Cl | C—H | CF3 | C—H | C—CF3 | Me | H | H | H | 1 |
| 2-735 | H | C—CF3 | C—H | C—Cl | C—H | CF3 | C—H | C—CF3 | Me | H | EtCO | H | 1 |

TABLE 2-1-continued

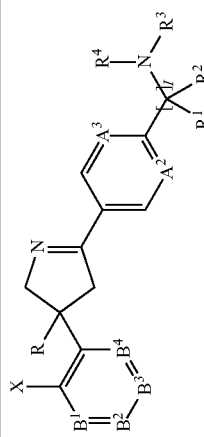

| Example No. | X | B¹ | B² | B³ | B⁴ | R | A² | A³ | R¹ | R² | R⁴ | I |
|---|---|---|---|---|---|---|---|---|---|---|---|---|
| 2-736 | H | C—CF3 | C—H | C—Cl | C—H | CF3 | C—H | C—CF3 | Me | H | CF3CH2CO | 1 |
| 2-737 | H | C—CF3 | C—H | C—Cl | C—H | CF3 | C—H | C—CF3 | Me | H | CH3SCH2CO | 1 |
| 2-738 | H | C—CF3 | C—H | C—Cl | C—H | CF3 | N | C—CF3 | H | H | H | 1 |
| 2-739 | H | C—CF3 | C—H | C—Cl | C—H | CF3 | N | C—CF3 | H | H | EtCO | 1 |
| 2-740 | H | C—CF3 | C—H | C—Cl | C—H | CF3 | N | C—CF3 | H | H | CF3CH2CO | 1 |
| 2-741 | H | C—CF3 | C—H | C—Cl | C—H | CF3 | N | C—CF3 | H | H | CH3SCH2CO | 1 |
| 2-742 | H | C—CF3 | C—H | C—Cl | C—H | CF3 | C—H | C—Cl | H | H | MeCO | 1 |
| 2-743 | H | C—CF3 | C—H | C—Cl | C—H | CF3 | C—H | C—Cl | H | H | CF3CH2CO | 1 |
| 2-744 | H | C—CF3 | C—H | C—Cl | C—H | CF3 | C—H | C—Cl | H | H | cyclo-PrCO | 1 |
| 2-745 | H | C—CF3 | C—H | C—Cl | C—H | CF3 | C—H | C—Cl | H | H | cyclo-PrCH2CO | 1 |
| 2-746 | H | C—CF3 | C—H | C—Cl | C—H | CF3 | C—H | C—Cl | H | H | CH3SCH2CO | 1 |
| 2-747 | H | C—CF3 | C—H | C—Cl | C—H | CF3 | C—H | C—Cl | H | H | CH3SOCH2CO | 1 |
| 2-748 | H | C—CF3 | C—H | C—Cl | C—H | CF3 | C—H | C—Cl | H | H | CH3SO2CH2CO | 1 |
| 2-749 | H | C—CF3 | C—H | C—Cl | C—H | CF3 | C—H | C—Cl | H | H | EtNHCO | 1 |
| 2-750 | H | C—CF3 | C—H | C—Cl | C—H | CF3 | C—H | C—Cl | Me | H | H | 1 |
| 2-751 | H | C—CF3 | C—H | C—Cl | C—H | CF3 | C—H | C—Cl | Me | H | EtCO | 1 |
| 2-752 | H | C—CF3 | C—H | C—Cl | C—H | CF3 | C—H | C—Cl | Me | H | CF3CH2CO | 1 |
| 2-753 | H | C—CF3 | C—H | C—Cl | C—H | CF3 | C—H | C—Cl | Me | H | CH3SCH2CO | 1 |
| 2-754 | H | C—CF3 | C—H | C—Cl | C—H | CF3 | N | C—Cl | H | H | H | 1 |
| 2-755 | H | C—CF3 | C—H | C—Cl | C—H | CF3 | N | C—Cl | H | H | EtCO | 1 |
| 2-756 | H | C—CF3 | C—H | C—Cl | C—H | CF3 | N | C—Cl | H | H | CF3CH2CO | 1 |
| 2-757 | H | C—CF3 | C—H | C—Cl | C—H | CF3 | N | C—Cl | H | H | CH3SCH2CO | 1 |
| 2-758 | H | C—CF3 | C—H | C—Cl | C—H | CF3 | C—H | C—Br | H | H | MeCO | 1 |
| 2-759 | H | C—CF3 | C—H | C—Cl | C—H | CF3 | C—H | C—Br | H | H | EtCO | 1 |
| 2-760 | H | C—CF3 | C—H | C—Cl | C—H | CF3 | C—H | C—Br | H | H | CF3CH2CO | 1 |
| 2-761 | H | C—CF3 | C—H | C—Cl | C—H | CF3 | C—H | C—Br | H | H | cyclo-PrCO | 1 |
| 2-762 | H | C—CF3 | C—H | C—Cl | C—H | CF3 | C—H | C—Br | H | H | cyclo-PrCH2CO | 1 |
| 2-763 | H | C—CF3 | C—H | C—Cl | C—H | CF3 | C—H | C—Br | H | H | CH3SCH2CO | 1 |
| 2-764 | H | C—CF3 | C—H | C—Cl | C—H | CF3 | C—H | C—Br | H | H | CH3SOCH2CO | 1 |
| 2-765 | H | C—CF3 | C—H | C—Cl | C—H | CF3 | C—H | C—Br | H | H | CH3SO2CH2CO | 1 |
| 2-766 | H | C—CF3 | C—H | C—Cl | C—H | CF3 | C—H | C—Br | H | H | EtNHCO | 1 |
| 2-767 | H | C—CF3 | C—H | C—Cl | C—H | CF3 | C—H | C—Br | Me | H | H | 1 |
| 2-768 | H | C—CF3 | C—H | C—Cl | C—H | CF3 | C—H | C—Br | Me | H | EtCO | 1 |
| 2-769 | H | C—CF3 | C—H | C—Cl | C—H | CF3 | C—H | C—Br | Me | H | CF3CH2CO | 1 |
| 2-770 | H | C—CF3 | C—H | C—Cl | C—H | CF3 | C—H | C—Br | Me | H | CH3SCH2CO | 1 |
| 2-771 | H | C—CF3 | C—H | C—Cl | C—H | CF3 | N | C—Br | H | H | H | 1 |
| 2-772 | H | C—CF3 | C—H | C—Cl | C—H | CF3 | N | C—Br | H | H | EtCO | 1 |
| 2-773 | H | C—CF3 | C—H | C—Cl | C—H | CF3 | N | C—Br | H | H | CF3CH2CO | 1 |
| 2-774 | H | C—CF3 | C—H | C—Cl | C—H | CF3 | N | C—Br | H | H | CH3SCH2CO | 1 |

TABLE 2-1-continued

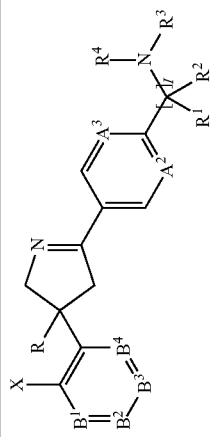

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-777 | H | C—CF3 | C—H | C—Cl | C—H | CF3 | C—H | C—CN | H | H | H | H | 1 |
| 2-778 | H | C—CF3 | C—H | C—Cl | C—H | CF3 | C—H | C—CN | H | H | MeCO | H | 1 |
| 2-779 | H | C—CF3 | C—H | C—Cl | C—H | CF3 | C—H | C—CN | H | H | EtCO | H | 1 |
| 2-780 | H | C—CF3 | C—H | C—Cl | C—H | CF3 | C—H | C—CN | H | H | CF3CH2CO | H | 1 |
| 2-781 | H | C—CF3 | C—H | C—Cl | C—H | CF3 | C—H | C—CN | H | H | cyclo-PrCO | H | 1 |
| 2-782 | H | C—CF3 | C—H | C—Cl | C—H | CF3 | C—H | C—CN | H | H | cyclo-PrCH2CO | H | 1 |
| 2-783 | H | C—CF3 | C—H | C—Cl | C—H | CF3 | C—H | C—CN | H | H | CH3SCH2CO | H | 1 |
| 2-784 | H | C—CF3 | C—H | C—Cl | C—H | CF3 | C—H | C—CN | H | H | CH3SOCH2CO | H | 1 |
| 2-785 | H | C—CF3 | C—H | C—Cl | C—H | CF3 | C—H | C—CN | H | H | CH3SO2CH2CO | H | 1 |
| 2-786 | H | C—CF3 | C—H | C—Cl | C—H | CF3 | C—H | C—CN | H | H | EtNHCO | H | 1 |
| 2-787 | H | C—CF3 | C—H | C—Cl | C—H | CF3 | C—H | C—CN | Me | H | EtCO | H | 1 |
| 2-788 | H | C—CF3 | C—H | C—Cl | C—H | CF3 | C—H | C—CN | Me | H | CF3CH2CO | H | 1 |
| 2-789 | H | C—CF3 | C—H | C—Cl | C—H | CF3 | N | C—CN | H | H | EtCO | H | 1 |
| 2-790 | H | C—CF3 | C—H | C—Cl | C—H | CF3 | N | C—CN | H | H | CF3CH2CO | H | 1 |
| 2-791 | H | C—CF3 | C—H | C—Cl | C—H | CF3 | C—H | C—Me | H | H | H | H | 1 |
| 2-792 | H | C—CF3 | C—H | C—Cl | C—H | CF3 | C—H | C—Me | H | H | MeCO | H | 1 |
| 2-793 | H | C—CF3 | C—H | C—Cl | C—H | CF3 | C—H | C—Me | H | H | EtCO | H | 1 |
| 2-794 | H | C—CF3 | C—H | C—Cl | C—H | CF3 | C—H | C—Me | H | H | CF3CH2CO | H | 1 |
| 2-795 | H | C—CF3 | C—H | C—Cl | C—H | CF3 | C—H | C—Me | H | H | cyclo-PrCO | H | 1 |
| 2-796 | H | C—CF3 | C—H | C—Cl | C—H | CF3 | C—H | C—Me | H | H | cyclo-PrCH2CO | H | 1 |
| 2-797 | H | C—CF3 | C—H | C—Cl | C—H | CF3 | C—H | C—Me | H | H | CH3SCH2CO | H | 1 |
| 2-798 | H | C—CF3 | C—H | C—Cl | C—H | CF3 | C—H | C—Me | H | H | CH3SOCH2CO | H | 1 |
| 2-799 | H | C—CF3 | C—H | C—Cl | C—H | CF3 | C—H | C—Me | H | H | CH3SO2CH2CO | H | 1 |
| 2-800 | H | C—CF3 | C—H | C—Cl | C—H | CF3 | C—H | C—Me | H | H | EtNHCO | H | 1 |
| 2-801 | H | C—CF3 | C—H | C—Cl | C—H | CF3 | C—H | C—Me | Me | H | EtCO | H | 1 |
| 2-802 | H | C—CF3 | C—H | C—Cl | C—H | CF3 | C—H | C—Me | Me | H | CF3CH2CO | H | 1 |
| 2-803 | H | C—CF3 | C—H | C—Cl | C—H | CF3 | N | C—Me | H | H | EtCO | H | 1 |
| 2-804 | H | C—CF3 | C—H | C—Cl | C—H | CF3 | N | C—Me | H | H | CF3CH2CO | H | 1 |
| 2-805 | H | C—CF3 | C—H | C—Cl | C—H | CF3 | C—H | C—NO2 | H | H | H | H | 1 |
| 2-806 | H | C—CF3 | C—H | C—Cl | C—H | CF3 | C—H | C—NO2 | H | H | MeCO | H | 1 |
| 2-807 | H | C—CF3 | C—H | C—Cl | C—H | CF3 | C—H | C—NO2 | H | H | EtCO | H | 1 |
| 2-808 | H | C—CF3 | C—H | C—Cl | C—H | CF3 | C—H | C—NO2 | H | H | CF3CH2CO | H | 1 |
| 2-809 | H | C—CF3 | C—H | C—Cl | C—H | CF3 | C—H | C—NO2 | H | H | cyclo-PrCO | H | 1 |
| 2-810 | H | C—CF3 | C—H | C—Cl | C—H | CF3 | C—H | C—NO2 | H | H | cyclo-PrCH2CO | H | 1 |
| 2-811 | H | C—CF3 | C—H | C—Cl | C—H | CF3 | C—H | C—NO2 | H | H | CH3SCH2CO | H | 1 |
| 2-812 | H | C—CF3 | C—H | C—Cl | C—H | CF3 | C—H | C—NO2 | H | H | CH3SOCH2CO | H | 1 |
| 2-813 | H | C—CF3 | C—H | C—Cl | C—H | CF3 | C—H | C—NO2 | H | H | CH3SO2CH2CO | H | 1 |
| 2-814 | H | C—CF3 | C—H | C—Cl | C—H | CF3 | C—H | C—NO2 | H | H | EtNHCO | H | 1 |
| 2-815 | H | C—CF3 | C—H | C—Cl | C—H | CF3 | C—H | C—NO2 | Me | H | EtCO | H | 1 |
| 2-816 | H | C—CF3 | C—H | C—Cl | C—H | CF3 | C—H | C—NO2 | Me | H | CF3CH2CO | H | 1 |
| 2-817 | H | C—CF3 | C—H | C—Cl | C—H | CF3 | N | C—NO2 | H | H | EtCO | H | 1 |

TABLE 2-1-continued

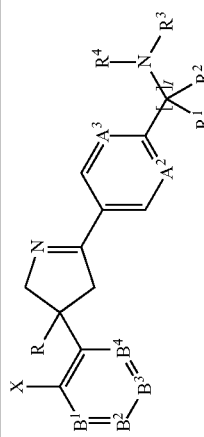

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-818 | H | C—CF3 | C—H | C—Cl | C—H | CF3 | N | C—NO2 | H | H | CF3CH2CO | H | 1 |
| 2-819 | H | C—CF3 | C—H | C—Cl | C—H | CF3 | C—H | C—SMe | H | H | H | H | 1 |
| 2-820 | H | C—CF3 | C—H | C—Cl | C—H | CF3 | C—H | C—SMe | H | H | MeCO | H | 1 |
| 2-821 | H | C—CF3 | C—H | C—Cl | C—H | CF3 | C—H | C—SMe | H | H | EtCO | H | 1 |
| 2-822 | H | C—CF3 | C—H | C—Cl | C—H | CF3 | C—H | C—SMe | H | H | CF3CH2CO | H | 1 |
| 2-823 | H | C—CF3 | C—H | C—Cl | C—H | CF3 | C—H | C—SMe | H | H | cyclo-PrCO | H | 1 |
| 2-824 | H | C—CF3 | C—H | C—Cl | C—H | CF3 | C—H | C—SMe | H | H | cyclo-PrCH2CO | H | 1 |
| 2-825 | H | C—CF3 | C—H | C—Cl | C—H | CF3 | C—H | C—SMe | H | H | CH3SCH2CO | H | 1 |
| 2-826 | H | C—CF3 | C—H | C—Cl | C—H | CF3 | C—H | C—SMe | H | H | CH3SOCH2CO | H | 1 |
| 2-827 | H | C—CF3 | C—H | C—Cl | C—H | CF3 | C—H | C—SMe | H | H | CH3SO2CH2CO | H | 1 |
| 2-828 | H | C—CF3 | C—H | C—Cl | C—H | CF3 | C—H | C—SMe | H | H | EtNHCO | H | 1 |
| 2-829 | H | C—CF3 | C—H | C—Cl | C—H | CF3 | C—H | C—SMe | Me | H | CF3CH2CO | H | 1 |
| 2-830 | H | C—CF3 | C—H | C—Cl | C—H | CF3 | C—H | C—SMe | Me | H | EtCO | H | 1 |
| 2-831 | H | C—CF3 | C—H | C—Cl | C—H | CF3 | C—H | C—SMe | H | H | CF3CH2CO | H | 1 |
| 2-832 | H | C—CF3 | C—H | C—Cl | C—H | CF3 | N | C—SOMe | H | H | EtCO | H | 1 |
| 2-833 | H | C—CF3 | C—H | C—Cl | C—H | CF3 | N | C—SOMe | H | H | H | H | 1 |
| 2-834 | H | C—CF3 | C—H | C—Cl | C—H | CF3 | C—H | C—SOMe | H | H | MeCO | H | 1 |
| 2-835 | H | C—CF3 | C—H | C—Cl | C—H | CF3 | C—H | C—SOMe | H | H | EtCO | H | 1 |
| 2-836 | H | C—CF3 | C—H | C—Cl | C—H | CF3 | C—H | C—SOMe | H | H | CF3CH2CO | H | 1 |
| 2-837 | H | C—CF3 | C—H | C—Cl | C—H | CF3 | C—H | C—SOMe | H | H | cyclo-PrCO | H | 1 |
| 2-838 | H | C—CF3 | C—H | C—Cl | C—H | CF3 | C—H | C—SOMe | H | H | cyclo-PrCH2CO | H | 1 |
| 2-839 | H | C—CF3 | C—H | C—Cl | C—H | CF3 | C—H | C—SOMe | H | H | CH3SCH2CO | H | 1 |
| 2-840 | H | C—CF3 | C—H | C—Cl | C—H | CF3 | C—H | C—SOMe | H | H | CH3SOCH2CO | H | 1 |
| 2-841 | H | C—CF3 | C—H | C—Cl | C—H | CF3 | C—H | C—SOMe | H | H | CH3SO2CH2CO | H | 1 |
| 2-842 | H | C—CF3 | C—H | C—Cl | C—H | CF3 | C—H | C—SOMe | H | H | EtNHCO | H | 1 |
| 2-843 | H | C—CF3 | C—H | C—Cl | C—H | CF3 | C—H | C—SOMe | Me | H | EtCO | H | 1 |
| 2-844 | H | C—CF3 | C—H | C—Cl | C—H | CF3 | C—H | C—SOMe | Me | H | CF3CH2CO | H | 1 |
| 2-845 | H | C—CF3 | C—H | C—Cl | C—H | CF3 | C—H | C—SOMe | H | H | EtCO | H | 1 |
| 2-846 | H | C—CF3 | C—H | C—Cl | C—H | CF3 | C—H | C—SOMe | H | H | CF3CH2CO | H | 1 |
| 2-847 | H | C—CF3 | C—H | C—Cl | C—H | CF3 | N | C—SO2Me | H | H | H | H | 1 |
| 2-848 | H | C—CF3 | C—H | C—Cl | C—H | CF3 | C—H | C—SO2Me | H | H | MeCO | H | 1 |
| 2-849 | H | C—CF3 | C—H | C—Cl | C—H | CF3 | C—H | C—SO2Me | H | H | EtCO | H | 1 |
| 2-850 | H | C—CF3 | C—H | C—Cl | C—H | CF3 | C—H | C—SO2Me | H | H | CF3CH2CO | H | 1 |
| 2-851 | H | C—CF3 | C—H | C—Cl | C—H | CF3 | C—H | C—SO2Me | H | H | cyclo-PrCO | H | 1 |
| 2-852 | H | C—CF3 | C—H | C—Cl | C—H | CF3 | C—H | C—SO2Me | H | H | cyclo-PrCH2CO | H | 1 |
| 2-853 | H | C—CF3 | C—H | C—Cl | C—H | CF3 | C—H | C—SO2Me | H | H | CH3SCH2CO | H | 1 |
| 2-854 | H | C—CF3 | C—H | C—Cl | C—H | CF3 | C—H | C—SO2Me | H | H | CH3SOCH2CO | H | 1 |
| 2-855 | H | C—CF3 | C—H | C—Cl | C—H | CF3 | C—H | C—SO2Me | H | H | CH3SO2CH2CO | H | 1 |
| 2-856 | H | C—CF3 | C—H | C—Cl | C—H | CF3 | C—H | C—SO2Me | H | H | EtNHCO | H | 1 |
| 2-857 | H | C—CF3 | C—H | C—Cl | C—H | CF3 | C—H | C—SO2Me | Me | H | EtCO | H | 1 |
| 2-858 | H | C—CF3 | C—H | C—Cl | C—H | CF3 | C—H | C—SO2Me | Me | H | CF3CH2CO | H | 1 |

TABLE 2-1-continued

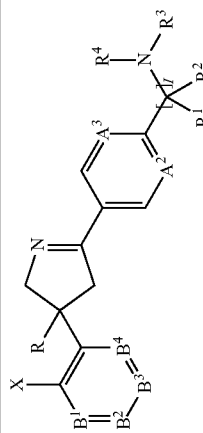

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-859 | H | C—CF3 | C—H | C—Cl | C—H | CF3 | N | C—SO2Me | H | H | EtCO | H | 1 |
| 2-860 | H | C—CF3 | C—H | C—Cl | C—H | CF3 | N | C—SO2Me | H | H | CF3CH2CO | H | 1 |
| 2-861 | H | C—CF3 | C—H | C—Cl | C—H | CF3 | C—H | C—SCF3 | H | H | H | H | 1 |
| 2-862 | H | C—CF3 | C—H | C—Cl | C—H | CF3 | C—H | C—SCF3 | H | H | MeCO | H | 1 |
| 2-863 | H | C—CF3 | C—H | C—Cl | C—H | CF3 | C—H | C—SCF3 | H | H | EtCO | H | 1 |
| 2-864 | H | C—CF3 | C—H | C—Cl | C—H | CF3 | C—H | C—SCF3 | H | H | CF3CH2CO | H | 1 |
| 2-865 | H | C—CF3 | C—H | C—Cl | C—H | CF3 | C—H | C—SCF3 | H | H | cyclo-PrCO | H | 1 |
| 2-866 | H | C—CF3 | C—H | C—Cl | C—H | CF3 | C—H | C—SCF3 | H | H | cyclo-PrCH2CO | H | 1 |
| 2-867 | H | C—CF3 | C—H | C—Cl | C—H | CF3 | C—H | C—SCF3 | H | H | CH3SCH2CO | H | 1 |
| 2-868 | H | C—CF3 | C—H | C—Cl | C—H | CF3 | C—H | C—SCF3 | H | H | CH3SOCH2CO | H | 1 |
| 2-869 | H | C—CF3 | C—H | C—Cl | C—H | CF3 | C—H | C—SCF3 | H | H | CH3SO2CH2CO | H | 1 |
| 2-870 | H | C—CF3 | C—H | C—Cl | C—H | CF3 | C—H | C—SCF3 | H | H | EtNHCO | H | 1 |
| 2-871 | H | C—CF3 | C—H | C—Cl | C—H | CF3 | C—H | C—SCF3 | Me | H | EtCO | H | 1 |
| 2-872 | H | C—CF3 | C—H | C—Cl | C—H | CF3 | C—H | C—SCF3 | Me | H | CF3CH2CO | H | 1 |
| 2-873 | H | C—CF3 | C—H | C—Cl | C—H | CF3 | C—H | C—SCF3 | H | H | EtCO | H | 1 |
| 2-874 | H | C—CF3 | C—H | C—Cl | C—H | CF3 | C—H | C—SCF3 | H | H | CF3CH2CO | H | 1 |
| 2-875 | H | C—CF3 | C—H | C—Cl | C—H | CF3 | C—H | C—SOCF3 | H | H | H | H | 1 |
| 2-876 | H | C—CF3 | C—H | C—Cl | C—H | CF3 | C—H | C—SOCF3 | H | H | MeCO | H | 1 |
| 2-877 | H | C—CF3 | C—H | C—Cl | C—H | CF3 | C—H | C—SOCF3 | H | H | EtCO | H | 1 |
| 2-878 | H | C—CF3 | C—H | C—Cl | C—H | CF3 | C—H | C—SOCF3 | H | H | CF3CH2CO | H | 1 |
| 2-879 | H | C—CF3 | C—H | C—Cl | C—H | CF3 | C—H | C—SOCF3 | H | H | cyclo-PrCO | H | 1 |
| 2-880 | H | C—CF3 | C—H | C—Cl | C—H | CF3 | C—H | C—SOCF3 | H | H | cyclo-PrCH2CO | H | 1 |
| 2-881 | H | C—CF3 | C—H | C—Cl | C—H | CF3 | C—H | C—SOCF3 | H | H | CH3SCH2CO | H | 1 |
| 2-882 | H | C—CF3 | C—H | C—Cl | C—H | CF3 | C—H | C—SOCF3 | H | H | CH3SOCH2CO | H | 1 |
| 2-883 | H | C—CF3 | C—H | C—Cl | C—H | CF3 | C—H | C—SOCF3 | H | H | CH3SO2CH2CO | H | 1 |
| 2-884 | H | C—CF3 | C—H | C—Cl | C—H | CF3 | C—H | C—SOCF3 | H | H | EtNHCO | H | 1 |
| 2-885 | H | C—CF3 | C—H | C—Cl | C—H | CF3 | C—H | C—SOCF3 | Me | H | EtCO | H | 1 |
| 2-886 | H | C—CF3 | C—H | C—Cl | C—H | CF3 | C—H | C—SOCF3 | Me | H | CF3CH2CO | H | 1 |
| 2-887 | H | C—CF3 | C—H | C—Cl | C—H | CF3 | N | C—SOCF3 | H | H | EtCO | H | 1 |
| 2-888 | H | C—CF3 | C—H | C—Cl | C—H | CF3 | C—H | C—SOCF3 | H | H | EtCO | H | 1 |
| 2-889 | H | C—CF3 | C—H | C—Cl | C—H | CF3 | C—H | C—SOCF3 | H | H | CF3CH2CO | H | 1 |
| 2-890 | H | C—CF3 | C—H | C—Cl | C—H | CF3 | C—H | C—H | H | H | H | H | 1 |
| 2-891 | H | C—CF3 | C—H | C—Cl | C—H | CF3 | C—H | C—H | H | H | MeCO | H | 1 |
| 2-892 | H | C—CF3 | C—H | C—Cl | C—H | CF3 | C—H | C—H | H | H | EtCO | H | 1 |
| 2-893 | H | C—CF3 | C—H | C—Cl | C—H | CF3 | C—H | C—H | H | H | CF3CH2CO | H | 1 |
| 2-894 | H | C—CF3 | C—H | C—Cl | C—H | CF3 | C—H | C—H | H | H | cyclo-PrCO | H | 1 |
| 2-895 | H | C—CF3 | C—H | C—Cl | C—H | CF3 | C—H | C—H | H | H | cyclo-PrCH2CO | H | 1 |
| 2-896 | H | C—CF3 | C—H | C—Cl | C—H | CF3 | C—H | C—H | H | H | CH3SCH2CO | H | 1 |
| 2-897 | H | C—CF3 | C—H | C—Cl | C—H | CF3 | C—H | C—H | H | H | CH3SOCH2CO | H | 1 |
| 2-898 | H | C—CF3 | C—H | C—Cl | C—H | CF3 | C—H | C—H | H | H | CH3SO2CH2CO | H | 1 |
| 2-899 | H | C—CF3 | C—H | C—Cl | C—H | CF3 | C—H | C—H | Me | H | EtNHCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-900 | H | C—CF3 | C—H | C—Cl | C—H | CF3 | C—H | C—H | Me | H | EtCO | H | 1 |
| 2-901 | H | C—CF3 | C—H | C—Cl | C—H | CF3 | C—H | C—H | Me | H | CF3CH2CO | H | 1 |
| 2-902 | H | C—CF3 | C—H | C—Cl | C—H | CF3 | C—H | C—H | Me | H | CH3SCH2CO | H | 1 |
| 2-903 | H | C—CF3 | C—H | C—Cl | C—H | CF3 | N | C—H | H | H | H | H | 1 |
| 2-904 | H | C—CF3 | C—H | C—Cl | C—H | CF3 | N | C—H | H | H | EtCO | H | 1 |
| 2-905 | H | C—CF3 | C—H | C—Cl | C—H | CF3 | C—H | C—F | H | H | CF3CH2CO | H | 1 |
| 2-906 | H | C—CF3 | C—H | C—Cl | C—H | CF3 | C—H | C—F | H | H | CH3SCH2CO | H | 1 |
| 2-907 | H | C—CF3 | C—H | C—Cl | C—H | CF3 | C—H | C—F | H | H | H | H | 1 |
| 2-908 | H | C—CF3 | C—H | C—Cl | C—H | CF3 | C—H | C—F | H | H | MeCO | H | 1 |
| 2-909 | H | C—CF3 | C—H | C—Cl | C—H | CF3 | C—H | C—F | H | H | EtCO | H | 1 |
| 2-910 | H | C—CF3 | C—H | C—Cl | C—H | CF3 | C—H | C—F | H | H | cyclo-PrCO | H | 1 |
| 2-911 | H | C—CF3 | C—H | C—Cl | C—H | CF3 | C—H | C—F | H | H | cyclo-PrCH2CO | H | 1 |
| 2-912 | H | C—CF3 | C—H | C—Cl | C—H | CF3 | C—H | C—F | H | H | CH3SCH2CO | H | 1 |
| 2-913 | H | C—CF3 | C—H | C—Cl | C—H | CF3 | C—H | C—F | H | H | CH3SCH2CO | H | 1 |
| 2-914 | H | C—CF3 | C—H | C—Cl | C—H | CF3 | C—H | C—F | H | H | CH3SOCH2CO | H | 1 |
| 2-915 | H | C—CF3 | C—H | C—Cl | C—H | CF3 | C—H | C—F | H | H | CH3SO2CH2CO | H | 1 |
| 2-916 | H | C—CF3 | C—H | C—Cl | C—H | CF3 | C—H | C—F | H | H | EtNHCO | H | 1 |
| 2-917 | H | C—CF3 | C—H | C—Cl | C—H | CF3 | C—H | C—F | Me | H | EtCO | H | 1 |
| 2-918 | H | C—CF3 | C—H | C—Cl | C—H | CF3 | C—H | C—F | Me | H | CF3CH2CO | H | 1 |
| 2-919 | H | C—CF3 | C—H | C—Cl | C—H | CF3 | N | C—F | H | H | EtCO | H | 1 |
| 2-920 | H | C—CF3 | C—H | C—Cl | C—H | CF3 | N | C—F | H | H | CF3CH2CO | H | 1 |
| 2-922 | H | C—CF3 | C—H | C—Cl | C—H | CF3 | C—H | C—I | H | H | H | H | 1 |
| 2-923 | H | C—CF3 | C—H | C—Cl | C—H | CF3 | C—H | C—I | H | H | MeCO | H | 1 |
| 2-924 | H | C—CF3 | C—H | C—Cl | C—H | CF3 | C—H | C—I | H | H | EtCO | H | 1 |
| 2-925 | H | C—CF3 | C—H | C—Cl | C—H | CF3 | C—H | C—I | H | H | CF3CH2CO | H | 1 |
| 2-926 | H | C—CF3 | C—H | C—Cl | C—H | CF3 | C—H | C—I | H | H | cyclo-PrCO | H | 1 |
| 2-927 | H | C—CF3 | C—H | C—Cl | C—H | CF3 | C—H | C—I | H | H | cyclo-PrCH2CO | H | 1 |
| 2-928 | H | C—CF3 | C—H | C—Cl | C—H | CF3 | C—H | C—I | H | H | CH3SCH2CO | H | 1 |
| 2-929 | H | C—CF3 | C—H | C—Cl | C—H | CF3 | C—H | C—I | H | H | CH3SOCH2CO | H | 1 |
| 2-930 | H | C—CF3 | C—H | C—Cl | C—H | CF3 | C—H | C—I | H | H | CH3SO2CH2CO | H | 1 |
| 2-931 | H | C—CF3 | C—H | C—Cl | C—H | CF3 | C—H | C—I | H | H | EtNHCO | H | 1 |
| 2-932 | H | C—CF3 | C—H | C—Cl | C—H | CF3 | C—H | C—I | Me | H | EtCO | H | 1 |
| 2-933 | H | C—CF3 | C—H | C—Cl | C—H | CF3 | C—H | C—I | Me | H | EtCO | H | 1 |
| 2-934 | H | C—CF3 | C—H | C—Cl | C—H | CF3 | N | C—I | H | H | CF3CH2CO | H | 1 |
| 2-935 | H | C—CF3 | C—H | C—Cl | C—H | CF3 | C—H | C—NH2 | H | H | H | H | 1 |
| 2-936 | H | C—CF3 | C—H | C—Cl | C—H | CF3 | C—H | C—NH2 | H | H | MeCO | H | 1 |
| 2-937 | H | C—CF3 | C—H | C—Cl | C—H | CF3 | C—H | C—NH2 | H | H | EtCO | H | 1 |
| 2-938 | H | C—CF3 | C—H | C—Cl | C—H | CF3 | C—H | C—NH2 | H | H | CF3CH2CO | H | 1 |
| 2-939 | H | C—CF3 | C—H | C—Cl | C—H | CF3 | C—H | C—NH2 | H | H | cyclo-PrCO | H | 1 |
| 2-940 | H | C—CF3 | C—H | C—Cl | C—H | CF3 | C—H | C—NH2 | H | H | cyclo-PrCH2CO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-941 | H | C—CF3 | C—H | C—Cl | C—H | CF3 | C—H | C—NH2 | H | H | CH3SCH2CO | H | 1 |
| 2-942 | H | C—CF3 | C—H | C—Cl | C—H | CF3 | C—H | C—NH2 | H | H | CH3SOCH2CO | H | 1 |
| 2-943 | H | C—CF3 | C—H | C—Cl | C—H | CF3 | C—H | C—NH2 | H | H | CH3SO2CH2CO | H | 1 |
| 2-944 | H | C—CF3 | C—H | C—Cl | C—H | CF3 | C—H | C—NH2 | H | H | EtNHCO | H | 1 |
| 2-945 | H | C—CF3 | C—H | C—Cl | C—H | CF3 | C—H | C—NH2 | Me | H | EtCO | H | 1 |
| 2-946 | H | C—CF3 | C—H | C—Cl | C—H | CF3 | C—H | C—NH2 | Me | H | CF3CH2CO | H | 1 |
| 2-947 | H | C—CF3 | C—H | C—Cl | C—H | CF3 | N | C—NH2 | H | H | EtCO | H | 1 |
| 2-948 | H | C—CF3 | C—H | C—Cl | C—H | CF3 | N | C—NH2 | H | H | CF3CH2CO | H | 1 |
| 2-949 | H | C—CF3 | C—H | C—Cl | C—H | CF3 | C—H | C—NHAc | H | H | H | H | 1 |
| 2-950 | H | C—CF3 | C—H | C—Cl | C—H | CF3 | C—H | C—NHAc | H | H | MeCO | H | 1 |
| 2-951 | H | C—CF3 | C—H | C—Cl | C—H | CF3 | C—H | C—NHAc | H | H | EtCO | H | 1 |
| 2-952 | H | C—CF3 | C—H | C—Cl | C—H | CF3 | C—H | C—NHAc | H | H | CF3CH2CO | H | 1 |
| 2-953 | H | C—CF3 | C—H | C—Cl | C—H | CF3 | C—H | C—NHAc | H | H | cyclo-PrCO | H | 1 |
| 2-954 | H | C—CF3 | C—H | C—Cl | C—H | CF3 | C—H | C—NHAc | H | H | cyclo-PrCH2CO | H | 1 |
| 2-955 | H | C—CF3 | C—H | C—Cl | C—H | CF3 | C—H | C—NHAc | H | H | CH3SCH2CO | H | 1 |
| 2-956 | H | C—CF3 | C—H | C—Cl | C—H | CF3 | C—H | C—NHAc | H | H | CH3SOCH2CO | H | 1 |
| 2-957 | H | C—CF3 | C—H | C—Cl | C—H | CF3 | C—H | C—NHAc | H | H | CH3SO2CH2CO | H | 1 |
| 2-958 | H | C—CF3 | C—H | C—Cl | C—H | CF3 | C—H | C—NHAc | H | H | EtNHCO | H | 1 |
| 2-959 | H | C—CF3 | C—H | C—Cl | C—H | CF3 | C—H | C—NHAc | Me | H | EtCO | H | 1 |
| 2-960 | H | C—CF3 | C—H | C—Cl | C—H | CF3 | C—H | C—NHAc | Me | H | CF3CH2CO | H | 1 |
| 2-961 | H | C—CF3 | C—H | C—Cl | C—H | CF3 | N | C—NHAc | H | H | EtCO | H | 1 |
| 2-962 | H | C—CF3 | C—H | C—Cl | C—H | CF3 | N | C—NHAc | H | H | CF3CH2CO | H | 1 |
| 2-963 | H | C—CF3 | C—H | C—Cl | C—H | CF3 | C—H | C—NHCOCF3 | H | H | H | H | 1 |
| 2-964 | H | C—CF3 | C—H | C—Cl | C—H | CF3 | C—H | C—NHCOCF3 | H | H | MeCO | H | 1 |
| 2-965 | H | C—CF3 | C—H | C—Cl | C—H | CF3 | C—H | C—NHCOCF3 | H | H | EtCO | H | 1 |
| 2-966 | H | C—CF3 | C—H | C—Cl | C—H | CF3 | C—H | C—NHCOCF3 | H | H | CF3CH2CO | H | 1 |
| 2-967 | H | C—CF3 | C—H | C—Cl | C—H | CF3 | C—H | C—NHCOCF3 | H | H | cyclo-PrCO | H | 1 |
| 2-968 | H | C—CF3 | C—H | C—Cl | C—H | CF3 | C—H | C—NHCOCF3 | H | H | cyclo-PrCH2CO | H | 1 |
| 2-969 | H | C—CF3 | C—H | C—Cl | C—H | CF3 | C—H | C—NHCOCF3 | H | H | CH3SCH2CO | H | 1 |
| 2-970 | H | C—CF3 | C—H | C—Cl | C—H | CF3 | C—H | C—NHCOCF3 | H | H | CH3SOCH2CO | H | 1 |
| 2-971 | H | C—CF3 | C—H | C—Cl | C—H | CF3 | C—H | C—NHCOCF3 | H | H | CH3SO2CH2CO | H | 1 |
| 2-972 | H | C—CF3 | C—H | C—Cl | C—H | CF3 | C—H | C—NHCOCF3 | H | H | EtNHCO | H | 1 |
| 2-973 | H | C—CF3 | C—H | C—Cl | C—H | CF3 | C—H | C—NHCOCF3 | Me | H | EtCO | H | 1 |
| 2-974 | H | C—CF3 | C—H | C—Cl | C—H | CF3 | C—H | C—NHCOCF3 | Me | H | CF3CH2CO | H | 1 |
| 2-975 | H | C—CF3 | C—H | C—Cl | C—H | CF3 | N | C—NHCOCF3 | H | H | EtCO | H | 1 |
| 2-976 | H | C—CF3 | C—H | C—Cl | C—H | CF3 | N | C—NHCOCF3 | H | H | CF3CH2CO | H | 1 |
| 2-977 | H | C—CF3 | C—H | C—Cl | C—H | CF3 | C—H | C—CH2OAc | H | H | H | H | 1 |
| 2-978 | H | C—CF3 | C—H | C—Cl | C—H | CF3 | C—H | C—CH2OAc | H | H | MeCO | H | 1 |
| 2-979 | H | C—CF3 | C—H | C—Cl | C—H | CF3 | C—H | C—CH2OAc | H | H | EtCO | H | 1 |
| 2-980 | H | C—CF3 | C—H | C—Cl | C—H | CF3 | C—H | C—CH2OAc | H | H | CF3CH2CO | H | 1 |
| 2-981 | H | C—CF3 | C—H | C—Cl | C—H | CF3 | C—H | C—CH2OAc | H | H | cyclo-PrCO | H | 1 |

TABLE 2-1-continued

| Example No. | X | B¹ | B² | B³ | B⁴ | R | A² | A³ | | R¹ | R² | R⁴ | R³ | I |
|---|---|---|---|---|---|---|---|---|---|---|---|---|---|---|
| 2-982 | H | C—CF3 | C—H | C—Cl | C—H | CF3 | C—H | C—CH2OAc | | H | H | cyclo-PrCH2CO | H | 1 |
| 2-983 | H | C—CF3 | C—H | C—Cl | C—H | CF3 | C—H | C—CH2OAc | | H | H | CH3SCH2CO | H | 1 |
| 2-984 | H | C—CF3 | C—H | C—Cl | C—H | CF3 | C—H | C—CH2OAc | | H | H | CH3SO2CH2CO | H | 1 |
| 2-985 | H | C—CF3 | C—H | C—Cl | C—H | CF3 | C—H | C—CH2OAc | | H | H | CH3OCH2CH2CO | H | 1 |
| 2-986 | H | C—CF3 | C—H | C—Cl | C—H | CF3 | C—H | C—CH2OAc | | H | H | CH3OCH(Me)CH2CO | H | 1 |
| 2-987 | H | C—CF3 | C—H | C—Cl | C—H | CF3 | C—H | C—CH2OAc | | H | H | EtNHCO | H | 1 |
| 2-988 | H | C—CF3 | C—H | C—Cl | C—H | CF3 | C—H | C—CH2OAc | | Me | H | EtCO | H | 1 |
| 2-989 | H | C—CF3 | C—H | C—Cl | C—H | CF3 | C—H | C—CH2OAc | | Me | H | CF3CH2CO | H | 1 |
| 2-990 | H | C—CF3 | C—H | C—Cl | C—H | CF3 | N | C—CH2OAc | | H | H | EtCO | H | 1 |
| 2-991 | H | C—CF3 | C—H | C—Cl | C—H | CF3 | N | C—CH2OAc | | H | H | CF3CH2CO | H | 1 |
| 2-992 | H | C—CF3 | C—H | C—Cl | C—H | CF3 | C—H | C—CH2OAc | | H | H | EtNHCO | H | 1 |
| 2-993 | H | C—CF3 | C—F | C—H | C—H | CF3 | C—H | C—CF3 | | H | H | H | H | 1 |
| 2-994 | H | C—CF3 | C—F | C—H | C—H | CF3 | C—H | C—CF3 | | H | H | CF3CH2CO | H | 1 |
| 2-995 | H | C—CF3 | C—F | C—H | C—H | CF3 | C—H | C—CF3 | | H | H | cyclo-PrCH2CO | H | 1 |
| 2-996 | H | C—CF3 | C—F | C—H | C—H | CF3 | C—H | C—CF3 | | H | H | CH3SCH2CO | H | 1 |
| 2-997 | H | C—CF3 | C—F | C—H | C—H | CF3 | C—H | C—CF3 | | H | H | CH3SOCH2CO | H | 1 |
| 2-998 | H | C—CF3 | C—F | C—H | C—H | CF3 | C—H | C—CF3 | | H | H | CH3SCH2CO | H | 1 |
| 2-999 | H | C—CF3 | C—F | C—H | C—H | CF3 | C—H | C—CF3 | | H | H | CH3SO2CH2CO | H | 1 |
| 2-1000 | H | C—CF3 | C—F | C—H | C—H | CF3 | C—H | C—CF3 | | Me | H | EtCO | H | 1 |
| 2-1001 | H | C—CF3 | C—F | C—H | C—H | CF3 | C—H | C—CF3 | | Me | H | CF3CH2CO | H | 1 |
| 2-1002 | H | C—CF3 | C—F | C—H | C—H | CF3 | N | C—CF3 | | Me | H | CH3SCH2CO | H | 1 |
| 2-1003 | H | C—CF3 | C—F | C—H | C—H | CF3 | N | C—CF3 | | H | H | EtCO | H | 1 |
| 2-1004 | H | C—CF3 | C—F | C—H | C—H | CF3 | N | C—CF3 | | H | H | H | H | 1 |
| 2-1005 | H | C—CF3 | C—F | C—H | C—H | CF3 | C—H | C—CF3 | | H | H | CF3CH2CO | H | 1 |
| 2-1006 | H | C—CF3 | C—F | C—H | C—H | CF3 | C—H | C—Cl | | H | H | EtCO | H | 1 |
| 2-1007 | H | C—CF3 | C—F | C—H | C—H | CF3 | C—H | C—Cl | | H | H | CF3CH2CO | H | 1 |
| 2-1008 | H | C—CF3 | C—F | C—H | C—H | CF3 | C—H | C—Cl | | H | H | CH3SCH2CO | H | 1 |
| 2-1009 | H | C—CF3 | C—F | C—H | C—H | CF3 | C—H | C—Cl | | H | H | H | H | 1 |
| 2-1010 | H | C—CF3 | C—F | C—H | C—H | CF3 | C—H | C—Cl | | H | H | MeCO | H | 1 |
| 2-1011 | H | C—CF3 | C—F | C—H | C—H | CF3 | C—H | C—Cl | | H | H | EtCO | H | 1 |
| 2-1012 | H | C—CF3 | C—F | C—H | C—H | CF3 | C—H | C—Cl | | H | H | CF3CH2CO | H | 1 |
| 2-1013 | H | C—CF3 | C—F | C—H | C—H | CF3 | C—H | C—Cl | | H | H | cyclo-PrCO | H | 1 |
| 2-1014 | H | C—CF3 | C—F | C—H | C—H | CF3 | C—H | C—Cl | | H | H | cyclo-PrCH2CO | H | 1 |
| 2-1015 | H | C—CF3 | C—F | C—H | C—H | CF3 | C—H | C—Cl | | H | H | CH3SCH2CO | H | 1 |
| 2-1016 | H | C—CF3 | C—F | C—H | C—H | CF3 | C—H | C—Cl | | H | H | CH3SOCH2CO | H | 1 |
| 2-1017 | H | C—CF3 | C—F | C—H | C—H | CF3 | C—H | C—Cl | | H | H | CH3SO2CH2CO | H | 1 |
| 2-1018 | H | C—CF3 | C—F | C—H | C—H | CF3 | C—H | C—Cl | | H | H | EtNHCO | H | 1 |
| 2-1019 | H | C—CF3 | C—F | C—H | C—H | CF3 | C—H | C—Cl | | Me | H | EtCO | H | 1 |
| 2-1020 | H | C—CF3 | C—F | C—H | C—H | CF3 | C—H | C—Cl | | Me | H | CF3CH2CO | H | 1 |
| 2-1021 | H | C—CF3 | C—F | C—H | C—H | CF3 | C—H | C—Cl | | Me | H | CH3SCH2CO | H | 1 |
| 2-1022 | H | C—CF3 | C—F | C—H | C—H | CF3 | N | C—Cl | | H | H | H | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1023 | H | C—CF3 | C—F | C—H | C—H | CF3 | N | C—Cl | H | H | EtCO | H | 1 |
| 2-1024 | H | C—CF3 | C—F | C—H | C—H | CF3 | N | C—Cl | H | H | CF3CH2CO | H | 1 |
| 2-1025 | H | C—CF3 | C—F | C—H | C—H | CF3 | N | C—Cl | H | H | CH3SCH2CO | H | 1 |
| 2-1026 | H | C—CF3 | C—F | C—H | C—H | CF3 | C—H | C—Br | H | H | H | H | 1 |
| 2-1027 | H | C—CF3 | C—F | C—H | C—H | CF3 | C—H | C—Br | H | H | MeCO | H | 1 |
| 2-1028 | H | C—CF3 | C—F | C—H | C—H | CF3 | C—H | C—Br | H | H | EtCO | H | 1 |
| 2-1029 | H | C—CF3 | C—F | C—H | C—H | CF3 | C—H | C—Br | H | H | CF3CH2CO | H | 1 |
| 2-1030 | H | C—CF3 | C—F | C—H | C—H | CF3 | C—H | C—Br | H | H | cyclo-PrCO | H | 1 |
| 2-1031 | H | C—CF3 | C—F | C—H | C—H | CF3 | C—H | C—Br | H | H | cyclo-PrCH2CO | H | 1 |
| 2-1032 | H | C—CF3 | C—F | C—H | C—H | CF3 | C—H | C—Br | H | H | CH3SCH2CO | H | 1 |
| 2-1033 | H | C—CF3 | C—F | C—H | C—H | CF3 | C—H | C—Br | H | H | CH3SOCH2CO | H | 1 |
| 2-1034 | H | C—CF3 | C—F | C—H | C—H | CF3 | C—H | C—Br | H | H | CH3SO2CH2CO | H | 1 |
| 2-1035 | H | C—CF3 | C—F | C—H | C—H | CF3 | C—H | C—Br | H | H | EtNHCO | H | 1 |
| 2-1036 | H | C—CF3 | C—F | C—H | C—H | CF3 | C—H | C—Br | Me | H | H | H | 1 |
| 2-1037 | H | C—CF3 | C—F | C—H | C—H | CF3 | C—H | C—Br | Me | H | EtCO | H | 1 |
| 2-1038 | H | C—CF3 | C—F | C—H | C—H | CF3 | C—H | C—Br | Me | H | CH3SCH2CO | H | 1 |
| 2-1039 | H | C—CF3 | C—F | C—H | C—H | CF3 | C—H | C—Br | H | H | CH3SCH2CO | H | 1 |
| 2-1040 | H | C—CF3 | C—F | C—H | C—H | CF3 | C—H | C—Br | H | H | H | H | 1 |
| 2-1041 | H | C—CF3 | C—F | C—H | C—H | CF3 | C—H | C—CN | H | H | EtCO | H | 1 |
| 2-1042 | H | C—CF3 | C—F | C—H | C—H | CF3 | C—H | C—CN | H | H | CF3CH2CO | H | 1 |
| 2-1043 | H | C—CF3 | C—F | C—H | C—H | CF3 | C—H | C—CN | H | H | CH3SCH2CO | H | 1 |
| 2-1044 | H | C—CF3 | C—F | C—H | C—H | CF3 | N | C—CN | H | H | H | H | 1 |
| 2-1045 | H | C—CF3 | C—F | C—H | C—H | CF3 | N | C—CN | H | H | MeCO | H | 1 |
| 2-1046 | H | C—CF3 | C—F | C—H | C—H | CF3 | N | C—CN | H | H | EtCO | H | 1 |
| 2-1047 | H | C—CF3 | C—F | C—H | C—H | CF3 | N | C—CN | H | H | CF3CH2CO | H | 1 |
| 2-1048 | H | C—CF3 | C—F | C—H | C—H | CF3 | N | C—CN | H | H | cyclo-PrCO | H | 1 |
| 2-1049 | H | C—CF3 | C—F | C—H | C—H | CF3 | N | C—CN | H | H | cyclo-PrCH2CO | H | 1 |
| 2-1050 | H | C—CF3 | C—F | C—H | C—H | CF3 | N | C—CN | H | H | CH3SCH2CO | H | 1 |
| 2-1051 | H | C—CF3 | C—F | C—H | C—H | CF3 | N | C—CN | H | H | CH3SOCH2CO | H | 1 |
| 2-1052 | H | C—CF3 | C—F | C—H | C—H | CF3 | N | C—CN | H | H | CH3SO2CH2CO | H | 1 |
| 2-1053 | H | C—CF3 | C—F | C—H | C—H | CF3 | N | C—CN | H | H | EtNHCO | H | 1 |
| 2-1054 | H | C—CF3 | C—F | C—H | C—H | CF3 | C—H | C—CN | Me | H | EtCO | H | 1 |
| 2-1055 | H | C—CF3 | C—F | C—H | C—H | CF3 | N | C—CN | Me | H | EtCO | H | 1 |
| 2-1056 | H | C—CF3 | C—F | C—H | C—H | CF3 | C—H | C—CN | H | H | EtCO | H | 1 |
| 2-1057 | H | C—CF3 | C—F | C—H | C—H | CF3 | C—H | C—CN | H | H | CF3CH2CO | H | 1 |
| 2-1058 | H | C—CF3 | C—F | C—H | C—H | CF3 | C—H | C—Me | H | H | H | H | 1 |
| 2-1059 | H | C—CF3 | C—F | C—H | C—H | CF3 | C—H | C—Me | H | H | MeCO | H | 1 |
| 2-1060 | H | C—CF3 | C—F | C—H | C—H | CF3 | C—H | C—Me | H | H | EtCO | H | 1 |
| 2-1061 | H | C—CF3 | C—F | C—H | C—H | CF3 | C—H | C—Me | H | H | CF3CH2CO | H | 1 |
| 2-1062 | H | C—CF3 | C—F | C—H | C—H | CF3 | C—H | C—Me | H | H | cyclo-PrCO | H | 1 |
| 2-1063 | H | C—CF3 | C—F | C—H | C—H | CF3 | C—H | C—Me | H | H | cyclo-PrCH2CO | H | 1 |

TABLE 2-1-continued

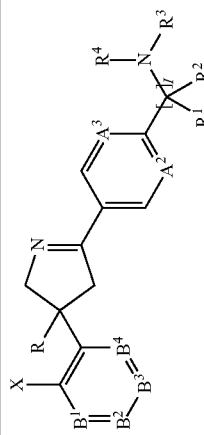

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1064 | H | C—CF3 | C—F | C—H | C—H | CF3 | C—H | C—Me | H | H | CH3SCH2CO | H | 1 |
| 2-1065 | H | C—CF3 | C—F | C—H | C—H | CF3 | C—H | C—Me | H | H | CH3SOCH2CO | H | 1 |
| 2-1066 | H | C—CF3 | C—F | C—H | C—H | CF3 | C—H | C—Me | H | H | CH3SO2CH2CO | H | 1 |
| 2-1067 | H | C—CF3 | C—F | C—H | C—H | CF3 | C—H | C—Me | H | H | EtNHCO | H | 1 |
| 2-1068 | H | C—CF3 | C—F | C—H | C—H | CF3 | C—H | C—Me | Me | H | EtCO | H | 1 |
| 2-1069 | H | C—CF3 | C—F | C—H | C—H | CF3 | C—H | C—Me | Me | H | CF3CH2CO | H | 1 |
| 2-1070 | H | C—CF3 | C—F | C—H | C—H | CF3 | C—H | C—Me | H | H | EtCO | H | 1 |
| 2-1071 | H | C—CF3 | C—F | C—H | C—H | CF3 | N | C—Me | H | H | CF3CH2CO | H | 1 |
| 2-1072 | H | C—CF3 | C—F | C—H | C—H | CF3 | C—H | C—Me | H | H | H | H | 1 |
| 2-1073 | H | C—CF3 | C—F | C—H | C—H | CF3 | C—H | C—NO2 | H | H | MeCO | H | 1 |
| 2-1074 | H | C—CF3 | C—F | C—H | C—H | CF3 | C—H | C—NO2 | H | H | EtCO | H | 1 |
| 2-1075 | H | C—CF3 | C—F | C—H | C—H | CF3 | C—H | C—NO2 | H | H | CF3CH2CO | H | 1 |
| 2-1076 | H | C—CF3 | C—F | C—H | C—H | CF3 | C—H | C—NO2 | H | H | cyclo-PrCO | H | 1 |
| 2-1077 | H | C—CF3 | C—F | C—H | C—H | CF3 | C—H | C—NO2 | H | H | cyclo-PrCH2CO | H | 1 |
| 2-1078 | H | C—CF3 | C—F | C—H | C—H | CF3 | C—H | C—NO2 | H | H | CH3SCH2CO | H | 1 |
| 2-1079 | H | C—CF3 | C—F | C—H | C—H | CF3 | C—H | C—NO2 | H | H | CH3SOCH2CO | H | 1 |
| 2-1080 | H | C—CF3 | C—F | C—H | C—H | CF3 | C—H | C—NO2 | H | H | CH3SO2CH2CO | H | 1 |
| 2-1081 | H | C—CF3 | C—F | C—H | C—H | CF3 | C—H | C—NO2 | H | H | EtNHCO | H | 1 |
| 2-1082 | H | C—CF3 | C—F | C—H | C—H | CF3 | C—H | C—NO2 | Me | H | EtCO | H | 1 |
| 2-1083 | H | C—CF3 | C—F | C—H | C—H | CF3 | C—H | C—NO2 | Me | H | CF3CH2CO | H | 1 |
| 2-1084 | H | C—CF3 | C—F | C—H | C—H | CF3 | C—H | C—NO2 | H | H | EtCO | H | 1 |
| 2-1085 | H | C—CF3 | C—F | C—H | C—H | CF3 | N | C—NO2 | H | H | CF3CH2CO | H | 1 |
| 2-1086 | H | C—CF3 | C—F | C—H | C—H | CF3 | C—H | C—NO2 | H | H | H | H | 1 |
| 2-1087 | H | C—CF3 | C—F | C—H | C—H | CF3 | C—H | C—SMe | H | H | MeCO | H | 1 |
| 2-1088 | H | C—CF3 | C—F | C—H | C—H | CF3 | C—H | C—SMe | H | H | EtCO | H | 1 |
| 2-1089 | H | C—CF3 | C—F | C—H | C—H | CF3 | C—H | C—SMe | H | H | CF3CH2CO | H | 1 |
| 2-1090 | H | C—CF3 | C—F | C—H | C—H | CF3 | C—H | C—SMe | H | H | cyclo-PrCO | H | 1 |
| 2-1091 | H | C—CF3 | C—F | C—H | C—H | CF3 | C—H | C—SMe | H | H | cyclo-PrCH2CO | H | 1 |
| 2-1092 | H | C—CF3 | C—F | C—H | C—H | CF3 | C—H | C—SMe | H | H | CH3SCH2CO | H | 1 |
| 2-1093 | H | C—CF3 | C—F | C—H | C—H | CF3 | C—H | C—SMe | H | H | CH3SOCH2CO | H | 1 |
| 2-1094 | H | C—CF3 | C—F | C—H | C—H | CF3 | C—H | C—SMe | H | H | CH3SO2CH2CO | H | 1 |
| 2-1095 | H | C—CF3 | C—F | C—H | C—H | CF3 | C—H | C—SMe | H | H | EtNHCO | H | 1 |
| 2-1096 | H | C—CF3 | C—F | C—H | C—H | CF3 | C—H | C—SMe | Me | H | EtCO | H | 1 |
| 2-1097 | H | C—CF3 | C—F | C—H | C—H | CF3 | C—H | C—SMe | Me | H | CF3CH2CO | H | 1 |
| 2-1098 | H | C—CF3 | C—F | C—H | C—H | CF3 | C—H | C—SMe | H | H | EtCO | H | 1 |
| 2-1099 | H | C—CF3 | C—F | C—H | C—H | CF3 | N | C—SMe | H | H | CF3CH2CO | H | 1 |
| 2-1100 | H | C—CF3 | C—F | C—H | C—H | CF3 | C—H | C—SMe | H | H | H | H | 1 |
| 2-1101 | H | C—CF3 | C—F | C—H | C—H | CF3 | C—H | C—SOMe | H | H | MeCO | H | 1 |
| 2-1102 | H | C—CF3 | C—F | C—H | C—H | CF3 | C—H | C—SOMe | H | H | EtCO | H | 1 |
| 2-1103 | H | C—CF3 | C—F | C—H | C—H | CF3 | C—H | C—SOMe | H | H | CF3CH2CO | H | 1 |
| 2-1104 | H | C—CF3 | C—F | C—H | C—H | CF3 | C—H | C—SOMe | H | H | cyclo-PrCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1105 | H | C—CF3 | C—F | C—H | C—H | CF3 | C—H | C—SOMe | H | H | cyclo-PrCH2CO | H | 1 |
| 2-1106 | H | C—CF3 | C—F | C—H | C—H | CF3 | C—H | C—SOMe | H | H | CH3SCH2CO | H | 1 |
| 2-1107 | H | C—CF3 | C—F | C—H | C—H | CF3 | C—H | C—SOMe | H | H | CH3SOCH2CO | H | 1 |
| 2-1108 | H | C—CF3 | C—F | C—H | C—H | CF3 | C—H | C—SOMe | H | H | CH3SO2CH2CO | H | 1 |
| 2-1109 | H | C—CF3 | C—F | C—H | C—H | CF3 | C—H | C—SOMe | H | H | EtNHCO | H | 1 |
| 2-1110 | H | C—CF3 | C—F | C—H | C—H | CF3 | C—H | C—SOMe | Me | H | EtCO | H | 1 |
| 2-1111 | H | C—CF3 | C—F | C—H | C—H | CF3 | C—H | C—SOMe | Me | H | CF3CH2CO | H | 1 |
| 2-1112 | H | C—CF3 | C—F | C—H | C—H | CF3 | N | C—SOMe | H | H | EtCO | H | 1 |
| 2-1113 | H | C—CF3 | C—F | C—H | C—H | CF3 | N | C—SOMe | H | H | CF3CH2CO | H | 1 |
| 2-1114 | H | C—CF3 | C—F | C—H | C—H | CF3 | C—H | C—SO2Me | H | H | H | H | 1 |
| 2-1115 | H | C—CF3 | C—F | C—H | C—H | CF3 | C—H | C—SO2Me | H | H | MeCO | H | 1 |
| 2-1116 | H | C—CF3 | C—F | C—H | C—H | CF3 | C—H | C—SO2Me | H | H | EtCO | H | 1 |
| 2-1117 | H | C—CF3 | C—F | C—H | C—H | CF3 | C—H | C—SO2Me | H | H | CF3CH2CO | H | 1 |
| 2-1118 | H | C—CF3 | C—F | C—H | C—H | CF3 | C—H | C—SO2Me | H | H | cyclo-PrCO | H | 1 |
| 2-1119 | H | C—CF3 | C—F | C—H | C—H | CF3 | C—H | C—SO2Me | H | H | cyclo-PrCH2CO | H | 1 |
| 2-1120 | H | C—CF3 | C—F | C—H | C—H | CF3 | C—H | C—SO2Me | H | H | CH3SCH2CO | H | 1 |
| 2-1121 | H | C—CF3 | C—F | C—H | C—H | CF3 | C—H | C—SO2Me | H | H | CH3SOCH2CO | H | 1 |
| 2-1122 | H | C—CF3 | C—F | C—H | C—H | CF3 | C—H | C—SO2Me | H | H | CH3SO2CH2CO | H | 1 |
| 2-1123 | H | C—CF3 | C—F | C—H | C—H | CF3 | C—H | C—SO2Me | H | H | EtNHCO | H | 1 |
| 2-1124 | H | C—CF3 | C—F | C—H | C—H | CF3 | C—H | C—SO2Me | Me | H | CF3CH2CO | H | 1 |
| 2-1125 | H | C—CF3 | C—F | C—H | C—H | CF3 | C—H | C—SO2Me | Me | H | EtCO | H | 1 |
| 2-1126 | H | C—CF3 | C—F | C—H | C—H | CF3 | N | C—SO2Me | H | H | EtCO | H | 1 |
| 2-1127 | H | C—CF3 | C—F | C—H | C—H | CF3 | N | C—SO2Me | H | H | CF3CH2CO | H | 1 |
| 2-1128 | H | C—CF3 | C—F | C—H | C—H | CF3 | C—H | C—SCF3 | H | H | H | H | 1 |
| 2-1129 | H | C—CF3 | C—F | C—H | C—H | CF3 | C—H | C—SCF3 | H | H | MeCO | H | 1 |
| 2-1130 | H | C—CF3 | C—F | C—H | C—H | CF3 | C—H | C—SCF3 | H | H | EtCO | H | 1 |
| 2-1131 | H | C—CF3 | C—F | C—H | C—H | CF3 | C—H | C—SCF3 | H | H | CF3CH2CO | H | 1 |
| 2-1132 | H | C—CF3 | C—F | C—H | C—H | CF3 | C—H | C—SCF3 | H | H | cyclo-PrCO | H | 1 |
| 2-1133 | H | C—CF3 | C—F | C—H | C—H | CF3 | C—H | C—SCF3 | H | H | cyclo-PrCH2CO | H | 1 |
| 2-1134 | H | C—CF3 | C—F | C—H | C—H | CF3 | C—H | C—SCF3 | H | H | CH3SCH2CO | H | 1 |
| 2-1135 | H | C—CF3 | C—F | C—H | C—H | CF3 | C—H | C—SCF3 | H | H | CH3SOCH2CO | H | 1 |
| 2-1136 | H | C—CF3 | C—F | C—H | C—H | CF3 | C—H | C—SCF3 | H | H | CH3SO2CH2CO | H | 1 |
| 2-1137 | H | C—CF3 | C—F | C—H | C—H | CF3 | C—H | C—SCF3 | H | H | EtNHCO | H | 1 |
| 2-1138 | H | C—CF3 | C—F | C—H | C—H | CF3 | C—H | C—SCF3 | Me | H | EtCO | H | 1 |
| 2-1139 | H | C—CF3 | C—F | C—H | C—H | CF3 | C—H | C—SCF3 | Me | H | CF3CH2CO | H | 1 |
| 2-1140 | H | C—CF3 | C—F | C—H | C—H | CF3 | N | C—SCF3 | H | H | EtCO | H | 1 |
| 2-1141 | H | C—CF3 | C—F | C—H | C—H | CF3 | C—H | C—SCF3 | H | H | CF3CH2CO | H | 1 |
| 2-1142 | H | C—CF3 | C—F | C—H | C—H | CF3 | C—H | C—SOCF3 | H | H | H | H | 1 |
| 2-1143 | H | C—CF3 | C—F | C—H | C—H | CF3 | C—H | C—SOCF3 | H | H | MeCO | H | 1 |
| 2-1144 | H | C—CF3 | C—F | C—H | C—H | CF3 | C—H | C—SOCF3 | H | H | EtCO | H | 1 |
| 2-1145 | H | C—CF3 | C—F | C—H | C—H | CF3 | C—H | C—SOCF3 | H | H | CF3CH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1146 | H | C—CF3 | C—F | C—H | C—H | CF3 | C—H | C—SOCF3 | H | H | cyclo-PrCO | H | 1 |
| 2-1147 | H | C—CF3 | C—F | C—H | C—H | CF3 | C—H | C—SOCF3 | H | H | cyclo-PrCH2CO | H | 1 |
| 2-1148 | H | C—CF3 | C—F | C—H | C—H | CF3 | C—H | C—SOCF3 | H | H | CH3SCH2CO | H | 1 |
| 2-1149 | H | C—CF3 | C—F | C—H | C—H | CF3 | C—H | C—SOCF3 | H | H | CH3SOCH2CO | H | 1 |
| 2-1150 | H | C—CF3 | C—F | C—H | C—H | CF3 | C—H | C—SOCF3 | H | H | CH3SO2CH2CO | H | 1 |
| 2-1151 | H | C—CF3 | C—F | C—H | C—H | CF3 | C—H | C—SOCF3 | Me | H | EtNHCO | H | 1 |
| 2-1152 | H | C—CF3 | C—F | C—H | C—H | CF3 | C—H | C—SOCF3 | Me | H | EtCO | H | 1 |
| 2-1153 | H | C—CF3 | C—F | C—H | C—H | CF3 | C—H | C—SOCF3 | H | H | CF3CH2CO | H | 1 |
| 2-1154 | H | C—CF3 | C—F | C—H | C—H | CF3 | N | C—SOCF3 | H | H | EtCO | H | 1 |
| 2-1155 | H | C—CF3 | C—F | C—H | C—H | CF3 | N | C—SOCF3 | H | H | CF3CH2CO | H | 1 |
| 2-1156 | H | C—CF3 | C—F | C—H | C—H | CF3 | C—H | C—H | H | H | H | H | 1 |
| 2-1157 | H | C—CF3 | C—F | C—H | C—H | CF3 | C—H | C—H | H | H | MeCO | H | 1 |
| 2-1158 | H | C—CF3 | C—F | C—H | C—H | CF3 | C—H | C—H | H | H | EtCO | H | 1 |
| 2-1159 | H | C—CF3 | C—F | C—H | C—H | CF3 | C—H | C—H | H | H | CF3CH2CO | H | 1 |
| 2-1160 | H | C—CF3 | C—F | C—H | C—H | CF3 | C—H | C—H | H | H | cyclo-PrCO | H | 1 |
| 2-1161 | H | C—CF3 | C—F | C—H | C—H | CF3 | C—H | C—H | H | H | cyclo-PrCH2CO | H | 1 |
| 2-1162 | H | C—CF3 | C—F | C—H | C—H | CF3 | C—H | C—H | H | H | CH3SCH2CO | H | 1 |
| 2-1163 | H | C—CF3 | C—F | C—H | C—H | CF3 | C—H | C—H | H | H | CH3SOCH2CO | H | 1 |
| 2-1164 | H | C—CF3 | C—F | C—H | C—H | CF3 | C—H | C—H | H | H | CH3SO2CH2CO | H | 1 |
| 2-1165 | H | C—CF3 | C—F | C—H | C—H | CF3 | C—H | C—H | Me | H | EtNHCO | H | 1 |
| 2-1166 | H | C—CF3 | C—F | C—H | C—H | CF3 | C—H | C—H | Me | H | EtCO | H | 1 |
| 2-1167 | H | C—CF3 | C—F | C—H | C—H | CF3 | C—H | C—H | Me | H | CF3CH2CO | H | 1 |
| 2-1168 | H | C—CF3 | C—F | C—H | C—H | CF3 | N | C—H | H | H | EtCO | H | 1 |
| 2-1169 | H | C—CF3 | C—F | C—H | C—H | CF3 | N | C—H | H | H | CF3CH2CO | H | 1 |
| 2-1170 | H | C—CF3 | C—F | C—H | C—H | CF3 | C—H | C—F | H | H | H | H | 1 |
| 2-1171 | H | C—CF3 | C—F | C—H | C—H | CF3 | C—H | C—F | H | H | EtCO | H | 1 |
| 2-1172 | H | C—CF3 | C—F | C—H | C—H | CF3 | C—H | C—F | H | H | CF3CH2CO | H | 1 |
| 2-1173 | H | C—CF3 | C—F | C—H | C—H | CF3 | C—H | C—F | H | H | CH3SCH2CO | H | 1 |
| 2-1174 | H | C—CF3 | C—F | C—H | C—H | CF3 | C—H | C—F | H | H | H | H | 1 |
| 2-1175 | H | C—CF3 | C—F | C—H | C—H | CF3 | C—H | C—F | H | H | MeCO | H | 1 |
| 2-1176 | H | C—CF3 | C—F | C—H | C—H | CF3 | C—H | C—F | H | H | EtCO | H | 1 |
| 2-1177 | H | C—CF3 | C—F | C—H | C—H | CF3 | C—H | C—F | H | H | CF3CH2CO | H | 1 |
| 2-1178 | H | C—CF3 | C—F | C—H | C—H | CF3 | C—H | C—F | H | H | cyclo-PrCO | H | 1 |
| 2-1179 | H | C—CF3 | C—F | C—H | C—H | CF3 | C—H | C—F | H | H | cyclo-PrCH2CO | H | 1 |
| 2-1180 | H | C—CF3 | C—F | C—H | C—H | CF3 | C—H | C—F | H | H | CH3SCH2CO | H | 1 |
| 2-1181 | H | C—CF3 | C—F | C—H | C—H | CF3 | C—H | C—F | H | H | CH3SOCH2CO | H | 1 |
| 2-1182 | H | C—CF3 | C—F | C—H | C—H | CF3 | C—H | C—F | H | H | CH3SO2CH2CO | H | 1 |
| 2-1183 | H | C—CF3 | C—F | C—H | C—H | CF3 | C—H | C—F | Me | H | EtNHCO | H | 1 |
| 2-1184 | H | C—CF3 | C—F | C—H | C—H | CF3 | C—H | C—F | Me | H | EtCO | H | 1 |
| 2-1185 | H | C—CF3 | C—F | C—H | C—H | CF3 | C—H | C—F | Me | H | CF3CH2CO | H | 1 |
| 2-1186 | H | C—CF3 | C—F | C—H | C—H | CF3 | N | C—F | H | H | EtCO | H | 1 |

TABLE 2-1-continued

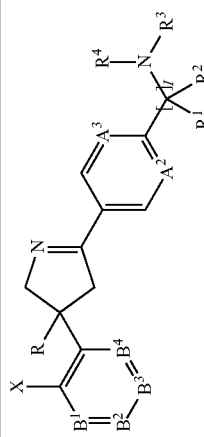

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1187 | H | C—CF3 | C—F | C—H | C—H | CF3 | N | C—F | H | H | CF3CH2CO | H | 1 |
| 2-1188 | H | C—CF3 | C—F | C—H | C—H | CF3 | C—H | C—I | H | H | H | H | 1 |
| 2-1189 | H | C—CF3 | C—F | C—H | C—H | CF3 | C—H | C—I | H | H | MeCO | H | 1 |
| 2-1190 | H | C—CF3 | C—F | C—H | C—H | CF3 | C—H | C—I | H | H | EtCO | H | 1 |
| 2-1191 | H | C—CF3 | C—F | C—H | C—H | CF3 | C—H | C—I | H | H | CF3CH2CO | H | 1 |
| 2-1192 | H | C—CF3 | C—F | C—H | C—H | CF3 | C—H | C—I | H | H | cyclo-PrCO | H | 1 |
| 2-1193 | H | C—CF3 | C—F | C—H | C—H | CF3 | C—H | C—I | H | H | cyclo-PrCH2CO | H | 1 |
| 2-1194 | H | C—CF3 | C—F | C—H | C—H | CF3 | C—H | C—I | H | H | CH3SCH2CO | H | 1 |
| 2-1195 | H | C—CF3 | C—F | C—H | C—H | CF3 | C—H | C—I | H | H | CH3SOCH2CO | H | 1 |
| 2-1196 | H | C—CF3 | C—F | C—H | C—H | CF3 | C—H | C—I | H | H | CH3SO2CH2CO | H | 1 |
| 2-1197 | H | C—CF3 | C—F | C—H | C—H | CF3 | C—H | C—I | H | H | EtNHCO | H | 1 |
| 2-1198 | H | C—CF3 | C—F | C—H | C—H | CF3 | C—H | C—I | Me | H | EtCO | H | 1 |
| 2-1199 | H | C—CF3 | C—F | C—H | C—H | CF3 | C—H | C—I | Me | H | CF3CH2CO | H | 1 |
| 2-1200 | H | C—CF3 | C—F | C—H | C—H | CF3 | C—H | C—I | H | H | EtCO | H | 1 |
| 2-1201 | H | C—CF3 | C—F | C—H | C—H | CF3 | C—H | C—I | H | H | CF3CH2CO | H | 1 |
| 2-1202 | H | C—CF3 | C—F | C—H | C—H | CF3 | N | C—NH2 | H | H | H | H | 1 |
| 2-1203 | H | C—CF3 | C—F | C—H | C—H | CF3 | N | C—NH2 | H | H | MeCO | H | 1 |
| 2-1204 | H | C—CF3 | C—F | C—H | C—H | CF3 | C—H | C—NH2 | H | H | EtCO | H | 1 |
| 2-1205 | H | C—CF3 | C—F | C—H | C—H | CF3 | C—H | C—NH2 | H | H | CF3CH2CO | H | 1 |
| 2-1206 | H | C—CF3 | C—F | C—H | C—H | CF3 | C—H | C—NH2 | H | H | cyclo-PrCO | H | 1 |
| 2-1207 | H | C—CF3 | C—F | C—H | C—H | CF3 | C—H | C—NH2 | H | H | cyclo-PrCH2CO | H | 1 |
| 2-1208 | H | C—CF3 | C—F | C—H | C—H | CF3 | C—H | C—NH2 | H | H | CH3SCH2CO | H | 1 |
| 2-1209 | H | C—CF3 | C—F | C—H | C—H | CF3 | C—H | C—NH2 | H | H | CH3SOCH2CO | H | 1 |
| 2-1210 | H | C—CF3 | C—F | C—H | C—H | CF3 | C—H | C—NH2 | H | H | CH3SO2CH2CO | H | 1 |
| 2-1211 | H | C—CF3 | C—F | C—H | C—H | CF3 | C—H | C—NH2 | H | H | EtNHCO | H | 1 |
| 2-1212 | H | C—CF3 | C—F | C—H | C—H | CF3 | C—H | C—NH2 | Me | H | EtCO | H | 1 |
| 2-1213 | H | C—CF3 | C—F | C—H | C—H | CF3 | C—H | C—NH2 | Me | H | CF3CH2CO | H | 1 |
| 2-1214 | H | C—CF3 | C—F | C—H | C—H | CF3 | N | C—NH2 | H | H | EtCO | H | 1 |
| 2-1215 | H | C—CF3 | C—F | C—H | C—H | CF3 | C—H | C—NH2 | H | H | CF3CH2CO | H | 1 |
| 2-1216 | H | C—CF3 | C—F | C—H | C—H | CF3 | C—H | C—NHAc | H | H | H | H | 1 |
| 2-1217 | H | C—CF3 | C—F | C—H | C—H | CF3 | C—H | C—NHAc | H | H | MeCO | H | 1 |
| 2-1218 | H | C—CF3 | C—F | C—H | C—H | CF3 | C—H | C—NHAc | H | H | EtCO | H | 1 |
| 2-1219 | H | C—CF3 | C—F | C—H | C—H | CF3 | C—H | C—NHAc | H | H | CF3CH2CO | H | 1 |
| 2-1220 | H | C—CF3 | C—F | C—H | C—H | CF3 | C—H | C—NHAc | H | H | cyclo-PrCO | H | 1 |
| 2-1221 | H | C—CF3 | C—F | C—H | C—H | CF3 | C—H | C—NHAc | H | H | cyclo-PrCH2CO | H | 1 |
| 2-1222 | H | C—CF3 | C—F | C—H | C—H | CF3 | C—H | C—NHAc | H | H | CH3SCH2CO | H | 1 |
| 2-1223 | H | C—CF3 | C—F | C—H | C—H | CF3 | C—H | C—NHAc | H | H | CH3SOCH2CO | H | 1 |
| 2-1224 | H | C—CF3 | C—F | C—H | C—H | CF3 | C—H | C—NHAc | H | H | CH3SO2CH2CO | H | 1 |
| 2-1225 | H | C—CF3 | C—F | C—H | C—H | CF3 | C—H | C—NHAc | H | H | EtNHCO | H | 1 |
| 2-1226 | H | C—CF3 | C—F | C—H | C—H | CF3 | C—H | C—NHAc | Me | H | EtCO | H | 1 |
| 2-1227 | H | C—CF3 | C—F | C—H | C—H | CF3 | C—H | C—NHAc | Me | H | CF3CH2CO | H | 1 |

TABLE 2-1-continued

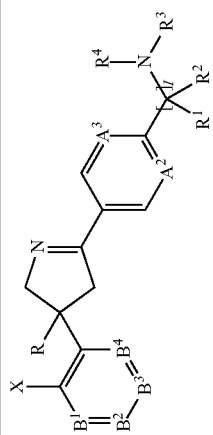

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1228 | H | C—CF3 | C—F | C—H | C—H | CF3 | N | C—NHAc | H | H | EtCO | H | 1 |
| 2-1229 | H | C—CF3 | C—F | C—H | C—H | CF3 | N | C—NHAc | H | H | CF3CH2CO | H | 1 |
| 2-1230 | H | C—CF3 | C—F | C—H | C—H | CF3 | C—H | C—NHCOCF3 | H | H | H | H | 1 |
| 2-1231 | H | C—CF3 | C—F | C—H | C—H | CF3 | C—H | C—NHCOCF3 | H | H | MeCO | H | 1 |
| 2-1232 | H | C—CF3 | C—F | C—H | C—H | CF3 | C—H | C—NHCOCF3 | H | H | EtCO | H | 1 |
| 2-1233 | H | C—CF3 | C—F | C—H | C—H | CF3 | C—H | C—NHCOCF3 | H | H | CF3CH2CO | H | 1 |
| 2-1234 | H | C—CF3 | C—F | C—H | C—H | CF3 | C—H | C—NHCOCF3 | H | H | cyclo-PrCO | H | 1 |
| 2-1235 | H | C—CF3 | C—F | C—H | C—H | CF3 | C—H | C—NHCOCF3 | H | H | cyclo-PrCH2CO | H | 1 |
| 2-1236 | H | C—CF3 | C—F | C—H | C—H | CF3 | C—H | C—NHCOCF3 | H | H | CH3SCH2CO | H | 1 |
| 2-1237 | H | C—CF3 | C—F | C—H | C—H | CF3 | C—H | C—NHCOCF3 | H | H | CH3SOCH2CO | H | 1 |
| 2-1238 | H | C—CF3 | C—F | C—H | C—H | CF3 | C—H | C—NHCOCF3 | H | H | CH3SO2CH2CO | H | 1 |
| 2-1239 | H | C—CF3 | C—F | C—H | C—H | CF3 | C—H | C—NHCOCF3 | H | H | EtNHCO | H | 1 |
| 2-1240 | H | C—CF3 | C—F | C—H | C—H | CF3 | C—H | C—NHCOCF3 | Me | H | EtCO | H | 1 |
| 2-1241 | H | C—CF3 | C—F | C—H | C—H | CF3 | C—H | C—NHCOCF3 | Me | H | CF3CH2CO | H | 1 |
| 2-1242 | H | C—CF3 | C—F | C—H | C—H | CF3 | N | C—CH2OAc | H | H | EtCO | H | 1 |
| 2-1243 | H | C—CF3 | C—F | C—H | C—H | CF3 | N | C—CH2OAc | H | H | CF3CH2CO | H | 1 |
| 2-1244 | H | C—CF3 | C—F | C—H | C—H | CF3 | C—H | C—CH2OAc | H | H | H | H | 1 |
| 2-1245 | H | C—CF3 | C—F | C—H | C—H | CF3 | C—H | C—CH2OAc | H | H | MeCO | H | 1 |
| 2-1246 | H | C—CF3 | C—F | C—H | C—H | CF3 | C—H | C—CH2OAc | H | H | EtCO | H | 1 |
| 2-1247 | H | C—CF3 | C—F | C—H | C—H | CF3 | C—H | C—CH2OAc | H | H | CF3CH2CO | H | 1 |
| 2-1248 | H | C—CF3 | C—F | C—H | C—H | CF3 | C—H | C—CH2OAc | H | H | cyclo-PrCO | H | 1 |
| 2-1249 | H | C—CF3 | C—F | C—H | C—H | CF3 | C—H | C—CH2OAc | H | H | cyclo-PrCH2CO | H | 1 |
| 2-1250 | H | C—CF3 | C—F | C—H | C—H | CF3 | C—H | C—CH2OAc | H | H | CH3SCH2CO | H | 1 |
| 2-1251 | H | C—CF3 | C—F | C—H | C—H | CF3 | C—H | C—CH2OAc | H | H | CH3SOCH2CO | H | 1 |
| 2-1252 | H | C—CF3 | C—F | C—H | C—H | CF3 | C—H | C—CH2OAc | H | H | CH3SO2CH2CO | H | 1 |
| 2-1253 | H | C—CF3 | C—F | C—H | C—H | CF3 | C—H | C—CH2OAc | H | H | EtNHCO | H | 1 |
| 2-1254 | H | C—CF3 | C—F | C—H | C—H | CF3 | C—H | C—CH2OAc | Me | H | EtCO | H | 1 |
| 2-1255 | H | C—CF3 | C—F | C—H | C—H | CF3 | C—H | C—CH2OAc | Me | H | CF3CH2CO | H | 1 |
| 2-1256 | H | C—CF3 | C—H | C—H | C—H | CF3 | N | C—CF3 | H | H | EtCO | H | 1 |
| 2-1257 | H | C—CF3 | C—H | C—H | C—H | CF3 | N | C—CF3 | H | H | CF3CH2CO | H | 1 |
| 2-1258 | H | C—CF3 | C—H | C—H | C—H | CF3 | C—H | C—CF3 | H | H | H | H | 1 |
| 2-1259 | H | C—CF3 | C—H | C—H | C—H | CF3 | C—H | C—CF3 | H | H | EtNHCO | H | 1 |
| 2-1260 | H | C—CF3 | C—H | C—H | C—H | CF3 | C—H | C—CF3 | H | H | cyclo-PrCO | H | 1 |
| 2-1261 | H | C—CF3 | C—H | C—H | C—H | CF3 | C—H | C—CF3 | H | H | cyclo-PrCH2CO | H | 1 |
| 2-1262 | H | C—CF3 | C—H | C—H | C—H | CF3 | C—H | C—CF3 | H | H | CH3SCH2CO | H | 1 |
| 2-1263 | H | C—CF3 | C—H | C—H | C—H | CF3 | C—H | C—CF3 | H | H | CH3SOCH2CO | H | 1 |
| 2-1264 | H | C—CF3 | C—H | C—H | C—H | CF3 | C—H | C—CF3 | H | H | CH3SO2CH2CO | H | 1 |
| 2-1265 | H | C—CF3 | C—H | C—H | C—H | CF3 | C—H | C—CF3 | Me | H | H | H | 1 |
| 2-1266 | H | C—CF3 | C—H | C—H | C—H | CF3 | C—H | C—CF3 | Me | H | EtCO | H | 1 |
| 2-1267 | H | C—CF3 | C—H | C—H | C—H | CF3 | C—H | C—CF3 | Me | H | CF3CH2CO | H | 1 |
| 2-1268 | H | C—CF3 | C—H | C—H | C—H | CF3 | C—H | C—CF3 | Me | H | CH3SCH2CO | H | 1 |

TABLE 2-1-continued

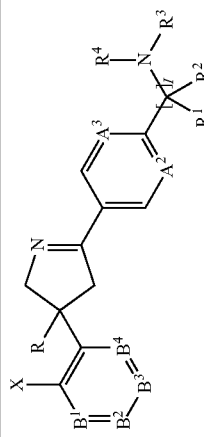

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1269 | H | C—CF3 | C—H | C—H | C—H | CF3 | N | C—CF3 | H | H | H | H | 1 |
| 2-1270 | H | C—CF3 | C—H | C—H | C—H | CF3 | N | C—CF3 | H | H | EtCO | H | 1 |
| 2-1271 | H | C—CF3 | C—H | C—H | C—H | CF3 | N | C—CF3 | H | H | CF3CH2CO | H | 1 |
| 2-1272 | H | C—CF3 | C—H | C—H | C—H | CF3 | N | C—CF3 | H | H | CH3SCH2CO | H | 1 |
| 2-1273 | H | C—CF3 | C—H | C—H | C—H | CF3 | C—H | C—Cl | H | H | H | H | 1 |
| 2-1274 | H | C—CF3 | C—H | C—H | C—H | CF3 | C—H | C—Cl | H | H | MeCO | H | 1 |
| 2-1275 | H | C—CF3 | C—H | C—H | C—H | CF3 | C—H | C—Cl | H | H | EtCO | H | 1 |
| 2-1276 | H | C—CF3 | C—H | C—H | C—H | CF3 | C—H | C—Cl | H | H | CF3CH2CO | H | 1 |
| 2-1277 | H | C—CF3 | C—H | C—H | C—H | CF3 | C—H | C—Cl | H | H | cyclo-PrCO | H | 1 |
| 2-1278 | H | C—CF3 | C—H | C—H | C—H | CF3 | C—H | C—Cl | H | H | cyclo-PrCH2CO | H | 1 |
| 2-1279 | H | C—CF3 | C—H | C—H | C—H | CF3 | C—H | C—Cl | H | H | CH3SCH2CO | H | 1 |
| 2-1280 | H | C—CF3 | C—H | C—H | C—H | CF3 | C—H | C—Cl | H | H | CH3SOCH2CO | H | 1 |
| 2-1281 | H | C—CF3 | C—H | C—H | C—H | CF3 | C—H | C—Cl | H | H | CH3SO2CH2CO | H | 1 |
| 2-1282 | H | C—CF3 | C—H | C—H | C—H | CF3 | C—H | C—Cl | H | H | EtNHCO | H | 1 |
| 2-1283 | H | C—CF3 | C—H | C—H | C—H | CF3 | C—H | C—Cl | Me | H | H | H | 1 |
| 2-1284 | H | C—CF3 | C—H | C—H | C—H | CF3 | C—H | C—Cl | Me | H | CF3CH2CO | H | 1 |
| 2-1285 | H | C—CF3 | C—H | C—H | C—H | CF3 | C—H | C—Cl | Me | H | CH3SCH2CO | H | 1 |
| 2-1286 | H | C—CF3 | C—H | C—H | C—H | CF3 | C—H | C—Cl | H | H | CF3CH2CO | H | 1 |
| 2-1287 | H | C—CF3 | C—H | C—H | C—H | CF3 | C—H | C—Cl | H | H | H | H | 1 |
| 2-1288 | H | C—CF3 | C—H | C—H | C—H | CF3 | C—H | C—Cl | H | H | CF3CH2CO | H | 1 |
| 2-1289 | H | C—CF3 | C—H | C—H | C—H | CF3 | C—H | C—Cl | H | H | CH3SCH2CO | H | 1 |
| 2-1290 | H | C—CF3 | C—H | C—H | C—H | CF3 | C—H | C—Cl | H | H | cyclo-PrCO | H | 1 |
| 2-1291 | H | C—CF3 | C—H | C—H | C—H | CF3 | C—H | C—Cl | H | H | cyclo-PrCH2CO | H | 1 |
| 2-1292 | H | C—CF3 | C—H | C—H | C—H | CF3 | C—H | C—Br | H | H | H | H | 1 |
| 2-1293 | H | C—CF3 | C—H | C—H | C—H | CF3 | C—H | C—Br | H | H | CF3CH2CO | H | 1 |
| 2-1294 | H | C—CF3 | C—H | C—H | C—H | CF3 | C—H | C—Br | H | H | CH3SCH2CO | H | 1 |
| 2-1295 | H | C—CF3 | C—H | C—H | C—H | CF3 | C—H | C—Br | H | H | H | H | 1 |
| 2-1296 | H | C—CF3 | C—H | C—H | C—H | CF3 | C—H | C—Br | H | H | CF3CH2CO | H | 1 |
| 2-1297 | H | C—CF3 | C—H | C—H | C—H | CF3 | C—H | C—Br | H | H | cyclo-PrCO | H | 1 |
| 2-1298 | H | C—CF3 | C—H | C—H | C—H | CF3 | C—H | C—Br | H | H | cyclo-PrCH2CO | H | 1 |
| 2-1299 | H | C—CF3 | C—H | C—H | C—H | CF3 | C—H | C—Br | H | H | CH3SCH2CO | H | 1 |
| 2-1300 | H | C—CF3 | C—H | C—H | C—H | CF3 | C—H | C—Br | H | H | CH3SO2CH2CO | H | 1 |
| 2-1301 | H | C—CF3 | C—H | C—H | C—H | CF3 | C—H | C—Br | H | H | EtNHCO | H | 1 |
| 2-1302 | H | C—CF3 | C—H | C—H | C—H | CF3 | N | C—Br | Me | H | EtCO | H | 1 |
| 2-1303 | H | C—CF3 | C—H | C—H | C—H | CF3 | N | C—Br | Me | H | CF3CH2CO | H | 1 |
| 2-1304 | H | C—CF3 | C—H | C—H | C—H | CF3 | N | C—Br | Me | H | CH3SCH2CO | H | 1 |
| 2-1305 | H | C—CF3 | C—H | C—H | C—H | CF3 | N | C—Br | H | H | H | H | 1 |
| 2-1306 | H | C—CF3 | C—H | C—H | C—H | CF3 | N | C—Br | H | H | EtCO | H | 1 |
| 2-1307 | H | C—CF3 | C—H | C—H | C—H | CF3 | N | C—Br | H | H | CF3CH2CO | H | 1 |
| 2-1308 | H | C—CF3 | C—H | C—H | C—H | CF3 | C—H | C—CN | H | H | CH3SCH2CO | H | 1 |
| 2-1309 | H | C—CF3 | C—H | C—H | C—H | CF3 | C—H | C—CN | H | H | MeCO | H | 1 |

TABLE 2-1-continued

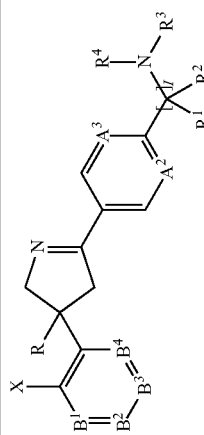

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1310 | H | C—CF3 | C—H | C—H | C—H | CF3 | C—H | C—CN | H | H | EtCO | H | 1 |
| 2-1311 | H | C—CF3 | C—H | C—H | C—H | CF3 | C—H | C—CN | H | H | CF3CH2CO | H | 1 |
| 2-1312 | H | C—CF3 | C—H | C—H | C—H | CF3 | C—H | C—CN | H | H | cyclo-PrCO | H | 1 |
| 2-1313 | H | C—CF3 | C—H | C—H | C—H | CF3 | C—H | C—CN | H | H | cyclo-PrCH2CO | H | 1 |
| 2-1314 | H | C—CF3 | C—H | C—H | C—H | CF3 | C—H | C—CN | H | H | CH3SCH2CO | H | 1 |
| 2-1315 | H | C—CF3 | C—H | C—H | C—H | CF3 | C—H | C—CN | H | H | CH3SOCH2CO | H | 1 |
| 2-1316 | H | C—CF3 | C—H | C—H | C—H | CF3 | C—H | C—CN | H | H | CH3SO2CH2CO | H | 1 |
| 2-1317 | H | C—CF3 | C—H | C—H | C—H | CF3 | C—H | C—CN | H | H | EtNHCO | H | 1 |
| 2-1318 | H | C—CF3 | C—H | C—H | C—H | CF3 | C—H | C—CN | Me | H | EtCO | H | 1 |
| 2-1319 | H | C—CF3 | C—H | C—H | C—H | CF3 | C—H | C—CN | Me | H | CF3CH2CO | H | 1 |
| 2-1320 | H | C—CF3 | C—H | C—H | C—H | CF3 | N | C—CN | H | H | EtCO | H | 1 |
| 2-1321 | H | C—CF3 | C—H | C—H | C—H | CF3 | C—H | N | H | H | EtCO | H | 1 |
| 2-1322 | H | C—CF3 | C—H | C—H | C—H | CF3 | C—H | C—CN | H | H | CF3CH2CO | H | 1 |
| 2-1323 | H | C—CF3 | C—H | C—H | C—H | CF3 | C—H | C—Me | H | H | H | H | 1 |
| 2-1324 | H | C—CF3 | C—H | C—H | C—H | CF3 | C—H | C—Me | H | H | MeCO | H | 1 |
| 2-1325 | H | C—CF3 | C—H | C—H | C—H | CF3 | C—H | C—Me | H | H | EtCO | H | 1 |
| 2-1326 | H | C—CF3 | C—H | C—H | C—H | CF3 | C—H | C—Me | H | H | cyclo-PrCO | H | 1 |
| 2-1327 | H | C—CF3 | C—H | C—H | C—H | CF3 | C—H | C—Me | H | H | cyclo-PrCH2CO | H | 1 |
| 2-1328 | H | C—CF3 | C—H | C—H | C—H | CF3 | C—H | C—Me | H | H | CH3SCH2CO | H | 1 |
| 2-1329 | H | C—CF3 | C—H | C—H | C—H | CF3 | C—H | C—Me | H | H | CH3SOCH2CO | H | 1 |
| 2-1330 | H | C—CF3 | C—H | C—H | C—H | CF3 | C—H | C—Me | H | H | CH3SO2CH2CO | H | 1 |
| 2-1331 | H | C—CF3 | C—H | C—H | C—H | CF3 | C—H | C—Me | H | H | EtNHCO | H | 1 |
| 2-1332 | H | C—CF3 | C—H | C—H | C—H | CF3 | C—H | C—Me | Me | H | EtCO | H | 1 |
| 2-1333 | H | C—CF3 | C—H | C—H | C—H | CF3 | C—H | C—Me | Me | H | CF3CH2CO | H | 1 |
| 2-1334 | H | C—CF3 | C—H | C—H | C—H | CF3 | N | C—Me | H | H | EtCO | H | 1 |
| 2-1335 | H | C—CF3 | C—H | C—H | C—H | CF3 | C—H | N | H | H | CF3CH2CO | H | 1 |
| 2-1336 | H | C—CF3 | C—H | C—H | C—H | CF3 | C—H | C—NO2 | H | H | H | H | 1 |
| 2-1337 | H | C—CF3 | C—H | C—H | C—H | CF3 | C—H | C—NO2 | H | H | MeCO | H | 1 |
| 2-1338 | H | C—CF3 | C—H | C—H | C—H | CF3 | C—H | C—NO2 | H | H | EtCO | H | 1 |
| 2-1339 | H | C—CF3 | C—H | C—H | C—H | CF3 | C—H | C—NO2 | H | H | CF3CH2CO | H | 1 |
| 2-1340 | H | C—CF3 | C—H | C—H | C—H | CF3 | C—H | C—NO2 | H | H | cyclo-PrCO | H | 1 |
| 2-1341 | H | C—CF3 | C—H | C—H | C—H | CF3 | C—H | C—NO2 | H | H | cyclo-PrCH2CO | H | 1 |
| 2-1342 | H | C—CF3 | C—H | C—H | C—H | CF3 | C—H | C—NO2 | H | H | CH3SCH2CO | H | 1 |
| 2-1343 | H | C—CF3 | C—H | C—H | C—H | CF3 | C—H | C—NO2 | H | H | CH3SOCH2CO | H | 1 |
| 2-1344 | H | C—CF3 | C—H | C—H | C—H | CF3 | C—H | C—NO2 | H | H | CH3SO2CH2CO | H | 1 |
| 2-1345 | H | C—CF3 | C—H | C—H | C—H | CF3 | C—H | C—NO2 | H | H | EtNHCO | H | 1 |
| 2-1346 | H | C—CF3 | C—H | C—H | C—H | CF3 | C—H | C—NO2 | Me | H | EtCO | H | 1 |
| 2-1347 | H | C—CF3 | C—H | C—H | C—H | CF3 | C—H | C—NO2 | Me | H | CF3CH2CO | H | 1 |
| 2-1348 | H | C—CF3 | C—H | C—H | C—H | CF3 | N | C—NO2 | H | H | EtCO | H | 1 |
| 2-1349 | H | C—CF3 | C—H | C—H | C—H | CF3 | N | C—NO2 | H | H | CF3CH2CO | H | 1 |
| 2-1350 | H | C—CF3 | C—H | C—H | C—H | CF3 | C—H | C—SMe | H | H | H | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1351 | H | C—CF3 | C—H | C—H | C—H | CF3 | C—H | C—SMe | H | H | MeCO | H | 1 |
| 2-1352 | H | C—CF3 | C—H | C—H | C—H | CF3 | C—H | C—SMe | H | H | EtCO | H | 1 |
| 2-1353 | H | C—CF3 | C—H | C—H | C—H | CF3 | C—H | C—SMe | H | H | CF3CH2CO | H | 1 |
| 2-1354 | H | C—CF3 | C—H | C—H | C—H | CF3 | C—H | C—SMe | H | H | cyclo-PrCO | H | 1 |
| 2-1355 | H | C—CF3 | C—H | C—H | C—H | CF3 | C—H | C—SMe | H | H | cyclo-PrCH2CO | H | 1 |
| 2-1356 | H | C—CF3 | C—H | C—H | C—H | CF3 | C—H | C—SMe | H | H | CH3SCH2CO | H | 1 |
| 2-1357 | H | C—CF3 | C—H | C—H | C—H | CF3 | C—H | C—SMe | H | H | CH3SOCH2CO | H | 1 |
| 2-1358 | H | C—CF3 | C—H | C—H | C—H | CF3 | C—H | C—SMe | H | H | CH3SO2CH2CO | H | 1 |
| 2-1359 | H | C—CF3 | C—H | C—H | C—H | CF3 | C—H | C—SMe | H | H | EtNHCO | H | 1 |
| 2-1360 | H | C—CF3 | C—H | C—H | C—H | CF3 | C—H | C—SMe | Me | H | EtCO | H | 1 |
| 2-1361 | H | C—CF3 | C—H | C—H | C—H | CF3 | C—H | C—SMe | Me | H | CF3CH2CO | H | 1 |
| 2-1362 | H | C—CF3 | C—H | C—H | C—H | CF3 | N | C—SMe | H | H | EtCO | H | 1 |
| 2-1363 | H | C—CF3 | C—H | C—H | C—H | CF3 | N | C—SMe | H | H | CF3CH2CO | H | 1 |
| 2-1364 | H | C—CF3 | C—H | C—H | C—H | CF3 | C—H | C—SOMe | H | H | H | H | 1 |
| 2-1365 | H | C—CF3 | C—H | C—H | C—H | CF3 | C—H | C—SOMe | H | H | MeCO | H | 1 |
| 2-1366 | H | C—CF3 | C—H | C—H | C—H | CF3 | C—H | C—SOMe | H | H | EtCO | H | 1 |
| 2-1367 | H | C—CF3 | C—H | C—H | C—H | CF3 | C—H | C—SOMe | H | H | CF3CH2CO | H | 1 |
| 2-1368 | H | C—CF3 | C—H | C—H | C—H | CF3 | C—H | C—SOMe | H | H | cyclo-PrCO | H | 1 |
| 2-1369 | H | C—CF3 | C—H | C—H | C—H | CF3 | C—H | C—SOMe | H | H | cyclo-PrCH2CO | H | 1 |
| 2-1370 | H | C—CF3 | C—H | C—H | C—H | CF3 | C—H | C—SOMe | H | H | CH3SCH2CO | H | 1 |
| 2-1371 | H | C—CF3 | C—H | C—H | C—H | CF3 | C—H | C—SOMe | H | H | CH3SOCH2CO | H | 1 |
| 2-1372 | H | C—CF3 | C—H | C—H | C—H | CF3 | C—H | C—SOMe | H | H | CH3SO2CH2CO | H | 1 |
| 2-1373 | H | C—CF3 | C—H | C—H | C—H | CF3 | C—H | C—SOMe | H | H | EtNHCO | H | 1 |
| 2-1374 | H | C—CF3 | C—H | C—H | C—H | CF3 | C—H | C—SOMe | Me | H | EtCO | H | 1 |
| 2-1375 | H | C—CF3 | C—H | C—H | C—H | CF3 | C—H | C—SOMe | Me | H | CF3CH2CO | H | 1 |
| 2-1376 | H | C—CF3 | C—H | C—H | C—H | CF3 | N | C—SOMe | H | H | EtCO | H | 1 |
| 2-1377 | H | C—CF3 | C—H | C—H | C—H | CF3 | N | C—SOMe | H | H | CF3CH2CO | H | 1 |
| 2-1378 | H | C—CF3 | C—H | C—H | C—H | CF3 | C—H | C—SO2Me | H | H | H | H | 1 |
| 2-1379 | H | C—CF3 | C—H | C—H | C—H | CF3 | C—H | C—SO2Me | H | H | MeCO | H | 1 |
| 2-1380 | H | C—CF3 | C—H | C—H | C—H | CF3 | C—H | C—SO2Me | H | H | EtCO | H | 1 |
| 2-1381 | H | C—CF3 | C—H | C—H | C—H | CF3 | C—H | C—SO2Me | H | H | CF3CH2CO | H | 1 |
| 2-1382 | H | C—CF3 | C—H | C—H | C—H | CF3 | C—H | C—SO2Me | H | H | cyclo-PrCO | H | 1 |
| 2-1383 | H | C—CF3 | C—H | C—H | C—H | CF3 | C—H | C—SO2Me | H | H | cyclo-PrCH2CO | H | 1 |
| 2-1384 | H | C—CF3 | C—H | C—H | C—H | CF3 | C—H | C—SO2Me | H | H | CH3SCH2CO | H | 1 |
| 2-1385 | H | C—CF3 | C—H | C—H | C—H | CF3 | C—H | C—SO2Me | H | H | CH3SOCH2CO | H | 1 |
| 2-1386 | H | C—CF3 | C—H | C—H | C—H | CF3 | C—H | C—SO2Me | H | H | CH3SO2CH2CO | H | 1 |
| 2-1387 | H | C—CF3 | C—H | C—H | C—H | CF3 | C—H | C—SO2Me | H | H | EtNHCO | H | 1 |
| 2-1388 | H | C—CF3 | C—H | C—H | C—H | CF3 | C—H | C—SO2Me | Me | H | EtCO | H | 1 |
| 2-1389 | H | C—CF3 | C—H | C—H | C—H | CF3 | C—H | C—SO2Me | Me | H | CF3CH2CO | H | 1 |
| 2-1390 | H | C—CF3 | C—H | C—H | C—H | CF3 | N | C—SO2Me | H | H | EtCO | H | 1 |
| 2-1391 | H | C—CF3 | C—H | C—H | C—H | CF3 | N | C—SO2Me | H | H | CF3CH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1392 | H | C—CF3 | C—H | C—H | C—H | CF3 | C—H | C—SCF3 | H | H | H | H | 1 |
| 2-1393 | H | C—CF3 | C—H | C—H | C—H | CF3 | C—H | C—SCF3 | H | H | MeCO | H | 1 |
| 2-1394 | H | C—CF3 | C—H | C—H | C—H | CF3 | C—H | C—SCF3 | H | H | EtCO | H | 1 |
| 2-1395 | H | C—CF3 | C—H | C—H | C—H | CF3 | C—H | C—SCF3 | H | H | CF3CH2CO | H | 1 |
| 2-1396 | H | C—CF3 | C—H | C—H | C—H | CF3 | C—H | C—SCF3 | H | H | cyclo-PrCO | H | 1 |
| 2-1397 | H | C—CF3 | C—H | C—H | C—H | CF3 | C—H | C—SCF3 | H | H | cyclo-PrCH2CO | H | 1 |
| 2-1398 | H | C—CF3 | C—H | C—H | C—H | CF3 | C—H | C—SCF3 | H | H | CH3SCH2CO | H | 1 |
| 2-1399 | H | C—CF3 | C—H | C—H | C—H | CF3 | C—H | C—SCF3 | H | H | CH3SOCH2CO | H | 1 |
| 2-1400 | H | C—CF3 | C—H | C—H | C—H | CF3 | C—H | C—SCF3 | H | H | CH3SO2CH2CO | H | 1 |
| 2-1401 | H | C—CF3 | C—H | C—H | C—H | CF3 | C—H | C—SCF3 | H | H | EtNHCO | H | 1 |
| 2-1402 | H | C—CF3 | C—H | C—H | C—H | CF3 | C—H | C—SCF3 | Me | H | EtCO | H | 1 |
| 2-1403 | H | C—CF3 | C—H | C—H | C—H | CF3 | C—H | C—SCF3 | Me | H | CF3CH2CO | H | 1 |
| 2-1404 | H | C—CF3 | C—H | C—H | C—H | CF3 | N | C—SCF3 | H | H | EtCO | H | 1 |
| 2-1405 | H | C—CF3 | C—H | C—H | C—H | CF3 | N | C—SCF3 | H | H | CF3CH2CO | H | 1 |
| 2-1406 | H | C—CF3 | C—H | C—H | C—H | CF3 | C—H | C—SOCF3 | H | H | H | H | 1 |
| 2-1407 | H | C—CF3 | C—H | C—H | C—H | CF3 | C—H | C—SOCF3 | H | H | MeCO | H | 1 |
| 2-1408 | H | C—CF3 | C—H | C—H | C—H | CF3 | C—H | C—SOCF3 | H | H | EtCO | H | 1 |
| 2-1409 | H | C—CF3 | C—H | C—H | C—H | CF3 | C—H | C—SOCF3 | H | H | CF3CH2CO | H | 1 |
| 2-1410 | H | C—CF3 | C—H | C—H | C—H | CF3 | C—H | C—SOCF3 | H | H | cyclo-PrCO | H | 1 |
| 2-1411 | H | C—CF3 | C—H | C—H | C—H | CF3 | C—H | C—SOCF3 | H | H | cyclo-PrCH2CO | H | 1 |
| 2-1412 | H | C—CF3 | C—H | C—H | C—H | CF3 | C—H | C—SOCF3 | H | H | CH3SCH2CO | H | 1 |
| 2-1413 | H | C—CF3 | C—H | C—H | C—H | CF3 | C—H | C—SOCF3 | H | H | CH3SOCH2CO | H | 1 |
| 2-1414 | H | C—CF3 | C—H | C—H | C—H | CF3 | C—H | C—SOCF3 | H | H | CH3SO2CH2CO | H | 1 |
| 2-1415 | H | C—CF3 | C—H | C—H | C—H | CF3 | C—H | C—SOCF3 | H | H | EtNHCO | H | 1 |
| 2-1416 | H | C—CF3 | C—H | C—H | C—H | CF3 | C—H | C—SOCF3 | Me | H | EtCO | H | 1 |
| 2-1417 | H | C—CF3 | C—H | C—H | C—H | CF3 | C—H | C—SOCF3 | Me | H | CF3CH2CO | H | 1 |
| 2-1418 | H | C—CF3 | C—H | C—H | C—H | CF3 | N | C—SOCF3 | H | H | EtCO | H | 1 |
| 2-1419 | H | C—CF3 | C—H | C—H | C—H | CF3 | N | C—SOCF3 | H | H | CF3CH2CO | H | 1 |
| 2-1420 | H | C—CF3 | C—H | C—H | C—H | CF3 | C—H | C—H | H | H | H | H | 1 |
| 2-1421 | H | C—CF3 | C—H | C—H | C—H | CF3 | C—H | C—H | H | H | MeCO | H | 1 |
| 2-1422 | H | C—CF3 | C—H | C—H | C—H | CF3 | C—H | C—H | H | H | EtCO | H | 1 |
| 2-1423 | H | C—CF3 | C—H | C—H | C—H | CF3 | C—H | C—H | H | H | CF3CH2CO | H | 1 |
| 2-1424 | H | C—CF3 | C—H | C—H | C—H | CF3 | C—H | C—H | H | H | cyclo-PrCO | H | 1 |
| 2-1425 | H | C—CF3 | C—H | C—H | C—H | CF3 | C—H | C—H | H | H | cyclo-PrCH2CO | H | 1 |
| 2-1426 | H | C—CF3 | C—H | C—H | C—H | CF3 | C—H | C—H | H | H | CH3SCH2CO | H | 1 |
| 2-1427 | H | C—CF3 | C—H | C—H | C—H | CF3 | C—H | C—H | H | H | CH3SOCH2CO | H | 1 |
| 2-1428 | H | C—CF3 | C—H | C—H | C—H | CF3 | C—H | C—H | H | H | CH3SO2CH2CO | H | 1 |
| 2-1429 | H | C—CF3 | C—H | C—H | C—H | CF3 | C—H | C—H | H | H | EtNHCO | H | 1 |
| 2-1430 | H | C—CF3 | C—H | C—H | C—H | CF3 | C—H | C—H | Me | H | H | H | 1 |
| 2-1431 | H | C—CF3 | C—H | C—H | C—H | CF3 | C—H | C—H | Me | H | EtCO | H | 1 |
| 2-1432 | H | C—CF3 | C—H | C—H | C—H | CF3 | C—H | C—H | Me | H | CF3CH2CO | H | 1 |

TABLE 2-1-continued

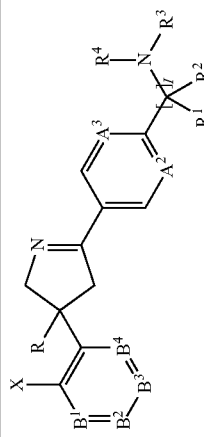

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1433 | H | C—CF3 | C—H | C—H | C—H | CF3 | C—H | C—H | Me | H | CH3SCH2CO | H | 1 |
| 2-1434 | H | C—CF3 | C—H | C—H | C—H | CF3 | N | C—H | H | H | H | H | 1 |
| 2-1435 | H | C—CF3 | C—H | C—H | C—H | CF3 | N | C—H | H | H | EtCO | H | 1 |
| 2-1436 | H | C—CF3 | C—H | C—H | C—H | CF3 | N | C—H | H | H | CF3CH2CO | H | 1 |
| 2-1437 | H | C—CF3 | C—H | C—H | C—H | CF3 | C—H | C—H | H | H | CH3SCH2CO | H | 1 |
| 2-1438 | H | C—CF3 | C—H | C—H | C—H | CF3 | C—H | C—F | H | H | H | H | 1 |
| 2-1439 | H | C—CF3 | C—H | C—H | C—H | CF3 | C—H | C—F | H | H | MeCO | H | 1 |
| 2-1440 | H | C—CF3 | C—H | C—H | C—H | CF3 | C—H | C—F | H | H | EtCO | H | 1 |
| 2-1441 | H | C—CF3 | C—H | C—H | C—H | CF3 | C—H | C—F | H | H | CF3CH2CO | H | 1 |
| 2-1442 | H | C—CF3 | C—H | C—H | C—H | CF3 | C—H | C—F | H | H | cyclo-PrCO | H | 1 |
| 2-1443 | H | C—CF3 | C—H | C—H | C—H | CF3 | C—H | C—F | H | H | cyclo-PrCH2CO | H | 1 |
| 2-1444 | H | C—CF3 | C—H | C—H | C—H | CF3 | C—H | C—F | H | H | CH3SCH2CO | H | 1 |
| 2-1445 | H | C—CF3 | C—H | C—H | C—H | CF3 | C—H | C—F | H | H | CH3SOCH2CO | H | 1 |
| 2-1446 | H | C—CF3 | C—H | C—H | C—H | CF3 | C—H | C—F | H | H | CH3SO2CH2CO | H | 1 |
| 2-1447 | H | C—CF3 | C—H | C—H | C—H | CF3 | C—H | C—F | H | H | EtNHCO | H | 1 |
| 2-1448 | H | C—CF3 | C—H | C—H | C—H | CF3 | C—H | C—F | Me | H | EtCO | H | 1 |
| 2-1449 | H | C—CF3 | C—H | C—H | C—H | CF3 | C—H | C—F | Me | H | CF3CH2CO | H | 1 |
| 2-1450 | H | C—CF3 | C—H | C—H | C—H | CF3 | C—H | C—I | H | H | EtCO | H | 1 |
| 2-1451 | H | C—CF3 | C—H | C—H | C—H | CF3 | C—H | C—I | H | H | CF3CH2CO | H | 1 |
| 2-1452 | H | C—CF3 | C—H | C—H | C—H | CF3 | C—H | C—I | H | H | H | H | 1 |
| 2-1453 | H | C—CF3 | C—H | C—H | C—H | CF3 | C—H | C—I | H | H | MeCO | H | 1 |
| 2-1454 | H | C—CF3 | C—H | C—H | C—H | CF3 | C—H | C—I | H | H | EtCO | H | 1 |
| 2-1455 | H | C—CF3 | C—H | C—H | C—H | CF3 | C—H | C—I | H | H | CF3CH2CO | H | 1 |
| 2-1456 | H | C—CF3 | C—H | C—H | C—H | CF3 | C—H | C—I | H | H | cyclo-PrCO | H | 1 |
| 2-1457 | H | C—CF3 | C—H | C—H | C—H | CF3 | C—H | C—I | H | H | cyclo-PrCH2CO | H | 1 |
| 2-1458 | H | C—CF3 | C—H | C—H | C—H | CF3 | C—H | C—I | H | H | CH3SCH2CO | H | 1 |
| 2-1459 | H | C—CF3 | C—H | C—H | C—H | CF3 | C—H | C—I | H | H | CH3SOCH2CO | H | 1 |
| 2-1460 | H | C—CF3 | C—H | C—H | C—H | CF3 | C—H | C—I | H | H | CH3SO2CH2CO | H | 1 |
| 2-1461 | H | C—CF3 | C—H | C—H | C—H | CF3 | C—H | C—I | H | H | EtNHCO | H | 1 |
| 2-1462 | H | C—CF3 | C—H | C—H | C—H | CF3 | C—H | C—I | Me | H | EtCO | H | 1 |
| 2-1463 | H | C—CF3 | C—H | C—H | C—H | CF3 | N | C—I | Me | H | CF3CH2CO | H | 1 |
| 2-1464 | H | C—CF3 | C—H | C—H | C—H | CF3 | N | C—I | H | H | EtCO | H | 1 |
| 2-1465 | H | C—CF3 | C—H | C—H | C—H | CF3 | N | C—I | H | H | CF3CH2CO | H | 1 |
| 2-1466 | H | C—CF3 | C—H | C—H | C—H | CF3 | C—H | C—NH2 | H | H | H | H | 1 |
| 2-1467 | H | C—CF3 | C—H | C—H | C—H | CF3 | C—H | C—NH2 | H | H | MeCO | H | 1 |
| 2-1468 | H | C—CF3 | C—H | C—H | C—H | CF3 | C—H | C—NH2 | H | H | EtCO | H | 1 |
| 2-1469 | H | C—CF3 | C—H | C—H | C—H | CF3 | C—H | C—NH2 | H | H | cyclo-PrCO | H | 1 |
| 2-1470 | H | C—CF3 | C—H | C—H | C—H | CF3 | C—H | C—NH2 | H | H | cyclo-PrCH2CO | H | 1 |
| 2-1471 | H | C—CF3 | C—H | C—H | C—H | CF3 | C—H | C—NH2 | H | H | CH3SCH2CO | H | 1 |
| 2-1472 | H | C—CF3 | C—H | C—H | C—H | CF3 | C—H | C—NH2 | H | H | CH3SOCH2CO | H | 1 |
| 2-1473 | H | C—CF3 | C—H | C—H | C—H | CF3 | C—H | C—NH2 | H | H | CH3SOCH2CO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-1474 | H | C—CF3 | C—H | C—H | C—H | CF3 | C—H | C—NH2 | H | H | CH3SO2CH2CO | H | 1 |
| 2-1475 | H | C—CF3 | C—H | C—H | C—H | CF3 | C—H | C—NH2 | H | H | EtNHCO | H | 1 |
| 2-1476 | H | C—CF3 | C—H | C—H | C—H | CF3 | C—H | C—NH2 | Me | H | EtCO | H | 1 |
| 2-1477 | H | C—CF3 | C—H | C—H | C—H | CF3 | N | C—NH2 | Me | H | CF3CH2CO | H | 1 |
| 2-1478 | H | C—CF3 | C—H | C—H | C—H | CF3 | N | C—NH2 | H | H | EtCO | H | 1 |
| 2-1479 | H | C—CF3 | C—H | C—H | C—H | CF3 | C—H | C—NH2 | H | H | CF3CH2CO | H | 1 |
| 2-1480 | H | C—CF3 | C—H | C—H | C—H | CF3 | C—H | C—NHAc | H | H | H | H | 1 |
| 2-1481 | H | C—CF3 | C—H | C—H | C—H | CF3 | C—H | C—NHAc | H | H | MeCO | H | 1 |
| 2-1482 | H | C—CF3 | C—H | C—H | C—H | CF3 | C—H | C—NHAc | H | H | EtCO | H | 1 |
| 2-1483 | H | C—CF3 | C—H | C—H | C—H | CF3 | C—H | C—NHAc | H | H | CF3CH2CO | H | 1 |
| 2-1484 | H | C—CF3 | C—H | C—H | C—H | CF3 | C—H | C—NHAc | H | H | cyclo-PrCO | H | 1 |
| 2-1485 | H | C—CF3 | C—H | C—H | C—H | CF3 | C—H | C—NHAc | H | H | cyclo-PrCH2CO | H | 1 |
| 2-1486 | H | C—CF3 | C—H | C—H | C—H | CF3 | C—H | C—NHAc | H | H | CH3SCH2CO | H | 1 |
| 2-1487 | H | C—CF3 | C—H | C—H | C—H | CF3 | C—H | C—NHAc | H | H | CH3SOCH2CO | H | 1 |
| 2-1488 | H | C—CF3 | C—H | C—H | C—H | CF3 | C—H | C—NHAc | H | H | CH3SO2CH2CO | H | 1 |
| 2-1489 | H | C—CF3 | C—H | C—H | C—H | CF3 | C—H | C—NHAc | H | H | EtNHCO | H | 1 |
| 2-1490 | H | C—CF3 | C—H | C—H | C—H | CF3 | C—H | C—NHAc | Me | H | EtCO | H | 1 |
| 2-1491 | H | C—CF3 | C—H | C—H | C—H | CF3 | C—H | C—NHAc | Me | H | CF3CH2CO | H | 1 |
| 2-1492 | H | C—CF3 | C—H | C—H | C—H | CF3 | N | C—NHAc | H | H | EtCO | H | 1 |
| 2-1493 | H | C—CF3 | C—H | C—H | C—H | CF3 | N | C—NHAc | H | H | CF3CH2CO | H | 1 |
| 2-1494 | H | C—CF3 | C—H | C—H | C—H | CF3 | C—H | C—NHCOCF3 | H | H | H | H | 1 |
| 2-1495 | H | C—CF3 | C—H | C—H | C—H | CF3 | C—H | C—NHCOCF3 | H | H | MeCO | H | 1 |
| 2-1496 | H | C—CF3 | C—H | C—H | C—H | CF3 | C—H | C—NHCOCF3 | H | H | EtCO | H | 1 |
| 2-1497 | H | C—CF3 | C—H | C—H | C—H | CF3 | C—H | C—NHCOCF3 | H | H | CF3CH2CO | H | 1 |
| 2-1498 | H | C—CF3 | C—H | C—H | C—H | CF3 | C—H | C—NHCOCF3 | H | H | cyclo-PrCO | H | 1 |
| 2-1499 | H | C—CF3 | C—H | C—H | C—H | CF3 | C—H | C—NHCOCF3 | H | H | cyclo-PrCH2CO | H | 1 |
| 2-1500 | H | C—CF3 | C—H | C—H | C—H | CF3 | C—H | C—NHCOCF3 | H | H | CH3SCH2CO | H | 1 |
| 2-1501 | H | C—CF3 | C—H | C—H | C—H | CF3 | C—H | C—NHCOCF3 | H | H | CH3SOCH2CO | H | 1 |
| 2-1502 | H | C—CF3 | C—H | C—H | C—H | CF3 | C—H | C—NHCOCF3 | H | H | CH3SO2CH2CO | H | 1 |
| 2-1503 | H | C—CF3 | C—H | C—H | C—H | CF3 | C—H | C—NHCOCF3 | H | H | EtNHCO | H | 1 |
| 2-1504 | H | C—CF3 | C—H | C—H | C—H | CF3 | C—H | C—NHCOCF3 | Me | H | EtCO | H | 1 |
| 2-1505 | H | C—CF3 | C—H | C—H | C—H | CF3 | C—H | C—NHCOCF3 | Me | H | CF3CH2CO | H | 1 |
| 2-1506 | H | C—CF3 | C—H | C—H | C—H | CF3 | N | C—NHCOCF3 | H | H | EtCO | H | 1 |
| 2-1507 | H | C—CF3 | C—H | C—H | C—H | CF3 | C—H | C—NHCOCF3 | H | H | CF3CH2CO | H | 1 |
| 2-1508 | H | C—CF3 | C—H | C—H | C—H | CF3 | C—H | C—CH2OAc | H | H | H | H | 1 |
| 2-1509 | H | C—CF3 | C—H | C—H | C—H | CF3 | C—H | C—CH2OAc | H | H | MeCO | H | 1 |
| 2-1510 | H | C—CF3 | C—H | C—H | C—H | CF3 | C—H | C—CH2OAc | H | H | EtCO | H | 1 |
| 2-1511 | H | C—CF3 | C—H | C—H | C—H | CF3 | C—H | C—CH2OAc | H | H | CF3CH2CO | H | 1 |
| 2-1512 | H | C—CF3 | C—H | C—H | C—H | CF3 | C—H | C—CH2OAc | H | H | cyclo-PrCO | H | 1 |
| 2-1513 | H | C—CF3 | C—H | C—H | C—H | CF3 | C—H | C—CH2OAc | H | H | cyclo-PrCH2CO | H | 1 |
| 2-1514 | H | C—CF3 | C—H | C—H | C—H | CF3 | C—H | C—CH2OAc | H | H | CH3SCH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1515 | H | C—CF3 | C—H | C—H | C—H | CF3 | C—H | C—CH2OAc | H | H | CH3SOCH2CO | H | 1 |
| 2-1516 | H | C—CF3 | C—H | C—H | C—H | CF3 | C—H | C—CH2OAc | H | H | CH3SO2CH2CO | H | 1 |
| 2-1517 | H | C—CF3 | C—H | C—H | C—H | CF3 | C—H | C—CH2OAc | H | H | EtNHCO | H | 1 |
| 2-1518 | H | C—CF3 | C—H | C—H | C—H | CF3 | C—H | C—CH2OAc | Me | H | EtCO | H | 1 |
| 2-1519 | H | C—CF3 | C—H | C—H | C—H | CF3 | C—H | C—CH2OAc | Me | H | CF3CH2CO | H | 1 |
| 2-1520 | H | C—CF3 | C—H | C—H | C—H | CF3 | N | C—CH2OAc | H | H | EtCO | H | 1 |
| 2-1521 | H | C—CF3 | C—H | C—H | C—H | CF3 | N | C—CH2OAc | H | H | CF3CH2CO | H | 1 |
| 2-1522 | H | C—Cl | C—H | C—Cl | C—H | CF3 | C—H | C—CF3 | H | H | H | H | 1 |
| 2-1523 | H | C—Cl | C—H | C—Cl | C—H | CF3 | C—H | C—CF3 | H | H | MeCO | H | 1 |
| 2-1524 | H | C—Cl | C—H | C—Cl | C—H | CF3 | C—H | C—CF3 | H | H | EtCO | H | 1 |
| 2-1525 | H | C—Cl | C—H | C—Cl | C—H | CF3 | C—H | C—CF3 | H | H | n-PrCO | H | 1 |
| 2-1526 | H | C—Cl | C—H | C—Cl | C—H | CF3 | C—H | C—CF3 | H | H | cyclo-PrCO | H | 1 |
| 2-1527 | H | C—Cl | C—F | C—Cl | C—H | CF3 | C—H | C—CF3 | H | H | EtNHCO | H | 1 |
| 2-1528 | H | C—Cl | C—F | C—Cl | C—H | CF3 | C—H | C—CF3 | H | H | CF3CH2CO | H | 1 |
| 2-1529 | H | C—Cl | C—F | C—Cl | C—H | CF3 | C—H | C—CF3 | H | H | cyclo-PrCH2CO | H | 1 |
| 2-1530 | H | C—Cl | C—F | C—Cl | C—H | CF3 | C—H | C—CF3 | H | H | CH3SOCH2CO | H | 1 |
| 2-1531 | H | C—Cl | C—F | C—Cl | C—H | CF3 | C—H | C—CF3 | H | H | CH3SCH2CO | H | 1 |
| 2-1532 | H | C—Cl | C—F | C—Cl | C—H | CF3 | C—H | C—CF3 | H | H | CH3SO2CH2CO | H | 1 |
| 2-1533 | H | C—Cl | C—F | C—Cl | C—H | CF3 | C—H | C—CF3 | Me | H | H | H | 1 |
| 2-1534 | H | C—Cl | C—F | C—Cl | C—H | CF3 | C—H | C—CF3 | Me | H | EtCO | H | 1 |
| 2-1535 | H | C—Cl | C—F | C—Cl | C—H | CF3 | C—H | C—CF3 | Me | H | CF3CH2CO | H | 1 |
| 2-1536 | H | C—Cl | C—F | C—Cl | C—H | CF3 | C—H | C—CF3 | Me | H | CH3SCH2CO | H | 1 |
| 2-1537 | H | C—Cl | C—F | C—Cl | C—H | CF3 | N | C—CF3 | H | H | H | H | 1 |
| 2-1538 | H | C—Cl | C—F | C—Cl | C—H | CF3 | N | C—CF3 | H | H | EtCO | H | 1 |
| 2-1539 | H | C—Cl | C—F | C—Cl | C—H | CF3 | N | C—CF3 | H | H | CF3CH2CO | H | 1 |
| 2-1540 | H | C—Cl | C—F | C—Cl | C—H | CF3 | N | C—CF3 | H | H | CH3SCH2CO | H | 1 |
| 2-1541 | H | C—Cl | C—F | C—Cl | C—H | CF3 | C—H | C—Cl | H | H | H | H | 1 |
| 2-1542 | H | C—Cl | C—F | C—Cl | C—H | CF3 | C—H | C—Cl | H | H | MeCO | H | 1 |
| 2-1543 | H | C—Cl | C—F | C—Cl | C—H | CF3 | C—H | C—Cl | H | H | EtCO | H | 1 |
| 2-1544 | H | C—Cl | C—F | C—Cl | C—H | CF3 | C—H | C—Cl | H | H | CF3CH2CO | H | 1 |
| 2-1545 | H | C—Cl | C—F | C—Cl | C—H | CF3 | C—H | C—Cl | H | H | cyclo-PrCO | H | 1 |
| 2-1546 | H | C—Cl | C—F | C—Cl | C—H | CF3 | C—H | C—Cl | H | H | cyclo-PrCH2CO | H | 1 |
| 2-1547 | H | C—Cl | C—F | C—Cl | C—H | CF3 | C—H | C—Cl | H | H | CH3SCH2CO | H | 1 |
| 2-1548 | H | C—Cl | C—F | C—Cl | C—H | CF3 | C—H | C—Cl | H | H | CH3SO2CH2CO | H | 1 |
| 2-1549 | H | C—Cl | C—F | C—Cl | C—H | CF3 | C—H | C—Cl | H | H | EtNHCO | H | 1 |
| 2-1550 | H | C—Cl | C—F | C—Cl | C—H | CF3 | C—H | C—Cl | Me | H | H | H | 1 |
| 2-1551 | H | C—Cl | C—F | C—Cl | C—H | CF3 | C—H | C—Cl | Me | H | EtCO | H | 1 |
| 2-1552 | H | C—Cl | C—F | C—Cl | C—H | CF3 | C—H | C—Cl | Me | H | CF3CH2CO | H | 1 |
| 2-1553 | H | C—Cl | C—F | C—Cl | C—H | CF3 | C—H | C—Cl | Me | H | CH3SCH2CO | H | 1 |
| 2-1554 | H | C—Cl | C—F | C—Cl | C—H | CF3 | N | C—Cl | H | H | H | H | 1 |
| 2-1555 | H | C—Cl | C—F | C—Cl | C—H | CF3 | N | C—Cl | H | H | H | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1556 | H | C—Cl | C—F | C—Cl | C—H | CF3 | N | C—Cl | H | H | EtCO | H | 1 |
| 2-1557 | H | C—Cl | C—F | C—Cl | C—H | CF3 | N | C—Cl | H | H | CF3CH2CO | H | 1 |
| 2-1558 | H | C—Cl | C—F | C—Cl | C—H | CF3 | N | C—Cl | H | H | CH3SCH2CO | H | 1 |
| 2-1559 | H | C—Cl | C—F | C—Cl | C—H | CF3 | C—H | C—Br | H | H | H | H | 1 |
| 2-1560 | H | C—Cl | C—F | C—Cl | C—H | CF3 | C—H | C—Br | H | H | MeCO | H | 1 |
| 2-1561 | H | C—Cl | C—F | C—Cl | C—H | CF3 | C—H | C—Br | H | H | EtCO | H | 1 |
| 2-1562 | H | C—Cl | C—F | C—Cl | C—H | CF3 | C—H | C—Br | H | H | CF3CH2CO | H | 1 |
| 2-1563 | H | C—Cl | C—F | C—Cl | C—H | CF3 | C—H | C—Br | H | H | cyclo-PrCO | H | 1 |
| 2-1564 | H | C—Cl | C—F | C—Cl | C—H | CF3 | C—H | C—Br | H | H | cyclo-PrCH2CO | H | 1 |
| 2-1565 | H | C—Cl | C—F | C—Cl | C—H | CF3 | C—H | C—Br | H | H | CH3SCH2CO | H | 1 |
| 2-1566 | H | C—Cl | C—F | C—Cl | C—H | CF3 | C—H | C—Br | H | H | CH3SOCH2CO | H | 1 |
| 2-1567 | H | C—Cl | C—F | C—Cl | C—H | CF3 | C—H | C—Br | H | H | CH3SO2CH2CO | H | 1 |
| 2-1568 | H | C—Cl | C—F | C—Cl | C—H | CF3 | C—H | C—Br | H | H | EtNHCO | H | 1 |
| 2-1569 | H | C—Cl | C—F | C—Cl | C—H | CF3 | C—H | C—Br | Me | H | H | H | 1 |
| 2-1570 | H | C—Cl | C—F | C—Cl | C—H | CF3 | C—H | C—Br | Me | H | EtCO | H | 1 |
| 2-1571 | H | C—Cl | C—F | C—Cl | C—H | CF3 | C—H | C—Br | Me | H | CF3CH2CO | H | 1 |
| 2-1572 | H | C—Cl | C—F | C—Cl | C—H | CF3 | C—H | C—Br | Me | H | CH3SCH2CO | H | 1 |
| 2-1573 | H | C—Cl | C—F | C—Cl | C—H | CF3 | C—H | C—Br | H | H | H | H | 1 |
| 2-1574 | H | C—Cl | C—F | C—Cl | C—H | CF3 | C—H | C—Br | H | H | EtCO | H | 1 |
| 2-1575 | H | C—Cl | C—F | C—Cl | C—H | CF3 | C—H | C—Br | H | H | CF3CH2CO | H | 1 |
| 2-1576 | H | C—Cl | C—F | C—Cl | C—H | CF3 | C—H | C—Br | H | H | CH3SCH2CO | H | 1 |
| 2-1577 | H | C—Cl | C—F | C—Cl | C—H | CF3 | N | C—CN | H | H | H | H | 1 |
| 2-1578 | H | C—Cl | C—F | C—Cl | C—H | CF3 | N | C—CN | H | H | MeCO | H | 1 |
| 2-1579 | H | C—Cl | C—F | C—Cl | C—H | CF3 | N | C—CN | H | H | EtCO | H | 1 |
| 2-1580 | H | C—Cl | C—F | C—Cl | C—H | CF3 | C—H | C—CN | H | H | CF3CH2CO | H | 1 |
| 2-1581 | H | C—Cl | C—F | C—Cl | C—H | CF3 | C—H | C—CN | H | H | cyclo-PrCO | H | 1 |
| 2-1582 | H | C—Cl | C—F | C—Cl | C—H | CF3 | C—H | C—CN | H | H | cyclo-PrCH2CO | H | 1 |
| 2-1583 | H | C—Cl | C—F | C—Cl | C—H | CF3 | C—H | C—CN | H | H | CH3SCH2CO | H | 1 |
| 2-1584 | H | C—Cl | C—F | C—Cl | C—H | CF3 | C—H | C—CN | H | H | CH3SOCH2CO | H | 1 |
| 2-1585 | H | C—Cl | C—F | C—Cl | C—H | CF3 | C—H | C—CN | H | H | CH3SO2CH2CO | H | 1 |
| 2-1586 | H | C—Cl | C—F | C—Cl | C—H | CF3 | C—H | C—CN | H | H | EtNHCO | H | 1 |
| 2-1587 | H | C—Cl | C—F | C—Cl | C—H | CF3 | C—H | C—CN | Me | H | EtCO | H | 1 |
| 2-1588 | H | C—Cl | C—F | C—Cl | C—H | CF3 | C—H | C—CN | Me | H | EtCO | H | 1 |
| 2-1589 | H | C—Cl | C—F | C—Cl | C—H | CF3 | N | C—CN | H | H | EtCO | H | 1 |
| 2-1590 | H | C—Cl | C—F | C—Cl | C—H | CF3 | C—H | C—CN | H | H | CF3CH2CO | H | 1 |
| 2-1591 | H | C—Cl | C—F | C—Cl | C—H | CF3 | C—H | C—Me | H | H | H | H | 1 |
| 2-1592 | H | C—Cl | C—F | C—Cl | C—H | CF3 | C—H | C—Me | H | H | MeCO | H | 1 |
| 2-1593 | H | C—Cl | C—F | C—Cl | C—H | CF3 | C—H | C—Me | H | H | EtCO | H | 1 |
| 2-1594 | H | C—Cl | C—F | C—Cl | C—H | CF3 | C—H | C—Me | H | H | CF3CH2CO | H | 1 |
| 2-1595 | H | C—Cl | C—F | C—Cl | C—H | CF3 | C—H | C—Me | H | H | cyclo-PrCO | H | 1 |
| 2-1596 | H | C—Cl | C—F | C—Cl | C—H | CF3 | C—H | C—Me | H | H | cyclo-PrCH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1597 | H | C—Cl | C—F | C—Cl | C—H | CF3 | C—H | C—Me | H | H | CH3SCH2CO | H | 1 |
| 2-1598 | H | C—Cl | C—F | C—Cl | C—H | CF3 | C—H | C—Me | H | H | CH3SOCH2CO | H | 1 |
| 2-1599 | H | C—Cl | C—F | C—Cl | C—H | CF3 | C—H | C—Me | H | H | CH3SO2CH2CO | H | 1 |
| 2-1600 | H | C—Cl | C—F | C—Cl | C—H | CF3 | C—H | C—Me | H | H | EtNHCO | H | 1 |
| 2-1601 | H | C—Cl | C—F | C—Cl | C—H | CF3 | C—H | C—Me | Me | H | EtCO | H | 1 |
| 2-1602 | H | C—Cl | C—F | C—Cl | C—H | CF3 | C—H | C—Me | Me | H | CF3CH2CO | H | 1 |
| 2-1603 | H | C—Cl | C—F | C—Cl | C—H | CF3 | C—H | C—Me | H | H | EtCO | H | 1 |
| 2-1604 | H | C—Cl | C—F | C—Cl | C—H | CF3 | N | C—Me | H | H | CF3CH2CO | H | 1 |
| 2-1605 | H | C—Cl | C—F | C—Cl | C—H | CF3 | N | C—Me | H | H | H | H | 1 |
| 2-1606 | H | C—Cl | C—F | C—Cl | C—H | CF3 | C—H | C—NO2 | H | H | MeCO | H | 1 |
| 2-1607 | H | C—Cl | C—F | C—Cl | C—H | CF3 | C—H | C—NO2 | H | H | EtCO | H | 1 |
| 2-1608 | H | C—Cl | C—F | C—Cl | C—H | CF3 | C—H | C—NO2 | H | H | CF3CH2CO | H | 1 |
| 2-1609 | H | C—Cl | C—F | C—Cl | C—H | CF3 | C—H | C—NO2 | H | H | cyclo-PrCO | H | 1 |
| 2-1610 | H | C—Cl | C—F | C—Cl | C—H | CF3 | C—H | C—NO2 | H | H | cyclo-PrCH2CO | H | 1 |
| 2-1611 | H | C—Cl | C—F | C—Cl | C—H | CF3 | C—H | C—NO2 | H | H | CH3SCH2CO | H | 1 |
| 2-1612 | H | C—Cl | C—F | C—Cl | C—H | CF3 | C—H | C—NO2 | H | H | CH3SOCH2CO | H | 1 |
| 2-1613 | H | C—Cl | C—F | C—Cl | C—H | CF3 | C—H | C—NO2 | H | H | CH3SO2CH2CO | H | 1 |
| 2-1614 | H | C—Cl | C—F | C—Cl | C—H | CF3 | C—H | C—NO2 | H | H | EtNHCO | H | 1 |
| 2-1615 | H | C—Cl | C—F | C—Cl | C—H | CF3 | C—H | C—NO2 | Me | H | EtCO | H | 1 |
| 2-1616 | H | C—Cl | C—F | C—Cl | C—H | CF3 | C—H | C—NO2 | Me | H | CF3CH2CO | H | 1 |
| 2-1617 | H | C—Cl | C—F | C—Cl | C—H | CF3 | C—H | C—NO2 | H | H | EtCO | H | 1 |
| 2-1618 | H | C—Cl | C—F | C—Cl | C—H | CF3 | N | C—NO2 | H | H | CF3CH2CO | H | 1 |
| 2-1619 | H | C—Cl | C—F | C—Cl | C—H | CF3 | C—H | C—SMe | H | H | H | H | 1 |
| 2-1620 | H | C—Cl | C—F | C—Cl | C—H | CF3 | C—H | C—SMe | H | H | MeCO | H | 1 |
| 2-1621 | H | C—Cl | C—F | C—Cl | C—H | CF3 | C—H | C—SMe | H | H | EtCO | H | 1 |
| 2-1622 | H | C—Cl | C—F | C—Cl | C—H | CF3 | C—H | C—SMe | H | H | CF3CH2CO | H | 1 |
| 2-1623 | H | C—Cl | C—F | C—Cl | C—H | CF3 | C—H | C—SMe | H | H | cyclo-PrCO | H | 1 |
| 2-1624 | H | C—Cl | C—F | C—Cl | C—H | CF3 | C—H | C—SMe | H | H | cyclo-PrCH2CO | H | 1 |
| 2-1625 | H | C—Cl | C—F | C—Cl | C—H | CF3 | C—H | C—SMe | H | H | CH3SCH2CO | H | 1 |
| 2-1626 | H | C—Cl | C—F | C—Cl | C—H | CF3 | C—H | C—SMe | H | H | CH3SOCH2CO | H | 1 |
| 2-1627 | H | C—Cl | C—F | C—Cl | C—H | CF3 | C—H | C—SMe | H | H | CH3SO2CH2CO | H | 1 |
| 2-1628 | H | C—Cl | C—F | C—Cl | C—H | CF3 | C—H | C—SMe | H | H | EtNHCO | H | 1 |
| 2-1629 | H | C—Cl | C—F | C—Cl | C—H | CF3 | C—H | C—SMe | Me | H | EtCO | H | 1 |
| 2-1630 | H | C—Cl | C—F | C—Cl | C—H | CF3 | C—H | C—SMe | Me | H | CF3CH2CO | H | 1 |
| 2-1631 | H | C—Cl | C—F | C—Cl | C—H | CF3 | C—H | C—SMe | H | H | EtCO | H | 1 |
| 2-1632 | H | C—Cl | C—F | C—Cl | C—H | CF3 | N | C—SMe | H | H | CF3CH2CO | H | 1 |
| 2-1633 | H | C—Cl | C—F | C—Cl | C—H | CF3 | C—H | C—SOMe | H | H | H | H | 1 |
| 2-1634 | H | C—Cl | C—F | C—Cl | C—H | CF3 | C—H | C—SOMe | H | H | MeCO | H | 1 |
| 2-1635 | H | C—Cl | C—F | C—Cl | C—H | CF3 | C—H | C—SOMe | H | H | EtCO | H | 1 |
| 2-1636 | H | C—Cl | C—F | C—Cl | C—H | CF3 | C—H | C—SOMe | H | H | CF3CH2CO | H | 1 |
| 2-1637 | H | C—Cl | C—F | C—Cl | C—H | CF3 | C—H | C—SOMe | H | H | cyclo-PrCO | H | 1 |

TABLE 2-1-continued

| Example No. | X | B¹ | B² | B³ | B⁴ | R | A² | A³ | R¹ | R² | R⁴ | I |
|---|---|---|---|---|---|---|---|---|---|---|---|---|
| 2-1638 | H | C-Cl | C-F | C-Cl | C-H | CF3 | C-H | C-SOMe | H | H | cyclo-PrCH2CO | 1 |
| 2-1639 | H | C-Cl | C-F | C-Cl | C-H | CF3 | C-H | C-SOMe | H | H | CH3SCH2CO | 1 |
| 2-1640 | H | C-Cl | C-F | C-Cl | C-H | CF3 | C-H | C-SOMe | H | H | CH3SOCH2CO | 1 |
| 2-1641 | H | C-Cl | C-F | C-Cl | C-H | CF3 | C-H | C-SOMe | H | H | CH3SO2CH2CO | 1 |
| 2-1642 | H | C-Cl | C-F | C-Cl | C-H | CF3 | C-H | C-SOMe | H | H | EtNHCO | 1 |
| 2-1643 | H | C-Cl | C-F | C-Cl | C-H | CF3 | C-H | C-SOMe | Me | H | EtCO | 1 |
| 2-1644 | H | C-Cl | C-F | C-Cl | C-H | CF3 | C-H | C-SOMe | Me | H | CF3CH2CO | 1 |
| 2-1645 | H | C-Cl | C-F | C-Cl | C-H | CF3 | N | C-SOMe | H | H | EtCO | 1 |
| 2-1646 | H | C-Cl | C-F | C-Cl | C-H | CF3 | N | C-SOMe | H | H | CF3CH2CO | 1 |
| 2-1647 | H | C-Cl | C-F | C-Cl | C-H | CF3 | C-H | C-SO2Me | H | H | H | 1 |
| 2-1648 | H | C-Cl | C-F | C-Cl | C-H | CF3 | C-H | C-SO2Me | H | H | MeCO | 1 |
| 2-1649 | H | C-Cl | C-F | C-Cl | C-H | CF3 | C-H | C-SO2Me | H | H | EtCO | 1 |
| 2-1650 | H | C-Cl | C-F | C-Cl | C-H | CF3 | C-H | C-SO2Me | H | H | CF3CH2CO | 1 |
| 2-1651 | H | C-Cl | C-F | C-Cl | C-H | CF3 | C-H | C-SO2Me | H | H | cyclo-PrCO | 1 |
| 2-1652 | H | C-Cl | C-F | C-Cl | C-H | CF3 | C-H | C-SO2Me | H | H | cyclo-PrCH2CO | 1 |
| 2-1653 | H | C-Cl | C-F | C-Cl | C-H | CF3 | C-H | C-SO2Me | H | H | CH3SCH2CO | 1 |
| 2-1654 | H | C-Cl | C-F | C-Cl | C-H | CF3 | C-H | C-SO2Me | H | H | CH3SOCH2CO | 1 |
| 2-1655 | H | C-Cl | C-F | C-Cl | C-H | CF3 | C-H | C-SO2Me | H | H | CH3SO2CH2CO | 1 |
| 2-1656 | H | C-Cl | C-F | C-Cl | C-H | CF3 | C-H | C-SO2Me | H | H | EtNHCO | 1 |
| 2-1657 | H | C-Cl | C-F | C-Cl | C-H | CF3 | C-H | C-SO2Me | Me | H | EtCO | 1 |
| 2-1658 | H | C-Cl | C-F | C-Cl | C-H | CF3 | C-H | C-SO2Me | Me | H | CF3CH2CO | 1 |
| 2-1659 | H | C-Cl | C-F | C-Cl | C-H | CF3 | N | C-SO2Me | H | H | EtCO | 1 |
| 2-1660 | H | C-Cl | C-F | C-Cl | C-H | CF3 | N | C-SO2Me | H | H | CF3CH2CO | 1 |
| 2-1661 | H | C-Cl | C-F | C-Cl | C-H | CF3 | C-H | C-SCF3 | H | H | H | 1 |
| 2-1662 | H | C-Cl | C-F | C-Cl | C-H | CF3 | C-H | C-SCF3 | H | H | MeCO | 1 |
| 2-1663 | H | C-Cl | C-F | C-Cl | C-H | CF3 | C-H | C-SCF3 | H | H | EtCO | 1 |
| 2-1664 | H | C-Cl | C-F | C-Cl | C-H | CF3 | C-H | C-SCF3 | H | H | CF3CH2CO | 1 |
| 2-1665 | H | C-Cl | C-F | C-Cl | C-H | CF3 | C-H | C-SCF3 | H | H | cyclo-PrCO | 1 |
| 2-1666 | H | C-Cl | C-F | C-Cl | C-H | CF3 | C-H | C-SCF3 | H | H | cyclo-PrCH2CO | 1 |
| 2-1667 | H | C-Cl | C-F | C-Cl | C-H | CF3 | C-H | C-SCF3 | H | H | CH3SCH2CO | 1 |
| 2-1668 | H | C-Cl | C-F | C-Cl | C-H | CF3 | C-H | C-SCF3 | H | H | CH3SOCH2CO | 1 |
| 2-1669 | H | C-Cl | C-F | C-Cl | C-H | CF3 | C-H | C-SCF3 | H | H | CH3SO2CH2CO | 1 |
| 2-1670 | H | C-Cl | C-F | C-Cl | C-H | CF3 | C-H | C-SCF3 | H | H | EtNHCO | 1 |
| 2-1671 | H | C-Cl | C-F | C-Cl | C-H | CF3 | C-H | C-SCF3 | Me | H | EtCO | 1 |
| 2-1672 | H | C-Cl | C-F | C-Cl | C-H | CF3 | C-H | C-SCF3 | Me | H | CF3CH2CO | 1 |
| 2-1673 | H | C-Cl | C-F | C-Cl | C-H | CF3 | N | C-SCF3 | H | H | EtCO | 1 |
| 2-1674 | H | C-Cl | C-F | C-Cl | C-H | CF3 | N | C-SCF3 | H | H | CF3CH2CO | 1 |
| 2-1675 | H | C-Cl | C-F | C-Cl | C-H | CF3 | C-H | C-SOCF3 | H | H | H | 1 |
| 2-1676 | H | C-Cl | C-F | C-Cl | C-H | CF3 | C-H | C-SOCF3 | H | H | MeCO | 1 |
| 2-1677 | H | C-Cl | C-F | C-Cl | C-H | CF3 | C-H | C-SOCF3 | H | H | EtCO | 1 |
| 2-1678 | H | C-Cl | C-F | C-Cl | C-H | CF3 | C-H | C-SOCF3 | H | H | CF3CH2CO | 1 |

TABLE 2-1-continued

| Example No. | X | B$^1$ | B$^2$ | B$^3$ | B$^4$ | R | A$^2$ | A$^3$ | R$^1$ | R$^2$ | R$^4$ | R$^3$ | I |
|---|---|---|---|---|---|---|---|---|---|---|---|---|---|
| 2-1679 | H | C—Cl | C—F | C—Cl | C—H | CF3 | C—H | C—SOCF3 | H | H | cyclo-PrCO | H | 1 |
| 2-1680 | H | C—Cl | C—F | C—Cl | C—H | CF3 | C—H | C—SOCF3 | H | H | cyclo-PrCH2CO | H | 1 |
| 2-1681 | H | C—Cl | C—F | C—Cl | C—H | CF3 | C—H | C—SOCF3 | H | H | CH3SCH2CO | H | 1 |
| 2-1682 | H | C—Cl | C—F | C—Cl | C—H | CF3 | C—H | C—SOCF3 | H | H | CH3SOCH2CO | H | 1 |
| 2-1683 | H | C—Cl | C—F | C—Cl | C—H | CF3 | C—H | C—SOCF3 | H | H | CH3SO2CH2CO | H | 1 |
| 2-1684 | H | C—Cl | C—F | C—Cl | C—H | CF3 | C—H | C—SOCF3 | H | H | EtNHCO | H | 1 |
| 2-1685 | H | C—Cl | C—F | C—Cl | C—H | CF3 | C—H | C—SOCF3 | Me | H | EtCO | H | 1 |
| 2-1686 | H | C—Cl | C—F | C—Cl | C—H | CF3 | C—H | C—SOCF3 | Me | H | CF3CH2CO | H | 1 |
| 2-1687 | H | C—Cl | C—F | C—Cl | C—H | CF3 | N | C—SOCF3 | H | H | EtCO | H | 1 |
| 2-1688 | H | C—Cl | C—F | C—Cl | C—H | CF3 | N | C—SOCF3 | H | H | CF3CH2CO | H | 1 |
| 2-1689 | H | C—Cl | C—F | C—Cl | C—H | CF3 | C—H | C—H | H | H | H | H | 1 |
| 2-1690 | H | C—Cl | C—F | C—Cl | C—H | CF3 | C—H | C—H | H | H | MeCO | H | 1 |
| 2-1691 | H | C—Cl | C—F | C—Cl | C—H | CF3 | C—H | C—H | H | H | EtCO | H | 1 |
| 2-1692 | H | C—Cl | C—F | C—Cl | C—H | CF3 | C—H | C—H | H | H | CF3CH2CO | H | 1 |
| 2-1693 | H | C—Cl | C—F | C—Cl | C—H | CF3 | C—H | C—H | H | H | cyclo-PrCO | H | 1 |
| 2-1694 | H | C—Cl | C—F | C—Cl | C—H | CF3 | C—H | C—H | H | H | cyclo-PrCH2CO | H | 1 |
| 2-1695 | H | C—Cl | C—F | C—Cl | C—H | CF3 | C—H | C—H | H | H | CH3SCH2CO | H | 1 |
| 2-1696 | H | C—Cl | C—F | C—Cl | C—H | CF3 | C—H | C—H | H | H | CH3SOCH2CO | H | 1 |
| 2-1697 | H | C—Cl | C—F | C—Cl | C—H | CF3 | C—H | C—H | H | H | CH3SO2CH2CO | H | 1 |
| 2-1698 | H | C—Cl | C—F | C—Cl | C—H | CF3 | C—H | C—H | H | H | EtNHCO | H | 1 |
| 2-1699 | H | C—Cl | C—F | C—Cl | C—H | CF3 | C—H | C—H | Me | H | H | H | 1 |
| 2-1700 | H | C—Cl | C—F | C—Cl | C—H | CF3 | C—H | C—H | Me | H | EtCO | H | 1 |
| 2-1701 | H | C—Cl | C—F | C—Cl | C—H | CF3 | C—H | C—H | Me | H | CF3CH2CO | H | 1 |
| 2-1702 | H | C—Cl | C—F | C—Cl | C—H | CF3 | C—H | C—H | Me | H | CH3SCH2CO | H | 1 |
| 2-1703 | H | C—Cl | C—F | C—Cl | C—H | CF3 | N | C—H | H | H | H | H | 1 |
| 2-1704 | H | C—Cl | C—F | C—Cl | C—H | CF3 | N | C—H | H | H | EtCO | H | 1 |
| 2-1705 | H | C—Cl | C—F | C—Cl | C—H | CF3 | N | C—H | H | H | CF3CH2CO | H | 1 |
| 2-1706 | H | C—Cl | C—F | C—Cl | C—H | CF3 | N | C—H | H | H | CH3SCH2CO | H | 1 |
| 2-1707 | H | C—Cl | C—F | C—Cl | C—H | CF3 | C—H | C—F | H | H | H | H | 1 |
| 2-1708 | H | C—Cl | C—F | C—Cl | C—H | CF3 | C—H | C—F | H | H | MeCO | H | 1 |
| 2-1709 | H | C—Cl | C—F | C—Cl | C—H | CF3 | C—H | C—F | H | H | EtCO | H | 1 |
| 2-1710 | H | C—Cl | C—F | C—Cl | C—H | CF3 | C—H | C—F | H | H | cyclo-PrCO | H | 1 |
| 2-1711 | H | C—Cl | C—F | C—Cl | C—H | CF3 | C—H | C—F | H | H | cyclo-PrCH2CO | H | 1 |
| 2-1712 | H | C—Cl | C—F | C—Cl | C—H | CF3 | C—H | C—F | H | H | CH3SCH2CO | H | 1 |
| 2-1713 | H | C—Cl | C—F | C—Cl | C—H | CF3 | C—H | C—F | H | H | CH3SOCH2CO | H | 1 |
| 2-1714 | H | C—Cl | C—F | C—Cl | C—H | CF3 | C—H | C—F | H | H | CH3SO2CH2CO | H | 1 |
| 2-1715 | H | C—Cl | C—F | C—Cl | C—H | CF3 | C—H | C—F | H | H | EtNHCO | H | 1 |
| 2-1716 | H | C—Cl | C—F | C—Cl | C—H | CF3 | C—H | C—F | Me | H | EtCO | H | 1 |
| 2-1717 | H | C—Cl | C—F | C—Cl | C—H | CF3 | C—H | C—F | Me | H | CF3CH2CO | H | 1 |
| 2-1718 | H | C—Cl | C—F | C—Cl | C—H | CF3 | N | C—F | H | H | EtCO | H | 1 |
| 2-1719 | H | C—Cl | C—F | C—Cl | C—H | CF3 | N | C—F | H | H | CF3CH2CO | H | 1 |

TABLE 2-1-continued

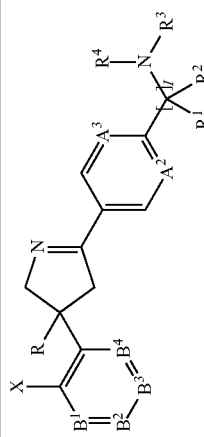

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1720 | H | C—Cl | C—F | C—Cl | C—H | CF3 | N | C—F | H | H | CF3CH2CO | H | 1 |
| 2-1721 | H | C—Cl | C—F | C—Cl | C—H | CF3 | C—H | C—I | H | H | H | H | 1 |
| 2-1722 | H | C—Cl | C—F | C—Cl | C—H | CF3 | C—H | C—I | H | H | MeCO | H | 1 |
| 2-1723 | H | C—Cl | C—F | C—Cl | C—H | CF3 | C—H | C—I | H | H | EtCO | H | 1 |
| 2-1724 | H | C—Cl | C—F | C—Cl | C—H | CF3 | C—H | C—I | H | H | CF3CH2CO | H | 1 |
| 2-1725 | H | C—Cl | C—F | C—Cl | C—H | CF3 | C—H | C—I | H | H | cyclo-PrCO | H | 1 |
| 2-1726 | H | C—Cl | C—F | C—Cl | C—H | CF3 | C—H | C—I | H | H | cyclo-PrCH2CO | H | 1 |
| 2-1727 | H | C—Cl | C—F | C—Cl | C—H | CF3 | C—H | C—I | H | H | CH3SCH2CO | H | 1 |
| 2-1728 | H | C—Cl | C—F | C—Cl | C—H | CF3 | C—H | C—I | H | H | CH3SOCH2CO | H | 1 |
| 2-1729 | H | C—Cl | C—F | C—Cl | C—H | CF3 | C—H | C—I | H | H | CH3SO2CH2CO | H | 1 |
| 2-1730 | H | C—Cl | C—F | C—Cl | C—H | CF3 | C—H | C—I | H | H | EtNHCO | H | 1 |
| 2-1731 | H | C—Cl | C—F | C—Cl | C—H | CF3 | C—H | C—I | Me | H | EtCO | H | 1 |
| 2-1732 | H | C—Cl | C—F | C—Cl | C—H | CF3 | C—H | C—I | Me | H | CF3CH2CO | H | 1 |
| 2-1733 | H | C—Cl | C—F | C—Cl | C—H | CF3 | N | C—I | H | H | EtCO | H | 1 |
| 2-1734 | H | C—Cl | C—F | C—Cl | C—H | CF3 | N | C—I | H | H | CF3CH2CO | H | 1 |
| 2-1735 | H | C—Cl | C—F | C—Cl | C—H | CF3 | C—H | C—NH2 | H | H | H | H | 1 |
| 2-1737 | H | C—Cl | C—F | C—Cl | C—H | CF3 | C—H | C—NH2 | H | H | MeCO | H | 1 |
| 2-1738 | H | C—Cl | C—F | C—Cl | C—H | CF3 | C—H | C—NH2 | H | H | EtCO | H | 1 |
| 2-1739 | H | C—Cl | C—F | C—Cl | C—H | CF3 | C—H | C—NH2 | H | H | CF3CH2CO | H | 1 |
| 2-1740 | H | C—Cl | C—F | C—Cl | C—H | CF3 | C—H | C—NH2 | H | H | cyclo-PrCO | H | 1 |
| 2-1741 | H | C—Cl | C—F | C—Cl | C—H | CF3 | C—H | C—NH2 | H | H | cyclo-PrCH2CO | H | 1 |
| 2-1742 | H | C—Cl | C—F | C—Cl | C—H | CF3 | C—H | C—NH2 | H | H | CH3SCH2CO | H | 1 |
| 2-1743 | H | C—Cl | C—F | C—Cl | C—H | CF3 | C—H | C—NH2 | H | H | CH3SOCH2CO | H | 1 |
| 2-1744 | H | C—Cl | C—F | C—Cl | C—H | CF3 | C—H | C—NH2 | H | H | CH3SO2CH2CO | H | 1 |
| 2-1745 | H | C—Cl | C—F | C—Cl | C—H | CF3 | C—H | C—NH2 | H | H | EtNHCO | H | 1 |
| 2-1746 | H | C—Cl | C—F | C—Cl | C—H | CF3 | C—H | C—NH2 | Me | H | EtCO | H | 1 |
| 2-1747 | H | C—Cl | C—F | C—Cl | C—H | CF3 | C—H | C—NH2 | Me | H | CF3CH2CO | H | 1 |
| 2-1748 | H | C—Cl | C—F | C—Cl | C—H | CF3 | N | C—NH2 | H | H | EtCO | H | 1 |
| 2-1749 | H | C—Cl | C—F | C—Cl | C—H | CF3 | N | C—NH2 | H | H | CF3CH2CO | H | 1 |
| 2-1750 | H | C—Cl | C—F | C—Cl | C—H | CF3 | C—H | C—NHAc | H | H | H | H | 1 |
| 2-1751 | H | C—Cl | C—F | C—Cl | C—H | CF3 | C—H | C—NHAc | H | H | MeCO | H | 1 |
| 2-1752 | H | C—Cl | C—F | C—Cl | C—H | CF3 | C—H | C—NHAc | H | H | EtCO | H | 1 |
| 2-1753 | H | C—Cl | C—F | C—Cl | C—H | CF3 | C—H | C—NHAc | H | H | CF3CH2CO | H | 1 |
| 2-1754 | H | C—Cl | C—F | C—Cl | C—H | CF3 | C—H | C—NHAc | H | H | cyclo-PrCO | H | 1 |
| 2-1755 | H | C—Cl | C—F | C—Cl | C—H | CF3 | C—H | C—NHAc | H | H | cyclo-PrCH2CO | H | 1 |
| 2-1756 | H | C—Cl | C—F | C—Cl | C—H | CF3 | C—H | C—NHAc | H | H | CH3SCH2CO | H | 1 |
| 2-1757 | H | C—Cl | C—F | C—Cl | C—H | CF3 | C—H | C—NHAc | H | H | CH3SOCH2CO | H | 1 |
| 2-1758 | H | C—Cl | C—F | C—Cl | C—H | CF3 | C—H | C—NHAc | H | H | CH3SO2CH2CO | H | 1 |
| 2-1759 | H | C—Cl | C—F | C—Cl | C—H | CF3 | C—H | C—NHAc | Me | H | EtNHCO | H | 1 |
| 2-1760 | H | C—Cl | C—F | C—Cl | C—H | CF3 | C—H | C—NHAc | Me | H | CF3CH2CO | H | 1 |

TABLE 2-1-continued

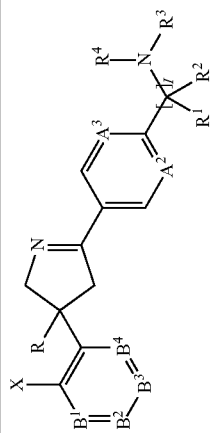

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1761 | H | C—Cl | C—F | C—Cl | C—H | CF3 | N | C—NHAc | H | H | EtCO | H | 1 |
| 2-1762 | H | C—Cl | C—F | C—Cl | C—H | CF3 | N | C—NHAc | H | H | CF3CH2CO | H | 1 |
| 2-1763 | H | C—Cl | C—F | C—Cl | C—H | CF3 | C—H | C—NHCOCF3 | H | H | H | H | 1 |
| 2-1764 | H | C—Cl | C—F | C—Cl | C—H | CF3 | C—H | C—NHCOCF3 | H | H | MeCO | H | 1 |
| 2-1765 | H | C—Cl | C—F | C—Cl | C—H | CF3 | C—H | C—NHCOCF3 | H | H | EtCO | H | 1 |
| 2-1766 | H | C—Cl | C—F | C—Cl | C—H | CF3 | C—H | C—NHCOCF3 | H | H | CF3CH2CO | H | 1 |
| 2-1767 | H | C—Cl | C—F | C—Cl | C—H | CF3 | C—H | C—NHCOCF3 | H | H | cyclo-PrCO | H | 1 |
| 2-1768 | H | C—Cl | C—F | C—Cl | C—H | CF3 | C—H | C—NHCOCF3 | H | H | cyclo-PrCH2CO | H | 1 |
| 2-1769 | H | C—Cl | C—F | C—Cl | C—H | CF3 | C—H | C—NHCOCF3 | H | H | CH3SCH2CO | H | 1 |
| 2-1770 | H | C—Cl | C—F | C—Cl | C—H | CF3 | C—H | C—NHCOCF3 | H | H | CH3SOCH2CO | H | 1 |
| 2-1771 | H | C—Cl | C—F | C—Cl | C—H | CF3 | C—H | C—NHCOCF3 | H | H | CH3SO2CH2CO | H | 1 |
| 2-1772 | H | C—Cl | C—F | C—Cl | C—H | CF3 | C—H | C—NHCOCF3 | H | H | EtNHCO | H | 1 |
| 2-1773 | H | C—Cl | C—F | C—Cl | C—H | CF3 | C—H | C—NHCOCF3 | Me | H | EtCO | H | 1 |
| 2-1774 | H | C—Cl | C—F | C—Cl | C—H | CF3 | C—H | C—NHCOCF3 | Me | H | CF3CH2CO | H | 1 |
| 2-1775 | H | C—Cl | C—F | C—Cl | C—H | CF3 | N | C—NHCOCF3 | H | H | EtCO | H | 1 |
| 2-1776 | H | C—Cl | C—F | C—Cl | C—H | CF3 | N | C—NHCOCF3 | H | H | CF3CH2CO | H | 1 |
| 2-1777 | H | C—Cl | C—F | C—Cl | C—H | CF3 | C—H | C—CH2OAc | H | H | H | H | 1 |
| 2-1778 | H | C—Cl | C—F | C—Cl | C—H | CF3 | C—H | C—CH2OAc | H | H | MeCO | H | 1 |
| 2-1779 | H | C—Cl | C—F | C—Cl | C—H | CF3 | C—H | C—CH2OAc | H | H | EtCO | H | 1 |
| 2-1780 | H | C—Cl | C—F | C—Cl | C—H | CF3 | C—H | C—CH2OAc | H | H | CF3CH2CO | H | 1 |
| 2-1781 | H | C—Cl | C—F | C—Cl | C—H | CF3 | C—H | C—CH2OAc | H | H | cyclo-PrCO | H | 1 |
| 2-1782 | H | C—Cl | C—F | C—Cl | C—H | CF3 | C—H | C—CH2OAc | H | H | cyclo-PrCH2CO | H | 1 |
| 2-1783 | H | C—Cl | C—F | C—Cl | C—H | CF3 | C—H | C—CH2OAc | H | H | CH3SCH2CO | H | 1 |
| 2-1784 | H | C—Cl | C—F | C—Cl | C—H | CF3 | C—H | C—CH2OAc | H | H | CH3SOCH2CO | H | 1 |
| 2-1785 | H | C—Cl | C—F | C—Cl | C—H | CF3 | C—H | C—CH2OAc | H | H | CH3SO2CH2CO | H | 1 |
| 2-1786 | H | C—Cl | C—F | C—Cl | C—H | CF3 | C—H | C—CH2OAc | H | H | EtNHCO | H | 1 |
| 2-1787 | H | C—Cl | C—F | C—Cl | C—H | CF3 | C—H | C—CH2OAc | Me | H | EtCO | H | 1 |
| 2-1788 | H | C—Cl | C—F | C—Cl | C—H | CF3 | C—H | C—CH2OAc | Me | H | CF3CH2CO | H | 1 |
| 2-1789 | H | C—Cl | C—F | C—Cl | C—H | CF3 | N | C—CH2OAc | H | H | EtCO | H | 1 |
| 2-1790 | H | C—Cl | C—F | C—Cl | C—H | CF3 | C—H | C—CH2OAc | H | H | CF3CH2CO | H | 1 |
| 2-1791 | H | C—Cl | C—Br | C—Cl | C—H | CF3 | C—H | C—CF3 | H | H | H | H | 1 |
| 2-1792 | H | C—Cl | C—Br | C—Cl | C—H | CF3 | C—H | C—CF3 | H | H | MeCO | H | 1 |
| 2-1793 | H | C—Cl | C—Br | C—Cl | C—H | CF3 | C—H | C—CF3 | H | H | EtCO | H | 1 |
| 2-1794 | H | C—Cl | C—Br | C—Cl | C—H | CF3 | C—H | C—CF3 | H | H | n-PrCO | H | 1 |
| 2-1795 | H | C—Cl | C—Br | C—Cl | C—H | CF3 | C—H | C—CF3 | H | H | cyclo-PrCO | H | 1 |
| 2-1796 | H | C—Cl | C—Br | C—Cl | C—H | CF3 | C—H | C—CF3 | H | H | EtNHCO | H | 1 |
| 2-1797 | H | C—Cl | C—Br | C—Cl | C—H | CF3 | C—H | C—CF3 | H | H | CF3CH2CO | H | 1 |
| 2-1798 | H | C—Cl | C—Br | C—Cl | C—H | CF3 | C—H | C—CF3 | H | H | cyclo-PrCH2CO | H | 1 |
| 2-1799 | H | C—Cl | C—Br | C—Cl | C—H | CF3 | C—H | C—CF3 | H | H | CH3SCH2CO | H | 1 |
| 2-1800 | H | C—Cl | C—Br | C—Cl | C—H | CF3 | C—H | C—CF3 | H | H | CH3SOCH2CO | H | 1 |
| 2-1801 | H | C—Cl | C—Br | C—Cl | C—H | CF3 | C—H | C—CF3 | H | H | CH3SO2CH2CO | H | 1 |

TABLE 2-1-continued

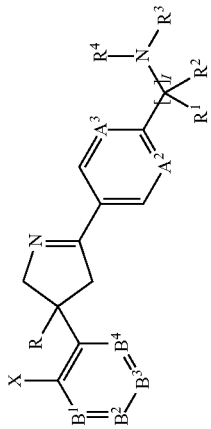

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1802 | H | C—Cl | C—Br | C—Cl | C—H | CF3 | C—H | C—CF3 | Me | H | H | H | 1 |
| 2-1803 | H | C—Cl | C—Br | C—Cl | C—H | CF3 | C—H | C—CF3 | Me | H | EtCO | H | 1 |
| 2-1804 | H | C—Cl | C—Br | C—Cl | C—H | CF3 | C—H | C—CF3 | Me | H | CF3CH2CO | H | 1 |
| 2-1805 | H | C—Cl | C—Br | C—Cl | C—H | CF3 | C—H | C—CF3 | Me | H | CH3SCH2CO | H | 1 |
| 2-1806 | H | C—Cl | C—Br | C—Cl | C—H | CF3 | N | C—CF3 | H | H | H | H | 1 |
| 2-1807 | H | C—Cl | C—Br | C—Cl | C—H | CF3 | N | C—CF3 | H | H | EtCO | H | 1 |
| 2-1808 | H | C—Cl | C—Br | C—Cl | C—H | CF3 | N | C—CF3 | H | H | CF3CH2CO | H | 1 |
| 2-1809 | H | C—Cl | C—Br | C—Cl | C—H | CF3 | N | C—CF3 | H | H | CH3SCH2CO | H | 1 |
| 2-1810 | H | C—Cl | C—Br | C—Cl | C—H | CF3 | C—H | C—Cl | H | H | H | H | 1 |
| 2-1811 | H | C—Cl | C—Br | C—Cl | C—H | CF3 | C—H | C—Cl | H | H | MeCO | H | 1 |
| 2-1812 | H | C—Cl | C—Br | C—Cl | C—H | CF3 | C—H | C—Cl | H | H | EtCO | H | 1 |
| 2-1813 | H | C—Cl | C—Br | C—Cl | C—H | CF3 | C—H | C—Cl | H | H | CF3CH2CO | H | 1 |
| 2-1814 | H | C—Cl | C—Br | C—Cl | C—H | CF3 | C—H | C—Cl | H | H | cyclo-PrCO | H | 1 |
| 2-1815 | H | C—Cl | C—Br | C—Cl | C—H | CF3 | C—H | C—Cl | H | H | cyclo-PrCH2CO | H | 1 |
| 2-1816 | H | C—Cl | C—Br | C—Cl | C—H | CF3 | C—H | C—Cl | H | H | CH3SCH2CO | H | 1 |
| 2-1817 | H | C—Cl | C—Br | C—Cl | C—H | CF3 | C—H | C—Cl | H | H | CH3SOCH2CO | H | 1 |
| 2-1818 | H | C—Cl | C—Br | C—Cl | C—H | CF3 | C—H | C—Cl | H | H | CH3SO2CH2CO | H | 1 |
| 2-1819 | H | C—Cl | C—Br | C—Cl | C—H | CF3 | C—H | C—Cl | H | H | EtNHCO | H | 1 |
| 2-1820 | H | C—Cl | C—Br | C—Cl | C—H | CF3 | C—H | C—Cl | Me | H | H | H | 1 |
| 2-1821 | H | C—Cl | C—Br | C—Cl | C—H | CF3 | C—H | C—Cl | Me | H | EtCO | H | 1 |
| 2-1822 | H | C—Cl | C—Br | C—Cl | C—H | CF3 | C—H | C—Cl | Me | H | CF3CH2CO | H | 1 |
| 2-1823 | H | C—Cl | C—Br | C—Cl | C—H | CF3 | C—H | C—Cl | Me | H | CH3SCH2CO | H | 1 |
| 2-1824 | H | C—Cl | C—Br | C—Cl | C—H | CF3 | N | C—Cl | H | H | H | H | 1 |
| 2-1825 | H | C—Cl | C—Br | C—Cl | C—H | CF3 | N | C—Cl | H | H | EtCO | H | 1 |
| 2-1826 | H | C—Cl | C—Br | C—Cl | C—H | CF3 | N | C—Cl | H | H | CF3CH2CO | H | 1 |
| 2-1827 | H | C—Cl | C—Br | C—Cl | C—H | CF3 | N | C—Cl | H | H | CH3SCH2CO | H | 1 |
| 2-1828 | H | C—Cl | C—Br | C—Cl | C—H | CF3 | C—H | C—Br | H | H | H | H | 1 |
| 2-1829 | H | C—Cl | C—Br | C—Cl | C—H | CF3 | C—H | C—Br | H | H | MeCO | H | 1 |
| 2-1830 | H | C—Cl | C—Br | C—Cl | C—H | CF3 | C—H | C—Br | H | H | EtCO | H | 1 |
| 2-1831 | H | C—Cl | C—Br | C—Cl | C—H | CF3 | C—H | C—Br | H | H | CF3CH2CO | H | 1 |
| 2-1832 | H | C—Cl | C—Br | C—Cl | C—H | CF3 | C—H | C—Br | H | H | cyclo-PrCO | H | 1 |
| 2-1833 | H | C—Cl | C—Br | C—Cl | C—H | CF3 | C—H | C—Br | H | H | cyclo-PrCH2CO | H | 1 |
| 2-1834 | H | C—Cl | C—Br | C—Cl | C—H | CF3 | C—H | C—Br | H | H | CH3SCH2CO | H | 1 |
| 2-1835 | H | C—Cl | C—Br | C—Cl | C—H | CF3 | C—H | C—Br | H | H | CH3SOCH2CO | H | 1 |
| 2-1836 | H | C—Cl | C—Br | C—Cl | C—H | CF3 | C—H | C—Br | H | H | CH3SO2CH2CO | H | 1 |
| 2-1837 | H | C—Cl | C—Br | C—Cl | C—H | CF3 | C—H | C—Br | H | H | EtNHCO | H | 1 |
| 2-1838 | H | C—Cl | C—Br | C—Cl | C—H | CF3 | C—H | C—Br | Me | H | H | H | 1 |
| 2-1839 | H | C—Cl | C—Br | C—Cl | C—H | CF3 | C—H | C—Br | Me | H | EtCO | H | 1 |
| 2-1840 | H | C—Cl | C—Br | C—Cl | C—H | CF3 | C—H | C—Br | Me | H | CF3CH2CO | H | 1 |
| 2-1841 | H | C—Cl | C—Br | C—Cl | C—H | CF3 | C—H | C—Br | Me | H | CH3SCH2CO | H | 1 |
| 2-1842 | H | C—Cl | C—Br | C—Cl | C—H | CF3 | N | C—Br | H | H | H | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-1843 | H | C—Cl | C—Br | C—Cl | C—H | CF3 | N | C—Br | H | H | EtCO | H | 1 |
| 2-1844 | H | C—Cl | C—Br | C—Cl | C—H | CF3 | N | C—Br | H | H | CF3CH2CO | H | 1 |
| 2-1845 | H | C—Cl | C—Br | C—Cl | C—H | CF3 | N | C—Br | H | H | CH3SCH2CO | H | 1 |
| 2-1846 | H | C—Cl | C—Br | C—Cl | C—H | CF3 | C—H | C—CN | H | H | H | H | 1 |
| 2-1847 | H | C—Cl | C—Br | C—Cl | C—H | CF3 | C—H | C—CN | H | H | MeCO | H | 1 |
| 2-1848 | H | C—Cl | C—Br | C—Cl | C—H | CF3 | C—H | C—CN | H | H | EtCO | H | 1 |
| 2-1849 | H | C—Cl | C—Br | C—Cl | C—H | CF3 | C—H | C—CN | H | H | CF3CH2CO | H | 1 |
| 2-1850 | H | C—Cl | C—Br | C—Cl | C—H | CF3 | C—H | C—CN | H | H | cyclo-PrCO | H | 1 |
| 2-1851 | H | C—Cl | C—Br | C—Cl | C—H | CF3 | C—H | C—CN | H | H | cyclo-PrCH2CO | H | 1 |
| 2-1852 | H | C—Cl | C—Br | C—Cl | C—H | CF3 | C—H | C—CN | H | H | CH3SCH2CO | H | 1 |
| 2-1853 | H | C—Cl | C—Br | C—Cl | C—H | CF3 | C—H | C—CN | H | H | CH3SOCH2CO | H | 1 |
| 2-1854 | H | C—Cl | C—Br | C—Cl | C—H | CF3 | C—H | C—CN | H | H | CH3SO2CH2CO | H | 1 |
| 2-1855 | H | C—Cl | C—Br | C—Cl | C—H | CF3 | C—H | C—CN | H | H | EtNHCO | H | 1 |
| 2-1856 | H | C—Cl | C—Br | C—Cl | C—H | CF3 | C—H | C—CN | Me | H | EtCO | H | 1 |
| 2-1857 | H | C—Cl | C—Br | C—Cl | C—H | CF3 | C—H | C—CN | Me | H | CF3CH2CO | H | 1 |
| 2-1858 | H | C—Cl | C—Br | C—Cl | C—H | CF3 | C—H | C—CN | H | H | EtCO | H | 1 |
| 2-1859 | H | C—Cl | C—Br | C—Cl | C—H | CF3 | N | C—CN | H | H | CF3CH2CO | H | 1 |
| 2-1860 | H | C—Cl | C—Br | C—Cl | C—H | CF3 | C—H | C—Me | H | H | H | H | 1 |
| 2-1861 | H | C—Cl | C—Br | C—Cl | C—H | CF3 | C—H | C—Me | H | H | MeCO | H | 1 |
| 2-1862 | H | C—Cl | C—Br | C—Cl | C—H | CF3 | C—H | C—Me | H | H | EtCO | H | 1 |
| 2-1863 | H | C—Cl | C—Br | C—Cl | C—H | CF3 | C—H | C—Me | H | H | CF3CH2CO | H | 1 |
| 2-1864 | H | C—Cl | C—Br | C—Cl | C—H | CF3 | C—H | C—Me | H | H | cyclo-PrCO | H | 1 |
| 2-1865 | H | C—Cl | C—Br | C—Cl | C—H | CF3 | C—H | C—Me | H | H | cyclo-PrCH2CO | H | 1 |
| 2-1866 | H | C—Cl | C—Br | C—Cl | C—H | CF3 | C—H | C—Me | H | H | CH3SCH2CO | H | 1 |
| 2-1867 | H | C—Cl | C—Br | C—Cl | C—H | CF3 | C—H | C—Me | H | H | CH3SOCH2CO | H | 1 |
| 2-1868 | H | C—Cl | C—Br | C—Cl | C—H | CF3 | C—H | C—Me | H | H | CH3SO2CH2CO | H | 1 |
| 2-1869 | H | C—Cl | C—Br | C—Cl | C—H | CF3 | C—H | C—Me | H | H | EtNHCO | H | 1 |
| 2-1870 | H | C—Cl | C—Br | C—Cl | C—H | CF3 | C—H | C—Me | Me | H | EtCO | H | 1 |
| 2-1871 | H | C—Cl | C—Br | C—Cl | C—H | CF3 | C—H | C—Me | Me | H | CF3CH2CO | H | 1 |
| 2-1872 | H | C—Cl | C—Br | C—Cl | C—H | CF3 | N | C—Me | H | H | EtCO | H | 1 |
| 2-1873 | H | C—Cl | C—Br | C—Cl | C—H | CF3 | N | C—Me | H | H | CF3CH2CO | H | 1 |
| 2-1874 | H | C—Cl | C—Br | C—Cl | C—H | CF3 | C—H | C—NO2 | H | H | H | H | 1 |
| 2-1875 | H | C—Cl | C—Br | C—Cl | C—H | CF3 | C—H | C—NO2 | H | H | MeCO | H | 1 |
| 2-1876 | H | C—Cl | C—Br | C—Cl | C—H | CF3 | C—H | C—NO2 | H | H | EtCO | H | 1 |
| 2-1877 | H | C—Cl | C—Br | C—Cl | C—H | CF3 | C—H | C—NO2 | H | H | CF3CH2CO | H | 1 |
| 2-1878 | H | C—Cl | C—Br | C—Cl | C—H | CF3 | C—H | C—NO2 | H | H | cyclo-PrCO | H | 1 |
| 2-1879 | H | C—Cl | C—Br | C—Cl | C—H | CF3 | C—H | C—NO2 | H | H | cyclo-PrCH2CO | H | 1 |
| 2-1880 | H | C—Cl | C—Br | C—Cl | C—H | CF3 | C—H | C—NO2 | H | H | CH3SCH2CO | H | 1 |
| 2-1881 | H | C—Cl | C—Br | C—Cl | C—H | CF3 | C—H | C—NO2 | H | H | CH3SOCH2CO | H | 1 |
| 2-1882 | H | C—Cl | C—Br | C—Cl | C—H | CF3 | C—H | C—NO2 | H | H | CH3SO2CH2CO | H | 1 |
| 2-1883 | H | C—Cl | C—Br | C—Cl | C—H | CF3 | C—H | C—NO2 | H | H | EtNHCO | H | 1 |

TABLE 2-1-continued

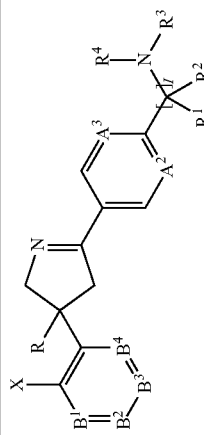

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1884 | H | C—Cl | C—Br | C—Cl | C—H | CF3 | C—H | C—NO2 | Me | H | EtCO | H | 1 |
| 2-1885 | H | C—Cl | C—Br | C—Cl | C—H | CF3 | C—H | C—NO2 | Me | H | CF3CH2CO | H | 1 |
| 2-1886 | H | C—Cl | C—Br | C—Cl | C—H | CF3 | N | C—NO2 | H | H | EtCO | H | 1 |
| 2-1887 | H | C—Cl | C—Br | C—Cl | C—H | CF3 | N | C—NO2 | H | H | CF3CH2CO | H | 1 |
| 2-1888 | H | C—Cl | C—Br | C—Cl | C—H | CF3 | C—H | C—SMe | H | H | H | H | 1 |
| 2-1889 | H | C—Cl | C—Br | C—Cl | C—H | CF3 | C—H | C—SMe | H | H | MeCO | H | 1 |
| 2-1890 | H | C—Cl | C—Br | C—Cl | C—H | CF3 | C—H | C—SMe | H | H | EtCO | H | 1 |
| 2-1891 | H | C—Cl | C—Br | C—Cl | C—H | CF3 | C—H | C—SMe | H | H | CF3CH2CO | H | 1 |
| 2-1892 | H | C—Cl | C—Br | C—Cl | C—H | CF3 | C—H | C—SMe | H | H | cyclo-PrCO | H | 1 |
| 2-1893 | H | C—Cl | C—Br | C—Cl | C—H | CF3 | C—H | C—SMe | H | H | cyclo-PrCH2CO | H | 1 |
| 2-1894 | H | C—Cl | C—Br | C—Cl | C—H | CF3 | C—H | C—SMe | H | H | CH3SCH2CO | H | 1 |
| 2-1895 | H | C—Cl | C—Br | C—Cl | C—H | CF3 | C—H | C—SMe | H | H | CH3SOCH2CO | H | 1 |
| 2-1896 | H | C—Cl | C—Br | C—Cl | C—H | CF3 | C—H | C—SMe | H | H | CH3SO2CH2CO | H | 1 |
| 2-1897 | H | C—Cl | C—Br | C—Cl | C—H | CF3 | C—H | C—SMe | H | H | EtNHCO | H | 1 |
| 2-1898 | H | C—Cl | C—Br | C—Cl | C—H | CF3 | C—H | C—SMe | Me | H | EtCO | H | 1 |
| 2-1899 | H | C—Cl | C—Br | C—Cl | C—H | CF3 | C—H | C—SMe | Me | H | CF3CH2CO | H | 1 |
| 2-1900 | H | C—Cl | C—Br | C—Cl | C—H | CF3 | N | C—SMe | H | H | EtCO | H | 1 |
| 2-1901 | H | C—Cl | C—Br | C—Cl | C—H | CF3 | N | C—SMe | H | H | CF3CH2CO | H | 1 |
| 2-1902 | H | C—Cl | C—Br | C—Cl | C—H | CF3 | C—H | C—SOMe | H | H | H | H | 1 |
| 2-1903 | H | C—Cl | C—Br | C—Cl | C—H | CF3 | C—H | C—SOMe | H | H | MeCO | H | 1 |
| 2-1904 | H | C—Cl | C—Br | C—Cl | C—H | CF3 | C—H | C—SOMe | H | H | EtCO | H | 1 |
| 2-1905 | H | C—Cl | C—Br | C—Cl | C—H | CF3 | C—H | C—SOMe | H | H | CF3CH2CO | H | 1 |
| 2-1906 | H | C—Cl | C—Br | C—Cl | C—H | CF3 | C—H | C—SOMe | H | H | cyclo-PrCO | H | 1 |
| 2-1907 | H | C—Cl | C—Br | C—Cl | C—H | CF3 | C—H | C—SOMe | H | H | cyclo-PrCH2CO | H | 1 |
| 2-1908 | H | C—Cl | C—Br | C—Cl | C—H | CF3 | C—H | C—SOMe | H | H | CH3SCH2CO | H | 1 |
| 2-1909 | H | C—Cl | C—Br | C—Cl | C—H | CF3 | C—H | C—SOMe | H | H | CH3SOCH2CO | H | 1 |
| 2-1910 | H | C—Cl | C—Br | C—Cl | C—H | CF3 | C—H | C—SOMe | H | H | CH3SO2CH2CO | H | 1 |
| 2-1911 | H | C—Cl | C—Br | C—Cl | C—H | CF3 | C—H | C—SOMe | H | H | EtNHCO | H | 1 |
| 2-1912 | H | C—Cl | C—Br | C—Cl | C—H | CF3 | C—H | C—SOMe | Me | H | EtCO | H | 1 |
| 2-1913 | H | C—Cl | C—Br | C—Cl | C—H | CF3 | C—H | C—SOMe | Me | H | CF3CH2CO | H | 1 |
| 2-1914 | H | C—Cl | C—Br | C—Cl | C—H | CF3 | N | C—SOMe | H | H | EtCO | H | 1 |
| 2-1915 | H | C—Cl | C—Br | C—Cl | C—H | CF3 | N | C—SOMe | H | H | CF3CH2CO | H | 1 |
| 2-1916 | H | C—Cl | C—Br | C—Cl | C—H | CF3 | C—H | C—SO2Me | H | H | H | H | 1 |
| 2-1917 | H | C—Cl | C—Br | C—Cl | C—H | CF3 | C—H | C—SO2Me | H | H | MeCO | H | 1 |
| 2-1918 | H | C—Cl | C—Br | C—Cl | C—H | CF3 | C—H | C—SO2Me | H | H | EtCO | H | 1 |
| 2-1919 | H | C—Cl | C—Br | C—Cl | C—H | CF3 | C—H | C—SO2Me | H | H | CF3CH2CO | H | 1 |
| 2-1920 | H | C—Cl | C—Br | C—Cl | C—H | CF3 | C—H | C—SO2Me | H | H | cyclo-PrCO | H | 1 |
| 2-1921 | H | C—Cl | C—Br | C—Cl | C—H | CF3 | C—H | C—SO2Me | H | H | cyclo-PrCH2CO | H | 1 |
| 2-1922 | H | C—Cl | C—Br | C—Cl | C—H | CF3 | C—H | C—SO2Me | H | H | CH3SCH2CO | H | 1 |
| 2-1923 | H | C—Cl | C—Br | C—Cl | C—H | CF3 | C—H | C—SO2Me | H | H | CH3SOCH2CO | H | 1 |
| 2-1924 | H | C—Cl | C—Br | C—Cl | C—H | CF3 | C—H | C—SO2Me | H | H | CH3SO2CH2CO | H | 1 |

TABLE 2-1-continued

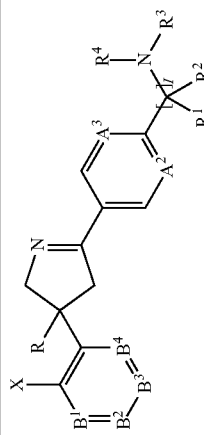

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1925 | H | C—Cl | C—Br | C—Cl | C—H | CF3 | C—H | C—SO2Me | H | H | EtNHCO | H | 1 |
| 2-1926 | H | C—Cl | C—Br | C—Cl | C—H | CF3 | C—H | C—SO2Me | Me | H | EtCO | H | 1 |
| 2-1927 | H | C—Cl | C—Br | C—Cl | C—H | CF3 | C—H | C—SO2Me | Me | H | CF3CH2CO | H | 1 |
| 2-1928 | H | C—Cl | C—Br | C—Cl | C—H | CF3 | N | C—SO2Me | H | H | EtCO | H | 1 |
| 2-1929 | H | C—Cl | C—Br | C—Cl | C—H | CF3 | C—H | C—SO2Me | H | H | CF3CH2CO | H | 1 |
| 2-1930 | H | C—Cl | C—Br | C—Cl | C—H | CF3 | C—H | C—SCF3 | H | H | H | H | 1 |
| 2-1931 | H | C—Cl | C—Br | C—Cl | C—H | CF3 | C—H | C—SCF3 | H | H | MeCO | H | 1 |
| 2-1932 | H | C—Cl | C—Br | C—Cl | C—H | CF3 | C—H | C—SCF3 | H | H | EtCO | H | 1 |
| 2-1933 | H | C—Cl | C—Br | C—Cl | C—H | CF3 | C—H | C—SCF3 | H | H | CF3CH2CO | H | 1 |
| 2-1934 | H | C—Cl | C—Br | C—Cl | C—H | CF3 | C—H | C—SCF3 | H | H | cyclo-PrCO | H | 1 |
| 2-1935 | H | C—Cl | C—Br | C—Cl | C—H | CF3 | C—H | C—SCF3 | H | H | cyclo-PrCH2CO | H | 1 |
| 2-1936 | H | C—Cl | C—Br | C—Cl | C—H | CF3 | C—H | C—SCF3 | H | H | CH3SCH2CO | H | 1 |
| 2-1937 | H | C—Cl | C—Br | C—Cl | C—H | CF3 | C—H | C—SCF3 | H | H | CH3SOCH2CO | H | 1 |
| 2-1938 | H | C—Cl | C—Br | C—Cl | C—H | CF3 | C—H | C—SCF3 | H | H | CH3SO2CH2CO | H | 1 |
| 2-1939 | H | C—Cl | C—Br | C—Cl | C—H | CF3 | C—H | C—SCF3 | H | H | EtNHCO | H | 1 |
| 2-1940 | H | C—Cl | C—Br | C—Cl | C—H | CF3 | C—H | C—SCF3 | Me | H | EtCO | H | 1 |
| 2-1941 | H | C—Cl | C—Br | C—Cl | C—H | CF3 | C—H | C—SCF3 | Me | H | CF3CH2CO | H | 1 |
| 2-1942 | H | C—Cl | C—Br | C—Cl | C—H | CF3 | N | C—SCF3 | H | H | EtCO | H | 1 |
| 2-1943 | H | C—Cl | C—Br | C—Cl | C—H | CF3 | N | C—SCF3 | H | H | CF3CH2CO | H | 1 |
| 2-1944 | H | C—Cl | C—Br | C—Cl | C—H | CF3 | C—H | C—SOCF3 | H | H | H | H | 1 |
| 2-1945 | H | C—Cl | C—Br | C—Cl | C—H | CF3 | C—H | C—SOCF3 | H | H | MeCO | H | 1 |
| 2-1946 | H | C—Cl | C—Br | C—Cl | C—H | CF3 | C—H | C—SOCF3 | H | H | EtCO | H | 1 |
| 2-1947 | H | C—Cl | C—Br | C—Cl | C—H | CF3 | C—H | C—SOCF3 | H | H | CF3CH2CO | H | 1 |
| 2-1948 | H | C—Cl | C—Br | C—Cl | C—H | CF3 | C—H | C—SOCF3 | H | H | cyclo-PrCO | H | 1 |
| 2-1949 | H | C—Cl | C—Br | C—Cl | C—H | CF3 | C—H | C—SOCF3 | H | H | cyclo-PrCH2CO | H | 1 |
| 2-1950 | H | C—Cl | C—Br | C—Cl | C—H | CF3 | C—H | C—SOCF3 | H | H | CH3SCH2CO | H | 1 |
| 2-1951 | H | C—Cl | C—Br | C—Cl | C—H | CF3 | C—H | C—SOCF3 | H | H | CH3SOCH2CO | H | 1 |
| 2-1952 | H | C—Cl | C—Br | C—Cl | C—H | CF3 | C—H | C—SOCF3 | H | H | CH3SO2CH2CO | H | 1 |
| 2-1953 | H | C—Cl | C—Br | C—Cl | C—H | CF3 | C—H | C—SOCF3 | H | H | EtNHCO | H | 1 |
| 2-1954 | H | C—Cl | C—Br | C—Cl | C—H | CF3 | C—H | C—SOCF3 | Me | H | EtCO | H | 1 |
| 2-1955 | H | C—Cl | C—Br | C—Cl | C—H | CF3 | C—H | C—SOCF3 | Me | H | CF3CH2CO | H | 1 |
| 2-1956 | H | C—Cl | C—Br | C—Cl | C—H | CF3 | N | C—SOCF3 | H | H | EtCO | H | 1 |
| 2-1957 | H | C—Cl | C—Br | C—Cl | C—H | CF3 | N | C—SOCF3 | H | H | CF3CH2CO | H | 1 |
| 2-1958 | H | C—Cl | C—Br | C—Cl | C—H | CF3 | C—H | C—H | H | H | H | H | 1 |
| 2-1959 | H | C—Cl | C—Br | C—Cl | C—H | CF3 | C—H | C—H | H | H | MeCO | H | 1 |
| 2-1960 | H | C—Cl | C—Br | C—Cl | C—H | CF3 | C—H | C—H | H | H | EtCO | H | 1 |
| 2-1961 | H | C—Cl | C—Br | C—Cl | C—H | CF3 | C—H | C—H | H | H | CF3CH2CO | H | 1 |
| 2-1962 | H | C—Cl | C—Br | C—Cl | C—H | CF3 | C—H | C—H | H | H | cyclo-PrCO | H | 1 |
| 2-1963 | H | C—Cl | C—Br | C—Cl | C—H | CF3 | C—H | C—H | H | H | cyclo-PrCH2CO | H | 1 |
| 2-1964 | H | C—Cl | C—Br | C—Cl | C—H | CF3 | C—H | C—H | H | H | CH3SCH2CO | H | 1 |
| 2-1965 | H | C—Cl | C—Br | C—Cl | C—H | CF3 | C—H | C—H | H | H | CH3SOCH2CO | H | 1 |

TABLE 2-1-continued

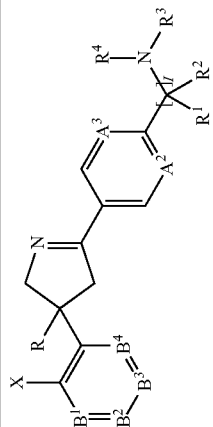

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-1966 | H | C—Cl | C—Br | C—Cl | C—H | CF3 | C—H | C—H | H | H | CH3SO2CH2CO | H | 1 |
| 2-1967 | H | C—Cl | C—Br | C—Cl | C—H | CF3 | C—H | C—H | H | H | EtNHCO | H | 1 |
| 2-1968 | H | C—Cl | C—Br | C—Cl | C—H | CF3 | C—H | C—H | Me | H | H | H | 1 |
| 2-1969 | H | C—Cl | C—Br | C—Cl | C—H | CF3 | C—H | C—H | Me | H | EtCO | H | 1 |
| 2-1970 | H | C—Cl | C—Br | C—Cl | C—H | CF3 | C—H | C—H | Me | H | CF3CH2CO | H | 1 |
| 2-1971 | H | C—Cl | C—Br | C—Cl | C—H | CF3 | C—H | C—H | Me | H | CH3SCH2CO | H | 1 |
| 2-1972 | H | C—Cl | C—Br | C—Cl | C—H | CF3 | N | C—H | H | H | H | H | 1 |
| 2-1973 | H | C—Cl | C—Br | C—Cl | C—H | CF3 | N | C—H | H | H | EtCO | H | 1 |
| 2-1974 | H | C—Cl | C—Br | C—Cl | C—H | CF3 | N | C—H | H | H | CF3CH2CO | H | 1 |
| 2-1975 | H | C—Cl | C—Br | C—Cl | C—H | CF3 | N | C—H | H | H | CH3SCH2CO | H | 1 |
| 2-1976 | H | C—Cl | C—Br | C—Cl | C—H | CF3 | C—H | C—F | H | H | H | H | 1 |
| 2-1977 | H | C—Cl | C—Br | C—Cl | C—H | CF3 | C—H | C—F | H | H | MeCO | H | 1 |
| 2-1978 | H | C—Cl | C—Br | C—Cl | C—H | CF3 | C—H | C—F | H | H | EtCO | H | 1 |
| 2-1979 | H | C—Cl | C—Br | C—Cl | C—H | CF3 | C—H | C—F | H | H | CF3CH2CO | H | 1 |
| 2-1980 | H | C—Cl | C—Br | C—Cl | C—H | CF3 | C—H | C—F | H | H | cyclo-PrCO | H | 1 |
| 2-1981 | H | C—Cl | C—Br | C—Cl | C—H | CF3 | C—H | C—F | H | H | cyclo-PrCH2CO | H | 1 |
| 2-1982 | H | C—Cl | C—Br | C—Cl | C—H | CF3 | C—H | C—F | H | H | CH3SCH2CO | H | 1 |
| 2-1983 | H | C—Cl | C—Br | C—Cl | C—H | CF3 | C—H | C—F | H | H | CH3SOCH2CO | H | 1 |
| 2-1984 | H | C—Cl | C—Br | C—Cl | C—H | CF3 | C—H | C—F | H | H | CH3SO2CH2CO | H | 1 |
| 2-1985 | H | C—Cl | C—Br | C—Cl | C—H | CF3 | C—H | C—F | H | H | EtNHCO | H | 1 |
| 2-1986 | H | C—Cl | C—Br | C—Cl | C—H | CF3 | C—H | C—F | Me | H | EtCO | H | 1 |
| 2-1987 | H | C—Cl | C—Br | C—Cl | C—H | CF3 | C—H | C—F | Me | H | CF3CH2CO | H | 1 |
| 2-1988 | H | C—Cl | C—Br | C—Cl | C—H | CF3 | N | C—F | H | H | EtCO | H | 1 |
| 2-1989 | H | C—Cl | C—Br | C—Cl | C—H | CF3 | N | C—F | H | H | CF3CH2CO | H | 1 |
| 2-1990 | H | C—Cl | C—Br | C—Cl | C—H | CF3 | C—H | C—I | H | H | H | H | 1 |
| 2-1991 | H | C—Cl | C—Br | C—Cl | C—H | CF3 | C—H | C—I | H | H | MeCO | H | 1 |
| 2-1992 | H | C—Cl | C—Br | C—Cl | C—H | CF3 | C—H | C—I | H | H | EtCO | H | 1 |
| 2-1993 | H | C—Cl | C—Br | C—Cl | C—H | CF3 | C—H | C—I | H | H | CF3CH2CO | H | 1 |
| 2-1994 | H | C—Cl | C—Br | C—Cl | C—H | CF3 | C—H | C—I | H | H | cyclo-PrCO | H | 1 |
| 2-1995 | H | C—Cl | C—Br | C—Cl | C—H | CF3 | C—H | C—I | H | H | cyclo-PrCH2CO | H | 1 |
| 2-1996 | H | C—Cl | C—Br | C—Cl | C—H | CF3 | C—H | C—I | H | H | CH3SCH2CO | H | 1 |
| 2-1997 | H | C—Cl | C—Br | C—Cl | C—H | CF3 | C—H | C—I | H | H | CH3SOCH2CO | H | 1 |
| 2-1998 | H | C—Cl | C—Br | C—Cl | C—H | CF3 | C—H | C—I | H | H | CH3SO2CH2CO | H | 1 |
| 2-1999 | H | C—Cl | C—Br | C—Cl | C—H | CF3 | C—H | C—I | H | H | EtNHCO | H | 1 |
| 2-2000 | H | C—Cl | C—Br | C—Cl | C—H | CF3 | C—H | C—I | Me | H | EtCO | H | 1 |
| 2-2001 | H | C—Cl | C—Br | C—Cl | C—H | CF3 | C—H | C—I | Me | H | CF3CH2CO | H | 1 |
| 2-2002 | H | C—Cl | C—Br | C—Cl | C—H | CF3 | N | C—I | H | H | EtCO | H | 1 |
| 2-2003 | H | C—Cl | C—Br | C—Cl | C—H | CF3 | N | C—I | H | H | CF3CH2CO | H | 1 |
| 2-2004 | H | C—Cl | C—Br | C—Cl | C—H | CF3 | C—H | C—NH2 | H | H | H | H | 1 |
| 2-2005 | H | C—Cl | C—Br | C—Cl | C—H | CF3 | C—H | C—NH2 | H | H | MeCO | H | 1 |
| 2-2006 | H | C—Cl | C—Br | C—Cl | C—H | CF3 | C—H | C—NH2 | H | H | EtCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2007 | H | C—Cl | C—Br | C—Cl | C—H | CF3 | C—H | C—NH2 | H | H | CF3CH2CO | H | 1 |
| 2-2008 | H | C—Cl | C—Br | C—Cl | C—H | CF3 | C—H | C—NH2 | H | H | cyclo-PrCO | H | 1 |
| 2-2009 | H | C—Cl | C—Br | C—Cl | C—H | CF3 | C—H | C—NH2 | H | H | cyclo-PrCH2CO | H | 1 |
| 2-2010 | H | C—Cl | C—Br | C—Cl | C—H | CF3 | C—H | C—NH2 | H | H | CH3SCH2CO | H | 1 |
| 2-2011 | H | C—Cl | C—Br | C—Cl | C—H | CF3 | C—H | C—NH2 | H | H | CH3SOCH2CO | H | 1 |
| 2-2012 | H | C—Cl | C—Br | C—Cl | C—H | CF3 | C—H | C—NH2 | H | H | CH3SO2CH2CO | H | 1 |
| 2-2013 | H | C—Cl | C—Br | C—Cl | C—H | CF3 | C—H | C—NH2 | H | H | EtNHCO | H | 1 |
| 2-2014 | H | C—Cl | C—Br | C—Cl | C—H | CF3 | C—H | C—NH2 | Me | H | EtCO | H | 1 |
| 2-2015 | H | C—Cl | C—Br | C—Cl | C—H | CF3 | C—H | C—NH2 | Me | H | CF3CH2CO | H | 1 |
| 2-2016 | H | C—Cl | C—Br | C—Cl | C—H | CF3 | N | C—NH2 | H | H | EtCO | H | 1 |
| 2-2017 | H | C—Cl | C—Br | C—Cl | C—H | CF3 | N | C—NH2 | H | H | CF3CH2CO | H | 1 |
| 2-2018 | H | C—Cl | C—Br | C—Cl | C—H | CF3 | C—H | C—NHAc | H | H | H | H | 1 |
| 2-2019 | H | C—Cl | C—Br | C—Cl | C—H | CF3 | C—H | C—NHAc | H | H | MeCO | H | 1 |
| 2-2020 | H | C—Cl | C—Br | C—Cl | C—H | CF3 | C—H | C—NHAc | H | H | EtCO | H | 1 |
| 2-2021 | H | C—Cl | C—Br | C—Cl | C—H | CF3 | C—H | C—NHAc | H | H | CF3CH2CO | H | 1 |
| 2-2022 | H | C—Cl | C—Br | C—Cl | C—H | CF3 | C—H | C—NHAc | H | H | cyclo-PrCO | H | 1 |
| 2-2023 | H | C—Cl | C—Br | C—Cl | C—H | CF3 | C—H | C—NHAc | H | H | cyclo-PrCH2CO | H | 1 |
| 2-2024 | H | C—Cl | C—Br | C—Cl | C—H | CF3 | C—H | C—NHAc | H | H | CH3SCH2CO | H | 1 |
| 2-2025 | H | C—Cl | C—Br | C—Cl | C—H | CF3 | C—H | C—NHAc | H | H | CH3SOCH2CO | H | 1 |
| 2-2026 | H | C—Cl | C—Br | C—Cl | C—H | CF3 | C—H | C—NHAc | H | H | CH3SO2CH2CO | H | 1 |
| 2-2027 | H | C—Cl | C—Br | C—Cl | C—H | CF3 | C—H | C—NHAc | H | H | EtNHCO | H | 1 |
| 2-2028 | H | C—Cl | C—Br | C—Cl | C—H | CF3 | C—H | C—NHAc | Me | H | EtCO | H | 1 |
| 2-2029 | H | C—Cl | C—Br | C—Cl | C—H | CF3 | C—H | C—NHAc | Me | H | CF3CH2CO | H | 1 |
| 2-2030 | H | C—Cl | C—Br | C—Cl | C—H | CF3 | N | C—NHAc | H | H | EtCO | H | 1 |
| 2-2031 | H | C—Cl | C—Br | C—Cl | C—H | CF3 | N | C—NHAc | H | H | CF3CH2CO | H | 1 |
| 2-2032 | H | C—Cl | C—Br | C—Cl | C—H | CF3 | C—H | C—NHCOCF3 | H | H | H | H | 1 |
| 2-2033 | H | C—Cl | C—Br | C—Cl | C—H | CF3 | C—H | C—NHCOCF3 | H | H | MeCO | H | 1 |
| 2-2034 | H | C—Cl | C—Br | C—Cl | C—H | CF3 | C—H | C—NHCOCF3 | H | H | EtCO | H | 1 |
| 2-2035 | H | C—Cl | C—Br | C—Cl | C—H | CF3 | C—H | C—NHCOCF3 | H | H | CF3CH2CO | H | 1 |
| 2-2036 | H | C—Cl | C—Br | C—Cl | C—H | CF3 | C—H | C—NHCOCF3 | H | H | cyclo-PrCO | H | 1 |
| 2-2037 | H | C—Cl | C—Br | C—Cl | C—H | CF3 | C—H | C—NHCOCF3 | H | H | cyclo-PrCH2CO | H | 1 |
| 2-2038 | H | C—Cl | C—Br | C—Cl | C—H | CF3 | C—H | C—NHCOCF3 | H | H | CH3SCH2CO | H | 1 |
| 2-2039 | H | C—Cl | C—Br | C—Cl | C—H | CF3 | C—H | C—NHCOCF3 | H | H | CH3SOCH2CO | H | 1 |
| 2-2040 | H | C—Cl | C—Br | C—Cl | C—H | CF3 | C—H | C—NHCOCF3 | H | H | CH3SO2CH2CO | H | 1 |
| 2-2041 | H | C—Cl | C—Br | C—Cl | C—H | CF3 | C—H | C—NHCOCF3 | H | H | EtNHCO | H | 1 |
| 2-2042 | H | C—Cl | C—Br | C—Cl | C—H | CF3 | C—H | C—NHCOCF3 | Me | H | EtCO | H | 1 |
| 2-2043 | H | C—Cl | C—Br | C—Cl | C—H | CF3 | C—H | C—NHCOCF3 | Me | H | CF3CH2CO | H | 1 |
| 2-2044 | H | C—Cl | C—Br | C—Cl | C—H | CF3 | N | C—NHCOCF3 | H | H | EtCO | H | 1 |
| 2-2045 | H | C—Cl | C—Br | C—Cl | C—H | CF3 | N | C—NHCOCF3 | H | H | CF3CH2CO | H | 1 |
| 2-2046 | H | C—Cl | C—Br | C—Cl | C—H | CF3 | C—H | C—CH2OAc | H | H | H | H | 1 |
| 2-2047 | H | C—Cl | C—Br | C—Cl | C—H | CF3 | C—H | C—CH2OAc | H | H | MeCO | H | 1 |

TABLE 2-1-continued

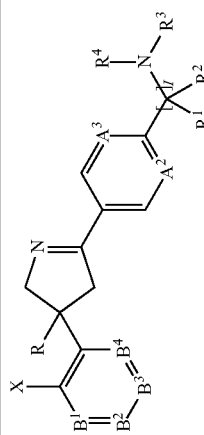

| Example No. | X | B¹ | B² | B³ | B⁴ | R | A² | A³ | | R¹ | R² | R⁴ | R³ | I |
|---|---|---|---|---|---|---|---|---|---|---|---|---|---|---|
| 2-2048 | H | C—Cl | C—Br | C—Cl | C—H | CF3 | C—H | C—CH2OAc | | H | H | EtCO | H | 1 |
| 2-2049 | H | C—Cl | C—Br | C—Cl | C—H | CF3 | C—H | C—CH2OAc | | H | H | CF3CH2CO | H | 1 |
| 2-2050 | H | C—Cl | C—Br | C—Cl | C—H | CF3 | C—H | C—CH2OAc | | H | H | cyclo-PrCO | H | 1 |
| 2-2051 | H | C—Cl | C—Br | C—Cl | C—H | CF3 | C—H | C—CH2OAc | | H | H | cyclo-PrCH2CO | H | 1 |
| 2-2052 | H | C—Cl | C—Br | C—Cl | C—H | CF3 | C—H | C—CH2OAc | | H | H | CH3SCH2CO | H | 1 |
| 2-2053 | H | C—Cl | C—Br | C—Cl | C—H | CF3 | C—H | C—CH2OAc | | H | H | CH3SOCH2CO | H | 1 |
| 2-2054 | H | C—Cl | C—Br | C—Cl | C—H | CF3 | C—H | C—CH2OAc | | H | H | CH3SO2CH2CO | H | 1 |
| 2-2055 | H | C—Cl | C—Br | C—Cl | C—H | CF3 | C—H | C—CH2OAc | | H | H | EtNHCO | H | 1 |
| 2-2056 | H | C—Cl | C—Br | C—Cl | C—H | CF3 | C—H | C—CH2OAc | | Me | H | EtCO | H | 1 |
| 2-2057 | H | C—Cl | C—Br | C—Cl | C—H | CF3 | C—H | C—CH2OAc | | Me | H | CF3CH2CO | H | 1 |
| 2-2058 | H | C—Cl | C—Br | C—Cl | C—H | CF3 | N | C—CH2OAc | | H | H | EtCO | H | 1 |
| 2-2059 | H | C—Cl | C—Br | C—Cl | C—H | CF3 | N | C—CH2OAc | | H | H | CF3CH2CO | H | 1 |
| 2-2060 | H | C—Br | C—H | C—Br | C—H | CF3 | C—H | C—CF3 | | H | H | H | H | 1 |
| 2-2061 | H | C—Br | C—H | C—Br | C—H | CF3 | C—H | C—CF3 | | H | H | CF3CH2CO | H | 1 |
| 2-2062 | H | C—Br | C—H | C—Br | C—H | CF3 | C—H | C—CF3 | | H | H | cyclo-PrCO | H | 1 |
| 2-2063 | H | C—Br | C—H | C—Br | C—H | CF3 | C—H | C—CF3 | | H | H | CH3SCH2CO | H | 1 |
| 2-2064 | H | C—Br | C—H | C—Br | C—H | CF3 | C—H | C—CF3 | | H | H | CH3SOCH2CO | H | 1 |
| 2-2065 | H | C—Br | C—H | C—Br | C—H | CF3 | C—H | C—CF3 | | H | H | CH3SO2CH2CO | H | 1 |
| 2-2066 | H | C—Br | C—H | C—Br | C—H | CF3 | C—H | C—CF3 | | H | H | EtNHCO | H | 1 |
| 2-2067 | H | C—Br | C—H | C—Br | C—H | CF3 | C—H | C—CF3 | | Me | H | EtCO | H | 1 |
| 2-2068 | H | C—Br | C—H | C—Br | C—H | CF3 | C—H | C—CF3 | | Me | H | CF3CH2CO | H | 1 |
| 2-2069 | H | C—Br | C—H | C—Br | C—H | CF3 | N | C—CF3 | | H | H | EtCO | H | 1 |
| 2-2070 | H | C—Br | C—H | C—Br | C—H | CF3 | N | C—CF3 | | H | H | CF3CH2CO | H | 1 |
| 2-2071 | H | C—Br | C—H | C—Br | C—H | CF3 | C—H | C—Cl | | H | H | H | H | 1 |
| 2-2072 | H | C—Br | C—H | C—Br | C—H | CF3 | C—H | C—Cl | | H | H | MeCO | H | 1 |
| 2-2073 | H | C—Br | C—H | C—Br | C—H | CF3 | C—H | C—Cl | | H | H | EtCO | H | 1 |
| 2-2074 | H | C—Br | C—H | C—Br | C—H | CF3 | C—H | C—Cl | | H | H | CF3CH2CO | H | 1 |
| 2-2075 | H | C—Br | C—H | C—Br | C—H | CF3 | C—H | C—Cl | | H | H | cyclo-PrCO | H | 1 |
| 2-2076 | H | C—Br | C—H | C—Br | C—H | CF3 | C—H | C—Cl | | H | H | cyclo-PrCH2CO | H | 1 |
| 2-2077 | H | C—Br | C—H | C—Br | C—H | CF3 | C—H | C—Cl | | H | H | CH3SCH2CO | H | 1 |
| 2-2078 | H | C—Br | C—H | C—Br | C—H | CF3 | C—H | C—Cl | | H | H | CH3SOCH2CO | H | 1 |
| 2-2079 | H | C—Br | C—H | C—Br | C—H | CF3 | C—H | C—Cl | | H | H | CH3SO2CH2CO | H | 1 |
| 2-2080 | H | C—Br | C—H | C—Br | C—H | CF3 | C—H | C—Cl | | H | H | EtNHCO | H | 1 |
| 2-2081 | H | C—Br | C—H | C—Br | C—H | CF3 | C—H | C—Cl | | Me | H | EtCO | H | 1 |
| 2-2082 | H | C—Br | C—H | C—Br | C—H | CF3 | C—H | C—Cl | | Me | H | CF3CH2CO | H | 1 |
| 2-2083 | H | C—Br | C—H | C—Br | C—H | CF3 | C—H | C—Cl | | H | H | EtCO | H | 1 |
| 2-2084 | H | C—Br | C—H | C—Br | C—H | CF3 | C—H | C—Cl | | H | H | CF3CH2CO | H | 1 |
| 2-2085 | H | C—Br | C—H | C—Br | C—H | CF3 | C—H | C—Cl | | H | H | H | H | 1 |
| 2-2086 | H | C—Br | C—H | C—Br | C—H | CF3 | C—H | C—Cl | | H | H | cyclo-PrCH2CO | H | 1 |
| 2-2087 | H | C—Br | C—H | C—Br | C—H | CF3 | C—H | C—Cl | | H | H | CH3SCH2CO | H | 1 |
| 2-2088 | H | C—Br | C—H | C—Br | C—H | CF3 | C—H | C—Cl | | H | H | CH3SOCH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2089 | H | C—Br | C—H | C—Br | C—H | CF3 | C—H | C—Cl | H | H | CH3SO2CH2CO | H | 1 |
| 2-2090 | H | C—Br | C—H | C—Br | C—H | CF3 | C—H | C—Cl | H | H | EtNHCO | H | 1 |
| 2-2091 | H | C—Br | C—H | C—Br | C—H | CF3 | C—H | C—Cl | Me | H | EtCO | H | 1 |
| 2-2092 | H | C—Br | C—H | C—Br | C—H | CF3 | C—H | C—Cl | Me | H | CF3CH2CO | H | 1 |
| 2-2093 | H | C—Br | C—H | C—Br | C—H | CF3 | N | C—Cl | H | H | EtCO | H | 1 |
| 2-2094 | H | C—Br | C—H | C—Br | C—H | CF3 | N | C—Cl | H | H | CF3CH2CO | H | 1 |
| 2-2095 | H | C—Br | C—H | C—Br | C—H | CF3 | C—H | C—Me | H | H | EtCO | H | 1 |
| 2-2096 | H | C—Br | C—H | C—Br | C—H | CF3 | C—H | C—Me | H | H | cyclo-PrCO | H | 1 |
| 2-2097 | H | C—Br | C—H | C—Br | C—H | CF3 | C—H | C—Me | H | H | H | H | 1 |
| 2-2098 | H | C—Br | C—H | C—Br | C—H | CF3 | C—H | C—Me | H | H | MeCO | H | 1 |
| 2-2099 | H | C—Br | C—H | C—Br | C—H | CF3 | C—H | C—Me | H | H | EtCO | H | 1 |
| 2-2100 | H | C—Br | C—H | C—Br | C—H | CF3 | C—H | C—Me | H | H | cyclo-PrCO | H | 1 |
| 2-2101 | H | C—Br | C—H | C—Br | C—H | CF3 | C—H | C—Me | H | H | CF3CH2CO | H | 1 |
| 2-2102 | H | C—Br | C—H | C—Br | C—H | CF3 | C—H | C—NO2 | H | H | H | H | 1 |
| 2-2103 | H | C—Br | C—H | C—Br | C—H | CF3 | C—H | C—NO2 | H | H | EtCO | H | 1 |
| 2-2104 | H | C—Br | C—H | C—Br | C—H | CF3 | C—H | C—NO2 | H | H | cyclo-PrCO | H | 1 |
| 2-2105 | H | C—Br | C—H | C—Br | C—H | CF3 | C—H | C—NO2 | H | H | CF3CH2CO | H | 1 |
| 2-2106 | H | C—Br | C—H | C—Br | C—H | CF3 | C—H | C—NO2 | H | H | H | H | 1 |
| 2-2107 | H | C—Br | C—H | C—Br | C—H | CF3 | C—H | C—NO2 | H | H | MeCO | H | 1 |
| 2-2108 | H | C—Br | C—H | C—Br | C—H | CF3 | C—H | C—NO2 | H | H | EtCO | H | 1 |
| 2-2109 | H | C—Br | C—H | C—Br | C—H | CF3 | C—H | C—NO2 | H | H | cyclo-PrCO | H | 1 |
| 2-2110 | H | C—Br | C—H | C—Br | C—H | CF3 | C—H | C—NO2 | H | H | CF3CH2CO | H | 1 |
| 2-2111 | H | C—Br | C—H | C—Br | C—H | CF3 | C—H | C—SMe | H | H | H | H | 1 |
| 2-2112 | H | C—Br | C—H | C—Br | C—H | CF3 | C—H | C—SMe | H | H | EtCO | H | 1 |
| 2-2113 | H | C—Br | C—H | C—Br | C—H | CF3 | C—H | C—SMe | H | H | cyclo-PrCO | H | 1 |
| 2-2114 | H | C—Br | C—H | C—Br | C—H | CF3 | C—H | C—SMe | H | H | H | H | 1 |
| 2-2115 | H | C—Br | C—H | C—Br | C—H | CF3 | C—H | C—SMe | H | H | MeCO | H | 1 |
| 2-2116 | H | C—Br | C—H | C—Br | C—H | CF3 | C—H | C—SMe | H | H | EtCO | H | 1 |
| 2-2117 | H | C—Br | C—H | C—Br | C—H | CF3 | C—H | C—SMe | H | H | cyclo-PrCO | H | 1 |
| 2-2118 | H | C—Br | C—H | C—Br | C—H | CF3 | C—H | C—SMe | H | H | CF3CH2CO | H | 1 |
| 2-2119 | H | C—Br | C—H | C—Br | C—H | CF3 | C—H | C—H | H | H | H | H | 1 |
| 2-2120 | H | C—Br | C—H | C—Br | C—H | CF3 | C—H | C—H | H | H | EtCO | H | 1 |
| 2-2121 | H | C—Br | C—H | C—Br | C—H | CF3 | C—H | C—H | H | H | cyclo-PrCO | H | 1 |
| 2-2122 | H | C—Br | C—H | C—Br | C—H | CF3 | C—H | C—H | H | H | H | H | 1 |
| 2-2123 | H | C—Br | C—H | C—Br | C—H | CF3 | C—H | C—H | H | H | MeCO | H | 1 |
| 2-2124 | H | C—Br | C—H | C—Br | C—H | CF3 | C—H | C—H | H | H | EtCO | H | 1 |
| 2-2125 | H | C—Br | C—H | C—Br | C—H | CF3 | C—H | C—H | H | H | cyclo-PrCO | H | 1 |
| 2-2126 | H | C—Br | C—H | C—Br | C—H | CF3 | C—H | C—H | H | H | CF3CH2CO | H | 1 |
| 2-2127 | H | C—Br | C—H | C—Br | C—H | CF3 | C—H | C—SOMe | H | H | EtCO | H | 1 |
| 2-2128 | H | C—Br | C—H | C—Br | C—H | CF3 | C—H | C—SOMe | H | H | CF3CH2CO | H | 1 |
| 2-2129 | H | C—Br | C—H | C—Br | C—H | CF3 | C—H | C—SO2Me | H | H | EtCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2130 | H | C—Br | C—H | C—Br | C—H | CF3 | C—H | C—SO2Me | H | H | CF3CH2CO | H | 1 |
| 2-2131 | H | C—Br | C—H | C—Br | C—H | CF3 | C—H | C—SCF3 | H | H | EtCO | H | 1 |
| 2-2132 | H | C—Br | C—H | C—Br | C—H | CF3 | C—H | C—SCF3 | H | H | CF3CH2CO | H | 1 |
| 2-2133 | H | C—Br | C—H | C—Br | C—H | CF3 | C—H | C—SOCF3 | H | H | EtCO | H | 1 |
| 2-2134 | H | C—Br | C—H | C—Br | C—H | CF3 | C—H | C—SOCF3 | H | H | CF3CH2CO | H | 1 |
| 2-2135 | H | C—Br | C—H | C—Br | C—H | CF3 | C—H | C—SO2CF3 | H | H | EtCO | H | 1 |
| 2-2136 | H | C—Br | C—H | C—Br | C—H | CF3 | C—H | C—SO2CF3 | H | H | CF3CH2CO | H | 1 |
| 2-2137 | H | C—Br | C—H | C—Br | C—H | CF3 | C—H | C—F | H | H | EtCO | H | 1 |
| 2-2138 | H | C—Br | C—H | C—Br | C—H | CF3 | C—H | C—F | H | H | CF3CH2CO | H | 1 |
| 2-2139 | H | C—Br | C—H | C—Br | C—H | CF3 | C—H | C—I | H | H | EtCO | H | 1 |
| 2-2140 | H | C—Br | C—H | C—Br | C—H | CF3 | C—H | C—I | H | H | CF3CH2CO | H | 1 |
| 2-2141 | H | C—Br | C—H | C—Br | C—H | CF3 | C—H | C—NH2 | H | H | EtCO | H | 1 |
| 2-2142 | H | C—Br | C—H | C—Br | C—H | CF3 | C—H | C—NH2 | H | H | CF3CH2CO | H | 1 |
| 2-2143 | H | C—Br | C—H | C—Br | C—H | CF3 | C—H | C—NHAc | H | H | EtCO | H | 1 |
| 2-2144 | H | C—Br | C—H | C—Br | C—H | CF3 | C—H | C—NHAc | H | H | CF3CH2CO | H | 1 |
| 2-2145 | H | C—Br | C—H | C—Br | C—H | CF3 | C—H | C—NHCOCF3 | H | H | EtCO | H | 1 |
| 2-2146 | H | C—Br | C—H | C—Br | C—H | CF3 | C—H | C—NHCOCF3 | H | H | CF3CH2CO | H | 1 |
| 2-2147 | H | C—Br | C—H | C—Br | C—H | CF3 | C—H | C—CH2OAc | H | H | EtCO | H | 1 |
| 2-2148 | H | C—Br | C—H | C—Br | C—H | CF3 | C—H | C—CH2OAc | H | H | CF3CH2CO | H | 1 |
| 2-2963 | F | C—CF3 | C—H | C—H | C—H | CF3 | C—H | C—CF3 | H | H | H | H | 1 |
| 2-2964 | F | C—CF3 | C—H | C—H | C—H | CF3 | C—H | C—CF3 | H | H | MeCO | H | 1 |
| 2-2965 | F | C—CF3 | C—H | C—H | C—H | CF3 | C—H | C—CF3 | H | H | EtCO | H | 1 |
| 2-2966 | F | C—CF3 | C—H | C—H | C—H | CF3 | C—H | C—CF3 | H | H | n-PrCO | H | 1 |
| 2-2967 | F | C—CF3 | C—H | C—H | C—H | CF3 | C—H | C—CF3 | H | H | cyclo-PrCO | H | 1 |
| 2-2968 | F | C—CF3 | C—H | C—H | C—H | CF3 | C—H | C—CF3 | H | H | EtNHCO | H | 1 |
| 2-2969 | F | C—CF3 | C—H | C—H | C—H | CF3 | C—H | C—CF3 | H | H | CF3CH2CO | H | 1 |
| 2-2970 | F | C—CF3 | C—H | C—H | C—H | CF3 | C—H | C—CF3 | H | H | cyclo-PrCH2CO | H | 1 |
| 2-2971 | F | C—CF3 | C—H | C—H | C—H | CF3 | C—H | C—CF3 | H | H | CH3SCH2CO | H | 1 |
| 2-2972 | F | C—CF3 | C—H | C—H | C—H | CF3 | N | C—CF3 | H | H | CH3SOCH2CO | H | 1 |
| 2-2973 | F | C—CF3 | C—H | C—H | C—H | CF3 | N | C—CF3 | H | H | CH3SO2CH2CO | H | 1 |
| 2-2974 | F | C—CF3 | C—H | C—H | C—H | CF3 | N | C—CF3 | H | H | H | H | 1 |
| 2-2975 | F | C—CF3 | C—H | C—H | C—H | CF3 | C—H | C—CF3 | Me | H | H | H | 1 |
| 2-2976 | F | C—CF3 | C—H | C—H | C—H | CF3 | C—H | C—CF3 | Me | H | EtCO | H | 1 |
| 2-2977 | F | C—CF3 | C—H | C—H | C—H | CF3 | C—H | C—CF3 | Me | H | CH3SCH2CO | H | 1 |
| 2-2978 | F | C—CF3 | C—H | C—H | C—H | CF3 | C—H | C—CF3 | H | H | H | H | 1 |
| 2-2979 | F | C—CF3 | C—H | C—H | C—H | CF3 | C—H | C—CF3 | H | H | EtCO | H | 1 |
| 2-2980 | F | C—CF3 | C—H | C—H | C—H | CF3 | C—H | C—CF3 | H | H | CH3SCH2CO | H | 1 |
| 2-2981 | F | C—CF3 | C—H | C—H | C—H | CF3 | C—H | C—Cl | H | H | H | H | 1 |
| 2-2982 | F | C—CF3 | C—H | C—H | C—H | CF3 | C—H | C—Cl | H | H | MeCO | H | 1 |
| 2-2983 | F | C—CF3 | C—H | C—H | C—H | CF3 | C—H | C—Cl | H | H | EtCO | H | 1 |
| 2-2984 | F | C—CF3 | C—H | C—H | C—H | CF3 | C—H | C—Cl | H | H | EtCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2985 | F | C—CF3 | C—H | C—H | C—H | CF3 | C—H | C—Cl | H | H | CF3CH2CO | H | 1 |
| 2-2986 | F | C—CF3 | C—H | C—H | C—H | CF3 | C—H | C—Cl | H | H | cyclo-PrCO | H | 1 |
| 2-2987 | F | C—CF3 | C—H | C—H | C—H | CF3 | C—H | C—Cl | H | H | cyclo-PrCH2CO | H | 1 |
| 2-2988 | F | C—CF3 | C—H | C—H | C—H | CF3 | C—H | C—Cl | H | H | CH3SCH2CO | H | 1 |
| 2-2989 | F | C—CF3 | C—H | C—H | C—H | CF3 | C—H | C—Cl | H | H | CH3SOCH2CO | H | 1 |
| 2-2990 | F | C—CF3 | C—H | C—H | C—H | CF3 | C—H | C—Cl | H | H | CH3SO2CH2CO | H | 1 |
| 2-2991 | F | C—CF3 | C—H | C—H | C—H | CF3 | C—H | C—Cl | Me | H | EtNHCO | H | 1 |
| 2-2992 | F | C—CF3 | C—H | C—H | C—H | CF3 | C—H | C—Cl | Me | H | H | H | 1 |
| 2-2993 | F | C—CF3 | C—H | C—H | C—H | CF3 | C—H | C—Cl | Me | H | EtCO | H | 1 |
| 2-2994 | F | C—CF3 | C—H | C—H | C—H | CF3 | C—H | C—Cl | H | H | CF3CH2CO | H | 1 |
| 2-2995 | F | C—CF3 | C—H | C—H | C—H | CF3 | C—H | C—Cl | H | H | CH3SCH2CO | H | 1 |
| 2-2996 | F | C—CF3 | C—H | C—H | C—H | CF3 | N | C—Cl | H | H | H | H | 1 |
| 2-2997 | F | C—CF3 | C—H | C—H | C—H | CF3 | N | C—Cl | H | H | EtCO | H | 1 |
| 2-2998 | F | C—CF3 | C—H | C—H | C—H | CF3 | N | C—Cl | H | H | CF3CH2CO | H | 1 |
| 2-2999 | F | C—CF3 | C—H | C—H | C—H | CF3 | N | C—Cl | H | H | CH3SCH2CO | H | 1 |
| 2-3000 | F | C—CF3 | C—H | C—H | C—H | CF3 | C—H | C—Br | H | H | H | H | 1 |
| 2-3001 | F | C—CF3 | C—H | C—H | C—H | CF3 | C—H | C—Br | H | H | MeCO | H | 1 |
| 2-3002 | F | C—CF3 | C—H | C—H | C—H | CF3 | C—H | C—Br | H | H | EtCO | H | 1 |
| 2-3003 | F | C—CF3 | C—H | C—H | C—H | CF3 | C—H | C—Br | H | H | CF3CH2CO | H | 1 |
| 2-3004 | F | C—CF3 | C—H | C—H | C—H | CF3 | C—H | C—Br | H | H | cyclo-PrCO | H | 1 |
| 2-3005 | F | C—CF3 | C—H | C—H | C—H | CF3 | C—H | C—Br | H | H | cyclo-PrCH2CO | H | 1 |
| 2-3006 | F | C—CF3 | C—H | C—H | C—H | CF3 | C—H | C—Br | H | H | CH3SCH2CO | H | 1 |
| 2-3007 | F | C—CF3 | C—H | C—H | C—H | CF3 | C—H | C—Br | H | H | CH3SOCH2CO | H | 1 |
| 2-3008 | F | C—CF3 | C—H | C—H | C—H | CF3 | C—H | C—Br | H | H | CH3SO2CH2CO | H | 1 |
| 2-3009 | F | C—CF3 | C—H | C—H | C—H | CF3 | C—H | C—Br | Me | H | EtNHCO | H | 1 |
| 2-3010 | F | C—CF3 | C—H | C—H | C—H | CF3 | C—H | C—Br | Me | H | H | H | 1 |
| 2-3011 | F | C—CF3 | C—H | C—H | C—H | CF3 | C—H | C—Br | Me | H | EtCO | H | 1 |
| 2-3012 | F | C—CF3 | C—H | C—H | C—H | CF3 | C—H | C—Br | H | H | CF3CH2CO | H | 1 |
| 2-3013 | F | C—CF3 | C—H | C—H | C—H | CF3 | C—H | C—Br | H | H | CH3SCH2CO | H | 1 |
| 2-3014 | F | C—CF3 | C—H | C—H | C—H | CF3 | N | C—Br | H | H | H | H | 1 |
| 2-3015 | F | C—CF3 | C—H | C—H | C—H | CF3 | N | C—Br | H | H | EtCO | H | 1 |
| 2-3016 | F | C—CF3 | C—H | C—H | C—H | CF3 | N | C—Br | H | H | CF3CH2CO | H | 1 |
| 2-3017 | F | C—CF3 | C—H | C—H | C—H | CF3 | N | C—Br | H | H | CH3SCH2CO | H | 1 |
| 2-3018 | F | C—CF3 | C—H | C—H | C—H | CF3 | C—H | C—CN | H | H | H | H | 1 |
| 2-3019 | F | C—CF3 | C—H | C—H | C—H | CF3 | C—H | C—CN | H | H | MeCO | H | 1 |
| 2-3020 | F | C—CF3 | C—H | C—H | C—H | CF3 | C—H | C—CN | H | H | EtCO | H | 1 |
| 2-3021 | F | C—CF3 | C—H | C—H | C—H | CF3 | C—H | C—CN | H | H | CF3CH2CO | H | 1 |
| 2-3022 | F | C—CF3 | C—H | C—H | C—H | CF3 | C—H | C—CN | H | H | cyclo-PrCO | H | 1 |
| 2-3023 | F | C—CF3 | C—H | C—H | C—H | CF3 | C—H | C—CN | H | H | cyclo-PrCH2CO | H | 1 |
| 2-3024 | F | C—CF3 | C—H | C—H | C—H | CF3 | C—H | C—CN | H | H | CH3SCH2CO | H | 1 |
| 2-3025 | F | C—CF3 | C—H | C—H | C—H | CF3 | C—H | C—CN | H | H | CH3SOCH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3026 | F | C—CF3 | C—H | C—H | C—H | CF3 | C—H | C—CN | H | H | CH3SO2CH2CO | H | 1 |
| 2-3027 | F | C—CF3 | C—H | C—H | C—H | CF3 | C—H | C—CN | H | H | EtNHCO | H | 1 |
| 2-3028 | F | C—CF3 | C—H | C—H | C—H | CF3 | C—H | C—CN | Me | H | CF3CH2CO | H | 1 |
| 2-3029 | F | C—CF3 | C—H | C—H | C—H | CF3 | N | C—CN | Me | H | EtCO | H | 1 |
| 2-3030 | F | C—CF3 | C—H | C—H | C—H | CF3 | N | C—CN | H | H | CF3CH2CO | H | 1 |
| 2-3031 | F | C—CF3 | C—H | C—H | C—H | CF3 | C—H | C—CN | H | H | EtCO | H | 1 |
| 2-3032 | F | C—CF3 | C—H | C—H | C—H | CF3 | C—H | C—Me | H | H | H | H | 1 |
| 2-3033 | F | C—CF3 | C—H | C—H | C—H | CF3 | C—H | C—Me | H | H | MeCO | H | 1 |
| 2-3034 | F | C—CF3 | C—H | C—H | C—H | CF3 | C—H | C—Me | H | H | EtCO | H | 1 |
| 2-3035 | F | C—CF3 | C—H | C—H | C—H | CF3 | C—H | C—Me | H | H | CF3CH2CO | H | 1 |
| 2-3036 | F | C—CF3 | C—H | C—H | C—H | CF3 | C—H | C—Me | H | H | cyclo-PrCO | H | 1 |
| 2-3037 | F | C—CF3 | C—H | C—H | C—H | CF3 | C—H | C—Me | H | H | cyclo-PrCH2CO | H | 1 |
| 2-3038 | F | C—CF3 | C—H | C—H | C—H | CF3 | C—H | C—Me | H | H | CH3SCH2CO | H | 1 |
| 2-3039 | F | C—CF3 | C—H | C—H | C—H | CF3 | C—H | C—Me | H | H | CH3SOCH2CO | H | 1 |
| 2-3040 | F | C—CF3 | C—H | C—H | C—H | CF3 | C—H | C—Me | H | H | CH3SO2CH2CO | H | 1 |
| 2-3041 | F | C—CF3 | C—H | C—H | C—H | CF3 | C—H | C—Me | H | H | EtNHCO | H | 1 |
| 2-3042 | F | C—CF3 | C—H | C—H | C—H | CF3 | C—H | C—Me | Me | H | EtCO | H | 1 |
| 2-3043 | F | C—CF3 | C—H | C—H | C—H | CF3 | C—H | C—Me | Me | H | CF3CH2CO | H | 1 |
| 2-3044 | F | C—CF3 | C—H | C—H | C—H | CF3 | N | C—Me | H | H | CF3CH2CO | H | 1 |
| 2-3045 | F | C—CF3 | C—H | C—H | C—H | CF3 | C—H | C—Me | H | H | H | H | 1 |
| 2-3046 | F | C—CF3 | C—H | C—H | C—H | CF3 | C—H | C—NO2 | H | H | MeCO | H | 1 |
| 2-3047 | F | C—CF3 | C—H | C—H | C—H | CF3 | C—H | C—NO2 | H | H | EtCO | H | 1 |
| 2-3048 | F | C—CF3 | C—H | C—H | C—H | CF3 | C—H | C—NO2 | H | H | CF3CH2CO | H | 1 |
| 2-3049 | F | C—CF3 | C—H | C—H | C—H | CF3 | C—H | C—NO2 | H | H | cyclo-PrCO | H | 1 |
| 2-3050 | F | C—CF3 | C—H | C—H | C—H | CF3 | C—H | C—NO2 | H | H | cyclo-PrCH2CO | H | 1 |
| 2-3051 | F | C—CF3 | C—H | C—H | C—H | CF3 | C—H | C—NO2 | H | H | CH3SCH2CO | H | 1 |
| 2-3052 | F | C—CF3 | C—H | C—H | C—H | CF3 | C—H | C—NO2 | H | H | CH3SOCH2CO | H | 1 |
| 2-3053 | F | C—CF3 | C—H | C—H | C—H | CF3 | C—H | C—NO2 | H | H | CH3SO2CH2CO | H | 1 |
| 2-3054 | F | C—CF3 | C—H | C—H | C—H | CF3 | C—H | C—NO2 | H | H | EtNHCO | H | 1 |
| 2-3055 | F | C—CF3 | C—H | C—H | C—H | CF3 | C—H | C—NO2 | Me | H | EtCO | H | 1 |
| 2-3056 | F | C—CF3 | C—H | C—H | C—H | CF3 | C—H | C—NO2 | Me | H | CF3CH2CO | H | 1 |
| 2-3057 | F | C—CF3 | C—H | C—H | C—H | CF3 | N | C—NO2 | H | H | EtCO | H | 1 |
| 2-3058 | F | C—CF3 | C—H | C—H | C—H | CF3 | C—H | C—SMe | H | H | CF3CH2CO | H | 1 |
| 2-3059 | F | C—CF3 | C—H | C—H | C—H | CF3 | C—H | C—SMe | H | H | EtCO | H | 1 |
| 2-3060 | F | C—CF3 | C—H | C—H | C—H | CF3 | C—H | C—SMe | H | H | H | H | 1 |
| 2-3061 | F | C—CF3 | C—H | C—H | C—H | CF3 | C—H | C—SMe | H | H | MeCO | H | 1 |
| 2-3062 | F | C—CF3 | C—H | C—H | C—H | CF3 | C—H | C—SMe | H | H | EtCO | H | 1 |
| 2-3063 | F | C—CF3 | C—H | C—H | C—H | CF3 | C—H | C—SMe | H | H | CF3CH2CO | H | 1 |
| 2-3064 | F | C—CF3 | C—H | C—H | C—H | CF3 | C—H | C—SMe | H | H | cyclo-PrCO | H | 1 |
| 2-3065 | F | C—CF3 | C—H | C—H | C—H | CF3 | C—H | C—SMe | H | H | cyclo-PrCH2CO | H | 1 |
| 2-3066 | F | C—CF3 | C—H | C—H | C—H | CF3 | C—H | C—SMe | H | H | CH3SCH2CO | H | 1 |

TABLE 2-1-continued

| Example No. | X | B¹ | B² | B³ | B⁴ | R | A² | A³ | R¹ | R² | R⁴ | R³ |
|---|---|---|---|---|---|---|---|---|---|---|---|---|
| 2-3067 | F | C—CF3 | C—H | C—H | C—H | CF3 | C—H | C—SMe | H | H | CH3SO2CH2CO | H |
| 2-3068 | F | C—CF3 | C—H | C—H | C—H | CF3 | C—H | C—SMe | H | H | EtNHCO | H |
| 2-3069 | F | C—CF3 | C—H | C—H | C—H | CF3 | C—H | C—SMe | Me | H | EtCO | H |
| 2-3070 | F | C—CF3 | C—H | C—H | C—H | CF3 | C—H | C—SMe | Me | H | CF3CH2CO | H |
| 2-3071 | F | C—CF3 | C—H | C—H | C—H | CF3 | N | C—SMe | H | H | EtCO | H |
| 2-3072 | F | C—CF3 | C—H | C—H | C—H | CF3 | N | C—SMe | H | H | CF3CH2CO | H |
| 2-3073 | F | C—CF3 | C—H | C—H | C—H | CF3 | C—H | C—SOMe | H | H | H | H |
| 2-3074 | F | C—CF3 | C—H | C—H | C—H | CF3 | C—H | C—SOMe | H | H | MeCO | H |
| 2-3075 | F | C—CF3 | C—H | C—H | C—H | CF3 | C—H | C—SOMe | H | H | EtCO | H |
| 2-3076 | F | C—CF3 | C—H | C—H | C—H | CF3 | C—H | C—SOMe | H | H | CF3CH2CO | H |
| 2-3077 | F | C—CF3 | C—H | C—H | C—H | CF3 | C—H | C—SOMe | H | H | cyclo-PrCO | H |
| 2-3078 | F | C—CF3 | C—H | C—H | C—H | CF3 | C—H | C—SOMe | H | H | cyclo-PrCH2CO | H |
| 2-3079 | F | C—CF3 | C—H | C—H | C—H | CF3 | C—H | C—SOMe | H | H | CH3SCH2CO | H |
| 2-3080 | F | C—CF3 | C—H | C—H | C—H | CF3 | C—H | C—SOMe | H | H | CH3SOCH2CO | H |
| 2-3081 | F | C—CF3 | C—H | C—H | C—H | CF3 | C—H | C—SOMe | H | H | CH3SO2CH2CO | H |
| 2-3082 | F | C—CF3 | C—H | C—H | C—H | CF3 | C—H | C—SOMe | H | H | EtNHCO | H |
| 2-3083 | F | C—CF3 | C—H | C—H | C—H | CF3 | C—H | C—SOMe | Me | H | EtCO | H |
| 2-3084 | F | C—CF3 | C—H | C—H | C—H | CF3 | C—H | C—SOMe | Me | H | CF3CH2CO | H |
| 2-3085 | F | C—CF3 | C—H | C—H | C—H | CF3 | N | C—SOMe | H | H | EtCO | H |
| 2-3086 | F | C—CF3 | C—H | C—H | C—H | CF3 | N | C—SOMe | H | H | CF3CH2CO | H |
| 2-3087 | F | C—CF3 | C—H | C—H | C—H | CF3 | C—H | C—SO2Me | H | H | H | H |
| 2-3088 | F | C—CF3 | C—H | C—H | C—H | CF3 | C—H | C—SO2Me | H | H | MeCO | H |
| 2-3089 | F | C—CF3 | C—H | C—H | C—H | CF3 | C—H | C—SO2Me | H | H | EtCO | H |
| 2-3090 | F | C—CF3 | C—H | C—H | C—H | CF3 | C—H | C—SO2Me | H | H | CF3CH2CO | H |
| 2-3091 | F | C—CF3 | C—H | C—H | C—H | CF3 | C—H | C—SO2Me | H | H | cyclo-PrCO | H |
| 2-3092 | F | C—CF3 | C—H | C—H | C—H | CF3 | C—H | C—SO2Me | H | H | cyclo-PrCH2CO | H |
| 2-3093 | F | C—CF3 | C—H | C—H | C—H | CF3 | C—H | C—SO2Me | H | H | CH3SCH2CO | H |
| 2-3094 | F | C—CF3 | C—H | C—H | C—H | CF3 | C—H | C—SO2Me | H | H | CH3SOCH2CO | H |
| 2-3095 | F | C—CF3 | C—H | C—H | C—H | CF3 | C—H | C—SO2Me | H | H | CH3SO2CH2CO | H |
| 2-3096 | F | C—CF3 | C—H | C—H | C—H | CF3 | C—H | C—SO2Me | H | H | EtNHCO | H |
| 2-3097 | F | C—CF3 | C—H | C—H | C—H | CF3 | C—H | C—SO2Me | Me | H | EtCO | H |
| 2-3098 | F | C—CF3 | C—H | C—H | C—H | CF3 | C—H | C—SO2Me | Me | H | CF3CH2CO | H |
| 2-3099 | F | C—CF3 | C—H | C—H | C—H | CF3 | N | C—SO2Me | H | H | EtCO | H |
| 2-3100 | F | C—CF3 | C—H | C—H | C—H | CF3 | N | C—SO2Me | H | H | CF3CH2CO | H |
| 2-3101 | F | C—CF3 | C—H | C—H | C—H | CF3 | C—H | C—SCF3 | H | H | H | H |
| 2-3102 | F | C—CF3 | C—H | C—H | C—H | CF3 | C—H | C—SCF3 | H | H | MeCO | H |
| 2-3103 | F | C—CF3 | C—H | C—H | C—H | CF3 | C—H | C—SCF3 | H | H | EtCO | H |
| 2-3104 | F | C—CF3 | C—H | C—H | C—H | CF3 | C—H | C—SCF3 | H | H | CF3CH2CO | H |
| 2-3105 | F | C—CF3 | C—H | C—H | C—H | CF3 | C—H | C—SCF3 | H | H | cyclo-PrCO | H |
| 2-3106 | F | C—CF3 | C—H | C—H | C—H | CF3 | C—H | C—SCF3 | H | H | cyclo-PrCH2CO | H |
| 2-3107 | F | C—CF3 | C—H | C—H | C—H | CF3 | C—H | C—SCF3 | H | H | CH3SCH2CO | H |

TABLE 2-1-continued

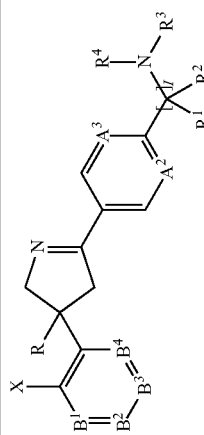

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3108 | F | C—CF3 | C—H | C—H | C—H | CF3 | C—H | C—SCF3 | H | H | CH3SOCH2CO | H | 1 |
| 2-3109 | F | C—CF3 | C—H | C—H | C—H | CF3 | C—H | C—SCF3 | H | H | CH3SO2CH2CO | H | 1 |
| 2-3110 | F | C—CF3 | C—H | C—H | C—H | CF3 | C—H | C—SCF3 | H | H | EtNHCO | H | 1 |
| 2-3111 | F | C—CF3 | C—H | C—H | C—H | CF3 | C—H | C—SCF3 | Me | H | EtCO | H | 1 |
| 2-3112 | F | C—CF3 | C—H | C—H | C—H | CF3 | C—H | C—SCF3 | Me | H | CF3CH2CO | H | 1 |
| 2-3113 | F | C—CF3 | C—H | C—H | C—H | CF3 | C—H | C—SCF3 | H | H | EtCO | H | 1 |
| 2-3114 | F | C—CF3 | C—H | C—H | C—H | CF3 | N | C—SCF3 | H | H | CF3CH2CO | H | 1 |
| 2-3115 | F | C—CF3 | C—H | C—H | C—H | CF3 | N | C—SCF3 | H | H | CF3CH2CO | H | 1 |
| 2-3116 | F | C—CF3 | C—H | C—H | C—H | CF3 | C—H | C—SCF3 | H | H | H | H | 1 |
| 2-3117 | F | C—CF3 | C—H | C—H | C—H | CF3 | C—H | C—SOCF3 | H | H | MeCO | H | 1 |
| 2-3118 | F | C—CF3 | C—H | C—H | C—H | CF3 | C—H | C—SOCF3 | H | H | EtCO | H | 1 |
| 2-3119 | F | C—CF3 | C—H | C—H | C—H | CF3 | C—H | C—SOCF3 | H | H | cyclo-PrCO | H | 1 |
| 2-3120 | F | C—CF3 | C—H | C—H | C—H | CF3 | C—H | C—SOCF3 | H | H | cyclo-PrCH2CO | H | 1 |
| 2-3121 | F | C—CF3 | C—H | C—H | C—H | CF3 | C—H | C—SOCF3 | H | H | CH3SCH2CO | H | 1 |
| 2-3122 | F | C—CF3 | C—H | C—H | C—H | CF3 | C—H | C—SOCF3 | H | H | CH3SOCH2CO | H | 1 |
| 2-3123 | F | C—CF3 | C—H | C—H | C—H | CF3 | C—H | C—SOCF3 | H | H | CH3SO2CH2CO | H | 1 |
| 2-3124 | F | C—CF3 | C—H | C—H | C—H | CF3 | C—H | C—SOCF3 | H | H | EtNHCO | H | 1 |
| 2-3125 | F | C—CF3 | C—H | C—H | C—H | CF3 | C—H | C—SOCF3 | Me | H | EtCO | H | 1 |
| 2-3126 | F | C—CF3 | C—H | C—H | C—H | CF3 | C—H | C—SOCF3 | Me | H | CF3CH2CO | H | 1 |
| 2-3127 | F | C—CF3 | C—H | C—H | C—H | CF3 | C—H | C—SOCF3 | H | H | EtCO | H | 1 |
| 2-3128 | F | C—CF3 | C—H | C—H | C—H | CF3 | N | C—SOCF3 | H | H | CF3CH2CO | H | 1 |
| 2-3129 | F | C—CF3 | C—H | C—H | C—H | CF3 | N | C—SOCF3 | H | H | CF3CH2CO | H | 1 |
| 2-3130 | F | C—CF3 | C—H | C—H | C—H | CF3 | C—H | C—H | H | H | H | H | 1 |
| 2-3131 | F | C—CF3 | C—H | C—H | C—H | CF3 | C—H | C—H | H | H | MeCO | H | 1 |
| 2-3132 | F | C—CF3 | C—H | C—H | C—H | CF3 | C—H | C—H | H | H | EtCO | H | 1 |
| 2-3133 | F | C—CF3 | C—H | C—H | C—H | CF3 | C—H | C—H | H | H | CF3CH2CO | H | 1 |
| 2-3134 | F | C—CF3 | C—H | C—H | C—H | CF3 | C—H | C—H | H | H | cyclo-PrCO | H | 1 |
| 2-3135 | F | C—CF3 | C—H | C—H | C—H | CF3 | C—H | C—H | H | H | cyclo-PrCH2CO | H | 1 |
| 2-3136 | F | C—CF3 | C—H | C—H | C—H | CF3 | C—H | C—H | H | H | CH3SCH2CO | H | 1 |
| 2-3137 | F | C—CF3 | C—H | C—H | C—H | CF3 | C—H | C—H | H | H | CH3SOCH2CO | H | 1 |
| 2-3138 | F | C—CF3 | C—H | C—H | C—H | CF3 | C—H | C—H | H | H | CH3SO2CH2CO | H | 1 |
| 2-3139 | F | C—CF3 | C—H | C—H | C—H | CF3 | C—H | C—H | H | H | EtNHCO | H | 1 |
| 2-3140 | F | C—CF3 | C—H | C—H | C—H | CF3 | C—H | C—H | Me | H | H | H | 1 |
| 2-3141 | F | C—CF3 | C—H | C—H | C—H | CF3 | C—H | C—H | Me | H | EtCO | H | 1 |
| 2-3142 | F | C—CF3 | C—H | C—H | C—H | CF3 | C—H | C—H | Me | H | CF3CH2CO | H | 1 |
| 2-3143 | F | C—CF3 | C—H | C—H | C—H | CF3 | C—H | C—H | H | H | CH3SCH2CO | H | 1 |
| 2-3144 | F | C—CF3 | C—H | C—H | C—H | CF3 | N | C—H | H | H | EtCO | H | 1 |
| 2-3145 | F | C—CF3 | C—H | C—H | C—H | CF3 | N | C—H | H | H | CF3CH2CO | H | 1 |
| 2-3146 | F | C—CF3 | C—H | C—H | C—H | CF3 | N | C—H | H | H | CH3SCH2CO | H | 1 |
| 2-3147 | F | C—CF3 | C—H | C—H | C—H | CF3 | C—H | C—F | H | H | H | H | 1 |
| 2-3148 | F | C—CF3 | C—H | C—H | C—H | CF3 | C—H | C—F | H | H | MeCO | H | 1 |

TABLE 2-1-continued

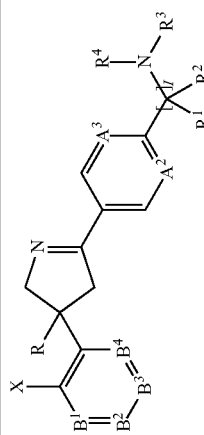

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3149 | F | C—CF3 | C—H | C—H | C—H | CF3 | C—H | C—F | H | H | EtCO | H | 1 |
| 2-3150 | F | C—CF3 | C—H | C—H | C—H | CF3 | C—H | C—F | H | H | CF3CH2CO | H | 1 |
| 2-3151 | F | C—CF3 | C—H | C—H | C—H | CF3 | C—H | C—F | H | H | cyclo-PrCO | H | 1 |
| 2-3152 | F | C—CF3 | C—H | C—H | C—H | CF3 | C—H | C—F | H | H | cyclo-PrCH2CO | H | 1 |
| 2-3153 | F | C—CF3 | C—H | C—H | C—H | CF3 | C—H | C—F | H | H | CH3SCH2CO | H | 1 |
| 2-3154 | F | C—CF3 | C—H | C—H | C—H | CF3 | C—H | C—F | H | H | CH3SOCH2CO | H | 1 |
| 2-3155 | F | C—CF3 | C—H | C—H | C—H | CF3 | C—H | C—F | H | H | CH3SO2CH2CO | H | 1 |
| 2-3156 | F | C—CF3 | C—H | C—H | C—H | CF3 | C—H | C—F | H | H | EtNHCO | H | 1 |
| 2-3157 | F | C—CF3 | C—H | C—H | C—H | CF3 | C—H | C—F | Me | H | EtCO | H | 1 |
| 2-3158 | F | C—CF3 | C—H | C—H | C—H | CF3 | C—H | C—F | Me | H | CF3CH2CO | H | 1 |
| 2-3159 | F | C—CF3 | C—H | C—H | C—H | CF3 | N | C—F | H | H | EtCO | H | 1 |
| 2-3160 | F | C—CF3 | C—H | C—H | C—H | CF3 | N | C—F | H | H | CF3CH2CO | H | 1 |
| 2-3161 | F | C—CF3 | C—H | C—H | C—H | CF3 | C—H | C—F | H | H | H | H | 1 |
| 2-3162 | F | C—CF3 | C—H | C—H | C—H | CF3 | C—H | C—I | H | H | MeCO | H | 1 |
| 2-3163 | F | C—CF3 | C—H | C—H | C—H | CF3 | C—H | C—I | H | H | EtCO | H | 1 |
| 2-3164 | F | C—CF3 | C—H | C—H | C—H | CF3 | C—H | C—I | H | H | CF3CH2CO | H | 1 |
| 2-3165 | F | C—CF3 | C—H | C—H | C—H | CF3 | C—H | C—I | H | H | cyclo-PrCO | H | 1 |
| 2-3166 | F | C—CF3 | C—H | C—H | C—H | CF3 | C—H | C—I | H | H | cyclo-PrCH2CO | H | 1 |
| 2-3167 | F | C—CF3 | C—H | C—H | C—H | CF3 | C—H | C—I | H | H | CH3SCH2CO | H | 1 |
| 2-3168 | F | C—CF3 | C—H | C—H | C—H | CF3 | C—H | C—I | H | H | CH3SOCH2CO | H | 1 |
| 2-3169 | F | C—CF3 | C—H | C—H | C—H | CF3 | C—H | C—I | H | H | CH3SO2CH2CO | H | 1 |
| 2-3170 | F | C—CF3 | C—H | C—H | C—H | CF3 | C—H | C—I | H | H | EtNHCO | H | 1 |
| 2-3171 | F | C—CF3 | C—H | C—H | C—H | CF3 | C—H | C—I | Me | H | EtCO | H | 1 |
| 2-3172 | F | C—CF3 | C—H | C—H | C—H | CF3 | C—H | C—I | Me | H | CF3CH2CO | H | 1 |
| 2-3173 | F | C—CF3 | C—H | C—H | C—H | CF3 | N | C—I | H | H | EtCO | H | 1 |
| 2-3174 | F | C—CF3 | C—H | C—H | C—H | CF3 | N | C—I | H | H | CF3CH2CO | H | 1 |
| 2-3175 | F | C—CF3 | C—H | C—H | C—H | CF3 | C—H | C—I | H | H | H | H | 1 |
| 2-3176 | F | C—CF3 | C—H | C—H | C—H | CF3 | C—H | C—NH2 | H | H | MeCO | H | 1 |
| 2-3177 | F | C—CF3 | C—H | C—H | C—H | CF3 | C—H | C—NH2 | H | H | EtCO | H | 1 |
| 2-3178 | F | C—CF3 | C—H | C—H | C—H | CF3 | C—H | C—NH2 | H | H | CF3CH2CO | H | 1 |
| 2-3179 | F | C—CF3 | C—H | C—H | C—H | CF3 | C—H | C—NH2 | H | H | cyclo-PrCO | H | 1 |
| 2-3180 | F | C—CF3 | C—H | C—H | C—H | CF3 | C—H | C—NH2 | H | H | cyclo-PrCH2CO | H | 1 |
| 2-3181 | F | C—CF3 | C—H | C—H | C—H | CF3 | C—H | C—NH2 | H | H | CH3SCH2CO | H | 1 |
| 2-3182 | F | C—CF3 | C—H | C—H | C—H | CF3 | C—H | C—NH2 | H | H | CH3SOCH2CO | H | 1 |
| 2-3183 | F | C—CF3 | C—H | C—H | C—H | CF3 | C—H | C—NH2 | H | H | CH3SO2CH2CO | H | 1 |
| 2-3184 | F | C—CF3 | C—H | C—H | C—H | CF3 | C—H | C—NH2 | H | H | EtNHCO | H | 1 |
| 2-3185 | F | C—CF3 | C—H | C—H | C—H | CF3 | C—H | C—NH2 | Me | H | EtCO | H | 1 |
| 2-3186 | F | C—CF3 | C—H | C—H | C—H | CF3 | C—H | C—NH2 | Me | H | CF3CH2CO | H | 1 |
| 2-3187 | F | C—CF3 | C—H | C—H | C—H | CF3 | N | C—NH2 | H | H | EtCO | H | 1 |
| 2-3188 | F | C—CF3 | C—H | C—H | C—H | CF3 | N | C—NH2 | H | H | CF3CH2CO | H | 1 |
| 2-3189 | F | C—CF3 | C—H | C—H | C—H | CF3 | C—H | C—NHAc | H | H | H | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3190 | F | C—CF3 | C—H | C—H | C—H | CF3 | C—H | C—NHAc | H | H | MeCO | H | 1 |
| 2-3191 | F | C—CF3 | C—H | C—H | C—H | CF3 | C—H | C—NHAc | H | H | EtCO | H | 1 |
| 2-3192 | F | C—CF3 | C—H | C—H | C—H | CF3 | C—H | C—NHAc | H | H | CF3CH2CO | H | 1 |
| 2-3193 | F | C—CF3 | C—H | C—H | C—H | CF3 | C—H | C—NHAc | H | H | cyclo-PrCO | H | 1 |
| 2-3194 | F | C—CF3 | C—H | C—H | C—H | CF3 | C—H | C—NHAc | H | H | cyclo-PrCH2CO | H | 1 |
| 2-3195 | F | C—CF3 | C—H | C—H | C—H | CF3 | C—H | C—NHAc | H | H | CH3SCH2CO | H | 1 |
| 2-3196 | F | C—CF3 | C—H | C—H | C—H | CF3 | C—H | C—NHAc | H | H | CH3SOCH2CO | H | 1 |
| 2-3197 | F | C—CF3 | C—H | C—H | C—H | CF3 | C—H | C—NHAc | H | H | CH3SO2CH2CO | H | 1 |
| 2-3198 | F | C—CF3 | C—H | C—H | C—H | CF3 | C—H | C—NHAc | H | H | EtNHCO | H | 1 |
| 2-3199 | F | C—CF3 | C—H | C—H | C—H | CF3 | C—H | C—NHAc | Me | H | EtCO | H | 1 |
| 2-3200 | F | C—CF3 | C—H | C—H | C—H | CF3 | C—H | C—NHAc | Me | H | CF3CH2CO | H | 1 |
| 2-3201 | F | C—CF3 | C—H | C—H | C—H | CF3 | N | C—NHAc | H | H | EtCO | H | 1 |
| 2-3202 | F | C—CF3 | C—H | C—H | C—H | CF3 | N | C—NHAc | H | H | CF3CH2CO | H | 1 |
| 2-3203 | F | C—CF3 | C—H | C—H | C—H | CF3 | C—H | C—NHCOCF3 | H | H | H | H | 1 |
| 2-3204 | F | C—CF3 | C—H | C—H | C—H | CF3 | C—H | C—NHCOCF3 | H | H | MeCO | H | 1 |
| 2-3205 | F | C—CF3 | C—H | C—H | C—H | CF3 | C—H | C—NHCOCF3 | H | H | EtCO | H | 1 |
| 2-3206 | F | C—CF3 | C—H | C—H | C—H | CF3 | C—H | C—NHCOCF3 | H | H | CF3CH2CO | H | 1 |
| 2-3207 | F | C—CF3 | C—H | C—H | C—H | CF3 | C—H | C—NHCOCF3 | H | H | cyclo-PrCO | H | 1 |
| 2-3208 | F | C—CF3 | C—H | C—H | C—H | CF3 | C—H | C—NHCOCF3 | H | H | cyclo-PrCH2CO | H | 1 |
| 2-3209 | F | C—CF3 | C—H | C—H | C—H | CF3 | C—H | C—NHCOCF3 | H | H | CH3SCH2CO | H | 1 |
| 2-3210 | F | C—CF3 | C—H | C—H | C—H | CF3 | C—H | C—NHCOCF3 | H | H | CH3SOCH2CO | H | 1 |
| 2-3211 | F | C—CF3 | C—H | C—H | C—H | CF3 | C—H | C—NHCOCF3 | H | H | CH3SO2CH2CO | H | 1 |
| 2-3212 | F | C—CF3 | C—H | C—H | C—H | CF3 | C—H | C—NHCOCF3 | H | H | EtNHCO | H | 1 |
| 2-3213 | F | C—CF3 | C—H | C—H | C—H | CF3 | C—H | C—NHCOCF3 | Me | H | EtCO | H | 1 |
| 2-3214 | F | C—CF3 | C—H | C—H | C—H | CF3 | C—H | C—NHCOCF3 | Me | H | CF3CH2CO | H | 1 |
| 2-3215 | F | C—CF3 | C—H | C—H | C—H | CF3 | N | C—NHCOCF3 | H | H | EtCO | H | 1 |
| 2-3216 | F | C—CF3 | C—H | C—H | C—H | CF3 | N | C—NHCOCF3 | H | H | CF3CH2CO | H | 1 |
| 2-3217 | F | C—CF3 | C—H | C—H | C—H | CF3 | C—H | C—CH2OAc | H | H | H | H | 1 |
| 2-3218 | F | C—CF3 | C—H | C—H | C—H | CF3 | C—H | C—CH2OAc | H | H | MeCO | H | 1 |
| 2-3219 | F | C—CF3 | C—H | C—H | C—H | CF3 | C—H | C—CH2OAc | H | H | EtCO | H | 1 |
| 2-3220 | F | C—CF3 | C—H | C—H | C—H | CF3 | C—H | C—CH2OAc | H | H | CF3CH2CO | H | 1 |
| 2-3221 | F | C—CF3 | C—H | C—H | C—H | CF3 | C—H | C—CH2OAc | H | H | cyclo-PrCO | H | 1 |
| 2-3222 | F | C—CF3 | C—H | C—H | C—H | CF3 | C—H | C—CH2OAc | H | H | cyclo-PrCH2CO | H | 1 |
| 2-3223 | F | C—CF3 | C—H | C—H | C—H | CF3 | C—H | C—CH2OAc | H | H | CH3SCH2CO | H | 1 |
| 2-3224 | F | C—CF3 | C—H | C—H | C—H | CF3 | C—H | C—CH2OAc | H | H | CH3SOCH2CO | H | 1 |
| 2-3225 | F | C—CF3 | C—H | C—H | C—H | CF3 | C—H | C—CH2OAc | H | H | CH3SO2CH2CO | H | 1 |
| 2-3226 | F | C—CF3 | C—H | C—H | C—H | CF3 | C—H | C—CH2OAc | H | H | EtNHCO | H | 1 |
| 2-3227 | F | C—CF3 | C—H | C—H | C—H | CF3 | C—H | C—CH2OAc | Me | H | EtCO | H | 1 |
| 2-3228 | F | C—CF3 | C—H | C—H | C—H | CF3 | C—H | C—CH2OAc | Me | H | CF3CH2CO | H | 1 |
| 2-3229 | F | C—CF3 | C—H | C—H | C—H | CF3 | N | C—CH2OAc | H | H | EtCO | H | 1 |
| 2-3230 | F | C—CF3 | C—H | C—H | C—H | CF3 | N | C—CH2OAc | H | H | CF3CH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3500 | H | C—Cl | C—Cl | C—CF3 | C—H | CF3 | C—H | C—CF3 | H | H | H | H | 1 |
| 2-3501 | H | C—Cl | C—Cl | C—CF3 | C—H | CF3 | C—H | C—CF3 | H | H | cyclo-PrCH2CO | H | 1 |
| 2-3502 | H | C—Cl | C—Cl | C—CF3 | C—H | CF3 | C—H | C—CF3 | H | H | CH3SCH2CO | H | 1 |
| 2-3503 | H | C—Cl | C—Cl | C—CF3 | C—H | CF3 | C—H | C—CF3 | H | H | CH3SOCH2CO | H | 1 |
| 2-3504 | H | C—Cl | C—Cl | C—CF3 | C—H | CF3 | C—H | C—CF3 | H | H | CH3SO2CH2CO | H | 1 |
| 2-3505 | H | C—Cl | C—Cl | C—CF3 | C—H | CF3 | C—H | C—CF3 | Me | H | EtCO | H | 1 |
| 2-3506 | H | C—Cl | C—Cl | C—CF3 | C—H | CF3 | C—H | C—CF3 | Me | H | CF3CH2CO | H | 1 |
| 2-3507 | H | C—Cl | C—Cl | C—CF3 | C—H | CF3 | N | C—CF3 | H | H | EtCO | H | 1 |
| 2-3508 | H | C—Cl | C—Cl | C—CF3 | C—H | CF3 | N | C—CF3 | H | H | CF3CH2CO | H | 1 |
| 2-3509 | H | C—Cl | C—Cl | C—CF3 | C—H | CF3 | C—H | C—Cl | H | H | H | H | 1 |
| 2-3510 | H | C—Cl | C—Cl | C—CF3 | C—H | CF3 | C—H | C—Cl | H | H | MeCO | H | 1 |
| 2-3511 | H | C—Cl | C—Cl | C—CF3 | C—H | CF3 | C—H | C—Cl | H | H | EtCO | H | 1 |
| 2-3512 | H | C—Cl | C—Cl | C—CF3 | C—H | CF3 | C—H | C—Cl | H | H | CF3CH2CO | H | 1 |
| 2-3513 | H | C—Cl | C—Cl | C—CF3 | C—H | CF3 | C—H | C—Cl | H | H | cyclo-PrCO | H | 1 |
| 2-3514 | H | C—Cl | C—Cl | C—CF3 | C—H | CF3 | C—H | C—Cl | H | H | cyclo-PrCH2CO | H | 1 |
| 2-3515 | H | C—Cl | C—Cl | C—CF3 | C—H | CF3 | C—H | C—Cl | H | H | CH3SCH2CO | H | 1 |
| 2-3516 | H | C—Cl | C—Cl | C—CF3 | C—H | CF3 | C—H | C—Cl | H | H | CH3SOCH2CO | H | 1 |
| 2-3517 | H | C—Cl | C—Cl | C—CF3 | C—H | CF3 | C—H | C—Cl | H | H | CH3SO2CH2CO | H | 1 |
| 2-3518 | H | C—Cl | C—Cl | C—CF3 | C—H | CF3 | C—H | C—Cl | H | H | EtNHCO | H | 1 |
| 2-3519 | H | C—Cl | C—Cl | C—CF3 | C—H | CF3 | C—H | C—Cl | Me | H | EtCO | H | 1 |
| 2-3520 | H | C—Cl | C—Cl | C—CF3 | C—H | CF3 | C—H | C—Cl | Me | H | CF3CH2CO | H | 1 |
| 2-3521 | H | C—Cl | C—Cl | C—CF3 | C—H | CF3 | N | C—Cl | H | H | EtCO | H | 1 |
| 2-3522 | H | C—Cl | C—Cl | C—CF3 | C—H | CF3 | N | C—Cl | H | H | CF3CH2CO | H | 1 |
| 2-3523 | H | C—Cl | C—Cl | C—CF3 | C—H | CF3 | C—H | C—Br | H | H | H | H | 1 |
| 2-3524 | H | C—Cl | C—Cl | C—CF3 | C—H | CF3 | C—H | C—Br | H | H | cyclo-PrCH2CO | H | 1 |
| 2-3525 | H | C—Cl | C—Cl | C—CF3 | C—H | CF3 | C—H | C—Br | H | H | CH3SCH2CO | H | 1 |
| 2-3526 | H | C—Cl | C—Cl | C—CF3 | C—H | CF3 | C—H | C—Br | H | H | CH3SOCH2CO | H | 1 |
| 2-3527 | H | C—Cl | C—Cl | C—CF3 | C—H | CF3 | C—H | C—Br | H | H | CH3SO2CH2CO | H | 1 |
| 2-3528 | H | C—Cl | C—Cl | C—CF3 | C—H | CF3 | C—H | C—Br | Me | H | EtCO | H | 1 |
| 2-3529 | H | C—Cl | C—Cl | C—CF3 | C—H | CF3 | C—H | C—Br | Me | H | CF3CH2CO | H | 1 |
| 2-3530 | H | C—Cl | C—Cl | C—CF3 | C—H | CF3 | N | C—Br | H | H | EtCO | H | 1 |
| 2-3531 | H | C—Cl | C—Cl | C—CF3 | C—H | CF3 | N | C—Br | H | H | CF3CH2CO | H | 1 |
| 2-3532 | H | C—Cl | C—Cl | C—CF3 | C—H | CF3 | C—H | C—CN | H | H | MeCO | H | 1 |
| 2-3533 | H | C—Cl | C—Cl | C—CF3 | C—H | CF3 | C—H | C—CN | H | H | EtCO | H | 1 |
| 2-3534 | H | C—Cl | C—Cl | C—CF3 | C—H | CF3 | C—H | C—CN | H | H | CF3CH2CO | H | 1 |
| 2-3535 | H | C—Cl | C—Cl | C—CF3 | C—H | CF3 | C—H | C—CN | H | H | cyclo-PrCO | H | 1 |
| 2-3536 | H | C—Cl | C—Cl | C—CF3 | C—H | CF3 | C—H | C—CN | H | H | ENHCO | H | 1 |
| 2-3537 | H | C—Cl | C—Cl | C—CF3 | C—H | CF3 | C—H | C—CN | Me | H | EtCO | H | 1 |
| 2-3538 | H | C—Cl | C—Cl | C—CF3 | C—H | CF3 | N | C—CN | H | H | EtCO | H | 1 |
| 2-3539 | H | C—Cl | C—Cl | C—CF3 | C—H | CF3 | C—H | C—Me | H | H | MeCO | H | 1 |
| 2-3540 | H | C—Cl | C—Cl | C—CF3 | C—H | CF3 | C—H | C—Me | H | H | MeCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3541 | H | C—Cl | C—Cl | C—CF3 | C—H | CF3 | C—H | C—Me | H | H | MeCO | H | 1 |
| 2-3542 | H | C—Cl | C—Cl | C—CF3 | C—H | CF3 | C—H | C—Me | H | H | EtCO | H | 1 |
| 2-3543 | H | C—Cl | C—Cl | C—CF3 | C—H | CF3 | C—H | C—Me | H | H | CF3CH2CO | H | 1 |
| 2-3544 | H | C—Cl | C—Cl | C—CF3 | C—H | CF3 | C—H | C—Me | H | H | cyclo-PrCO | H | 1 |
| 2-3545 | H | C—Cl | C—Cl | C—CF3 | C—H | CF3 | C—H | C—Me | H | H | CH3SCH2CO | H | 1 |
| 2-3546 | H | C—Cl | C—Cl | C—CF3 | C—H | CF3 | C—H | C—Me | H | H | EtNHCO | H | 1 |
| 2-3547 | H | C—Cl | C—Cl | C—CF3 | C—H | CF3 | C—H | C—Me | Me | H | EtCO | H | 1 |
| 2-3548 | H | C—Cl | C—Cl | C—CF3 | C—H | CF3 | N | C—Me | H | H | EtCO | H | 1 |
| 2-3549 | H | C—Cl | C—Cl | C—CF3 | C—H | CF3 | C—H | C—NO2 | H | H | MeCO | H | 1 |
| 2-3550 | H | C—Cl | C—Cl | C—CF3 | C—H | CF3 | C—H | C—NO2 | H | H | MeCO | H | 1 |
| 2-3551 | H | C—Cl | C—Cl | C—CF3 | C—H | CF3 | C—H | C—NO2 | H | H | CF3CH2CO | H | 1 |
| 2-3552 | H | C—Cl | C—Cl | C—CF3 | C—H | CF3 | C—H | C—NO2 | H | H | cyclo-PrCO | H | 1 |
| 2-3553 | H | C—Cl | C—Cl | C—CF3 | C—H | CF3 | C—H | C—NO2 | H | H | CH3SCH2CO | H | 1 |
| 2-3554 | H | C—Cl | C—Cl | C—CF3 | C—H | CF3 | C—H | C—NO2 | H | H | EtNHCO | H | 1 |
| 2-3555 | H | C—Cl | C—Cl | C—CF3 | C—H | CF3 | C—H | C—NO2 | Me | H | EtCO | H | 1 |
| 2-3556 | H | C—Cl | C—Cl | C—CF3 | C—H | CF3 | N | C—NO2 | H | H | EtCO | H | 1 |
| 2-3557 | H | C—Cl | C—Cl | C—CF3 | C—H | CF3 | C—H | C—SMe | H | H | EtCO | H | 1 |
| 2-3558 | H | C—Cl | C—Cl | C—CF3 | C—H | CF3 | C—H | C—SMe | H | H | MeCO | H | 1 |
| 2-3559 | H | C—Cl | C—Cl | C—CF3 | C—H | CF3 | C—H | C—SMe | H | H | MeCO | H | 1 |
| 2-3560 | H | C—Cl | C—Cl | C—CF3 | C—H | CF3 | C—H | C—SMe | H | H | EtCO | H | 1 |
| 2-3561 | H | C—Cl | C—Cl | C—CF3 | C—H | CF3 | C—H | C—SMe | H | H | CF3CH2CO | H | 1 |
| 2-3562 | H | C—Cl | C—Cl | C—CF3 | C—H | CF3 | C—H | C—SMe | H | H | cyclo-PrCO | H | 1 |
| 2-3563 | H | C—Cl | C—Cl | C—CF3 | C—H | CF3 | C—H | C—SMe | H | H | CH3SCH2CO | H | 1 |
| 2-3564 | H | C—Cl | C—Cl | C—CF3 | C—H | CF3 | C—H | C—SMe | H | H | EtNHCO | H | 1 |
| 2-3565 | H | C—Cl | C—Cl | C—CF3 | C—H | CF3 | C—H | C—SMe | Me | H | EtCO | H | 1 |
| 2-3566 | H | C—Cl | C—Cl | C—CF3 | C—H | CF3 | N | C—SMe | H | H | EtCO | H | 1 |
| 2-3567 | H | C—Cl | C—Cl | C—CF3 | C—H | CF3 | C—H | C—H | H | H | MeCO | H | 1 |
| 2-3568 | H | C—Cl | C—Cl | C—CF3 | C—H | CF3 | C—H | C—H | H | H | MeCO | H | 1 |
| 2-3569 | H | C—Cl | C—Cl | C—CF3 | C—H | CF3 | C—H | C—H | H | H | EtCO | H | 1 |
| 2-3570 | H | C—Cl | C—Cl | C—CF3 | C—H | CF3 | C—H | C—H | H | H | CF3CH2CO | H | 1 |
| 2-3571 | H | C—Cl | C—Cl | C—CF3 | C—H | CF3 | C—H | C—H | H | H | cyclo-PrCO | H | 1 |
| 2-3572 | H | C—Cl | C—Cl | C—CF3 | C—H | CF3 | C—H | C—H | H | H | CH3SCH2CO | H | 1 |
| 2-3573 | H | C—Cl | C—Cl | C—CF3 | C—H | CF3 | C—H | C—H | H | H | EtNHCO | H | 1 |
| 2-3574 | H | C—Cl | C—Cl | C—CF3 | C—H | CF3 | C—H | C—H | Me | H | EtCO | H | 1 |
| 2-3575 | H | C—Cl | C—Cl | C—CF3 | C—H | CF3 | N | C—H | H | H | EtCO | H | 1 |
| 2-3576 | H | C—Cl | C—Cl | C—CF3 | C—H | CF3 | C—H | C—SOMe | H | H | MeCO | H | 1 |
| 2-3577 | H | C—Cl | C—Cl | C—CF3 | C—H | CF3 | C—H | C—SOMe | H | H | EtCO | H | 1 |
| 2-3578 | H | C—Cl | C—Cl | C—CF3 | C—H | CF3 | C—H | C—SO2Me | H | H | CF3CH2CO | H | 1 |
| 2-3579 | H | C—Cl | C—Cl | C—CF3 | C—H | CF3 | C—H | C—SO2Me | H | H | EtCO | H | 1 |
| 2-3580 | H | C—Cl | C—Cl | C—CF3 | C—H | CF3 | C—H | C—SCF3 | H | H | CF3CH2CO | H | 1 |
| 2-3581 | H | C—Cl | C—Cl | C—CF3 | C—H | CF3 | C—H | C—SCF3 | H | H | EtCO | H | 1 |

TABLE 2-1-continued

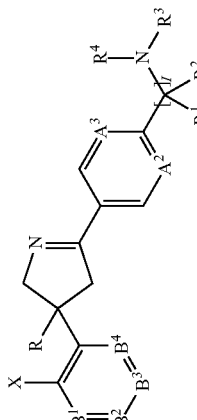

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3582 | H | C—Cl | C—Cl | C—CF3 | C—H | CF3 | C—H | C—SOCF3 | H | H | EtCO | H | 1 |
| 2-3583 | H | C—Cl | C—Cl | C—CF3 | C—H | CF3 | C—H | C—SOCF3 | H | H | CF3CH2CO | H | 1 |
| 2-3584 | H | C—Cl | C—Cl | C—CF3 | C—H | CF3 | C—H | C—SO2CF3 | H | H | EtCO | H | 1 |
| 2-3585 | H | C—Cl | C—Cl | C—CF3 | C—H | CF3 | C—H | C—SO2CF3 | H | H | CF3CH2CO | H | 1 |
| 2-3586 | H | C—Cl | C—Cl | C—CF3 | C—H | CF3 | C—H | C—F | H | H | EtCO | H | 1 |
| 2-3587 | H | C—Cl | C—Cl | C—CF3 | C—H | CF3 | C—H | C—F | H | H | CF3CH2CO | H | 1 |
| 2-3588 | H | C—Cl | C—Cl | C—CF3 | C—H | CF3 | C—H | C—I | H | H | EtCO | H | 1 |
| 2-3589 | H | C—Cl | C—Cl | C—CF3 | C—H | CF3 | C—H | C—I | H | H | CF3CH2CO | H | 1 |
| 2-3590 | H | C—Cl | C—Cl | C—CF3 | C—H | CF3 | C—H | C—NH2 | H | H | EtCO | H | 1 |
| 2-3591 | H | C—Cl | C—Cl | C—CF3 | C—H | CF3 | C—H | C—NH2 | H | H | CF3CH2CO | H | 1 |
| 2-3592 | H | C—Cl | C—Cl | C—CF3 | C—H | CF3 | C—H | C—NHAc | H | H | EtCO | H | 1 |
| 2-3593 | H | C—Cl | C—Cl | C—CF3 | C—H | CF3 | C—H | C—NHAc | H | H | CF3CH2CO | H | 1 |
| 2-3594 | H | C—Cl | C—Cl | C—CF3 | C—H | CF3 | C—H | C—NHCOCF3 | H | H | EtCO | H | 1 |
| 2-3595 | H | C—Cl | C—Cl | C—CF3 | C—H | CF3 | C—H | C—NHCOCF3 | H | H | CF3CH2CO | H | 1 |
| 2-3596 | H | C—Cl | C—Cl | C—CF3 | C—H | CF3 | C—H | C—CH2OAc | H | H | EtCO | H | 1 |
| 2-3597 | H | C—Cl | C—Cl | C—CF3 | C—H | CF3 | C—H | C—CH2OAc | H | H | CF3CH2CO | H | 1 |
| 2-3598 | H | C—Cl | C—Cl | C—Cl | C—H | CF3 | C—H | C—CF3 | H | H | H | H | 1 |
| 2-3599 | H | C—Cl | C—Cl | C—Cl | C—H | CF3 | C—H | C—CF3 | H | H | CH3CO | H | 1 |
| 2-3600 | H | C—Cl | C—Cl | C—Cl | C—H | CF3 | C—H | C—CF3 | H | H | EtCO | H | 1 |
| 2-3601 | H | C—Cl | C—Cl | C—Cl | C—H | CF3 | C—H | C—CF3 | H | H | cyclo-PrCO | H | 1 |
| 2-3602 | H | C—Cl | C—Cl | C—Cl | C—H | CF3 | C—H | C—CF3 | H | H | cyclo-PrCH2CO | H | 1 |
| 2-3603 | H | C—Cl | C—Cl | C—Cl | C—H | CF3 | C—H | C—CF3 | H | H | EtNHCO | H | 1 |
| 2-3604 | H | C—Cl | C—Cl | C—Cl | C—H | CF3 | C—H | C—CF3 | H | H | CH3SCH2CO | H | 1 |
| 2-3605 | H | C—Cl | C—Cl | C—Cl | C—H | CF3 | C—H | C—CF3 | H | H | CH3SOCH2CO | H | 1 |
| 2-3606 | H | C—Cl | C—Cl | C—Cl | C—H | CF3 | C—H | C—CF3 | H | H | CH3SO2CH2CO | H | 1 |
| 2-3607 | H | C—Cl | C—Cl | C—Cl | C—H | CF3 | C—H | C—CF3 | Me | H | EtCO | H | 1 |
| 2-3608 | H | C—Cl | C—Cl | C—Cl | C—H | CF3 | C—H | C—CF3 | Me | H | CF3CH2CO | H | 1 |
| 2-3609 | H | C—Cl | C—Cl | C—Cl | C—H | CF3 | N | C—CF3 | H | H | EtCO | H | 1 |
| 2-3610 | H | C—Cl | C—Cl | C—Cl | C—H | CF3 | N | C—CF3 | H | H | CF3CH2CO | H | 1 |
| 2-3611 | H | C—Cl | C—Cl | C—Cl | C—H | CF3 | C—H | C—Cl | H | H | H | H | 1 |
| 2-3612 | H | C—Cl | C—Cl | C—Cl | C—H | CF3 | C—H | C—Cl | H | H | MeCO | H | 1 |
| 2-3613 | H | C—Cl | C—Cl | C—Cl | C—H | CF3 | C—H | C—Cl | H | H | EtCO | H | 1 |
| 2-3614 | H | C—Cl | C—Cl | C—Cl | C—H | CF3 | C—H | C—Cl | H | H | CF3CH2CO | H | 1 |
| 2-3615 | H | C—Cl | C—Cl | C—Cl | C—H | CF3 | C—H | C—Cl | H | H | cyclo-PrCO | H | 1 |
| 2-3616 | H | C—Cl | C—Cl | C—Cl | C—H | CF3 | C—H | C—Cl | H | H | cyclo-PrCH2CO | H | 1 |
| 2-3617 | H | C—Cl | C—Cl | C—Cl | C—H | CF3 | C—H | C—Cl | H | H | CH3SCH2CO | H | 1 |
| 2-3618 | H | C—Cl | C—Cl | C—Cl | C—H | CF3 | C—H | C—Cl | H | H | CH3SOCH2CO | H | 1 |
| 2-3619 | H | C—Cl | C—Cl | C—Cl | C—H | CF3 | C—H | C—Cl | H | H | CH3SO2CH2CO | H | 1 |
| 2-3620 | H | C—Cl | C—Cl | C—Cl | C—H | CF3 | C—H | C—Cl | H | H | EtNHCO | H | 1 |
| 2-3621 | H | C—Cl | C—Cl | C—Cl | C—H | CF3 | C—H | C—Cl | Me | H | EtCO | H | 1 |
| 2-3622 | H | C—Cl | C—Cl | C—Cl | C—H | CF3 | C—H | C—Cl | Me | H | EtCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3623 | H | C—Cl | C—CF3 | C—Cl | C—H | CF3 | C—H | C—Cl | Me | H | CF3CH2CO | H | 1 |
| 2-3624 | H | C—Cl | C—CF3 | C—Cl | C—H | CF3 | N | C—Cl | H | H | EtCO | H | 1 |
| 2-3625 | H | C—Cl | C—CF3 | C—Cl | C—H | CF3 | N | C—Cl | H | H | CF3CH2CO | H | 1 |
| 2-3626 | H | C—Cl | C—CF3 | C—Cl | C—H | CF3 | C—H | C—Br | H | H | H | H | 1 |
| 2-3627 | H | C—Cl | C—CF3 | C—Cl | C—H | CF3 | C—H | C—Br | H | H | MeCO | H | 1 |
| 2-3628 | H | C—Cl | C—CF3 | C—Cl | C—H | CF3 | C—H | C—Br | H | H | EtCO | H | 1 |
| 2-3629 | H | C—Cl | C—CF3 | C—Cl | C—H | CF3 | C—H | C—Br | H | H | cyc-PrCO | H | 1 |
| 2-3630 | H | C—Cl | C—CF3 | C—Cl | C—H | CF3 | C—H | C—Br | H | H | CF3CH2CO | H | 1 |
| 2-3631 | H | C—Cl | C—CF3 | C—Cl | C—H | CF3 | C—H | C—Br | H | H | CH3SCH2CO | H | 1 |
| 2-3632 | H | C—Cl | C—CF3 | C—Cl | C—H | CF3 | C—H | C—Br | H | H | CH3SOCH2CO | H | 1 |
| 2-3633 | H | C—Cl | C—CF3 | C—Cl | C—H | CF3 | C—H | C—Br | H | H | CH3SO2CH2CO | H | 1 |
| 2-3634 | H | C—Cl | C—CF3 | C—Cl | C—H | CF3 | C—H | C—Br | Me | H | EtCO | H | 1 |
| 2-3635 | H | C—Cl | C—CF3 | C—Cl | C—H | CF3 | C—H | C—Br | Me | H | CF3CH2CO | H | 1 |
| 2-3636 | H | C—Cl | C—CF3 | C—Cl | C—H | CF3 | N | C—Br | H | H | EtCO | H | 1 |
| 2-3637 | H | C—Cl | C—CF3 | C—Cl | C—H | CF3 | N | C—Br | H | H | CF3CH2CO | H | 1 |
| 2-3638 | H | C—Cl | C—CF3 | C—Cl | C—H | CF3 | C—H | C—CN | H | H | EtCO | H | 1 |
| 2-3639 | H | C—Cl | C—CF3 | C—Cl | C—H | CF3 | C—H | C—CN | H | H | CF3CH2CO | H | 1 |
| 2-3640 | H | C—Cl | C—CF3 | C—Cl | C—H | CF3 | N | C—CN | H | H | EtCO | H | 1 |
| 2-3641 | H | C—Cl | C—CF3 | C—Cl | C—H | CF3 | C—H | C—Me | H | H | MeCO | H | 1 |
| 2-3642 | H | C—Cl | C—CF3 | C—Cl | C—H | CF3 | C—H | C—Me | H | H | MeCO | H | 1 |
| 2-3643 | H | C—Cl | C—CF3 | C—Cl | C—H | CF3 | C—H | C—Me | H | H | EtCO | H | 1 |
| 2-3644 | H | C—Cl | C—CF3 | C—Cl | C—H | CF3 | C—H | C—Me | H | H | CF3CH2CO | H | 1 |
| 2-3645 | H | C—Cl | C—CF3 | C—Cl | C—H | CF3 | C—H | C—Me | H | H | cyclo-PrCO | H | 1 |
| 2-3646 | H | C—Cl | C—CF3 | C—Cl | C—H | CF3 | C—H | C—Me | H | H | CH3SCH2CO | H | 1 |
| 2-3647 | H | C—Cl | C—CF3 | C—Cl | C—H | CF3 | C—H | C—Me | H | H | EtNHCO | H | 1 |
| 2-3648 | H | C—Cl | C—CF3 | C—Cl | C—H | CF3 | C—H | C—Me | Me | H | EtCO | H | 1 |
| 2-3649 | H | C—Cl | C—CF3 | C—Cl | C—H | CF3 | N | C—Me | H | H | EtCO | H | 1 |
| 2-3650 | H | C—Cl | C—CF3 | C—Cl | C—H | CF3 | C—H | C—NO2 | H | H | MeCO | H | 1 |
| 2-3651 | H | C—Cl | C—CF3 | C—Cl | C—H | CF3 | C—H | C—NO2 | H | H | EtCO | H | 1 |
| 2-3652 | H | C—Cl | C—CF3 | C—Cl | C—H | CF3 | C—H | C—NO2 | H | H | CF3CH2CO | H | 1 |
| 2-3653 | H | C—Cl | C—CF3 | C—Cl | C—H | CF3 | C—H | C—NO2 | H | H | cyclo-PrCO | H | 1 |
| 2-3654 | H | C—Cl | C—CF3 | C—Cl | C—H | CF3 | C—H | C—NO2 | H | H | CH3SCH2CO | H | 1 |
| 2-3655 | H | C—Cl | C—CF3 | C—Cl | C—H | CF3 | C—H | C—NO2 | H | H | EtNHCO | H | 1 |
| 2-3656 | H | C—Cl | C—CF3 | C—Cl | C—H | CF3 | C—H | C—NO2 | Me | H | EtCO | H | 1 |
| 2-3657 | H | C—Cl | C—CF3 | C—Cl | C—H | CF3 | N | C—NO2 | H | H | EtCO | H | 1 |
| 2-3658 | H | C—Cl | C—CF3 | C—Cl | C—H | CF3 | C—H | C—SMe | H | H | MeCO | H | 1 |
| 2-3659 | H | C—Cl | C—CF3 | C—Cl | C—H | CF3 | C—H | C—SMe | H | H | EtCO | H | 1 |
| 2-3660 | H | C—Cl | C—CF3 | C—Cl | C—H | CF3 | C—H | C—SMe | H | H | MeCO | H | 1 |
| 2-3661 | H | C—Cl | C—CF3 | C—Cl | C—H | CF3 | C—H | C—SMe | H | H | EtCO | H | 1 |
| 2-3662 | H | C—Cl | C—CF3 | C—Cl | C—H | CF3 | C—H | C—SMe | H | H | CF3CH2CO | H | 1 |
| 2-3663 | H | C—Cl | C—CF3 | C—Cl | C—H | CF3 | C—H | C—SMe | H | H | cyclo-PrCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3664 | H | C—Cl | C—CF3 | C—Cl | C—H | CF3 | C—H | C—SMe | H | H | CH3SCH2CO | H | 1 |
| 2-3665 | H | C—Cl | C—CF3 | C—Cl | C—H | CF3 | C—H | C—SMe | H | H | EtNHCO | H | 1 |
| 2-3666 | H | C—Cl | C—CF3 | C—Cl | C—H | CF3 | N | C—SMe | Me | H | EtCO | H | 1 |
| 2-3667 | H | C—Cl | C—CF3 | C—Cl | C—H | CF3 | C—H | C—SMe | H | H | EtCO | H | 1 |
| 2-3668 | H | C—Cl | C—CF3 | C—Cl | C—H | CF3 | C—H | C—H | H | H | MeCO | H | 1 |
| 2-3669 | H | C—Cl | C—CF3 | C—Cl | C—H | CF3 | C—H | C—H | H | H | MeCO | H | 1 |
| 2-3670 | H | C—Cl | C—CF3 | C—Cl | C—H | CF3 | C—H | C—H | H | H | EtCO | H | 1 |
| 2-3671 | H | C—Cl | C—CF3 | C—Cl | C—H | CF3 | C—H | C—H | H | H | CF3CH2CO | H | 1 |
| 2-3672 | H | C—Cl | C—CF3 | C—Cl | C—H | CF3 | C—H | C—H | H | H | cyclo-PrCO | H | 1 |
| 2-3673 | H | C—Cl | C—CF3 | C—Cl | C—H | CF3 | C—H | C—H | H | H | CH3SCH2CO | H | 1 |
| 2-3674 | H | C—Cl | C—CF3 | C—Cl | C—H | CF3 | C—H | C—H | Me | H | EtNHCO | H | 1 |
| 2-3675 | H | C—Cl | C—CF3 | C—Cl | C—H | CF3 | N | C—H | H | H | EtCO | H | 1 |
| 2-3676 | H | C—Cl | C—CF3 | C—Cl | C—H | CF3 | C—H | C—H | H | H | EtCO | H | 1 |
| 2-3677 | H | C—Cl | C—CF3 | C—Cl | C—H | CF3 | C—H | C—SOMe | H | H | EtCO | H | 1 |
| 2-3678 | H | C—Cl | C—CF3 | C—Cl | C—H | CF3 | C—H | C—SOMe | H | H | CF3CH2CO | H | 1 |
| 2-3679 | H | C—Cl | C—CF3 | C—Cl | C—H | CF3 | C—H | C—SO2Me | H | H | EtCO | H | 1 |
| 2-3680 | H | C—Cl | C—CF3 | C—Cl | C—H | CF3 | C—H | C—SO2Me | H | H | CF3CH2CO | H | 1 |
| 2-3681 | H | C—Cl | C—CF3 | C—Cl | C—H | CF3 | C—H | C—SCF3 | H | H | EtCO | H | 1 |
| 2-3682 | H | C—Cl | C—CF3 | C—Cl | C—H | CF3 | C—H | C—SCF3 | H | H | CF3CH2CO | H | 1 |
| 2-3683 | H | C—Cl | C—CF3 | C—Cl | C—H | CF3 | C—H | C—SOCF3 | H | H | EtCO | H | 1 |
| 2-3684 | H | C—Cl | C—CF3 | C—Cl | C—H | CF3 | C—H | C—SOCF3 | H | H | CF3CH2CO | H | 1 |
| 2-3685 | H | C—Cl | C—CF3 | C—Cl | C—H | CF3 | C—H | C—SO2CF3 | H | H | EtCO | H | 1 |
| 2-3686 | H | C—Cl | C—CF3 | C—Cl | C—H | CF3 | C—H | C—SO2CF3 | H | H | CF3CH2CO | H | 1 |
| 2-3687 | H | C—Cl | C—CF3 | C—Cl | C—H | CF3 | C—H | C—F | H | H | EtCO | H | 1 |
| 2-3688 | H | C—Cl | C—CF3 | C—Cl | C—H | CF3 | C—H | C—F | H | H | CF3CH2CO | H | 1 |
| 2-3689 | H | C—Cl | C—CF3 | C—Cl | C—H | CF3 | C—H | C—I | H | H | EtCO | H | 1 |
| 2-3690 | H | C—Cl | C—CF3 | C—Cl | C—H | CF3 | C—H | C—I | H | H | CF3CH2CO | H | 1 |
| 2-3691 | H | C—Cl | C—CF3 | C—Cl | C—H | CF3 | C—H | C—NH2 | H | H | EtCO | H | 1 |
| 2-3692 | H | C—Cl | C—CF3 | C—Cl | C—H | CF3 | C—H | C—NH2 | H | H | CF3CH2CO | H | 1 |
| 2-3693 | H | C—Cl | C—CF3 | C—Cl | C—H | CF3 | C—H | C—NHAc | H | H | EtCO | H | 1 |
| 2-3694 | H | C—Cl | C—CF3 | C—Cl | C—H | CF3 | C—H | C—NHAc | H | H | CF3CH2CO | H | 1 |
| 2-3695 | H | C—Cl | C—CF3 | C—Cl | C—H | CF3 | C—H | C—NHCOCF3 | H | H | EtCO | H | 1 |
| 2-3696 | H | C—Cl | C—CF3 | C—Cl | C—H | CF3 | C—H | C—NHCOCF3 | H | H | CF3CH2CO | H | 1 |
| 2-3697 | H | C—Cl | C—CF3 | C—Cl | C—H | CF3 | C—H | C—CH2OAc | H | H | EtCO | H | 1 |
| 2-3698 | H | C—Cl | C—CF3 | C—Cl | C—H | CF3 | C—H | C—CH2OAc | H | H | CF3CH2CO | H | 1 |
| 2-3699 | H | C—Br | C—Cl | C—Br | C—H | CF3 | C—H | C—CF3 | H | H | H | H | 1 |
| 2-3700 | H | C—Br | C—Cl | C—Br | C—H | CF3 | C—H | C—CF3 | H | H | CH3CO | H | 1 |
| 2-3701 | H | C—Br | C—Cl | C—Br | C—H | CF3 | C—H | C—CF3 | H | H | EtCO | H | 1 |
| 2-3702 | H | C—Br | C—Cl | C—Br | C—H | CF3 | C—H | C—CF3 | H | H | CF3CH2CO | H | 1 |
| 2-3703 | H | C—Br | C—Cl | C—Br | C—H | CF3 | C—H | C—CF3 | H | H | cyclo-PrCO | H | 1 |
| 2-3704 | H | C—Br | C—Cl | C—Br | C—H | CF3 | C—H | C—CF3 | H | H | cyclo-PrCH2CO | H | 1 |

TABLE 2-1-continued

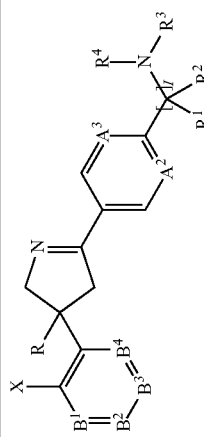

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3705 | H | C—Br | C—Cl | C—Br | C—H | CF3 | C—H | C—CF3 | H | H | EtNHCO | H | 1 |
| 2-3706 | H | C—Br | C—Cl | C—Br | C—H | CF3 | C—H | C—CF3 | H | H | CH3SCH2CO | H | 1 |
| 2-3707 | H | C—Br | C—Cl | C—Br | C—H | CF3 | C—H | C—CF3 | H | H | CH3SOCH2CO | H | 1 |
| 2-3708 | H | C—Br | C—Cl | C—Br | C—H | CF3 | C—H | C—CF3 | H | H | CH3SO2CH2CO | H | 1 |
| 2-3709 | H | C—Br | C—Cl | C—Br | C—H | CF3 | C—H | C—CF3 | Me | H | EtCO | H | 1 |
| 2-3710 | H | C—Br | C—Cl | C—Br | C—H | CF3 | C—H | C—CF3 | Me | H | CF3CH2CO | H | 1 |
| 2-3711 | H | C—Br | C—Cl | C—Br | C—H | CF3 | N | C—CF3 | H | H | EtCO | H | 1 |
| 2-3712 | H | C—Br | C—Cl | C—Br | C—H | CF3 | C—H | C—CF3 | H | H | CF3CH2CO | H | 1 |
| 2-3713 | H | C—Br | C—Cl | C—Br | C—H | CF3 | C—H | C—Cl | H | H | H | H | 1 |
| 2-3714 | H | C—Br | C—Cl | C—Br | C—H | CF3 | C—H | C—Cl | H | H | MeCO | H | 1 |
| 2-3715 | H | C—Br | C—Cl | C—Br | C—H | CF3 | C—H | C—Cl | H | H | EtCO | H | 1 |
| 2-3716 | H | C—Br | C—Cl | C—Br | C—H | CF3 | C—H | C—Cl | H | H | CF3CH2CO | H | 1 |
| 2-3717 | H | C—Br | C—Cl | C—Br | C—H | CF3 | C—H | C—Cl | H | H | cyclo-PrCO | H | 1 |
| 2-3718 | H | C—Br | C—Cl | C—Br | C—H | CF3 | C—H | C—Cl | H | H | cyclo-PrCH2CO | H | 1 |
| 2-3719 | H | C—Br | C—Cl | C—Br | C—H | CF3 | C—H | C—Cl | H | H | CH3SCH2CO | H | 1 |
| 2-3720 | H | C—Br | C—Cl | C—Br | C—H | CF3 | C—H | C—Cl | H | H | CH3SOCH2CO | H | 1 |
| 2-3721 | H | C—Br | C—Cl | C—Br | C—H | CF3 | C—H | C—Cl | H | H | CH3SO2CH2CO | H | 1 |
| 2-3722 | H | C—Br | C—Cl | C—Br | C—H | CF3 | C—H | C—Cl | H | H | EtNHCO | H | 1 |
| 2-3723 | H | C—Br | C—Cl | C—Br | C—H | CF3 | C—H | C—Cl | Me | H | EtCO | H | 1 |
| 2-3724 | H | C—Br | C—Cl | C—Br | C—H | CF3 | C—H | C—Cl | Me | H | CF3CH2CO | H | 1 |
| 2-3725 | H | C—Br | C—Cl | C—Br | C—H | CF3 | N | C—Cl | H | H | EtCO | H | 1 |
| 2-3726 | H | C—Br | C—Cl | C—Br | C—H | CF3 | C—H | C—Cl | H | H | EtCO | H | 1 |
| 2-3727 | H | C—Br | C—Cl | C—Br | C—H | CF3 | C—H | C—Br | H | H | H | H | 1 |
| 2-3728 | H | C—Br | C—Cl | C—Br | C—H | CF3 | C—H | C—Br | H | H | MeCO | H | 1 |
| 2-3729 | H | C—Br | C—Cl | C—Br | C—H | CF3 | C—H | C—Br | H | H | EtCO | H | 1 |
| 2-3730 | H | C—Br | C—Cl | C—Br | C—H | CF3 | C—H | C—Br | H | H | cyc-PrCO | H | 1 |
| 2-3731 | H | C—Br | C—Cl | C—Br | C—H | CF3 | C—H | C—Br | H | H | CF3CH2CO | H | 1 |
| 2-3732 | H | C—Br | C—Cl | C—Br | C—H | CF3 | C—H | C—Br | H | H | CH3SCH2CO | H | 1 |
| 2-3733 | H | C—Br | C—Cl | C—Br | C—H | CF3 | C—H | C—Br | H | H | CH3SOCH2CO | H | 1 |
| 2-3734 | H | C—Br | C—Cl | C—Br | C—H | CF3 | C—H | C—Br | H | H | CH3SO2CH2CO | H | 1 |
| 2-3735 | H | C—Br | C—Cl | C—Br | C—H | CF3 | C—H | C—Br | Me | H | EtCO | H | 1 |
| 2-3736 | H | C—Br | C—Cl | C—Br | C—H | CF3 | C—H | C—Br | Me | H | CF3CH2CO | H | 1 |
| 2-3737 | H | C—Br | C—Cl | C—Br | C—H | CF3 | N | C—Br | H | H | EtCO | H | 1 |
| 2-3738 | H | C—Br | C—Cl | C—Br | C—H | CF3 | C—H | C—Br | H | H | CF3CH2CO | H | 1 |
| 2-3739 | H | C—Br | C—Cl | C—Br | C—H | CF3 | C—H | C—CN | H | H | EtCO | H | 1 |
| 2-3740 | H | C—Br | C—Cl | C—Br | C—H | CF3 | C—H | C—CN | H | H | CF3CH2CO | H | 1 |
| 2-3741 | H | C—Br | C—Cl | C—Br | C—H | CF3 | N | C—CN | H | H | EtCO | H | 1 |
| 2-3742 | H | C—Br | C—Cl | C—Br | C—H | CF3 | C—H | C—Me | H | H | EtCO | H | 1 |
| 2-3743 | H | C—Br | C—Cl | C—Br | C—H | CF3 | C—H | C—Me | H | H | MeCO | H | 1 |
| 2-3744 | H | C—Br | C—Cl | C—Br | C—H | CF3 | C—H | C—Me | H | H | MeCO | H | 1 |
| 2-3745 | H | C—Br | C—Cl | C—Br | C—H | CF3 | C—H | C—Me | H | H | CF3CH2CO | H | 1 |

TABLE 2-1-continued

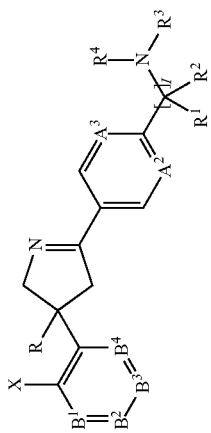

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3746 | H | C—Br | C—Cl | C—Br | C—H | CF3 | C—H | C—Me | H | H | cyclo-PrCO | H | 1 |
| 2-3747 | H | C—Br | C—Cl | C—Br | C—H | CF3 | C—H | C—Me | H | H | CH3SCH2CO | H | 1 |
| 2-3748 | H | C—Br | C—Cl | C—Br | C—H | CF3 | C—H | C—Me | H | H | EtNHCO | H | 1 |
| 2-3749 | H | C—Br | C—Cl | C—Br | C—H | CF3 | C—H | C—Me | Me | H | EtCO | H | 1 |
| 2-3750 | H | C—Br | C—Cl | C—Br | C—H | CF3 | N | C—Me | H | H | EtCO | H | 1 |
| 2-3751 | H | C—Br | C—Cl | C—Br | C—H | CF3 | C—H | C—NO2 | H | H | EtCO | H | 1 |
| 2-3752 | H | C—Br | C—Cl | C—Br | C—H | CF3 | C—H | C—NO2 | H | H | MeCO | H | 1 |
| 2-3753 | H | C—Br | C—Cl | C—Br | C—H | CF3 | C—H | C—NO2 | H | H | MeCO | H | 1 |
| 2-3754 | H | C—Br | C—Cl | C—Br | C—H | CF3 | C—H | C—NO2 | H | H | CF3CH2CO | H | 1 |
| 2-3755 | H | C—Br | C—Cl | C—Br | C—H | CF3 | C—H | C—NO2 | H | H | cyclo-PrCO | H | 1 |
| 2-3756 | H | C—Br | C—Cl | C—Br | C—H | CF3 | C—H | C—NO2 | H | H | CH3SCH2CO | H | 1 |
| 2-3757 | H | C—Br | C—Cl | C—Br | C—H | CF3 | C—H | C—NO2 | H | H | EtNHCO | H | 1 |
| 2-3758 | H | C—Br | C—Cl | C—Br | C—H | CF3 | C—H | C—NO2 | Me | H | EtCO | H | 1 |
| 2-3759 | H | C—Br | C—Cl | C—Br | C—H | CF3 | N | C—NO2 | H | H | EtCO | H | 1 |
| 2-3760 | H | C—Br | C—Cl | C—Br | C—H | CF3 | C—H | C—SMe | H | H | EtCO | H | 1 |
| 2-3761 | H | C—Br | C—Cl | C—Br | C—H | CF3 | C—H | C—SMe | H | H | MeCO | H | 1 |
| 2-3762 | H | C—Br | C—Cl | C—Br | C—H | CF3 | C—H | C—SMe | H | H | MeCO | H | 1 |
| 2-3763 | H | C—Br | C—Cl | C—Br | C—H | CF3 | C—H | C—SMe | H | H | CF3CH2CO | H | 1 |
| 2-3764 | H | C—Br | C—Cl | C—Br | C—H | CF3 | C—H | C—SMe | H | H | cyclo-PrCO | H | 1 |
| 2-3765 | H | C—Br | C—Cl | C—Br | C—H | CF3 | C—H | C—SMe | H | H | CH3SCH2CO | H | 1 |
| 2-3766 | H | C—Br | C—Cl | C—Br | C—H | CF3 | C—H | C—SMe | H | H | EtNHCO | H | 1 |
| 2-3767 | H | C—Br | C—Cl | C—Br | C—H | CF3 | C—H | C—SMe | Me | H | EtCO | H | 1 |
| 2-3768 | H | C—Br | C—Cl | C—Br | C—H | CF3 | N | C—SMe | H | H | EtCO | H | 1 |
| 2-3769 | H | C—Br | C—Cl | C—Br | C—H | CF3 | C—H | C—H | H | H | MeCO | H | 1 |
| 2-3770 | H | C—Br | C—Cl | C—Br | C—H | CF3 | C—H | C—H | H | H | MeCO | H | 1 |
| 2-3771 | H | C—Br | C—Cl | C—Br | C—H | CF3 | C—H | C—H | H | H | EtCO | H | 1 |
| 2-3772 | H | C—Br | C—Cl | C—Br | C—H | CF3 | C—H | C—H | H | H | CF3CH2CO | H | 1 |
| 2-3773 | H | C—Br | C—Cl | C—Br | C—H | CF3 | C—H | C—H | H | H | cyclo-PrCO | H | 1 |
| 2-3774 | H | C—Br | C—Cl | C—Br | C—H | CF3 | C—H | C—H | H | H | CH3SCH2CO | H | 1 |
| 2-3775 | H | C—Br | C—Cl | C—Br | C—H | CF3 | C—H | C—H | H | H | EtNHCO | H | 1 |
| 2-3776 | H | C—Br | C—Cl | C—Br | C—H | CF3 | C—H | C—H | Me | H | EtCO | H | 1 |
| 2-3777 | H | C—Br | C—Cl | C—Br | C—H | CF3 | N | C—H | H | H | EtCO | H | 1 |
| 2-3778 | H | C—Br | C—Cl | C—Br | C—H | CF3 | C—H | C—SOMe | H | H | EtCO | H | 1 |
| 2-3779 | H | C—Br | C—Cl | C—Br | C—H | CF3 | C—H | C—SOMe | H | H | EtCO | H | 1 |
| 2-3780 | H | C—Br | C—Cl | C—Br | C—H | CF3 | C—H | C—SO2Me | H | H | CF3CH2CO | H | 1 |
| 2-3781 | H | C—Br | C—Cl | C—Br | C—H | CF3 | C—H | C—SO2Me | H | H | EtCO | H | 1 |
| 2-3782 | H | C—Br | C—Cl | C—Br | C—H | CF3 | C—H | C—SCF3 | H | H | EtCO | H | 1 |
| 2-3783 | H | C—Br | C—Cl | C—Br | C—H | CF3 | C—H | C—SCF3 | H | H | CF3CH2CO | H | 1 |
| 2-3784 | H | C—Br | C—Cl | C—Br | C—H | CF3 | C—H | C—SOCF3 | H | H | EtCO | H | 1 |
| 2-3785 | H | C—Br | C—Cl | C—Br | C—H | CF3 | C—H | C—SOCF3 | H | H | CF3CH2CO | H | 1 |
| 2-3786 | H | C—Br | C—Cl | C—Br | C—H | CF3 | C—H | C—SO2CF3 | H | H | EtCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3787 | H | C—Cl | C—Cl | C—Br | C—H | CF3 | C—H | C—SO2CF3 | H | H | CF3CH2CO | H | 1 |
| 2-3788 | H | C—Br | C—Cl | C—Br | C—H | CF3 | C—H | C—F | H | H | EtCO | H | 1 |
| 2-3789 | H | C—Br | C—Cl | C—Br | C—H | CF3 | C—H | C—F | H | H | CF3CH2CO | H | 1 |
| 2-3790 | H | C—Br | C—Cl | C—Br | C—H | CF3 | C—H | C—I | H | H | EtCO | H | 1 |
| 2-3791 | H | C—Br | C—Cl | C—Br | C—H | CF3 | C—H | C—I | H | H | CF3CH2CO | H | 1 |
| 2-3792 | H | C—Br | C—Cl | C—Br | C—H | CF3 | C—H | C—NH2 | H | H | EtCO | H | 1 |
| 2-3793 | H | C—Br | C—Cl | C—Br | C—H | CF3 | C—H | C—NH2 | H | H | CF3CH2CO | H | 1 |
| 2-3794 | H | C—Br | C—Cl | C—Br | C—H | CF3 | C—H | C—NHAc | H | H | EtCO | H | 1 |
| 2-3795 | H | C—Br | C—Cl | C—Br | C—H | CF3 | C—H | C—NHAc | H | H | CF3CH2CO | H | 1 |
| 2-3796 | H | C—Br | C—Cl | C—Br | C—H | CF3 | C—H | C—NHCOCF3 | H | H | EtCO | H | 1 |
| 2-3797 | H | C—Br | C—Cl | C—Br | C—H | CF3 | C—H | C—NHCOCF3 | H | H | CF3CH2CO | H | 1 |
| 2-3798 | H | C—Br | C—Cl | C—Br | C—H | CF3 | C—H | C—CH2OAc | H | H | EtCO | H | 1 |
| 2-3799 | H | C—Br | C—Cl | C—Br | C—H | CF3 | C—H | C—CH2OAc | H | H | CF3CH2CO | H | 1 |
| 2-3800 | H | C—Cl | C—Cl | C—Br | C—H | CF3 | C—H | C—CF3 | H | H | H | H | 1 |
| 2-3801 | H | C—Cl | C—Cl | C—Br | C—H | CF3 | C—H | C—CF3 | H | H | CH3CO | H | 1 |
| 2-3802 | H | C—Cl | C—Cl | C—Br | C—H | CF3 | C—H | C—CF3 | H | H | EtCO | H | 1 |
| 2-3803 | H | C—Cl | C—Cl | C—Br | C—H | CF3 | C—H | C—CF3 | H | H | CF3CH2CO | H | 1 |
| 2-3804 | H | C—Cl | C—Cl | C—Br | C—H | CF3 | C—H | C—CF3 | H | H | cyclo-PrCO | H | 1 |
| 2-3805 | H | C—Cl | C—Cl | C—Br | C—H | CF3 | C—H | C—CF3 | H | H | cyclo-PrCH2CO | H | 1 |
| 2-3806 | H | C—Cl | C—Cl | C—Br | C—H | CF3 | C—H | C—CF3 | H | H | EtNHCO | H | 1 |
| 2-3807 | H | C—Cl | C—Cl | C—Br | C—H | CF3 | C—H | C—CF3 | H | H | CH3SCH2CO | H | 1 |
| 2-3808 | H | C—Cl | C—Cl | C—Br | C—H | CF3 | C—H | C—CF3 | H | H | CH3SOCH2CO | H | 1 |
| 2-3809 | H | C—Cl | C—Cl | C—Br | C—H | CF3 | C—H | C—CF3 | H | H | CH3SO2CH2CO | H | 1 |
| 2-3810 | H | C—Cl | C—Cl | C—Br | C—H | CF3 | C—H | C—CF3 | Me | H | EtCO | H | 1 |
| 2-3811 | H | C—Cl | C—Cl | C—Br | C—H | CF3 | C—H | C—CF3 | Me | H | CF3CH2CO | H | 1 |
| 2-3812 | H | C—Cl | C—Cl | C—Br | C—H | CF3 | N | C—CF3 | H | H | EtCO | H | 1 |
| 2-3813 | H | C—Cl | C—Cl | C—Br | C—H | CF3 | N | C—CF3 | H | H | CF3CH2CO | H | 1 |
| 2-3814 | H | C—Cl | C—Cl | C—Br | C—H | CF3 | C—H | C—Cl | H | H | H | H | 1 |
| 2-3815 | H | C—Cl | C—Cl | C—Br | C—H | CF3 | C—H | C—Cl | H | H | MeCO | H | 1 |
| 2-3816 | H | C—Cl | C—Cl | C—Br | C—H | CF3 | C—H | C—Cl | H | H | EtCO | H | 1 |
| 2-3817 | H | C—Cl | C—Cl | C—Br | C—H | CF3 | C—H | C—Cl | H | H | CF3CH2CO | H | 1 |
| 2-3818 | H | C—Cl | C—Cl | C—Br | C—H | CF3 | C—H | C—Cl | H | H | cyclo-PrCO | H | 1 |
| 2-3819 | H | C—Cl | C—Cl | C—Br | C—H | CF3 | C—H | C—Cl | H | H | cyclo-PrCH2CO | H | 1 |
| 2-3820 | H | C—Cl | C—Cl | C—Br | C—H | CF3 | C—H | C—Cl | H | H | CH3SCH2CO | H | 1 |
| 2-3821 | H | C—Cl | C—Cl | C—Br | C—H | CF3 | C—H | C—Cl | H | H | CH3SOCH2CO | H | 1 |
| 2-3822 | H | C—Cl | C—Cl | C—Br | C—H | CF3 | C—H | C—Cl | H | H | CH3SO2CH2CO | H | 1 |
| 2-3823 | H | C—Cl | C—Cl | C—Br | C—H | CF3 | C—H | C—Cl | H | H | EtNHCO | H | 1 |
| 2-3824 | H | C—Cl | C—Cl | C—Br | C—H | CF3 | C—H | C—Cl | Me | H | EtCO | H | 1 |
| 2-3825 | H | C—Cl | C—Cl | C—Br | C—H | CF3 | C—H | C—Cl | Me | H | CF3CH2CO | H | 1 |
| 2-3826 | H | C—Cl | C—Cl | C—Br | C—H | CF3 | N | C—Cl | H | H | EtCO | H | 1 |
| 2-3827 | H | C—Cl | C—Cl | C—Br | C—H | CF3 | N | C—Cl | H | H | CF3CH2CO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-3828 | H | C—Cl | C—Cl | C—Br | C—H | CF3 | C—H | C—Br | H | H | H | H | 1 |
| 2-3829 | H | C—Cl | C—Cl | C—Br | C—H | CF3 | C—H | C—Br | H | H | MeCO | H | 1 |
| 2-3830 | H | C—Cl | C—Cl | C—Br | C—H | CF3 | C—H | C—Br | H | H | EtCO | H | 1 |
| 2-3831 | H | C—Cl | C—Cl | C—Br | C—H | CF3 | C—H | C—Br | H | H | cyc-PrCO | H | 1 |
| 2-3832 | H | C—Cl | C—Cl | C—Br | C—H | CF3 | C—H | C—Br | H | H | CF3CH2CO | H | 1 |
| 2-3833 | H | C—Cl | C—Cl | C—Br | C—H | CF3 | C—H | C—Br | H | H | CH3SCH2CO | H | 1 |
| 2-3834 | H | C—Cl | C—Cl | C—Br | C—H | CF3 | C—H | C—Br | H | H | CH3SOCH2CO | H | 1 |
| 2-3835 | H | C—Cl | C—Cl | C—Br | C—H | CF3 | C—H | C—Br | H | H | CH3SO2CH2CO | H | 1 |
| 2-3836 | H | C—Cl | C—Cl | C—Br | C—H | CF3 | C—H | C—Br | Me | H | EtCO | H | 1 |
| 2-3837 | H | C—Cl | C—Cl | C—Br | C—H | CF3 | C—H | C—Br | Me | H | CF3CH2CO | H | 1 |
| 2-3838 | H | C—Cl | C—Cl | C—Br | C—H | CF3 | C—H | C—Br | H | H | EtCO | H | 1 |
| 2-3839 | H | C—Cl | C—Cl | C—Br | C—H | CF3 | N | C—Br | H | H | EtCO | H | 1 |
| 2-3840 | H | C—Cl | C—Cl | C—Br | C—H | CF3 | C—H | C—CN | H | H | CF3CH2CO | H | 1 |
| 2-3841 | H | C—Cl | C—Cl | C—Br | C—H | CF3 | C—H | C—CN | H | H | EtCO | H | 1 |
| 2-3842 | H | C—Cl | C—Cl | C—Br | C—H | CF3 | N | C—CN | H | H | EtCO | H | 1 |
| 2-3843 | H | C—Cl | C—Cl | C—Br | C—H | CF3 | C—H | C—Me | H | H | EtCO | H | 1 |
| 2-3844 | H | C—Cl | C—Cl | C—Br | C—H | CF3 | C—H | C—Me | H | H | MeCO | H | 1 |
| 2-3845 | H | C—Cl | C—Cl | C—Br | C—H | CF3 | C—H | C—Me | H | H | MeCO | H | 1 |
| 2-3846 | H | C—Cl | C—Cl | C—Br | C—H | CF3 | C—H | C—Me | H | H | EtCO | H | 1 |
| 2-3847 | H | C—Cl | C—Cl | C—Br | C—H | CF3 | C—H | C—Me | H | H | CF3CH2CO | H | 1 |
| 2-3848 | H | C—Cl | C—Cl | C—Br | C—H | CF3 | C—H | C—Me | H | H | cyclo-PrCO | H | 1 |
| 2-3849 | H | C—Cl | C—Cl | C—Br | C—H | CF3 | C—H | C—Me | H | H | CH3SCH2CO | H | 1 |
| 2-3850 | H | C—Cl | C—Cl | C—Br | C—H | CF3 | C—H | C—Me | H | H | EtNHCO | H | 1 |
| 2-3851 | H | C—Cl | C—Cl | C—Br | C—H | CF3 | N | C—Me | Me | H | EtCO | H | 1 |
| 2-3852 | H | C—Cl | C—Cl | C—Br | C—H | CF3 | C—H | C—NO2 | H | H | MeCO | H | 1 |
| 2-3853 | H | C—Cl | C—Cl | C—Br | C—H | CF3 | C—H | C—NO2 | H | H | MeCO | H | 1 |
| 2-3854 | H | C—Cl | C—Cl | C—Br | C—H | CF3 | C—H | C—NO2 | H | H | EtCO | H | 1 |
| 2-3855 | H | C—Cl | C—Cl | C—Br | C—H | CF3 | C—H | C—NO2 | H | H | CF3CH2CO | H | 1 |
| 2-3856 | H | C—Cl | C—Cl | C—Br | C—H | CF3 | C—H | C—NO2 | H | H | cyclo-PrCO | H | 1 |
| 2-3857 | H | C—Cl | C—Cl | C—Br | C—H | CF3 | C—H | C—NO2 | H | H | CH3SCH2CO | H | 1 |
| 2-3858 | H | C—Cl | C—Cl | C—Br | C—H | CF3 | C—H | C—NO2 | H | H | EtNHCO | H | 1 |
| 2-3859 | H | C—Cl | C—Cl | C—Br | C—H | CF3 | C—H | C—NO2 | Me | H | EtCO | H | 1 |
| 2-3860 | H | C—Cl | C—Cl | C—Br | C—H | CF3 | N | C—NO2 | H | H | EtCO | H | 1 |
| 2-3861 | H | C—Cl | C—Cl | C—Br | C—H | CF3 | C—H | C—SMe | H | H | MeCO | H | 1 |
| 2-3862 | H | C—Cl | C—Cl | C—Br | C—H | CF3 | C—H | C—SMe | H | H | MeCO | H | 1 |
| 2-3863 | H | C—Cl | C—Cl | C—Br | C—H | CF3 | C—H | C—SMe | H | H | EtCO | H | 1 |
| 2-3864 | H | C—Cl | C—Cl | C—Br | C—H | CF3 | C—H | C—SMe | H | H | CF3CH2CO | H | 1 |
| 2-3865 | H | C—Cl | C—Cl | C—Br | C—H | CF3 | C—H | C—SMe | H | H | cyclo-PrCO | H | 1 |
| 2-3866 | H | C—Cl | C—Cl | C—Br | C—H | CF3 | C—H | C—SMe | H | H | CH3SCH2CO | H | 1 |
| 2-3867 | H | C—Cl | C—Cl | C—Br | C—H | CF3 | C—H | C—SMe | H | H | EtNHCO | H | 1 |
| 2-3868 | H | C—Cl | C—Cl | C—Br | C—H | CF3 | C—H | C—SMe | Me | H | EtCO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-3869 | H | C—Cl | C—Cl | C—Br | C—H | CF3 | N | C—SMe | H | H | EtCO | H | 1 |
| 2-3870 | H | C—Cl | C—Cl | C—Br | C—H | CF3 | C—H | C—H | H | H | MeCO | H | 1 |
| 2-3871 | H | C—Cl | C—Cl | C—Br | C—H | CF3 | C—H | C—H | H | H | MeCO | H | 1 |
| 2-3872 | H | C—Cl | C—Cl | C—Br | C—H | CF3 | C—H | C—H | H | H | EtCO | H | 1 |
| 2-3873 | H | C—Cl | C—Cl | C—Br | C—H | CF3 | C—H | C—H | H | H | CF3CH2CO | H | 1 |
| 2-3874 | H | C—Cl | C—Cl | C—Br | C—H | CF3 | C—H | C—H | H | H | cyclo-PrCO | H | 1 |
| 2-3875 | H | C—Cl | C—Cl | C—Br | C—H | CF3 | C—H | C—H | H | H | CH3SCH2CO | H | 1 |
| 2-3876 | H | C—Cl | C—Cl | C—Br | C—H | CF3 | C—H | C—H | H | H | EtNHCO | H | 1 |
| 2-3877 | H | C—Cl | C—Cl | C—Br | C—H | CF3 | C—H | C—H | Me | H | EtCO | H | 1 |
| 2-3878 | H | C—Cl | C—Cl | C—Br | C—H | CF3 | N | C—H | H | H | EtCO | H | 1 |
| 2-3879 | H | C—Cl | C—Cl | C—Br | C—H | CF3 | C—H | C—SOMe | H | H | EtCO | H | 1 |
| 2-3880 | H | C—Cl | C—Cl | C—Br | C—H | CF3 | C—H | C—SOMe | H | H | EtCO | H | 1 |
| 2-3881 | H | C—Cl | C—Cl | C—Br | C—H | CF3 | C—H | C—SO2Me | H | H | EtCO | H | 1 |
| 2-3882 | H | C—Cl | C—Cl | C—Br | C—H | CF3 | C—H | C—SO2Me | H | H | CF3CH2CO | H | 1 |
| 2-3883 | H | C—Cl | C—Cl | C—Br | C—H | CF3 | C—H | C—SCF3 | H | H | EtCO | H | 1 |
| 2-3884 | H | C—Cl | C—Cl | C—Br | C—H | CF3 | C—H | C—SCF3 | H | H | EtCO | H | 1 |
| 2-3885 | H | C—Cl | C—Cl | C—Br | C—H | CF3 | C—H | C—SOCF3 | H | H | EtCO | H | 1 |
| 2-3886 | H | C—Cl | C—Cl | C—Br | C—H | CF3 | C—H | C—SOCF3 | H | H | CF3CH2CO | H | 1 |
| 2-3887 | H | C—Cl | C—Cl | C—Br | C—H | CF3 | C—H | C—SO2CF3 | H | H | EtCO | H | 1 |
| 2-3888 | H | C—Cl | C—Cl | C—Br | C—H | CF3 | C—H | C—SO2CF3 | H | H | EtCO | H | 1 |
| 2-3889 | H | C—Cl | C—Cl | C—Br | C—H | CF3 | C—H | C—F | H | H | EtCO | H | 1 |
| 2-3890 | H | C—Cl | C—Cl | C—Br | C—H | CF3 | C—H | C—F | H | H | CF3CH2CO | H | 1 |
| 2-3891 | H | C—Cl | C—Cl | C—Br | C—H | CF3 | C—H | C—I | H | H | EtCO | H | 1 |
| 2-3892 | H | C—Cl | C—Cl | C—Br | C—H | CF3 | C—H | C—I | H | H | CF3CH2CO | H | 1 |
| 2-3893 | H | C—Cl | C—Cl | C—Br | C—H | CF3 | C—H | C—NH2 | H | H | EtCO | H | 1 |
| 2-3894 | H | C—Cl | C—Cl | C—Br | C—H | CF3 | C—H | C—NH2 | H | H | CF3CH2CO | H | 1 |
| 2-3895 | H | C—Cl | C—Cl | C—Br | C—H | CF3 | C—H | C—NHAc | H | H | EtCO | H | 1 |
| 2-3896 | H | C—Cl | C—Cl | C—Br | C—H | CF3 | C—H | C—NHAc | H | H | CF3CH2CO | H | 1 |
| 2-3897 | H | C—Cl | C—Cl | C—Br | C—H | CF3 | C—H | C—NHCOCF3 | H | H | EtCO | H | 1 |
| 2-3898 | H | C—Cl | C—Cl | C—Br | C—H | CF3 | C—H | C—NHCOCF3 | H | H | CF3CH2CO | H | 1 |
| 2-3899 | H | C—Cl | C—Cl | C—Br | C—H | CF3 | C—H | C—CH2OAc | H | H | EtCO | H | 1 |
| 2-3900 | H | C—Cl | C—Cl | C—Br | C—H | CF3 | C—H | C—CH2OAc | H | H | CF3CH2CO | H | 1 |
| 2-3901 | H | C—Cl | C—Cl | C—H | C—H | CF3 | C—H | C—CF3 | H | H | H | H | 1 |
| 2-3902 | H | C—Cl | C—CF3 | C—H | C—H | CF3 | C—H | C—CF3 | H | H | CH3CO | H | 1 |
| 2-3903 | H | C—Cl | C—CF3 | C—H | C—H | CF3 | C—H | C—CF3 | H | H | EtCO | H | 1 |
| 2-3904 | H | C—Cl | C—CF3 | C—H | C—H | CF3 | C—H | C—CF3 | H | H | CF3CH2CO | H | 1 |
| 2-3905 | H | C—Cl | C—CF3 | C—H | C—H | CF3 | C—H | C—CF3 | H | H | cyclo-PrCO | H | 1 |
| 2-3906 | H | C—Cl | C—CF3 | C—H | C—H | CF3 | C—H | C—CF3 | H | H | cyclo-PrCH2CO | H | 1 |
| 2-3907 | H | C—Cl | C—CF3 | C—H | C—H | CF3 | C—H | C—CF3 | H | H | EtNHCO | H | 1 |
| 2-3908 | H | C—Cl | C—CF3 | C—H | C—H | CF3 | C—H | C—CF3 | H | H | CH3SCH2CO | H | 1 |
| 2-3909 | H | C—Cl | C—CF3 | C—H | C—H | CF3 | C—H | C—CF3 | H | H | CH3SOCH2CO | H | 1 |

TABLE 2-1-continued

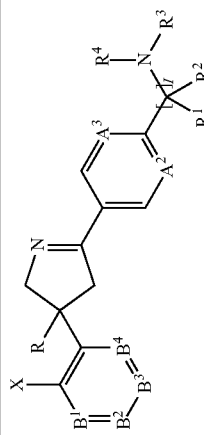

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3910 | H | C—Cl | C—CF3 | C—H | C—H | CF3 | C—H | C—Cl | H | H | CH3SO2CH2CO | H | 1 |
| 2-3911 | H | C—Cl | C—CF3 | C—H | C—H | CF3 | C—H | C—Cl | Me | H | EtCO | H | 1 |
| 2-3912 | H | C—Cl | C—CF3 | C—H | C—H | CF3 | C—H | C—Cl | Me | H | CF3CH2CO | H | 1 |
| 2-3913 | H | C—Cl | C—CF3 | C—H | C—H | CF3 | N | C—Cl | H | H | EtCO | H | 1 |
| 2-3914 | H | C—Cl | C—CF3 | C—H | C—H | CF3 | C—H | C—Cl | H | H | CF3CH2CO | H | 1 |
| 2-3915 | H | C—Cl | C—CF3 | C—H | C—H | CF3 | C—H | C—Cl | H | H | H | H | 1 |
| 2-3916 | H | C—Cl | C—CF3 | C—H | C—H | CF3 | C—H | C—Cl | H | H | MeCO | H | 1 |
| 2-3917 | H | C—Cl | C—CF3 | C—H | C—H | CF3 | C—H | C—Cl | H | H | EtCO | H | 1 |
| 2-3918 | H | C—Cl | C—CF3 | C—H | C—H | CF3 | C—H | C—Cl | H | H | CF3CH2CO | H | 1 |
| 2-3919 | H | C—Cl | C—CF3 | C—H | C—H | CF3 | C—H | C—Cl | H | H | cyclo-PrCO | H | 1 |
| 2-3920 | H | C—Cl | C—CF3 | C—H | C—H | CF3 | C—H | C—Cl | H | H | cyclo-PrCH2CO | H | 1 |
| 2-3921 | H | C—Cl | C—CF3 | C—H | C—H | CF3 | C—H | C—Cl | H | H | CH3SCH2CO | H | 1 |
| 2-3922 | H | C—Cl | C—CF3 | C—H | C—H | CF3 | C—H | C—Cl | H | H | CH3SOCH2CO | H | 1 |
| 2-3923 | H | C—Cl | C—CF3 | C—H | C—H | CF3 | C—H | C—Cl | H | H | CH3SO2CH2CO | H | 1 |
| 2-3924 | H | C—Cl | C—CF3 | C—H | C—H | CF3 | C—H | C—Cl | H | H | EtNHCO | H | 1 |
| 2-3925 | H | C—Cl | C—CF3 | C—H | C—H | CF3 | C—H | C—Cl | Me | H | EtCO | H | 1 |
| 2-3926 | H | C—Cl | C—CF3 | C—H | C—H | CF3 | C—H | C—Cl | Me | H | CF3CH2CO | H | 1 |
| 2-3927 | H | C—Cl | C—CF3 | C—H | C—H | CF3 | N | C—Cl | H | H | EtCO | H | 1 |
| 2-3928 | H | C—Cl | C—CF3 | C—H | C—H | CF3 | N | C—Cl | H | H | CF3CH2CO | H | 1 |
| 2-3929 | H | C—Cl | C—CF3 | C—H | C—H | CF3 | C—H | C—Br | H | H | H | H | 1 |
| 2-3930 | H | C—Cl | C—CF3 | C—H | C—H | CF3 | C—H | C—Br | H | H | MeCO | H | 1 |
| 2-3931 | H | C—Cl | C—CF3 | C—H | C—H | CF3 | C—H | C—Br | H | H | EtCO | H | 1 |
| 2-3932 | H | C—Cl | C—CF3 | C—H | C—H | CF3 | C—H | C—Br | H | H | CF3CH2CO | H | 1 |
| 2-3933 | H | C—Cl | C—CF3 | C—H | C—H | CF3 | C—H | C—Br | H | H | cyc-PrCO | H | 1 |
| 2-3934 | H | C—Cl | C—CF3 | C—H | C—H | CF3 | C—H | C—Br | H | H | CH3SCH2CO | H | 1 |
| 2-3935 | H | C—Cl | C—CF3 | C—H | C—H | CF3 | C—H | C—Br | H | H | CH3SOCH2CO | H | 1 |
| 2-3936 | H | C—Cl | C—CF3 | C—H | C—H | CF3 | C—H | C—Br | H | H | CH3SO2CH2CO | H | 1 |
| 2-3937 | H | C—Cl | C—CF3 | C—H | C—H | CF3 | C—H | C—Br | Me | H | EtCO | H | 1 |
| 2-3938 | H | C—Cl | C—CF3 | C—H | C—H | CF3 | C—H | C—Br | H | H | EtCO | H | 1 |
| 2-3939 | H | C—Cl | C—CF3 | C—H | C—H | CF3 | C—H | C—Br | H | H | CF3CH2CO | H | 1 |
| 2-3940 | H | C—Cl | C—CF3 | C—H | C—H | CF3 | N | C—Br | H | H | EtCO | H | 1 |
| 2-3941 | H | C—Cl | C—CF3 | C—H | C—H | CF3 | N | C—CN | H | H | CF3CH2CO | H | 1 |
| 2-3942 | H | C—Cl | C—CF3 | C—H | C—H | CF3 | C—H | C—CN | H | H | EtCO | H | 1 |
| 2-3943 | H | C—Cl | C—CF3 | C—H | C—H | CF3 | N | C—CN | H | H | EtCO | H | 1 |
| 2-3944 | H | C—Cl | C—CF3 | C—H | C—H | CF3 | C—H | C—Me | H | H | MeCO | H | 1 |
| 2-3945 | H | C—Cl | C—CF3 | C—H | C—H | CF3 | C—H | C—Me | H | H | MeCO | H | 1 |
| 2-3946 | H | C—Cl | C—CF3 | C—H | C—H | CF3 | C—H | C—Me | H | H | MeCO | H | 1 |
| 2-3947 | H | C—Cl | C—CF3 | C—H | C—H | CF3 | C—H | C—Me | H | H | CF3CH2CO | H | 1 |
| 2-3948 | H | C—Cl | C—CF3 | C—H | C—H | CF3 | C—H | C—Me | H | H | cyclo-PrCO | H | 1 |
| 2-3949 | H | C—Cl | C—CF3 | C—H | C—H | CF3 | C—H | C—Me | H | H | CH3SCH2CO | H | 1 |
| 2-3950 | H | C—Cl | C—CF3 | C—H | C—H | CF3 | C—H | C—Me | H | H | EtNHCO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-3951 | H | C—Cl | C—CF3 | C—H | C—H | CF3 | C—H | C—Me | Me | H | EtCO | H | 1 |
| 2-3952 | H | C—Cl | C—CF3 | C—H | C—H | CF3 | N | C—Me | H | H | EtCO | H | 1 |
| 2-3953 | H | C—Cl | C—CF3 | C—H | C—H | CF3 | C—H | C—NO2 | H | H | MeCO | H | 1 |
| 2-3954 | H | C—Cl | C—CF3 | C—H | C—H | CF3 | C—H | C—NO2 | H | H | MeCO | H | 1 |
| 2-3955 | H | C—Cl | C—CF3 | C—H | C—H | CF3 | C—H | C—NO2 | H | H | EtCO | H | 1 |
| 2-3956 | H | C—Cl | C—CF3 | C—H | C—H | CF3 | C—H | C—NO2 | H | H | CF3CH2CO | H | 1 |
| 2-3957 | H | C—Cl | C—CF3 | C—H | C—H | CF3 | C—H | C—NO2 | H | H | cyclo-PrCO | H | 1 |
| 2-3958 | H | C—Cl | C—CF3 | C—H | C—H | CF3 | C—H | C—NO2 | H | H | CH3SCH2CO | H | 1 |
| 2-3959 | H | C—Cl | C—CF3 | C—H | C—H | CF3 | C—H | C—NO2 | H | H | EtNHCO | H | 1 |
| 2-3960 | H | C—Cl | C—CF3 | C—H | C—H | CF3 | N | C—NO2 | H | H | EtCO | H | 1 |
| 2-3961 | H | C—Cl | C—CF3 | C—H | C—H | CF3 | C—H | C—SMe | Me | H | EtCO | H | 1 |
| 2-3962 | H | C—Cl | C—CF3 | C—H | C—H | CF3 | C—H | C—SMe | H | H | MeCO | H | 1 |
| 2-3963 | H | C—Cl | C—CF3 | C—H | C—H | CF3 | C—H | C—SMe | H | H | MeCO | H | 1 |
| 2-3964 | H | C—Cl | C—CF3 | C—H | C—H | CF3 | C—H | C—SMe | H | H | EtCO | H | 1 |
| 2-3965 | H | C—Cl | C—CF3 | C—H | C—H | CF3 | C—H | C—SMe | H | H | CF3CH2CO | H | 1 |
| 2-3966 | H | C—Cl | C—CF3 | C—H | C—H | CF3 | C—H | C—SMe | H | H | cyclo-PrCO | H | 1 |
| 2-3967 | H | C—Cl | C—CF3 | C—H | C—H | CF3 | C—H | C—SMe | H | H | CH3SCH2CO | H | 1 |
| 2-3968 | H | C—Cl | C—CF3 | C—H | C—H | CF3 | C—H | C—SMe | H | H | EtNHCO | H | 1 |
| 2-3969 | H | C—Cl | C—CF3 | C—H | C—H | CF3 | N | C—SMe | H | H | EtCO | H | 1 |
| 2-3970 | H | C—Cl | C—CF3 | C—H | C—H | CF3 | C—H | C—H | Me | H | EtCO | H | 1 |
| 2-3971 | H | C—Cl | C—CF3 | C—H | C—H | CF3 | C—H | C—H | H | H | MeCO | H | 1 |
| 2-3972 | H | C—Cl | C—CF3 | C—H | C—H | CF3 | C—H | C—H | H | H | MeCO | H | 1 |
| 2-3973 | H | C—Cl | C—CF3 | C—H | C—H | CF3 | C—H | C—H | H | H | EtCO | H | 1 |
| 2-3974 | H | C—Cl | C—CF3 | C—H | C—H | CF3 | C—H | C—H | H | H | CF3CH2CO | H | 1 |
| 2-3975 | H | C—Cl | C—CF3 | C—H | C—H | CF3 | C—H | C—H | H | H | cyclo-PrCO | H | 1 |
| 2-3976 | H | C—Cl | C—CF3 | C—H | C—H | CF3 | C—H | C—H | H | H | CH3SCH2CO | H | 1 |
| 2-3977 | H | C—Cl | C—CF3 | C—H | C—H | CF3 | C—H | C—H | H | H | EtNHCO | H | 1 |
| 2-3978 | H | C—Cl | C—CF3 | C—H | C—H | CF3 | N | C—H | Me | H | EtCO | H | 1 |
| 2-3979 | H | C—Cl | C—CF3 | C—H | C—H | CF3 | C—H | C—SOMe | H | H | EtCO | H | 1 |
| 2-3980 | H | C—Cl | C—CF3 | C—H | C—H | CF3 | C—H | C—SOMe | H | H | EtCO | H | 1 |
| 2-3981 | H | C—Cl | C—CF3 | C—H | C—H | CF3 | C—H | C—SO2Me | H | H | EtCO | H | 1 |
| 2-3982 | H | C—Cl | C—CF3 | C—H | C—H | CF3 | C—H | C—SO2Me | H | H | CF3CH2CO | H | 1 |
| 2-3983 | H | C—Cl | C—CF3 | C—H | C—H | CF3 | C—H | C—SCF3 | H | H | EtCO | H | 1 |
| 2-3984 | H | C—Cl | C—CF3 | C—H | C—H | CF3 | C—H | C—SCF3 | H | H | CF3CH2CO | H | 1 |
| 2-3985 | H | C—Cl | C—CF3 | C—H | C—H | CF3 | C—H | C—SOCF3 | H | H | EtCO | H | 1 |
| 2-3986 | H | C—Cl | C—CF3 | C—H | C—H | CF3 | C—H | C—SOCF3 | H | H | CF3CH2CO | H | 1 |
| 2-3987 | H | C—Cl | C—CF3 | C—H | C—H | CF3 | C—H | C—SO2CF3 | H | H | EtCO | H | 1 |
| 2-3988 | H | C—Cl | C—CF3 | C—H | C—H | CF3 | C—H | C—SO2CF3 | H | H | CF3CH2CO | H | 1 |
| 2-3989 | H | C—Cl | C—CF3 | C—H | C—H | CF3 | C—H | C—F | H | H | EtCO | H | 1 |
| 2-3990 | H | C—Cl | C—CF3 | C—H | C—H | CF3 | C—H | C—F | H | H | CF3CH2CO | H | 1 |
| 2-3991 | H | C—Cl | C—CF3 | C—H | C—H | CF3 | C—H | C—F | H | H | CF3CH2CO | H | 1 |

TABLE 2-1-continued

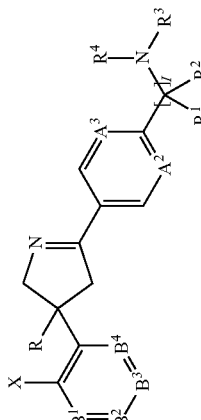

| Example No. | X | B¹ | B² | B³ | B⁴ | R | A² | A³ | | R¹ | R² | R⁴ | R³ | I |
|---|---|---|---|---|---|---|---|---|---|---|---|---|---|---|
| 2-3992 | H | C—Cl | C—CF3 | C—H | C—H | CF3 | C—H | C—I | | H | H | EtCO | H | 1 |
| 2-3993 | H | C—Cl | C—CF3 | C—H | C—H | CF3 | C—H | C—I | | H | H | CF3CH2CO | H | 1 |
| 2-3994 | H | C—Cl | C—CF3 | C—H | C—H | CF3 | C—H | C—NH2 | | H | H | EtCO | H | 1 |
| 2-3995 | H | C—Cl | C—CF3 | C—H | C—H | CF3 | C—H | C—NH2 | | H | H | CF3CH2CO | H | 1 |
| 2-3996 | H | C—Cl | C—CF3 | C—H | C—H | CF3 | C—H | C—NHAc | | H | H | EtCO | H | 1 |
| 2-3997 | H | C—Cl | C—CF3 | C—H | C—H | CF3 | C—H | C—NHAc | | H | H | CF3CH2CO | H | 1 |
| 2-3998 | H | C—Cl | C—CF3 | C—H | C—H | CF3 | C—H | C—NHCOCF3 | | H | H | EtCO | H | 1 |
| 2-3999 | H | C—Cl | C—CF3 | C—H | C—H | CF3 | C—H | C—NHCOCF3 | | H | H | CF3CH2CO | H | 1 |
| 2-4000 | H | C—Cl | C—CF3 | C—H | C—H | CF3 | C—H | C—CH2OAc | | H | H | EtCO | H | 1 |
| 2-4001 | H | C—Cl | C—CF3 | C—H | C—H | CF3 | C—H | C—CH2OAc | | H | H | CF3CH2CO | H | 1 |
| 2-4103 | F | C—Cl | C—F | C—Cl | C—H | CF3 | C—H | C—CF3 | | H | H | H | H | 1 |
| 2-4104 | F | C—Cl | C—F | C—Cl | C—H | CF3 | C—H | C—CF3 | | H | H | CH3CO | H | 1 |
| 2-4105 | F | C—Cl | C—F | C—Cl | C—H | CF3 | C—H | C—CF3 | | H | H | EtCO | H | 1 |
| 2-4106 | F | C—Cl | C—F | C—Cl | C—H | CF3 | C—H | C—CF3 | | H | H | CF3CH2CO | H | 1 |
| 2-4107 | F | C—Cl | C—F | C—Cl | C—H | CF3 | C—H | C—CF3 | | H | H | cyclo-PrCO | H | 1 |
| 2-4108 | F | C—Cl | C—F | C—Cl | C—H | CF3 | C—H | C—CF3 | | H | H | EtNHCO | H | 1 |
| 2-4109 | F | C—Cl | C—F | C—Cl | C—H | CF3 | C—H | C—CF3 | | H | H | CH3SCH2CO | H | 1 |
| 2-4110 | F | C—Cl | C—F | C—Cl | C—H | CF3 | C—H | C—CF3 | | H | H | CH3SOCH2CO | H | 1 |
| 2-4111 | F | C—Cl | C—F | C—Cl | C—H | CF3 | C—H | C—CF3 | | H | H | CH3SO2CH2CO | H | 1 |
| 2-4112 | F | C—Cl | C—F | C—Cl | C—H | CF3 | C—H | C—CF3 | | H | H | EtCO | H | 1 |
| 2-4113 | F | C—Cl | C—F | C—Cl | C—H | CF3 | C—H | C—CF3 | | Me | H | CF3CH2CO | H | 1 |
| 2-4114 | F | C—Cl | C—F | C—Cl | C—H | CF3 | N | C—CF3 | | Me | H | EtCO | H | 1 |
| 2-4115 | F | C—Cl | C—F | C—Cl | C—H | CF3 | N | C—CF3 | | H | H | CF3CH2CO | H | 1 |
| 2-4116 | F | C—Cl | C—F | C—Cl | C—H | CF3 | C—H | C—Cl | | H | H | H | H | 1 |
| 2-4117 | F | C—Cl | C—F | C—Cl | C—H | CF3 | C—H | C—Cl | | H | H | MeCO | H | 1 |
| 2-4118 | F | C—Cl | C—F | C—Cl | C—H | CF3 | C—H | C—Cl | | H | H | EtCO | H | 1 |
| 2-4119 | F | C—Cl | C—F | C—Cl | C—H | CF3 | C—H | C—Cl | | H | H | CF3CH2CO | H | 1 |
| 2-4120 | F | C—Cl | C—F | C—Cl | C—H | CF3 | C—H | C—Cl | | H | H | cyclo-PrCO | H | 1 |
| 2-4121 | F | C—Cl | C—F | C—Cl | C—H | CF3 | C—H | C—Cl | | H | H | cyclo-PrCH2CO | H | 1 |
| 2-4122 | F | C—Cl | C—F | C—Cl | C—H | CF3 | C—H | C—Cl | | H | H | CH3SCH2CO | H | 1 |
| 2-4123 | F | C—Cl | C—F | C—Cl | C—H | CF3 | C—H | C—Cl | | H | H | CH3SOCH2CO | H | 1 |
| 2-4124 | F | C—Cl | C—F | C—Cl | C—H | CF3 | C—H | C—Cl | | H | H | CH3SO2CH2CO | H | 1 |
| 2-4125 | F | C—Cl | C—F | C—Cl | C—H | CF3 | C—H | C—Cl | | H | H | EtNHCO | H | 1 |
| 2-4126 | F | C—Cl | C—F | C—Cl | C—H | CF3 | C—H | C—Cl | | Me | H | EtCO | H | 1 |
| 2-4127 | F | C—Cl | C—F | C—Cl | C—H | CF3 | N | C—Cl | | Me | H | EtCO | H | 1 |
| 2-4128 | F | C—Cl | C—F | C—Cl | C—H | CF3 | N | C—Cl | | H | H | CF3CH2CO | H | 1 |
| 2-4129 | F | C—Cl | C—F | C—Cl | C—H | CF3 | C—H | C—Br | | H | H | CF3CH2CO | H | 1 |
| 2-4131 | F | C—Cl | C—F | C—Cl | C—H | CF3 | C—H | C—Br | | H | H | H | H | 1 |
| 2-4132 | F | C—Cl | C—F | C—Cl | C—H | CF3 | C—H | C—Br | | H | H | MeCO | H | 1 |
| 2-4133 | F | C—Cl | C—F | C—Cl | C—H | CF3 | C—H | C—Br | | H | H | EtCO | H | 1 |

TABLE 2-1-continued

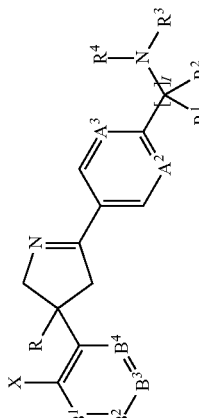

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4134 | F | C—Cl | C—F | C—Cl | C—H | CF3 | C—H | C—Br | H | H | cyc-PrCO | H | 1 |
| 2-4135 | F | C—Cl | C—F | C—Cl | C—H | CF3 | C—H | C—Br | H | H | CF3CH2CO | H | 1 |
| 2-4136 | F | C—Cl | C—F | C—Cl | C—H | CF3 | C—H | C—Br | H | H | CH3SCH2CO | H | 1 |
| 2-4137 | F | C—Cl | C—F | C—Cl | C—H | CF3 | C—H | C—Br | H | H | CH3SOCH2CO | H | 1 |
| 2-4138 | F | C—Cl | C—F | C—Cl | C—H | CF3 | C—H | C—Br | H | H | CH3SO2CH2CO | H | 1 |
| 2-4139 | F | C—Cl | C—F | C—Cl | C—H | CF3 | C—H | C—Br | Me | H | EtCO | H | 1 |
| 2-4140 | F | C—Cl | C—F | C—Cl | C—H | CF3 | C—H | C—Br | Me | H | CF3CH2CO | H | 1 |
| 2-4141 | F | C—Cl | C—F | C—Cl | C—H | CF3 | N | C—Br | H | H | EtCO | H | 1 |
| 2-4142 | F | C—Cl | C—F | C—Cl | C—H | CF3 | C—H | C—CN | H | H | CF3CH2CO | H | 1 |
| 2-4143 | F | C—Cl | C—F | C—Cl | C—H | CF3 | C—H | C—CN | H | H | EtCO | H | 1 |
| 2-4144 | F | C—Cl | C—F | C—Cl | C—H | CF3 | N | C—CN | H | H | CF3CH2CO | H | 1 |
| 2-4145 | F | C—Cl | C—F | C—Cl | C—H | CF3 | C—H | C—Me | H | H | EtCO | H | 1 |
| 2-4146 | F | C—Cl | C—F | C—Cl | C—H | CF3 | C—H | C—Me | H | H | MeCO | H | 1 |
| 2-4147 | F | C—Cl | C—F | C—Cl | C—H | CF3 | C—H | C—Me | H | H | MeCO | H | 1 |
| 2-4148 | F | C—Cl | C—F | C—Cl | C—H | CF3 | C—H | C—Me | H | H | EtCO | H | 1 |
| 2-4149 | F | C—Cl | C—F | C—Cl | C—H | CF3 | C—H | C—Me | H | H | CF3CH2CO | H | 1 |
| 2-4150 | F | C—Cl | C—F | C—Cl | C—H | CF3 | C—H | C—Me | H | H | cyclo-PrCO | H | 1 |
| 2-4151 | F | C—Cl | C—F | C—Cl | C—H | CF3 | C—H | C—Me | H | H | CH3SCH2CO | H | 1 |
| 2-4152 | F | C—Cl | C—F | C—Cl | C—H | CF3 | C—H | C—Me | H | H | EtNHCO | H | 1 |
| 2-4153 | F | C—Cl | C—F | C—Cl | C—H | CF3 | C—H | C—Me | Me | H | EtCO | H | 1 |
| 2-4154 | F | C—Cl | C—F | C—Cl | C—H | CF3 | N | C—Me | H | H | EtCO | H | 1 |
| 2-4155 | F | C—Cl | C—F | C—Cl | C—H | CF3 | C—H | C—NO2 | H | H | MeCO | H | 1 |
| 2-4156 | F | C—Cl | C—F | C—Cl | C—H | CF3 | C—H | C—NO2 | H | H | MeCO | H | 1 |
| 2-4157 | F | C—Cl | C—F | C—Cl | C—H | CF3 | C—H | C—NO2 | H | H | EtCO | H | 1 |
| 2-4158 | F | C—Cl | C—F | C—Cl | C—H | CF3 | C—H | C—NO2 | H | H | CF3CH2CO | H | 1 |
| 2-4159 | F | C—Cl | C—F | C—Cl | C—H | CF3 | C—H | C—NO2 | H | H | cyclo-PrCO | H | 1 |
| 2-4160 | F | C—Cl | C—F | C—Cl | C—H | CF3 | C—H | C—NO2 | H | H | CH3SCH2CO | H | 1 |
| 2-4161 | F | C—Cl | C—F | C—Cl | C—H | CF3 | C—H | C—NO2 | H | H | EtNHCO | H | 1 |
| 2-4162 | F | C—Cl | C—F | C—Cl | C—H | CF3 | C—H | C—NO2 | Me | H | EtCO | H | 1 |
| 2-4163 | F | C—Cl | C—F | C—Cl | C—H | CF3 | N | C—NO2 | H | H | EtCO | H | 1 |
| 2-4164 | F | C—Cl | C—F | C—Cl | C—H | CF3 | C—H | C—SMe | H | H | MeCO | H | 1 |
| 2-4165 | F | C—Cl | C—F | C—Cl | C—H | CF3 | C—H | C—SMe | H | H | MeCO | H | 1 |
| 2-4166 | F | C—Cl | C—F | C—Cl | C—H | CF3 | C—H | C—SMe | H | H | EtCO | H | 1 |
| 2-4167 | F | C—Cl | C—F | C—Cl | C—H | CF3 | C—H | C—SMe | H | H | CF3CH2CO | H | 1 |
| 2-4168 | F | C—Cl | C—F | C—Cl | C—H | CF3 | C—H | C—SMe | H | H | cyclo-PrCO | H | 1 |
| 2-4169 | F | C—Cl | C—F | C—Cl | C—H | CF3 | C—H | C—SMe | H | H | CH3SCH2CO | H | 1 |
| 2-4170 | F | C—Cl | C—F | C—Cl | C—H | CF3 | C—H | C—SMe | H | H | EtNHCO | H | 1 |
| 2-4171 | F | C—Cl | C—F | C—Cl | C—H | CF3 | C—H | C—SMe | Me | H | EtCO | H | 1 |
| 2-4172 | F | C—Cl | C—F | C—Cl | C—H | CF3 | N | C—SMe | H | H | EtCO | H | 1 |
| 2-4173 | F | C—Cl | C—F | C—Cl | C—H | CF3 | C—H | C—H | H | H | MeCO | H | 1 |
| 2-4174 | F | C—Cl | C—F | C—Cl | C—H | CF3 | C—H | C—H | H | H | MeCO | H | 1 |

TABLE 2-1-continued

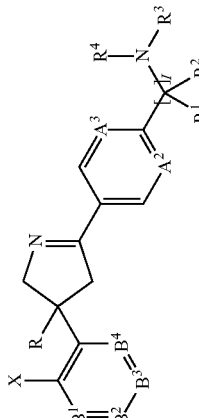

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4175 | F | C—Cl | C—F | C—Cl | C—H | CF3 | C—H | C—H | H | H | EtCO | H | 1 |
| 2-4176 | F | C—Cl | C—F | C—Cl | C—H | CF3 | C—H | C—H | H | H | CF3CH2CO | H | 1 |
| 2-4177 | F | C—Cl | C—F | C—Cl | C—H | CF3 | C—H | C—H | H | H | cyclo-PrCO | H | 1 |
| 2-4178 | F | C—Cl | C—F | C—Cl | C—H | CF3 | C—H | C—H | H | H | CH3SCH2CO | H | 1 |
| 2-4179 | F | C—Cl | C—F | C—Cl | C—H | CF3 | C—H | C—H | H | H | EtNHCO | H | 1 |
| 2-4180 | F | C—Cl | C—F | C—Cl | C—H | CF3 | C—H | C—H | Me | H | EtCO | H | 1 |
| 2-4181 | F | C—Cl | C—F | C—Cl | C—H | CF3 | N | C—H | H | H | EtCO | H | 1 |
| 2-4182 | F | C—Cl | C—F | C—Cl | C—H | CF3 | C—H | C—SOMe | H | H | EtCO | H | 1 |
| 2-4183 | F | C—Cl | C—F | C—Cl | C—H | CF3 | C—H | C—SOMe | H | H | CF3CH2CO | H | 1 |
| 2-4184 | F | C—Cl | C—F | C—Cl | C—H | CF3 | C—H | C—SO2Me | H | H | EtCO | H | 1 |
| 2-4185 | F | C—Cl | C—F | C—Cl | C—H | CF3 | C—H | C—SO2Me | H | H | CF3CH2CO | H | 1 |
| 2-4186 | F | C—Cl | C—F | C—Cl | C—H | CF3 | C—H | C—SCF3 | H | H | EtCO | H | 1 |
| 2-4187 | F | C—Cl | C—F | C—Cl | C—H | CF3 | C—H | C—SCF3 | H | H | CF3CH2CO | H | 1 |
| 2-4188 | F | C—Cl | C—F | C—Cl | C—H | CF3 | C—H | C—SOCF3 | H | H | EtCO | H | 1 |
| 2-4189 | F | C—Cl | C—F | C—Cl | C—H | CF3 | C—H | C—SOCF3 | H | H | CF3CH2CO | H | 1 |
| 2-4190 | F | C—Cl | C—F | C—Cl | C—H | CF3 | C—H | C—SO2CF3 | H | H | EtCO | H | 1 |
| 2-4191 | F | C—Cl | C—F | C—Cl | C—H | CF3 | C—H | C—SO2CF3 | H | H | CF3CH2CO | H | 1 |
| 2-4192 | F | C—Cl | C—F | C—Cl | C—H | CF3 | C—H | C—F | H | H | EtCO | H | 1 |
| 2-4193 | F | C—Cl | C—F | C—Cl | C—H | CF3 | C—H | C—F | H | H | CF3CH2CO | H | 1 |
| 2-4194 | F | C—Cl | C—F | C—Cl | C—H | CF3 | C—H | C—I | H | H | EtCO | H | 1 |
| 2-4195 | F | C—Cl | C—F | C—Cl | C—H | CF3 | C—H | C—I | H | H | CF3CH2CO | H | 1 |
| 2-4196 | F | C—Cl | C—F | C—Cl | C—H | CF3 | C—H | C—NH2 | H | H | EtCO | H | 1 |
| 2-4197 | F | C—Cl | C—F | C—Cl | C—H | CF3 | C—H | C—NH2 | H | H | CF3CH2CO | H | 1 |
| 2-4198 | F | C—Cl | C—F | C—Cl | C—H | CF3 | C—H | C—NHAc | H | H | EtCO | H | 1 |
| 2-4199 | F | C—Cl | C—F | C—Cl | C—H | CF3 | C—H | C—NHAc | H | H | CF3CH2CO | H | 1 |
| 2-4200 | F | C—Cl | C—F | C—Cl | C—H | CF3 | C—H | C—NHCOCF3 | H | H | EtCO | H | 1 |
| 2-4201 | F | C—Cl | C—F | C—Cl | C—H | CF3 | C—H | C—NHCOCF3 | H | H | CF3CH2CO | H | 1 |
| 2-4202 | F | C—Cl | C—F | C—Cl | C—H | CF3 | C—H | C—CH2OAc | H | H | EtCO | H | 1 |
| 2-4203 | F | C—Cl | C—F | C—Cl | C—H | CF3 | C—H | C—CH2OAc | H | H | CF3CH2CO | H | 1 |
| 2-4406 | H | C—Cl | —OCH2O— | | C—H | CF3 | C—H | C—CF3 | H | H | H | H | 1 |
| 2-4407 | H | C—Cl | —OCH2O— | | C—H | CF3 | C—H | C—CF3 | H | H | CH3CO | H | 1 |
| 2-4408 | H | C—Cl | —OCH2O— | | C—H | CF3 | C—H | C—CF3 | H | H | EtCO | H | 1 |
| 2-4409 | H | C—Cl | —OCH2O— | | C—H | CF3 | C—H | C—CF3 | H | H | CF3CH2CO | H | 1 |
| 2-4410 | H | C—Cl | —OCH2O— | | C—H | CF3 | C—H | C—CF3 | H | H | cyclo-PrCO | H | 1 |
| 2-4411 | H | C—Cl | —OCH2O— | | C—H | CF3 | C—H | C—CF3 | H | H | cyclo-PrCH2CO | H | 1 |
| 2-4412 | H | C—Cl | —OCH2O— | | C—H | CF3 | C—H | C—CF3 | H | H | EtNHCO | H | 1 |
| 2-4413 | H | C—Cl | —OCH2O— | | C—H | CF3 | C—H | C—CF3 | H | H | CH3SCH2CO | H | 1 |
| 2-4414 | H | C—Cl | —OCH2O— | | C—H | CF3 | C—H | C—CF3 | H | H | CH3SOCH2CO | H | 1 |
| 2-4415 | H | C—Cl | —OCH2O— | | C—H | CF3 | C—H | C—CF3 | H | H | CH3SO2CH2CO | H | 1 |
| 2-4416 | H | C—Cl | —OCH2O— | | C—H | CF3 | C—H | C—CF3 | Me | H | EtCO | H | 1 |
| 2-4417 | H | C—Cl | —OCH2O— | | C—H | CF3 | C—H | C—CF3 | Me | H | CF3CH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4418 | H | C—Cl | —OCH2O— | | C—H | CF3 | N | C—CF3 | H | H | EtCO | H | 1 |
| 2-4419 | H | C—Cl | —OCH2O— | | C—H | CF3 | N | C—CF3 | H | H | CF3CH2CO | H | 1 |
| 2-4420 | H | C—Cl | —OCH2O— | | C—H | CF3 | C—H | C—Cl | H | H | H | H | 1 |
| 2-4421 | H | C—Cl | —OCH2O— | | C—H | CF3 | C—H | C—Cl | H | H | MeCO | H | 1 |
| 2-4422 | H | C—Cl | —OCH2O— | | C—H | CF3 | C—H | C—Cl | H | H | EtCO | H | 1 |
| 2-4423 | H | C—Cl | —OCH2O— | | C—H | CF3 | C—H | C—Cl | H | H | CF3CH2CO | H | 1 |
| 2-4424 | H | C—Cl | —OCH2O— | | C—H | CF3 | C—H | C—Cl | H | H | cyclo-PrCO | H | 1 |
| 2-4425 | H | C—Cl | —OCH2O— | | C—H | CF3 | C—H | C—Cl | H | H | cyclo-PrCH2CO | H | 1 |
| 2-4426 | H | C—Cl | —OCH2O— | | C—H | CF3 | C—H | C—Cl | H | H | CH3SCH2CO | H | 1 |
| 2-4427 | H | C—Cl | —OCH2O— | | C—H | CF3 | C—H | C—Cl | H | H | CH3SOCH2CO | H | 1 |
| 2-4428 | H | C—Cl | —OCH2O— | | C—H | CF3 | C—H | C—Cl | H | H | CH3SO2CH2CO | H | 1 |
| 2-4429 | H | C—Cl | —OCH2O— | | C—H | CF3 | C—H | C—Cl | H | H | EtNHCO | H | 1 |
| 2-4430 | H | C—Cl | —OCH2O— | | C—H | CF3 | C—H | C—Cl | Me | H | EtCO | H | 1 |
| 2-4431 | H | C—Cl | —OCH2O— | | C—H | CF3 | C—H | C—Cl | Me | H | CF3CH2CO | H | 1 |
| 2-4432 | H | C—Cl | —OCH2O— | | C—H | CF3 | C—H | C—Br | H | H | EtCO | H | 1 |
| 2-4433 | H | C—Cl | —OCH2O— | | C—H | CF3 | N | C—Br | H | H | CF3CH2CO | H | 1 |
| 2-4434 | H | C—Cl | —OCH2O— | | C—H | CF3 | C—H | C—Br | H | H | H | H | 1 |
| 2-4435 | H | C—Cl | —OCH2O— | | C—H | CF3 | C—H | C—Br | H | H | MeCO | H | 1 |
| 2-4436 | H | C—Cl | —OCH2O— | | C—H | CF3 | C—H | C—Br | H | H | EtCO | H | 1 |
| 2-4437 | H | C—Cl | —OCH2O— | | C—H | CF3 | C—H | C—Br | H | H | cyc-PrCO | H | 1 |
| 2-4438 | H | C—Cl | —OCH2O— | | C—H | CF3 | C—H | C—Br | H | H | CF3CH2CO | H | 1 |
| 2-4439 | H | C—Cl | —OCH2O— | | C—H | CF3 | C—H | C—Br | H | H | CH3SCH2CO | H | 1 |
| 2-4440 | H | C—Cl | —OCH2O— | | C—H | CF3 | C—H | C—Br | H | H | CH3SOCH2CO | H | 1 |
| 2-4441 | H | C—Cl | —OCH2O— | | C—H | CF3 | C—H | C—Br | H | H | CH3SO2CH2CO | H | 1 |
| 2-4442 | H | C—Cl | —OCH2O— | | C—H | CF3 | C—H | C—Br | Me | H | EtCO | H | 1 |
| 2-4443 | H | C—Cl | —OCH2O— | | C—H | CF3 | C—H | C—Br | Me | H | CF3CH2CO | H | 1 |
| 2-4444 | H | C—Cl | —OCH2O— | | C—H | CF3 | C—H | C—Br | H | H | EtCO | H | 1 |
| 2-4445 | H | C—Cl | —OCH2O— | | C—H | CF3 | C—H | C—Br | H | H | CF3CH2CO | H | 1 |
| 2-4446 | H | C—Cl | —OCH2O— | | C—H | CF3 | N | C—CN | H | H | EtCO | H | 1 |
| 2-4447 | H | C—Cl | —OCH2O— | | C—H | CF3 | C—H | C—CN | H | H | CF3CH2CO | H | 1 |
| 2-4448 | H | C—Cl | —OCH2O— | | C—H | CF3 | C—H | C—CN | H | H | EtCO | H | 1 |
| 2-4449 | H | C—Cl | —OCH2O— | | C—H | CF3 | N | C—Me | H | H | MeCO | H | 1 |
| 2-4450 | H | C—Cl | —OCH2O— | | C—H | CF3 | C—H | C—Me | H | H | MeCO | H | 1 |
| 2-4451 | H | C—Cl | —OCH2O— | | C—H | CF3 | C—H | C—Me | H | H | EtCO | H | 1 |
| 2-4452 | H | C—Cl | —OCH2O— | | C—H | CF3 | C—H | C—Me | H | H | CF3CH2CO | H | 1 |
| 2-4453 | H | C—Cl | —OCH2O— | | C—H | CF3 | C—H | C—Me | H | H | cyclo-PrCO | H | 1 |
| 2-4454 | H | C—Cl | —OCH2O— | | C—H | CF3 | C—H | C—Me | H | H | CH3SCH2CO | H | 1 |
| 2-4455 | H | C—Cl | —OCH2O— | | C—H | CF3 | C—H | C—Me | H | H | EtNHCO | H | 1 |
| 2-4456 | H | C—Cl | —OCH2O— | | C—H | CF3 | C—H | C—Me | Me | H | EtCO | H | 1 |
| 2-4457 | H | C—Cl | —OCH2O— | | C—H | CF3 | N | C—Me | H | H | EtCO | H | 1 |
| 2-4458 | H | C—Cl | —OCH2O— | | C—H | CF3 | C—H | C—NO2 | H | H | MeCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4459 | H | C—Cl | —OCH2O— | | C—H | CF3 | C—H | C—NO2 | H | H | MeCO | H | 1 |
| 2-4460 | H | C—Cl | —OCH2O— | | C—H | CF3 | C—H | C—NO2 | H | H | EtCO | H | 1 |
| 2-4461 | H | C—Cl | —OCH2O— | | C—H | CF3 | C—H | C—NO2 | H | H | CF3CH2CO | H | 1 |
| 2-4462 | H | C—Cl | —OCH2O— | | C—H | CF3 | C—H | C—NO2 | H | H | cyclo-PrCO | H | 1 |
| 2-4463 | H | C—Cl | —OCH2O— | | C—H | CF3 | C—H | C—NO2 | H | H | CH3SCH2CO | H | 1 |
| 2-4464 | H | C—Cl | —OCH2O— | | C—H | CF3 | C—H | C—NO2 | H | H | EtNHCO | H | 1 |
| 2-4465 | H | C—Cl | —OCH2O— | | C—H | CF3 | C—H | C—NO2 | Me | H | EtCO | H | 1 |
| 2-4466 | H | C—Cl | —OCH2O— | | C—H | CF3 | N | C—NO2 | H | H | EtCO | H | 1 |
| 2-4467 | H | C—Cl | —OCH2O— | | C—H | CF3 | C—H | C—SMe | H | H | MeCO | H | 1 |
| 2-4468 | H | C—Cl | —OCH2O— | | C—H | CF3 | C—H | C—SMe | H | H | MeCO | H | 1 |
| 2-4469 | H | C—Cl | —OCH2O— | | C—H | CF3 | C—H | C—SMe | H | H | EtCO | H | 1 |
| 2-4470 | H | C—Cl | —OCH2O— | | C—H | CF3 | C—H | C—SMe | H | H | CF3CH2CO | H | 1 |
| 2-4471 | H | C—Cl | —OCH2O— | | C—H | CF3 | C—H | C—SMe | H | H | cyclo-PrCO | H | 1 |
| 2-4472 | H | C—Cl | —OCH2O— | | C—H | CF3 | C—H | C—SMe | H | H | CH3SCH2CO | H | 1 |
| 2-4473 | H | C—Cl | —OCH2O— | | C—H | CF3 | C—H | C—SMe | H | H | EtNHCO | H | 1 |
| 2-4474 | H | C—Cl | —OCH2O— | | C—H | CF3 | C—H | C—SMe | Me | H | EtCO | H | 1 |
| 2-4475 | H | C—Cl | —OCH2O— | | C—H | CF3 | N | C—SMe | H | H | EtCO | H | 1 |
| 2-4476 | H | C—Cl | —OCH2O— | | C—H | CF3 | C—H | C—H | H | H | MeCO | H | 1 |
| 2-4477 | H | C—Cl | —OCH2O— | | C—H | CF3 | C—H | C—H | H | H | MeCO | H | 1 |
| 2-4478 | H | C—Cl | —OCH2O— | | C—H | CF3 | C—H | C—H | H | H | EtCO | H | 1 |
| 2-4479 | H | C—Cl | —OCH2O— | | C—H | CF3 | C—H | C—H | H | H | CF3CH2CO | H | 1 |
| 2-4480 | H | C—Cl | —OCH2O— | | C—H | CF3 | C—H | C—H | H | H | cyclo-PrCO | H | 1 |
| 2-4481 | H | C—Cl | —OCH2O— | | C—H | CF3 | C—H | C—H | H | H | CH3SCH2CO | H | 1 |
| 2-4482 | H | C—Cl | —OCH2O— | | C—H | CF3 | C—H | C—H | H | H | EtNHCO | H | 1 |
| 2-4483 | H | C—Cl | —OCH2O— | | C—H | CF3 | C—H | C—H | Me | H | EtCO | H | 1 |
| 2-4484 | H | C—Cl | —OCH2O— | | C—H | CF3 | N | C—H | H | H | EtCO | H | 1 |
| 2-4485 | H | C—Cl | —OCH2O— | | C—H | CF3 | C—H | C—SOMe | H | H | EtCO | H | 1 |
| 2-4486 | H | C—Cl | —OCH2O— | | C—H | CF3 | C—H | C—SOMe | H | H | CF3CH2CO | H | 1 |
| 2-4487 | H | C—Cl | —OCH2O— | | C—H | CF3 | C—H | C—SO2Me | H | H | EtCO | H | 1 |
| 2-4488 | H | C—Cl | —OCH2O— | | C—H | CF3 | C—H | C—SO2Me | H | H | CF3CH2CO | H | 1 |
| 2-4489 | H | C—Cl | —OCH2O— | | C—H | CF3 | C—H | C—SCF3 | H | H | EtCO | H | 1 |
| 2-4490 | H | C—Cl | —OCH2O— | | C—H | CF3 | C—H | C—SCF3 | H | H | CF3CH2CO | H | 1 |
| 2-4491 | H | C—Cl | —OCH2O— | | C—H | CF3 | C—H | C—SOCF3 | H | H | EtCO | H | 1 |
| 2-4492 | H | C—Cl | —OCH2O— | | C—H | CF3 | C—H | C—SOCF3 | H | H | CF3CH2CO | H | 1 |
| 2-4493 | H | C—Cl | —OCH2O— | | C—H | CF3 | C—H | C—SO2CF3 | H | H | EtCO | H | 1 |
| 2-4494 | H | C—Cl | —OCH2O— | | C—H | CF3 | C—H | C—SO2CF3 | H | H | CF3CH2CO | H | 1 |
| 2-4495 | H | C—Cl | —OCH2O— | | C—H | CF3 | C—H | C—F | H | H | EtCO | H | 1 |
| 2-4496 | H | C—Cl | —OCH2O— | | C—H | CF3 | C—H | C—F | H | H | CF3CH2CO | H | 1 |
| 2-4497 | H | C—Cl | —OCH2O— | | C—H | CF3 | C—H | C—I | H | H | EtCO | H | 1 |
| 2-4498 | H | C—Cl | —OCH2O— | | C—H | CF3 | C—H | C—I | H | H | CF3CH2CO | H | 1 |
| 2-4499 | H | C—Cl | —OCH2O— | | C—H | CF3 | C—H | C—NH2 | H | H | EtCO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4500 | H | C—Cl | | —OCH2O— | C—H | CF3 | C—H | C—NH2 | H | H | CF3CH2CO | H | 1 |
| 2-4501 | H | C—Cl | | —OCH2O— | C—H | CF3 | C—H | C—NHAc | H | H | EtCO | H | 1 |
| 2-4502 | H | C—Cl | | —OCH2O— | C—H | CF3 | C—H | C—NHAc | H | H | CF3CH2CO | H | 1 |
| 2-4503 | H | C—Cl | | —OCH2O— | C—H | CF3 | C—H | C—NHCOCF3 | H | H | EtCO | H | 1 |
| 2-4504 | H | C—Cl | | —OCH2O— | C—H | CF3 | C—H | C—NHCOCF3 | H | H | CF3CH2CO | H | 1 |
| 2-4505 | H | C—Cl | | —OCH2O— | C—H | CF3 | C—H | C—CH2OAc | H | H | EtCO | H | 1 |
| 2-4506 | H | C—Cl | | —OCH2O— | C—H | CF3 | C—H | C—CH2OAc | H | H | CF3CH2CO | H | 1 |
| 2-4507 | H | C—Cl | | —OCH2O— | C—H | CF3 | C—H | C—CF3 | H | H | H | H | 1 |
| 2-4508 | H | C—Cl | | —OCF2O— | C—H | CF3 | C—H | C—CF3 | H | H | CH3CO | H | 1 |
| 2-4509 | H | C—Cl | | —OCF2O— | C—H | CF3 | C—H | C—CF3 | H | H | EtCO | H | 1 |
| 2-4510 | H | C—Cl | | —OCF2O— | C—H | CF3 | C—H | C—CF3 | H | H | cyclo-PrCO | H | 1 |
| 2-4511 | H | C—Cl | | —OCF2O— | C—H | CF3 | C—H | C—CF3 | H | H | cyclo-PrCH2CO | H | 1 |
| 2-4512 | H | C—Cl | | —OCF2O— | C—H | CF3 | C—H | C—CF3 | H | H | EtNHCO | H | 1 |
| 2-4513 | H | C—Cl | | —OCF2O— | C—H | CF3 | C—H | C—CF3 | H | H | CH3SCH2CO | H | 1 |
| 2-4514 | H | C—Cl | | —OCF2O— | C—H | CF3 | C—H | C—CF3 | H | H | CH3SOCH2CO | H | 1 |
| 2-4515 | H | C—Cl | | —OCF2O— | C—H | CF3 | C—H | C—CF3 | H | H | CH3SO2CH2CO | H | 1 |
| 2-4516 | H | C—Cl | | —OCF2O— | C—H | CF3 | C—H | C—CF3 | H | H | CH3SO2CH2CO | H | 1 |
| 2-4517 | H | C—Cl | | —OCF2O— | C—H | CF3 | C—H | C—CF3 | Me | H | EtCO | H | 1 |
| 2-4518 | H | C—Cl | | —OCF2O— | C—H | CF3 | C—H | C—CF3 | Me | H | CF3CH2CO | H | 1 |
| 2-4519 | H | C—Cl | | —OCF2O— | C—H | CF3 | N | C—CF3 | H | H | EtCO | H | 1 |
| 2-4520 | H | C—Cl | | —OCF2O— | C—H | CF3 | N | C—CF3 | H | H | CF3CH2CO | H | 1 |
| 2-4521 | H | C—Cl | | —OCF2O— | C—H | CF3 | C—H | C—Cl | H | H | H | H | 1 |
| 2-4522 | H | C—Cl | | —OCF2O— | C—H | CF3 | C—H | C—Cl | H | H | MeCO | H | 1 |
| 2-4523 | H | C—Cl | | —OCF2O— | C—H | CF3 | C—H | C—Cl | H | H | EtCO | H | 1 |
| 2-4524 | H | C—Cl | | —OCF2O— | C—H | CF3 | C—H | C—Cl | H | H | CF3CH2CO | H | 1 |
| 2-4525 | H | C—Cl | | —OCF2O— | C—H | CF3 | C—H | C—Cl | H | H | cyclo-PrCO | H | 1 |
| 2-4526 | H | C—Cl | | —OCF2O— | C—H | CF3 | C—H | C—Cl | H | H | cyclo-PrCH2CO | H | 1 |
| 2-4527 | H | C—Cl | | —OCF2O— | C—H | CF3 | C—H | C—Cl | H | H | CH3SCH2CO | H | 1 |
| 2-4528 | H | C—Cl | | —OCF2O— | C—H | CF3 | C—H | C—Cl | H | H | CH3SOCH2CO | H | 1 |
| 2-4529 | H | C—Cl | | —OCF2O— | C—H | CF3 | C—H | C—Cl | H | H | CH3SO2CH2CO | H | 1 |
| 2-4530 | H | C—Cl | | —OCF2O— | C—H | CF3 | C—H | C—Cl | H | H | EtNHCO | H | 1 |
| 2-4531 | H | C—Cl | | —OCF2O— | C—H | CF3 | C—H | C—Cl | Me | H | EtCO | H | 1 |
| 2-4532 | H | C—Cl | | —OCF2O— | C—H | CF3 | C—H | C—Cl | Me | H | CF3CH2CO | H | 1 |
| 2-4533 | H | C—Cl | | —OCF2O— | C—H | CF3 | N | C—Cl | H | H | EtCO | H | 1 |
| 2-4534 | H | C—Cl | | —OCF2O— | C—H | CF3 | N | C—Cl | H | H | CF3CH2CO | H | 1 |
| 2-4535 | H | C—Cl | | —OCF2O— | C—H | CF3 | C—H | C—Br | H | H | H | H | 1 |
| 2-4536 | H | C—Cl | | —OCF2O— | C—H | CF3 | C—H | C—Br | H | H | MeCO | H | 1 |
| 2-4537 | H | C—Cl | | —OCF2O— | C—H | CF3 | C—H | C—Br | H | H | EtCO | H | 1 |
| 2-4538 | H | C—Cl | | —OCF2O— | C—H | CF3 | C—H | C—Br | H | H | cyc-PrCO | H | 1 |
| 2-4539 | H | C—Cl | | —OCF2O— | C—H | CF3 | C—H | C—Br | H | H | CF3CH2CO | H | 1 |
| 2-4540 | H | C—Cl | | —OCF2O— | C—H | CF3 | C—H | C—Br | H | H | CH3SCH2CO | H | 1 |

TABLE 2-1-continued

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-4541 | H | C—Cl | —OCF2O— | | C—H | CF3 | C—H | C—Br | H | H | CH3SOCH2CO | H | 1 |
| 2-4542 | H | C—Cl | —OCF2O— | | C—H | CF3 | C—H | C—Br | H | H | CH3SO2CH2CO | H | 1 |
| 2-4543 | H | C—Cl | —OCF2O— | | C—H | CF3 | C—H | C—Br | Me | H | EtCO | H | 1 |
| 2-4544 | H | C—Cl | —OCF2O— | | C—H | CF3 | N | C—Br | Me | H | CF3CH2CO | H | 1 |
| 2-4545 | H | C—Cl | —OCF2O— | | C—H | CF3 | N | C—Br | H | H | EtCO | H | 1 |
| 2-4546 | H | C—Cl | —OCF2O— | | C—H | CF3 | C—H | C—Br | H | H | CF3CH2CO | H | 1 |
| 2-4547 | H | C—Cl | —OCF2O— | | C—H | CF3 | C—H | C—CN | H | H | EtCO | H | 1 |
| 2-4548 | H | C—Cl | —OCF2O— | | C—H | CF3 | N | C—CN | H | H | CF3CH2CO | H | 1 |
| 2-4549 | H | C—Cl | —OCF2O— | | C—H | CF3 | C—H | C—CN | H | H | EtCO | H | 1 |
| 2-4550 | H | C—Cl | —OCF2O— | | C—H | CF3 | C—H | C—Me | H | H | MeCO | H | 1 |
| 2-4551 | H | C—Cl | —OCF2O— | | C—H | CF3 | C—H | C—Me | H | H | MeCO | H | 1 |
| 2-4552 | H | C—Cl | —OCF2O— | | C—H | CF3 | C—H | C—Me | H | H | EtCO | H | 1 |
| 2-4553 | H | C—Cl | —OCF2O— | | C—H | CF3 | C—H | C—Me | H | H | CF3CH2CO | H | 1 |
| 2-4554 | H | C—Cl | —OCF2O— | | C—H | CF3 | C—H | C—Me | H | H | cyclo-PrCO | H | 1 |
| 2-4555 | H | C—Cl | —OCF2O— | | C—H | CF3 | C—H | C—Me | H | H | CH3SCH2CO | H | 1 |
| 2-4556 | H | C—Cl | —OCF2O— | | C—H | CF3 | C—H | C—Me | H | H | EtNHCO | H | 1 |
| 2-4557 | H | C—Cl | —OCF2O— | | C—H | CF3 | C—H | C—Me | Me | H | EtCO | H | 1 |
| 2-4558 | H | C—Cl | —OCF2O— | | C—H | CF3 | N | C—Me | H | H | EtCO | H | 1 |
| 2-4559 | H | C—Cl | —OCF2O— | | C—H | CF3 | C—H | C—NO2 | H | H | MeCO | H | 1 |
| 2-4560 | H | C—Cl | —OCF2O— | | C—H | CF3 | C—H | C—NO2 | H | H | EtCO | H | 1 |
| 2-4561 | H | C—Cl | —OCF2O— | | C—H | CF3 | C—H | C—NO2 | H | H | EtCO | H | 1 |
| 2-4562 | H | C—Cl | —OCF2O— | | C—H | CF3 | C—H | C—NO2 | H | H | CF3CH2CO | H | 1 |
| 2-4563 | H | C—Cl | —OCF2O— | | C—H | CF3 | C—H | C—NO2 | H | H | cyclo-PrCO | H | 1 |
| 2-4564 | H | C—Cl | —OCF2O— | | C—H | CF3 | C—H | C—NO2 | H | H | CH3SCH2CO | H | 1 |
| 2-4565 | H | C—Cl | —OCF2O— | | C—H | CF3 | C—H | C—NO2 | H | H | EtNHCO | H | 1 |
| 2-4566 | H | C—Cl | —OCF2O— | | C—H | CF3 | C—H | C—NO2 | Me | H | EtCO | H | 1 |
| 2-4567 | H | C—Cl | —OCF2O— | | C—H | CF3 | N | C—NO2 | H | H | EtCO | H | 1 |
| 2-4568 | H | C—Cl | —OCF2O— | | C—H | CF3 | C—H | C—SMe | H | H | MeCO | H | 1 |
| 2-4569 | H | C—Cl | —OCF2O— | | C—H | CF3 | C—H | C—SMe | H | H | EtCO | H | 1 |
| 2-4570 | H | C—Cl | —OCF2O— | | C—H | CF3 | C—H | C—SMe | H | H | EtCO | H | 1 |
| 2-4571 | H | C—Cl | —OCF2O— | | C—H | CF3 | C—H | C—SMe | H | H | CF3CH2CO | H | 1 |
| 2-4572 | H | C—Cl | —OCF2O— | | C—H | CF3 | C—H | C—SMe | H | H | cyclo-PrCO | H | 1 |
| 2-4573 | H | C—Cl | —OCF2O— | | C—H | CF3 | C—H | C—SMe | H | H | CH3SCH2CO | H | 1 |
| 2-4574 | H | C—Cl | —OCF2O— | | C—H | CF3 | C—H | C—SMe | H | H | EtNHCO | H | 1 |
| 2-4575 | H | C—Cl | —OCF2O— | | C—H | CF3 | C—H | C—SMe | Me | H | EtCO | H | 1 |
| 2-4576 | H | C—Cl | —OCF2O— | | C—H | CF3 | N | C—SMe | H | H | EtCO | H | 1 |
| 2-4577 | H | C—Cl | —OCF2O— | | C—H | CF3 | C—H | C—H | H | H | MeCO | H | 1 |
| 2-4578 | H | C—Cl | —OCF2O— | | C—H | CF3 | C—H | C—H | H | H | MeCO | H | 1 |
| 2-4579 | H | C—Cl | —OCF2O— | | C—H | CF3 | C—H | C—H | H | H | EtCO | H | 1 |
| 2-4580 | H | C—Cl | —OCF2O— | | C—H | CF3 | C—H | C—H | H | H | CF3CH2CO | H | 1 |
| 2-4581 | H | C—Cl | —OCF2O— | | C—H | CF3 | C—H | C—H | H | H | cyclo-PrCO | H | 1 |

TABLE 2-1-continued

| Example No. | X | B¹ | B² | B³ | B⁴ | R | A² | A³ | R¹ | R² | R⁴ | R³ | 1 |
|---|---|---|---|---|---|---|---|---|---|---|---|---|---|
| 2-4582 | H | C—Cl | | —OCF2O— | C—H | CF3 | C—H | C—H | H | H | CH3SCH2CO | H | 1 |
| 2-4583 | H | C—Cl | | —OCF2O— | C—H | CF3 | C—H | C—H | H | H | EtNHCO | H | 1 |
| 2-4584 | H | C—Cl | | —OCF2O— | C—H | CF3 | N | C—H | Me | H | EtCO | H | 1 |
| 2-4585 | H | C—Cl | | —OCF2O— | C—H | CF3 | C—H | C—H | H | H | EtCO | H | 1 |
| 2-4586 | H | C—Cl | | —OCF2O— | C—H | CF3 | C—H | C—SOMe | H | H | CF3CH2CO | H | 1 |
| 2-4587 | H | C—Cl | | —OCF2O— | C—H | CF3 | C—H | C—SOMe | H | H | EtCO | H | 1 |
| 2-4588 | H | C—Cl | | —OCF2O— | C—H | CF3 | C—H | C—SO2Me | H | H | CF3CH2CO | H | 1 |
| 2-4589 | H | C—Cl | | —OCF2O— | C—H | CF3 | C—H | C—SO2Me | H | H | EtCO | H | 1 |
| 2-4590 | H | C—Cl | | —OCF2O— | C—H | CF3 | C—H | C—SCF3 | H | H | CF3CH2CO | H | 1 |
| 2-4591 | H | C—Cl | | —OCF2O— | C—H | CF3 | C—H | C—SCF3 | H | H | EtCO | H | 1 |
| 2-4592 | H | C—Cl | | —OCF2O— | C—H | CF3 | C—H | C—SOCF3 | H | H | CF3CH2CO | H | 1 |
| 2-4593 | H | C—Cl | | —OCF2O— | C—H | CF3 | C—H | C—SOCF3 | H | H | EtCO | H | 1 |
| 2-4594 | H | C—Cl | | —OCF2O— | C—H | CF3 | C—H | C—SO2CF3 | H | H | CF3CH2CO | H | 1 |
| 2-4595 | H | C—Cl | | —OCF2O— | C—H | CF3 | C—H | C—SO2CF3 | H | H | EtCO | H | 1 |
| 2-4596 | H | C—Cl | | —OCF2O— | C—H | CF3 | C—H | C—F | H | H | CF3CH2CO | H | 1 |
| 2-4597 | H | C—Cl | | —OCF2O— | C—H | CF3 | C—H | C—F | H | H | EtCO | H | 1 |
| 2-4598 | H | C—Cl | | —OCF2O— | C—H | CF3 | C—H | C—I | H | H | CF3CH2CO | H | 1 |
| 2-4599 | H | C—Cl | | —OCF2O— | C—H | CF3 | C—H | C—I | H | H | EtCO | H | 1 |
| 2-4600 | H | C—Cl | | —OCF2O— | C—H | CF3 | C—H | C—NH2 | H | H | CF3CH2CO | H | 1 |
| 2-4601 | H | C—Cl | | —OCF2O— | C—H | CF3 | C—H | C—NH2 | H | H | EtCO | H | 1 |
| 2-4602 | H | C—Cl | | —OCF2O— | C—H | CF3 | C—H | C—NHAc | H | H | CF3CH2CO | H | 1 |
| 2-4603 | H | C—Cl | | —OCF2O— | C—H | CF3 | C—H | C—NHAc | H | H | EtCO | H | 1 |
| 2-4604 | H | C—Cl | | —OCF2O— | C—H | CF3 | C—H | C—NHCOCF3 | H | H | CF3CH2CO | H | 1 |
| 2-4605 | H | C—Cl | | —OCF2O— | C—H | CF3 | C—H | C—NHCOCF3 | H | H | EtCO | H | 1 |
| 2-4606 | H | C—Cl | | —OCF2O— | C—H | CF3 | C—H | C—CH2OAc | H | H | CF3CH2CO | H | 1 |
| 2-4607 | H | C—Cl | | —OCF2O— | C—H | CF3 | C—H | C—CH2OAc | H | H | EtCO | H | 1 |
| 2-4810 | H | C—CF3 | C—H | C—F | C—H | CF3 | C—H | C—CF3 | H | H | MeCO | H | 1 |
| 2-4811 | H | C—CF3 | C—H | C—F | C—H | CF3 | C—H | C—CF3 | H | H | EtCO | H | 1 |
| 2-4812 | H | C—CF3 | C—H | C—F | C—H | CF3 | C—H | C—CF3 | H | H | EtNHCO | H | 1 |
| 2-4813 | H | C—CF3 | C—H | C—F | C—H | CF3 | C—H | C—CF3 | H | H | H | H | 1 |
| 2-4814 | H | C—CF3 | C—H | C—F | C—H | CF3 | C—H | C—CF3 | H | H | cyclo-PrCO | H | 1 |
| 2-4815 | H | C—CF3 | C—H | C—F | C—H | CF3 | C—H | C—CF3 | H | H | cyclo-PrCH2CO | H | 1 |
| 2-4816 | H | C—CF3 | C—H | C—F | C—H | CF3 | C—H | C—CF3 | H | H | CH3SCH2CO | H | 1 |
| 2-4817 | H | C—CF3 | C—H | C—F | C—H | CF3 | C—H | C—CF3 | H | H | CH3SOCH2CO | H | 1 |
| 2-4818 | H | C—CF3 | C—H | C—F | C—H | CF3 | C—H | C—CF3 | H | H | CH3SO2CH2CO | H | 1 |
| 2-4819 | H | C—CF3 | C—H | C—F | C—H | CF3 | C—H | C—CF3 | H | H | H | H | 1 |
| 2-4820 | H | C—CF3 | C—H | C—F | C—H | CF3 | C—H | C—CF3 | Me | H | EtCO | H | 1 |
| 2-4821 | H | C—CF3 | C—H | C—F | C—H | CF3 | C—H | C—CF3 | Me | H | CF3CH2CO | H | 1 |
| 2-4822 | H | C—CF3 | C—H | C—F | C—H | CF3 | C—H | C—CF3 | Me | H | CH3SCH2CO | H | 1 |
| 2-4823 | H | C—CF3 | C—H | C—F | C—H | CF3 | C—H | C—CF3 | H | H | H | H | 1 |
| 2-4824 | H | C—CF3 | C—H | C—F | C—H | CF3 | N | C—CF3 | H | H | H | H | 1 |

TABLE 2-1-continued

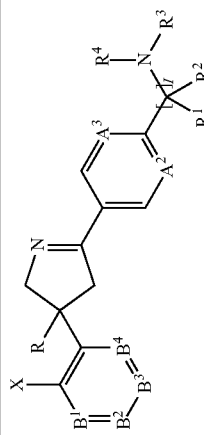

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4825 | H | C—CF3 | C—H | C—F | C—H | CF3 | N | C—CF3 | H | H | EtCO | H | 1 |
| 2-4826 | H | C—CF3 | C—H | C—F | C—H | CF3 | N | C—CF3 | H | H | CF3CH2CO | H | 1 |
| 2-4827 | H | C—CF3 | C—H | C—F | C—H | CF3 | C—H | C—CF3 | H | H | CH3SCH2CO | H | 1 |
| 2-4828 | H | C—CF3 | C—H | C—F | C—H | CF3 | C—H | C—Cl | H | H | H | H | 1 |
| 2-4830 | H | C—CF3 | C—H | C—F | C—H | CF3 | C—H | C—Cl | H | H | MeCO | H | 1 |
| 2-4831 | H | C—CF3 | C—H | C—F | C—H | CF3 | C—H | C—Cl | H | H | EtCO | H | 1 |
| 2-4832 | H | C—CF3 | C—H | C—F | C—H | CF3 | C—H | C—Cl | H | H | cyclo-PrCO | H | 1 |
| 2-4833 | H | C—CF3 | C—H | C—F | C—H | CF3 | C—H | C—Cl | H | H | cyclo-PrCH2CO | H | 1 |
| 2-4834 | H | C—CF3 | C—H | C—F | C—H | CF3 | C—H | C—Cl | H | H | CH3SCH2CO | H | 1 |
| 2-4835 | H | C—CF3 | C—H | C—F | C—H | CF3 | C—H | C—Cl | H | H | CH3SOCH2CO | H | 1 |
| 2-4836 | H | C—CF3 | C—H | C—F | C—H | CF3 | C—H | C—Cl | H | H | CH3SO2CH2CO | H | 1 |
| 2-4837 | H | C—CF3 | C—H | C—F | C—H | CF3 | C—H | C—Cl | H | H | EtNHCO | H | 1 |
| 2-4838 | H | C—CF3 | C—H | C—F | C—H | CF3 | C—H | C—Cl | Me | H | H | H | 1 |
| 2-4839 | H | C—CF3 | C—H | C—F | C—H | CF3 | C—H | C—Cl | Me | H | EtCO | H | 1 |
| 2-4840 | H | C—CF3 | C—H | C—F | C—H | CF3 | C—H | C—Cl | Me | H | CF3CH2CO | H | 1 |
| 2-4841 | H | C—CF3 | C—H | C—F | C—H | CF3 | C—H | C—Cl | Me | H | CH3SCH2CO | H | 1 |
| 2-4842 | H | C—CF3 | C—H | C—F | C—H | CF3 | C—H | C—Cl | H | H | H | H | 1 |
| 2-4843 | H | C—CF3 | C—H | C—F | C—H | CF3 | C—H | C—Cl | H | H | EtCO | H | 1 |
| 2-4844 | H | C—CF3 | C—H | C—F | C—H | CF3 | C—H | C—Cl | H | H | CF3CH2CO | H | 1 |
| 2-4845 | H | C—CF3 | C—H | C—F | C—H | CF3 | C—H | C—Cl | H | H | CH3SCH2CO | H | 1 |
| 2-4846 | H | C—CF3 | C—H | C—F | C—H | CF3 | C—H | C—Br | H | H | H | H | 1 |
| 2-4847 | H | C—CF3 | C—H | C—F | C—H | CF3 | C—H | C—Br | H | H | MeCO | H | 1 |
| 2-4848 | H | C—CF3 | C—H | C—F | C—H | CF3 | C—H | C—Br | H | H | EtCO | H | 1 |
| 2-4849 | H | C—CF3 | C—H | C—F | C—H | CF3 | C—H | C—Br | H | H | CF3CH2CO | H | 1 |
| 2-4850 | H | C—CF3 | C—H | C—F | C—H | CF3 | C—H | C—Br | H | H | cyclo-PrCO | H | 1 |
| 2-4851 | H | C—CF3 | C—H | C—F | C—H | CF3 | C—H | C—Br | H | H | cyclo-PrCH2CO | H | 1 |
| 2-4852 | H | C—CF3 | C—H | C—F | C—H | CF3 | N | C—Br | H | H | CH3SCH2CO | H | 1 |
| 2-4853 | H | C—CF3 | C—H | C—F | C—H | CF3 | N | C—Br | H | H | CH3SOCH2CO | H | 1 |
| 2-4854 | H | C—CF3 | C—H | C—F | C—H | CF3 | N | C—Br | H | H | CH3SO2CH2CO | H | 1 |
| 2-4855 | H | C—CF3 | C—H | C—F | C—H | CF3 | C—H | C—Br | H | H | EtNHCO | H | 1 |
| 2-4856 | H | C—CF3 | C—H | C—F | C—H | CF3 | C—H | C—Br | Me | H | H | H | 1 |
| 2-4857 | H | C—CF3 | C—H | C—F | C—H | CF3 | C—H | C—Br | Me | H | EtCO | H | 1 |
| 2-4858 | H | C—CF3 | C—H | C—F | C—H | CF3 | C—H | C—Br | Me | H | CF3CH2CO | H | 1 |
| 2-4859 | H | C—CF3 | C—H | C—F | C—H | CF3 | C—H | C—Br | Me | H | CH3SCH2CO | H | 1 |
| 2-4860 | H | C—CF3 | C—H | C—F | C—H | CF3 | C—H | C—Br | H | H | EtCO | H | 1 |
| 2-4861 | H | C—CF3 | C—H | C—F | C—H | CF3 | C—H | C—Br | H | H | CF3CH2CO | H | 1 |
| 2-4862 | H | C—CF3 | C—H | C—F | C—H | CF3 | C—H | C—Br | H | H | CH3SCH2CO | H | 1 |
| 2-4863 | H | C—CF3 | C—H | C—F | C—H | CF3 | C—H | C—CN | H | H | EtCO | H | 1 |
| 2-4864 | H | C—CF3 | C—H | C—F | C—H | CF3 | C—H | C—CN | H | H | H | H | 1 |
| 2-4865 | H | C—CF3 | C—H | C—F | C—H | CF3 | C—H | C—CN | H | H | MeCO | H | 1 |

TABLE 2-1-continued

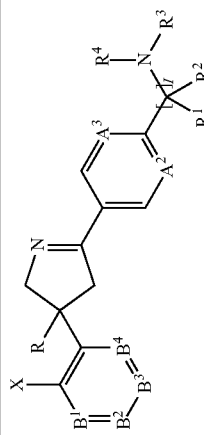

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4866 | H | C—CF3 | C—H | C—F | C—H | CF3 | C—H | C—CN | H | H | EtCO | H | 1 |
| 2-4867 | H | C—CF3 | C—H | C—F | C—H | CF3 | C—H | C—CN | H | H | CF3CH2CO | H | 1 |
| 2-4868 | H | C—CF3 | C—H | C—F | C—H | CF3 | C—H | C—CN | H | H | cyclo-PrCO | H | 1 |
| 2-4869 | H | C—CF3 | C—H | C—F | C—H | CF3 | C—H | C—CN | H | H | cyclo-PrCH2CO | H | 1 |
| 2-4870 | H | C—CF3 | C—H | C—F | C—H | CF3 | C—H | C—CN | H | H | CH3SCH2CO | H | 1 |
| 2-4871 | H | C—CF3 | C—H | C—F | C—H | CF3 | C—H | C—CN | H | H | CH3SOCH2CO | H | 1 |
| 2-4872 | H | C—CF3 | C—H | C—F | C—H | CF3 | C—H | C—CN | H | H | CH3SO2CH2CO | H | 1 |
| 2-4873 | H | C—CF3 | C—H | C—F | C—H | CF3 | C—H | C—CN | H | H | EtNHCO | H | 1 |
| 2-4874 | H | C—CF3 | C—H | C—F | C—H | CF3 | C—H | C—CN | Me | H | EtCO | H | 1 |
| 2-4875 | H | C—CF3 | C—H | C—F | C—H | CF3 | C—H | C—CN | Me | H | CF3CH2CO | H | 1 |
| 2-4876 | H | C—CF3 | C—H | C—F | C—H | CF3 | N | C—CN | H | H | EtCO | H | 1 |
| 2-4877 | H | C—CF3 | C—H | C—F | C—H | CF3 | C—H | C—CN | H | H | EtCO | H | 1 |
| 2-4878 | H | C—CF3 | C—H | C—F | C—H | CF3 | C—H | C—Me | H | H | H | H | 1 |
| 2-4879 | H | C—CF3 | C—H | C—F | C—H | CF3 | C—H | C—Me | H | H | MeCO | H | 1 |
| 2-4880 | H | C—CF3 | C—H | C—F | C—H | CF3 | C—H | C—Me | H | H | EtCO | H | 1 |
| 2-4881 | H | C—CF3 | C—H | C—F | C—H | CF3 | C—H | C—Me | H | H | CF3CH2CO | H | 1 |
| 2-4882 | H | C—CF3 | C—H | C—F | C—H | CF3 | C—H | C—Me | H | H | cyclo-PrCO | H | 1 |
| 2-4883 | H | C—CF3 | C—H | C—F | C—H | CF3 | C—H | C—Me | H | H | cyclo-PrCH2CO | H | 1 |
| 2-4884 | H | C—CF3 | C—H | C—F | C—H | CF3 | C—H | C—Me | H | H | CH3SCH2CO | H | 1 |
| 2-4885 | H | C—CF3 | C—H | C—F | C—H | CF3 | C—H | C—Me | H | H | CH3SOCH2CO | H | 1 |
| 2-4886 | H | C—CF3 | C—H | C—F | C—H | CF3 | C—H | C—Me | H | H | CH3SO2CH2CO | H | 1 |
| 2-4887 | H | C—CF3 | C—H | C—F | C—H | CF3 | C—H | C—Me | H | H | EtNHCO | H | 1 |
| 2-4888 | H | C—CF3 | C—H | C—F | C—H | CF3 | C—H | C—Me | Me | H | EtCO | H | 1 |
| 2-4889 | H | C—CF3 | C—H | C—F | C—H | CF3 | C—H | C—Me | Me | H | CF3CH2CO | H | 1 |
| 2-4890 | H | C—CF3 | C—H | C—F | C—H | CF3 | N | C—Me | H | H | EtCO | H | 1 |
| 2-4891 | H | C—CF3 | C—H | C—F | C—H | CF3 | C—H | C—Me | H | H | CF3CH2CO | H | 1 |
| 2-4892 | H | C—CF3 | C—H | C—F | C—H | CF3 | C—H | C—NO2 | H | H | H | H | 1 |
| 2-4893 | H | C—CF3 | C—H | C—F | C—H | CF3 | C—H | C—NO2 | H | H | MeCO | H | 1 |
| 2-4894 | H | C—CF3 | C—H | C—F | C—H | CF3 | C—H | C—NO2 | H | H | EtCO | H | 1 |
| 2-4895 | H | C—CF3 | C—H | C—F | C—H | CF3 | C—H | C—NO2 | H | H | CF3CH2CO | H | 1 |
| 2-4896 | H | C—CF3 | C—H | C—F | C—H | CF3 | C—H | C—NO2 | H | H | cyclo-PrCO | H | 1 |
| 2-4897 | H | C—CF3 | C—H | C—F | C—H | CF3 | C—H | C—NO2 | H | H | cyclo-PrCH2CO | H | 1 |
| 2-4898 | H | C—CF3 | C—H | C—F | C—H | CF3 | C—H | C—NO2 | H | H | CH3SCH2CO | H | 1 |
| 2-4899 | H | C—CF3 | C—H | C—F | C—H | CF3 | C—H | C—NO2 | H | H | CH3SOCH2CO | H | 1 |
| 2-4900 | H | C—CF3 | C—H | C—F | C—H | CF3 | C—H | C—NO2 | H | H | CH3SO2CH2CO | H | 1 |
| 2-4901 | H | C—CF3 | C—H | C—F | C—H | CF3 | C—H | C—NO2 | H | H | EtNHCO | H | 1 |
| 2-4902 | H | C—CF3 | C—H | C—F | C—H | CF3 | C—H | C—NO2 | Me | H | EtCO | H | 1 |
| 2-4903 | H | C—CF3 | C—H | C—F | C—H | CF3 | C—H | C—NO2 | Me | H | CF3CH2CO | H | 1 |
| 2-4904 | H | C—CF3 | C—H | C—F | C—H | CF3 | N | C—NO2 | H | H | EtCO | H | 1 |
| 2-4905 | H | C—CF3 | C—H | C—F | C—H | CF3 | C—H | C—NO2 | H | H | CF3CH2CO | H | 1 |
| 2-4906 | H | C—CF3 | C—H | C—F | C—H | CF3 | C—H | C—SMe | H | H | H | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4907 | H | C—CF3 | C—H | C—F | C—H | CF3 | C—H | C—SMe | H | H | MeCO | H | 1 |
| 2-4908 | H | C—CF3 | C—H | C—F | C—H | CF3 | C—H | C—SMe | H | H | EtCO | H | 1 |
| 2-4909 | H | C—CF3 | C—H | C—F | C—H | CF3 | C—H | C—SMe | H | H | CF3CH2CO | H | 1 |
| 2-4910 | H | C—CF3 | C—H | C—F | C—H | CF3 | C—H | C—SMe | H | H | cyclo-PrCO | H | 1 |
| 2-4911 | H | C—CF3 | C—H | C—F | C—H | CF3 | C—H | C—SMe | H | H | cyclo-PrCH2CO | H | 1 |
| 2-4912 | H | C—CF3 | C—H | C—F | C—H | CF3 | C—H | C—SMe | H | H | CH3SCH2CO | H | 1 |
| 2-4913 | H | C—CF3 | C—H | C—F | C—H | CF3 | C—H | C—SMe | H | H | CH3SOCH2CO | H | 1 |
| 2-4914 | H | C—CF3 | C—H | C—F | C—H | CF3 | C—H | C—SMe | H | H | CH3SO2CH2CO | H | 1 |
| 2-4915 | H | C—CF3 | C—H | C—F | C—H | CF3 | C—H | C—SMe | H | H | EtNHCO | H | 1 |
| 2-4916 | H | C—CF3 | C—H | C—F | C—H | CF3 | C—H | C—SMe | Me | H | EtCO | H | 1 |
| 2-4917 | H | C—CF3 | C—H | C—F | C—H | CF3 | C—H | C—SMe | Me | H | CF3CH2CO | H | 1 |
| 2-4918 | H | C—CF3 | C—H | C—F | C—H | CF3 | N | C—SMe | H | H | EtCO | H | 1 |
| 2-4919 | H | C—CF3 | C—H | C—F | C—H | CF3 | N | C—SMe | H | H | CF3CH2CO | H | 1 |
| 2-4920 | H | C—CF3 | C—H | C—F | C—H | CF3 | C—H | C—SOMe | H | H | H | H | 1 |
| 2-4921 | H | C—CF3 | C—H | C—F | C—H | CF3 | C—H | C—SOMe | H | H | MeCO | H | 1 |
| 2-4922 | H | C—CF3 | C—H | C—F | C—H | CF3 | C—H | C—SOMe | H | H | EtCO | H | 1 |
| 2-4923 | H | C—CF3 | C—H | C—F | C—H | CF3 | C—H | C—SOMe | H | H | CF3CH2CO | H | 1 |
| 2-4924 | H | C—CF3 | C—H | C—F | C—H | CF3 | C—H | C—SOMe | H | H | cyclo-PrCO | H | 1 |
| 2-4925 | H | C—CF3 | C—H | C—F | C—H | CF3 | C—H | C—SOMe | H | H | cyclo-PrCH2CO | H | 1 |
| 2-4926 | H | C—CF3 | C—H | C—F | C—H | CF3 | C—H | C—SOMe | H | H | CH3SCH2CO | H | 1 |
| 2-4927 | H | C—CF3 | C—H | C—F | C—H | CF3 | C—H | C—SOMe | H | H | CH3SOCH2CO | H | 1 |
| 2-4928 | H | C—CF3 | C—H | C—F | C—H | CF3 | C—H | C—SOMe | H | H | CH3SO2CH2CO | H | 1 |
| 2-4929 | H | C—CF3 | C—H | C—F | C—H | CF3 | C—H | C—SOMe | H | H | EtNHCO | H | 1 |
| 2-4930 | H | C—CF3 | C—H | C—F | C—H | CF3 | C—H | C—SOMe | Me | H | EtCO | H | 1 |
| 2-4931 | H | C—CF3 | C—H | C—F | C—H | CF3 | C—H | C—SOMe | Me | H | CF3CH2CO | H | 1 |
| 2-4932 | H | C—CF3 | C—H | C—F | C—H | CF3 | N | C—SOMe | H | H | EtCO | H | 1 |
| 2-4933 | H | C—CF3 | C—H | C—F | C—H | CF3 | N | C—SOMe | H | H | CF3CH2CO | H | 1 |
| 2-4934 | H | C—CF3 | C—H | C—F | C—H | CF3 | C—H | C—SO2Me | H | H | H | H | 1 |
| 2-4935 | H | C—CF3 | C—H | C—F | C—H | CF3 | C—H | C—SO2Me | H | H | MeCO | H | 1 |
| 2-4936 | H | C—CF3 | C—H | C—F | C—H | CF3 | C—H | C—SO2Me | H | H | EtCO | H | 1 |
| 2-4937 | H | C—CF3 | C—H | C—F | C—H | CF3 | C—H | C—SO2Me | H | H | CF3CH2CO | H | 1 |
| 2-4938 | H | C—CF3 | C—H | C—F | C—H | CF3 | C—H | C—SO2Me | H | H | cyclo-PrCO | H | 1 |
| 2-4939 | H | C—CF3 | C—H | C—F | C—H | CF3 | C—H | C—SO2Me | H | H | cyclo-PrCH2CO | H | 1 |
| 2-4940 | H | C—CF3 | C—H | C—F | C—H | CF3 | C—H | C—SO2Me | H | H | CH3SCH2CO | H | 1 |
| 2-4941 | H | C—CF3 | C—H | C—F | C—H | CF3 | C—H | C—SO2Me | H | H | CH3SOCH2CO | H | 1 |
| 2-4942 | H | C—CF3 | C—H | C—F | C—H | CF3 | C—H | C—SO2Me | H | H | CH3SO2CH2CO | H | 1 |
| 2-4943 | H | C—CF3 | C—H | C—F | C—H | CF3 | C—H | C—SO2Me | H | H | EtNHCO | H | 1 |
| 2-4944 | H | C—CF3 | C—H | C—F | C—H | CF3 | C—H | C—SO2Me | Me | H | EtCO | H | 1 |
| 2-4945 | H | C—CF3 | C—H | C—F | C—H | CF3 | C—H | C—SO2Me | Me | H | CF3CH2CO | H | 1 |
| 2-4946 | H | C—CF3 | C—H | C—F | C—H | CF3 | N | C—SO2Me | H | H | EtCO | H | 1 |
| 2-4947 | H | C—CF3 | C—H | C—F | C—H | CF3 | N | C—SO2Me | H | H | CF3CH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4948 | H | C—CF3 | C—H | C—F | C—H | CF3 | C—H | C—SCF3 | H | H | H | H | 1 |
| 2-4949 | H | C—CF3 | C—H | C—F | C—H | CF3 | C—H | C—SCF3 | H | H | MeCO | H | 1 |
| 2-4950 | H | C—CF3 | C—H | C—F | C—H | CF3 | C—H | C—SCF3 | H | H | EtCO | H | 1 |
| 2-4951 | H | C—CF3 | C—H | C—F | C—H | CF3 | C—H | C—SCF3 | H | H | CF3CH2CO | H | 1 |
| 2-4952 | H | C—CF3 | C—H | C—F | C—H | CF3 | C—H | C—SCF3 | H | H | cyclo-PrCO | H | 1 |
| 2-4953 | H | C—CF3 | C—H | C—F | C—H | CF3 | C—H | C—SCF3 | H | H | cyclo-PrCH2CO | H | 1 |
| 2-4954 | H | C—CF3 | C—H | C—F | C—H | CF3 | C—H | C—SCF3 | H | H | CH3SCH2CO | H | 1 |
| 2-4955 | H | C—CF3 | C—H | C—F | C—H | CF3 | C—H | C—SCF3 | H | H | CH3SOCH2CO | H | 1 |
| 2-4956 | H | C—CF3 | C—H | C—F | C—H | CF3 | C—H | C—SCF3 | H | H | CH3SO2CH2CO | H | 1 |
| 2-4957 | H | C—CF3 | C—H | C—F | C—H | CF3 | C—H | C—SCF3 | H | H | EtNHCO | H | 1 |
| 2-4958 | H | C—CF3 | C—H | C—F | C—H | CF3 | C—H | C—SCF3 | Me | H | EtCO | H | 1 |
| 2-4959 | H | C—CF3 | C—H | C—F | C—H | CF3 | C—H | C—SCF3 | Me | H | CF3CH2CO | H | 1 |
| 2-4960 | H | C—CF3 | C—H | C—F | C—H | CF3 | N | C—SCF3 | H | H | EtCO | H | 1 |
| 2-4961 | H | C—CF3 | C—H | C—F | C—H | CF3 | N | C—SCF3 | H | H | CF3CH2CO | H | 1 |
| 2-4962 | H | C—CF3 | C—H | C—F | C—H | CF3 | C—H | C—SOCF3 | H | H | H | H | 1 |
| 2-4963 | H | C—CF3 | C—H | C—F | C—H | CF3 | C—H | C—SOCF3 | H | H | MeCO | H | 1 |
| 2-4964 | H | C—CF3 | C—H | C—F | C—H | CF3 | C—H | C—SOCF3 | H | H | EtCO | H | 1 |
| 2-4965 | H | C—CF3 | C—H | C—F | C—H | CF3 | C—H | C—SOCF3 | H | H | CF3CH2CO | H | 1 |
| 2-4966 | H | C—CF3 | C—H | C—F | C—H | CF3 | C—H | C—SOCF3 | H | H | cyclo-PrCO | H | 1 |
| 2-4967 | H | C—CF3 | C—H | C—F | C—H | CF3 | C—H | C—SOCF3 | H | H | cyclo-PrCH2CO | H | 1 |
| 2-4968 | H | C—CF3 | C—H | C—F | C—H | CF3 | C—H | C—SOCF3 | H | H | CH3SCH2CO | H | 1 |
| 2-4969 | H | C—CF3 | C—H | C—F | C—H | CF3 | C—H | C—SOCF3 | H | H | CH3SOCH2CO | H | 1 |
| 2-4970 | H | C—CF3 | C—H | C—F | C—H | CF3 | C—H | C—SOCF3 | H | H | CH3SO2CH2CO | H | 1 |
| 2-4971 | H | C—CF3 | C—H | C—F | C—H | CF3 | C—H | C—SOCF3 | H | H | EtNHCO | H | 1 |
| 2-4972 | H | C—CF3 | C—H | C—F | C—H | CF3 | C—H | C—SOCF3 | Me | H | EtCO | H | 1 |
| 2-4973 | H | C—CF3 | C—H | C—F | C—H | CF3 | C—H | C—SOCF3 | Me | H | CF3CH2CO | H | 1 |
| 2-4974 | H | C—CF3 | C—H | C—F | C—H | CF3 | N | C—SOCF3 | H | H | EtCO | H | 1 |
| 2-4975 | H | C—CF3 | C—H | C—F | C—H | CF3 | N | C—SOCF3 | H | H | CF3CH2CO | H | 1 |
| 2-4976 | H | C—CF3 | C—H | C—F | C—H | CF3 | C—H | C—H | H | H | H | H | 1 |
| 2-4977 | H | C—CF3 | C—H | C—F | C—H | CF3 | C—H | C—H | H | H | MeCO | H | 1 |
| 2-4978 | H | C—CF3 | C—H | C—F | C—H | CF3 | C—H | C—H | H | H | EtCO | H | 1 |
| 2-4979 | H | C—CF3 | C—H | C—F | C—H | CF3 | C—H | C—H | H | H | CF3CH2CO | H | 1 |
| 2-4980 | H | C—CF3 | C—H | C—F | C—H | CF3 | C—H | C—H | H | H | cyclo-PrCO | H | 1 |
| 2-4981 | H | C—CF3 | C—H | C—F | C—H | CF3 | C—H | C—H | H | H | cyclo-PrCH2CO | H | 1 |
| 2-4982 | H | C—CF3 | C—H | C—F | C—H | CF3 | C—H | C—H | H | H | CH3SCH2CO | H | 1 |
| 2-4983 | H | C—CF3 | C—H | C—F | C—H | CF3 | C—H | C—H | H | H | CH3SOCH2CO | H | 1 |
| 2-4984 | H | C—CF3 | C—H | C—F | C—H | CF3 | C—H | C—H | H | H | CH3SO2CH2CO | H | 1 |
| 2-4985 | H | C—CF3 | C—H | C—F | C—H | CF3 | C—H | C—H | H | H | EtNHCO | H | 1 |
| 2-4986 | H | C—CF3 | C—H | C—F | C—H | CF3 | C—H | C—H | Me | H | H | H | 1 |
| 2-4987 | H | C—CF3 | C—H | C—F | C—H | CF3 | C—H | C—H | Me | H | EtCO | H | 1 |
| 2-4988 | H | C—CF3 | C—H | C—F | C—H | CF3 | C—H | C—H | Me | H | CF3CH2CO | H | 1 |

TABLE 2-1-continued

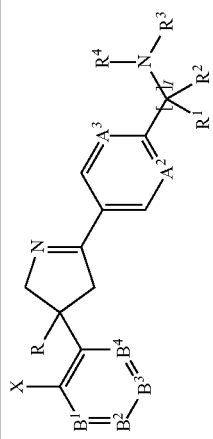

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4989 | H | C—CF3 | C—H | C—F | C—H | CF3 | C—H | C—H | Me | H | CH3SCH2CO | H | 1 |
| 2-4990 | H | C—CF3 | C—H | C—F | C—H | CF3 | N | C—H | H | H | H | H | 1 |
| 2-4991 | H | C—CF3 | C—H | C—F | C—H | CF3 | N | C—H | H | H | EtCO | H | 1 |
| 2-4992 | H | C—CF3 | C—H | C—F | C—H | CF3 | N | C—H | H | H | CF3CH2CO | H | 1 |
| 2-4993 | H | C—CF3 | C—H | C—F | C—H | CF3 | C—H | C—F | H | H | CH3SCH2CO | H | 1 |
| 2-4994 | H | C—CF3 | C—H | C—F | C—H | CF3 | C—H | C—F | H | H | H | H | 1 |
| 2-4995 | H | C—CF3 | C—H | C—F | C—H | CF3 | C—H | C—F | H | H | MeCO | H | 1 |
| 2-4996 | H | C—CF3 | C—H | C—F | C—H | CF3 | C—H | C—F | H | H | EtCO | H | 1 |
| 2-4997 | H | C—CF3 | C—H | C—F | C—H | CF3 | C—H | C—F | H | H | CF3CH2CO | H | 1 |
| 2-4998 | H | C—CF3 | C—H | C—F | C—H | CF3 | C—H | C—F | H | H | cyclo-PrCO | H | 1 |
| 2-4999 | H | C—CF3 | C—H | C—F | C—H | CF3 | C—H | C—F | H | H | cyclo-PrCH2CO | H | 1 |
| 2-5000 | H | C—CF3 | C—H | C—F | C—H | CF3 | C—H | C—F | H | H | CH3SCH2CO | H | 1 |
| 2-5001 | H | C—CF3 | C—H | C—F | C—H | CF3 | C—H | C—F | H | H | CH3SOCH2CO | H | 1 |
| 2-5002 | H | C—CF3 | C—H | C—F | C—H | CF3 | C—H | C—F | H | H | CH3SO2CH2CO | H | 1 |
| 2-5003 | H | C—CF3 | C—H | C—F | C—H | CF3 | C—H | C—F | H | H | EtNHCO | H | 1 |
| 2-5004 | H | C—CF3 | C—H | C—F | C—H | CF3 | C—H | C—F | Me | H | CF3CH2CO | H | 1 |
| 2-5005 | H | C—CF3 | C—H | C—F | C—H | CF3 | C—H | C—F | Me | H | EtCO | H | 1 |
| 2-5006 | H | C—CF3 | C—H | C—F | C—H | CF3 | C—H | C—F | H | H | EtCO | H | 1 |
| 2-5007 | H | C—CF3 | C—H | C—F | C—H | CF3 | C—H | C—F | H | H | CF3CH2CO | H | 1 |
| 2-5008 | H | C—CF3 | C—H | C—F | C—H | CF3 | C—H | C—I | H | H | H | H | 1 |
| 2-5009 | H | C—CF3 | C—H | C—F | C—H | CF3 | C—H | C—I | H | H | MeCO | H | 1 |
| 2-5010 | H | C—CF3 | C—H | C—F | C—H | CF3 | C—H | C—I | H | H | EtCO | H | 1 |
| 2-5011 | H | C—CF3 | C—H | C—F | C—H | CF3 | C—H | C—I | H | H | CF3CH2CO | H | 1 |
| 2-5012 | H | C—CF3 | C—H | C—F | C—H | CF3 | C—H | C—I | H | H | cyclo-PrCO | H | 1 |
| 2-5013 | H | C—CF3 | C—H | C—F | C—H | CF3 | C—H | C—I | H | H | cyclo-PrCH2CO | H | 1 |
| 2-5014 | H | C—CF3 | C—H | C—F | C—H | CF3 | C—H | C—I | H | H | CH3SCH2CO | H | 1 |
| 2-5015 | H | C—CF3 | C—H | C—F | C—H | CF3 | C—H | C—I | H | H | CH3SOCH2CO | H | 1 |
| 2-5016 | H | C—CF3 | C—H | C—F | C—H | CF3 | C—H | C—I | H | H | CH3SO2CH2CO | H | 1 |
| 2-5017 | H | C—CF3 | C—H | C—F | C—H | CF3 | C—H | C—I | H | H | EtNHCO | H | 1 |
| 2-5018 | H | C—CF3 | C—H | C—F | C—H | CF3 | C—H | C—I | Me | H | EtCO | H | 1 |
| 2-5019 | H | C—CF3 | C—H | C—F | C—H | CF3 | C—H | C—I | Me | H | CF3CH2CO | H | 1 |
| 2-5020 | H | C—CF3 | C—H | C—F | C—H | CF3 | N | C—I | H | H | EtCO | H | 1 |
| 2-5021 | H | C—CF3 | C—H | C—F | C—H | CF3 | C—H | C—NH2 | H | H | H | H | 1 |
| 2-5022 | H | C—CF3 | C—H | C—F | C—H | CF3 | C—H | C—NH2 | H | H | MeCO | H | 1 |
| 2-5023 | H | C—CF3 | C—H | C—F | C—H | CF3 | C—H | C—NH2 | H | H | EtCO | H | 1 |
| 2-5024 | H | C—CF3 | C—H | C—F | C—H | CF3 | C—H | C—NH2 | H | H | CF3CH2CO | H | 1 |
| 2-5025 | H | C—CF3 | C—H | C—F | C—H | CF3 | C—H | C—NH2 | H | H | cyclo-PrCO | H | 1 |
| 2-5026 | H | C—CF3 | C—H | C—F | C—H | CF3 | C—H | C—NH2 | H | H | cyclo-PrCH2CO | H | 1 |
| 2-5027 | H | C—CF3 | C—H | C—F | C—H | CF3 | C—H | C—NH2 | H | H | CH3SCH2CO | H | 1 |
| 2-5028 | H | C—CF3 | C—H | C—F | C—H | CF3 | C—H | C—NH2 | H | H | CH3SOCH2CO | H | 1 |
| 2-5029 | H | C—CF3 | C—H | C—F | C—H | CF3 | C—H | C—NH2 | H | H | CH3SOCH2CO | H | 1 |

TABLE 2-1-continued

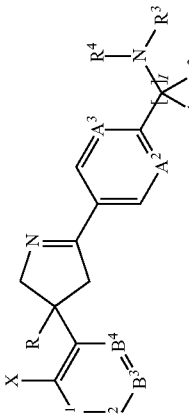

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-5030 | H | C—CF3 | C—H | C—F | C—H | CF3 | C—H | C—NH2 | H | H | CH3SO2CH2CO | H | 1 |
| 2-5031 | H | C—CF3 | C—H | C—F | C—H | CF3 | C—H | C—NH2 | H | H | EtNHCO | H | 1 |
| 2-5032 | H | C—CF3 | C—H | C—F | C—H | CF3 | C—H | C—NH2 | Me | H | EtCO | H | 1 |
| 2-5033 | H | C—CF3 | C—H | C—F | C—H | CF3 | C—H | C—NH2 | Me | H | CF3CH2CO | H | 1 |
| 2-5034 | H | C—CF3 | C—H | C—F | C—H | CF3 | N | C—NH2 | H | H | EtCO | H | 1 |
| 2-5035 | H | C—CF3 | C—H | C—F | C—H | CF3 | N | C—NH2 | H | H | CF3CH2CO | H | 1 |
| 2-5036 | H | C—CF3 | C—H | C—F | C—H | CF3 | C—H | C—NHAc | H | H | H | H | 1 |
| 2-5037 | H | C—CF3 | C—H | C—F | C—H | CF3 | C—H | C—NHAc | H | H | MeCO | H | 1 |
| 2-5038 | H | C—CF3 | C—H | C—F | C—H | CF3 | C—H | C—NHAc | H | H | EtCO | H | 1 |
| 2-5039 | H | C—CF3 | C—H | C—F | C—H | CF3 | C—H | C—NHAc | H | H | CF3CH2CO | H | 1 |
| 2-5040 | H | C—CF3 | C—H | C—F | C—H | CF3 | C—H | C—NHAc | H | H | cyclo-PrCO | H | 1 |
| 2-5041 | H | C—CF3 | C—H | C—F | C—H | CF3 | C—H | C—NHAc | H | H | cyclo-PrCH2CO | H | 1 |
| 2-5042 | H | C—CF3 | C—H | C—F | C—H | CF3 | C—H | C—NHAc | H | H | CH3SCH2CO | H | 1 |
| 2-5043 | H | C—CF3 | C—H | C—F | C—H | CF3 | C—H | C—NHAc | H | H | CH3SOCH2CO | H | 1 |
| 2-5044 | H | C—CF3 | C—H | C—F | C—H | CF3 | C—H | C—NHAc | H | H | CH3SO2CH2CO | H | 1 |
| 2-5045 | H | C—CF3 | C—H | C—F | C—H | CF3 | C—H | C—NHAc | H | H | EtNHCO | H | 1 |
| 2-5046 | H | C—CF3 | C—H | C—F | C—H | CF3 | C—H | C—NHAc | Me | H | EtCO | H | 1 |
| 2-5047 | H | C—CF3 | C—H | C—F | C—H | CF3 | C—H | C—NHAc | Me | H | CF3CH2CO | H | 1 |
| 2-5048 | H | C—CF3 | C—H | C—F | C—H | CF3 | N | C—NHAc | H | H | EtCO | H | 1 |
| 2-5049 | H | C—CF3 | C—H | C—F | C—H | CF3 | N | C—NHAc | H | H | CF3CH2CO | H | 1 |
| 2-5050 | H | C—CF3 | C—H | C—F | C—H | CF3 | C—H | C—NHCOCF3 | H | H | H | H | 1 |
| 2-5051 | H | C—CF3 | C—H | C—F | C—H | CF3 | C—H | C—NHCOCF3 | H | H | MeCO | H | 1 |
| 2-5052 | H | C—CF3 | C—H | C—F | C—H | CF3 | C—H | C—NHCOCF3 | H | H | EtCO | H | 1 |
| 2-5053 | H | C—CF3 | C—H | C—F | C—H | CF3 | C—H | C—NHCOCF3 | H | H | CF3CH2CO | H | 1 |
| 2-5054 | H | C—CF3 | C—H | C—F | C—H | CF3 | C—H | C—NHCOCF3 | H | H | cyclo-PrCO | H | 1 |
| 2-5055 | H | C—CF3 | C—H | C—F | C—H | CF3 | C—H | C—NHCOCF3 | H | H | cyclo-PrCH2CO | H | 1 |
| 2-5056 | H | C—CF3 | C—H | C—F | C—H | CF3 | C—H | C—NHCOCF3 | H | H | CH3SCH2CO | H | 1 |
| 2-5057 | H | C—CF3 | C—H | C—F | C—H | CF3 | C—H | C—NHCOCF3 | H | H | CH3SOCH2CO | H | 1 |
| 2-5058 | H | C—CF3 | C—H | C—F | C—H | CF3 | C—H | C—NHCOCF3 | H | H | CH3SO2CH2CO | H | 1 |
| 2-5059 | H | C—CF3 | C—H | C—F | C—H | CF3 | C—H | C—NHCOCF3 | H | H | EtNHCO | H | 1 |
| 2-5060 | H | C—CF3 | C—H | C—F | C—H | CF3 | C—H | C—NHCOCF3 | Me | H | EtCO | H | 1 |
| 2-5061 | H | C—CF3 | C—H | C—F | C—H | CF3 | C—H | C—NHCOCF3 | Me | H | CF3CH2CO | H | 1 |
| 2-5062 | H | C—CF3 | C—H | C—F | C—H | CF3 | N | C—NHCOCF3 | H | H | EtCO | H | 1 |
| 2-5063 | H | C—CF3 | C—H | C—F | C—H | CF3 | C—H | C—NHCOCF3 | H | H | CF3CH2CO | H | 1 |
| 2-5064 | H | C—CF3 | C—H | C—F | C—H | CF3 | C—H | C—CH2OAc | H | H | H | H | 1 |
| 2-5065 | H | C—CF3 | C—H | C—F | C—H | CF3 | C—H | C—CH2OAc | H | H | MeCO | H | 1 |
| 2-5066 | H | C—CF3 | C—H | C—F | C—H | CF3 | C—H | C—CH2OAc | H | H | EtCO | H | 1 |
| 2-5067 | H | C—CF3 | C—H | C—F | C—H | CF3 | C—H | C—CH2OAc | H | H | CF3CH2CO | H | 1 |
| 2-5068 | H | C—CF3 | C—H | C—F | C—H | CF3 | C—H | C—CH2OAc | H | H | cyclo-PrCO | H | 1 |
| 2-5069 | H | C—CF3 | C—H | C—F | C—H | CF3 | C—H | C—CH2OAc | H | H | cyclo-PrCH2CO | H | 1 |
| 2-5070 | H | C—CF3 | C—H | C—F | C—H | CF3 | C—H | C—CH2OAc | H | H | CH3SCH2CO | H | 1 |

TABLE 2-1-continued

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-5071 | H | C—CF3 | C—H | C—F | C—H | CF3 | C—H | C—CH2OAc | H | H | CH3SOCH2CO | H | 1 |
| 2-5072 | H | C—CF3 | C—H | C—F | C—H | CF3 | C—H | C—CH2OAc | H | H | CH3SO2CH2CO | H | 1 |
| 2-5073 | H | C—CF3 | C—H | C—F | C—H | CF3 | C—H | C—CH2OAc | H | H | EtNHCO | H | 1 |
| 2-5074 | H | C—CF3 | C—H | C—F | C—H | CF3 | C—H | C—CH2OAc | Me | H | EtCO | H | 1 |
| 2-5075 | H | C—CF3 | C—H | C—F | C—H | CF3 | C—H | C—CH2OAc | Me | H | CF3CH2CO | H | 1 |
| 2-5076 | H | C—CF3 | C—H | C—F | C—H | CF3 | N | C—CH2OAc | H | H | EtCO | H | 1 |
| 2-5077 | H | C—CF3 | C—H | C—F | C—H | CF3 | N | C—CH2OAc | H | H | CF3CH2CO | H | 1 |
| 2-5078 | H | C—Br | C—H | C—H | C—H | CF3 | C—H | C—CF3 | H | H | H | H | 1 |
| 2-5079 | H | C—Br | C—H | C—H | C—H | CF3 | C—H | C—CF3 | H | H | EtCO | H | 1 |
| 2-5080 | H | C—Br | C—H | C—F | C—H | CF3 | C—H | C—CF3 | H | H | CF3CH2CO | H | 1 |
| 2-5081 | H | C—Br | C—H | C—F | C—H | CF3 | C—H | C—CF3 | H | H | H | H | 1 |
| 2-5082 | H | C—Br | C—H | C—F | C—H | CF3 | C—H | C—CF3 | H | H | EtCO | H | 1 |
| 2-5083 | H | C—Cl | C—Me | C—Cl | C—H | CF3 | C—H | C—CF3 | H | H | CF3CH2CO | H | 1 |
| 2-5084 | H | C—Cl | C—Me | C—Cl | C—H | CF3 | C—H | C—CF3 | H | H | H | H | 1 |
| 2-5085 | H | C—Cl | C—Me | C—Cl | C—H | CF3 | C—H | C—CF3 | H | H | EtCO | H | 1 |
| 2-5086 | H | C—CF3 | C—H | C—CF3 | C—H | CF3 | C—H | C—CH2OH | H | H | EtCO | H | 1 |
| 2-5087 | H | C—Cl | C—H | C—Cl | C—H | CF3 | C—H | C—CH2OH | H | H | CF3CH2CO | H | 1 |
| 2-5088 | H | C—Cl | C—Cl | C—Cl | C—H | CF3 | C—H | C—CH2OH | H | H | EtCO | H | 1 |
| 2-5089 | H | C—Cl | C—Cl | C—Cl | C—H | CF3 | C—H | C—CH2OH | H | H | EtCO | H | 1 |
| 2-5090 | H | C—Cl | C—Cl | C—Cl | C—H | CF3 | C—H | C—CH2OH | H | H | CF3CH2CO | H | 1 |

TABLE 2-2

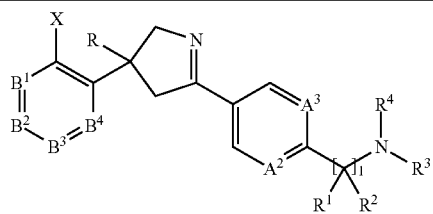

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-2149 | H | C—Cl | N | C—Cl | C—H | CF₃ | C—H | C—CF₃ | H | H | H | H | 1 |
| 2-2150 | H | C—Cl | N | C—Cl | C—H | CF₃ | C—H | C—CF₃ | H | H | MeCO | H | 1 |
| 2-2151 | H | C—Cl | N | C—Cl | C—H | CF₃ | C—H | C—CF₃ | H | H | EtCO | H | 1 |
| 2-2152 | H | C—Cl | N | C—Cl | C—H | CF₃ | C—H | C—CF₃ | H | H | n-PrCO | H | 1 |
| 2-2153 | H | C—Cl | N | C—Cl | C—H | CF₃ | C—H | C—CF₃ | H | H | cyclo-PrCO | H | 1 |
| 2-2154 | H | C—Cl | N | C—Cl | C—H | CF₃ | C—H | C—CF₃ | H | H | EtNHCO | H | 1 |
| 2-2155 | H | C—Cl | N | C—Cl | C—H | CF₃ | C—H | C—CF₃ | H | H | CF3CH2CO | H | 1 |
| 2-2156 | H | C—Cl | N | C—Cl | C—H | CF₃ | C—H | C—CF₃ | H | H | cyclo-PrCH2CO | H | 1 |
| 2-2157 | H | C—Cl | N | C—Cl | C—H | CF₃ | C—H | C—CF₃ | H | H | CH3SCH2CO | H | 1 |
| 2-2158 | H | C—Cl | N | C—Cl | C—H | CF₃ | C—H | C—CF₃ | H | H | CH3SOCH2CO | H | 1 |
| 2-2159 | H | C—Cl | N | C—Cl | C—H | CF₃ | C—H | C—CF₃ | H | H | CH3SO2CH2CO | H | 1 |
| 2-2160 | H | C—Cl | N | C—Cl | C—H | CF₃ | C—H | C—CF₃ | H | H | CH3OCH2CH2CO | H | 1 |
| 2-2161 | H | C—Cl | N | C—Cl | C—H | CF₃ | C—H | C—CF₃ | H | H | CH3OCH(Me)CH2CO | H | 1 |
| 2-2162 | H | C—Cl | N | C—Cl | C—H | CF₃ | C—H | C—CF₃ | Me | H | H | H | 1 |
| 2-2163 | H | C—Cl | N | C—Cl | C—H | CF₃ | C—H | C—CF₃ | Me | H | EtCO | H | 1 |
| 2-2164 | H | C—Cl | N | C—Cl | C—H | CF₃ | C—H | C—CF₃ | Me | H | CF3CH2CO | H | 1 |
| 2-2165 | H | C—Cl | N | C—Cl | C—H | CF₃ | C—H | C—CF₃ | Me | H | CH3SCH2CO | H | 1 |
| 2-2166 | H | C—Cl | N | C—Cl | C—H | CF₃ | N | C—CF₃ | H | H | H | H | 1 |
| 2-2167 | H | C—Cl | N | C—Cl | C—H | CF₃ | N | C—CF₃ | H | H | EtCO | H | 1 |
| 2-2168 | H | C—Cl | N | C—Cl | C—H | CF₃ | N | C—CF₃ | H | H | CF3CH2CO | H | 1 |
| 2-2169 | H | C—Cl | N | C—Cl | C—H | CF₃ | N | C—CF₃ | H | H | CH3SCH2CO | H | 1 |
| 2-2170 | H | C—Cl | N | C—Cl | C—H | CF₃ | C—H | C—Cl | H | H | H | H | 1 |
| 2-2171 | H | C—Cl | N | C—Cl | C—H | CF₃ | C—H | C—Cl | H | H | MeCO | H | 1 |
| 2-2172 | H | C—Cl | N | C—Cl | C—H | CF₃ | C—H | C—Cl | H | H | CF3CH2CO | H | 1 |
| 2-2173 | H | C—Cl | N | C—Cl | C—H | CF₃ | C—H | C—Cl | H | H | cyclo-PrCO | H | 1 |
| 2-2174 | H | C—Cl | N | C—Cl | C—H | CF₃ | C—H | C—Cl | H | H | cyclo-PrCH2CO | H | 1 |
| 2-2175 | H | C—Cl | N | C—Cl | C—H | CF₃ | C—H | C—Cl | H | H | CH3SCH2CO | H | 1 |
| 2-2176 | H | C—Cl | N | C—Cl | C—H | CF₃ | C—H | C—Cl | H | H | CH3SOCH2CO | H | 1 |
| 2-2177 | H | C—Cl | N | C—Cl | C—H | CF₃ | C—H | C—Cl | H | H | CH3SO2CH2CO | H | 1 |
| 2-2178 | H | C—Cl | N | C—Cl | C—H | CF₃ | C—H | C—Cl | H | H | CH3OCH2CH2CO | H | 1 |
| 2-2179 | H | C—Cl | N | C—Cl | C—H | CF₃ | C—H | C—Cl | H | H | CH3OCH(Me)CH2CO | H | 1 |
| 2-2180 | H | C—Cl | N | C—Cl | C—H | CF₃ | C—H | C—Cl | H | H | EtNHCO | H | 1 |
| 2-2181 | H | C—Cl | N | C—Cl | C—H | CF₃ | C—H | C—Cl | Me | H | H | H | 1 |
| 2-2182 | H | C—Cl | N | C—Cl | C—H | CF₃ | C—H | C—Cl | Me | H | EtCO | H | 1 |
| 2-2183 | H | C—Cl | N | C—Cl | C—H | CF₃ | C—H | C—Cl | Me | H | CF3CH2CO | H | 1 |
| 2-2184 | H | C—Cl | N | C—Cl | C—H | CF₃ | C—H | C—Cl | Me | H | CH3SCH2CO | H | 1 |
| 2-2185 | H | C—Cl | N | C—Cl | C—H | CF₃ | N | C—Cl | H | H | H | H | 1 |
| 2-2186 | H | C—Cl | N | C—Cl | C—H | CF₃ | N | C—Cl | H | H | EtCO | H | 1 |
| 2-2187 | H | C—Cl | N | C—Cl | C—H | CF₃ | N | C—Cl | H | H | CF3CH2CO | H | 1 |
| 2-2188 | H | C—Cl | N | C—Cl | C—H | CF₃ | N | C—Cl | H | H | CH3SCH2CO | H | 1 |
| 2-2189 | H | C—Cl | N | C—Cl | C—H | CF₃ | C—H | C—Br | H | H | H | H | 1 |
| 2-2190 | H | C—Cl | N | C—Cl | C—H | CF₃ | C—H | C—Br | H | H | MeCO | H | 1 |
| 2-2191 | H | C—Cl | N | C—Cl | C—H | CF₃ | C—H | C—Br | H | H | EtCO | H | 1 |
| 2-2192 | H | C—Cl | N | C—Cl | C—H | CF₃ | C—H | C—Br | H | H | CF3CH2CO | H | 1 |
| 2-2193 | H | C—Cl | N | C—Cl | C—H | CF₃ | C—H | C—Br | H | H | cyclo-PrCO | H | 1 |
| 2-2194 | H | C—Cl | N | C—Cl | C—H | CF₃ | C—H | C—Br | H | H | cyclo-PrCH2CO | H | 1 |
| 2-2195 | H | C—Cl | N | C—Cl | C—H | CF₃ | C—H | C—Br | H | H | CH3SCH2CO | H | 1 |
| 2-2196 | H | C—Cl | N | C—Cl | C—H | CF₃ | C—H | C—Br | H | H | CH3SOCH2CO | H | 1 |
| 2-2197 | H | C—Cl | N | C—Cl | C—H | CF₃ | C—H | C—Br | H | H | CH3SO2CH2CO | H | 1 |
| 2-2198 | H | C—Cl | N | C—Cl | C—H | CF₃ | C—H | C—Br | H | H | EtNHCO | H | 1 |
| 2-2199 | H | C—Cl | N | C—Cl | C—H | CF₃ | C—H | C—Br | Me | H | H | H | 1 |
| 2-2200 | H | C—Cl | N | C—Cl | C—H | CF₃ | C—H | C—Br | Me | H | EtCO | H | 1 |
| 2-2201 | H | C—Cl | N | C—Cl | C—H | CF₃ | C—H | C—Br | Me | H | CF3CH2CO | H | 1 |
| 2-2202 | H | C—Cl | N | C—Cl | C—H | CF₃ | C—H | C—Br | Me | H | CH3SCH2CO | H | 1 |
| 2-2203 | H | C—Cl | N | C—Cl | C—H | CF₃ | N | C—Br | H | H | H | H | 1 |
| 2-2204 | H | C—Cl | N | C—Cl | C—H | CF₃ | N | C—Br | H | H | EtCO | H | 1 |
| 2-2205 | H | C—Cl | N | C—Cl | C—H | CF₃ | N | C—Br | H | H | CF3CH2CO | H | 1 |
| 2-2206 | H | C—Cl | N | C—Cl | C—H | CF₃ | N | C—Br | H | H | CH3SCH2CO | H | 1 |
| 2-2207 | H | C—Cl | N | C—Cl | C—H | CF₃ | C—H | C—CN | H | H | H | H | 1 |
| 2-2208 | H | C—Cl | N | C—Cl | C—H | CF₃ | C—H | C—CN | H | H | MeCO | H | 1 |
| 2-2209 | H | C—Cl | N | C—Cl | C—H | CF₃ | C—H | C—CN | H | H | EtCO | H | 1 |
| 2-2210 | H | C—Cl | N | C—Cl | C—H | CF₃ | C—H | C—CN | H | H | CF3CH2CO | H | 1 |
| 2-2211 | H | C—Cl | N | C—Cl | C—H | CF₃ | C—H | C—CN | H | H | cyclo-PrCO | H | 1 |
| 2-2212 | H | C—Cl | N | C—Cl | C—H | CF₃ | C—H | C—CN | H | H | cyclo-PrCH2CO | H | 1 |
| 2-2213 | H | C—Cl | N | C—Cl | C—H | CF₃ | C—H | C—CN | H | H | CH3SCH2CO | H | 1 |
| 2-2214 | H | C—Cl | N | C—Cl | C—H | CF₃ | C—H | C—CN | H | H | CH3SOCH2CO | H | 1 |
| 2-2215 | H | C—Cl | N | C—Cl | C—H | CF₃ | C—H | C—CN | H | H | CH3SO2CH2CO | H | 1 |

TABLE 2-2-continued

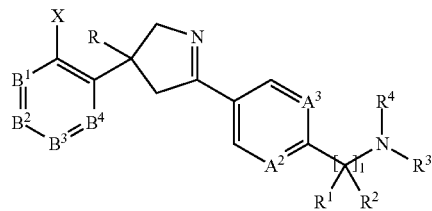

| Example No. | X | B$^1$ | B$^2$ | B$^3$ | B$^4$ | R | A$^2$ | A$^3$ | R$^1$ | R$^2$ | R$^4$ | R$^3$ | I |
|---|---|---|---|---|---|---|---|---|---|---|---|---|---|
| 2-2216 | H | C—Cl | N | C—Cl | C—H | CF$_3$ | C—H | C—CN | H | H | EtNHCO | H | 1 |
| 2-2217 | H | C—Cl | N | C—Cl | C—H | CF$_3$ | C—H | C—CN | Me | H | EtCO | H | 1 |
| 2-2218 | H | C—Cl | N | C—Cl | C—H | CF$_3$ | C—H | C—CN | Me | H | CF3CH2CO | H | 1 |
| 2-2219 | H | C—Cl | N | C—Cl | C—H | CF$_3$ | N | C—CN | H | H | EtCO | H | 1 |
| 2-2220 | H | C—Cl | N | C—Cl | C—H | CF$_3$ | N | C—CN | H | H | CF3CH2CO | H | 1 |
| 2-2221 | H | C—Cl | N | C—Cl | C—H | CF$_3$ | C—H | C—Me | H | H | H | H | 1 |
| 2-2222 | H | C—Cl | N | C—Cl | C—H | CF$_3$ | C—H | C—Me | H | H | MeCO | H | 1 |
| 2-2223 | H | C—Cl | N | C—Cl | C—H | CF$_3$ | C—H | C—Me | H | H | EtCO | H | 1 |
| 2-2224 | H | C—Cl | N | C—Cl | C—H | CF$_3$ | C—H | C—Me | H | H | CF3CH2CO | H | 1 |
| 2-2225 | H | C—Cl | N | C—Cl | C—H | CF$_3$ | C—H | C—Me | H | H | cyclo-PrCO | H | 1 |
| 2-2226 | H | C—Cl | N | C—Cl | C—H | CF$_3$ | C—H | C—Me | H | H | cyclo-PrCH2CO | H | 1 |
| 2-2227 | H | C—Cl | N | C—Cl | C—H | CF$_3$ | C—H | C—Me | H | H | CH3SCH2CO | H | 1 |
| 2-2228 | H | C—Cl | N | C—Cl | C—H | CF$_3$ | C—H | C—Me | H | H | CH3SOCH2CO | H | 1 |
| 2-2229 | H | C—Cl | N | C—Cl | C—H | CF$_3$ | C—H | C—Me | H | H | CH3SO2CH2CO | H | 1 |
| 2-2230 | H | C—Cl | N | C—Cl | C—H | CF$_3$ | C—H | C—Me | H | H | CH3OCH2CH2CO | H | 1 |
| 2-2231 | H | C—Cl | N | C—Cl | C—H | CF$_3$ | C—H | C—Me | H | H | CH3OCH(Me)CH2CO | H | 1 |
| 2-2232 | H | C—Cl | N | C—Cl | C—H | CF$_3$ | C—H | C—Me | H | H | EtNHCO | H | 1 |
| 2-2233 | H | C—Cl | N | C—Cl | C—H | CF$_3$ | C—H | C—Me | Me | H | EtCO | H | 1 |
| 2-2234 | H | C—Cl | N | C—Cl | C—H | CF$_3$ | C—H | C—Me | Me | H | CF3CH2CO | H | 1 |
| 2-2235 | H | C—Cl | N | C—Cl | C—H | CF$_3$ | N | C—Me | H | H | EtCO | H | 1 |
| 2-2236 | H | C—Cl | N | C—Cl | C—H | CF$_3$ | N | C—Me | H | H | CF3CH2CO | H | 1 |
| 2-2237 | H | C—Cl | N | C—Cl | C—H | CF$_3$ | C—H | C—NO2 | H | H | H | H | 1 |
| 2-2238 | H | C—Cl | N | C—Cl | C—H | CF$_3$ | C—H | C—NO2 | H | H | MeCO | H | 1 |
| 2-2239 | H | C—Cl | N | C—Cl | C—H | CF$_3$ | C—H | C—NO2 | H | H | EtCO | H | 1 |
| 2-2240 | H | C—Cl | N | C—Cl | C—H | CF$_3$ | C—H | C—NO2 | H | H | CF3CH2CO | H | 1 |
| 2-2241 | H | C—Cl | N | C—Cl | C—H | CF$_3$ | C—H | C—NO2 | H | H | cyclo-PrCO | H | 1 |
| 2-2242 | H | C—Cl | N | C—Cl | C—H | CF$_3$ | C—H | C—NO2 | H | H | cyclo-PrCH2CO | H | 1 |
| 2-2243 | H | C—Cl | N | C—Cl | C—H | CF$_3$ | C—H | C—NO2 | H | H | CH3SCH2CO | H | 1 |
| 2-2244 | H | C—Cl | N | C—Cl | C—H | CF$_3$ | C—H | C—NO2 | H | H | CH3SOCH2CO | H | 1 |
| 2-2245 | H | C—Cl | N | C—Cl | C—H | CF$_3$ | C—H | C—NO2 | H | H | CH3SO2CH2CO | H | 1 |
| 2-2246 | H | C—Cl | N | C—Cl | C—H | CF$_3$ | C—H | C—NO2 | H | H | CH3OCH2CH2CO | H | 1 |
| 2-2247 | H | C—Cl | N | C—Cl | C—H | CF$_3$ | C—H | C—NO2 | H | H | CH3OCH(Me)CH2CO | H | 1 |
| 2-2248 | H | C—Cl | N | C—Cl | C—H | CF$_3$ | C—H | C—NO2 | H | H | EtNHCO | H | 1 |
| 2-2249 | H | C—Cl | N | C—Cl | C—H | CF$_3$ | C—H | C—NO2 | Me | H | EtCO | H | 1 |
| 2-2250 | H | C—Cl | N | C—Cl | C—H | CF$_3$ | C—H | C—NO2 | Me | H | CF3CH2CO | H | 1 |
| 2-2251 | H | C—Cl | N | C—Cl | C—H | CF$_3$ | N | C—NO2 | H | H | EtCO | H | 1 |
| 2-2252 | H | C—Cl | N | C—Cl | C—H | CF$_3$ | N | C—NO2 | H | H | CF3CH2CO | H | 1 |
| 2-2253 | H | C—Cl | N | C—Cl | C—H | CF$_3$ | C—H | C—SMe | H | H | H | H | 1 |
| 2-2254 | H | C—Cl | N | C—Cl | C—H | CF$_3$ | C—H | C—SMe | H | H | MeCO | H | 1 |
| 2-2255 | H | C—Cl | N | C—Cl | C—H | CF$_3$ | C—H | C—SMe | H | H | EtCO | H | 1 |
| 2-2256 | H | C—Cl | N | C—Cl | C—H | CF$_3$ | C—H | C—SMe | H | H | CF3CH2CO | H | 1 |
| 2-2257 | H | C—Cl | N | C—Cl | C—H | CF$_3$ | C—H | C—SMe | H | H | cyclo-PrCO | H | 1 |
| 2-2258 | H | C—Cl | N | C—Cl | C—H | CF$_3$ | C—H | C—SMe | H | H | cyclo-PrCH2CO | H | 1 |
| 2-2259 | H | C—Cl | N | C—Cl | C—H | CF$_3$ | C—H | C—SMe | H | H | CH3SCH2CO | H | 1 |
| 2-2260 | H | C—Cl | N | C—Cl | C—H | CF$_3$ | C—H | C—SMe | H | H | CH3SOCH2CO | H | 1 |
| 2-2261 | H | C—Cl | N | C—Cl | C—H | CF$_3$ | C—H | C—SMe | H | H | CH3SO2CH2CO | H | 1 |
| 2-2262 | H | C—Cl | N | C—Cl | C—H | CF$_3$ | C—H | C—SMe | H | H | CH3OCH2CH2CO | H | 1 |
| 2-2263 | H | C—Cl | N | C—Cl | C—H | CF$_3$ | C—H | C—SMe | H | H | CH3OCH(Me)CH2CO | H | 1 |
| 2-2264 | H | C—Cl | N | C—Cl | C—H | CF$_3$ | C—H | C—SMe | H | H | EtNHCO | H | 1 |
| 2-2265 | H | C—Cl | N | C—Cl | C—H | CF$_3$ | C—H | C—SMe | Me | H | EtCO | H | 1 |
| 2-2266 | H | C—Cl | N | C—Cl | C—H | CF$_3$ | C—H | C—SMe | Me | H | CF3CH2CO | H | 1 |
| 2-2267 | H | C—Cl | N | C—Cl | C—H | CF$_3$ | N | C—SMe | H | H | EtCO | H | 1 |
| 2-2268 | H | C—Cl | N | C—Cl | C—H | CF$_3$ | N | C—SMe | H | H | CF3CH2CO | H | 1 |
| 2-2269 | H | C—Cl | N | C—Cl | C—H | CF$_3$ | C—H | C—SOMe | H | H | H | H | 1 |
| 2-2270 | H | C—Cl | N | C—Cl | C—H | CF$_3$ | C—H | C—SOMe | H | H | MeCO | H | 1 |
| 2-2271 | H | C—Cl | N | C—Cl | C—H | CF$_3$ | C—H | C—SOMe | H | H | EtCO | H | 1 |
| 2-2272 | H | C—Cl | N | C—Cl | C—H | CF$_3$ | C—H | C—SOMe | H | H | CF3CH2CO | H | 1 |
| 2-2273 | H | C—Cl | N | C—Cl | C—H | CF$_3$ | C—H | C—SOMe | H | H | cyclo-PrCO | H | 1 |
| 2-2274 | H | C—Cl | N | C—Cl | C—H | CF$_3$ | C—H | C—SOMe | H | H | cyclo-PrCH2CO | H | 1 |
| 2-2275 | H | C—Cl | N | C—Cl | C—H | CF$_3$ | C—H | C—SOMe | H | H | CH3SCH2CO | H | 1 |
| 2-2276 | H | C—Cl | N | C—Cl | C—H | CF$_3$ | C—H | C—SOMe | H | H | CH3SOCH2CO | H | 1 |
| 2-2277 | H | C—Cl | N | C—Cl | C—H | CF$_3$ | C—H | C—SOMe | H | H | CH3SO2CH2CO | H | 1 |
| 2-2278 | H | C—Cl | N | C—Cl | C—H | CF$_3$ | C—H | C—SOMe | H | H | EtNHCO | H | 1 |
| 2-2279 | H | C—Cl | N | C—Cl | C—H | CF$_3$ | C—H | C—SOMe | Me | H | EtCO | H | 1 |
| 2-2280 | H | C—Cl | N | C—Cl | C—H | CF$_3$ | C—H | C—SOMe | Me | H | CF3CH2CO | H | 1 |
| 2-2281 | H | C—Cl | N | C—Cl | C—H | CF$_3$ | N | C—SOMe | H | H | EtCO | H | 1 |
| 2-2282 | H | C—Cl | N | C—Cl | C—H | CF$_3$ | N | C—SOMe | H | H | CF3CH2CO | H | 1 |

TABLE 2-2-continued

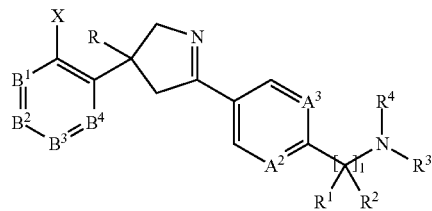

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-2283 | H | C—Cl | N | C—Cl | C—H | CF₃ | C—H | C—SO2Me | H | H | H | H | 1 |
| 2-2284 | H | C—Cl | N | C—Cl | C—H | CF₃ | C—H | C—SO2Me | H | H | MeCO | H | 1 |
| 2-2285 | H | C—Cl | N | C—Cl | C—H | CF₃ | C—H | C—SO2Me | H | H | EtCO | H | 1 |
| 2-2286 | H | C—Cl | N | C—Cl | C—H | CF₃ | C—H | C—SO2Me | H | H | CF3CH2CO | H | 1 |
| 2-2287 | H | C—Cl | N | C—Cl | C—H | CF₃ | C—H | C—SO2Me | H | H | cyclo-PrCO | H | 1 |
| 2-2288 | H | C—Cl | N | C—Cl | C—H | CF₃ | C—H | C—SO2Me | H | H | cyclo-PrCH2CO | H | 1 |
| 2-2289 | H | C—Cl | N | C—Cl | C—H | CF₃ | C—H | C—SO2Me | H | H | CH3SCH2CO | H | 1 |
| 2-2290 | H | C—Cl | N | C—Cl | C—H | CF₃ | C—H | C—SO2Me | H | H | CH3SOCH2CO | H | 1 |
| 2-2291 | H | C—Cl | N | C—Cl | C—H | CF₃ | C—H | C—SO2Me | H | H | CH3SO2CH2CO | H | 1 |
| 2-2292 | H | C—Cl | N | C—Cl | C—H | CF₃ | C—H | C—SO2Me | H | H | EtNHCO | H | 1 |
| 2-2293 | H | C—Cl | N | C—Cl | C—H | CF₃ | C—H | C—SO2Me | Me | H | EtCO | H | 1 |
| 2-2294 | H | C—Cl | N | C—Cl | C—H | CF₃ | C—H | C—SO2Me | Me | H | CF3CH2CO | H | 1 |
| 2-2295 | H | C—Cl | N | C—Cl | C—H | CF₃ | N | C—SO2Me | H | H | EtCO | H | 1 |
| 2-2296 | H | C—Cl | N | C—Cl | C—H | CF₃ | N | C—SO2Me | H | H | CF3CH2CO | H | 1 |
| 2-2297 | H | C—Cl | N | C—Cl | C—H | CF₃ | C—H | C—SCF3 | H | H | H | H | 1 |
| 2-2298 | H | C—Cl | N | C—Cl | C—H | CF₃ | C—H | C—SCF3 | H | H | MeCO | H | 1 |
| 2-2299 | H | C—Cl | N | C—Cl | C—H | CF₃ | C—H | C—SCF3 | H | H | EtCO | H | 1 |
| 2-2300 | H | C—Cl | N | C—Cl | C—H | CF₃ | C—H | C—SCF3 | H | H | CF3CH2CO | H | 1 |
| 2-2301 | H | C—Cl | N | C—Cl | C—H | CF₃ | C—H | C—SCF3 | H | H | cyclo-PrCO | H | 1 |
| 2-2302 | H | C—Cl | N | C—Cl | C—H | CF₃ | C—H | C—SCF3 | H | H | cyclo-PrCH2CO | H | 1 |
| 2-2303 | H | C—Cl | N | C—Cl | C—H | CF₃ | C—H | C—SCF3 | H | H | CH3SCH2CO | H | 1 |
| 2-2304 | H | C—Cl | N | C—Cl | C—H | CF₃ | C—H | C—SCF3 | H | H | CH3SOCH2CO | H | 1 |
| 2-2305 | H | C—Cl | N | C—Cl | C—H | CF₃ | C—H | C—SCF3 | H | H | CH3SO2CH2CO | H | 1 |
| 2-2306 | H | C—Cl | N | C—Cl | C—H | CF₃ | C—H | C—SCF3 | H | H | EtNHCO | H | 1 |
| 2-2307 | H | C—Cl | N | C—Cl | C—H | CF₃ | C—H | C—SCF3 | Me | H | EtCO | H | 1 |
| 2-2308 | H | C—Cl | N | C—Cl | C—H | CF₃ | C—H | C—SCF3 | Me | H | CF3CH2CO | H | 1 |
| 2-2309 | H | C—Cl | N | C—Cl | C—H | CF₃ | N | C—SCF3 | H | H | EtCO | H | 1 |
| 2-2310 | H | C—Cl | N | C—Cl | C—H | CF₃ | N | C—SCF3 | H | H | CF3CH2CO | H | 1 |
| 2-2311 | H | C—Cl | N | C—Cl | C—H | CF₃ | C—H | C—SOCF3 | H | H | H | H | 1 |
| 2-2312 | H | C—Cl | N | C—Cl | C—H | CF₃ | C—H | C—SOCF3 | H | H | MeCO | H | 1 |
| 2-2313 | H | C—Cl | N | C—Cl | C—H | CF₃ | C—H | C—SOCF3 | H | H | EtCO | H | 1 |
| 2-2314 | H | C—Cl | N | C—Cl | C—H | CF₃ | C—H | C—SOCF3 | H | H | CF3CH2CO | H | 1 |
| 2-2315 | H | C—Cl | N | C—Cl | C—H | CF₃ | C—H | C—SOCF3 | H | H | cyclo-PrCO | H | 1 |
| 2-2316 | H | C—Cl | N | C—Cl | C—H | CF₃ | C—H | C—SOCF3 | H | H | cyclo-PrCH2CO | H | 1 |
| 2-2317 | H | C—Cl | N | C—Cl | C—H | CF₃ | C—H | C—SOCF3 | H | H | CH3SCH2CO | H | 1 |
| 2-2318 | H | C—Cl | N | C—Cl | C—H | CF₃ | C—H | C—SOCF3 | H | H | CH3SOCH2CO | H | 1 |
| 2-2319 | H | C—Cl | N | C—Cl | C—H | CF₃ | C—H | C—SOCF3 | H | H | CH3SO2CH2CO | H | 1 |
| 2-2320 | H | C—Cl | N | C—Cl | C—H | CF₃ | C—H | C—SOCF3 | H | H | EtNHCO | H | 1 |
| 2-2321 | H | C—Cl | N | C—Cl | C—H | CF₃ | C—H | C—SOCF3 | Me | H | EtCO | H | 1 |
| 2-2322 | H | C—Cl | N | C—Cl | C—H | CF₃ | C—H | C—SOCF3 | Me | H | CF3CH2CO | H | 1 |
| 2-2323 | H | C—Cl | N | C—Cl | C—H | CF₃ | N | C—SOCF3 | H | H | EtCO | H | 1 |
| 2-2324 | H | C—Cl | N | C—Cl | C—H | CF₃ | N | C—SOCF3 | H | H | CF3CH2CO | H | 1 |
| 2-2325 | H | C—Cl | N | C—Cl | C—H | CF₃ | C—H | C—H | H | H | H | H | 1 |
| 2-2326 | H | C—Cl | N | C—Cl | C—H | CF₃ | C—H | C—H | H | H | MeCO | H | 1 |
| 2-2327 | H | C—Cl | N | C—Cl | C—H | CF₃ | C—H | C—H | H | H | EtCO | H | 1 |
| 2-2328 | H | C—Cl | N | C—Cl | C—H | CF₃ | C—H | C—H | H | H | CF3CH2CO | H | 1 |
| 2-2329 | H | C—Cl | N | C—Cl | C—H | CF₃ | C—H | C—H | H | H | cyclo-PrCO | H | 1 |
| 2-2330 | H | C—Cl | N | C—Cl | C—H | CF₃ | C—H | C—H | H | H | cyclo-PrCH2CO | H | 1 |
| 2-2331 | H | C—Cl | N | C—Cl | C—H | CF₃ | C—H | C—H | H | H | CH3SCH2CO | H | 1 |
| 2-2332 | H | C—Cl | N | C—Cl | C—H | CF₃ | C—H | C—H | H | H | CH3SOCH2CO | H | 1 |
| 2-2333 | H | C—Cl | N | C—Cl | C—H | CF₃ | C—H | C—H | H | H | CH3SO2CH2CO | H | 1 |
| 2-2334 | H | C—Cl | N | C—Cl | C—H | CF₃ | C—H | C—H | H | H | EtNHCO | H | 1 |
| 2-2335 | H | C—Cl | N | C—Cl | C—H | CF₃ | C—H | C—H | Me | H | H | H | 1 |
| 2-2336 | H | C—Cl | N | C—Cl | C—H | CF₃ | C—H | C—H | Me | H | EtCO | H | 1 |
| 2-2337 | H | C—Cl | N | C—Cl | C—H | CF₃ | C—H | C—H | Me | H | CF3CH2CO | H | 1 |
| 2-2338 | H | C—Cl | N | C—Cl | C—H | CF₃ | C—H | C—H | Me | H | CH3SCH2CO | H | 1 |
| 2-2339 | H | C—Cl | N | C—Cl | C—H | CF₃ | N | C—H | H | H | H | H | 1 |
| 2-2340 | H | C—Cl | N | C—Cl | C—H | CF₃ | N | C—H | H | H | EtCO | H | 1 |
| 2-2341 | H | C—Cl | N | C—Cl | C—H | CF₃ | N | C—H | H | H | CF3CH2CO | H | 1 |
| 2-2342 | H | C—Cl | N | C—Cl | C—H | CF₃ | N | C—H | H | H | CH3SCH2CO | H | 1 |
| 2-2343 | H | C—Cl | N | C—Cl | C—H | CF₃ | C—H | C—F | H | H | H | H | 1 |
| 2-2344 | H | C—Cl | N | C—Cl | C—H | CF₃ | C—H | C—F | H | H | MeCO | H | 1 |
| 2-2345 | H | C—Cl | N | C—Cl | C—H | CF₃ | C—H | C—F | H | H | EtCO | H | 1 |
| 2-2346 | H | C—Cl | N | C—Cl | C—H | CF₃ | C—H | C—F | H | H | CF3CH2CO | H | 1 |
| 2-2347 | H | C—Cl | N | C—Cl | C—H | CF₃ | C—H | C—F | H | H | cyclo-PrCO | H | 1 |
| 2-2348 | H | C—Cl | N | C—Cl | C—H | CF₃ | C—H | C—F | H | H | cyclo-PrCH2CO | H | 1 |
| 2-2349 | H | C—Cl | N | C—Cl | C—H | CF₃ | C—H | C—F | H | H | CH3SCH2CO | H | 1 |

TABLE 2-2-continued

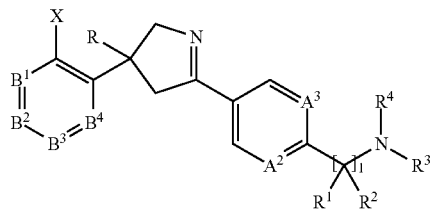

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2350 | H | C—Cl | N | C—Cl | C—H | CF₃ | C—H | C—F | H | H | CH3SOCH2CO | H | 1 |
| 2-2351 | H | C—Cl | N | C—Cl | C—H | CF₃ | C—H | C—F | H | H | CH3SO2CH2CO | H | 1 |
| 2-2352 | H | C—Cl | N | C—Cl | C—H | CF₃ | C—H | C—F | H | H | EtNHCO | H | 1 |
| 2-2353 | H | C—Cl | N | C—Cl | C—H | CF₃ | C—H | C—F | Me | H | EtCO | H | 1 |
| 2-2354 | H | C—Cl | N | C—Cl | C—H | CF₃ | C—H | C—F | Me | H | CF3CH2CO | H | 1 |
| 2-2355 | H | C—Cl | N | C—Cl | C—H | CF₃ | N | C—F | H | H | EtCO | H | 1 |
| 2-2356 | H | C—Cl | N | C—Cl | C—H | CF₃ | N | C—F | H | H | CF3CH2CO | H | 1 |
| 2-2357 | H | C—Cl | N | C—Cl | C—H | CF₃ | C—H | C—I | H | H | H | H | 1 |
| 2-2358 | H | C—Cl | N | C—Cl | C—H | CF₃ | C—H | C—I | H | H | MeCO | H | 1 |
| 2-2359 | H | C—Cl | N | C—Cl | C—H | CF₃ | C—H | C—I | H | H | EtCO | H | 1 |
| 2-2360 | H | C—Cl | N | C—Cl | C—H | CF₃ | C—H | C—I | H | H | CF3CH2CO | H | 1 |
| 2-2361 | H | C—Cl | N | C—Cl | C—H | CF₃ | C—H | C—I | H | H | cyclo-PrCO | H | 1 |
| 2-2362 | H | C—Cl | N | C—Cl | C—H | CF₃ | C—H | C—I | H | H | cyclo-PrCH2CO | H | 1 |
| 2-2363 | H | C—Cl | N | C—Cl | C—H | CF₃ | C—H | C—I | H | H | CH3SCH2CO | H | 1 |
| 2-2364 | H | C—Cl | N | C—Cl | C—H | CF₃ | C—H | C—I | H | H | CH3SOCH2CO | H | 1 |
| 2-2365 | H | C—Cl | N | C—Cl | C—H | CF₃ | C—H | C—I | H | H | CH3SO2CH2CO | H | 1 |
| 2-2366 | H | C—Cl | N | C—Cl | C—H | CF₃ | C—H | C—I | H | H | EtNHCO | H | 1 |
| 2-2367 | H | C—Cl | N | C—Cl | C—H | CF₃ | C—H | C—I | Me | H | EtCO | H | 1 |
| 2-2368 | H | C—Cl | N | C—Cl | C—H | CF₃ | C—H | C—I | Me | H | CF3CH2CO | H | 1 |
| 2-2369 | H | C—Cl | N | C—Cl | C—H | CF₃ | N | C—I | H | H | EtCO | H | 1 |
| 2-2370 | H | C—Cl | N | C—Cl | C—H | CF₃ | N | C—I | H | H | CF3CH2CO | H | 1 |
| 2-2371 | H | C—Cl | N | C—Cl | C—H | CF₃ | C—H | C—NH2 | H | H | H | H | 1 |
| 2-2372 | H | C—Cl | N | C—Cl | C—H | CF₃ | C—H | C—NH2 | H | H | MeCO | H | 1 |
| 2-2373 | H | C—Cl | N | C—Cl | C—H | CF₃ | C—H | C—NH2 | H | H | EtCO | H | 1 |
| 2-2374 | H | C—Cl | N | C—Cl | C—H | CF₃ | C—H | C—NH2 | H | H | CF3CH2CO | H | 1 |
| 2-2375 | H | C—Cl | N | C—Cl | C—H | CF₃ | C—H | C—NH2 | H | H | cyclo-PrCO | H | 1 |
| 2-2376 | H | C—Cl | N | C—Cl | C—H | CF₃ | C—H | C—NH2 | H | H | cyclo-PrCH2CO | H | 1 |
| 2-2377 | H | C—Cl | N | C—Cl | C—H | CF₃ | C—H | C—NH2 | H | H | CH3SCH2CO | H | 1 |
| 2-2378 | H | C—Cl | N | C—Cl | C—H | CF₃ | C—H | C—NH2 | H | H | CH3SOCH2CO | H | 1 |
| 2-2379 | H | C—Cl | N | C—Cl | C—H | CF₃ | C—H | C—NH2 | H | H | CH3SO2CH2CO | H | 1 |
| 2-2380 | H | C—Cl | N | C—Cl | C—H | CF₃ | C—H | C—NH2 | H | H | EtNHCO | H | 1 |
| 2-2381 | H | C—Cl | N | C—Cl | C—H | CF₃ | C—H | C—NH2 | Me | H | EtCO | H | 1 |
| 2-2382 | H | C—Cl | N | C—Cl | C—H | CF₃ | C—H | C—NH2 | Me | H | CF3CH2CO | H | 1 |
| 2-2383 | H | C—Cl | N | C—Cl | C—H | CF₃ | N | C—NH2 | H | H | EtCO | H | 1 |
| 2-2384 | H | C—Cl | N | C—Cl | C—H | CF₃ | N | C—NH2 | H | H | CF3CH2CO | H | 1 |
| 2-2385 | H | C—Cl | N | C—Cl | C—H | CF₃ | C—H | C—NHAc | H | H | H | H | 1 |
| 2-2386 | H | C—Cl | N | C—Cl | C—H | CF₃ | C—H | C—NHAc | H | H | MeCO | H | 1 |
| 2-2387 | H | C—Cl | N | C—Cl | C—H | CF₃ | C—H | C—NHAc | H | H | EtCO | H | 1 |
| 2-2388 | H | C—Cl | N | C—Cl | C—H | CF₃ | C—H | C—NHAc | H | H | CF3CH2CO | H | 1 |
| 2-2389 | H | C—Cl | N | C—Cl | C—H | CF₃ | C—H | C—NHAc | H | H | cyclo-PrCO | H | 1 |
| 2-2390 | H | C—Cl | N | C—Cl | C—H | CF₃ | C—H | C—NHAc | H | H | cyclo-PrCH2CO | H | 1 |
| 2-2391 | H | C—Cl | N | C—Cl | C—H | CF₃ | C—H | C—NHAc | H | H | CH3SCH2CO | H | 1 |
| 2-2392 | H | C—Cl | N | C—Cl | C—H | CF₃ | C—H | C—NHAc | H | H | CH3SOCH2CO | H | 1 |
| 2-2393 | H | C—Cl | N | C—Cl | C—H | CF₃ | C—H | C—NHAc | H | H | CH3SO2CH2CO | H | 1 |
| 2-2394 | H | C—Cl | N | C—Cl | C—H | CF₃ | C—H | C—NHAc | H | H | EtNHCO | H | 1 |
| 2-2395 | H | C—Cl | N | C—Cl | C—H | CF₃ | C—H | C—NHAc | Me | H | EtCO | H | 1 |
| 2-2396 | H | C—Cl | N | C—Cl | C—H | CF₃ | C—H | C—NHAc | Me | H | CF3CH2CO | H | 1 |
| 2-2397 | H | C—Cl | N | C—Cl | C—H | CF₃ | N | C—NHAc | H | H | EtCO | H | 1 |
| 2-2398 | H | C—Cl | N | C—Cl | C—H | CF₃ | N | C—NHAc | H | H | CF3CH2CO | H | 1 |
| 2-2399 | H | C—Cl | N | C—Cl | C—H | CF₃ | C—H | C—NHCOCF3 | H | H | H | H | 1 |
| 2-2400 | H | C—Cl | N | C—Cl | C—H | CF₃ | C—H | C—NHCOCF3 | H | H | MeCO | H | 1 |
| 2-2401 | H | C—Cl | N | C—Cl | C—H | CF₃ | C—H | C—NHCOCF3 | H | H | EtCO | H | 1 |
| 2-2402 | H | C—Cl | N | C—Cl | C—H | CF₃ | C—H | C—NHCOCF3 | H | H | CF3CH2CO | H | 1 |
| 2-2403 | H | C—Cl | N | C—Cl | C—H | CF₃ | C—H | C—NHCOCF3 | H | H | cyclo-PrCO | H | 1 |
| 2-2404 | H | C—Cl | N | C—Cl | C—H | CF₃ | C—H | C—NHCOCF3 | H | H | cyclo-PrCH2CO | H | 1 |
| 2-2405 | H | C—Cl | N | C—Cl | C—H | CF₃ | C—H | C—NHCOCF3 | H | H | CH3SCH2CO | H | 1 |
| 2-2406 | H | C—Cl | N | C—Cl | C—H | CF₃ | C—H | C—NHCOCF3 | H | H | CH3SOCH2CO | H | 1 |
| 2-2407 | H | C—Cl | N | C—Cl | C—H | CF₃ | C—H | C—NHCOCF3 | H | H | CH3SO2CH2CO | H | 1 |
| 2-2408 | H | C—Cl | N | C—Cl | C—H | CF₃ | C—H | C—NHCOCF3 | H | H | EtNHCO | H | 1 |
| 2-2409 | H | C—Cl | N | C—Cl | C—H | CF₃ | C—H | C—NHCOCF3 | Me | H | EtCO | H | 1 |
| 2-2410 | H | C—Cl | N | C—Cl | C—H | CF₃ | C—H | C—NHCOCF3 | Me | H | CF3CH2CO | H | 1 |
| 2-2411 | H | C—Cl | N | C—Cl | C—H | CF₃ | N | C—NHCOCF3 | H | H | EtCO | H | 1 |
| 2-2412 | H | C—Cl | N | C—Cl | C—H | CF₃ | N | C—NHCOCF3 | H | H | CF3CH2CO | H | 1 |
| 2-2413 | H | C—Cl | N | C—Cl | C—H | CF₃ | C—H | C—CH2OAc | H | H | H | H | 1 |
| 2-2414 | H | C—Cl | N | C—Cl | C—H | CF₃ | C—H | C—CH2OAc | H | H | MeCO | H | 1 |
| 2-2415 | H | C—Cl | N | C—Cl | C—H | CF₃ | C—H | C—CH2OAc | H | H | EtCO | H | 1 |
| 2-2416 | H | C—Cl | N | C—Cl | C—H | CF₃ | C—H | C—CH2OAc | H | H | CF3CH2CO | H | 1 |

TABLE 2-2-continued

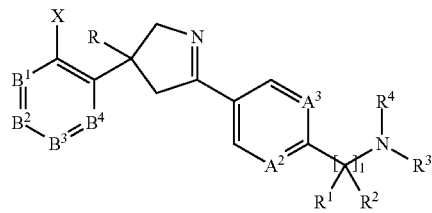

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2417 | H | C—Cl | N | C—Cl | C—H | CF₃ | C—H | C—CH2OAc | H | H | cyclo-PrCO | H | 1 |
| 2-2418 | H | C—Cl | N | C—Cl | C—H | CF₃ | C—H | C—CH2OAc | H | H | cyclo-PrCH2CO | H | 1 |
| 2-2419 | H | C—Cl | N | C—Cl | C—H | CF₃ | C—H | C—CH2OAc | H | H | CH3SCH2CO | H | 1 |
| 2-2420 | H | C—Cl | N | C—Cl | C—H | CF₃ | C—H | C—CH2OAc | H | H | CH3SOCH2CO | H | 1 |
| 2-2421 | H | C—Cl | N | C—Cl | C—H | CF₃ | C—H | C—CH2OAc | H | H | CH3SO2CH2CO | H | 1 |
| 2-2422 | H | C—Cl | N | C—Cl | C—H | CF₃ | C—H | C—CH2OAc | H | H | EtNHCO | H | 1 |
| 2-2423 | H | C—Cl | N | C—Cl | C—H | CF₃ | C—H | C—CH2OAc | Me | H | EtCO | H | 1 |
| 2-2424 | H | C—Cl | N | C—Cl | C—H | CF₃ | C—H | C—CH2OAc | Me | H | CF3CH2CO | H | 1 |
| 2-2425 | H | C—Cl | N | C—Cl | C—H | CF₃ | N | C—CH2OAc | H | H | EtCO | H | 1 |
| 2-2426 | H | C—Cl | N | C—Cl | C—H | CF₃ | N | C—CH2OAc | H | H | CF3CH2CO | H | 1 |
| 2-2427 | H | C—CF3 | N | C—H | C—H | CF₃ | C—H | C—CF₃ | H | H | H | H | 1 |
| 2-2428 | H | C—CF3 | N | C—H | C—H | CF₃ | C—H | C—CF₃ | H | H | MeCO | H | 1 |
| 2-2429 | H | C—CF3 | N | C—H | C—H | CF₃ | C—H | C—CF₃ | H | H | EtCO | H | 1 |
| 2-2430 | H | C—CF3 | N | C—H | C—H | CF₃ | C—H | C—CF₃ | H | H | n-PrCO | H | 1 |
| 2-2431 | H | C—CF3 | N | C—H | C—H | CF₃ | C—H | C—CF₃ | H | H | cyclo-PrCO | H | 1 |
| 2-2432 | H | C—CF3 | N | C—H | C—H | CF₃ | C—H | C—CF₃ | H | H | EtNHCO | H | 1 |
| 2-2433 | H | C—CF3 | N | C—H | C—H | CF₃ | C—H | C—CF₃ | H | H | CF3CH2CO | H | 1 |
| 2-2434 | H | C—CF3 | N | C—H | C—H | CF₃ | C—H | C—CF₃ | H | H | cyclo-PrCH2CO | H | 1 |
| 2-2435 | H | C—CF3 | N | C—H | C—H | CF₃ | C—H | C—CF₃ | H | H | CH3SCH2CO | H | 1 |
| 2-2436 | H | C—CF3 | N | C—H | C—H | CF₃ | C—H | C—CF₃ | H | H | CH3SOCH2CO | H | 1 |
| 2-2437 | H | C—CF3 | N | C—H | C—H | CF₃ | C—H | C—CF₃ | H | H | CH3SO2CH2CO | H | 1 |
| 2-2438 | H | C—CF3 | N | C—H | C—H | CF₃ | C—H | C—CF₃ | Me | H | H | H | 1 |
| 2-2439 | H | C—CF3 | N | C—H | C—H | CF₃ | C—H | C—CF₃ | Me | H | EtCO | H | 1 |
| 2-2440 | H | C—CF3 | N | C—H | C—H | CF₃ | C—H | C—CF₃ | Me | H | CF3CH2CO | H | 1 |
| 2-2441 | H | C—CF3 | N | C—H | C—H | CF₃ | C—H | C—CF₃ | Me | H | CH3SCH2CO | H | 1 |
| 2-2442 | H | C—CF3 | N | C—H | C—H | CF₃ | N | C—CF₃ | H | H | H | H | 1 |
| 2-2443 | H | C—CF3 | N | C—H | C—H | CF₃ | N | C—CF₃ | H | H | EtCO | H | 1 |
| 2-2444 | H | C—CF3 | N | C—H | C—H | CF₃ | N | C—CF₃ | H | H | CF3CH2CO | H | 1 |
| 2-2445 | H | C—CF3 | N | C—H | C—H | CF₃ | N | C—CF₃ | H | H | CH3SCH2CO | H | 1 |
| 2-2446 | H | C—CF3 | N | C—H | C—H | CF₃ | C—H | C—Cl | H | H | H | H | 1 |
| 2-2447 | H | C—CF3 | N | C—H | C—H | CF₃ | C—H | C—Cl | H | H | MeCO | H | 1 |
| 2-2448 | H | C—CF3 | N | C—H | C—H | CF₃ | C—H | C—Cl | H | H | CF3CH2CO | H | 1 |
| 2-2449 | H | C—CF3 | N | C—H | C—H | CF₃ | C—H | C—Cl | H | H | cyclo-PrCO | H | 1 |
| 2-2450 | H | C—CF3 | N | C—H | C—H | CF₃ | C—H | C—Cl | H | H | cyclo-PrCH2CO | H | 1 |
| 2-2451 | H | C—CF3 | N | C—H | C—H | CF₃ | C—H | C—Cl | H | H | CH3SCH2CO | H | 1 |
| 2-2452 | H | C—CF3 | N | C—H | C—H | CF₃ | C—H | C—Cl | H | H | CH3SOCH2CO | H | 1 |
| 2-2453 | H | C—CF3 | N | C—H | C—H | CF₃ | C—H | C—Cl | H | H | CH3SO2CH2CO | H | 1 |
| 2-2454 | H | C—CF3 | N | C—H | C—H | CF₃ | C—H | C—Cl | H | H | EtNHCO | H | 1 |
| 2-2455 | H | C—CF3 | N | C—H | C—H | CF₃ | C—H | C—Cl | Me | H | H | H | 1 |
| 2-2456 | H | C—CF3 | N | C—H | C—H | CF₃ | C—H | C—Cl | Me | H | EtCO | H | 1 |
| 2-2457 | H | C—CF3 | N | C—H | C—H | CF₃ | C—H | C—Cl | Me | H | CF3CH2CO | H | 1 |
| 2-2458 | H | C—CF3 | N | C—H | C—H | CF₃ | C—H | C—Cl | Me | H | CH3SCH2CO | H | 1 |
| 2-2459 | H | C—CF3 | N | C—H | C—H | CF₃ | N | C—Cl | H | H | H | H | 1 |
| 2-2460 | H | C—CF3 | N | C—H | C—H | CF₃ | N | C—Cl | H | H | EtCO | H | 1 |
| 2-2461 | H | C—CF3 | N | C—H | C—H | CF₃ | N | C—Cl | H | H | CF3CH2CO | H | 1 |
| 2-2462 | H | C—CF3 | N | C—H | C—H | CF₃ | N | C—Cl | H | H | CH3SCH2CO | H | 1 |
| 2-2463 | H | C—CF3 | N | C—H | C—H | CF₃ | C—H | C—Br | H | H | H | H | 1 |
| 2-2464 | H | C—CF3 | N | C—H | C—H | CF₃ | C—H | C—Br | H | H | MeCO | H | 1 |
| 2-2465 | H | C—CF3 | N | C—H | C—H | CF₃ | C—H | C—Br | H | H | EtCO | H | 1 |
| 2-2466 | H | C—CF3 | N | C—H | C—H | CF₃ | C—H | C—Br | H | H | CF3CH2CO | H | 1 |
| 2-2467 | H | C—CF3 | N | C—H | C—H | CF₃ | C—H | C—Br | H | H | cyclo-PrCO | H | 1 |
| 2-2468 | H | C—CF3 | N | C—H | C—H | CF₃ | C—H | C—Br | H | H | cyclo-PrCH2CO | H | 1 |
| 2-2469 | H | C—CF3 | N | C—H | C—H | CF₃ | C—H | C—Br | H | H | CH3SCH2CO | H | 1 |
| 2-2470 | H | C—CF3 | N | C—H | C—H | CF₃ | C—H | C—Br | H | H | CH3SOCH2CO | H | 1 |
| 2-2471 | H | C—CF3 | N | C—H | C—H | CF₃ | C—H | C—Br | H | H | CH3SO2CH2CO | H | 1 |
| 2-2472 | H | C—CF3 | N | C—H | C—H | CF₃ | C—H | C—Br | H | H | EtNHCO | H | 1 |
| 2-2473 | H | C—CF3 | N | C—H | C—H | CF₃ | C—H | C—Br | Me | H | H | H | 1 |
| 2-2474 | H | C—CF3 | N | C—H | C—H | CF₃ | C—H | C—Br | Me | H | EtCO | H | 1 |
| 2-2475 | H | C—CF3 | N | C—H | C—H | CF₃ | C—H | C—Br | Me | H | CF3CH2CO | H | 1 |
| 2-2476 | H | C—CF3 | N | C—H | C—H | CF₃ | C—H | C—Br | Me | H | CH3SCH2CO | H | 1 |
| 2-2477 | H | C—CF3 | N | C—H | C—H | CF₃ | N | C—Br | H | H | H | H | 1 |
| 2-2478 | H | C—CF3 | N | C—H | C—H | CF₃ | N | C—Br | H | H | EtCO | H | 1 |
| 2-2479 | H | C—CF3 | N | C—H | C—H | CF₃ | N | C—Br | H | H | CF3CH2CO | H | 1 |
| 2-2480 | H | C—CF3 | N | C—H | C—H | CF₃ | N | C—Br | H | H | CH3SCH2CO | H | 1 |
| 2-2481 | H | C—CF3 | N | C—H | C—H | CF₃ | C—H | C—CN | H | H | H | H | 1 |
| 2-2482 | H | C—CF3 | N | C—H | C—H | CF₃ | C—H | C—CN | H | H | MeCO | H | 1 |
| 2-2483 | H | C—CF3 | N | C—H | C—H | CF₃ | C—H | C—CN | H | H | EtCO | H | 1 |

TABLE 2-2-continued

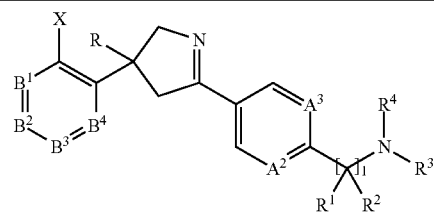

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2484 | H | C—CF3 | N | C—H | C—H | CF₃ | C—H | C—CN | H | H | CF3CH2CO | H | 1 |
| 2-2485 | H | C—CF3 | N | C—H | C—H | CF₃ | C—H | C—CN | H | H | cyclo-PrCO | H | 1 |
| 2-2486 | H | C—CF3 | N | C—H | C—H | CF₃ | C—H | C—CN | H | H | cyclo-PrCH2CO | H | 1 |
| 2-2487 | H | C—CF3 | N | C—H | C—H | CF₃ | C—H | C—CN | H | H | CH3SCH2CO | H | 1 |
| 2-2488 | H | C—CF3 | N | C—H | C—H | CF₃ | C—H | C—CN | H | H | CH3SOCH2CO | H | 1 |
| 2-2489 | H | C—CF3 | N | C—H | C—H | CF₃ | C—H | C—CN | H | H | CH3SO2CH2CO | H | 1 |
| 2-2490 | H | C—CF3 | N | C—H | C—H | CF₃ | C—H | C—CN | H | H | EtNHCO | H | 1 |
| 2-2491 | H | C—CF3 | N | C—H | C—H | CF₃ | C—H | C—CN | Me | H | EtCO | H | 1 |
| 2-2492 | H | C—CF3 | N | C—H | C—H | CF₃ | C—H | C—CN | Me | H | CF3CH2CO | H | 1 |
| 2-2493 | H | C—CF3 | N | C—H | C—H | CF₃ | N | C—CN | H | H | EtCO | H | 1 |
| 2-2494 | H | C—CF3 | N | C—H | C—H | CF₃ | N | C—CN | H | H | CF3CH2CO | H | 1 |
| 2-2495 | H | C—CF3 | N | C—H | C—H | CF₃ | C—H | C—Me | H | H | H | H | 1 |
| 2-2496 | H | C—CF3 | N | C—H | C—H | CF₃ | C—H | C—Me | H | H | MeCO | H | 1 |
| 2-2497 | H | C—CF3 | N | C—H | C—H | CF₃ | C—H | C—Me | H | H | EtCO | H | 1 |
| 2-2498 | H | C—CF3 | N | C—H | C—H | CF₃ | C—H | C—Me | H | H | CF3CH2CO | H | 1 |
| 2-2499 | H | C—CF3 | N | C—H | C—H | CF₃ | C—H | C—Me | H | H | cyclo-PrCO | H | 1 |
| 2-2500 | H | C—CF3 | N | C—H | C—H | CF₃ | C—H | C—Me | H | H | cyclo-PrCH2CO | H | 1 |
| 2-2501 | H | C—CF3 | N | C—H | C—H | CF₃ | C—H | C—Me | H | H | CH3SCH2CO | H | 1 |
| 2-2502 | H | C—CF3 | N | C—H | C—H | CF₃ | C—H | C—Me | H | H | CH3SOCH2CO | H | 1 |
| 2-2503 | H | C—CF3 | N | C—H | C—H | CF₃ | C—H | C—Me | H | H | CH3SO2CH2CO | H | 1 |
| 2-2504 | H | C—CF3 | N | C—H | C—H | CF₃ | C—H | C—Me | H | H | EtNHCO | H | 1 |
| 2-2505 | H | C—CF3 | N | C—H | C—H | CF₃ | C—H | C—Me | Me | H | EtCO | H | 1 |
| 2-2506 | H | C—CF3 | N | C—H | C—H | CF₃ | C—H | C—Me | Me | H | CF3CH2CO | H | 1 |
| 2-2507 | H | C—CF3 | N | C—H | C—H | CF₃ | N | C—Me | H | H | EtCO | H | 1 |
| 2-2508 | H | C—CF3 | N | C—H | C—H | CF₃ | N | C—Me | H | H | CF3CH2CO | H | 1 |
| 2-2509 | H | C—CF3 | N | C—H | C—H | CF₃ | C—H | C—NO2 | H | H | H | H | 1 |
| 2-2510 | H | C—CF3 | N | C—H | C—H | CF₃ | C—H | C—NO2 | H | H | MeCO | H | 1 |
| 2-2511 | H | C—CF3 | N | C—H | C—H | CF₃ | C—H | C—NO2 | H | H | EtCO | H | 1 |
| 2-2512 | H | C—CF3 | N | C—H | C—H | CF₃ | C—H | C—NO2 | H | H | CF3CH2CO | H | 1 |
| 2-2513 | H | C—CF3 | N | C—H | C—H | CF₃ | C—H | C—NO2 | H | H | cyclo-PrCO | H | 1 |
| 2-2514 | H | C—CF3 | N | C—H | C—H | CF₃ | C—H | C—NO2 | H | H | cyclo-PrCH2CO | H | 1 |
| 2-2515 | H | C—CF3 | N | C—H | C—H | CF₃ | C—H | C—NO2 | H | H | CH3SCH2CO | H | 1 |
| 2-2516 | H | C—CF3 | N | C—H | C—H | CF₃ | C—H | C—NO2 | H | H | CH3SOCH2CO | H | 1 |
| 2-2517 | H | C—CF3 | N | C—H | C—H | CF₃ | C—H | C—NO2 | H | H | CH3SO2CH2CO | H | 1 |
| 2-2518 | H | C—CF3 | N | C—H | C—H | CF₃ | C—H | C—NO2 | H | H | EtNHCO | H | 1 |
| 2-2519 | H | C—CF3 | N | C—H | C—H | CF₃ | C—H | C—NO2 | Me | H | EtCO | H | 1 |
| 2-2520 | H | C—CF3 | N | C—H | C—H | CF₃ | C—H | C—NO2 | Me | H | CF3CH2CO | H | 1 |
| 2-2521 | H | C—CF3 | N | C—H | C—H | CF₃ | N | C—NO2 | H | H | EtCO | H | 1 |
| 2-2522 | H | C—CF3 | N | C—H | C—H | CF₃ | N | C—NO2 | H | H | CF3CH2CO | H | 1 |
| 2-2523 | H | C—CF3 | N | C—H | C—H | CF₃ | C—H | C—SMe | H | H | H | H | 1 |
| 2-2524 | H | C—CF3 | N | C—H | C—H | CF₃ | C—H | C—SMe | H | H | MeCO | H | 1 |
| 2-2525 | H | C—CF3 | N | C—H | C—H | CF₃ | C—H | C—SMe | H | H | EtCO | H | 1 |
| 2-2526 | H | C—CF3 | N | C—H | C—H | CF₃ | C—H | C—SMe | H | H | CF3CH2CO | H | 1 |
| 2-2527 | H | C—CF3 | N | C—H | C—H | CF₃ | C—H | C—SMe | H | H | cyclo-PrCO | H | 1 |
| 2-2528 | H | C—CF3 | N | C—H | C—H | CF₃ | C—H | C—SMe | H | H | cyclo-PrCH2CO | H | 1 |
| 2-2529 | H | C—CF3 | N | C—H | C—H | CF₃ | C—H | C—SMe | H | H | CH3SCH2CO | H | 1 |
| 2-2530 | H | C—CF3 | N | C—H | C—H | CF₃ | C—H | C—SMe | H | H | CH3SOCH2CO | H | 1 |
| 2-2531 | H | C—CF3 | N | C—H | C—H | CF₃ | C—H | C—SMe | H | H | CH3SO2CH2CO | H | 1 |
| 2-2532 | H | C—CF3 | N | C—H | C—H | CF₃ | C—H | C—SMe | H | H | EtNHCO | H | 1 |
| 2-2533 | H | C—CF3 | N | C—H | C—H | CF₃ | C—H | C—SMe | Me | H | EtCO | H | 1 |
| 2-2534 | H | C—CF3 | N | C—H | C—H | CF₃ | C—H | C—SMe | Me | H | CF3CH2CO | H | 1 |
| 2-2535 | H | C—CF3 | N | C—H | C—H | CF₃ | N | C—SMe | H | H | EtCO | H | 1 |
| 2-2536 | H | C—CF3 | N | C—H | C—H | CF₃ | N | C—SMe | H | H | CF3CH2CO | H | 1 |
| 2-2537 | H | C—CF3 | N | C—H | C—H | CF₃ | C—H | C—SOMe | H | H | H | H | 1 |
| 2-2538 | H | C—CF3 | N | C—H | C—H | CF₃ | C—H | C—SOMe | H | H | MeCO | H | 1 |
| 2-2539 | H | C—CF3 | N | C—H | C—H | CF₃ | C—H | C—SOMe | H | H | EtCO | H | 1 |
| 2-2540 | H | C—CF3 | N | C—H | C—H | CF₃ | C—H | C—SOMe | H | H | CF3CH2CO | H | 1 |
| 2-2541 | H | C—CF3 | N | C—H | C—H | CF₃ | C—H | C—SOMe | H | H | cyclo-PrCO | H | 1 |
| 2-2542 | H | C—CF3 | N | C—H | C—H | CF₃ | C—H | C—SOMe | H | H | cyclo-PrCH2CO | H | 1 |
| 2-2543 | H | C—CF3 | N | C—H | C—H | CF₃ | C—H | C—SOMe | H | H | CH3SCH2CO | H | 1 |
| 2-2544 | H | C—CF3 | N | C—H | C—H | CF₃ | C—H | C—SOMe | H | H | CH3SOCH2CO | H | 1 |
| 2-2545 | H | C—CF3 | N | C—H | C—H | CF₃ | C—H | C—SOMe | H | H | CH3SO2CH2CO | H | 1 |
| 2-2546 | H | C—CF3 | N | C—H | C—H | CF₃ | C—H | C—SOMe | H | H | EtNHCO | H | 1 |
| 2-2547 | H | C—CF3 | N | C—H | C—H | CF₃ | C—H | C—SOMe | Me | H | EtCO | H | 1 |
| 2-2548 | H | C—CF3 | N | C—H | C—H | CF₃ | C—H | C—SOMe | Me | H | CF3CH2CO | H | 1 |
| 2-2549 | H | C—CF3 | N | C—H | C—H | CF₃ | N | C—SOMe | H | H | EtCO | H | 1 |
| 2-2550 | H | C—CF3 | N | C—H | C—H | CF₃ | N | C—SOMe | H | H | CF3CH2CO | H | 1 |

TABLE 2-2-continued

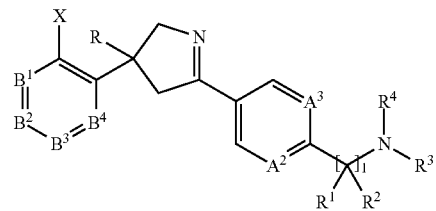

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2551 | H | C—CF3 | N | C—H | C—H | CF₃ | C—H | C—SO2Me | H | H | H | H | 1 |
| 2-2552 | H | C—CF3 | N | C—H | C—H | CF₃ | C—H | C—SO2Me | H | H | MeCO | H | 1 |
| 2-2553 | H | C—CF3 | N | C—H | C—H | CF₃ | C—H | C—SO2Me | H | H | EtCO | H | 1 |
| 2-2554 | H | C—CF3 | N | C—H | C—H | CF₃ | C—H | C—SO2Me | H | H | CF3CH2CO | H | 1 |
| 2-2555 | H | C—CF3 | N | C—H | C—H | CF₃ | C—H | C—SO2Me | H | H | cyclo-PrCO | H | 1 |
| 2-2556 | H | C—CF3 | N | C—H | C—H | CF₃ | C—H | C—SO2Me | H | H | cyclo-PrCH2CO | H | 1 |
| 2-2557 | H | C—CF3 | N | C—H | C—H | CF₃ | C—H | C—SO2Me | H | H | CH3SCH2CO | H | 1 |
| 2-2558 | H | C—CF3 | N | C—H | C—H | CF₃ | C—H | C—SO2Me | H | H | CH3SOCH2CO | H | 1 |
| 2-2559 | H | C—CF3 | N | C—H | C—H | CF₃ | C—H | C—SO2Me | H | H | CH3SO2CH2CO | H | 1 |
| 2-2560 | H | C—CF3 | N | C—H | C—H | CF₃ | C—H | C—SO2Me | H | H | EtNHCO | H | 1 |
| 2-2561 | H | C—CF3 | N | C—H | C—H | CF₃ | C—H | C—SO2Me | Me | H | EtCO | H | 1 |
| 2-2562 | H | C—CF3 | N | C—H | C—H | CF₃ | C—H | C—SO2Me | Me | H | CF3CH2CO | H | 1 |
| 2-2563 | H | C—CF3 | N | C—H | C—H | CF₃ | N | C—SO2Me | H | H | EtCO | H | 1 |
| 2-2564 | H | C—CF3 | N | C—H | C—H | CF₃ | N | C—SO2Me | H | H | CF3CH2CO | H | 1 |
| 2-2565 | H | C—CF3 | N | C—H | C—H | CF₃ | C—H | C—SCF3 | H | H | H | H | 1 |
| 2-2566 | H | C—CF3 | N | C—H | C—H | CF₃ | C—H | C—SCF3 | H | H | MeCO | H | 1 |
| 2-2567 | H | C—CF3 | N | C—H | C—H | CF₃ | C—H | C—SCF3 | H | H | EtCO | H | 1 |
| 2-2568 | H | C—CF3 | N | C—H | C—H | CF₃ | C—H | C—SCF3 | H | H | CF3CH2CO | H | 1 |
| 2-2569 | H | C—CF3 | N | C—H | C—H | CF₃ | C—H | C—SCF3 | H | H | cyclo-PrCO | H | 1 |
| 2-2570 | H | C—CF3 | N | C—H | C—H | CF₃ | C—H | C—SCF3 | H | H | cyclo-PrCH2CO | H | 1 |
| 2-2571 | H | C—CF3 | N | C—H | C—H | CF₃ | C—H | C—SCF3 | H | H | CH3SCH2CO | H | 1 |
| 2-2572 | H | C—CF3 | N | C—H | C—H | CF₃ | C—H | C—SCF3 | H | H | CH3SOCH2CO | H | 1 |
| 2-2573 | H | C—CF3 | N | C—H | C—H | CF₃ | C—H | C—SCF3 | H | H | CH3SO2CH2CO | H | 1 |
| 2-2574 | H | C—CF3 | N | C—H | C—H | CF₃ | C—H | C—SCF3 | H | H | EtNHCO | H | 1 |
| 2-2575 | H | C—CF3 | N | C—H | C—H | CF₃ | C—H | C—SCF3 | Me | H | EtCO | H | 1 |
| 2-2576 | H | C—CF3 | N | C—H | C—H | CF₃ | C—H | C—SCF3 | Me | H | CF3CH2CO | H | 1 |
| 2-2577 | H | C—CF3 | N | C—H | C—H | CF₃ | N | C—SCF3 | H | H | EtCO | H | 1 |
| 2-2578 | H | C—CF3 | N | C—H | C—H | CF₃ | N | C—SCF3 | H | H | CF3CH2CO | H | 1 |
| 2-2579 | H | C—CF3 | N | C—H | C—H | CF₃ | C—H | C—SOCF3 | H | H | H | H | 1 |
| 2-2580 | H | C—CF3 | N | C—H | C—H | CF₃ | C—H | C—SOCF3 | H | H | MeCO | H | 1 |
| 2-2581 | H | C—CF3 | N | C—H | C—H | CF₃ | C—H | C—SOCF3 | H | H | EtCO | H | 1 |
| 2-2582 | H | C—CF3 | N | C—H | C—H | CF₃ | C—H | C—SOCF3 | H | H | CF3CH2CO | H | 1 |
| 2-2583 | H | C—CF3 | N | C—H | C—H | CF₃ | C—H | C—SOCF3 | H | H | cyclo-PrCO | H | 1 |
| 2-2584 | H | C—CF3 | N | C—H | C—H | CF₃ | C—H | C—SOCF3 | H | H | cyclo-PrCH2CO | H | 1 |
| 2-2585 | H | C—CF3 | N | C—H | C—H | CF₃ | C—H | C—SOCF3 | H | H | CH3SCH2CO | H | 1 |
| 2-2586 | H | C—CF3 | N | C—H | C—H | CF₃ | C—H | C—SOCF3 | H | H | CH3SOCH2CO | H | 1 |
| 2-2587 | H | C—CF3 | N | C—H | C—H | CF₃ | C—H | C—SOCF3 | H | H | CH3SO2CH2CO | H | 1 |
| 2-2588 | H | C—CF3 | N | C—H | C—H | CF₃ | C—H | C—SOCF3 | H | H | EtNHCO | H | 1 |
| 2-2589 | H | C—CF3 | N | C—H | C—H | CF₃ | C—H | C—SOCF3 | Me | H | EtCO | H | 1 |
| 2-2590 | H | C—CF3 | N | C—H | C—H | CF₃ | C—H | C—SOCF3 | Me | H | CF3CH2CO | H | 1 |
| 2-2591 | H | C—CF3 | N | C—H | C—H | CF₃ | N | C—SOCF3 | H | H | EtCO | H | 1 |
| 2-2592 | H | C—CF3 | N | C—H | C—H | CF₃ | N | C—SOCF3 | H | H | CF3CH2CO | H | 1 |
| 2-2593 | H | C—CF3 | N | C—H | C—H | CF₃ | C—H | C—H | H | H | H | H | 1 |
| 2-2594 | H | C—CF3 | N | C—H | C—H | CF₃ | C—H | C—H | H | H | MeCO | H | 1 |
| 2-2595 | H | C—CF3 | N | C—H | C—H | CF₃ | C—H | C—H | H | H | EtCO | H | 1 |
| 2-2596 | H | C—CF3 | N | C—H | C—H | CF₃ | C—H | C—H | H | H | CF3CH2CO | H | 1 |
| 2-2597 | H | C—CF3 | N | C—H | C—H | CF₃ | C—H | C—H | H | H | cyclo-PrCO | H | 1 |
| 2-2598 | H | C—CF3 | N | C—H | C—H | CF₃ | C—H | C—H | H | H | cyclo-PrCH2CO | H | 1 |
| 2-2599 | H | C—CF3 | N | C—H | C—H | CF₃ | C—H | C—H | H | H | CH3SCH2CO | H | 1 |
| 2-2600 | H | C—CF3 | N | C—H | C—H | CF₃ | C—H | C—H | H | H | CH3SOCH2CO | H | 1 |
| 2-2601 | H | C—CF3 | N | C—H | C—H | CF₃ | C—H | C—H | H | H | CH3SO2CH2CO | H | 1 |
| 2-2602 | H | C—CF3 | N | C—H | C—H | CF₃ | C—H | C—H | H | H | EtNHCO | H | 1 |
| 2-2603 | H | C—CF3 | N | C—H | C—H | CF₃ | C—H | C—H | Me | H | H | H | 1 |
| 2-2604 | H | C—CF3 | N | C—H | C—H | CF₃ | C—H | C—H | Me | H | EtCO | H | 1 |
| 2-2605 | H | C—CF3 | N | C—H | C—H | CF₃ | C—H | C—H | Me | H | CF3CH2CO | H | 1 |
| 2-2606 | H | C—CF3 | N | C—H | C—H | CF₃ | C—H | C—H | Me | H | CH3SCH2CO | H | 1 |
| 2-2607 | H | C—CF3 | N | C—H | C—H | CF₃ | N | C—H | H | H | H | H | 1 |
| 2-2608 | H | C—CF3 | N | C—H | C—H | CF₃ | N | C—H | H | H | EtCO | H | 1 |
| 2-2609 | H | C—CF3 | N | C—H | C—H | CF₃ | N | C—H | H | H | CF3CH2CO | H | 1 |
| 2-2610 | H | C—CF3 | N | C—H | C—H | CF₃ | N | C—H | H | H | CH3SCH2CO | H | 1 |
| 2-2611 | H | C—CF3 | N | C—H | C—H | CF₃ | C—H | C—F | H | H | H | H | 1 |
| 2-2612 | H | C—CF3 | N | C—H | C—H | CF₃ | C—H | C—F | H | H | MeCO | H | 1 |
| 2-2613 | H | C—CF3 | N | C—H | C—H | CF₃ | C—H | C—F | H | H | EtCO | H | 1 |
| 2-2614 | H | C—CF3 | N | C—H | C—H | CF₃ | C—H | C—F | H | H | CF3CH2CO | H | 1 |
| 2-2615 | H | C—CF3 | N | C—H | C—H | CF₃ | C—H | C—F | H | H | cyclo-PrCO | H | 1 |
| 2-2616 | H | C—CF3 | N | C—H | C—H | CF₃ | C—H | C—F | H | H | cyclo-PrCH2CO | H | 1 |
| 2-2617 | H | C—CF3 | N | C—H | C—H | CF₃ | C—H | C—F | H | H | CH3SCH2CO | H | 1 |

TABLE 2-2-continued

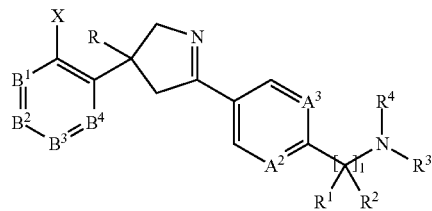

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2618 | H | C—CF3 | N | C—H | C—H | CF₃ | C—H | C—F | H | H | CH3SOCH2CO | H | 1 |
| 2-2619 | H | C—CF3 | N | C—H | C—H | CF₃ | C—H | C—F | H | H | CH3SO2CH2CO | H | 1 |
| 2-2620 | H | C—CF3 | N | C—H | C—H | CF₃ | C—H | C—F | H | H | EtNHCO | H | 1 |
| 2-2621 | H | C—CF3 | N | C—H | C—H | CF₃ | C—H | C—F | Me | H | EtCO | H | 1 |
| 2-2622 | H | C—CF3 | N | C—H | C—H | CF₃ | C—H | C—F | Me | H | CF3CH2CO | H | 1 |
| 2-2623 | H | C—CF3 | N | C—H | C—H | CF₃ | N | C—F | H | H | EtCO | H | 1 |
| 2-2624 | H | C—CF3 | N | C—H | C—H | CF₃ | N | C—F | H | H | CF3CH2CO | H | 1 |
| 2-2625 | H | C—CF3 | N | C—H | C—H | CF₃ | C—H | C—I | H | H | H | H | 1 |
| 2-2626 | H | C—CF3 | N | C—H | C—H | CF₃ | C—H | C—I | H | H | MeCO | H | 1 |
| 2-2627 | H | C—CF3 | N | C—H | C—H | CF₃ | C—H | C—I | H | H | EtCO | H | 1 |
| 2-2628 | H | C—CF3 | N | C—H | C—H | CF₃ | C—H | C—I | H | H | CF3CH2CO | H | 1 |
| 2-2629 | H | C—CF3 | N | C—H | C—H | CF₃ | C—H | C—I | H | H | cyclo-PrCO | H | 1 |
| 2-2630 | H | C—CF3 | N | C—H | C—H | CF₃ | C—H | C—I | H | H | cyclo-PrCH2CO | H | 1 |
| 2-2631 | H | C—CF3 | N | C—H | C—H | CF₃ | C—H | C—I | H | H | CH3SCH2CO | H | 1 |
| 2-2632 | H | C—CF3 | N | C—H | C—H | CF₃ | C—H | C—I | H | H | CH3SOCH2CO | H | 1 |
| 2-2633 | H | C—CF3 | N | C—H | C—H | CF₃ | C—H | C—I | H | H | CH3SO2CH2CO | H | 1 |
| 2-2634 | H | C—CF3 | N | C—H | C—H | CF₃ | C—H | C—I | H | H | EtNHCO | H | 1 |
| 2-2635 | H | C—CF3 | N | C—H | C—H | CF₃ | C—H | C—I | Me | H | EtCO | H | 1 |
| 2-2636 | H | C—CF3 | N | C—H | C—H | CF₃ | C—H | C—I | Me | H | CF3CH2CO | H | 1 |
| 2-2637 | H | C—CF3 | N | C—H | C—H | CF₃ | N | C—I | H | H | EtCO | H | 1 |
| 2-2638 | H | C—CF3 | N | C—H | C—H | CF₃ | N | C—I | H | H | CF3CH2CO | H | 1 |
| 2-2639 | H | C—CF3 | N | C—H | C—H | CF₃ | C—H | C—NH2 | H | H | H | H | 1 |
| 2-2640 | H | C—CF3 | N | C—H | C—H | CF₃ | C—H | C—NH2 | H | H | MeCO | H | 1 |
| 2-2641 | H | C—CF3 | N | C—H | C—H | CF₃ | C—H | C—NH2 | H | H | EtCO | H | 1 |
| 2-2642 | H | C—CF3 | N | C—H | C—H | CF₃ | C—H | C—NH2 | H | H | CF3CH2CO | H | 1 |
| 2-2643 | H | C—CF3 | N | C—H | C—H | CF₃ | C—H | C—NH2 | H | H | cyclo-PrCO | H | 1 |
| 2-2644 | H | C—CF3 | N | C—H | C—H | CF₃ | C—H | C—NH2 | H | H | cyclo-PrCH2CO | H | 1 |
| 2-2645 | H | C—CF3 | N | C—H | C—H | CF₃ | C—H | C—NH2 | H | H | CH3SCH2CO | H | 1 |
| 2-2646 | H | C—CF3 | N | C—H | C—H | CF₃ | C—H | C—NH2 | H | H | CH3SOCH2CO | H | 1 |
| 2-2647 | H | C—CF3 | N | C—H | C—H | CF₃ | C—H | C—NH2 | H | H | CH3SO2CH2CO | H | 1 |
| 2-2648 | H | C—CF3 | N | C—H | C—H | CF₃ | C—H | C—NH2 | H | H | EtNHCO | H | 1 |
| 2-2649 | H | C—CF3 | N | C—H | C—H | CF₃ | C—H | C—NH2 | Me | H | EtCO | H | 1 |
| 2-2650 | H | C—CF3 | N | C—H | C—H | CF₃ | C—H | C—NH2 | Me | H | CF3CH2CO | H | 1 |
| 2-2651 | H | C—CF3 | N | C—H | C—H | CF₃ | N | C—NH2 | H | H | EtCO | H | 1 |
| 2-2652 | H | C—CF3 | N | C—H | C—H | CF₃ | N | C—NH2 | H | H | CF3CH2CO | H | 1 |
| 2-2653 | H | C—CF3 | N | C—H | C—H | CF₃ | C—H | C—NHAc | H | H | H | H | 1 |
| 2-2654 | H | C—CF3 | N | C—H | C—H | CF₃ | C—H | C—NHAc | H | H | MeCO | H | 1 |
| 2-2655 | H | C—CF3 | N | C—H | C—H | CF₃ | C—H | C—NHAc | H | H | EtCO | H | 1 |
| 2-2656 | H | C—CF3 | N | C—H | C—H | CF₃ | C—H | C—NHAc | H | H | CF3CH2CO | H | 1 |
| 2-2657 | H | C—CF3 | N | C—H | C—H | CF₃ | C—H | C—NHAc | H | H | cyclo-PrCO | H | 1 |
| 2-2658 | H | C—CF3 | N | C—H | C—H | CF₃ | C—H | C—NHAc | H | H | cyclo-PrCH2CO | H | 1 |
| 2-2659 | H | C—CF3 | N | C—H | C—H | CF₃ | C—H | C—NHAc | H | H | CH3SCH2CO | H | 1 |
| 2-2660 | H | C—CF3 | N | C—H | C—H | CF₃ | C—H | C—NHAc | H | H | CH3SOCH2CO | H | 1 |
| 2-2661 | H | C—CF3 | N | C—H | C—H | CF₃ | C—H | C—NHAc | H | H | CH3SO2CH2CO | H | 1 |
| 2-2662 | H | C—CF3 | N | C—H | C—H | CF₃ | C—H | C—NHAc | H | H | EtNHCO | H | 1 |
| 2-2663 | H | C—CF3 | N | C—H | C—H | CF₃ | C—H | C—NHAc | Me | H | EtCO | H | 1 |
| 2-2664 | H | C—CF3 | N | C—H | C—H | CF₃ | C—H | C—NHAc | Me | H | CF3CH2CO | H | 1 |
| 2-2665 | H | C—CF3 | N | C—H | C—H | CF₃ | N | C—NHAc | H | H | EtCO | H | 1 |
| 2-2666 | H | C—CF3 | N | C—H | C—H | CF₃ | N | C—NHAc | H | H | CF3CH2CO | H | 1 |
| 2-2667 | H | C—CF3 | N | C—H | C—H | CF₃ | C—H | C—NHCOCF3 | H | H | H | H | 1 |
| 2-2668 | H | C—CF3 | N | C—H | C—H | CF₃ | C—H | C—NHCOCF3 | H | H | MeCO | H | 1 |
| 2-2669 | H | C—CF3 | N | C—H | C—H | CF₃ | C—H | C—NHCOCF3 | H | H | EtCO | H | 1 |
| 2-2670 | H | C—CF3 | N | C—H | C—H | CF₃ | C—H | C—NHCOCF3 | H | H | CF3CH2CO | H | 1 |
| 2-2671 | H | C—CF3 | N | C—H | C—H | CF₃ | C—H | C—NHCOCF3 | H | H | cyclo-PrCO | H | 1 |
| 2-2672 | H | C—CF3 | N | C—H | C—H | CF₃ | C—H | C—NHCOCF3 | H | H | cyclo-PrCH2CO | H | 1 |
| 2-2673 | H | C—CF3 | N | C—H | C—H | CF₃ | C—H | C—NHCOCF3 | H | H | CH3SCH2CO | H | 1 |
| 2-2674 | H | C—CF3 | N | C—H | C—H | CF₃ | C—H | C—NHCOCF3 | H | H | CH3SOCH2CO | H | 1 |
| 2-2675 | H | C—CF3 | N | C—H | C—H | CF₃ | C—H | C—NHCOCF3 | H | H | CH3SO2CH2CO | H | 1 |
| 2-2676 | H | C—CF3 | N | C—H | C—H | CF₃ | C—H | C—NHCOCF3 | H | H | EtNHCO | H | 1 |
| 2-2677 | H | C—CF3 | N | C—H | C—H | CF₃ | C—H | C—NHCOCF3 | Me | H | EtCO | H | 1 |
| 2-2678 | H | C—CF3 | N | C—H | C—H | CF₃ | C—H | C—NHCOCF3 | Me | H | CF3CH2CO | H | 1 |
| 2-2679 | H | C—CF3 | N | C—H | C—H | CF₃ | N | C—NHCOCF3 | H | H | EtCO | H | 1 |
| 2-2680 | H | C—CF3 | N | C—H | C—H | CF₃ | N | C—NHCOCF3 | H | H | CF3CH2CO | H | 1 |
| 2-2681 | H | C—CF3 | N | C—H | C—H | CF₃ | C—H | C—CH2OAc | H | H | H | H | 1 |
| 2-2682 | H | C—CF3 | N | C—H | C—H | CF₃ | C—H | C—CH2OAc | H | H | MeCO | H | 1 |
| 2-2683 | H | C—CF3 | N | C—H | C—H | CF₃ | C—H | C—CH2OAc | H | H | EtCO | H | 1 |
| 2-2684 | H | C—CF3 | N | C—H | C—H | CF₃ | C—H | C—CH2OAc | H | H | CF3CH2CO | H | 1 |

TABLE 2-2-continued

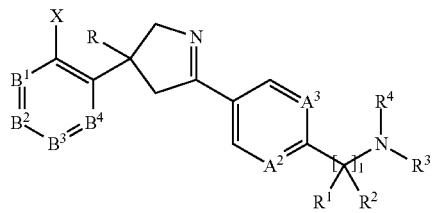

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2685 | H | C—CF3 | N | C—H | C—H | CF₃ | C—H | C—CH2OAc | H | H | cyclo-PrCO | H | 1 |
| 2-2686 | H | C—CF3 | N | C—H | C—H | CF₃ | C—H | C—CH2OAc | H | H | cyclo-PrCH2CO | H | 1 |
| 2-2687 | H | C—CF3 | N | C—H | C—H | CF₃ | C—H | C—CH2OAc | H | H | CH3SCH2CO | H | 1 |
| 2-2688 | H | C—CF3 | N | C—H | C—H | CF₃ | C—H | C—CH2OAc | H | H | CH3SOCH2CO | H | 1 |
| 2-2689 | H | C—CF3 | N | C—H | C—H | CF₃ | C—H | C—CH2OAc | H | H | CH3SO2CH2CO | H | 1 |
| 2-2690 | H | C—CF3 | N | C—H | C—H | CF₃ | C—H | C—CH2OAc | H | H | EtNHCO | H | 1 |
| 2-2691 | H | C—CF3 | N | C—H | C—H | CF₃ | C—H | C—CH2OAc | Me | H | EtCO | H | 1 |
| 2-2692 | H | C—CF3 | N | C—H | C—H | CF₃ | C—H | C—CH2OAc | Me | H | CF3CH2CO | H | 1 |
| 2-2693 | H | C—CF3 | N | C—H | C—H | CF₃ | N | C—CH2OAc | H | H | EtCO | H | 1 |
| 2-2694 | H | C—CF3 | N | C—H | C—H | CF₃ | N | C—CH2OAc | H | H | CF3CH2CO | H | 1 |
| 2-2695 | H | C—CF3 | N | C—CF3 | C—H | CF₃ | C—H | C—CF₃ | H | H | H | H | 1 |
| 2-2696 | H | C—CF3 | N | C—CF3 | C—H | CF₃ | C—H | C—CF₃ | H | H | MeCO | H | 1 |
| 2-2697 | H | C—CF3 | N | C—CF3 | C—H | CF₃ | C—H | C—CF₃ | H | H | EtCO | H | 1 |
| 2-2698 | H | C—CF3 | N | C—CF3 | C—H | CF₃ | C—H | C—CF₃ | H | H | n-PrCO | H | 1 |
| 2-2699 | H | C—CF3 | N | C—CF3 | C—H | CF₃ | C—H | C—CF₃ | H | H | cyclo-PrCO | H | 1 |
| 2-2700 | H | C—CF3 | N | C—CF3 | C—H | CF₃ | C—H | C—CF₃ | H | H | EtNHCO | H | 1 |
| 2-2701 | H | C—CF3 | N | C—CF3 | C—H | CF₃ | C—H | C—CF₃ | H | H | CF3CH2CO | H | 1 |
| 2-2702 | H | C—CF3 | N | C—CF3 | C—H | CF₃ | C—H | C—CF₃ | H | H | cyclo-PrCH2CO | H | 1 |
| 2-2703 | H | C—CF3 | N | C—CF3 | C—H | CF₃ | C—H | C—CF₃ | H | H | CH3SCH2CO | H | 1 |
| 2-2704 | H | C—CF3 | N | C—CF3 | C—H | CF₃ | C—H | C—CF₃ | H | H | CH3SOCH2CO | H | 1 |
| 2-2705 | H | C—CF3 | N | C—CF3 | C—H | CF₃ | C—H | C—CF₃ | H | H | CH3SO2CH2CO | H | 1 |
| 2-2706 | H | C—CF3 | N | C—CF3 | C—H | CF₃ | C—H | C—CF₃ | Me | H | H | H | 1 |
| 2-2707 | H | C—CF3 | N | C—CF3 | C—H | CF₃ | C—H | C—CF₃ | Me | H | EtCO | H | 1 |
| 2-2708 | H | C—CF3 | N | C—CF3 | C—H | CF₃ | C—H | C—CF₃ | Me | H | CF3CH2CO | H | 1 |
| 2-2709 | H | C—CF3 | N | C—CF3 | C—H | CF₃ | C—H | C—CF₃ | Me | H | CH3SCH2CO | H | 1 |
| 2-2710 | H | C—CF3 | N | C—CF3 | C—H | CF₃ | N | C—CF₃ | H | H | H | H | 1 |
| 2-2711 | H | C—CF3 | N | C—CF3 | C—H | CF₃ | N | C—CF₃ | H | H | EtCO | H | 1 |
| 2-2712 | H | C—CF3 | N | C—CF3 | C—H | CF₃ | N | C—CF₃ | H | H | CF3CH2CO | H | 1 |
| 2-2713 | H | C—CF3 | N | C—CF3 | C—H | CF₃ | N | C—CF₃ | H | H | CH3SCH2CO | H | 1 |
| 2-2714 | H | C—CF3 | N | C—CF3 | C—H | CF₃ | C—H | C—Cl | H | H | H | H | 1 |
| 2-2715 | H | C—CF3 | N | C—CF3 | C—H | CF₃ | C—H | C—Cl | H | H | MeCO | H | 1 |
| 2-2716 | H | C—CF3 | N | C—CF3 | C—H | CF₃ | C—H | C—Cl | H | H | CF3CH2CO | H | 1 |
| 2-2717 | H | C—CF3 | N | C—CF3 | C—H | CF₃ | C—H | C—Cl | H | H | cyclo-PrCO | H | 1 |
| 2-2718 | H | C—CF3 | N | C—CF3 | C—H | CF₃ | C—H | C—Cl | H | H | cyclo-PrCH2CO | H | 1 |
| 2-2719 | H | C—CF3 | N | C—CF3 | C—H | CF₃ | C—H | C—Cl | H | H | CH3SCH2CO | H | 1 |
| 2-2720 | H | C—CF3 | N | C—CF3 | C—H | CF₃ | C—H | C—Cl | H | H | CH3SOCH2CO | H | 1 |
| 2-2721 | H | C—CF3 | N | C—CF3 | C—H | CF₃ | C—H | C—Cl | H | H | CH3SO2CH2CO | H | 1 |
| 2-2722 | H | C—CF3 | N | C—CF3 | C—H | CF₃ | C—H | C—Cl | H | H | EtNHCO | H | 1 |
| 2-2723 | H | C—CF3 | N | C—CF3 | C—H | CF₃ | C—H | C—Cl | Me | H | H | H | 1 |
| 2-2724 | H | C—CF3 | N | C—CF3 | C—H | CF₃ | C—H | C—Cl | Me | H | EtCO | H | 1 |
| 2-2725 | H | C—CF3 | N | C—CF3 | C—H | CF₃ | C—H | C—Cl | Me | H | CF3CH2CO | H | 1 |
| 2-2726 | H | C—CF3 | N | C—CF3 | C—H | CF₃ | C—H | C—Cl | Me | H | CH3SCH2CO | H | 1 |
| 2-2727 | H | C—CF3 | N | C—CF3 | C—H | CF₃ | N | C—Cl | H | H | H | H | 1 |
| 2-2728 | H | C—CF3 | N | C—CF3 | C—H | CF₃ | N | C—Cl | H | H | EtCO | H | 1 |
| 2-2729 | H | C—CF3 | N | C—CF3 | C—H | CF₃ | N | C—Cl | H | H | CF3CH2CO | H | 1 |
| 2-2730 | H | C—CF3 | N | C—CF3 | C—H | CF₃ | N | C—Cl | H | H | CH3SCH2CO | H | 1 |
| 2-2731 | H | C—CF3 | N | C—CF3 | C—H | CF₃ | C—H | C—Br | H | H | H | H | 1 |
| 2-2732 | H | C—CF3 | N | C—CF3 | C—H | CF₃ | C—H | C—Br | H | H | MeCO | H | 1 |
| 2-2733 | H | C—CF3 | N | C—CF3 | C—H | CF₃ | C—H | C—Br | H | H | EtCO | H | 1 |
| 2-2734 | H | C—CF3 | N | C—CF3 | C—H | CF₃ | C—H | C—Br | H | H | CF3CH2CO | H | 1 |
| 2-2735 | H | C—CF3 | N | C—CF3 | C—H | CF₃ | C—H | C—Br | H | H | cyclo-PrCO | H | 1 |
| 2-2736 | H | C—CF3 | N | C—CF3 | C—H | CF₃ | C—H | C—Br | H | H | cyclo-PrCH2CO | H | 1 |
| 2-2737 | H | C—CF3 | N | C—CF3 | C—H | CF₃ | C—H | C—Br | H | H | CH3SCH2CO | H | 1 |
| 2-2738 | H | C—CF3 | N | C—CF3 | C—H | CF₃ | C—H | C—Br | H | H | CH3SOCH2CO | H | 1 |
| 2-2739 | H | C—CF3 | N | C—CF3 | C—H | CF₃ | C—H | C—Br | H | H | CH3SO2CH2CO | H | 1 |
| 2-2740 | H | C—CF3 | N | C—CF3 | C—H | CF₃ | C—H | C—Br | H | H | EtNHCO | H | 1 |
| 2-2741 | H | C—CF3 | N | C—CF3 | C—H | CF₃ | C—H | C—Br | Me | H | H | H | 1 |
| 2-2742 | H | C—CF3 | N | C—CF3 | C—H | CF₃ | C—H | C—Br | Me | H | EtCO | H | 1 |
| 2-2743 | H | C—CF3 | N | C—CF3 | C—H | CF₃ | C—H | C—Br | Me | H | CF3CH2CO | H | 1 |
| 2-2744 | H | C—CF3 | N | C—CF3 | C—H | CF₃ | C—H | C—Br | Me | H | CH3SCH2CO | H | 1 |
| 2-2745 | H | C—CF3 | N | C—CF3 | C—H | CF₃ | N | C—Br | H | H | H | H | 1 |
| 2-2746 | H | C—CF3 | N | C—CF3 | C—H | CF₃ | N | C—Br | H | H | EtCO | H | 1 |
| 2-2747 | H | C—CF3 | N | C—CF3 | C—H | CF₃ | N | C—Br | H | H | CF3CH2CO | H | 1 |
| 2-2748 | H | C—CF3 | N | C—CF3 | C—H | CF₃ | N | C—Br | H | H | CH3SCH2CO | H | 1 |
| 2-2749 | H | C—CF3 | N | C—CF3 | C—H | CF₃ | C—H | C—CN | H | H | H | H | 1 |
| 2-2750 | H | C—CF3 | N | C—CF3 | C—H | CF₃ | C—H | C—CN | H | H | MeCO | H | 1 |
| 2-2751 | H | C—CF3 | N | C—CF3 | C—H | CF₃ | C—H | C—CN | H | H | EtCO | H | 1 |

TABLE 2-2-continued

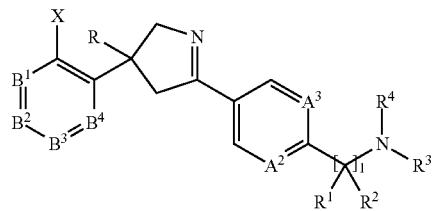

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2752 | H | C—CF3 | N | C—CF3 | C—H | CF₃ | C—H | C—CN | H | H | CF3CH2CO | H | 1 |
| 2-2753 | H | C—CF3 | N | C—CF3 | C—H | CF₃ | C—H | C—CN | H | H | cyclo-PrCO | H | 1 |
| 2-2754 | H | C—CF3 | N | C—CF3 | C—H | CF₃ | C—H | C—CN | H | H | cyclo-PrCH2CO | H | 1 |
| 2-2755 | H | C—CF3 | N | C—CF3 | C—H | CF₃ | C—H | C—CN | H | H | CH3SCH2CO | H | 1 |
| 2-2756 | H | C—CF3 | N | C—CF3 | C—H | CF₃ | C—H | C—CN | H | H | CH3SOCH2CO | H | 1 |
| 2-2757 | H | C—CF3 | N | C—CF3 | C—H | CF₃ | C—H | C—CN | H | H | CH3SO2CH2CO | H | 1 |
| 2-2758 | H | C—CF3 | N | C—CF3 | C—H | CF₃ | C—H | C—CN | H | H | EtNHCO | H | 1 |
| 2-2759 | H | C—CF3 | N | C—CF3 | C—H | CF₃ | C—H | C—CN | Me | H | EtCO | H | 1 |
| 2-2760 | H | C—CF3 | N | C—CF3 | C—H | CF₃ | C—H | C—CN | Me | H | CF3CH2CO | H | 1 |
| 2-2761 | H | C—CF3 | N | C—CF3 | C—H | CF₃ | N | C—CN | H | H | EtCO | H | 1 |
| 2-2762 | H | C—CF3 | N | C—CF3 | C—H | CF₃ | N | C—CN | H | H | CF3CH2CO | H | 1 |
| 2-2763 | H | C—CF3 | N | C—CF3 | C—H | CF₃ | C—H | C—Me | H | H | H | H | 1 |
| 2-2764 | H | C—CF3 | N | C—CF3 | C—H | CF₃ | C—H | C—Me | H | H | MeCO | H | 1 |
| 2-2765 | H | C—CF3 | N | C—CF3 | C—H | CF₃ | C—H | C—Me | H | H | EtCO | H | 1 |
| 2-2766 | H | C—CF3 | N | C—CF3 | C—H | CF₃ | C—H | C—Me | H | H | CF3CH2CO | H | 1 |
| 2-2767 | H | C—CF3 | N | C—CF3 | C—H | CF₃ | C—H | C—Me | H | H | cyclo-PrCO | H | 1 |
| 2-2768 | H | C—CF3 | N | C—CF3 | C—H | CF₃ | C—H | C—Me | H | H | cyclo-PrCH2CO | H | 1 |
| 2-2769 | H | C—CF3 | N | C—CF3 | C—H | CF₃ | C—H | C—Me | H | H | CH3SCH2CO | H | 1 |
| 2-2770 | H | C—CF3 | N | C—CF3 | C—H | CF₃ | C—H | C—Me | H | H | CH3SOCH2CO | H | 1 |
| 2-2771 | H | C—CF3 | N | C—CF3 | C—H | CF₃ | C—H | C—Me | H | H | CH3SO2CH2CO | H | 1 |
| 2-2772 | H | C—CF3 | N | C—CF3 | C—H | CF₃ | C—H | C—Me | H | H | EtNHCO | H | 1 |
| 2-2773 | H | C—CF3 | N | C—CF3 | C—H | CF₃ | C—H | C—Me | Me | H | EtCO | H | 1 |
| 2-2774 | H | C—CF3 | N | C—CF3 | C—H | CF₃ | C—H | C—Me | Me | H | CF3CH2CO | H | 1 |
| 2-2775 | H | C—CF3 | N | C—CF3 | C—H | CF₃ | N | C—Me | H | H | EtCO | H | 1 |
| 2-2776 | H | C—CF3 | N | C—CF3 | C—H | CF₃ | N | C—Me | H | H | CF3CH2CO | H | 1 |
| 2-2777 | H | C—CF3 | N | C—CF3 | C—H | CF₃ | C—H | C—NO2 | H | H | H | H | 1 |
| 2-2778 | H | C—CF3 | N | C—CF3 | C—H | CF₃ | C—H | C—NO2 | H | H | MeCO | H | 1 |
| 2-2779 | H | C—CF3 | N | C—CF3 | C—H | CF₃ | C—H | C—NO2 | H | H | EtCO | H | 1 |
| 2-2780 | H | C—CF3 | N | C—CF3 | C—H | CF₃ | C—H | C—NO2 | H | H | CF3CH2CO | H | 1 |
| 2-2781 | H | C—CF3 | N | C—CF3 | C—H | CF₃ | C—H | C—NO2 | H | H | cyclo-PrCO | H | 1 |
| 2-2782 | H | C—CF3 | N | C—CF3 | C—H | CF₃ | C—H | C—NO2 | H | H | cyclo-PrCH2CO | H | 1 |
| 2-2783 | H | C—CF3 | N | C—CF3 | C—H | CF₃ | C—H | C—NO2 | H | H | CH3SCH2CO | H | 1 |
| 2-2784 | H | C—CF3 | N | C—CF3 | C—H | CF₃ | C—H | C—NO2 | H | H | CH3SOCH2CO | H | 1 |
| 2-2785 | H | C—CF3 | N | C—CF3 | C—H | CF₃ | C—H | C—NO2 | H | H | CH3SO2CH2CO | H | 1 |
| 2-2786 | H | C—CF3 | N | C—CF3 | C—H | CF₃ | C—H | C—NO2 | H | H | EtNHCO | H | 1 |
| 2-2787 | H | C—CF3 | N | C—CF3 | C—H | CF₃ | C—H | C—NO2 | Me | H | EtCO | H | 1 |
| 2-2788 | H | C—CF3 | N | C—CF3 | C—H | CF₃ | C—H | C—NO2 | Me | H | CF3CH2CO | H | 1 |
| 2-2789 | H | C—CF3 | N | C—CF3 | C—H | CF₃ | N | C—NO2 | H | H | EtCO | H | 1 |
| 2-2790 | H | C—CF3 | N | C—CF3 | C—H | CF₃ | N | C—NO2 | H | H | CF3CH2CO | H | 1 |
| 2-2791 | H | C—CF3 | N | C—CF3 | C—H | CF₃ | C—H | C—SMe | H | H | H | H | 1 |
| 2-2792 | H | C—CF3 | N | C—CF3 | C—H | CF₃ | C—H | C—SMe | H | H | MeCO | H | 1 |
| 2-2793 | H | C—CF3 | N | C—CF3 | C—H | CF₃ | C—H | C—SMe | H | H | EtCO | H | 1 |
| 2-2794 | H | C—CF3 | N | C—CF3 | C—H | CF₃ | C—H | C—SMe | H | H | CF3CH2CO | H | 1 |
| 2-2795 | H | C—CF3 | N | C—CF3 | C—H | CF₃ | C—H | C—SMe | H | H | cyclo-PrCO | H | 1 |
| 2-2796 | H | C—CF3 | N | C—CF3 | C—H | CF₃ | C—H | C—SMe | H | H | cyclo-PrCH2CO | H | 1 |
| 2-2797 | H | C—CF3 | N | C—CF3 | C—H | CF₃ | C—H | C—SMe | H | H | CH3SCH2CO | H | 1 |
| 2-2798 | H | C—CF3 | N | C—CF3 | C—H | CF₃ | C—H | C—SMe | H | H | CH3SOCH2CO | H | 1 |
| 2-2799 | H | C—CF3 | N | C—CF3 | C—H | CF₃ | C—H | C—SMe | H | H | CH3SO2CH2CO | H | 1 |
| 2-2800 | H | C—CF3 | N | C—CF3 | C—H | CF₃ | C—H | C—SMe | H | H | EtNHCO | H | 1 |
| 2-2801 | H | C—CF3 | N | C—CF3 | C—H | CF₃ | C—H | C—SMe | Me | H | EtCO | H | 1 |
| 2-2802 | H | C—CF3 | N | C—CF3 | C—H | CF₃ | C—H | C—SMe | Me | H | CF3CH2CO | H | 1 |
| 2-2803 | H | C—CF3 | N | C—CF3 | C—H | CF₃ | N | C—SMe | H | H | EtCO | H | 1 |
| 2-2804 | H | C—CF3 | N | C—CF3 | C—H | CF₃ | N | C—SMe | H | H | CF3CH2CO | H | 1 |
| 2-2805 | H | C—CF3 | N | C—CF3 | C—H | CF₃ | C—H | C—SOMe | H | H | H | H | 1 |
| 2-2806 | H | C—CF3 | N | C—CF3 | C—H | CF₃ | C—H | C—SOMe | H | H | MeCO | H | 1 |
| 2-2807 | H | C—CF3 | N | C—CF3 | C—H | CF₃ | C—H | C—SOMe | H | H | EtCO | H | 1 |
| 2-2808 | H | C—CF3 | N | C—CF3 | C—H | CF₃ | C—H | C—SOMe | H | H | CF3CH2CO | H | 1 |
| 2-2809 | H | C—CF3 | N | C—CF3 | C—H | CF₃ | C—H | C—SOMe | H | H | cyclo-PrCO | H | 1 |
| 2-2810 | H | C—CF3 | N | C—CF3 | C—H | CF₃ | C—H | C—SOMe | H | H | cyclo-PrCH2CO | H | 1 |
| 2-2811 | H | C—CF3 | N | C—CF3 | C—H | CF₃ | C—H | C—SOMe | H | H | CH3SCH2CO | H | 1 |
| 2-2812 | H | C—CF3 | N | C—CF3 | C—H | CF₃ | C—H | C—SOMe | H | H | CH3SOCH2CO | H | 1 |
| 2-2813 | H | C—CF3 | N | C—CF3 | C—H | CF₃ | C—H | C—SOMe | H | H | CH3SO2CH2CO | H | 1 |
| 2-2814 | H | C—CF3 | N | C—CF3 | C—H | CF₃ | C—H | C—SOMe | H | H | EtNHCO | H | 1 |
| 2-2815 | H | C—CF3 | N | C—CF3 | C—H | CF₃ | C—H | C—SOMe | Me | H | EtCO | H | 1 |
| 2-2816 | H | C—CF3 | N | C—CF3 | C—H | CF₃ | C—H | C—SOMe | Me | H | CF3CH2CO | H | 1 |
| 2-2817 | H | C—CF3 | N | C—CF3 | C—H | CF₃ | N | C—SOMe | H | H | EtCO | H | 1 |
| 2-2818 | H | C—CF3 | N | C—CF3 | C—H | CF₃ | N | C—SOMe | H | H | CF3CH2CO | H | 1 |

TABLE 2-2-continued

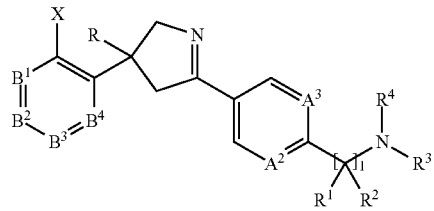

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2819 | H | C—CF3 | N | C—CF3 | C—H | CF3 | C—H | C—SO2Me | H | H | H | H | 1 |
| 2-2820 | H | C—CF3 | N | C—CF3 | C—H | CF3 | C—H | C—SO2Me | H | H | MeCO | H | 1 |
| 2-2821 | H | C—CF3 | N | C—CF3 | C—H | CF3 | C—H | C—SO2Me | H | H | EtCO | H | 1 |
| 2-2822 | H | C—CF3 | N | C—CF3 | C—H | CF3 | C—H | C—SO2Me | H | H | CF3CH2CO | H | 1 |
| 2-2823 | H | C—CF3 | N | C—CF3 | C—H | CF3 | C—H | C—SO2Me | H | H | cyclo-PrCO | H | 1 |
| 2-2824 | H | C—CF3 | N | C—CF3 | C—H | CF3 | C—H | C—SO2Me | H | H | cyclo-PrCH2CO | H | 1 |
| 2-2825 | H | C—CF3 | N | C—CF3 | C—H | CF3 | C—H | C—SO2Me | H | H | CH3SCH2CO | H | 1 |
| 2-2826 | H | C—CF3 | N | C—CF3 | C—H | CF3 | C—H | C—SO2Me | H | H | CH3SOCH2CO | H | 1 |
| 2-2827 | H | C—CF3 | N | C—CF3 | C—H | CF3 | C—H | C—SO2Me | H | H | CH3SO2CH2CO | H | 1 |
| 2-2828 | H | C—CF3 | N | C—CF3 | C—H | CF3 | C—H | C—SO2Me | H | H | EtNHCO | H | 1 |
| 2-2829 | H | C—CF3 | N | C—CF3 | C—H | CF3 | C—H | C—SO2Me | Me | H | EtCO | H | 1 |
| 2-2830 | H | C—CF3 | N | C—CF3 | C—H | CF3 | C—H | C—SO2Me | Me | H | CF3CH2CO | H | 1 |
| 2-2831 | H | C—CF3 | N | C—CF3 | C—H | CF3 | N | C—SO2Me | H | H | EtCO | H | 1 |
| 2-2832 | H | C—CF3 | N | C—CF3 | C—H | CF3 | N | C—SO2Me | H | H | CF3CH2CO | H | 1 |
| 2-2833 | H | C—CF3 | N | C—CF3 | C—H | CF3 | C—H | C—SCF3 | H | H | H | H | 1 |
| 2-2834 | H | C—CF3 | N | C—CF3 | C—H | CF3 | C—H | C—SCF3 | H | H | MeCO | H | 1 |
| 2-2835 | H | C—CF3 | N | C—CF3 | C—H | CF3 | C—H | C—SCF3 | H | H | EtCO | H | 1 |
| 2-2836 | H | C—CF3 | N | C—CF3 | C—H | CF3 | C—H | C—SCF3 | H | H | CF3CH2CO | H | 1 |
| 2-2837 | H | C—CF3 | N | C—CF3 | C—H | CF3 | C—H | C—SCF3 | H | H | cyclo-PrCO | H | 1 |
| 2-2838 | H | C—CF3 | N | C—CF3 | C—H | CF3 | C—H | C—SCF3 | H | H | cyclo-PrCH2CO | H | 1 |
| 2-2839 | H | C—CF3 | N | C—CF3 | C—H | CF3 | C—H | C—SCF3 | H | H | CH3SCH2CO | H | 1 |
| 2-2840 | H | C—CF3 | N | C—CF3 | C—H | CF3 | C—H | C—SCF3 | H | H | CH3SOCH2CO | H | 1 |
| 2-2841 | H | C—CF3 | N | C—CF3 | C—H | CF3 | C—H | C—SCF3 | H | H | CH3SO2CH2CO | H | 1 |
| 2-2842 | H | C—CF3 | N | C—CF3 | C—H | CF3 | C—H | C—SCF3 | H | H | EtNHCO | H | 1 |
| 2-2843 | H | C—CF3 | N | C—CF3 | C—H | CF3 | C—H | C—SCF3 | Me | H | EtCO | H | 1 |
| 2-2844 | H | C—CF3 | N | C—CF3 | C—H | CF3 | C—H | C—SCF3 | Me | H | CF3CH2CO | H | 1 |
| 2-2845 | H | C—CF3 | N | C—CF3 | C—H | CF3 | N | C—SCF3 | H | H | EtCO | H | 1 |
| 2-2846 | H | C—CF3 | N | C—CF3 | C—H | CF3 | N | C—SCF3 | H | H | CF3CH2CO | H | 1 |
| 2-2847 | H | C—CF3 | N | C—CF3 | C—H | CF3 | C—H | C—SOCF3 | H | H | H | H | 1 |
| 2-2848 | H | C—CF3 | N | C—CF3 | C—H | CF3 | C—H | C—SOCF3 | H | H | MeCO | H | 1 |
| 2-2849 | H | C—CF3 | N | C—CF3 | C—H | CF3 | C—H | C—SOCF3 | H | H | EtCO | H | 1 |
| 2-2850 | H | C—CF3 | N | C—CF3 | C—H | CF3 | C—H | C—SOCF3 | H | H | CF3CH2CO | H | 1 |
| 2-2851 | H | C—CF3 | N | C—CF3 | C—H | CF3 | C—H | C—SOCF3 | H | H | cyclo-PrCO | H | 1 |
| 2-2852 | H | C—CF3 | N | C—CF3 | C—H | CF3 | C—H | C—SOCF3 | H | H | cyclo-PrCH2CO | H | 1 |
| 2-2853 | H | C—CF3 | N | C—CF3 | C—H | CF3 | C—H | C—SOCF3 | H | H | CH3SCH2CO | H | 1 |
| 2-2854 | H | C—CF3 | N | C—CF3 | C—H | CF3 | C—H | C—SOCF3 | H | H | CH3SOCH2CO | H | 1 |
| 2-2855 | H | C—CF3 | N | C—CF3 | C—H | CF3 | C—H | C—SOCF3 | H | H | CH3SO2CH2CO | H | 1 |
| 2-2856 | H | C—CF3 | N | C—CF3 | C—H | CF3 | C—H | C—SOCF3 | H | H | EtNHCO | H | 1 |
| 2-2857 | H | C—CF3 | N | C—CF3 | C—H | CF3 | C—H | C—SOCF3 | Me | H | EtCO | H | 1 |
| 2-2858 | H | C—CF3 | N | C—CF3 | C—H | CF3 | C—H | C—SOCF3 | Me | H | CF3CH2CO | H | 1 |
| 2-2859 | H | C—CF3 | N | C—CF3 | C—H | CF3 | N | C—SOCF3 | H | H | EtCO | H | 1 |
| 2-2860 | H | C—CF3 | N | C—CF3 | C—H | CF3 | N | C—SOCF3 | H | H | CF3CH2CO | H | 1 |
| 2-2861 | H | C—CF3 | N | C—CF3 | C—H | CF3 | C—H | C—H | H | H | H | H | 1 |
| 2-2862 | H | C—CF3 | N | C—CF3 | C—H | CF3 | C—H | C—H | H | H | MeCO | H | 1 |
| 2-2863 | H | C—CF3 | N | C—CF3 | C—H | CF3 | C—H | C—H | H | H | EtCO | H | 1 |
| 2-2864 | H | C—CF3 | N | C—CF3 | C—H | CF3 | C—H | C—H | H | H | CF3CH2CO | H | 1 |
| 2-2865 | H | C—CF3 | N | C—CF3 | C—H | CF3 | C—H | C—H | H | H | cyclo-PrCO | H | 1 |
| 2-2866 | H | C—CF3 | N | C—CF3 | C—H | CF3 | C—H | C—H | H | H | cyclo-PrCH2CO | H | 1 |
| 2-2867 | H | C—CF3 | N | C—CF3 | C—H | CF3 | C—H | C—H | H | H | CH3SCH2CO | H | 1 |
| 2-2868 | H | C—CF3 | N | C—CF3 | C—H | CF3 | C—H | C—H | H | H | CH3SOCH2CO | H | 1 |
| 2-2869 | H | C—CF3 | N | C—CF3 | C—H | CF3 | C—H | C—H | H | H | CH3SO2CH2CO | H | 1 |
| 2-2870 | H | C—CF3 | N | C—CF3 | C—H | CF3 | C—H | C—H | H | H | EtNHCO | H | 1 |
| 2-2871 | H | C—CF3 | N | C—CF3 | C—H | CF3 | C—H | C—H | Me | H | H | H | 1 |
| 2-2872 | H | C—CF3 | N | C—CF3 | C—H | CF3 | C—H | C—H | Me | H | EtCO | H | 1 |
| 2-2873 | H | C—CF3 | N | C—CF3 | C—H | CF3 | C—H | C—H | Me | H | CF3CH2CO | H | 1 |
| 2-2874 | H | C—CF3 | N | C—CF3 | C—H | CF3 | C—H | C—H | Me | H | CH3SCH2CO | H | 1 |
| 2-2875 | H | C—CF3 | N | C—CF3 | C—H | CF3 | N | C—H | H | H | H | H | 1 |
| 2-2876 | H | C—CF3 | N | C—CF3 | C—H | CF3 | N | C—H | H | H | EtCO | H | 1 |
| 2-2877 | H | C—CF3 | N | C—CF3 | C—H | CF3 | N | C—H | H | H | CF3CH2CO | H | 1 |
| 2-2878 | H | C—CF3 | N | C—CF3 | C—H | CF3 | N | C—H | H | H | CH3SCH2CO | H | 1 |
| 2-2879 | H | C—CF3 | N | C—CF3 | C—H | CF3 | C—H | C—F | H | H | H | H | 1 |
| 2-2880 | H | C—CF3 | N | C—CF3 | C—H | CF3 | C—H | C—F | H | H | MeCO | H | 1 |
| 2-2881 | H | C—CF3 | N | C—CF3 | C—H | CF3 | C—H | C—F | H | H | EtCO | H | 1 |
| 2-2882 | H | C—CF3 | N | C—CF3 | C—H | CF3 | C—H | C—F | H | H | CF3CH2CO | H | 1 |
| 2-2883 | H | C—CF3 | N | C—CF3 | C—H | CF3 | C—H | C—F | H | H | cyclo-PrCO | H | 1 |
| 2-2884 | H | C—CF3 | N | C—CF3 | C—H | CF3 | C—H | C—F | H | H | cyclo-PrCH2CO | H | 1 |
| 2-2885 | H | C—CF3 | N | C—CF3 | C—H | CF3 | C—H | C—F | H | H | CH3SCH2CO | H | 1 |

TABLE 2-2-continued

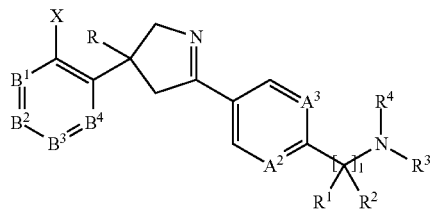

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2886 | H | C—CF3 | N | C—CF3 | C—H | CF₃ | C—H | C—F | H | H | CH3SOCH2CO | H | 1 |
| 2-2887 | H | C—CF3 | N | C—CF3 | C—H | CF₃ | C—H | C—F | H | H | CH3SO2CH2CO | H | 1 |
| 2-2888 | H | C—CF3 | N | C—CF3 | C—H | CF₃ | C—H | C—F | H | H | EtNHCO | H | 1 |
| 2-2889 | H | C—CF3 | N | C—CF3 | C—H | CF₃ | C—H | C—F | Me | H | EtCO | H | 1 |
| 2-2890 | H | C—CF3 | N | C—CF3 | C—H | CF₃ | C—H | C—F | Me | H | CF3CH2CO | H | 1 |
| 2-2891 | H | C—CF3 | N | C—CF3 | C—H | CF₃ | N | C—F | H | H | EtCO | H | 1 |
| 2-2892 | H | C—CF3 | N | C—CF3 | C—H | CF₃ | N | C—F | H | H | CF3CH2CO | H | 1 |
| 2-2893 | H | C—CF3 | N | C—CF3 | C—H | CF₃ | C—H | C—I | H | H | H | H | 1 |
| 2-2894 | H | C—CF3 | N | C—CF3 | C—H | CF₃ | C—H | C—I | H | H | MeCO | H | 1 |
| 2-2895 | H | C—CF3 | N | C—CF3 | C—H | CF₃ | C—H | C—I | H | H | EtCO | H | 1 |
| 2-2896 | H | C—CF3 | N | C—CF3 | C—H | CF₃ | C—H | C—I | H | H | CF3CH2CO | H | 1 |
| 2-2897 | H | C—CF3 | N | C—CF3 | C—H | CF₃ | C—H | C—I | H | H | cyclo-PrCO | H | 1 |
| 2-2898 | H | C—CF3 | N | C—CF3 | C—H | CF₃ | C—H | C—I | H | H | cyclo-PrCH2CO | H | 1 |
| 2-2899 | H | C—CF3 | N | C—CF3 | C—H | CF₃ | C—H | C—I | H | H | CH3SCH2CO | H | 1 |
| 2-2900 | H | C—CF3 | N | C—CF3 | C—H | CF₃ | C—H | C—I | H | H | CH3SOCH2CO | H | 1 |
| 2-2901 | H | C—CF3 | N | C—CF3 | C—H | CF₃ | C—H | C—I | H | H | CH3SO2CH2CO | H | 1 |
| 2-2902 | H | C—CF3 | N | C—CF3 | C—H | CF₃ | C—H | C—I | H | H | EtNHCO | H | 1 |
| 2-2903 | H | C—CF3 | N | C—CF3 | C—H | CF₃ | C—H | C—I | Me | H | EtCO | H | 1 |
| 2-2904 | H | C—CF3 | N | C—CF3 | C—H | CF₃ | C—H | C—I | Me | H | CF3CH2CO | H | 1 |
| 2-2905 | H | C—CF3 | N | C—CF3 | C—H | CF₃ | N | C—I | H | H | EtCO | H | 1 |
| 2-2906 | H | C—CF3 | N | C—CF3 | C—H | CF₃ | N | C—I | H | H | CF3CH2CO | H | 1 |
| 2-2907 | H | C—CF3 | N | C—CF3 | C—H | CF₃ | C—H | C—NH2 | H | H | H | H | 1 |
| 2-2908 | H | C—CF3 | N | C—CF3 | C—H | CF₃ | C—H | C—NH2 | H | H | MeCO | H | 1 |
| 2-2909 | H | C—CF3 | N | C—CF3 | C—H | CF₃ | C—H | C—NH2 | H | H | EtCO | H | 1 |
| 2-2910 | H | C—CF3 | N | C—CF3 | C—H | CF₃ | C—H | C—NH2 | H | H | CF3CH2CO | H | 1 |
| 2-2911 | H | C—CF3 | N | C—CF3 | C—H | CF₃ | C—H | C—NH2 | H | H | cyclo-PrCO | H | 1 |
| 2-2912 | H | C—CF3 | N | C—CF3 | C—H | CF₃ | C—H | C—NH2 | H | H | cyclo-PrCH2CO | H | 1 |
| 2-2913 | H | C—CF3 | N | C—CF3 | C—H | CF₃ | C—H | C—NH2 | H | H | CH3SCH2CO | H | 1 |
| 2-2914 | H | C—CF3 | N | C—CF3 | C—H | CF₃ | C—H | C—NH2 | H | H | CH3SOCH2CO | H | 1 |
| 2-2915 | H | C—CF3 | N | C—CF3 | C—H | CF₃ | C—H | C—NH2 | H | H | CH3SO2CH2CO | H | 1 |
| 2-2916 | H | C—CF3 | N | C—CF3 | C—H | CF₃ | C—H | C—NH2 | H | H | EtNHCO | H | 1 |
| 2-2917 | H | C—CF3 | N | C—CF3 | C—H | CF₃ | C—H | C—NH2 | Me | H | EtCO | H | 1 |
| 2-2918 | H | C—CF3 | N | C—CF3 | C—H | CF₃ | C—H | C—NH2 | Me | H | CF3CH2CO | H | 1 |
| 2-2919 | H | C—CF3 | N | C—CF3 | C—H | CF₃ | N | C—NH2 | H | H | EtCO | H | 1 |
| 2-2920 | H | C—CF3 | N | C—CF3 | C—H | CF₃ | N | C—NH2 | H | H | CF3CH2CO | H | 1 |
| 2-2921 | H | C—CF3 | N | C—CF3 | C—H | CF₃ | C—H | C—NHAc | H | H | H | H | 1 |
| 2-2922 | H | C—CF3 | N | C—CF3 | C—H | CF₃ | C—H | C—NHAc | H | H | MeCO | H | 1 |
| 2-2923 | H | C—CF3 | N | C—CF3 | C—H | CF₃ | C—H | C—NHAc | H | H | EtCO | H | 1 |
| 2-2924 | H | C—CF3 | N | C—CF3 | C—H | CF₃ | C—H | C—NHAc | H | H | CF3CH2CO | H | 1 |
| 2-2925 | H | C—CF3 | N | C—CF3 | C—H | CF₃ | C—H | C—NHAc | H | H | cyclo-PrCO | H | 1 |
| 2-2926 | H | C—CF3 | N | C—CF3 | C—H | CF₃ | C—H | C—NHAc | H | H | cyclo-PrCH2CO | H | 1 |
| 2-2927 | H | C—CF3 | N | C—CF3 | C—H | CF₃ | C—H | C—NHAc | H | H | CH3SCH2CO | H | 1 |
| 2-2928 | H | C—CF3 | N | C—CF3 | C—H | CF₃ | C—H | C—NHAc | H | H | CH3SOCH2CO | H | 1 |
| 2-2929 | H | C—CF3 | N | C—CF3 | C—H | CF₃ | C—H | C—NHAc | H | H | CH3SO2CH2CO | H | 1 |
| 2-2930 | H | C—CF3 | N | C—CF3 | C—H | CF₃ | C—H | C—NHAc | H | H | EtNHCO | H | 1 |
| 2-2931 | H | C—CF3 | N | C—CF3 | C—H | CF₃ | C—H | C—NHAc | Me | H | EtCO | H | 1 |
| 2-2932 | H | C—CF3 | N | C—CF3 | C—H | CF₃ | C—H | C—NHAc | Me | H | CF3CH2CO | H | 1 |
| 2-2933 | H | C—CF3 | N | C—CF3 | C—H | CF₃ | N | C—NHAc | H | H | EtCO | H | 1 |
| 2-2934 | H | C—CF3 | N | C—CF3 | C—H | CF₃ | N | C—NHAc | H | H | CF3CH2CO | H | 1 |
| 2-2935 | H | C—CF3 | N | C—CF3 | C—H | CF₃ | C—H | C—NHCOCF3 | H | H | H | H | 1 |
| 2-2936 | H | C—CF3 | N | C—CF3 | C—H | CF₃ | C—H | C—NHCOCF3 | H | H | MeCO | H | 1 |
| 2-2937 | H | C—CF3 | N | C—CF3 | C—H | CF₃ | C—H | C—NHCOCF3 | H | H | EtCO | H | 1 |
| 2-2938 | H | C—CF3 | N | C—CF3 | C—H | CF₃ | C—H | C—NHCOCF3 | H | H | CF3CH2CO | H | 1 |
| 2-2939 | H | C—CF3 | N | C—CF3 | C—H | CF₃ | C—H | C—NHCOCF3 | H | H | cyclo-PrCO | H | 1 |
| 2-2940 | H | C—CF3 | N | C—CF3 | C—H | CF₃ | C—H | C—NHCOCF3 | H | H | cyclo-PrCH2CO | H | 1 |
| 2-2941 | H | C—CF3 | N | C—CF3 | C—H | CF₃ | C—H | C—NHCOCF3 | H | H | CH3SCH2CO | H | 1 |
| 2-2942 | H | C—CF3 | N | C—CF3 | C—H | CF₃ | C—H | C—NHCOCF3 | H | H | CH3SOCH2CO | H | 1 |
| 2-2943 | H | C—CF3 | N | C—CF3 | C—H | CF₃ | C—H | C—NHCOCF3 | H | H | CH3SO2CH2CO | H | 1 |
| 2-2944 | H | C—CF3 | N | C—CF3 | C—H | CF₃ | C—H | C—NHCOCF3 | H | H | EtNHCO | H | 1 |
| 2-2945 | H | C—CF3 | N | C—CF3 | C—H | CF₃ | C—H | C—NHCOCF3 | Me | H | EtCO | H | 1 |
| 2-2946 | H | C—CF3 | N | C—CF3 | C—H | CF₃ | C—H | C—NHCOCF3 | Me | H | CF3CH2CO | H | 1 |
| 2-2947 | H | C—CF3 | N | C—CF3 | C—H | CF₃ | N | C—NHCOCF3 | H | H | EtCO | H | 1 |
| 2-2948 | H | C—CF3 | N | C—CF3 | C—H | CF₃ | N | C—NHCOCF3 | H | H | CF3CH2CO | H | 1 |
| 2-2949 | H | C—CF3 | N | C—CF3 | C—H | CF₃ | C—H | C—CH2OAc | H | H | H | H | 1 |
| 2-2950 | H | C—CF3 | N | C—CF3 | C—H | CF₃ | C—H | C—CH2OAc | H | H | MeCO | H | 1 |
| 2-2951 | H | C—CF3 | N | C—CF3 | C—H | CF₃ | C—H | C—CH2OAc | H | H | EtCO | H | 1 |
| 2-2952 | H | C—CF3 | N | C—CF3 | C—H | CF₃ | C—H | C—CH2OAc | H | H | CF3CH2CO | H | 1 |

TABLE 2-2-continued

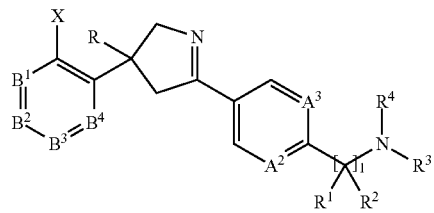

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-2953 | H | C—CF3 | N | C—CF3 | C—H | CF₃ | C—H | C—CH2OAc | H | H | cyclo-PrCO | H | 1 |
| 2-2954 | H | C—CF3 | N | C—CF3 | C—H | CF₃ | C—H | C—CH2OAc | H | H | cyclo-PrCH2CO | H | 1 |
| 2-2955 | H | C—CF3 | N | C—CF3 | C—H | CF₃ | C—H | C—CH2OAc | H | H | CH3SCH2CO | H | 1 |
| 2-2956 | H | C—CF3 | N | C—CF3 | C—H | CF₃ | C—H | C—CH2OAc | H | H | CH3SOCH2CO | H | 1 |
| 2-2957 | H | C—CF3 | N | C—CF3 | C—H | CF₃ | C—H | C—CH2OAc | H | H | CH3SO2CH2CO | H | 1 |
| 2-2958 | H | C—CF3 | N | C—CF3 | C—H | CF₃ | C—H | C—CH2OAc | H | H | EtNHCO | H | 1 |
| 2-2959 | H | C—CF3 | N | C—CF3 | C—H | CF₃ | C—H | C—CH2OAc | Me | H | EtCO | H | 1 |
| 2-2960 | H | C—CF3 | N | C—CF3 | C—H | CF₃ | C—H | C—CH2OAc | Me | H | CF3CH2CO | H | 1 |
| 2-2961 | H | C—CF3 | N | C—CF3 | C—H | CF₃ | N | C—CH2OAc | H | H | EtCO | H | 1 |
| 2-2962 | H | C—CF3 | N | C—CF3 | C—H | CF₃ | N | C—CH2OAc | H | H | CF3CH2CO | H | 1 |
| 2-3231 | H | C—CF3 | C—H | C—CF3 | N | CF₃ | C—H | C—CF₃ | H | H | H | H | 1 |
| 2-3232 | H | C—CF3 | C—H | C—CF3 | N | CF₃ | C—H | C—CF₃ | H | H | MeCO | H | 1 |
| 2-3233 | H | C—CF3 | C—H | C—CF3 | N | CF₃ | C—H | C—CF₃ | H | H | EtCO | H | 1 |
| 2-3234 | H | C—CF3 | C—H | C—CF3 | N | CF₃ | C—H | C—CF₃ | H | H | n-PrCO | H | 1 |
| 2-3235 | H | C—CF3 | C—H | C—CF3 | N | CF₃ | C—H | C—CF₃ | H | H | cyclo-PrCO | H | 1 |
| 2-3236 | H | C—CF3 | C—H | C—CF3 | N | CF₃ | C—H | C—CF₃ | H | H | EtNHCO | H | 1 |
| 2-3237 | H | C—CF3 | C—H | C—CF3 | N | CF₃ | C—H | C—CF₃ | H | H | CF3CH2CO | H | 1 |
| 2-3238 | H | C—CF3 | C—H | C—CF3 | N | CF₃ | C—H | C—CF₃ | H | H | cyclo-PrCH2CO | H | 1 |
| 2-3239 | H | C—CF3 | C—H | C—CF3 | N | CF₃ | C—H | C—CF₃ | H | H | CH3SCH2CO | H | 1 |
| 2-3240 | H | C—CF3 | C—H | C—CF3 | N | CF₃ | C—H | C—CF₃ | H | H | CH3SOCH2CO | H | 1 |
| 2-3241 | H | C—CF3 | C—H | C—CF3 | N | CF₃ | C—H | C—CF₃ | H | H | CH3SO2CH2CO | H | 1 |
| 2-3242 | H | C—CF3 | C—H | C—CF3 | N | CF₃ | C—H | C—CF₃ | Me | H | H | H | 1 |
| 2-3243 | H | C—CF3 | C—H | C—CF3 | N | CF₃ | C—H | C—CF₃ | Me | H | EtCO | H | 1 |
| 2-3244 | H | C—CF3 | C—H | C—CF3 | N | CF₃ | C—H | C—CF₃ | Me | H | CF3CH2CO | H | 1 |
| 2-3245 | H | C—CF3 | C—H | C—CF3 | N | CF₃ | C—H | C—CF₃ | Me | H | CH3SCH2CO | H | 1 |
| 2-3246 | H | C—CF3 | C—H | C—CF3 | N | CF₃ | N | C—CF₃ | H | H | H | H | 1 |
| 2-3247 | H | C—CF3 | C—H | C—CF3 | N | CF₃ | N | C—CF₃ | H | H | EtCO | H | 1 |
| 2-3248 | H | C—CF3 | C—H | C—CF3 | N | CF₃ | N | C—CF₃ | H | H | CF3CH2CO | H | 1 |
| 2-3249 | H | C—CF3 | C—H | C—CF3 | N | CF₃ | N | C—CF₃ | H | H | CH3SCH2CO | H | 1 |
| 2-3250 | H | C—CF3 | C—H | C—CF3 | N | CF₃ | C—H | C—Cl | H | H | H | H | 1 |
| 2-3251 | H | C—CF3 | C—H | C—CF3 | N | CF₃ | C—H | C—Cl | H | H | MeCO | H | 1 |
| 2-3252 | H | C—CF3 | C—H | C—CF3 | N | CF₃ | C—H | C—Cl | H | H | EtCO | H | 1 |
| 2-3253 | H | C—CF3 | C—H | C—CF3 | N | CF₃ | C—H | C—Cl | H | H | CF3CH2CO | H | 1 |
| 2-3254 | H | C—CF3 | C—H | C—CF3 | N | CF₃ | C—H | C—Cl | H | H | cyclo-PrCO | H | 1 |
| 2-3255 | H | C—CF3 | C—H | C—CF3 | N | CF₃ | C—H | C—Cl | H | H | cyclo-PrCH2CO | H | 1 |
| 2-3256 | H | C—CF3 | C—H | C—CF3 | N | CF₃ | C—H | C—Cl | H | H | CH3SCH2CO | H | 1 |
| 2-3257 | H | C—CF3 | C—H | C—CF3 | N | CF₃ | C—H | C—Cl | H | H | CH3SOCH2CO | H | 1 |
| 2-3258 | H | C—CF3 | C—H | C—CF3 | N | CF₃ | C—H | C—Cl | H | H | CH3SO2CH2CO | H | 1 |
| 2-3259 | H | C—CF3 | C—H | C—CF3 | N | CF₃ | C—H | C—Cl | H | H | EtNHCO | H | 1 |
| 2-3260 | H | C—CF3 | C—H | C—CF3 | N | CF₃ | C—H | C—Cl | Me | H | H | H | 1 |
| 2-3261 | H | C—CF3 | C—H | C—CF3 | N | CF₃ | C—H | C—Cl | Me | H | EtCO | H | 1 |
| 2-3262 | H | C—CF3 | C—H | C—CF3 | N | CF₃ | C—H | C—Cl | Me | H | CF3CH2CO | H | 1 |
| 2-3263 | H | C—CF3 | C—H | C—CF3 | N | CF₃ | C—H | C—Cl | Me | H | CH3SCH2CO | H | 1 |
| 2-3264 | H | C—CF3 | C—H | C—CF3 | N | CF₃ | N | C—Cl | H | H | H | H | 1 |
| 2-3265 | H | C—CF3 | C—H | C—CF3 | N | CF₃ | N | C—Cl | H | H | EtCO | H | 1 |
| 2-3266 | H | C—CF3 | C—H | C—CF3 | N | CF₃ | N | C—Cl | H | H | CF3CH2CO | H | 1 |
| 2-3267 | H | C—CF3 | C—H | C—CF3 | N | CF₃ | N | C—Cl | H | H | CH3SCH2CO | H | 1 |
| 2-3268 | H | C—CF3 | C—H | C—CF3 | N | CF₃ | C—H | C—Br | H | H | H | H | 1 |
| 2-3269 | H | C—CF3 | C—H | C—CF3 | N | CF₃ | C—H | C—Br | H | H | MeCO | H | 1 |
| 2-3270 | H | C—CF3 | C—H | C—CF3 | N | CF₃ | C—H | C—Br | H | H | EtCO | H | 1 |
| 2-3271 | H | C—CF3 | C—H | C—CF3 | N | CF₃ | C—H | C—Br | H | H | CF3CH2CO | H | 1 |
| 2-3272 | H | C—CF3 | C—H | C—CF3 | N | CF₃ | C—H | C—Br | H | H | cyclo-PrCO | H | 1 |
| 2-3273 | H | C—CF3 | C—H | C—CF3 | N | CF₃ | C—H | C—Br | H | H | cyclo-PrCH2CO | H | 1 |
| 2-3274 | H | C—CF3 | C—H | C—CF3 | N | CF₃ | C—H | C—Br | H | H | CH3SCH2CO | H | 1 |
| 2-3275 | H | C—CF3 | C—H | C—CF3 | N | CF₃ | C—H | C—Br | H | H | CH3SOCH2CO | H | 1 |
| 2-3276 | H | C—CF3 | C—H | C—CF3 | N | CF₃ | C—H | C—Br | H | H | CH3SO2CH2CO | H | 1 |
| 2-3277 | H | C—CF3 | C—H | C—CF3 | N | CF₃ | C—H | C—Br | H | H | EtNHCO | H | 1 |
| 2-3278 | H | C—CF3 | C—H | C—CF3 | N | CF₃ | C—H | C—Br | Me | H | H | H | 1 |
| 2-3279 | H | C—CF3 | C—H | C—CF3 | N | CF₃ | C—H | C—Br | Me | H | EtCO | H | 1 |
| 2-3280 | H | C—CF3 | C—H | C—CF3 | N | CF₃ | C—H | C—Br | Me | H | CF3CH2CO | H | 1 |
| 2-3281 | H | C—CF3 | C—H | C—CF3 | N | CF₃ | C—H | C—Br | Me | H | CH3SCH2CO | H | 1 |
| 2-3282 | H | C—CF3 | C—H | C—CF3 | N | CF₃ | N | C—Br | H | H | H | H | 1 |
| 2-3283 | H | C—CF3 | C—H | C—CF3 | N | CF₃ | N | C—Br | H | H | EtCO | H | 1 |
| 2-3284 | H | C—CF3 | C—H | C—CF3 | N | CF₃ | N | C—Br | H | H | CF3CH2CO | H | 1 |
| 2-3285 | H | C—CF3 | C—H | C—CF3 | N | CF₃ | N | C—Br | H | H | CH3SCH2CO | H | 1 |
| 2-3286 | H | C—CF3 | C—H | C—CF3 | N | CF₃ | C—H | C—CN | H | H | H | H | 1 |
| 2-3287 | H | C—CF3 | C—H | C—CF3 | N | CF₃ | C—H | C—CN | H | H | MeCO | H | 1 |

TABLE 2-2-continued

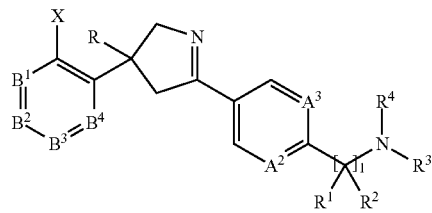

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3288 | H | C—CF3 | C—H | C—CF3 | N | CF₃ | C—H | C—CN | H | H | EtCO | H | 1 |
| 2-3289 | H | C—CF3 | C—H | C—CF3 | N | CF₃ | C—H | C—CN | H | H | CF3CH2CO | H | 1 |
| 2-3290 | H | C—CF3 | C—H | C—CF3 | N | CF₃ | C—H | C—CN | H | H | cyclo-PrCO | H | 1 |
| 2-3291 | H | C—CF3 | C—H | C—CF3 | N | CF₃ | C—H | C—CN | H | H | cyclo-PrCH2CO | H | 1 |
| 2-3292 | H | C—CF3 | C—H | C—CF3 | N | CF₃ | C—H | C—CN | H | H | CH3SCH2CO | H | 1 |
| 2-3293 | H | C—CF3 | C—H | C—CF3 | N | CF₃ | C—H | C—CN | H | H | CH3SOCH2CO | H | 1 |
| 2-3294 | H | C—CF3 | C—H | C—CF3 | N | CF₃ | C—H | C—CN | H | H | CH3SO2CH2CO | H | 1 |
| 2-3295 | H | C—CF3 | C—H | C—CF3 | N | CF₃ | C—H | C—CN | H | H | EtNHCO | H | 1 |
| 2-3296 | H | C—CF3 | C—H | C—CF3 | N | CF₃ | C—H | C—CN | Me | H | EtCO | H | 1 |
| 2-3297 | H | C—CF3 | C—H | C—CF3 | N | CF₃ | C—H | C—CN | Me | H | CF3CH2CO | H | 1 |
| 2-3298 | H | C—CF3 | C—H | C—CF3 | N | CF₃ | N | C—CN | H | H | EtCO | H | 1 |
| 2-3299 | H | C—CF3 | C—H | C—CF3 | N | CF₃ | N | C—CN | H | H | CF3CH2CO | H | 1 |
| 2-3300 | H | C—CF3 | C—H | C—CF3 | N | CF₃ | C—H | C—Me | H | H | H | H | 1 |
| 2-3301 | H | C—CF3 | C—H | C—CF3 | N | CF₃ | C—H | C—Me | H | H | MeCO | H | 1 |
| 2-3302 | H | C—CF3 | C—H | C—CF3 | N | CF₃ | C—H | C—Me | H | H | EtCO | H | 1 |
| 2-3303 | H | C—CF3 | C—H | C—CF3 | N | CF₃ | C—H | C—Me | H | H | CF3CH2CO | H | 1 |
| 2-3304 | H | C—CF3 | C—H | C—CF3 | N | CF₃ | C—H | C—Me | H | H | cyclo-PrCO | H | 1 |
| 2-3305 | H | C—CF3 | C—H | C—CF3 | N | CF₃ | C—H | C—Me | H | H | cyclo-PrCH2CO | H | 1 |
| 2-3306 | H | C—CF3 | C—H | C—CF3 | N | CF₃ | C—H | C—Me | H | H | CH3SCH2CO | H | 1 |
| 2-3307 | H | C—CF3 | C—H | C—CF3 | N | CF₃ | C—H | C—Me | H | H | CH3SOCH2CO | H | 1 |
| 2-3308 | H | C—CF3 | C—H | C—CF3 | N | CF₃ | C—H | C—Me | H | H | CH3SO2CH2CO | H | 1 |
| 2-3309 | H | C—CF3 | C—H | C—CF3 | N | CF₃ | C—H | C—Me | H | H | EtNHCO | H | 1 |
| 2-3310 | H | C—CF3 | C—H | C—CF3 | N | CF₃ | C—H | C—Me | Me | H | EtCO | H | 1 |
| 2-3311 | H | C—CF3 | C—H | C—CF3 | N | CF₃ | C—H | C—Me | Me | H | CF3CH2CO | H | 1 |
| 2-3312 | H | C—CF3 | C—H | C—CF3 | N | CF₃ | N | C—Me | H | H | EtCO | H | 1 |
| 2-3313 | H | C—CF3 | C—H | C—CF3 | N | CF₃ | N | C—Me | H | H | CF3CH2CO | H | 1 |
| 2-3314 | H | C—CF3 | C—H | C—CF3 | N | CF₃ | C—H | C—NO2 | H | H | H | H | 1 |
| 2-3315 | H | C—CF3 | C—H | C—CF3 | N | CF₃ | C—H | C—NO2 | H | H | MeCO | H | 1 |
| 2-3316 | H | C—CF3 | C—H | C—CF3 | N | CF₃ | C—H | C—NO2 | H | H | EtCO | H | 1 |
| 2-3317 | H | C—CF3 | C—H | C—CF3 | N | CF₃ | C—H | C—NO2 | H | H | CF3CH2CO | H | 1 |
| 2-3318 | H | C—CF3 | C—H | C—CF3 | N | CF₃ | C—H | C—NO2 | H | H | cyclo-PrCO | H | 1 |
| 2-3319 | H | C—CF3 | C—H | C—CF3 | N | CF₃ | C—H | C—NO2 | H | H | cyclo-PrCH2CO | H | 1 |
| 2-3320 | H | C—CF3 | C—H | C—CF3 | N | CF₃ | C—H | C—NO2 | H | H | CH3SCH2CO | H | 1 |
| 2-3321 | H | C—CF3 | C—H | C—CF3 | N | CF₃ | C—H | C—NO2 | H | H | CH3SOCH2CO | H | 1 |
| 2-3322 | H | C—CF3 | C—H | C—CF3 | N | CF₃ | C—H | C—NO2 | H | H | CH3SO2CH2CO | H | 1 |
| 2-3323 | H | C—CF3 | C—H | C—CF3 | N | CF₃ | C—H | C—NO2 | H | H | EtNHCO | H | 1 |
| 2-3324 | H | C—CF3 | C—H | C—CF3 | N | CF₃ | C—H | C—NO2 | Me | H | EtCO | H | 1 |
| 2-3325 | H | C—CF3 | C—H | C—CF3 | N | CF₃ | C—H | C—NO2 | Me | H | CF3CH2CO | H | 1 |
| 2-3326 | H | C—CF3 | C—H | C—CF3 | N | CF₃ | N | C—NO2 | H | H | EtCO | H | 1 |
| 2-3327 | H | C—CF3 | C—H | C—CF3 | N | CF₃ | N | C—NO2 | H | H | CF3CH2CO | H | 1 |
| 2-3328 | H | C—CF3 | C—H | C—CF3 | N | CF₃ | C—H | C—SMe | H | H | H | H | 1 |
| 2-3329 | H | C—CF3 | C—H | C—CF3 | N | CF₃ | C—H | C—SMe | H | H | MeCO | H | 1 |
| 2-3330 | H | C—CF3 | C—H | C—CF3 | N | CF₃ | C—H | C—SMe | H | H | EtCO | H | 1 |
| 2-3331 | H | C—CF3 | C—H | C—CF3 | N | CF₃ | C—H | C—SMe | H | H | CF3CH2CO | H | 1 |
| 2-3332 | H | C—CF3 | C—H | C—CF3 | N | CF₃ | C—H | C—SMe | H | H | cyclo-PrCO | H | 1 |
| 2-3333 | H | C—CF3 | C—H | C—CF3 | N | CF₃ | C—H | C—SMe | H | H | cyclo-PrCH2CO | H | 1 |
| 2-3334 | H | C—CF3 | C—H | C—CF3 | N | CF₃ | C—H | C—SMe | H | H | CH3SCH2CO | H | 1 |
| 2-3335 | H | C—CF3 | C—H | C—CF3 | N | CF₃ | C—H | C—SMe | H | H | CH3SOCH2CO | H | 1 |
| 2-3336 | H | C—CF3 | C—H | C—CF3 | N | CF₃ | C—H | C—SMe | H | H | CH3SO2CH2CO | H | 1 |
| 2-3337 | H | C—CF3 | C—H | C—CF3 | N | CF₃ | C—H | C—SMe | H | H | EtNHCO | H | 1 |
| 2-3338 | H | C—CF3 | C—H | C—CF3 | N | CF₃ | C—H | C—SMe | Me | H | EtCO | H | 1 |
| 2-3339 | H | C—CF3 | C—H | C—CF3 | N | CF₃ | C—H | C—SMe | Me | H | CF3CH2CO | H | 1 |
| 2-3340 | H | C—CF3 | C—H | C—CF3 | N | CF₃ | N | C—SMe | H | H | EtCO | H | 1 |
| 2-3341 | H | C—CF3 | C—H | C—CF3 | N | CF₃ | N | C—SMe | H | H | CF3CH2CO | H | 1 |
| 2-3342 | H | C—CF3 | C—H | C—CF3 | N | CF₃ | C—H | C—SOMe | H | H | H | H | 1 |
| 2-3343 | H | C—CF3 | C—H | C—CF3 | N | CF₃ | C—H | C—SOMe | H | H | MeCO | H | 1 |
| 2-3344 | H | C—CF3 | C—H | C—CF3 | N | CF₃ | C—H | C—SOMe | H | H | EtCO | H | 1 |
| 2-3345 | H | C—CF3 | C—H | C—CF3 | N | CF₃ | C—H | C—SOMe | H | H | CF3CH2CO | H | 1 |
| 2-3346 | H | C—CF3 | C—H | C—CF3 | N | CF₃ | C—H | C—SOMe | H | H | cyclo-PrCO | H | 1 |
| 2-3347 | H | C—CF3 | C—H | C—CF3 | N | CF₃ | C—H | C—SOMe | H | H | cyclo-PrCH2CO | H | 1 |
| 2-3348 | H | C—CF3 | C—H | C—CF3 | N | CF₃ | C—H | C—SOMe | H | H | CH3SCH2CO | H | 1 |
| 2-3349 | H | C—CF3 | C—H | C—CF3 | N | CF₃ | C—H | C—SOMe | H | H | CH3SOCH2CO | H | 1 |
| 2-3350 | H | C—CF3 | C—H | C—CF3 | N | CF₃ | C—H | C—SOMe | H | H | CH3SO2CH2CO | H | 1 |
| 2-3351 | H | C—CF3 | C—H | C—CF3 | N | CF₃ | C—H | C—SOMe | H | H | EtNHCO | H | 1 |
| 2-3352 | H | C—CF3 | C—H | C—CF3 | N | CF₃ | C—H | C—SOMe | Me | H | EtCO | H | 1 |
| 2-3353 | H | C—CF3 | C—H | C—CF3 | N | CF₃ | C—H | C—SOMe | Me | H | CF3CH2CO | H | 1 |
| 2-3354 | H | C—CF3 | C—H | C—CF3 | N | CF₃ | N | C—SOMe | H | H | EtCO | H | 1 |

TABLE 2-2-continued

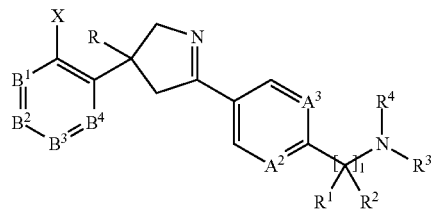

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3355 | H | C—CF3 | C—H | C—CF3 | N | CF₃ | N | C—SOMe | H | H | CF3CH2CO | H | 1 |
| 2-3356 | H | C—CF3 | C—H | C—CF3 | N | CF₃ | C—H | C—SO2Me | H | H | H | H | 1 |
| 2-3357 | H | C—CF3 | C—H | C—CF3 | N | CF₃ | C—H | C—SO2Me | H | H | MeCO | H | 1 |
| 2-3358 | H | C—CF3 | C—H | C—CF3 | N | CF₃ | C—H | C—SO2Me | H | H | EtCO | H | 1 |
| 2-3359 | H | C—CF3 | C—H | C—CF3 | N | CF₃ | C—H | C—SO2Me | H | H | CF3CH2CO | H | 1 |
| 2-3360 | H | C—CF3 | C—H | C—CF3 | N | CF₃ | C—H | C—SO2Me | H | H | cyclo-PrCO | H | 1 |
| 2-3361 | H | C—CF3 | C—H | C—CF3 | N | CF₃ | C—H | C—SO2Me | H | H | cyclo-PrCH2CO | H | 1 |
| 2-3362 | H | C—CF3 | C—H | C—CF3 | N | CF₃ | C—H | C—SO2Me | H | H | CH3SCH2CO | H | 1 |
| 2-3363 | H | C—CF3 | C—H | C—CF3 | N | CF₃ | C—H | C—SO2Me | H | H | CH3SOCH2CO | H | 1 |
| 2-3364 | H | C—CF3 | C—H | C—CF3 | N | CF₃ | C—H | C—SO2Me | H | H | CH3SO2CH2CO | H | 1 |
| 2-3365 | H | C—CF3 | C—H | C—CF3 | N | CF₃ | C—H | C—SO2Me | H | H | EtNHCO | H | 1 |
| 2-3366 | H | C—CF3 | C—H | C—CF3 | N | CF₃ | C—H | C—SO2Me | Me | H | EtCO | H | 1 |
| 2-3367 | H | C—CF3 | C—H | C—CF3 | N | CF₃ | C—H | C—SO2Me | Me | H | CF3CH2CO | H | 1 |
| 2-3368 | H | C—CF3 | C—H | C—CF3 | N | CF₃ | N | C—SO2Me | H | H | EtCO | H | 1 |
| 2-3369 | H | C—CF3 | C—H | C—CF3 | N | CF₃ | N | C—SO2Me | H | H | CF3CH2CO | H | 1 |
| 2-3370 | H | C—CF3 | C—H | C—CF3 | N | CF₃ | C—H | C—SCF3 | H | H | H | H | 1 |
| 2-3371 | H | C—CF3 | C—H | C—CF3 | N | CF₃ | C—H | C—SCF3 | H | H | MeCO | H | 1 |
| 2-3372 | H | C—CF3 | C—H | C—CF3 | N | CF₃ | C—H | C—SCF3 | H | H | EtCO | H | 1 |
| 2-3373 | H | C—CF3 | C—H | C—CF3 | N | CF₃ | C—H | C—SCF3 | H | H | CF3CH2CO | H | 1 |
| 2-3374 | H | C—CF3 | C—H | C—CF3 | N | CF₃ | C—H | C—SCF3 | H | H | cyclo-PrCO | H | 1 |
| 2-3375 | H | C—CF3 | C—H | C—CF3 | N | CF₃ | C—H | C—SCF3 | H | H | cyclo-PrCH2CO | H | 1 |
| 2-3376 | H | C—CF3 | C—H | C—CF3 | N | CF₃ | C—H | C—SCF3 | H | H | CH3SCH2CO | H | 1 |
| 2-3377 | H | C—CF3 | C—H | C—CF3 | N | CF₃ | C—H | C—SCF3 | H | H | CH3SOCH2CO | H | 1 |
| 2-3378 | H | C—CF3 | C—H | C—CF3 | N | CF₃ | C—H | C—SCF3 | H | H | CH3SO2CH2CO | H | 1 |
| 2-3379 | H | C—CF3 | C—H | C—CF3 | N | CF₃ | C—H | C—SCF3 | H | H | EtNHCO | H | 1 |
| 2-3380 | H | C—CF3 | C—H | C—CF3 | N | CF₃ | C—H | C—SCF3 | Me | H | EtCO | H | 1 |
| 2-3381 | H | C—CF3 | C—H | C—CF3 | N | CF₃ | C—H | C—SCF3 | Me | H | CF3CH2CO | H | 1 |
| 2-3382 | H | C—CF3 | C—H | C—CF3 | N | CF₃ | N | C—SCF3 | H | H | EtCO | H | 1 |
| 2-3383 | H | C—CF3 | C—H | C—CF3 | N | CF₃ | N | C—SCF3 | H | H | CF3CH2CO | H | 1 |
| 2-3384 | H | C—CF3 | C—H | C—CF3 | N | CF₃ | C—H | C—SOCF3 | H | H | H | H | 1 |
| 2-3385 | H | C—CF3 | C—H | C—CF3 | N | CF₃ | C—H | C—SOCF3 | H | H | MeCO | H | 1 |
| 2-3386 | H | C—CF3 | C—H | C—CF3 | N | CF₃ | C—H | C—SOCF3 | H | H | EtCO | H | 1 |
| 2-3387 | H | C—CF3 | C—H | C—CF3 | N | CF₃ | C—H | C—SOCF3 | H | H | CF3CH2CO | H | 1 |
| 2-3388 | H | C—CF3 | C—H | C—CF3 | N | CF₃ | C—H | C—SOCF3 | H | H | cyclo-PrCO | H | 1 |
| 2-3389 | H | C—CF3 | C—H | C—CF3 | N | CF₃ | C—H | C—SOCF3 | H | H | cyclo-PrCH2CO | H | 1 |
| 2-3390 | H | C—CF3 | C—H | C—CF3 | N | CF₃ | C—H | C—SOCF3 | H | H | CH3SCH2CO | H | 1 |
| 2-3391 | H | C—CF3 | C—H | C—CF3 | N | CF₃ | C—H | C—SOCF3 | H | H | CH3SOCH2CO | H | 1 |
| 2-3392 | H | C—CF3 | C—H | C—CF3 | N | CF₃ | C—H | C—SOCF3 | H | H | CH3SO2CH2CO | H | 1 |
| 2-3393 | H | C—CF3 | C—H | C—CF3 | N | CF₃ | C—H | C—SOCF3 | H | H | EtNHCO | H | 1 |
| 2-3394 | H | C—CF3 | C—H | C—CF3 | N | CF₃ | C—H | C—SOCF3 | Me | H | EtCO | H | 1 |
| 2-3395 | H | C—CF3 | C—H | C—CF3 | N | CF₃ | C—H | C—SOCF3 | Me | H | CF3CH2CO | H | 1 |
| 2-3396 | H | C—CF3 | C—H | C—CF3 | N | CF₃ | N | C—SOCF3 | H | H | EtCO | H | 1 |
| 2-3397 | H | C—CF3 | C—H | C—CF3 | N | CF₃ | N | C—SOCF3 | H | H | CF3CH2CO | H | 1 |
| 2-3398 | H | C—CF3 | C—H | C—CF3 | N | CF₃ | C—H | C—H | H | H | H | H | 1 |
| 2-3399 | H | C—CF3 | C—H | C—CF3 | N | CF₃ | C—H | C—H | H | H | MeCO | H | 1 |
| 2-3400 | H | C—CF3 | C—H | C—CF3 | N | CF₃ | C—H | C—H | H | H | EtCO | H | 1 |
| 2-3401 | H | C—CF3 | C—H | C—CF3 | N | CF₃ | C—H | C—H | H | H | CF3CH2CO | H | 1 |
| 2-3402 | H | C—CF3 | C—H | C—CF3 | N | CF₃ | C—H | C—H | H | H | cyclo-PrCO | H | 1 |
| 2-3403 | H | C—CF3 | C—H | C—CF3 | N | CF₃ | C—H | C—H | H | H | cyclo-PrCH2CO | H | 1 |
| 2-3404 | H | C—CF3 | C—H | C—CF3 | N | CF₃ | C—H | C—H | H | H | CH3SCH2CO | H | 1 |
| 2-3405 | H | C—CF3 | C—H | C—CF3 | N | CF₃ | C—H | C—H | H | H | CH3SOCH2CO | H | 1 |
| 2-3406 | H | C—CF3 | C—H | C—CF3 | N | CF₃ | C—H | C—H | H | H | CH3SO2CH2CO | H | 1 |
| 2-3407 | H | C—CF3 | C—H | C—CF3 | N | CF₃ | C—H | C—H | H | H | EtNHCO | H | 1 |
| 2-3408 | H | C—CF3 | C—H | C—CF3 | N | CF₃ | C—H | C—H | Me | H | H | H | 1 |
| 2-3409 | H | C—CF3 | C—H | C—CF3 | N | CF₃ | C—H | C—H | Me | H | EtCO | H | 1 |
| 2-3410 | H | C—CF3 | C—H | C—CF3 | N | CF₃ | C—H | C—H | Me | H | CF3CH2CO | H | 1 |
| 2-3411 | H | C—CF3 | C—H | C—CF3 | N | CF₃ | C—H | C—H | Me | H | CH3SCH2CO | H | 1 |
| 2-3412 | H | C—CF3 | C—H | C—CF3 | N | CF₃ | N | C—H | H | H | H | H | 1 |
| 2-3413 | H | C—CF3 | C—H | C—CF3 | N | CF₃ | N | C—H | H | H | EtCO | H | 1 |
| 2-3414 | H | C—CF3 | C—H | C—CF3 | N | CF₃ | N | C—H | H | H | CF3CH2CO | H | 1 |
| 2-3415 | H | C—CF3 | C—H | C—CF3 | N | CF₃ | N | C—H | H | H | CH3SCH2CO | H | 1 |
| 2-3416 | H | C—CF3 | C—H | C—CF3 | N | CF₃ | C—H | C—F | H | H | H | H | 1 |
| 2-3417 | H | C—CF3 | C—H | C—CF3 | N | CF₃ | C—H | C—F | H | H | MeCO | H | 1 |
| 2-3418 | H | C—CF3 | C—H | C—CF3 | N | CF₃ | C—H | C—F | H | H | EtCO | H | 1 |
| 2-3419 | H | C—CF3 | C—H | C—CF3 | N | CF₃ | C—H | C—F | H | H | CF3CH2CO | H | 1 |
| 2-3420 | H | C—CF3 | C—H | C—CF3 | N | CF₃ | C—H | C—F | H | H | cyclo-PrCO | H | 1 |
| 2-3421 | H | C—CF3 | C—H | C—CF3 | N | CF₃ | C—H | C—F | H | H | cyclo-PrCH2CO | H | 1 |

TABLE 2-2-continued

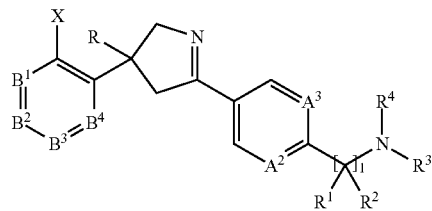

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3422 | H | C—CF3 | C—H | C—CF3 | N | CF₃ | C—H | C—F | H | H | CH3SCH2CO | H | 1 |
| 2-3423 | H | C—CF3 | C—H | C—CF3 | N | CF₃ | C—H | C—F | H | H | CH3SOCH2CO | H | 1 |
| 2-3424 | H | C—CF3 | C—H | C—CF3 | N | CF₃ | C—H | C—F | H | H | CH3SO2CH2CO | H | 1 |
| 2-3425 | H | C—CF3 | C—H | C—CF3 | N | CF₃ | C—H | C—F | H | H | EtNHCO | H | 1 |
| 2-3426 | H | C—CF3 | C—H | C—CF3 | N | CF₃ | C—H | C—F | Me | H | EtCO | H | 1 |
| 2-3427 | H | C—CF3 | C—H | C—CF3 | N | CF₃ | C—H | C—F | Me | H | CF3CH2CO | H | 1 |
| 2-3428 | H | C—CF3 | C—H | C—CF3 | N | CF₃ | N | C—F | H | H | EtCO | H | 1 |
| 2-3429 | H | C—CF3 | C—H | C—CF3 | N | CF₃ | N | C—F | H | H | CF3CH2CO | H | 1 |
| 2-3430 | H | C—CF3 | C—H | C—CF3 | N | CF₃ | C—H | C—I | H | H | H | H | 1 |
| 2-3431 | H | C—CF3 | C—H | C—CF3 | N | CF₃ | C—H | C—I | H | H | MeCO | H | 1 |
| 2-3432 | H | C—CF3 | C—H | C—CF3 | N | CF₃ | C—H | C—I | H | H | EtCO | H | 1 |
| 2-3433 | H | C—CF3 | C—H | C—CF3 | N | CF₃ | C—H | C—I | H | H | CF3CH2CO | H | 1 |
| 2-3434 | H | C—CF3 | C—H | C—CF3 | N | CF₃ | C—H | C—I | H | H | cyclo-PrCO | H | 1 |
| 2-3435 | H | C—CF3 | C—H | C—CF3 | N | CF₃ | C—H | C—I | H | H | cyclo-PrCH2CO | H | 1 |
| 2-3436 | H | C—CF3 | C—H | C—CF3 | N | CF₃ | C—H | C—I | H | H | CH3SCH2CO | H | 1 |
| 2-3437 | H | C—CF3 | C—H | C—CF3 | N | CF₃ | C—H | C—I | H | H | CH3SOCH2CO | H | 1 |
| 2-3438 | H | C—CF3 | C—H | C—CF3 | N | CF₃ | C—H | C—I | H | H | CH3SO2CH2CO | H | 1 |
| 2-3439 | H | C—CF3 | C—H | C—CF3 | N | CF₃ | C—H | C—I | H | H | EtNHCO | H | 1 |
| 2-3440 | H | C—CF3 | C—H | C—CF3 | N | CF₃ | C—H | C—I | Me | H | EtCO | H | 1 |
| 2-3441 | H | C—CF3 | C—H | C—CF3 | N | CF₃ | C—H | C—I | Me | H | CF3CH2CO | H | 1 |
| 2-3442 | H | C—CF3 | C—H | C—CF3 | N | CF₃ | N | C—I | H | H | EtCO | H | 1 |
| 2-3443 | H | C—CF3 | C—H | C—CF3 | N | CF₃ | N | C—I | H | H | CF3CH2CO | H | 1 |
| 2-3444 | H | C—CF3 | C—H | C—CF3 | N | CF₃ | C—H | C—NH2 | H | H | H | H | 1 |
| 2-3445 | H | C—CF3 | C—H | C—CF3 | N | CF₃ | C—H | C—NH2 | H | H | MeCO | H | 1 |
| 2-3446 | H | C—CF3 | C—H | C—CF3 | N | CF₃ | C—H | C—NH2 | H | H | EtCO | H | 1 |
| 2-3447 | H | C—CF3 | C—H | C—CF3 | N | CF₃ | C—H | C—NH2 | H | H | CF3CH2CO | H | 1 |
| 2-3448 | H | C—CF3 | C—H | C—CF3 | N | CF₃ | C—H | C—NH2 | H | H | cyclo-PrCO | H | 1 |
| 2-3449 | H | C—CF3 | C—H | C—CF3 | N | CF₃ | C—H | C—NH2 | H | H | cyclo-PrCH2CO | H | 1 |
| 2-3450 | H | C—CF3 | C—H | C—CF3 | N | CF₃ | C—H | C—NH2 | H | H | CH3SCH2CO | H | 1 |
| 2-3451 | H | C—CF3 | C—H | C—CF3 | N | CF₃ | C—H | C—NH2 | H | H | CH3SOCH2CO | H | 1 |
| 2-3452 | H | C—CF3 | C—H | C—CF3 | N | CF₃ | C—H | C—NH2 | H | H | CH3SO2CH2CO | H | 1 |
| 2-3453 | H | C—CF3 | C—H | C—CF3 | N | CF₃ | C—H | C—NH2 | H | H | EtNHCO | H | 1 |
| 2-3454 | H | C—CF3 | C—H | C—CF3 | N | CF₃ | C—H | C—NH2 | Me | H | EtCO | H | 1 |
| 2-3455 | H | C—CF3 | C—H | C—CF3 | N | CF₃ | C—H | C—NH2 | Me | H | CF3CH2CO | H | 1 |
| 2-3456 | H | C—CF3 | C—H | C—CF3 | N | CF₃ | N | C—NH2 | H | H | EtCO | H | 1 |
| 2-3457 | H | C—CF3 | C—H | C—CF3 | N | CF₃ | N | C—NH2 | H | H | CF3CH2CO | H | 1 |
| 2-3458 | H | C—CF3 | C—H | C—CF3 | N | CF₃ | C—H | C—NHAc | H | H | H | H | 1 |
| 2-3459 | H | C—CF3 | C—H | C—CF3 | N | CF₃ | C—H | C—NHAc | H | H | MeCO | H | 1 |
| 2-3460 | H | C—CF3 | C—H | C—CF3 | N | CF₃ | C—H | C—NHAc | H | H | EtCO | H | 1 |
| 2-3461 | H | C—CF3 | C—H | C—CF3 | N | CF₃ | C—H | C—NHAc | H | H | CF3CH2CO | H | 1 |
| 2-3462 | H | C—CF3 | C—H | C—CF3 | N | CF₃ | C—H | C—NHAc | H | H | cyclo-PrCO | H | 1 |
| 2-3463 | H | C—CF3 | C—H | C—CF3 | N | CF₃ | C—H | C—NHAc | H | H | cyclo-PrCH2CO | H | 1 |
| 2-3464 | H | C—CF3 | C—H | C—CF3 | N | CF₃ | C—H | C—NHAc | H | H | CH3SCH2CO | H | 1 |
| 2-3465 | H | C—CF3 | C—H | C—CF3 | N | CF₃ | C—H | C—NHAc | H | H | CH3SOCH2CO | H | 1 |
| 2-3466 | H | C—CF3 | C—H | C—CF3 | N | CF₃ | C—H | C—NHAc | H | H | CH3SO2CH2CO | H | 1 |
| 2-3467 | H | C—CF3 | C—H | C—CF3 | N | CF₃ | C—H | C—NHAc | H | H | EtNHCO | H | 1 |
| 2-3468 | H | C—CF3 | C—H | C—CF3 | N | CF₃ | C—H | C—NHAc | Me | H | EtCO | H | 1 |
| 2-3469 | H | C—CF3 | C—H | C—CF3 | N | CF₃ | C—H | C—NHAc | Me | H | CF3CH2CO | H | 1 |
| 2-3470 | H | C—CF3 | C—H | C—CF3 | N | CF₃ | N | C—NHAc | H | H | EtCO | H | 1 |
| 2-3471 | H | C—CF3 | C—H | C—CF3 | N | CF₃ | N | C—NHAc | H | H | CF3CH2CO | H | 1 |
| 2-3472 | H | C—CF3 | C—H | C—CF3 | N | CF₃ | C—H | C—NHCOCF3 | H | H | H | H | 1 |
| 2-3473 | H | C—CF3 | C—H | C—CF3 | N | CF₃ | C—H | C—NHCOCF3 | H | H | MeCO | H | 1 |
| 2-3474 | H | C—CF3 | C—H | C—CF3 | N | CF₃ | C—H | C—NHCOCF3 | H | H | EtCO | H | 1 |
| 2-3475 | H | C—CF3 | C—H | C—CF3 | N | CF₃ | C—H | C—NHCOCF3 | H | H | CF3CH2CO | H | 1 |
| 2-3476 | H | C—CF3 | C—H | C—CF3 | N | CF₃ | C—H | C—NHCOCF3 | H | H | cyclo-PrCO | H | 1 |
| 2-3477 | H | C—CF3 | C—H | C—CF3 | N | CF₃ | C—H | C—NHCOCF3 | H | H | cyclo-PrCH2CO | H | 1 |
| 2-3478 | H | C—CF3 | C—H | C—CF3 | N | CF₃ | C—H | C—NHCOCF3 | H | H | CH3SCH2CO | H | 1 |
| 2-3479 | H | C—CF3 | C—H | C—CF3 | N | CF₃ | C—H | C—NHCOCF3 | H | H | CH3SOCH2CO | H | 1 |
| 2-3480 | H | C—CF3 | C—H | C—CF3 | N | CF₃ | C—H | C—NHCOCF3 | H | H | CH3SO2CH2CO | H | 1 |
| 2-3481 | H | C—CF3 | C—H | C—CF3 | N | CF₃ | C—H | C—NHCOCF3 | H | H | EtNHCO | H | 1 |
| 2-3482 | H | C—CF3 | C—H | C—CF3 | N | CF₃ | C—H | C—NHCOCF3 | Me | H | EtCO | H | 1 |
| 2-3483 | H | C—CF3 | C—H | C—CF3 | N | CF₃ | C—H | C—NHCOCF3 | Me | H | CF3CH2CO | H | 1 |
| 2-3484 | H | C—CF3 | C—H | C—CF3 | N | CF₃ | N | C—NHCOCF3 | H | H | EtCO | H | 1 |
| 2-3485 | H | C—CF3 | C—H | C—CF3 | N | CF₃ | N | C—NHCOCF3 | H | H | CF3CH2CO | H | 1 |
| 2-3486 | H | C—CF3 | C—H | C—CF3 | N | CF₃ | C—H | C—CH2OAc | H | H | H | H | 1 |
| 2-3487 | H | C—CF3 | C—H | C—CF3 | N | CF₃ | C—H | C—CH2OAc | H | H | MeCO | H | 1 |
| 2-3488 | H | C—CF3 | C—H | C—CF3 | N | CF₃ | C—H | C—CH2OAc | H | H | EtCO | H | 1 |

TABLE 2-2-continued

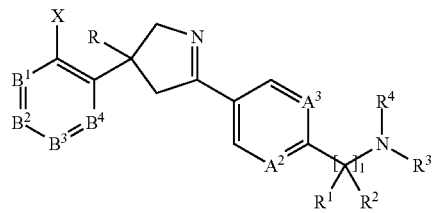

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-3489 | H | C—CF3 | C—H | C—CF3 | N | CF₃ | C—H | C—CH2OAc | H | H | CF3CH2CO | H | 1 |
| 2-3490 | H | C—CF3 | C—H | C—CF3 | N | CF₃ | C—H | C—CH2OAc | H | H | cyclo-PrCO | H | 1 |
| 2-3491 | H | C—CF3 | C—H | C—CF3 | N | CF₃ | C—H | C—CH2OAc | H | H | cyclo-PrCH2CO | H | 1 |
| 2-3492 | H | C—CF3 | C—H | C—CF3 | N | CF₃ | C—H | C—CH2OAc | H | H | CH3SCH2CO | H | 1 |
| 2-3493 | H | C—CF3 | C—H | C—CF3 | N | CF₃ | C—H | C—CH2OAc | H | H | CH3SOCH2CO | H | 1 |
| 2-3494 | H | C—CF3 | C—H | C—CF3 | N | CF₃ | C—H | C—CH2OAc | H | H | CH3SO2CH2CO | H | 1 |
| 2-3495 | H | C—CF3 | C—H | C—CF3 | N | CF₃ | C—H | C—CH2OAc | H | H | EtNHCO | H | 1 |
| 2-3496 | H | C—CF3 | C—H | C—CF3 | N | CF₃ | C—H | C—CH2OAc | Me | H | EtCO | H | 1 |
| 2-3497 | H | C—CF3 | C—H | C—CF3 | N | CF₃ | C—H | C—CH2OAc | Me | H | CF3CH2CO | H | 1 |
| 2-3498 | H | C—CF3 | C—H | C—CF3 | N | CF₃ | N | C—CH2OAc | H | H | EtCO | H | 1 |
| 2-3499 | H | C—CF3 | C—H | C—CF3 | N | CF₃ | N | C—CH2OAc | H | H | CF3CH2CO | H | 1 |
| 2-4002 | H | C—C2F5 | N | C—H | C—H | CF₃ | C—H | C—CF3 | H | H | H | H | 1 |
| 2-4003 | H | C—C2F5 | N | C—H | C—H | CF₃ | C—H | C—CF3 | H | H | CH3CO | H | 1 |
| 2-4004 | H | C—C2F5 | N | C—H | C—H | CF₃ | C—H | C—CF3 | H | H | EtCO | H | 1 |
| 2-4005 | H | C—C2F5 | N | C—H | C—H | CF₃ | C—H | C—CF3 | H | H | CF3CH2CO | H | 1 |
| 2-4006 | H | C—C2F5 | N | C—H | C—H | CF₃ | C—H | C—CF3 | H | H | cyclo-PrCO | H | 1 |
| 2-4007 | H | C—C2F5 | N | C—H | C—H | CF₃ | C—H | C—CF3 | H | H | cyclo-PrCH2CO | H | 1 |
| 2-4008 | H | C—C2F5 | N | C—H | C—H | CF₃ | C—H | C—CF3 | H | H | EtNHCO | H | 1 |
| 2-4009 | H | C—C2F5 | N | C—H | C—H | CF₃ | C—H | C—CF3 | H | H | CH3SCH2CO | H | 1 |
| 2-4010 | H | C—C2F5 | N | C—H | C—H | CF₃ | C—H | C—CF3 | H | H | CH3SOCH2CO | H | 1 |
| 2-4011 | H | C—C2F5 | N | C—H | C—H | CF₃ | C—H | C—CF3 | H | H | CH3SO2CH2CO | H | 1 |
| 2-4012 | H | C—C2F5 | N | C—H | C—H | CF₃ | C—H | C—CF3 | Me | H | EtCO | H | 1 |
| 2-4013 | H | C—C2F5 | N | C—H | C—H | CF₃ | C—H | C—CF3 | Me | H | CF3CH2CO | H | 1 |
| 2-4014 | H | C—C2F5 | N | C—H | C—H | CF₃ | N | C—CF3 | H | H | EtCO | H | 1 |
| 2-4015 | H | C—C2F5 | N | C—H | C—H | CF₃ | N | C—CF3 | H | H | CF3CH2CO | H | 1 |
| 2-4016 | H | C—C2F5 | N | C—H | C—H | CF₃ | C—H | C—Cl | H | H | H | H | 1 |
| 2-4017 | H | C—C2F5 | N | C—H | C—H | CF₃ | C—H | C—Cl | H | H | MeCO | H | 1 |
| 2-4018 | H | C—C2F5 | N | C—H | C—H | CF₃ | C—H | C—Cl | H | H | EtCO | H | 1 |
| 2-4019 | H | C—C2F5 | N | C—H | C—H | CF₃ | C—H | C—Cl | H | H | CF3CH2CO | H | 1 |
| 2-4020 | H | C—C2F5 | N | C—H | C—H | CF₃ | C—H | C—Cl | H | H | cyclo-PrCO | H | 1 |
| 2-4021 | H | C—C2F5 | N | C—H | C—H | CF₃ | C—H | C—Cl | H | H | cyclo-PrCH2CO | H | 1 |
| 2-4022 | H | C—C2F5 | N | C—H | C—H | CF₃ | C—H | C—Cl | H | H | CH3SCH2CO | H | 1 |
| 2-4023 | H | C—C2F5 | N | C—H | C—H | CF₃ | C—H | C—Cl | H | H | CH3SOCH2CO | H | 1 |
| 2-4024 | H | C—C2F5 | N | C—H | C—H | CF₃ | C—H | C—Cl | H | H | CH3SO2CH2CO | H | 1 |
| 2-4025 | H | C—C2F5 | N | C—H | C—H | CF₃ | C—H | C—Cl | H | H | EtNHCO | H | 1 |
| 2-4026 | H | C—C2F5 | N | C—H | C—H | CF₃ | C—H | C—Cl | Me | H | EtCO | H | 1 |
| 2-4027 | H | C—C2F5 | N | C—H | C—H | CF₃ | C—H | C—Cl | Me | H | CF3CH2CO | H | 1 |
| 2-4028 | H | C—C2F5 | N | C—H | C—H | CF₃ | N | C—Cl | H | H | EtCO | H | 1 |
| 2-4029 | H | C—C2F5 | N | C—H | C—H | CF₃ | N | C—Cl | H | H | CF3CH2CO | H | 1 |
| 2-4030 | H | C—C2F5 | N | C—H | C—H | CF₃ | C—H | C—Br | H | H | H | H | 1 |
| 2-4031 | H | C—C2F5 | N | C—H | C—H | CF₃ | C—H | C—Br | H | H | MeCO | H | 1 |
| 2-4032 | H | C—C2F5 | N | C—H | C—H | CF₃ | C—H | C—Br | H | H | EtCO | H | 1 |
| 2-4033 | H | C—C2F5 | N | C—H | C—H | CF₃ | C—H | C—Br | H | H | cyc-PrCO | H | 1 |
| 2-4034 | H | C—C2F5 | N | C—H | C—H | CF₃ | C—H | C—Br | H | H | CF3CH2CO | H | 1 |
| 2-4035 | H | C—C2F5 | N | C—H | C—H | CF₃ | C—H | C—Br | H | H | CH3SCH2CO | H | 1 |
| 2-4036 | H | C—C2F5 | N | C—H | C—H | CF₃ | C—H | C—Br | H | H | CH3SOCH2CO | H | 1 |
| 2-4037 | H | C—C2F5 | N | C—H | C—H | CF₃ | C—H | C—Br | H | H | CH3SO2CH2CO | H | 1 |
| 2-4038 | H | C—C2F5 | N | C—H | C—H | CF₃ | C—H | C—Br | Me | H | EtCO | H | 1 |
| 2-4039 | H | C—C2F5 | N | C—H | C—H | CF₃ | C—H | C—Br | Me | H | CF3CH2CO | H | 1 |
| 2-4040 | H | C—C2F5 | N | C—H | C—H | CF₃ | N | C—Br | H | H | EtCO | H | 1 |
| 2-4041 | H | C—C2F5 | N | C—H | C—H | CF₃ | N | C—Br | H | H | CF3CH2CO | H | 1 |
| 2-4042 | H | C—C2F5 | N | C—H | C—H | CF₃ | C—H | C—CN | H | H | EtCO | H | 1 |
| 2-4043 | H | C—C2F5 | N | C—H | C—H | CF₃ | C—H | C—CN | H | H | CF3CH2CO | H | 1 |
| 2-4044 | H | C—C2F5 | N | C—H | C—H | CF₃ | N | C—CN | H | H | EtCO | H | 1 |
| 2-4045 | H | C—C2F5 | N | C—H | C—H | CF₃ | C—H | C—Me | H | H | MeCO | H | 1 |
| 2-4046 | H | C—C2F5 | N | C—H | C—H | CF₃ | C—H | C—Me | H | H | MeCO | H | 1 |
| 2-4047 | H | C—C2F5 | N | C—H | C—H | CF₃ | C—H | C—Me | H | H | EtCO | H | 1 |
| 2-4048 | H | C—C2F5 | N | C—H | C—H | CF₃ | C—H | C—Me | H | H | CF3CH2CO | H | 1 |
| 2-4049 | H | C—C2F5 | N | C—H | C—H | CF₃ | C—H | C—Me | H | H | cyclo-PrCO | H | 1 |
| 2-4050 | H | C—C2F5 | N | C—H | C—H | CF₃ | C—H | C—Me | H | H | CH3SCH2CO | H | 1 |
| 2-4051 | H | C—C2F5 | N | C—H | C—H | CF₃ | C—H | C—Me | H | H | EtNHCO | H | 1 |
| 2-4052 | H | C—C2F5 | N | C—H | C—H | CF₃ | C—H | C—Me | Me | H | EtCO | H | 1 |
| 2-4053 | H | C—C2F5 | N | C—H | C—H | CF₃ | N | C—Me | H | H | EtCO | H | 1 |
| 2-4054 | H | C—C2F5 | N | C—H | C—H | CF₃ | C—H | C—NO2 | H | H | MeCO | H | 1 |
| 2-4055 | H | C—C2F5 | N | C—H | C—H | CF₃ | C—H | C—NO2 | H | H | MeCO | H | 1 |
| 2-4056 | H | C—C2F5 | N | C—H | C—H | CF₃ | C—H | C—NO2 | H | H | EtCO | H | 1 |
| 2-4057 | H | C—C2F5 | N | C—H | C—H | CF₃ | C—H | C—NO2 | H | H | CF3CH2CO | H | 1 |

TABLE 2-2-continued

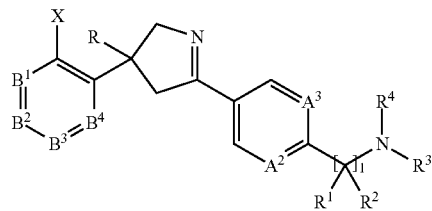

| Example No. | X | B¹ | B² | B³ | B⁴ | R | A² | A³ | R¹ | R² | R⁴ | R³ | l |
|---|---|---|---|---|---|---|---|---|---|---|---|---|---|
| 2-4058 | H | C—C2F5 | N | C—H | C—H | CF₃ | C—H | C—NO2 | H | H | cyclo-PrCO | H | 1 |
| 2-4059 | H | C—C2F5 | N | C—H | C—H | CF₃ | C—H | C—NO2 | H | H | CH3SCH2CO | H | 1 |
| 2-4060 | H | C—C2F5 | N | C—H | C—H | CF₃ | C—H | C—NO2 | H | H | EtNHCO | H | 1 |
| 2-4061 | H | C—C2F5 | N | C—H | C—H | CF₃ | C—H | C—NO2 | Me | H | EtCO | H | 1 |
| 2-4062 | H | C—C2F5 | N | C—H | C—H | CF₃ | N | C—NO2 | H | H | EtCO | H | 1 |
| 2-4063 | H | C—C2F5 | N | C—H | C—H | CF₃ | C—H | C—SMe | H | H | MeCO | H | 1 |
| 2-4064 | H | C—C2F5 | N | C—H | C—H | CF₃ | C—H | C—SMe | H | H | MeCO | H | 1 |
| 2-4065 | H | C—C2F5 | N | C—H | C—H | CF₃ | C—H | C—SMe | H | H | EtCO | H | 1 |
| 2-4066 | H | C—C2F5 | N | C—H | C—H | CF₃ | C—H | C—SMe | H | H | CF3CH2CO | H | 1 |
| 2-4067 | H | C—C2F5 | N | C—H | C—H | CF₃ | C—H | C—SMe | H | H | cyclo-PrCO | H | 1 |
| 2-4068 | H | C—C2F5 | N | C—H | C—H | CF₃ | C—H | C—SMe | H | H | CH3SCH2CO | H | 1 |
| 2-4069 | H | C—C2F5 | N | C—H | C—H | CF₃ | C—H | C—SMe | H | H | EtNHCO | H | 1 |
| 2-4070 | H | C—C2F5 | N | C—H | C—H | CF₃ | C—H | C—SMe | Me | H | EtCO | H | 1 |
| 2-4071 | H | C—C2F5 | N | C—H | C—H | CF₃ | N | C—SMe | H | H | EtCO | H | 1 |
| 2-4072 | H | C—C2F5 | N | C—H | C—H | CF₃ | C—H | C—H | H | H | MeCO | H | 1 |
| 2-4073 | H | C—C2F5 | N | C—H | C—H | CF₃ | C—H | C—H | H | H | MeCO | H | 1 |
| 2-4074 | H | C—C2F5 | N | C—H | C—H | CF₃ | C—H | C—H | H | H | EtCO | H | 1 |
| 2-4075 | H | C—C2F5 | N | C—H | C—H | CF₃ | C—H | C—H | H | H | CF3CH2CO | H | 1 |
| 2-4076 | H | C—C2F5 | N | C—H | C—H | CF₃ | C—H | C—H | H | H | cyclo-PrCO | H | 1 |
| 2-4077 | H | C—C2F5 | N | C—H | C—H | CF₃ | C—H | C—H | H | H | CH3SCH2CO | H | 1 |
| 2-4078 | H | C—C2F5 | N | C—H | C—H | CF₃ | C—H | C—H | H | H | EtNHCO | H | 1 |
| 2-4079 | H | C—C2F5 | N | C—H | C—H | CF₃ | C—H | C—H | Me | H | EtCO | H | 1 |
| 2-4080 | H | C—C2F5 | N | C—H | C—H | CF₃ | N | C—H | H | H | EtCO | H | 1 |
| 2-4081 | H | C—C2F5 | N | C—H | C—H | CF₃ | C—H | C—SOMe | H | H | EtCO | H | 1 |
| 2-4082 | H | C—C2F5 | N | C—H | C—H | CF₃ | C—H | C—SOMe | H | H | CF₃CH₂CO | H | 1 |
| 2-4083 | H | C—C2F5 | N | C—H | C—H | CF₃ | C—H | C—SO2Me | H | H | EtCO | H | 1 |
| 2-4084 | H | C—C2F5 | N | C—H | C—H | CF₃ | C—H | C—SO2Me | H | H | CF₃CH₂CO | H | 1 |
| 2-4085 | H | C—C2F5 | N | C—H | C—H | CF₃ | C—H | C—SCF3 | H | H | EtCO | H | 1 |
| 2-4086 | H | C—C2F5 | N | C—H | C—H | CF₃ | C—H | C—SCF3 | H | H | CF₃CH₂CO | H | 1 |
| 2-4087 | H | C—C2F5 | N | C—H | C—H | CF₃ | C—H | C—SOCF3 | H | H | EtCO | H | 1 |
| 2-4088 | H | C—C2F5 | N | C—H | C—H | CF₃ | C—H | C—SOCF3 | H | H | CF₃CH₂CO | H | 1 |
| 2-4089 | H | C—C2F5 | N | C—H | C—H | CF₃ | C—H | C—SO2CF3 | H | H | EtCO | H | 1 |
| 2-4090 | H | C—C2F5 | N | C—H | C—H | CF₃ | C—H | C—SO2CF3 | H | H | CF₃CH₂CO | H | 1 |
| 2-4091 | H | C—C2F5 | N | C—H | C—H | CF₃ | C—H | C—F | H | H | EtCO | H | 1 |
| 2-4092 | H | C—C2F5 | N | C—H | C—H | CF₃ | C—H | C—F | H | H | CF₃CH₂CO | H | 1 |
| 2-4093 | H | C—C2F5 | N | C—H | C—H | CF₃ | C—H | C—I | H | H | EtCO | H | 1 |
| 2-4094 | H | C—C2F5 | N | C—H | C—H | CF₃ | C—H | C—I | H | H | CF₃CH₂CO | H | 1 |
| 2-4095 | H | C—C2F5 | N | C—H | C—H | CF₃ | C—H | C—NH2 | H | H | EtCO | H | 1 |
| 2-4096 | H | C—C2F5 | N | C—H | C—H | CF₃ | C—H | C—NH2 | H | H | CF₃CH₂CO | H | 1 |
| 2-4097 | H | C—C2F5 | N | C—H | C—H | CF₃ | C—H | C—NHAc | H | H | EtCO | H | 1 |
| 2-4098 | H | C—C2F5 | N | C—H | C—H | CF₃ | C—H | C—NHAc | H | H | CF₃CH₂CO | H | 1 |
| 2-4099 | H | C—C2F5 | N | C—H | C—H | CF₃ | C—H | C—NHCOCF3 | H | H | EtCO | H | 1 |
| 2-4100 | H | C—C2F5 | N | C—H | C—H | CF₃ | C—H | C—NHCOCF3 | H | H | CF₃CH₂CO | H | 1 |
| 2-4101 | H | C—C2F5 | N | C—H | C—H | CF₃ | C—H | C—CH2OAc | H | H | EtCO | H | 1 |
| 2-4102 | H | C—C2F5 | N | C—H | C—H | CF₃ | C—H | C—CH2OAc | H | H | CF₃CH₂CO | H | 1 |
| 2-4204 | H | C—CF3 | C—H | C—Cl | N | CF₃ | C—H | C—CF3 | H | H | H | H | 1 |
| 2-4205 | H | C—CF3 | C—H | C—Cl | N | CF₃ | C—H | C—CF3 | H | H | CH3CO | H | 1 |
| 2-4206 | H | C—CF3 | C—H | C—Cl | N | CF₃ | C—H | C—CF3 | H | H | EtCO | H | 1 |
| 2-4207 | H | C—CF3 | C—H | C—Cl | N | CF₃ | C—H | C—CF3 | H | H | CF₃CH₂CO | H | 1 |
| 2-4208 | H | C—CF3 | C—H | C—Cl | N | CF₃ | C—H | C—CF3 | H | H | cyclo-PrCO | H | 1 |
| 2-4209 | H | C—CF3 | C—H | C—Cl | N | CF₃ | C—H | C—CF3 | H | H | cyclo-PrCH2CO | H | 1 |
| 2-4210 | H | C—CF3 | C—H | C—Cl | N | CF₃ | C—H | C—CF3 | H | H | EtNHCO | H | 1 |
| 2-4211 | H | C—CF3 | C—H | C—Cl | N | CF₃ | C—H | C—CF3 | H | H | CH3SCH2CO | H | 1 |
| 2-4212 | H | C—CF3 | C—H | C—Cl | N | CF₃ | C—H | C—CF3 | H | H | CH3SOCH2CO | H | 1 |
| 2-4213 | H | C—CF3 | C—H | C—Cl | N | CF₃ | C—H | C—CF3 | H | H | CH3SO2CH2CO | H | 1 |
| 2-4214 | H | C—CF3 | C—H | C—Cl | N | CF₃ | C—H | C—CF3 | Me | H | EtCO | H | 1 |
| 2-4215 | H | C—CF3 | C—H | C—Cl | N | CF₃ | C—H | C—CF3 | Me | H | CF₃CH₂CO | H | 1 |
| 2-4216 | H | C—CF3 | C—H | C—Cl | N | CF₃ | N | C—CF3 | H | H | EtCO | H | 1 |
| 2-4217 | H | C—CF3 | C—H | C—Cl | N | CF₃ | N | C—CF3 | H | H | CF3CH2CO | H | 1 |
| 2-4218 | H | C—CF3 | C—H | C—Cl | N | CF₃ | C—H | C—Cl | H | H | H | H | 1 |
| 2-4219 | H | C—CF3 | C—H | C—Cl | N | CF₃ | C—H | C—Cl | H | H | MeCO | H | 1 |
| 2-4220 | H | C—CF3 | C—H | C—Cl | N | CF₃ | C—H | C—Cl | H | H | EtCO | H | 1 |
| 2-4221 | H | C—CF3 | C—H | C—Cl | N | CF₃ | C—H | C—Cl | H | H | CF3CH2CO | H | 1 |
| 2-4222 | H | C—CF3 | C—H | C—Cl | N | CF₃ | C—H | C—Cl | H | H | cyclo-PrCO | H | 1 |
| 2-4223 | H | C—CF3 | C—H | C—Cl | N | CF₃ | C—H | C—Cl | H | H | cyclo-PrCH2CO | H | 1 |
| 2-4224 | H | C—CF3 | C—H | C—Cl | N | CF₃ | C—H | C—Cl | H | H | CH3SCH2CO | H | 1 |
| 2-4225 | H | C—CF3 | C—H | C—Cl | N | CF₃ | C—H | C—Cl | H | H | CH3SOCH2CO | H | 1 |

TABLE 2-2-continued

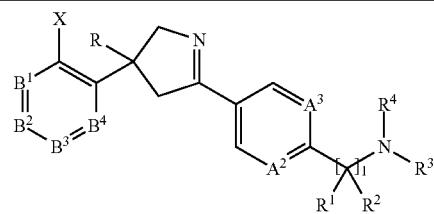

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4226 | H | C—CF3 | C—H | C—Cl | N | CF₃ | C—H | C—Cl | H | H | CH3SO2CH2CO | H | 1 |
| 2-4227 | H | C—CF3 | C—H | C—Cl | N | CF₃ | C—H | C—Cl | H | H | EtNHCO | H | 1 |
| 2-4228 | H | C—CF3 | C—H | C—Cl | N | CF₃ | C—H | C—Cl | Me | H | EtCO | H | 1 |
| 2-4229 | H | C—CF3 | C—H | C—Cl | N | CF₃ | C—H | C—Cl | Me | H | CF3CH2CO | H | 1 |
| 2-4230 | H | C—CF3 | C—H | C—Cl | N | CF₃ | N | C—Cl | H | H | EtCO | H | 1 |
| 2-4231 | H | C—CF3 | C—H | C—Cl | N | CF₃ | N | C—Cl | H | H | CF3CH2CO | H | 1 |
| 2-4232 | H | C—CF3 | C—H | C—Cl | N | CF₃ | C—H | C—Br | H | H | H | H | 1 |
| 2-4233 | H | C—CF3 | C—H | C—Cl | N | CF₃ | C—H | C—Br | H | H | MeCO | H | 1 |
| 2-4234 | H | C—CF3 | C—H | C—Cl | N | CF₃ | C—H | C—Br | H | H | EtCO | H | 1 |
| 2-4235 | H | C—CF3 | C—H | C—Cl | N | CF₃ | C—H | C—Br | H | H | cyc-PrCO | H | 1 |
| 2-4236 | H | C—CF3 | C—H | C—Cl | N | CF₃ | C—H | C—Br | H | H | CF₃CH₂CO | H | 1 |
| 2-4237 | H | C—CF3 | C—H | C—Cl | N | CF₃ | C—H | C—Br | H | H | CH3SCH2CO | H | 1 |
| 2-4238 | H | C—CF3 | C—H | C—Cl | N | CF₃ | C—H | C—Br | H | H | CH3SOCH2CO | H | 1 |
| 2-4239 | H | C—CF3 | C—H | C—Cl | N | CF₃ | C—H | C—Br | H | H | CH3SO2CH2CO | H | 1 |
| 2-4240 | H | C—CF3 | C—H | C—Cl | N | CF₃ | C—H | C—Br | Me | H | EtCO | H | 1 |
| 2-4241 | H | C—CF3 | C—H | C—Cl | N | CF₃ | C—H | C—Br | Me | H | CF3CH2CO | H | 1 |
| 2-4242 | H | C—CF3 | C—H | C—Cl | N | CF₃ | N | C—Br | H | H | EtCO | H | 1 |
| 2-4243 | H | C—CF3 | C—H | C—Cl | N | CF₃ | N | C—Br | H | H | CF3CH2CO | H | 1 |
| 2-4244 | H | C—CF3 | C—H | C—Cl | N | CF₃ | C—H | C—CN | H | H | EtCO | H | 1 |
| 2-4245 | H | C—CF3 | C—H | C—Cl | N | CF₃ | C—H | C—CN | H | H | CF3CH2CO | H | 1 |
| 2-4246 | H | C—CF3 | C—H | C—Cl | N | CF₃ | N | C—CN | H | H | EtCO | H | 1 |
| 2-4247 | H | C—CF3 | C—H | C—Cl | N | CF₃ | C—H | C—Me | H | H | MeCO | H | 1 |
| 2-4248 | H | C—CF3 | C—H | C—Cl | N | CF₃ | C—H | C—Me | H | H | MeCO | H | 1 |
| 2-4249 | H | C—CF3 | C—H | C—Cl | N | CF₃ | C—H | C—Me | H | H | EtCO | H | 1 |
| 2-4250 | H | C—CF3 | C—H | C—Cl | N | CF₃ | C—H | C—Me | H | H | CF3CH2CO | H | 1 |
| 2-4251 | H | C—CF3 | C—H | C—Cl | N | CF₃ | C—H | C—Me | H | H | cyclo-PrCO | H | 1 |
| 2-4252 | H | C—CF3 | C—H | C—Cl | N | CF₃ | C—H | C—Me | H | H | CH3SCH2CO | H | 1 |
| 2-4253 | H | C—CF3 | C—H | C—Cl | N | CF₃ | C—H | C—Me | H | H | EtNHCO | H | 1 |
| 2-4254 | H | C—CF3 | C—H | C—Cl | N | CF₃ | C—H | C—Me | Me | H | EtCO | H | 1 |
| 2-4255 | H | C—CF3 | C—H | C—Cl | N | CF₃ | N | C—Me | H | H | EtCO | H | 1 |
| 2-4256 | H | C—CF3 | C—H | C—Cl | N | CF₃ | C—H | C—NO2 | H | H | MeCO | H | 1 |
| 2-4257 | H | C—CF3 | C—H | C—Cl | N | CF₃ | C—H | C—NO2 | H | H | MeCO | H | 1 |
| 2-4258 | H | C—CF3 | C—H | C—Cl | N | CF₃ | C—H | C—NO2 | H | H | EtCO | H | 1 |
| 2-4259 | H | C—CF3 | C—H | C—Cl | N | CF₃ | C—H | C—NO2 | H | H | CF3CH2CO | H | 1 |
| 2-4260 | H | C—CF3 | C—H | C—Cl | N | CF₃ | C—H | C—NO2 | H | H | cyclo-PrCO | H | 1 |
| 2-4261 | H | C—CF3 | C—H | C—Cl | N | CF₃ | C—H | C—NO2 | H | H | CH3SCH2CO | H | 1 |
| 2-4262 | H | C—CF3 | C—H | C—Cl | N | CF₃ | C—H | C—NO2 | H | H | EtNHCO | H | 1 |
| 2-4263 | H | C—CF3 | C—H | C—Cl | N | CF₃ | C—H | C—NO2 | Me | H | EtCO | H | 1 |
| 2-4264 | H | C—CF3 | C—H | C—Cl | N | CF₃ | N | C—NO2 | H | H | EtCO | H | 1 |
| 2-4265 | H | C—CF3 | C—H | C—Cl | N | CF₃ | C—H | C—SMe | H | H | MeCO | H | 1 |
| 2-4266 | H | C—CF3 | C—H | C—Cl | N | CF₃ | C—H | C—SMe | H | H | MeCO | H | 1 |
| 2-4267 | H | C—CF3 | C—H | C—Cl | N | CF₃ | C—H | C—SMe | H | H | EtCO | H | 1 |
| 2-4268 | H | C—CF3 | C—H | C—Cl | N | CF₃ | C—H | C—SMe | H | H | CF3CH2CO | H | 1 |
| 2-4269 | H | C—CF3 | C—H | C—Cl | N | CF₃ | C—H | C—SMe | H | H | cyclo-PrCO | H | 1 |
| 2-4270 | H | C—CF3 | C—H | C—Cl | N | CF₃ | C—H | C—SMe | H | H | CH3SCH2CO | H | 1 |
| 2-4271 | H | C—CF3 | C—H | C—Cl | N | CF₃ | C—H | C—SMe | H | H | EtNHCO | H | 1 |
| 2-4272 | H | C—CF3 | C—H | C—Cl | N | CF₃ | C—H | C—SMe | Me | H | EtCO | H | 1 |
| 2-4273 | H | C—CF3 | C—H | C—Cl | N | CF₃ | N | C—SMe | H | H | EtCO | H | 1 |
| 2-4274 | H | C—CF3 | C—H | C—Cl | N | CF₃ | C—H | C—H | H | H | MeCO | H | 1 |
| 2-4275 | H | C—CF3 | C—H | C—Cl | N | CF₃ | C—H | C—H | H | H | MeCO | H | 1 |
| 2-4276 | H | C—CF3 | C—H | C—Cl | N | CF₃ | C—H | C—H | H | H | EtCO | H | 1 |
| 2-4277 | H | C—CF3 | C—H | C—Cl | N | CF₃ | C—H | C—H | H | H | CF3CH2CO | H | 1 |
| 2-4278 | H | C—CF3 | C—H | C—Cl | N | CF₃ | C—H | C—H | H | H | cyclo-PrCO | H | 1 |
| 2-4279 | H | C—CF3 | C—H | C—Cl | N | CF₃ | C—H | C—H | H | H | CH3SCH2CO | H | 1 |
| 2-4280 | H | C—CF3 | C—H | C—Cl | N | CF₃ | C—H | C—H | H | H | EtNHCO | H | 1 |
| 2-4281 | H | C—CF3 | C—H | C—Cl | N | CF₃ | C—H | C—H | Me | H | EtCO | H | 1 |
| 2-4282 | H | C—CF3 | C—H | C—Cl | N | CF₃ | N | C—H | H | H | EtCO | H | 1 |
| 2-4283 | H | C—CF3 | C—H | C—Cl | N | CF₃ | C—H | C—SOMe | H | H | EtCO | H | 1 |
| 2-4284 | H | C—CF3 | C—H | C—Cl | N | CF₃ | C—H | C—SOMe | H | H | CF₃CH₂CO | H | 1 |
| 2-4285 | H | C—CF3 | C—H | C—Cl | N | CF₃ | C—H | C—SO2Me | H | H | EtCO | H | 1 |
| 2-4286 | H | C—CF3 | C—H | C—Cl | N | CF₃ | C—H | C—SO2Me | H | H | CF₃CH₂CO | H | 1 |
| 2-4287 | H | C—CF3 | C—H | C—Cl | N | CF₃ | C—H | C—SCF3 | H | H | EtCO | H | 1 |
| 2-4288 | H | C—CF3 | C—H | C—Cl | N | CF₃ | C—H | C—SCF3 | H | H | CF₃CH₂CO | H | 1 |
| 2-4289 | H | C—CF3 | C—H | C—Cl | N | CF₃ | C—H | C—SOCF3 | H | H | EtCO | H | 1 |
| 2-4290 | H | C—CF3 | C—H | C—Cl | N | CF₃ | C—H | C—SOCF3 | H | H | CF₃CH₂CO | H | 1 |
| 2-4291 | H | C—CF3 | C—H | C—Cl | N | CF₃ | C—H | C—SO2CF3 | H | H | EtCO | H | 1 |
| 2-4292 | H | C—CF3 | C—H | C—Cl | N | CF₃ | C—H | C—SO2CF3 | H | H | CF₃CH₂CO | H | 1 |

TABLE 2-2-continued

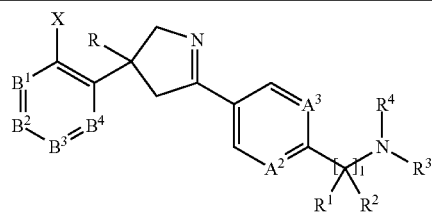

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4293 | H | C—CF3 | C—H | C—Cl | N | CF₃ | C—H | C—F | H | H | EtCO | H | 1 |
| 2-4294 | H | C—CF3 | C—H | C—Cl | N | CF₃ | C—H | C—F | H | H | CF₃CH₂CO | H | 1 |
| 2-4295 | H | C—CF3 | C—H | C—Cl | N | CF₃ | C—H | C—I | H | H | EtCO | H | 1 |
| 2-4296 | H | C—CF3 | C—H | C—Cl | N | CF₃ | C—H | C—I | H | H | CF₃CH₂CO | H | 1 |
| 2-4297 | H | C—CF3 | C—H | C—Cl | N | CF₃ | C—H | C—NH2 | H | H | EtCO | H | 1 |
| 2-4298 | H | C—CF3 | C—H | C—Cl | N | CF₃ | C—H | C—NH2 | H | H | CF₃CH₂CO | H | 1 |
| 2-4299 | H | C—CF3 | C—H | C—Cl | N | CF₃ | C—H | C—NHAc | H | H | EtCO | H | 1 |
| 2-4300 | H | C—CF3 | C—H | C—Cl | N | CF₃ | C—H | C—NHAc | H | H | CF₃CH₂CO | H | 1 |
| 2-4301 | H | C—CF3 | C—H | C—Cl | N | CF₃ | C—H | C—NHCOCF3 | H | H | EtCO | H | 1 |
| 2-4302 | H | C—CF3 | C—H | C—Cl | N | CF₃ | C—H | C—NHCOCF3 | H | H | CF₃CH₂CO | H | 1 |
| 2-4303 | H | C—CF3 | C—H | C—Cl | N | CF₃ | C—H | C—CH2OAc | H | H | EtCO | H | 1 |
| 2-4304 | H | C—CF3 | C—H | C—Cl | N | CF₃ | C—H | C—CH2OAc | H | H | CF₃CH₂CO | H | 1 |
| 2-4305 | H | C—CF3 | C—H | C—Br | N | CF₃ | C—H | C—CF3 | H | H | H | H | 1 |
| 2-4306 | H | C—CF3 | C—H | C—Br | N | CF₃ | C—H | C—CF3 | H | H | CH3CO | H | 1 |
| 2-4307 | H | C—CF3 | C—H | C—Br | N | CF₃ | C—H | C—CF3 | H | H | EtCO | H | 1 |
| 2-4308 | H | C—CF3 | C—H | C—Br | N | CF₃ | C—H | C—CF3 | H | H | CF₃CH₂CO | H | 1 |
| 2-4309 | H | C—CF3 | C—H | C—Br | N | CF₃ | C—H | C—CF3 | H | H | cyclo-PrCO | H | 1 |
| 2-4310 | H | C—CF3 | C—H | C—Br | N | CF₃ | C—H | C—CF3 | H | H | cyclo-PrCH2CO | H | 1 |
| 2-4311 | H | C—CF3 | C—H | C—Br | N | CF₃ | C—H | C—CF3 | H | H | EtNHCO | H | 1 |
| 2-4312 | H | C—CF3 | C—H | C—Br | N | CF₃ | C—H | C—CF3 | H | H | CH3SCH2CO | H | 1 |
| 2-4313 | H | C—CF3 | C—H | C—Br | N | CF₃ | C—H | C—CF3 | H | H | CH3SOCH2CO | H | 1 |
| 2-4314 | H | C—CF3 | C—H | C—Br | N | CF₃ | C—H | C—CF3 | H | H | CH3SO2CH2CO | H | 1 |
| 2-4315 | H | C—CF3 | C—H | C—Br | N | CF₃ | C—H | C—CF3 | Me | H | EtCO | H | 1 |
| 2-4316 | H | C—CF3 | C—H | C—Br | N | CF₃ | C—H | C—CF3 | Me | H | CF3CH2CO | H | 1 |
| 2-4317 | H | C—CF3 | C—H | C—Br | N | CF₃ | N | C—CF3 | H | H | EtCO | H | 1 |
| 2-4318 | H | C—CF3 | C—H | C—Br | N | CF₃ | N | C—CF3 | H | H | CF3CH2CO | H | 1 |
| 2-4319 | H | C—CF3 | C—H | C—Br | N | CF₃ | C—H | C—Cl | H | H | H | H | 1 |
| 2-4320 | H | C—CF3 | C—H | C—Br | N | CF₃ | C—H | C—Cl | H | H | MeCO | H | 1 |
| 2-4321 | H | C—CF3 | C—H | C—Br | N | CF₃ | C—H | C—Cl | H | H | EtCO | H | 1 |
| 2-4322 | H | C—CF3 | C—H | C—Br | N | CF₃ | C—H | C—Cl | H | H | CF3CH2CO | H | 1 |
| 2-4323 | H | C—CF3 | C—H | C—Br | N | CF₃ | C—H | C—Cl | H | H | cyclo-PrCO | H | 1 |
| 2-4324 | H | C—CF3 | C—H | C—Br | N | CF₃ | C—H | C—Cl | H | H | cyclo-PrCH2CO | H | 1 |
| 2-4325 | H | C—CF3 | C—H | C—Br | N | CF₃ | C—H | C—Cl | H | H | CH3SCH2CO | H | 1 |
| 2-4326 | H | C—CF3 | C—H | C—Br | N | CF₃ | C—H | C—Cl | H | H | CH3SOCH2CO | H | 1 |
| 2-4327 | H | C—CF3 | C—H | C—Br | N | CF₃ | C—H | C—Cl | H | H | CH3SO2CH2CO | H | 1 |
| 2-4328 | H | C—CF3 | C—H | C—Br | N | CF₃ | C—H | C—Cl | H | H | EtNHCO | H | 1 |
| 2-4329 | H | C—CF3 | C—H | C—Br | N | CF₃ | C—H | C—Cl | Me | H | EtCO | H | 1 |
| 2-4330 | H | C—CF3 | C—H | C—Br | N | CF₃ | C—H | C—Cl | Me | H | CF3CH2CO | H | 1 |
| 2-4331 | H | C—CF3 | C—H | C—Br | N | CF₃ | N | C—Cl | H | H | EtCO | H | 1 |
| 2-4332 | H | C—CF3 | C—H | C—Br | N | CF₃ | N | C—Cl | H | H | CF3CH2CO | H | 1 |
| 2-4333 | H | C—CF3 | C—H | C—Br | N | CF₃ | C—H | C—Br | H | H | H | H | 1 |
| 2-4334 | H | C—CF3 | C—H | C—Br | N | CF₃ | C—H | C—Br | H | H | MeCO | H | 1 |
| 2-4335 | H | C—CF3 | C—H | C—Br | N | CF₃ | C—H | C—Br | H | H | EtCO | H | 1 |
| 2-4336 | H | C—CF3 | C—H | C—Br | N | CF₃ | C—H | C—Br | H | H | cyc-PrCO | H | 1 |
| 2-4337 | H | C—CF3 | C—H | C—Br | N | CF₃ | C—H | C—Br | H | H | CF₃CH₂CO | H | 1 |
| 2-4338 | H | C—CF3 | C—H | C—Br | N | CF₃ | C—H | C—Br | H | H | CH3SCH2CO | H | 1 |
| 2-4339 | H | C—CF3 | C—H | C—Br | N | CF₃ | C—H | C—Br | H | H | CH3SOCH2CO | H | 1 |
| 2-4340 | H | C—CF3 | C—H | C—Br | N | CF₃ | C—H | C—Br | H | H | CH3SO2CH2CO | H | 1 |
| 2-4341 | H | C—CF3 | C—H | C—Br | N | CF₃ | C—H | C—Br | Me | H | EtCO | H | 1 |
| 2-4342 | H | C—CF3 | C—H | C—Br | N | CF₃ | C—H | C—Br | Me | H | CF3CH2CO | H | 1 |
| 2-4343 | H | C—CF3 | C—H | C—Br | N | CF₃ | N | C—Br | H | H | EtCO | H | 1 |
| 2-4344 | H | C—CF3 | C—H | C—Br | N | CF₃ | N | C—Br | H | H | CF3CH2CO | H | 1 |
| 2-4345 | H | C—CF3 | C—H | C—Br | N | CF₃ | C—H | C—CN | H | H | EtCO | H | 1 |
| 2-4346 | H | C—CF3 | C—H | C—Br | N | CF₃ | C—H | C—CN | H | H | CF3CH2CO | H | 1 |
| 2-4347 | H | C—CF3 | C—H | C—Br | N | CF₃ | N | C—CN | H | H | EtCO | H | 1 |
| 2-4348 | H | C—CF3 | C—H | C—Br | N | CF₃ | C—H | C—Me | H | H | MeCO | H | 1 |
| 2-4349 | H | C—CF3 | C—H | C—Br | N | CF₃ | C—H | C—Me | H | H | MeCO | H | 1 |
| 2-4350 | H | C—CF3 | C—H | C—Br | N | CF₃ | C—H | C—Me | H | H | EtCO | H | 1 |
| 2-4351 | H | C—CF3 | C—H | C—Br | N | CF₃ | C—H | C—Me | H | H | CF3CH2CO | H | 1 |
| 2-4352 | H | C—CF3 | C—H | C—Br | N | CF₃ | C—H | C—Me | H | H | cyclo-PrCO | H | 1 |
| 2-4353 | H | C—CF3 | C—H | C—Br | N | CF₃ | C—H | C—Me | H | H | CH3SCH2CO | H | 1 |
| 2-4354 | H | C—CF3 | C—H | C—Br | N | CF₃ | C—H | C—Me | H | H | EtNHCO | H | 1 |
| 2-4355 | H | C—CF3 | C—H | C—Br | N | CF₃ | C—H | C—Me | Me | H | EtCO | H | 1 |
| 2-4356 | H | C—CF3 | C—H | C—Br | N | CF₃ | N | C—Me | H | H | EtCO | H | 1 |
| 2-4357 | H | C—CF3 | C—H | C—Br | N | CF₃ | C—H | C—NO2 | H | H | MeCO | H | 1 |
| 2-4358 | H | C—CF3 | C—H | C—Br | N | CF₃ | C—H | C—NO2 | H | H | MeCO | H | 1 |
| 2-4359 | H | C—CF3 | C—H | C—Br | N | CF₃ | C—H | C—NO2 | H | H | EtCO | H | 1 |

TABLE 2-2-continued

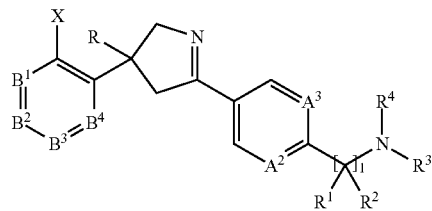

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4360 | H | C—CF3 | C—H | C—Br | N | CF₃ | C—H | C—NO2 | H | H | CF3CH2CO | H | 1 |
| 2-4361 | H | C—CF3 | C—H | C—Br | N | CF₃ | C—H | C—NO2 | H | H | cyclo-PrCO | H | 1 |
| 2-4362 | H | C—CF3 | C—H | C—Br | N | CF₃ | C—H | C—NO2 | H | H | CH3SCH2CO | H | 1 |
| 2-4363 | H | C—CF3 | C—H | C—Br | N | CF₃ | C—H | C—NO2 | H | H | EtNHCO | H | 1 |
| 2-4364 | H | C—CF3 | C—H | C—Br | N | CF₃ | C—H | C—NO2 | Me | H | EtCO | H | 1 |
| 2-4365 | H | C—CF3 | C—H | C—Br | N | CF₃ | N | C—NO2 | H | H | EtCO | H | 1 |
| 2-4366 | H | C—CF3 | C—H | C—Br | N | CF₃ | C—H | C—SMe | H | H | MeCO | H | 1 |
| 2-4367 | H | C—CF3 | C—H | C—Br | N | CF₃ | C—H | C—SMe | H | H | MeCO | H | 1 |
| 2-4368 | H | C—CF3 | C—H | C—Br | N | CF₃ | C—H | C—SMe | H | H | EtCO | H | 1 |
| 2-4369 | H | C—CF3 | C—H | C—Br | N | CF₃ | C—H | C—SMe | H | H | CF3CH2CO | H | 1 |
| 2-4370 | H | C—CF3 | C—H | C—Br | N | CF₃ | C—H | C—SMe | H | H | cyclo-PrCO | H | 1 |
| 2-4371 | H | C—CF3 | C—H | C—Br | N | CF₃ | C—H | C—SMe | H | H | CH3SCH2CO | H | 1 |
| 2-4372 | H | C—CF3 | C—H | C—Br | N | CF₃ | C—H | C—SMe | H | H | EtNHCO | H | 1 |
| 2-4373 | H | C—CF3 | C—H | C—Br | N | CF₃ | C—H | C—SMe | Me | H | EtCO | H | 1 |
| 2-4374 | H | C—CF3 | C—H | C—Br | N | CF₃ | N | C—SMe | H | H | EtCO | H | 1 |
| 2-4375 | H | C—CF3 | C—H | C—Br | N | CF₃ | C—H | C—H | H | H | MeCO | H | 1 |
| 2-4376 | H | C—CF3 | C—H | C—Br | N | CF₃ | C—H | C—H | H | H | MeCO | H | 1 |
| 2-4377 | H | C—CF3 | C—H | C—Br | N | CF₃ | C—H | C—H | H | H | EtCO | H | 1 |
| 2-4378 | H | C—CF3 | C—H | C—Br | N | CF₃ | C—H | C—H | H | H | CF3CH2CO | H | 1 |
| 2-4379 | H | C—CF3 | C—H | C—Br | N | CF₃ | C—H | C—H | H | H | cyclo-PrCO | H | 1 |
| 2-4380 | H | C—CF3 | C—H | C—Br | N | CF₃ | C—H | C—H | H | H | CH3SCH2CO | H | 1 |
| 2-4381 | H | C—CF3 | C—H | C—Br | N | CF₃ | C—H | C—H | H | H | EtNHCO | H | 1 |
| 2-4382 | H | C—CF3 | C—H | C—Br | N | CF₃ | C—H | C—H | Me | H | EtCO | H | 1 |
| 2-4383 | H | C—CF3 | C—H | C—Br | N | CF₃ | N | C—H | H | H | EtCO | H | 1 |
| 2-4384 | H | C—CF3 | C—H | C—Br | N | CF₃ | C—H | C—SOMe | H | H | EtCO | H | 1 |
| 2-4385 | H | C—CF3 | C—H | C—Br | N | CF₃ | C—H | C—SOMe | H | H | CF₃CH₂CO | H | 1 |
| 2-4386 | H | C—CF3 | C—H | C—Br | N | CF₃ | C—H | C—SO2Me | H | H | EtCO | H | 1 |
| 2-4387 | H | C—CF3 | C—H | C—Br | N | CF₃ | C—H | C—SO2Me | H | H | CF₃CH₂CO | H | 1 |
| 2-4388 | H | C—CF3 | C—H | C—Br | N | CF₃ | C—H | C—SCF3 | H | H | EtCO | H | 1 |
| 2-4389 | H | C—CF3 | C—H | C—Br | N | CF₃ | C—H | C—SCF3 | H | H | CF₃CH₂CO | H | 1 |
| 2-4390 | H | C—CF3 | C—H | C—Br | N | CF₃ | C—H | C—SOCF3 | H | H | EtCO | H | 1 |
| 2-4391 | H | C—CF3 | C—H | C—Br | N | CF₃ | C—H | C—SOCF3 | H | H | CF₃CH₂CO | H | 1 |
| 2-4392 | H | C—CF3 | C—H | C—Br | N | CF₃ | C—H | C—SO2CF3 | H | H | EtCO | H | 1 |
| 2-4393 | H | C—CF3 | C—H | C—Br | N | CF₃ | C—H | C—SO2CF3 | H | H | CF₃CH₂CO | H | 1 |
| 2-4394 | H | C—CF3 | C—H | C—Br | N | CF₃ | C—H | C—F | H | H | EtCO | H | 1 |
| 2-4395 | H | C—CF3 | C—H | C—Br | N | CF₃ | C—H | C—F | H | H | CF₃CH₂CO | H | 1 |
| 2-4396 | H | C—CF3 | C—H | C—Br | N | CF₃ | C—H | C—I | H | H | EtCO | H | 1 |
| 2-4397 | H | C—CF3 | C—H | C—Br | N | CF₃ | C—H | C—I | H | H | CF₃CH₂CO | H | 1 |
| 2-4398 | H | C—CF3 | C—H | C—Br | N | CF₃ | C—H | C—NH2 | H | H | EtCO | H | 1 |
| 2-4399 | H | C—CF3 | C—H | C—Br | N | CF₃ | C—H | C—NH2 | H | H | CF₃CH₂CO | H | 1 |
| 2-4400 | H | C—CF3 | C—H | C—Br | N | CF₃ | C—H | C—NHAc | H | H | EtCO | H | 1 |
| 2-4401 | H | C—CF3 | C—H | C—Br | N | CF₃ | C—H | C—NHAc | H | H | CF₃CH₂CO | H | 1 |
| 2-4402 | H | C—CF3 | C—H | C—Br | N | CF₃ | C—H | C—NHCOCF3 | H | H | EtCO | H | 1 |
| 2-4403 | H | C—CF3 | C—H | C—Br | N | CF₃ | C—H | C—NHCOCF3 | H | H | CF₃CH₂CO | H | 1 |
| 2-4404 | H | C—CF3 | C—H | C—Br | N | CF₃ | C—H | C—CH2OAc | H | H | EtCO | H | 1 |
| 2-4405 | H | C—CF3 | C—H | C—Br | N | CF₃ | C—H | C—CH2OAc | H | H | CF₃CH₂CO | H | 1 |
| 2-4608 | H | C—H | C—H | C—CF3 | N | CF₃ | C—H | C—CF3 | H | H | H | H | 1 |
| 2-4609 | H | C—H | C—H | C—CF3 | N | CF₃ | C—H | C—CF3 | H | H | CH3CO | H | 1 |
| 2-4610 | H | C—H | C—H | C—CF3 | N | CF₃ | C—H | C—CF3 | H | H | EtCO | H | 1 |
| 2-4611 | H | C—H | C—H | C—CF3 | N | CF₃ | C—H | C—CF3 | H | H | CF₃CH₂CO | H | 1 |
| 2-4612 | H | C—H | C—H | C—CF3 | N | CF₃ | C—H | C—CF3 | H | H | cyclo-PrCO | H | 1 |
| 2-4613 | H | C—H | C—H | C—CF3 | N | CF₃ | C—H | C—CF3 | H | H | cyclo-PrCH2CO | H | 1 |
| 2-4614 | H | C—H | C—H | C—CF3 | N | CF₃ | C—H | C—CF3 | H | H | EtNHCO | H | 1 |
| 2-4615 | H | C—H | C—H | C—CF3 | N | CF₃ | C—H | C—CF3 | H | H | CH3SCH2CO | H | 1 |
| 2-4616 | H | C—H | C—H | C—CF3 | N | CF₃ | C—H | C—CF3 | H | H | CH3SOCH2CO | H | 1 |
| 2-4617 | H | C—H | C—H | C—CF3 | N | CF₃ | C—H | C—CF3 | H | H | CH3SO2CH2CO | H | 1 |
| 2-4618 | H | C—H | C—H | C—CF3 | N | CF₃ | C—H | C—CF3 | Me | H | EtCO | H | 1 |
| 2-4619 | H | C—H | C—H | C—CF3 | N | CF₃ | C—H | C—CF3 | Me | H | CF3CH2CO | H | 1 |
| 2-4620 | H | C—H | C—H | C—CF3 | N | CF₃ | N | C—CF3 | H | H | EtCO | H | 1 |
| 2-4621 | H | C—H | C—H | C—CF3 | N | CF₃ | N | C—CF3 | H | H | CF3CH2CO | H | 1 |
| 2-4622 | H | C—H | C—H | C—CF3 | N | CF₃ | C—H | C—Cl | H | H | H | H | 1 |
| 2-4623 | H | C—H | C—H | C—CF3 | N | CF₃ | C—H | C—Cl | H | H | MeCO | H | 1 |
| 2-4624 | H | C—H | C—H | C—CF3 | N | CF₃ | C—H | C—Cl | H | H | EtCO | H | 1 |
| 2-4625 | H | C—H | C—H | C—CF3 | N | CF₃ | C—H | C—Cl | H | H | CF3CH2CO | H | 1 |
| 2-4626 | H | C—H | C—H | C—CF3 | N | CF₃ | C—H | C—Cl | H | H | cyclo-PrCO | H | 1 |
| 2-4627 | H | C—H | C—H | C—CF3 | N | CF₃ | C—H | C—Cl | H | H | cyclo-PrCH2CO | H | 1 |
| 2-4628 | H | C—H | C—H | C—CF3 | N | CF₃ | C—H | C—Cl | H | H | CH3SCH2CO | H | 1 |

TABLE 2-2-continued

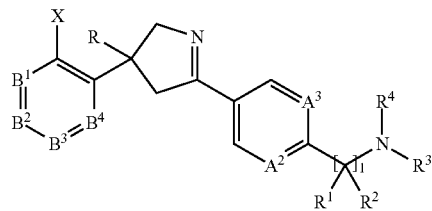

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4629 | H | C—H | C—H | C—CF3 | N | CF₃ | C—H | C—Cl | H | H | CH3SOCH2CO | H | 1 |
| 2-4630 | H | C—H | C—H | C—CF3 | N | CF₃ | C—H | C—Cl | H | H | CH3SO2CH2CO | H | 1 |
| 2-4631 | H | C—H | C—H | C—CF3 | N | CF₃ | C—H | C—Cl | H | H | EtNHCO | H | 1 |
| 2-4632 | H | C—H | C—H | C—CF3 | N | CF₃ | C—H | C—Cl | Me | H | EtCO | H | 1 |
| 2-4633 | H | C—H | C—H | C—CF3 | N | CF₃ | C—H | C—Cl | Me | H | CF3CH2CO | H | 1 |
| 2-4634 | H | C—H | C—H | C—CF3 | N | CF₃ | N | C—Cl | H | H | EtCO | H | 1 |
| 2-4635 | H | C—H | C—H | C—CF3 | N | CF₃ | N | C—Cl | H | H | CF3CH2CO | H | 1 |
| 2-4636 | H | C—H | C—H | C—CF3 | N | CF₃ | C—H | C—Br | H | H | H | H | 1 |
| 2-4637 | H | C—H | C—H | C—CF3 | N | CF₃ | C—H | C—Br | H | H | MeCO | H | 1 |
| 2-4638 | H | C—H | C—H | C—CF3 | N | CF₃ | C—H | C—Br | H | H | EtCO | H | 1 |
| 2-4639 | H | C—H | C—H | C—CF3 | N | CF₃ | C—H | C—Br | H | H | cyc-PrCO | H | 1 |
| 2-4640 | H | C—H | C—H | C—CF3 | N | CF₃ | C—H | C—Br | H | H | $CF_3CH_2CO$ | H | 1 |
| 2-4641 | H | C—H | C—H | C—CF3 | N | CF₃ | C—H | C—Br | H | H | CH3SCH2CO | H | 1 |
| 2-4642 | H | C—H | C—H | C—CF3 | N | CF₃ | C—H | C—Br | H | H | CH3SOCH2CO | H | 1 |
| 2-4643 | H | C—H | C—H | C—CF3 | N | CF₃ | C—H | C—Br | H | H | CH3SO2CH2CO | H | 1 |
| 2-4644 | H | C—H | C—H | C—CF3 | N | CF₃ | C—H | C—Br | Me | H | EtCO | H | 1 |
| 2-4645 | H | C—H | C—H | C—CF3 | N | CF₃ | C—H | C—Br | Me | H | CF3CH2CO | H | 1 |
| 2-4646 | H | C—H | C—H | C—CF3 | N | CF₃ | N | C—Br | H | H | EtCO | H | 1 |
| 2-4647 | H | C—H | C—H | C—CF3 | N | CF₃ | N | C—Br | H | H | CF3CH2CO | H | 1 |
| 2-4648 | H | C—H | C—H | C—CF3 | N | CF₃ | C—H | C—CN | H | H | EtCO | H | 1 |
| 2-4649 | H | C—H | C—H | C—CF3 | N | CF₃ | C—H | C—CN | H | H | CF3CH2CO | H | 1 |
| 2-4650 | H | C—H | C—H | C—CF3 | N | CF₃ | N | C—CN | H | H | EtCO | H | 1 |
| 2-4651 | H | C—H | C—H | C—CF3 | N | CF₃ | C—H | C—Me | H | H | MeCO | H | 1 |
| 2-4652 | H | C—H | C—H | C—CF3 | N | CF₃ | C—H | C—Me | H | H | MeCO | H | 1 |
| 2-4653 | H | C—H | C—H | C—CF3 | N | CF₃ | C—H | C—Me | H | H | EtCO | H | 1 |
| 2-4654 | H | C—H | C—H | C—CF3 | N | CF₃ | C—H | C—Me | H | H | CF3CH2CO | H | 1 |
| 2-4655 | H | C—H | C—H | C—CF3 | N | CF₃ | C—H | C—Me | H | H | cyclo-PrCO | H | 1 |
| 2-4656 | H | C—H | C—H | C—CF3 | N | CF₃ | C—H | C—Me | H | H | CH3SCH2CO | H | 1 |
| 2-4657 | H | C—H | C—H | C—CF3 | N | CF₃ | C—H | C—Me | H | H | EtNHCO | H | 1 |
| 2-4658 | H | C—H | C—H | C—CF3 | N | CF₃ | C—H | C—Me | Me | H | EtCO | H | 1 |
| 2-4659 | H | C—H | C—H | C—CF3 | N | CF₃ | N | C—Me | H | H | EtCO | H | 1 |
| 2-4660 | H | C—H | C—H | C—CF3 | N | CF₃ | C—H | C—NO2 | H | H | MeCO | H | 1 |
| 2-4661 | H | C—H | C—H | C—CF3 | N | CF₃ | C—H | C—NO2 | H | H | MeCO | H | 1 |
| 2-4662 | H | C—H | C—H | C—CF3 | N | CF₃ | C—H | C—NO2 | H | H | EtCO | H | 1 |
| 2-4663 | H | C—H | C—H | C—CF3 | N | CF₃ | C—H | C—NO2 | H | H | CF3CH2CO | H | 1 |
| 2-4664 | H | C—H | C—H | C—CF3 | N | CF₃ | C—H | C—NO2 | H | H | cyclo-PrCO | H | 1 |
| 2-4665 | H | C—H | C—H | C—CF3 | N | CF₃ | C—H | C—NO2 | H | H | CH3SCH2CO | H | 1 |
| 2-4666 | H | C—H | C—H | C—CF3 | N | CF₃ | C—H | C—NO2 | H | H | EtNHCO | H | 1 |
| 2-4667 | H | C—H | C—H | C—CF3 | N | CF₃ | C—H | C—NO2 | Me | H | EtCO | H | 1 |
| 2-4668 | H | C—H | C—H | C—CF3 | N | CF₃ | N | C—NO2 | H | H | EtCO | H | 1 |
| 2-4669 | H | C—H | C—H | C—CF3 | N | CF₃ | C—H | C—SMe | H | H | MeCO | H | 1 |
| 2-4670 | H | C—H | C—H | C—CF3 | N | CF₃ | C—H | C—SMe | H | H | MeCO | H | 1 |
| 2-4671 | H | C—H | C—H | C—CF3 | N | CF₃ | C—H | C—SMe | H | H | EtCO | H | 1 |
| 2-4672 | H | C—H | C—H | C—CF3 | N | CF₃ | C—H | C—SMe | H | H | CF3CH2CO | H | 1 |
| 2-4673 | H | C—H | C—H | C—CF3 | N | CF₃ | C—H | C—SMe | H | H | cyclo-PrCO | H | 1 |
| 2-4674 | H | C—H | C—H | C—CF3 | N | CF₃ | C—H | C—SMe | H | H | CH3SCH2CO | H | 1 |
| 2-4675 | H | C—H | C—H | C—CF3 | N | CF₃ | C—H | C—SMe | H | H | EtNHCO | H | 1 |
| 2-4676 | H | C—H | C—H | C—CF3 | N | CF₃ | C—H | C—SMe | Me | H | EtCO | H | 1 |
| 2-4677 | H | C—H | C—H | C—CF3 | N | CF₃ | N | C—SMe | H | H | EtCO | H | 1 |
| 2-4678 | H | C—H | C—H | C—CF3 | N | CF₃ | C—H | C—H | H | H | MeCO | H | 1 |
| 2-4679 | H | C—H | C—H | C—CF3 | N | CF₃ | C—H | C—H | H | H | MeCO | H | 1 |
| 2-4680 | H | C—H | C—H | C—CF3 | N | CF₃ | C—H | C—H | H | H | EtCO | H | 1 |
| 2-4681 | H | C—H | C—H | C—CF3 | N | CF₃ | C—H | C—H | H | H | CF3CH2CO | H | 1 |
| 2-4682 | H | C—H | C—H | C—CF3 | N | CF₃ | C—H | C—H | H | H | cyclo-PrCO | H | 1 |
| 2-4683 | H | C—H | C—H | C—CF3 | N | CF₃ | C—H | C—H | H | H | CH3SCH2CO | H | 1 |
| 2-4684 | H | C—H | C—H | C—CF3 | N | CF₃ | C—H | C—H | H | H | EtNHCO | H | 1 |
| 2-4685 | H | C—H | C—H | C—CF3 | N | CF₃ | C—H | C—H | Me | H | EtCO | H | 1 |
| 2-4686 | H | C—H | C—H | C—CF3 | N | CF₃ | N | C—H | H | H | EtCO | H | 1 |
| 2-4687 | H | C—H | C—H | C—CF3 | N | CF₃ | C—H | C—SOMe | H | H | EtCO | H | 1 |
| 2-4688 | H | C—H | C—H | C—CF3 | N | CF₃ | C—H | C—SOMe | H | H | $CF_3CH_2CO$ | H | 1 |
| 2-4689 | H | C—H | C—H | C—CF3 | N | CF₃ | C—H | C—SO2Me | H | H | EtCO | H | 1 |
| 2-4690 | H | C—H | C—H | C—CF3 | N | CF₃ | C—H | C—SO2Me | H | H | $CF_3CH_2CO$ | H | 1 |
| 2-4691 | H | C—H | C—H | C—CF3 | N | CF₃ | C—H | C—SCF3 | H | H | EtCO | H | 1 |
| 2-4692 | H | C—H | C—H | C—CF3 | N | CF₃ | C—H | C—SCF3 | H | H | $CF_3CH_2CO$ | H | 1 |
| 2-4693 | H | C—H | C—H | C—CF3 | N | CF₃ | C—H | C—SOCF3 | H | H | EtCO | H | 1 |
| 2-4694 | H | C—H | C—H | C—CF3 | N | CF₃ | C—H | C—SOCF3 | H | H | $CF_3CH_2CO$ | H | 1 |
| 2-4695 | H | C—H | C—H | C—CF3 | N | CF₃ | C—H | C—SO2CF3 | H | H | EtCO | H | 1 |

TABLE 2-2-continued

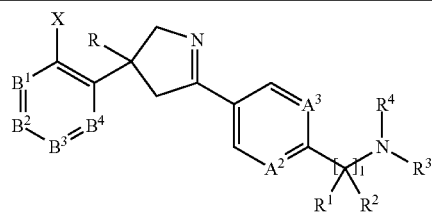

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4696 | H | C—H | C—H | C—CF3 | N | CF₃ | C—H | C—SO2CF3 | H | H | CF₃CH₂CO | H | 1 |
| 2-4697 | H | C—H | C—H | C—CF3 | N | CF₃ | C—H | C—F | H | H | EtCO | H | 1 |
| 2-4698 | H | C—H | C—H | C—CF3 | N | CF₃ | C—H | C—F | H | H | CF₃CH₂CO | H | 1 |
| 2-4699 | H | C—H | C—H | C—CF3 | N | CF₃ | C—H | C—I | H | H | EtCO | H | 1 |
| 2-4700 | H | C—H | C—H | C—CF3 | N | CF₃ | C—H | C—I | H | H | CF₃CH₂CO | H | 1 |
| 2-4701 | H | C—H | C—H | C—CF3 | N | CF₃ | C—H | C—NH2 | H | H | EtCO | H | 1 |
| 2-4702 | H | C—H | C—H | C—CF3 | N | CF₃ | C—H | C—NH2 | H | H | CF₃CH₂CO | H | 1 |
| 2-4703 | H | C—H | C—H | C—CF3 | N | CF₃ | C—H | C—NHAc | H | H | EtCO | H | 1 |
| 2-4704 | H | C—H | C—H | C—CF3 | N | CF₃ | C—H | C—NHAc | H | H | CF₃CH₂CO | H | 1 |
| 2-4705 | H | C—H | C—H | C—CF3 | N | CF₃ | C—H | C—NHCOCF3 | H | H | EtCO | H | 1 |
| 2-4706 | H | C—H | C—H | C—CF3 | N | CF₃ | C—H | C—NHCOCF3 | H | H | CF₃CH₂CO | H | 1 |
| 2-4707 | H | C—H | C—H | C—CF3 | N | CF₃ | C—H | C—CH2OAc | H | H | EtCO | H | 1 |
| 2-4708 | H | C—H | C—H | C—CF3 | N | CF₃ | C—H | C—CH2OAc | H | H | CF₃CH₂CO | H | 1 |
| 2-4709 | H | C—CF3 | C—H | C—H | N | CF₃ | C—H | C—CF3 | H | H | H | H | 1 |
| 2-4710 | H | C—CF3 | C—H | C—H | N | CF₃ | C—H | C—CF3 | H | H | CH3CO | H | 1 |
| 2-4711 | H | C—CF3 | C—H | C—H | N | CF₃ | C—H | C—CF3 | H | H | EtCO | H | 1 |
| 2-4712 | H | C—CF3 | C—H | C—H | N | CF₃ | C—H | C—CF3 | H | H | CF₃CH₂CO | H | 1 |
| 2-4713 | H | C—CF3 | C—H | C—H | N | CF₃ | C—H | C—CF3 | H | H | cyclo-PrCO | H | 1 |
| 2-4714 | H | C—CF3 | C—H | C—H | N | CF₃ | C—H | C—CF3 | H | H | cyclo-PrCH2CO | H | 1 |
| 2-4715 | H | C—CF3 | C—H | C—H | N | CF₃ | C—H | C—CF3 | H | H | EtNHCO | H | 1 |
| 2-4716 | H | C—CF3 | C—H | C—H | N | CF₃ | C—H | C—CF3 | H | H | CH3SCH2CO | H | 1 |
| 2-4717 | H | C—CF3 | C—H | C—H | N | CF₃ | C—H | C—CF3 | H | H | CH3SOCH2CO | H | 1 |
| 2-4718 | H | C—CF3 | C—H | C—H | N | CF₃ | C—H | C—CF3 | H | H | CH3SO2CH2CO | H | 1 |
| 2-4719 | H | C—CF3 | C—H | C—H | N | CF₃ | C—H | C—CF3 | Me | H | EtCO | H | 1 |
| 2-4720 | H | C—CF3 | C—H | C—H | N | CF₃ | C—H | C—CF3 | Me | H | CF3CH2CO | H | 1 |
| 2-4721 | H | C—CF3 | C—H | C—H | N | CF₃ | N | C—CF3 | H | H | EtCO | H | 1 |
| 2-4722 | H | C—CF3 | C—H | C—H | N | CF₃ | N | C—CF3 | H | H | CF3CH2CO | H | 1 |
| 2-4723 | H | C—CF3 | C—H | C—H | N | CF₃ | C—H | C—Cl | H | H | H | H | 1 |
| 2-4724 | H | C—CF3 | C—H | C—H | N | CF₃ | C—H | C—Cl | H | H | MeCO | H | 1 |
| 2-4725 | H | C—CF3 | C—H | C—H | N | CF₃ | C—H | C—Cl | H | H | EtCO | H | 1 |
| 2-4726 | H | C—CF3 | C—H | C—H | N | CF₃ | C—H | C—Cl | H | H | CF3CH2CO | H | 1 |
| 2-4727 | H | C—CF3 | C—H | C—H | N | CF₃ | C—H | C—Cl | H | H | cyclo-PrCO | H | 1 |
| 2-4728 | H | C—CF3 | C—H | C—H | N | CF₃ | C—H | C—Cl | H | H | cyclo-PrCH2CO | H | 1 |
| 2-4729 | H | C—CF3 | C—H | C—H | N | CF₃ | C—H | C—Cl | H | H | CH3SCH2CO | H | 1 |
| 2-4730 | H | C—CF3 | C—H | C—H | N | CF₃ | C—H | C—Cl | H | H | CH3SOCH2CO | H | 1 |
| 2-4731 | H | C—CF3 | C—H | C—H | N | CF₃ | C—H | C—Cl | H | H | CH3SO2CH2CO | H | 1 |
| 2-4732 | H | C—CF3 | C—H | C—H | N | CF₃ | C—H | C—Cl | H | H | EtNHCO | H | 1 |
| 2-4733 | H | C—CF3 | C—H | C—H | N | CF₃ | C—H | C—Cl | Me | H | EtCO | H | 1 |
| 2-4734 | H | C—CF3 | C—H | C—H | N | CF₃ | C—H | C—Cl | Me | H | CF3CH2CO | H | 1 |
| 2-4735 | H | C—CF3 | C—H | C—H | N | CF₃ | N | C—Cl | H | H | EtCO | H | 1 |
| 2-4736 | H | C—CF3 | C—H | C—H | N | CF₃ | N | C—Cl | H | H | CF3CH2CO | H | 1 |
| 2-4737 | H | C—CF3 | C—H | C—H | N | CF₃ | C—H | C—Br | H | H | H | H | 1 |
| 2-4738 | H | C—CF3 | C—H | C—H | N | CF₃ | C—H | C—Br | H | H | MeCO | H | 1 |
| 2-4739 | H | C—CF3 | C—H | C—H | N | CF₃ | C—H | C—Br | H | H | EtCO | H | 1 |
| 2-4740 | H | C—CF3 | C—H | C—H | N | CF₃ | C—H | C—Br | H | H | cyc-PrCO | H | 1 |
| 2-4741 | H | C—CF3 | C—H | C—H | N | CF₃ | C—H | C—Br | H | H | CF₃CH₂CO | H | 1 |
| 2-4742 | H | C—CF3 | C—H | C—H | N | CF₃ | C—H | C—Br | H | H | CH3SCH2CO | H | 1 |
| 2-4743 | H | C—CF3 | C—H | C—H | N | CF₃ | C—H | C—Br | H | H | CH3SOCH2CO | H | 1 |
| 2-4744 | H | C—CF3 | C—H | C—H | N | CF₃ | C—H | C—Br | H | H | CH3SO2CH2CO | H | 1 |
| 2-4745 | H | C—CF3 | C—H | C—H | N | CF₃ | C—H | C—Br | Me | H | EtCO | H | 1 |
| 2-4746 | H | C—CF3 | C—H | C—H | N | CF₃ | C—H | C—Br | Me | H | CF3CH2CO | H | 1 |
| 2-4747 | H | C—CF3 | C—H | C—H | N | CF₃ | N | C—Br | H | H | EtCO | H | 1 |
| 2-4748 | H | C—CF3 | C—H | C—H | N | CF₃ | N | C—Br | H | H | CF3CH2CO | H | 1 |
| 2-4749 | H | C—CF3 | C—H | C—H | N | CF₃ | C—H | C—CN | H | H | EtCO | H | 1 |
| 2-4750 | H | C—CF3 | C—H | C—H | N | CF₃ | C—H | C—CN | H | H | CF3CH2CO | H | 1 |
| 2-4751 | H | C—CF3 | C—H | C—H | N | CF₃ | N | C—CN | H | H | EtCO | H | 1 |
| 2-4752 | H | C—CF3 | C—H | C—H | N | CF₃ | C—H | C—Me | H | H | MeCO | H | 1 |
| 2-4753 | H | C—CF3 | C—H | C—H | N | CF₃ | C—H | C—Me | H | H | MeCO | H | 1 |
| 2-4754 | H | C—CF3 | C—H | C—H | N | CF₃ | C—H | C—Me | H | H | EtCO | H | 1 |
| 2-4755 | H | C—CF3 | C—H | C—H | N | CF₃ | C—H | C—Me | H | H | CF3CH2CO | H | 1 |
| 2-4756 | H | C—CF3 | C—H | C—H | N | CF₃ | C—H | C—Me | H | H | cyclo-PrCO | H | 1 |
| 2-4757 | H | C—CF3 | C—H | C—H | N | CF₃ | C—H | C—Me | H | H | CH3SCH2CO | H | 1 |
| 2-4758 | H | C—CF3 | C—H | C—H | N | CF₃ | C—H | C—Me | H | H | EtNHCO | H | 1 |
| 2-4759 | H | C—CF3 | C—H | C—H | N | CF₃ | C—H | C—Me | Me | H | EtCO | H | 1 |
| 2-4760 | H | C—CF3 | C—H | C—H | N | CF₃ | N | C—Me | H | H | EtCO | H | 1 |
| 2-4761 | H | C—CF3 | C—H | C—H | N | CF₃ | C—H | C—NO2 | H | H | MeCO | H | 1 |
| 2-4762 | H | C—CF3 | C—H | C—H | N | CF₃ | C—H | C—NO2 | H | H | MeCO | H | 1 |

TABLE 2-2-continued

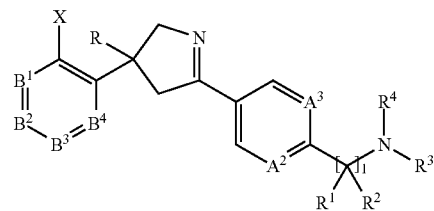

| Example No. | X | B¹ | B² | B³ | B⁴ | R | A² | A³ | R¹ | R² | R⁴ | R³ | I |
|---|---|---|---|---|---|---|---|---|---|---|---|---|---|
| 2-4763 | H | C—CF3 | C—H | C—H | N | CF₃ | C—H | C—NO2 | H | H | EtCO | H | 1 |
| 2-4764 | H | C—CF3 | C—H | C—H | N | CF₃ | C—H | C—NO2 | H | H | CF3CH2CO | H | 1 |
| 2-4765 | H | C—CF3 | C—H | C—H | N | CF₃ | C—H | C—NO2 | H | H | cyclo-PrCO | H | 1 |
| 2-4766 | H | C—CF3 | C—H | C—H | N | CF₃ | C—H | C—NO2 | H | H | CH3SCH2CO | H | 1 |
| 2-4767 | H | C—CF3 | C—H | C—H | N | CF₃ | C—H | C—NO2 | H | H | EtNHCO | H | 1 |
| 2-4768 | H | C—CF3 | C—H | C—H | N | CF₃ | C—H | C—NO2 | Me | H | EtCO | H | 1 |
| 2-4769 | H | C—CF3 | C—H | C—H | N | CF₃ | N | C—NO2 | H | H | EtCO | H | 1 |
| 2-4770 | H | C—CF3 | C—H | C—H | N | CF₃ | C—H | C—SMe | H | H | MeCO | H | 1 |
| 2-4771 | H | C—CF3 | C—H | C—H | N | CF₃ | C—H | C—SMe | H | H | MeCO | H | 1 |
| 2-4772 | H | C—CF3 | C—H | C—H | N | CF₃ | C—H | C—SMe | H | H | EtCO | H | 1 |
| 2-4773 | H | C—CF3 | C—H | C—H | N | CF₃ | C—H | C—SMe | H | H | CF3CH2CO | H | 1 |
| 2-4774 | H | C—CF3 | C—H | C—H | N | CF₃ | C—H | C—SMe | H | H | cyclo-PrCO | H | 1 |
| 2-4775 | H | C—CF3 | C—H | C—H | N | CF₃ | C—H | C—SMe | H | H | CH3SCH2CO | H | 1 |
| 2-4776 | H | C—CF3 | C—H | C—H | N | CF₃ | C—H | C—SMe | H | H | EtNHCO | H | 1 |
| 2-4777 | H | C—CF3 | C—H | C—H | N | CF₃ | C—H | C—SMe | Me | H | EtCO | H | 1 |
| 2-4778 | H | C—CF3 | C—H | C—H | N | CF₃ | N | C—SMe | H | H | EtCO | H | 1 |
| 2-4779 | H | C—CF3 | C—H | C—H | N | CF₃ | C—H | C—H | H | H | MeCO | H | 1 |
| 2-4780 | H | C—CF3 | C—H | C—H | N | CF₃ | C—H | C—H | H | H | MeCO | H | 1 |
| 2-4781 | H | C—CF3 | C—H | C—H | N | CF₃ | C—H | C—H | H | H | EtCO | H | 1 |
| 2-4782 | H | C—CF3 | C—H | C—H | N | CF₃ | C—H | C—H | H | H | CF3CH2CO | H | 1 |
| 2-4783 | H | C—CF3 | C—H | C—H | N | CF₃ | C—H | C—H | H | H | cyclo-PrCO | H | 1 |
| 2-4784 | H | C—CF3 | C—H | C—H | N | CF₃ | C—H | C—H | H | H | CH3SCH2CO | H | 1 |
| 2-4785 | H | C—CF3 | C—H | C—H | N | CF₃ | C—H | C—H | H | H | EtNHCO | H | 1 |
| 2-4786 | H | C—CF3 | C—H | C—H | N | CF₃ | C—H | C—H | Me | H | EtCO | H | 1 |
| 2-4787 | H | C—CF3 | C—H | C—H | N | CF₃ | N | C—H | H | H | EtCO | H | 1 |
| 2-4788 | H | C—CF3 | C—H | C—H | N | CF₃ | C—H | C—SOMe | H | H | EtCO | H | 1 |
| 2-4789 | H | C—CF3 | C—H | C—H | N | CF₃ | C—H | C—SOMe | H | H | CF₃CH₂CO | H | 1 |
| 2-4790 | H | C—CF3 | C—H | C—H | N | CF₃ | C—H | C—SO2Me | H | H | EtCO | H | 1 |
| 2-4791 | H | C—CF3 | C—H | C—H | N | CF₃ | C—H | C—SO2Me | H | H | CF₃CH₂CO | H | 1 |
| 2-4792 | H | C—CF3 | C—H | C—H | N | CF₃ | C—H | C—SCF3 | H | H | EtCO | H | 1 |
| 2-4793 | H | C—CF3 | C—H | C—H | N | CF₃ | C—H | C—SCF3 | H | H | CF₃CH₂CO | H | 1 |
| 2-4794 | H | C—CF3 | C—H | C—H | N | CF₃ | C—H | C—SOCF3 | H | H | EtCO | H | 1 |
| 2-4795 | H | C—CF3 | C—H | C—H | N | CF₃ | C—H | C—SOCF3 | H | H | CF₃CH₂CO | H | 1 |
| 2-4796 | H | C—CF3 | C—H | C—H | N | CF₃ | C—H | C—SO2CF3 | H | H | EtCO | H | 1 |
| 2-4797 | H | C—CF3 | C—H | C—H | N | CF₃ | C—H | C—SO2CF3 | H | H | CF₃CH₂CO | H | 1 |
| 2-4798 | H | C—CF3 | C—H | C—H | N | CF₃ | C—H | C—F | H | H | EtCO | H | 1 |
| 2-4799 | H | C—CF3 | C—H | C—H | N | CF₃ | C—H | C—F | H | H | CF₃CH₂CO | H | 1 |
| 2-4800 | H | C—CF3 | C—H | C—H | N | CF₃ | C—H | C—I | H | H | EtCO | H | 1 |
| 2-4801 | H | C—CF3 | C—H | C—H | N | CF₃ | C—H | C—I | H | H | CF₃CH₂CO | H | 1 |
| 2-4802 | H | C—CF3 | C—H | C—H | N | CF₃ | C—H | C—NH2 | H | H | EtCO | H | 1 |
| 2-4803 | H | C—CF3 | C—H | C—H | N | CF₃ | C—H | C—NH2 | H | H | CF₃CH₂CO | H | 1 |
| 2-4804 | H | C—CF3 | C—H | C—H | N | CF₃ | C—H | C—NHAc | H | H | EtCO | H | 1 |
| 2-4805 | H | C—CF3 | C—H | C—H | N | CF₃ | C—H | C—NHAc | H | H | CF₃CH₂CO | H | 1 |
| 2-4806 | H | C—CF3 | C—H | C—H | N | CF₃ | C—H | C—NHCOCF3 | H | H | EtCO | H | 1 |
| 2-4807 | H | C—CF3 | C—H | C—H | N | CF₃ | C—H | C—NHCOCF3 | H | H | CF₃CH₂CO | H | 1 |
| 2-4808 | H | C—CF3 | C—H | C—H | N | CF₃ | C—H | C—CH2OAc | H | H | EtCO | H | 1 |
| 2-4809 | H | C—CF3 | C—H | C—H | N | CF₃ | C—H | C—CH2OAc | H | H | CF₃CH₂CO | H | 1 |
| 2-5091 | H | C—CF3 | N | C—CF3 | C—H | CF₃ | C—H | C—H | Me | H | MeCO | H | 1 |
| 2-5092 | H | C—CF3 | N | C—CF3 | C—H | CF₃ | C—H | C—H | Me | H | CH3SOCH2CO | H | 1 |
| 2-5093 | H | C—CF3 | N | C—CF3 | C—H | CF₃ | C—H | C—H | Me | H | CH3SO2CH2CO | H | 1 |
| 2-5094 | H | C—CF3 | N | C—CF3 | C—H | CF₃ | C—H | C—H | Me | H | CH3OCH2CH2CO | H | 1 |

TABLE 3-1

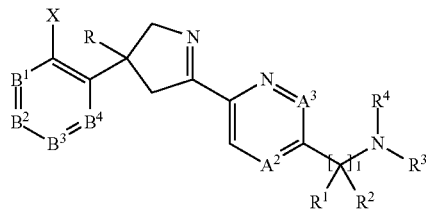

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 3 | — | 1 | H | C—Cl | C—Cl | C—Cl | C—H | CF3 | C—H | C—CF3 | H | H | cyclo-PrCH2CO | H | 1 |
| 3 | — | 2 | H | C—Cl | C—Cl | C—Cl | C—H | CF3 | C—H | C—CF3 | H | H | n-PrCO | H | 1 |
| 3 | — | 3 | H | C—Cl | C—Cl | C—Cl | C—H | CF3 | C—H | C—CF3 | H | H | CH3OCH2CH2CO | H | 1 |
| 3 | — | 4 | H | C—Cl | C—Cl | C—Cl | C—H | CF3 | C—H | C—CF3 | H | H | CH3OCH(Me)CH2CO | H | 1 |
| 3 | — | 5 | H | C—Cl | C—Cl | C—Cl | C—H | CF3 | C—H | C—CF3 | H | H | H | H | 1 |
| 3 | — | 6 | H | C—Cl | C—Cl | C—Cl | C—H | CF3 | C—H | C—CF3 | Me | H | EtCO | H | 1 |
| 3 | — | 7 | H | C—Cl | C—Cl | C—Cl | C—H | CF3 | C—H | C—CF3 | Me | H | CF3CH2CO | H | 1 |
| 3 | — | 8 | H | C—Cl | C—Cl | C—Cl | C—H | CF3 | C—H | C—CF3 | Me | Me | EtCO | H | 1 |
| 3 | — | 9 | H | C—Cl | C—Cl | C—Cl | C—H | CF3 | C—H | C—CF3 | Me | Me | CF3CH2CO | H | 1 |
| 3 | — | 10 | H | C—Cl | C—Cl | C—Cl | C—H | CF3 | C—H | C—CF3 | —CH2CH2— | | EtCO | H | 1 |
| 3 | — | 11 | H | C—Cl | C—Cl | C—Cl | C—H | CF3 | C—H | C—CF3 | —CH2CH2— | | CF3CH2CO | H | 1 |
| 3 | — | 12 | H | C—Cl | C—Cl | C—Cl | C—H | CF3 | C—H | C—Cl | H | H | H | H | 1 |
| 3 | — | 13 | H | C—Cl | C—Cl | C—Cl | C—H | CF3 | C—H | C—Cl | H | H | MeCO | H | 1 |
| 3 | — | 14 | H | C—Cl | C—Cl | C—Cl | C—H | CF3 | C—H | C—Cl | H | H | EtCO | H | 1 |
| 3 | — | 15 | H | C—Cl | C—Cl | C—Cl | C—H | CF3 | C—H | C—Cl | H | H | n-PrCO | H | 1 |
| 3 | — | 16 | H | C—Cl | C—Cl | C—Cl | C—H | CF3 | C—H | C—Cl | H | H | cyclo-PrCO | H | 1 |
| 3 | — | 17 | H | C—Cl | C—Cl | C—Cl | C—H | CF3 | C—H | C—Cl | H | H | cyclo-PrCH2CO | H | 1 |
| 3 | — | 18 | H | C—Cl | C—Cl | C—Cl | C—H | CF3 | C—H | C—Cl | H | H | CF3CH2CO | H | 1 |
| 3 | — | 19 | H | C—Cl | C—Cl | C—Cl | C—H | CF3 | C—H | C—Cl | H | H | CH3SCH2CO | H | 1 |
| 3 | — | 20 | H | C—Cl | C—Cl | C—Cl | C—H | CF3 | C—H | C—Cl | H | H | CH3SO2CH2CO | H | 1 |
| 3 | — | 21 | H | C—Cl | C—Cl | C—Cl | C—H | CF3 | C—H | C—Cl | H | H | CH3OCH2CH2CO | H | 1 |
| 3 | — | 22 | H | C—Cl | C—Cl | C—Cl | C—H | CF3 | C—H | C—Cl | H | H | CH3OCH(Me)CH2CO | H | 1 |
| 3 | — | 23 | H | C—Cl | C—Cl | C—Cl | C—H | CF3 | C—H | C—Cl | H | H | EtNHCO | H | 1 |
| 3 | — | 24 | H | C—Cl | C—Cl | C—Cl | C—H | CF3 | C—H | C—Me | H | H | MeCO | H | 1 |
| 3 | — | 25 | H | C—Cl | C—Cl | C—Cl | C—H | CF3 | C—H | C—Me | H | H | EtCO | H | 1 |
| 3 | — | 26 | H | C—Cl | C—Cl | C—Cl | C—H | CF3 | C—H | C—Me | H | H | n-PrCO | H | 1 |
| 3 | — | 27 | H | C—Cl | C—Cl | C—Cl | C—H | CF3 | C—H | C—Me | H | H | cyclo-PrCO | H | 1 |
| 3 | — | 28 | H | C—Cl | C—Cl | C—Cl | C—H | CF3 | C—H | C—Me | H | H | cyclo-PrCH2CO | H | 1 |
| 3 | — | 29 | H | C—Cl | C—Cl | C—Cl | C—H | CF3 | C—H | C—Me | H | H | CF3CH2CO | H | 1 |
| 3 | — | 30 | H | C—Cl | C—Cl | C—Cl | C—H | CF3 | C—H | C—Me | H | H | CH3SCH2CO | H | 1 |
| 3 | — | 31 | H | C—Cl | C—Cl | C—Cl | C—H | CF3 | C—H | C—Me | H | H | CH3SO2CH2CO | H | 1 |
| 3 | — | 32 | H | C—Cl | C—Cl | C—Cl | C—H | CF3 | C—H | C—Me | H | H | CH3OCH2CH2CO | H | 1 |
| 3 | — | 33 | H | C—Cl | C—Cl | C—Cl | C—H | CF3 | C—H | C—Me | H | H | CH3OCH(Me)CH2CO | H | 1 |
| 3 | — | 34 | H | C—Cl | C—Cl | C—Cl | C—H | CF3 | C—H | C—Me | H | H | EtNHCO | H | 1 |
| 3 | — | 35 | H | C—Cl | C—Cl | C—Cl | C—H | CF3 | C—H | C—SMe | H | H | H | H | 1 |
| 3 | — | 36 | H | C—Cl | C—Cl | C—Cl | C—H | CF3 | C—H | C—SMe | H | H | MeCO | H | 1 |
| 3 | — | 37 | H | C—Cl | C—Cl | C—Cl | C—H | CF3 | C—H | C—SMe | H | H | EtCO | H | 1 |
| 3 | — | 38 | H | C—Cl | C—Cl | C—Cl | C—H | CF3 | C—H | C—SMe | H | H | cyclo-PrCO | H | 1 |
| 3 | — | 39 | H | C—Cl | C—Cl | C—Cl | C—H | CF3 | C—H | C—SMe | H | H | cyclo-PrCH2CO | H | 1 |
| 3 | — | 40 | H | C—Cl | C—Cl | C—Cl | C—H | CF3 | C—H | C—SMe | H | H | CF3CH2CO | H | 1 |
| 3 | — | 41 | H | C—Cl | C—Cl | C—Cl | C—H | CF3 | C—H | C—SMe | H | H | CH3SCH2CO | H | 1 |
| 3 | — | 42 | H | C—Cl | C—Cl | C—Cl | C—H | CF3 | C—H | C—SMe | H | H | CH3SO2CH2CO | H | 1 |
| 3 | — | 43 | H | C—Cl | C—Cl | C—Cl | C—H | CF3 | C—H | C—SMe | H | H | CH3OCH2CH2CO | H | 1 |
| 3 | — | 44 | H | C—Cl | C—Cl | C—Cl | C—H | CF3 | C—H | C—SMe | H | H | CH3OCH(Me)CH2CO | H | 1 |
| 3 | — | 45 | H | C—Cl | C—Cl | C—Cl | C—H | CF3 | C—H | C—SMe | H | H | EtNHCO | H | 1 |
| 3 | — | 46 | H | C—Cl | C—Cl | C—Cl | C—H | CF3 | C—H | C—SO2Me | H | H | H | H | 1 |
| 3 | — | 47 | H | C—Cl | C—Cl | C—Cl | C—H | CF3 | C—H | C—SO2Me | H | H | MeCO | H | 1 |
| 3 | — | 48 | H | C—Cl | C—Cl | C—Cl | C—H | CF3 | C—H | C—SO2Me | H | H | EtCO | H | 1 |
| 3 | — | 49 | H | C—Cl | C—Cl | C—Cl | C—H | CF3 | C—H | C—SO2Me | H | H | cyclo-PrCO | H | 1 |
| 3 | — | 50 | H | C—Cl | C—Cl | C—Cl | C—H | CF3 | C—H | C—SO2Me | H | H | cyclo-PrCH2CO | H | 1 |
| 3 | — | 51 | H | C—Cl | C—Cl | C—Cl | C—H | CF3 | C—H | C—SO2Me | H | H | CF3CH2CO | H | 1 |
| 3 | — | 52 | H | C—Cl | C—Cl | C—Cl | C—H | CF3 | C—H | C—SO2Me | H | H | CH3SCH2CO | H | 1 |
| 3 | — | 53 | H | C—Cl | C—Cl | C—Cl | C—H | CF3 | C—H | C—SO2Me | H | H | CH3SO2CH2CO | H | 1 |
| 3 | — | 54 | H | C—Cl | C—Cl | C—Cl | C—H | CF3 | C—H | C—SO2Me | H | H | EtNHCO | H | 1 |
| 3 | — | 55 | H | C—Cl | C—Cl | C—Cl | C—H | CF3 | C—H | C—SCF3 | H | H | H | H | 1 |
| 3 | — | 56 | H | C—Cl | C—Cl | C—Cl | C—H | CF3 | C—H | C—SCF3 | H | H | MeCO | H | 1 |
| 3 | — | 57 | H | C—Cl | C—Cl | C—Cl | C—H | CF3 | C—H | C—SCF3 | H | H | EtCO | H | 1 |
| 3 | — | 58 | H | C—Cl | C—Cl | C—Cl | C—H | CF3 | C—H | C—SCF3 | H | H | cyclo-PrCO | H | 1 |
| 3 | — | 59 | H | C—Cl | C—Cl | C—Cl | C—H | CF3 | C—H | C—SCF3 | H | H | cyclo-PrCH2CO | H | 1 |
| 3 | — | 60 | H | C—Cl | C—Cl | C—Cl | C—H | CF3 | C—H | C—SCF3 | H | H | CF3CH2CO | H | 1 |
| 3 | — | 61 | H | C—Cl | C—Cl | C—Cl | C—H | CF3 | C—H | C—SCF3 | H | H | CH3SCH2CO | H | 1 |
| 3 | — | 62 | H | C—Cl | C—Cl | C—Cl | C—H | CF3 | C—H | C—SCF3 | H | H | CH3SO2CH2CO | H | 1 |
| 3 | — | 63 | H | C—Cl | C—Cl | C—Cl | C—H | CF3 | C—H | C—SCF3 | H | H | EtNHCO | H | 1 |
| 3 | — | 64 | H | C—Cl | C—Cl | C—Cl | C—H | CF3 | C—H | C—SOCF3 | H | H | MeCO | H | 1 |
| 3 | — | 65 | H | C—Cl | C—Cl | C—Cl | C—H | CF3 | C—H | C—SOCF3 | H | H | EtCO | H | 1 |
| 3 | — | 66 | H | C—Cl | C—Cl | C—Cl | C—H | CF3 | C—H | C—SOCF3 | H | H | cyclo-PrCO | H | 1 |
| 3 | — | 67 | H | C—Cl | C—Cl | C—Cl | C—H | CF3 | C—H | C—SOCF3 | H | H | cyclo-PrCH2CO | H | 1 |

TABLE 3-1-continued

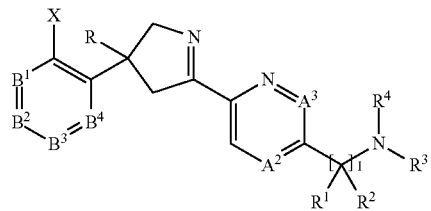

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 3 | — | 68 | H | C—Cl | C—Cl | C—Cl | C—H | CF3 | C—H | C—SOCF3 | H | H | CF3CH2CO | H | 1 |
| 3 | — | 69 | H | C—Cl | C—Cl | C—Cl | C—H | CF3 | C—H | C—SOCF3 | H | H | CH3SCH2CO | H | 1 |
| 3 | — | 70 | H | C—Cl | C—Cl | C—Cl | C—H | CF3 | C—H | C—SOCF3 | H | H | CH3SO2CH2CO | H | 1 |
| 3 | — | 71 | H | C—Cl | C—Cl | C—Cl | C—H | CF3 | C—H | C—SOCF3 | H | H | EtNHCO | H | 1 |
| 3 | — | 72 | H | C—Cl | C—Cl | C—Cl | C—H | CF3 | C—H | C—SO2CF3 | H | H | H | H | 1 |
| 3 | — | 73 | H | C—Cl | C—Cl | C—Cl | C—H | CF3 | C—H | C—SO2CF3 | H | H | MeCO | H | 1 |
| 3 | — | 74 | H | C—Cl | C—Cl | C—Cl | C—H | CF3 | C—H | C—SO2CF3 | H | H | EtCO | H | 1 |
| 3 | — | 75 | H | C—Cl | C—Cl | C—Cl | C—H | CF3 | C—H | C—SO2CF3 | H | H | cyclo-PrCO | H | 1 |
| 3 | — | 76 | H | C—Cl | C—Cl | C—Cl | C—H | CF3 | C—H | C—SO2CF3 | H | H | cyclo-PrCH2CO | H | 1 |
| 3 | — | 77 | H | C—Cl | C—Cl | C—Cl | C—H | CF3 | C—H | C—SO2CF3 | H | H | CF3CH2CO | H | 1 |
| 3 | — | 78 | H | C—Cl | C—Cl | C—Cl | C—H | CF3 | C—H | C—SO2CF3 | H | H | CH3SCH2CO | H | 1 |
| 3 | — | 79 | H | C—Cl | C—Cl | C—Cl | C—H | CF3 | C—H | C—SO2CF3 | H | H | CH3SO2CH2CO | H | 1 |
| 3 | — | 80 | H | C—Cl | C—Cl | C—Cl | C—H | CF3 | C—H | C—SO2CF3 | H | H | EtNHCO | H | 1 |
| 3 | — | 81 | H | C—Cl | C—Cl | C—Cl | C—H | CF3 | C—H | C—H | H | H | H | H | 1 |
| 3 | — | 82 | H | C—Cl | C—Cl | C—Cl | C—H | CF3 | C—H | C—H | H | H | MeCO | H | 1 |
| 3 | — | 83 | H | C—Cl | C—Cl | C—Cl | C—H | CF3 | C—H | C—H | H | H | EtCO | H | 1 |
| 3 | — | 84 | H | C—Cl | C—Cl | C—Cl | C—H | CF3 | C—H | C—H | H | H | cyclo-PrCO | H | 1 |
| 3 | — | 85 | H | C—Cl | C—Cl | C—Cl | C—H | CF3 | C—H | C—H | H | H | cyclo-PrCH2CO | H | 1 |
| 3 | — | 86 | H | C—Cl | C—Cl | C—Cl | C—H | CF3 | C—H | C—H | H | H | CF3CH2CO | H | 1 |
| 3 | — | 87 | H | C—Cl | C—Cl | C—Cl | C—H | CF3 | C—H | C—H | H | H | CH3SCH2CO | H | 1 |
| 3 | — | 88 | H | C—Cl | C—Cl | C—Cl | C—H | CF3 | C—H | C—H | H | H | CH3SO2CH2CO | H | 1 |
| 3 | — | 89 | H | C—Cl | C—Cl | C—Cl | C—H | CF3 | C—H | C—H | H | H | EtNHCO | H | 1 |
| 3 | — | 90 | H | C—Cl | C—H | C—Cl | C—H | CF3 | C—H | C—H | H | H | H | H | 1 |
| 3 | — | 91 | H | C—Cl | C—H | C—Cl | C—H | CF3 | C—H | C—CF3 | H | H | H | H | 1 |
| 3 | — | 92 | H | C—Cl | C—H | C—Cl | C—H | CF3 | C—H | C—Cl | H | H | H | H | 1 |
| 3 | — | 93 | H | C—CF3 | C—H | C—CF3 | C—H | CF3 | C—H | C—CF3 | H | H | H | H | 1 |
| 3 | — | 94 | H | C—CF3 | C—H | C—CF3 | C—H | CF3 | C—H | C—CF3 | H | H | CH3OCH2CH2CO | H | 1 |
| 3 | — | 95 | H | C—CF3 | C—H | C—CF3 | C—H | CF3 | C—H | C—CF3 | H | H | CH3OCH(Me)CH2CO | H | 1 |
| 3 | — | 96 | H | C—CF3 | C—H | C—CF3 | C—H | CF3 | C—H | C—CF3 | H | H | cyclo-PrCH2CO | H | 1 |
| 3 | — | 97 | H | C—CF3 | C—H | C—CF3 | C—H | CF3 | C—H | C—Cl | H | H | MeCO | H | 1 |
| 3 | — | 98 | H | C—CF3 | C—H | C—CF3 | C—H | CF3 | C—H | C—Cl | H | H | EtCO | H | 1 |
| 3 | — | 99 | H | C—CF3 | C—H | C—CF3 | C—H | CF3 | C—H | C—Cl | H | H | CF3CH2CO | H | 1 |
| 3 | — | 100 | H | C—CF3 | C—H | C—CF3 | C—H | CF3 | C—H | C—Cl | H | H | cyclo-PrCO | H | 1 |
| 3 | — | 101 | H | C—CF3 | C—H | C—CF3 | C—H | CF3 | C—H | C—Cl | H | H | EtNHCO | H | 1 |
| 3 | — | 102 | H | C—CF3 | C—H | C—CF3 | C—H | CF3 | C—H | C—Cl | H | H | CH3SCH2CO | H | 1 |
| 3 | — | 103 | H | C—CF3 | C—H | C—CF3 | C—H | CF3 | C—H | C—Cl | H | H | CH3SOCH2CO | H | 1 |
| 3 | — | 104 | H | C—CF3 | C—H | C—CF3 | C—H | CF3 | C—H | C—Cl | H | H | CH3SO2CH2CO | H | 1 |
| 3 | — | 105 | H | C—CF3 | C—H | C—CF3 | C—H | CF3 | C—H | C—Cl | H | H | tert-BuOC(=O) | H | 1 |
| 3 | — | 106 | H | C—CF3 | C—H | C—CF3 | C—H | CF3 | C—H | C—Cl | H | H | H | H | 1 |
| 3 | — | 107 | H | C—CF3 | C—H | C—CF3 | C—H | CF3 | C—H | C—Cl | H | H | CH3OCH2CH2CO | H | 1 |
| 3 | — | 108 | H | C—CF3 | C—H | C—CF3 | C—H | CF3 | C—H | C—Cl | H | H | CH3OCH(Me)CH2CO | H | 1 |
| 3 | — | 109 | H | C—CF3 | C—H | C—CF3 | C—H | CF3 | C—H | C—Cl | H | H | cyclo-PrCH2CO | H | 1 |
| 3 | — | 110 | H | C—CF3 | C—H | C—CF3 | C—H | CF3 | C—H | C—SMe | H | H | H | H | 1 |
| 3 | — | 111 | H | C—CF3 | C—H | C—CF3 | C—H | CF3 | C—H | C—SMe | H | H | EtCO | H | 1 |
| 3 | — | 112 | H | C—CF3 | C—H | C—CF3 | C—H | CF3 | C—H | C—SMe | H | H | CF3CH2CO | H | 1 |
| 3 | — | 113 | H | C—CF3 | C—H | C—CF3 | C—H | CF3 | C—H | C—SCF3 | H | H | H | H | 1 |
| 3 | — | 114 | H | C—CF3 | C—H | C—CF3 | C—H | CF3 | C—H | C—SCF3 | H | H | EtCO | H | 1 |
| 3 | — | 115 | H | C—CF3 | C—H | C—CF3 | C—H | CF3 | C—H | C—SCF3 | H | H | CF3CH2CO | H | 1 |
| 3 | — | 116 | H | C—CF3 | C—H | C—CF3 | C—H | CF3 | C—H | C—Me | H | H | H | H | 1 |
| 3 | — | 117 | H | C—CF3 | C—H | C—CF3 | C—H | CF3 | C—H | C—Me | H | H | EtCO | H | 1 |
| 3 | — | 118 | H | C—CF3 | C—H | C—CF3 | C—H | CF3 | C—H | C—Me | H | H | CF3CH2CO | H | 1 |
| 3 | — | 119 | H | C—CF3 | C—H | C—Cl | C—H | CF3 | C—H | C—CF3 | H | H | H | H | 1 |
| 3 | — | 120 | H | C—CF3 | C—H | C—Cl | C—H | CF3 | C—H | C—CF3 | H | H | MeCO | H | 1 |
| 3 | — | 121 | H | C—CF3 | C—H | C—Cl | C—H | CF3 | C—H | C—CF3 | H | H | EtCO | H | 1 |
| 3 | — | 122 | H | C—CF3 | C—H | C—Cl | C—H | CF3 | C—H | C—CF3 | H | H | CF3CH2CO | H | 1 |
| 3 | — | 123 | H | C—CF3 | C—H | C—Cl | C—H | CF3 | C—H | C—CF3 | H | H | cyclo-PrCO | H | 1 |
| 3 | — | 124 | H | C—CF3 | C—H | C—Cl | C—H | CF3 | C—H | C—CF3 | H | H | EtNHCO | H | 1 |
| 3 | — | 125 | H | C—CF3 | C—H | C—Cl | C—H | CF3 | C—H | C—CF3 | H | H | CH3SCH2CO | H | 1 |
| 3 | — | 126 | H | C—CF3 | C—H | C—Cl | C—H | CF3 | C—H | C—CF3 | H | H | CH3SOCH2CO | H | 1 |
| 3 | — | 127 | H | C—CF3 | C—H | C—Cl | C—H | CF3 | C—H | C—CF3 | H | H | CH3SO2CH2CO | H | 1 |
| 3 | — | 128 | H | C—CF3 | C—H | C—Cl | C—H | CF3 | C—H | C—CF3 | H | H | tert-BuOC(=O) | H | 1 |
| 3 | — | 129 | H | C—CF3 | C—H | C—Cl | C—H | CF3 | C—H | C—CF3 | Me | H | EtCO | H | 1 |
| 3 | — | 130 | H | C—CF3 | C—H | C—Cl | C—H | CF3 | C—H | C—CF3 | Me | H | CF3CH2CO | H | 1 |
| 3 | — | 131 | H | C—CF3 | C—H | C—Cl | C—H | CF3 | C—H | C—CF3 | —CH2CH2— | | EtCO | H | 1 |
| 3 | — | 132 | H | C—CF3 | C—H | C—Cl | C—H | CF3 | C—H | C—CF3 | —CH2CH2— | | CF3CH2CO | H | 1 |
| 3 | — | 133 | H | C—CF3 | C—H | C—Cl | C—H | CF3 | C—H | C—CF3 | Me | H | CF3CH2CO | H | 1 |
| 3 | — | 134 | H | C—CF3 | C—H | C—Cl | C—H | CF3 | C—H | C—H | H | H | EtCO | H | 1 |

TABLE 3-1-continued

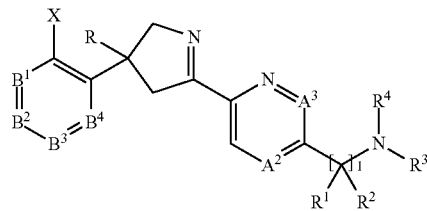

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 3 | — | 135 | H | C—CF3 | C—H | C—Cl | C—H | CF3 | C—H | C—H | H | H | CF3CH2CO | H | 1 |
| 3 | — | 136 | H | C—CF3 | C—H | C—Cl | C—H | CF3 | C—H | C—Cl | H | H | H | H | 1 |
| 3 | — | 137 | H | C—CF3 | C—H | C—Cl | C—H | CF3 | C—H | C—Cl | H | H | EtCO | H | 1 |
| 3 | — | 138 | H | C—CF3 | C—H | C—Cl | C—H | CF3 | C—H | C—Cl | H | H | CF3CH2CO | H | 1 |
| 3 | — | 139 | H | C—CF3 | C—H | C—Cl | C—H | CF3 | C—H | C—SMe | H | H | H | H | 1 |
| 3 | — | 140 | H | C—CF3 | C—H | C—Cl | C—H | CF3 | C—H | C—SMe | H | H | EtCO | H | 1 |
| 3 | — | 141 | H | C—CF3 | C—H | C—Cl | C—H | CF3 | C—H | C—SMe | H | H | CF3CH2CO | H | 1 |
| 3 | — | 142 | H | C—CF3 | C—H | C—Cl | C—H | CF3 | C—H | C—SMe | H | H | H | H | 1 |
| 3 | — | 143 | H | C—CF3 | C—H | C—Cl | C—H | CF3 | C—H | C—SCF3 | H | H | EtCO | H | 1 |
| 3 | — | 144 | H | C—CF3 | C—H | C—Cl | C—H | CF3 | C—H | C—SCF3 | H | H | CF3CH2CO | H | 1 |
| 3 | — | 145 | H | C—CF3 | C—H | C—Cl | C—H | CF3 | C—H | C—Me | H | H | H | H | 1 |
| 3 | — | 146 | H | C—CF3 | C—H | C—Cl | C—H | CF3 | C—H | C—Me | H | H | EtCO | H | 1 |
| 3 | — | 147 | H | C—CF3 | C—H | C—Cl | C—H | CF3 | C—H | C—Me | H | H | CF3CH2CO | H | 1 |
| 3 | — | 148 | H | C—CF3 | C—F | C—H | C—H | CF3 | C—H | C—CF3 | H | H | H | H | 1 |
| 3 | — | 149 | H | C—CF3 | C—F | C—H | C—H | CF3 | C—H | C—CF3 | H | H | MeCO | H | 1 |
| 3 | — | 150 | H | C—CF3 | C—F | C—H | C—H | CF3 | C—H | C—CF3 | H | H | EtCO | H | 1 |
| 3 | — | 151 | H | C—CF3 | C—F | C—H | C—H | CF3 | C—H | C—CF3 | H | H | CF3CH2CO | H | 1 |
| 3 | — | 152 | H | C—CF3 | C—F | C—H | C—H | CF3 | C—H | C—CF3 | H | H | cyclo-PrCO | H | 1 |
| 3 | — | 153 | H | C—CF3 | C—F | C—H | C—H | CF3 | C—H | C—CF3 | H | H | EtNHCO | H | 1 |
| 3 | — | 154 | H | C—CF3 | C—F | C—H | C—H | CF3 | C—H | C—CF3 | H | H | CH3SCH2CO | H | 1 |
| 3 | — | 155 | H | C—CF3 | C—F | C—H | C—H | CF3 | C—H | C—CF3 | H | H | CH3SOCH2CO | H | 1 |
| 3 | — | 156 | H | C—CF3 | C—F | C—H | C—H | CF3 | C—H | C—CF3 | H | H | CH3SO2CH2CO | H | 1 |
| 3 | — | 157 | H | C—CF3 | C—F | C—H | C—H | CF3 | C—H | C—CF3 | H | H | tert-BuOC(=O) | H | 1 |
| 3 | — | 158 | H | C—CF3 | C—F | C—H | C—H | CF3 | C—H | C—CF3 | Me | H | EtCO | H | 1 |
| 3 | — | 159 | H | C—CF3 | C—F | C—H | C—H | CF3 | C—H | C—CF3 | Me | H | CF3CH2CO | H | 1 |
| 3 | — | 160 | H | C—CF3 | C—F | C—H | C—H | CF3 | C—H | C—CF3 | —CH2CH2— | | EtCO | H | 1 |
| 3 | — | 161 | H | C—CF3 | C—F | C—H | C—H | CF3 | C—H | C—CF3 | —CH2CH2— | | CF3CH2CO | H | 1 |
| 3 | — | 162 | H | C—CF3 | C—F | C—H | C—H | CF3 | C—H | C—H | H | H | H | H | 1 |
| 3 | — | 163 | H | C—CF3 | C—F | C—H | C—H | CF3 | C—H | C—H | H | H | EtCO | H | 1 |
| 3 | — | 164 | H | C—CF3 | C—F | C—H | C—H | CF3 | C—H | C—H | H | H | CF3CH2CO | H | 1 |
| 3 | — | 165 | H | C—CF3 | C—F | C—H | C—H | CF3 | C—H | C—Cl | H | H | H | H | 1 |
| 3 | — | 166 | H | C—CF3 | C—F | C—H | C—H | CF3 | C—H | C—Cl | H | H | EtCO | H | 1 |
| 3 | — | 167 | H | C—CF3 | C—F | C—H | C—H | CF3 | C—H | C—Cl | H | H | CF3CH2CO | H | 1 |
| 3 | — | 168 | H | C—CF3 | C—F | C—H | C—H | CF3 | C—H | C—SMe | H | H | H | H | 1 |
| 3 | — | 169 | H | C—CF3 | C—F | C—H | C—H | CF3 | C—H | C—SMe | H | H | EtCO | H | 1 |
| 3 | — | 170 | H | C—CF3 | C—F | C—H | C—H | CF3 | C—H | C—SMe | H | H | CF3CH2CO | H | 1 |
| 3 | — | 171 | H | C—CF3 | C—F | C—H | C—H | CF3 | C—H | C—SCF3 | H | H | H | H | 1 |
| 3 | — | 172 | H | C—CF3 | C—F | C—H | C—H | CF3 | C—H | C—SCF3 | H | H | EtCO | H | 1 |
| 3 | — | 173 | H | C—CF3 | C—F | C—H | C—H | CF3 | C—H | C—SCF3 | H | H | CF3CH2CO | H | 1 |
| 3 | — | 174 | H | C—CF3 | C—F | C—H | C—H | CF3 | C—H | C—Me | H | H | H | H | 1 |
| 3 | — | 175 | H | C—CF3 | C—F | C—H | C—H | CF3 | C—H | C—Me | H | H | EtCO | H | 1 |
| 3 | — | 176 | H | C—CF3 | C—F | C—H | C—H | CF3 | C—H | C—Me | H | H | CF3CH2CO | H | 1 |
| 3 | — | 177 | H | C—CF3 | C—H | C—H | C—H | CF3 | C—H | C—CF3 | H | H | H | H | 1 |
| 3 | — | 178 | H | C—CF3 | C—H | C—H | C—H | CF3 | C—H | C—CF3 | H | H | MeCO | H | 1 |
| 3 | — | 179 | H | C—CF3 | C—H | C—H | C—H | CF3 | C—H | C—CF3 | H | H | EtCO | H | 1 |
| 3 | — | 180 | H | C—CF3 | C—H | C—H | C—H | CF3 | C—H | C—CF3 | H | H | CF3CH2CO | H | 1 |
| 3 | — | 181 | H | C—CF3 | C—H | C—H | C—H | CF3 | C—H | C—CF3 | H | H | cyclo-PrCO | H | 1 |
| 3 | — | 182 | H | C—CF3 | C—H | C—H | C—H | CF3 | C—H | C—CF3 | H | H | EtNHCO | H | 1 |
| 3 | — | 183 | H | C—CF3 | C—H | C—H | C—H | CF3 | C—H | C—CF3 | H | H | CH3SCH2CO | H | 1 |
| 3 | — | 184 | H | C—CF3 | C—H | C—H | C—H | CF3 | C—H | C—CF3 | H | H | CH3SOCH2CO | H | 1 |
| 3 | — | 185 | H | C—CF3 | C—H | C—H | C—H | CF3 | C—H | C—CF3 | H | H | CH3SO2CH2CO | H | 1 |
| 3 | — | 186 | H | C—CF3 | C—H | C—H | C—H | CF3 | C—H | C—CF3 | H | H | tert-BuOC(=O) | H | 1 |
| 3 | — | 187 | H | C—CF3 | C—H | C—H | C—H | CF3 | C—H | C—CF3 | Me | H | EtCO | H | 1 |
| 3 | — | 188 | H | C—CF3 | C—H | C—H | C—H | CF3 | C—H | C—CF3 | Me | H | CF3CH2CO | H | 1 |
| 3 | — | 189 | H | C—CF3 | C—H | C—H | C—H | CF3 | C—H | C—CF3 | —CH2CH2— | | EtCO | H | 1 |
| 3 | — | 190 | H | C—CF3 | C—H | C—H | C—H | CF3 | C—H | C—CF3 | —CH2CH2— | | CF3CH2CO | H | 1 |
| 3 | — | 191 | H | C—CF3 | C—H | C—H | C—H | CF3 | C—H | C—H | H | H | H | H | 1 |
| 3 | — | 192 | H | C—CF3 | C—H | C—H | C—H | CF3 | C—H | C—H | H | H | EtCO | H | 1 |
| 3 | — | 193 | H | C—CF3 | C—H | C—H | C—H | CF3 | C—H | C—H | H | H | CF3CH2CO | H | 1 |
| 3 | — | 194 | H | C—CF3 | C—H | C—H | C—H | CF3 | C—H | C—Cl | H | H | H | H | 1 |
| 3 | — | 195 | H | C—CF3 | C—H | C—H | C—H | CF3 | C—H | C—Cl | H | H | EtCO | H | 1 |
| 3 | — | 196 | H | C—CF3 | C—H | C—H | C—H | CF3 | C—H | C—Cl | H | H | CF3CH2CO | H | 1 |
| 3 | — | 197 | H | C—CF3 | C—H | C—H | C—H | CF3 | C—H | C—SMe | H | H | H | H | 1 |
| 3 | — | 198 | H | C—CF3 | C—H | C—H | C—H | CF3 | C—H | C—SMe | H | H | EtCO | H | 1 |
| 3 | — | 199 | H | C—CF3 | C—H | C—H | C—H | CF3 | C—H | C—SMe | H | H | CF3CH2CO | H | 1 |
| 3 | — | 200 | H | C—CF3 | C—H | C—H | C—H | CF3 | C—H | C—SCF3 | H | H | H | H | 1 |
| 3 | — | 201 | H | C—CF3 | C—H | C—H | C—H | CF3 | C—H | C—SCF3 | H | H | EtCO | H | 1 |

TABLE 3-1-continued

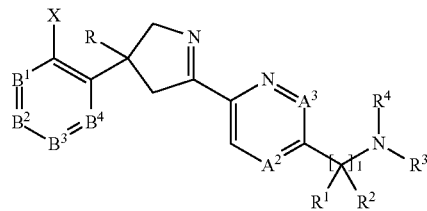

| Example No. | | | X | B¹ | B² | B³ | B⁴ | R | A² | A³ | R¹ | R² | R⁴ | R³ | l |
|---|---|---|---|---|---|---|---|---|---|---|---|---|---|---|---|
| 3 | — | 202 | H | C—CF3 | C—H | C—H | C—H | CF3 | C—H | C—SCF3 | H | H | CF3CH2CO | H | 1 |
| 3 | — | 203 | H | C—CF3 | C—H | C—H | C—H | CF3 | C—H | C—Me | H | H | H | H | 1 |
| 3 | — | 204 | H | C—CF3 | C—H | C—H | C—H | CF3 | C—H | C—Me | H | H | EtCO | H | 1 |
| 3 | — | 205 | H | C—CF3 | C—H | C—H | C—H | CF3 | C—H | C—Me | H | H | CF3CH2CO | H | 1 |
| 3 | — | 206 | H | C—Cl | C—F | C—Cl | C—H | CF3 | C—H | C—CF3 | H | H | H | H | 1 |
| 3 | — | 207 | H | C—Cl | C—F | C—Cl | C—H | CF3 | C—H | C—CF3 | H | H | MeCO | H | 1 |
| 3 | — | 208 | H | C—Cl | C—F | C—Cl | C—H | CF3 | C—H | C—CF3 | H | H | EtCO | H | 1 |
| 3 | — | 209 | H | C—Cl | C—F | C—Cl | C—H | CF3 | C—H | C—CF3 | H | H | CF3CH2CO | H | 1 |
| 3 | — | 210 | H | C—Cl | C—F | C—Cl | C—H | CF3 | C—H | C—CF3 | H | H | cyclo-PrCO | H | 1 |
| 3 | — | 211 | H | C—Cl | C—F | C—Cl | C—H | CF3 | C—H | C—CF3 | H | H | EtNHCO | H | 1 |
| 3 | — | 212 | H | C—Cl | C—F | C—Cl | C—H | CF3 | C—H | C—CF3 | H | H | CH3SCH2CO | H | 1 |
| 3 | — | 213 | H | C—Cl | C—F | C—Cl | C—H | CF3 | C—H | C—CF3 | H | H | CH3SOCH2CO | H | 1 |
| 3 | — | 214 | H | C—Cl | C—F | C—Cl | C—H | CF3 | C—H | C—CF3 | H | H | CH3SO2CH2CO | H | 1 |
| 3 | — | 215 | H | C—Cl | C—F | C—Cl | C—H | CF3 | C—H | C—CF3 | H | H | tert-BuOC(=O) | H | 1 |
| 3 | — | 216 | H | C—Cl | C—F | C—Cl | C—H | CF3 | C—H | C—CF3 | Me | H | EtCO | H | 1 |
| 3 | — | 217 | H | C—Cl | C—F | C—Cl | C—H | CF3 | C—H | C—CF3 | Me | H | CF3CH2CO | H | 1 |
| 3 | — | 218 | H | C—Cl | C—F | C—Cl | C—H | CF3 | C—H | C—CF3 | —CH2CH2— | | EtCO | H | 1 |
| 3 | — | 219 | H | C—Cl | C—F | C—Cl | C—H | CF3 | C—H | C—CF3 | —CH2CH2— | | CF3CH2CO | H | 1 |
| 3 | — | 220 | H | C—Cl | C—F | C—Cl | C—H | CF3 | C—H | C—CF3 | H | H | H | H | 1 |
| 3 | — | 221 | H | C—Cl | C—F | C—Cl | C—H | CF3 | C—H | C—H | H | H | EtCO | H | 1 |
| 3 | — | 222 | H | C—Cl | C—F | C—Cl | C—H | CF3 | C—H | C—H | H | H | CF3CH2CO | H | 1 |
| 3 | — | 223 | H | C—Cl | C—F | C—Cl | C—H | CF3 | C—H | C—Cl | H | H | H | H | 1 |
| 3 | — | 224 | H | C—Cl | C—F | C—Cl | C—H | CF3 | C—H | C—Cl | H | H | EtCO | H | 1 |
| 3 | — | 225 | H | C—Cl | C—F | C—Cl | C—H | CF3 | C—H | C—Cl | H | H | CF3CH2CO | H | 1 |
| 3 | — | 226 | H | C—Cl | C—F | C—Cl | C—H | CF3 | C—H | C—SMe | H | H | H | H | 1 |
| 3 | — | 227 | H | C—Cl | C—F | C—Cl | C—H | CF3 | C—H | C—SMe | H | H | EtCO | H | 1 |
| 3 | — | 228 | H | C—Cl | C—F | C—Cl | C—H | CF3 | C—H | C—SMe | H | H | CF3CH2CO | H | 1 |
| 3 | — | 229 | H | C—Cl | C—F | C—Cl | C—H | CF3 | C—H | C—SCF3 | H | H | H | H | 1 |
| 3 | — | 230 | H | C—Cl | C—F | C—Cl | C—H | CF3 | C—H | C—SCF3 | H | H | EtCO | H | 1 |
| 3 | — | 231 | H | C—Cl | C—F | C—Cl | C—H | CF3 | C—H | C—SCF3 | H | H | CF3CH2CO | H | 1 |
| 3 | — | 232 | H | C—Cl | C—F | C—Cl | C—H | CF3 | C—H | C—Me | H | H | H | H | 1 |
| 3 | — | 233 | H | C—Cl | C—F | C—Cl | C—H | CF3 | C—H | C—Me | H | H | EtCO | H | 1 |
| 3 | — | 234 | H | C—Cl | C—F | C—Cl | C—H | CF3 | C—H | C—Me | H | H | CF3CH2CO | H | 1 |
| 3 | — | 322 | F | C—CF3 | C—H | C—H | C—H | CF3 | C—H | C—CF3 | H | H | H | H | 1 |
| 3 | — | 323 | F | C—CF3 | C—H | C—H | C—H | CF3 | C—H | C—CF3 | H | H | MeCO | H | 1 |
| 3 | — | 324 | F | C—CF3 | C—H | C—H | C—H | CF3 | C—H | C—CF3 | H | H | EtCO | H | 1 |
| 3 | — | 325 | F | C—CF3 | C—H | C—H | C—H | CF3 | C—H | C—CF3 | H | H | CF3CH2CO | H | 1 |
| 3 | — | 326 | F | C—CF3 | C—H | C—H | C—H | CF3 | C—H | C—CF3 | H | H | cyclo-PrCO | H | 1 |
| 3 | — | 327 | F | C—CF3 | C—H | C—H | C—H | CF3 | C—H | C—CF3 | H | H | EtNHCO | H | 1 |
| 3 | — | 328 | F | C—CF3 | C—H | C—H | C—H | CF3 | C—H | C—CF3 | H | H | CH3SCH2CO | H | 1 |
| 3 | — | 329 | F | C—CF3 | C—H | C—H | C—H | CF3 | C—H | C—CF3 | H | H | CH3SOCH2CO | H | 1 |
| 3 | — | 330 | F | C—CF3 | C—H | C—H | C—H | CF3 | C—H | C—CF3 | H | H | CH3SO2CH2CO | H | 1 |
| 3 | — | 331 | F | C—CF3 | C—H | C—H | C—H | CF3 | C—H | C—CF3 | H | H | tert-BuOC(=O) | H | 1 |
| 3 | — | 332 | F | C—CF3 | C—H | C—H | C—H | CF3 | C—H | C—CF3 | Me | H | EtCO | H | 1 |
| 3 | — | 333 | F | C—CF3 | C—H | C—H | C—H | CF3 | C—H | C—CF3 | Me | H | CF3CH2CO | H | 1 |
| 3 | — | 334 | F | C—CF3 | C—H | C—H | C—H | CF3 | C—H | C—CF3 | —CH2CH2— | | EtCO | H | 1 |
| 3 | — | 335 | F | C—CF3 | C—H | C—H | C—H | CF3 | C—H | C—CF3 | —CH2CH2— | | CF3CH2CO | H | 1 |
| 3 | — | 336 | F | C—CF3 | C—H | C—H | C—H | CF3 | C—H | C—H | H | H | H | H | 1 |
| 3 | — | 337 | F | C—CF3 | C—H | C—H | C—H | CF3 | C—H | C—H | H | H | EtCO | H | 1 |
| 3 | — | 338 | F | C—CF3 | C—H | C—H | C—H | CF3 | C—H | C—H | H | H | CF3CH2CO | H | 1 |
| 3 | — | 339 | F | C—CF3 | C—H | C—H | C—H | CF3 | C—H | C—Cl | H | H | H | H | 1 |
| 3 | — | 340 | F | C—CF3 | C—H | C—H | C—H | CF3 | C—H | C—Cl | H | H | EtCO | H | 1 |
| 3 | — | 341 | F | C—CF3 | C—H | C—H | C—H | CF3 | C—H | C—Cl | H | H | CF3CH2CO | H | 1 |
| 3 | — | 342 | F | C—CF3 | C—H | C—H | C—H | CF3 | C—H | C—SMe | H | H | H | H | 1 |
| 3 | — | 343 | F | C—CF3 | C—H | C—H | C—H | CF3 | C—H | C—SMe | H | H | EtCO | H | 1 |
| 3 | — | 344 | F | C—CF3 | C—H | C—H | C—H | CF3 | C—H | C—SMe | H | H | CF3CH2CO | H | 1 |
| 3 | — | 345 | F | C—CF3 | C—H | C—H | C—H | CF3 | C—H | C—SCF3 | H | H | H | H | 1 |
| 3 | — | 346 | F | C—CF3 | C—H | C—H | C—H | CF3 | C—H | C—SCF3 | H | H | EtCO | H | 1 |
| 3 | — | 347 | F | C—CF3 | C—H | C—H | C—H | CF3 | C—H | C—SCF3 | H | H | CF3CH2CO | H | 1 |
| 3 | — | 348 | F | C—CF3 | C—H | C—H | C—H | CF3 | C—H | C—Me | H | H | H | H | 1 |
| 3 | — | 349 | F | C—CF3 | C—H | C—H | C—H | CF3 | C—H | C—Me | H | H | EtCO | H | 1 |
| 3 | — | 350 | F | C—CF3 | C—H | C—H | C—H | CF3 | C—H | C—Me | H | H | CF3CH2CO | H | 1 |
| 3 | — | 366 | H | C—CF3 | C—Cl | C—Cl | C—H | CF3 | C—H | C—CF3 | H | H | H | H | 1 |
| 3 | — | 367 | H | C—CF3 | C—Cl | C—Cl | C—H | CF3 | C—H | C—CF3 | H | H | EtCO | H | 1 |
| 3 | — | 368 | H | C—CF3 | C—Cl | C—Cl | C—H | CF3 | C—H | C—CF3 | H | H | CF3CH2CO | H | 1 |
| 3 | — | 369 | H | C—Cl | C—CF3 | C—Cl | C—H | CF3 | C—H | C—CF3 | H | H | H | H | 1 |
| 3 | — | 370 | H | C—Cl | C—CF3 | C—Cl | C—H | CF3 | C—H | C—CF3 | H | H | EtCO | H | 1 |

TABLE 3-1-continued

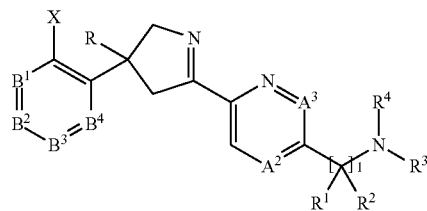

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 3 | — | 371 | H | C—Cl | C—CF3 | C—Cl | C—H | CF3 | C—H | C—CF3 | H | H | CF3CH2CO | H | 1 |
| 3 | — | 372 | H | C—Br | C—Cl | C—Br | C—H | CF3 | C—H | C—CF3 | H | H | H | H | 1 |
| 3 | — | 373 | H | C—Br | C—Cl | C—Br | C—H | CF3 | C—H | C—CF3 | H | H | EtCO | H | 1 |
| 3 | — | 374 | H | C—Br | C—Cl | C—Br | C—H | CF3 | C—H | C—CF3 | H | H | CF3CH2CO | H | 1 |
| 3 | — | 375 | H | C—Cl | C—Cl | C—Br | C—H | CF3 | C—H | C—CF3 | H | H | H | H | 1 |
| 3 | — | 376 | H | C—Cl | C—Cl | C—Br | C—H | CF3 | C—H | C—CF3 | H | H | EtCO | H | 1 |
| 3 | — | 377 | H | C—Cl | C—Cl | C—Br | C—H | CF3 | C—H | C—CF3 | H | H | CF3CH2CO | H | 1 |
| 3 | — | 378 | H | C—Cl | C—CF3 | C—H | C—H | CF3 | C—H | C—CF3 | H | H | H | H | 1 |
| 3 | — | 379 | H | C—Cl | C—CF3 | C—H | C—H | CF3 | C—H | C—CF3 | H | H | EtCO | H | 1 |
| 3 | — | 380 | H | C—Cl | C—CF3 | C—H | C—H | CF3 | C—H | C—CF3 | H | H | CF3CH2CO | H | 1 |
| 3 | — | 381 | F | C—Cl | C—F | C—Cl | C—H | CF3 | C—H | C—CF3 | H | H | H | H | 1 |
| 3 | — | 382 | F | C—Cl | C—F | C—Cl | C—H | CF3 | C—H | C—CF3 | H | H | EtCO | H | 1 |
| 3 | — | 383 | F | C—Cl | C—F | C—Cl | C—H | CF3 | C—H | C—CF3 | H | H | CF3CH2CO | H | 1 |
| 3 | — | 384 | H | C—Cl | —OCH2O— | | C—H | CF3 | C—H | C—CF3 | H | H | H | H | 1 |
| 3 | — | 385 | H | C—Cl | —OCH2O— | | C—H | CF3 | C—H | C—CF3 | H | H | EtCO | H | 1 |
| 3 | — | 386 | H | C—Cl | —OCH2O— | | C—H | CF3 | C—H | C—CF3 | H | H | CF3CH2CO | H | 1 |
| 3 | — | 387 | H | C—Cl | —OCF2O— | | C—H | CF3 | C—H | C—CF3 | H | H | H | H | 1 |
| 3 | — | 388 | H | C—Cl | —OCF2O— | | C—H | CF3 | C—H | C—CF3 | H | H | EtCO | H | 1 |
| 3 | — | 389 | H | C—Cl | —OCF2O— | | C—H | CF3 | C—H | C—CF3 | H | H | CF3CH2CO | H | 1 |
| 3 | — | 390 | H | C—Cl | C—Cl | C—Cl | C—H | CF3 | C—H | C—Br | H | H | H | H | 1 |
| 3 | — | 391 | H | C—Cl | C—Cl | C—Cl | C—H | CF3 | C—H | C—Br | H | H | MeCO | H | 1 |
| 3 | — | 392 | H | C—Cl | C—Cl | C—Cl | C—H | CF3 | C—H | C—Br | H | H | EtCO | H | 1 |
| 3 | — | 393 | H | C—Cl | C—Cl | C—Cl | C—H | CF3 | C—H | C—Br | H | H | n-PrCO | H | 1 |
| 3 | — | 394 | H | C—Cl | C—Cl | C—Cl | C—H | CF3 | C—H | C—Br | H | H | cyclo-PrCO | H | 1 |
| 3 | — | 395 | H | C—Cl | C—Cl | C—Cl | C—H | CF3 | C—H | C—Br | H | H | cyclo-PrCH2CO | H | 1 |
| 3 | — | 396 | H | C—Cl | C—Cl | C—Cl | C—H | CF3 | C—H | C—Br | H | H | CF3CH2CO | H | 1 |
| 3 | — | 397 | H | C—Cl | C—Cl | C—Cl | C—H | CF3 | C—H | C—Br | H | H | CH3SCH2CO | H | 1 |
| 3 | — | 398 | H | C—Cl | C—Cl | C—Cl | C—H | CF3 | C—H | C—Br | H | H | CH3SO2CH2CO | H | 1 |
| 3 | — | 399 | H | C—Cl | C—Cl | C—Cl | C—H | CF3 | C—H | C—Br | H | H | CH3OCH2CH2CO | H | 1 |
| 3 | — | 400 | H | C—Cl | C—Cl | C—Cl | C—H | CF3 | C—H | C—Br | H | H | CH3OCH(Me)CH2CO | H | 1 |
| 3 | — | 401 | H | C—Cl | C—Cl | C—Cl | C—H | CF3 | C—H | C—Br | H | H | EtNHCO | H | 1 |
| 3 | — | 402 | H | C—Cl | C—H | C—Cl | C—H | CF3 | C—H | C—Br | H | H | H | H | 1 |
| 3 | — | 403 | H | C—CF3 | C—H | C—CF3 | C—H | CF3 | C—H | C—Br | H | H | MeCO | H | 1 |
| 3 | — | 404 | H | C—CF3 | C—H | C—CF3 | C—H | CF3 | C—H | C—Br | H | H | EtCO | H | 1 |
| 3 | — | 405 | H | C—CF3 | C—H | C—CF3 | C—H | CF3 | C—H | C—Br | H | H | CF3CH2CO | H | 1 |
| 3 | — | 406 | H | C—CF3 | C—H | C—CF3 | C—H | CF3 | C—H | C—Br | H | H | cyclo-PrCO | H | 1 |
| 3 | — | 407 | H | C—CF3 | C—H | C—CF3 | C—H | CF3 | C—H | C—Br | H | H | EtNHCO | H | 1 |
| 3 | — | 408 | H | C—CF3 | C—H | C—CF3 | C—H | CF3 | C—H | C—Br | H | H | CH3SCH2CO | H | 1 |
| 3 | — | 409 | H | C—CF3 | C—H | C—CF3 | C—H | CF3 | C—H | C—Br | H | H | CH3SOCH2CO | H | 1 |
| 3 | — | 410 | H | C—CF3 | C—H | C—CF3 | C—H | CF3 | C—H | C—Br | H | H | CH3SO2CH2CO | H | 1 |
| 3 | — | 411 | H | C—CF3 | C—H | C—CF3 | C—H | CF3 | C—H | C—Br | CN | H | tert-BuOC(=O) | H | 1 |
| 3 | — | 412 | H | C—CF3 | C—H | C—CF3 | C—H | CF3 | C—H | C—Br | H | H | H | H | 1 |
| 3 | — | 413 | H | C—CF3 | C—H | C—CF3 | C—H | CF3 | C—H | C—Br | H | H | cyclo-PrCH2CO | H | 1 |
| 3 | — | 414 | H | C—CF3 | C—H | C—Cl | C—H | CF3 | C—H | C—Br | H | H | H | H | 1 |
| 3 | — | 415 | H | C—CF3 | C—H | C—Cl | C—H | CF3 | C—H | C—Br | H | H | EtCO | H | 1 |
| 3 | — | 416 | H | C—CF3 | C—H | C—Cl | C—H | CF3 | C—H | C—Br | H | H | CF3CH2CO | H | 1 |
| 3 | — | 417 | H | C—CF3 | C—F | C—H | C—H | CF3 | C—H | C—Br | H | H | H | H | 1 |
| 3 | — | 418 | H | C—CF3 | C—F | C—H | C—H | CF3 | C—H | C—Br | H | H | EtCO | H | 1 |
| 3 | — | 419 | H | C—CF3 | C—F | C—H | C—H | CF3 | C—H | C—Br | H | H | CF3CH2CO | H | 1 |
| 3 | — | 420 | H | C—CF3 | C—H | C—H | C—H | CF3 | C—H | C—Br | H | H | H | H | 1 |
| 3 | — | 421 | H | C—CF3 | C—H | C—H | C—H | CF3 | C—H | C—Br | H | H | EtCO | H | 1 |
| 3 | — | 422 | H | C—CF3 | C—H | C—H | C—H | CF3 | C—H | C—Br | H | H | CF3CH2CO | H | 1 |
| 3 | — | 423 | H | C—Cl | C—F | C—Cl | C—H | CF3 | C—H | C—Br | H | H | H | H | 1 |
| 3 | — | 424 | H | C—Cl | C—F | C—Cl | C—H | CF3 | C—H | C—Br | H | H | EtCO | H | 1 |
| 3 | — | 425 | H | C—Cl | C—F | C—Cl | C—H | CF3 | C—H | C—Br | H | H | CF3CH2CO | H | 1 |
| 3 | — | 435 | F | C—CF3 | C—H | C—H | C—H | CF3 | C—H | C—Br | H | H | H | H | 1 |
| 3 | — | 436 | F | C—CF3 | C—H | C—H | C—H | CF3 | C—H | C—Br | H | H | EtCO | H | 1 |
| 3 | — | 437 | F | C—CF3 | C—H | C—H | C—H | CF3 | C—H | C—Br | H | H | CF3CH2CO | H | 1 |

TABLE 3-2

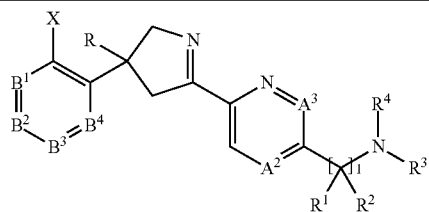

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 3 | — | 235 | H | C—Cl | N | C—Cl | C—H | CF3 | C—H | C—CF3 | H | H | H | H | 1 |
| 3 | — | 236 | H | C—Cl | N | C—Cl | C—H | CF3 | C—H | C—CF3 | H | H | MeCO | H | 1 |
| 3 | — | 237 | H | C—Cl | N | C—Cl | C—H | CF3 | C—H | C—CF3 | H | H | EtCO | H | 1 |
| 3 | — | 238 | H | C—Cl | N | C—Cl | C—H | CF3 | C—H | C—CF3 | H | H | CF3CH2CO | H | 1 |
| 3 | — | 239 | H | C—Cl | N | C—Cl | C—H | CF3 | C—H | C—CF3 | H | H | cyclo-PrCO | H | 1 |
| 3 | — | 240 | H | C—Cl | N | C—Cl | C—H | CF3 | C—H | C—CF3 | H | H | EtNHCO | H | 1 |
| 3 | — | 241 | H | C—Cl | N | C—Cl | C—H | CF3 | C—H | C—CF3 | H | H | CH3SCH2CO | H | 1 |
| 3 | — | 242 | H | C—Cl | N | C—Cl | C—H | CF3 | C—H | C—CF3 | H | H | CH3SOCH2CO | H | 1 |
| 3 | — | 243 | H | C—Cl | N | C—Cl | C—H | CF3 | C—H | C—CF3 | H | H | CH3SO2CH2CO | H | 1 |
| 3 | — | 244 | H | C—Cl | N | C—Cl | C—H | CF3 | C—H | C—CF3 | H | H | tert-BuOC(=O) | H | 1 |
| 3 | — | 245 | H | C—Cl | N | C—Cl | C—H | CF3 | C—H | C—CF3 | Me | H | EtCO | H | 1 |
| 3 | — | 246 | H | C—Cl | N | C—Cl | C—H | CF3 | C—H | C—CF3 | Me | H | CF3CH2CO | H | 1 |
| 3 | — | 247 | H | C—Cl | N | C—Cl | C—H | CF3 | C—H | C—CF3 | —CH2CH2— | | EtCO | H | 1 |
| 3 | — | 248 | H | C—Cl | N | C—Cl | C—H | CF3 | C—H | C—CF3 | —CH2CH2— | | CF3CH2CO | H | 1 |
| 3 | — | 249 | H | C—Cl | N | C—Cl | C—H | CF3 | C—H | C—H | H | H | H | H | 1 |
| 3 | — | 250 | H | C—Cl | N | C—Cl | C—H | CF3 | C—H | C—H | H | H | EtCO | H | 1 |
| 3 | — | 251 | H | C—Cl | N | C—Cl | C—H | CF3 | C—H | C—H | H | H | CF3CH2CO | H | 1 |
| 3 | — | 252 | H | C—Cl | N | C—Cl | C—H | CF3 | C—H | C—Cl | H | H | H | H | 1 |
| 3 | — | 253 | H | C—Cl | N | C—Cl | C—H | CF3 | C—H | C—Cl | H | H | EtCO | H | 1 |
| 3 | — | 254 | H | C—Cl | N | C—Cl | C—H | CF3 | C—H | C—Cl | H | H | CF3CH2CO | H | 1 |
| 3 | — | 255 | H | C—Cl | N | C—Cl | C—H | CF3 | C—H | C—SMe | H | H | H | H | 1 |
| 3 | — | 256 | H | C—Cl | N | C—Cl | C—H | CF3 | C—H | C—Sme | H | H | EtCO | H | 1 |
| 3 | — | 257 | H | C—Cl | N | C—Cl | C—H | CF3 | C—H | C—Sme | H | H | CF3CH2CO | H | 1 |
| 3 | — | 258 | H | C—Cl | N | C—Cl | C—H | CF3 | C—H | C—SCF3 | H | H | H | H | 1 |
| 3 | — | 259 | H | C—Cl | N | C—Cl | C—H | CF3 | C—H | C—SCF3 | H | H | EtCO | H | 1 |
| 3 | — | 260 | H | C—Cl | N | C—Cl | C—H | CF3 | C—H | C—SCF3 | H | H | CF3CH2CO | H | 1 |
| 3 | — | 261 | H | C—Cl | N | C—Cl | C—H | CF3 | C—H | C—Me | H | H | H | H | 1 |
| 3 | — | 262 | H | C—Cl | N | C—Cl | C—H | CF3 | C—H | C—Me | H | H | EtCO | H | 1 |
| 3 | — | 263 | H | C—Cl | N | C—Cl | C—H | CF3 | C—H | C—Me | H | H | CF3CH2CO | H | 1 |
| 3 | — | 264 | H | C—CF3 | N | C—H | C—H | CF3 | C—H | C—CF3 | H | H | H | H | 1 |
| 3 | — | 265 | H | C—CF3 | N | C—H | C—H | CF3 | C—H | C—CF3 | H | H | MeCO | H | 1 |
| 3 | — | 266 | H | C—CF3 | N | C—H | C—H | CF3 | C—H | C—CF3 | H | H | EtCO | H | 1 |
| 3 | — | 267 | H | C—CF3 | N | C—H | C—H | CF3 | C—H | C—CF3 | H | H | CF3CH2CO | H | 1 |
| 3 | — | 268 | H | C—CF3 | N | C—H | C—H | CF3 | C—H | C—CF3 | H | H | cyclo-PrCO | H | 1 |
| 3 | — | 269 | H | C—CF3 | N | C—H | C—H | CF3 | C—H | C—CF3 | H | H | EtNHCO | H | 1 |
| 3 | — | 270 | H | C—CF3 | N | C—H | C—H | CF3 | C—H | C—CF3 | H | H | CH3SCH2CO | H | 1 |
| 3 | — | 271 | H | C—CF3 | N | C—H | C—H | CF3 | C—H | C—CF3 | H | H | CH3SOCH2CO | H | 1 |
| 3 | — | 272 | H | C—CF3 | N | C—H | C—H | CF3 | C—H | C—CF3 | H | H | CH3SO2CH2CO | H | 1 |
| 3 | — | 273 | H | C—CF3 | N | C—H | C—H | CF3 | C—H | C—CF3 | H | H | tert-BuOC(=O) | H | 1 |
| 3 | — | 274 | H | C—CF3 | N | C—H | C—H | CF3 | C—H | C—CF3 | Me | H | EtCO | H | 1 |
| 3 | — | 275 | H | C—CF3 | N | C—H | C—H | CF3 | C—H | C—CF3 | Me | H | CF3CH2CO | H | 1 |
| 3 | — | 276 | H | C—CF3 | N | C—H | C—H | CF3 | C—H | C—CF3 | —CH2CH2— | | EtCO | H | 1 |
| 3 | — | 277 | H | C—CF3 | N | C—H | C—H | CF3 | C—H | C—CF3 | —CH2CH2— | | CF3CH2CO | H | 1 |
| 3 | — | 278 | H | C—CF3 | N | C—H | C—H | CF3 | C—H | C—H | H | H | H | H | 1 |
| 3 | — | 279 | H | C—CF3 | N | C—H | C—H | CF3 | C—H | C—H | H | H | EtCO | H | 1 |
| 3 | — | 280 | H | C—CF3 | N | C—H | C—H | CF3 | C—H | C—H | H | H | CF3CH2CO | H | 1 |
| 3 | — | 281 | H | C—CF3 | N | C—H | C—H | CF3 | C—H | C—Cl | H | H | H | H | 1 |
| 3 | — | 282 | H | C—CF3 | N | C—H | C—H | CF3 | C—H | C—Cl | H | H | EtCO | H | 1 |
| 3 | — | 283 | H | C—CF3 | N | C—H | C—H | CF3 | C—H | C—Cl | H | H | CF3CH2CO | H | 1 |
| 3 | — | 284 | H | C—CF3 | N | C—H | C—H | CF3 | C—H | C—SMe | H | H | H | H | 1 |
| 3 | — | 285 | H | C—CF3 | N | C—H | C—H | CF3 | C—H | C—Sme | H | H | EtCO | H | 1 |
| 3 | — | 286 | H | C—CF3 | N | C—H | C—H | CF3 | C—H | C—Sme | H | H | CF3CH2CO | H | 1 |
| 3 | — | 287 | H | C—CF3 | N | C—H | C—H | CF3 | C—H | C—SCF3 | H | H | H | H | 1 |
| 3 | — | 288 | H | C—CF3 | N | C—H | C—H | CF3 | C—H | C—SCF3 | H | H | EtCO | H | 1 |
| 3 | — | 289 | H | C—CF3 | N | C—H | C—H | CF3 | C—H | C—SCF3 | H | H | CF3CH2CO | H | 1 |
| 3 | — | 290 | H | C—CF3 | N | C—H | C—H | CF3 | C—H | C—Me | H | H | H | H | 1 |
| 3 | — | 291 | H | C—CF3 | N | C—H | C—H | CF3 | C—H | C—Me | H | H | EtCO | H | 1 |
| 3 | — | 292 | H | C—CF3 | N | C—H | C—H | CF3 | C—H | C—Me | H | H | CF3CH2CO | H | 1 |
| 3 | — | 293 | H | C—CF3 | N | C—CF3 | C—H | CF3 | C—H | C—CF3 | H | H | H | H | 1 |
| 3 | — | 294 | H | C—CF3 | N | C—CF3 | C—H | CF3 | C—H | C—CF3 | H | H | MeCO | H | 1 |
| 3 | — | 295 | H | C—CF3 | N | C—CF3 | C—H | CF3 | C—H | C—CF3 | H | H | EtCO | H | 1 |
| 3 | — | 296 | H | C—CF3 | N | C—CF3 | C—H | CF3 | C—H | C—CF3 | H | H | CF3CH2CO | H | 1 |
| 3 | — | 297 | H | C—CF3 | N | C—CF3 | C—H | CF3 | C—H | C—CF3 | H | H | cyclo-PrCO | H | 1 |
| 3 | — | 298 | H | C—CF3 | N | C—CF3 | C—H | CF3 | C—H | C—CF3 | H | H | EtNHCO | H | 1 |
| 3 | — | 299 | H | C—CF3 | N | C—CF3 | C—H | CF3 | C—H | C—CF3 | H | H | CH3SCH2CO | H | 1 |
| 3 | — | 300 | H | C—CF3 | N | C—CF3 | C—H | CF3 | C—H | C—CF3 | H | H | CH3SOCH2CO | H | 1 |
| 3 | — | 301 | H | C—CF3 | N | C—CF3 | C—H | CF3 | C—H | C—CF3 | H | H | CH3SO2CH2CO | H | 1 |

TABLE 3-2-continued

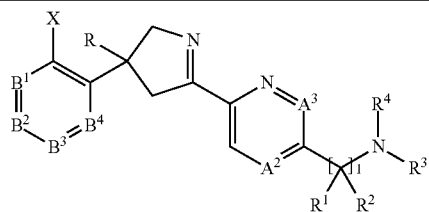

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 3 | — | 302 | H | C—CF3 | N | C—CF3 | C—H | CF3 | C—H | C—CF3 | H | H | tert-BuOC(=O) | H | 1 |
| 3 | — | 303 | H | C—CF3 | N | C—CF3 | C—H | CF3 | C—H | C—CF3 | Me | H | EtCO | H | 1 |
| 3 | — | 304 | H | C—CF3 | N | C—CF3 | C—H | CF3 | C—H | C—CF3 | Me | H | CF3CH2CO | H | 1 |
| 3 | — | 305 | H | C—CF3 | N | C—CF3 | C—H | CF3 | C—H | C—CF3 | —CH2CH2— | | EtCO | H | 1 |
| 3 | — | 306 | H | C—CF3 | N | C—CF3 | C—H | CF3 | C—H | C—CF3 | —CH2CH2— | | CF3CH2CO | H | 1 |
| 3 | — | 307 | H | C—CF3 | N | C—CF3 | C—H | CF3 | C—H | C—H | H | H | H | H | 1 |
| 3 | — | 308 | H | C—CF3 | N | C—CF3 | C—H | CF3 | C—H | C—H | H | H | EtCO | H | 1 |
| 3 | — | 309 | H | C—CF3 | N | C—CF3 | C—H | CF3 | C—H | C—H | H | H | CF3CH2CO | H | 1 |
| 3 | — | 310 | H | C—CF3 | N | C—CF3 | C—H | CF3 | C—H | C—Cl | H | H | H | H | 1 |
| 3 | — | 311 | H | C—CF3 | N | C—CF3 | C—H | CF3 | C—H | C—Cl | H | H | EtCO | H | 1 |
| 3 | — | 312 | H | C—CF3 | N | C—CF3 | C—H | CF3 | C—H | C—Cl | H | H | CF3CH2CO | H | 1 |
| 3 | — | 313 | H | C—CF3 | N | C—CF3 | C—H | CF3 | C—H | C—SMe | H | H | H | H | 1 |
| 3 | — | 314 | H | C—CF3 | N | C—CF3 | C—H | CF3 | C—H | C—SMe | H | H | EtCO | H | 1 |
| 3 | — | 315 | H | C—CF3 | N | C—CF3 | C—H | CF3 | C—H | C—SMe | H | H | CF3CH2CO | H | 1 |
| 3 | — | 316 | H | C—CF3 | N | C—CF3 | C—H | CF3 | C—H | C—SCF3 | H | H | H | H | 1 |
| 3 | — | 317 | H | C—CF3 | N | C—CF3 | C—H | CF3 | C—H | C—SCF3 | H | H | EtCO | H | 1 |
| 3 | — | 318 | H | C—CF3 | N | C—CF3 | C—H | CF3 | C—H | C—SCF3 | H | H | CF3CH2CO | H | 1 |
| 3 | — | 319 | H | C—CF3 | N | C—CF3 | C—H | CF3 | C—H | C—Me | H | H | H | H | 1 |
| 3 | — | 320 | H | C—CF3 | N | C—CF3 | C—H | CF3 | C—H | C—Me | H | H | EtCO | H | 1 |
| 3 | — | 321 | H | C—CF3 | N | C—CF3 | C—H | CF3 | C—H | C—Me | H | H | CF3CH2CO | H | 1 |
| 3 | — | 351 | H | C—CF3 | C—H | C—Cl | N | CF3 | C—H | C—CF3 | H | H | H | H | 1 |
| 3 | — | 352 | H | C—CF3 | C—H | C—Cl | N | CF3 | C—H | C—CF3 | H | H | EtCO | H | 1 |
| 3 | — | 353 | H | C—CF3 | C—H | C—Cl | N | CF3 | C—H | C—CF3 | H | H | CF3CH2CO | H | 1 |
| 3 | — | 354 | H | C—CF3 | C—H | C—Br | N | CF3 | C—H | C—CF3 | H | H | H | H | 1 |
| 3 | — | 355 | H | C—CF3 | C—H | C—Br | N | CF3 | C—H | C—CF3 | H | H | EtCO | H | 1 |
| 3 | — | 356 | H | C—CF3 | C—H | C—Br | N | CF3 | C—H | C—CF3 | H | H | CF3CH2CO | H | 1 |
| 3 | — | 357 | H | C—CF3 | C—H | C—H | N | CF3 | C—H | C—CF3 | H | H | H | H | 1 |
| 3 | — | 358 | H | C—CF3 | C—H | C—H | N | CF3 | C—H | C—CF3 | H | H | EtCO | H | 1 |
| 3 | — | 359 | H | C—CF3 | C—H | C—H | N | CF3 | C—H | C—CF3 | H | H | CF3CH2CO | H | 1 |
| 3 | — | 360 | H | C—H | C—H | C—CF3 | N | CF3 | C—H | C—CF3 | H | H | H | H | 1 |
| 3 | — | 361 | H | C—H | C—H | C—CF3 | N | CF3 | C—H | C—CF3 | H | H | EtCO | H | 1 |
| 3 | — | 362 | H | C—H | C—H | C—CF3 | N | CF3 | C—H | C—CF3 | H | H | CF3CH2CO | H | 1 |
| 3 | — | 363 | H | C—CF3 | C—H | C—CF3 | N | CF3 | C—H | C—CF3 | H | H | H | H | 1 |
| 3 | — | 364 | H | C—CF3 | C—H | C—CF3 | N | CF3 | C—H | C—CF3 | H | H | EtCO | H | 1 |
| 3 | — | 365 | H | C—CF3 | C—H | C—CF3 | N | CF3 | C—H | C—CF3 | H | H | CF3CH2CO | H | 1 |
| 3 | — | 426 | H | C—Cl | C—H | C—Cl | C—H | CF3 | C—H | C—Br | H | H | H | H | 1 |
| 3 | — | 427 | H | C—Cl | N | C—Cl | C—H | CF3 | C—H | C—Br | H | H | EtCO | H | 1 |
| 3 | — | 428 | H | C—Cl | N | C—Cl | C—H | CF3 | C—H | C—Br | H | H | CF3CH2CO | H | 1 |
| 3 | — | 429 | H | C—CF3 | N | C—H | C—H | CF3 | C—H | C—Br | H | H | H | H | 1 |
| 3 | — | 430 | H | C—CF3 | N | C—H | C—H | CF3 | C—H | C—Br | H | H | EtCO | H | 1 |
| 3 | — | 431 | H | C—CF3 | N | C—H | C—H | CF3 | C—H | C—Br | H | H | CF3CH2CO | H | 1 |
| 3 | — | 432 | H | C—CF3 | N | C—CF3 | C—H | CF3 | C—H | C—Br | H | H | H | H | 1 |
| 3 | — | 433 | H | C—CF3 | N | C—CF3 | C—H | CF3 | C—H | C—Br | H | H | EtCO | H | 1 |
| 3 | — | 434 | H | C—CF3 | N | C—CF3 | C—H | CF3 | C—H | C—Br | H | H | CF3CH2CO | H | 1 |

TABLE 4-1

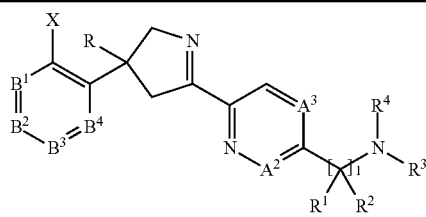

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 4 | — | 1 | H | C—Cl | C—H | C—Cl | C—H | CF3 | C—H | C—CF3 | H | H | tert-BuOC(=O) | H | 1 |
| 4 | — | 2 | H | C—Cl | C—Cl | C—Cl | C—H | CF3 | C—H | C—CF3 | H | H | tert-BuOC(=O) | H | 1 |
| 4 | — | 3 | H | C—CF3 | C—H | C—CF3 | C—H | CF3 | C—H | C—CF3 | CN | H | tert-BuOC(=O) | H | 1 |
| 4 | — | 4 | H | C—Cl | C—Cl | C—Cl | C—H | CF3 | C—H | C—CF3 | H | H | cyclo-PrCH2CO | H | 1 |
| 4 | — | 5 | H | C—Cl | C—Cl | C—Cl | C—H | CF3 | C—H | C—CF3 | H | H | n-PrCO | H | 1 |

TABLE 4-1-continued

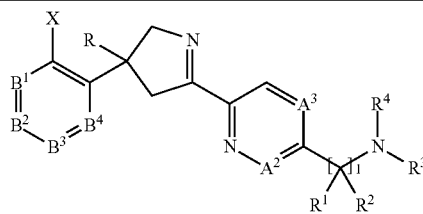

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 4 | — | 6 | H | C—Cl | C—Cl | C—Cl | C—H | CF3 | C—H | C—CF3 | H | H | CH3OCH2CH2CO | H | 1 |
| 4 | — | 7 | H | C—Cl | C—Cl | C—Cl | C—H | CF3 | C—H | C—CF3 | H | H | CH3OCH(Me)CH2CO | H | 1 |
| 4 | — | 8 | H | C—Cl | C—Cl | C—Cl | C—H | CF3 | C—H | C—CF3 | H | H | H | H | 1 |
| 4 | — | 9 | H | C—Cl | C—Cl | C—Cl | C—H | CF3 | C—H | C—CF3 | Me | H | EtCO | H | 1 |
| 4 | — | 10 | H | C—Cl | C—Cl | C—Cl | C—H | CF3 | C—H | C—CF3 | Me | H | CF3CH2CO | H | 1 |
| 4 | — | 11 | H | C—Cl | C—Cl | C—Cl | C—H | CF3 | C—H | C—CF3 | Me | Me | EtCO | H | 1 |
| 4 | — | 12 | H | C—Cl | C—Cl | C—Cl | C—H | CF3 | C—H | C—CF3 | Me | Me | CF3CH2CO | H | 1 |
| 4 | — | 13 | H | C—Cl | C—Cl | C—Cl | C—H | CF3 | C—H | C—CF3 | —CH2CH2— | | EtCO | H | 1 |
| 4 | — | 14 | H | C—Cl | C—Cl | C—Cl | C—H | CF3 | C—H | C—CF3 | —CH2CH2— | | CF3CH2CO | H | 1 |
| 4 | — | 15 | H | C—Cl | C—Cl | C—Cl | C—H | CF3 | C—H | C—Cl | H | H | H | H | 1 |
| 4 | — | 16 | H | C—Cl | C—Cl | C—Cl | C—H | CF3 | C—H | C—Cl | H | H | MeCO | H | 1 |
| 4 | — | 17 | H | C—Cl | C—Cl | C—Cl | C—H | CF3 | C—H | C—Cl | H | H | EtCO | H | 1 |
| 4 | — | 18 | H | C—Cl | C—Cl | C—Cl | C—H | CF3 | C—H | C—Cl | H | H | n-PrCO | H | 1 |
| 4 | — | 19 | H | C—Cl | C—Cl | C—Cl | C—H | CF3 | C—H | C—Cl | H | H | cyclo-PrCO | H | 1 |
| 4 | — | 20 | H | C—Cl | C—Cl | C—Cl | C—H | CF3 | C—H | C—Cl | H | H | cyclo-PrCH2CO | H | 1 |
| 4 | — | 21 | H | C—Cl | C—Cl | C—Cl | C—H | CF3 | C—H | C—Cl | H | H | CF3CH2CO | H | 1 |
| 4 | — | 22 | H | C—Cl | C—Cl | C—Cl | C—H | CF3 | C—H | C—Cl | H | H | CH3SCH2CO | H | 1 |
| 4 | — | 23 | H | C—Cl | C—Cl | C—Cl | C—H | CF3 | C—H | C—Cl | H | H | CH3SO2CH2CO | H | 1 |
| 4 | — | 24 | H | C—Cl | C—Cl | C—Cl | C—H | CF3 | C—H | C—Cl | H | H | CH3OCH2CH2CO | H | 1 |
| 4 | — | 25 | H | C—Cl | C—Cl | C—Cl | C—H | CF3 | C—H | C—Cl | H | H | CH3OCH(Me)CH2CO | H | 1 |
| 4 | — | 26 | H | C—Cl | C—Cl | C—Cl | C—H | CF3 | C—H | C—Cl | H | H | EtNHCO | H | 1 |
| 4 | — | 27 | H | C—Cl | C—Cl | C—Cl | C—H | CF3 | C—H | C—Me | H | H | MeCO | H | 1 |
| 4 | — | 28 | H | C—Cl | C—Cl | C—Cl | C—H | CF3 | C—H | C—Me | H | H | EtCO | H | 1 |
| 4 | — | 29 | H | C—Cl | C—Cl | C—Cl | C—H | CF3 | C—H | C—Me | H | H | n-PrCO | H | 1 |
| 4 | — | 30 | H | C—Cl | C—Cl | C—Cl | C—H | CF3 | C—H | C—Me | H | H | cyclo-PrCO | H | 1 |
| 4 | — | 31 | H | C—Cl | C—Cl | C—Cl | C—H | CF3 | C—H | C—Me | H | H | cyclo-PrCH2CO | H | 1 |
| 4 | — | 32 | H | C—Cl | C—Cl | C—Cl | C—H | CF3 | C—H | C—Me | H | H | CF3CH2CO | H | 1 |
| 4 | — | 33 | H | C—Cl | C—Cl | C—Cl | C—H | CF3 | C—H | C—Me | H | H | CH3SCH2CO | H | 1 |
| 4 | — | 34 | H | C—Cl | C—Cl | C—Cl | C—H | CF3 | C—H | C—Me | H | H | CH3SO2CH2CO | H | 1 |
| 4 | — | 35 | H | C—Cl | C—Cl | C—Cl | C—H | CF3 | C—H | C—Me | H | H | CH3OCH2CH2CO | H | 1 |
| 4 | — | 36 | H | C—Cl | C—Cl | C—Cl | C—H | CF3 | C—H | C—Me | H | H | CH3OCH(Me)CH2CO | H | 1 |
| 4 | — | 37 | H | C—Cl | C—Cl | C—Cl | C—H | CF3 | C—H | C—Me | H | H | EtNHCO | H | 1 |
| 4 | — | 38 | H | C—Cl | C—Cl | C—Cl | C—H | CF3 | C—H | C—SMe | H | H | H | H | 1 |
| 4 | — | 39 | H | C—Cl | C—Cl | C—Cl | C—H | CF3 | C—H | C—Sme | H | H | MeCO | H | 1 |
| 4 | — | 40 | H | C—Cl | C—Cl | C—Cl | C—H | CF3 | C—H | C—Sme | H | H | EtCO | H | 1 |
| 4 | — | 41 | H | C—Cl | C—Cl | C—Cl | C—H | CF3 | C—H | C—Sme | H | H | cyclo-PrCO | H | 1 |
| 4 | — | 42 | H | C—Cl | C—Cl | C—Cl | C—H | CF3 | C—H | C—Sme | H | H | cyclo-PrCH2CO | H | 1 |
| 4 | — | 43 | H | C—Cl | C—Cl | C—Cl | C—H | CF3 | C—H | C—Sme | H | H | CF3CH2CO | H | 1 |
| 4 | — | 44 | H | C—Cl | C—Cl | C—Cl | C—H | CF3 | C—H | C—Sme | H | H | CH3SCH2CO | H | 1 |
| 4 | — | 45 | H | C—Cl | C—Cl | C—Cl | C—H | CF3 | C—H | C—Sme | H | H | CH3SO2CH2CO | H | 1 |
| 4 | — | 46 | H | C—Cl | C—Cl | C—Cl | C—H | CF3 | C—H | C—Sme | H | H | CH3OCH2CH2CO | H | 1 |
| 4 | — | 47 | H | C—Cl | C—Cl | C—Cl | C—H | CF3 | C—H | C—Sme | H | H | CH3OCH(Me)CH2CO | H | 1 |
| 4 | — | 48 | H | C—Cl | C—Cl | C—Cl | C—H | CF3 | C—H | C—Sme | H | H | EtNHCO | H | 1 |
| 4 | — | 49 | H | C—Cl | C—Cl | C—Cl | C—H | CF3 | C—H | C—SO2Me | H | H | H | H | 1 |
| 4 | — | 50 | H | C—Cl | C—Cl | C—Cl | C—H | CF3 | C—H | C—SO2Me | H | H | MeCO | H | 1 |
| 4 | — | 51 | H | C—Cl | C—Cl | C—Cl | C—H | CF3 | C—H | C—SO2Me | H | H | EtCO | H | 1 |
| 4 | — | 52 | H | C—Cl | C—Cl | C—Cl | C—H | CF3 | C—H | C—SO2Me | H | H | cyclo-PrCO | H | 1 |
| 4 | — | 53 | H | C—Cl | C—Cl | C—Cl | C—H | CF3 | C—H | C—SO2Me | H | H | cyclo-PrCH2CO | H | 1 |
| 4 | — | 54 | H | C—Cl | C—Cl | C—Cl | C—H | CF3 | C—H | C—SO2Me | H | H | CF3CH2CO | H | 1 |
| 4 | — | 55 | H | C—Cl | C—Cl | C—Cl | C—H | CF3 | C—H | C—SO2Me | H | H | CH3SCH2CO | H | 1 |
| 4 | — | 56 | H | C—Cl | C—Cl | C—Cl | C—H | CF3 | C—H | C—SO2Me | H | H | CH3SO2CH2CO | H | 1 |
| 4 | — | 57 | H | C—Cl | C—Cl | C—Cl | C—H | CF3 | C—H | C—SO2Me | H | H | EtNHCO | H | 1 |
| 4 | — | 58 | H | C—Cl | C—Cl | C—Cl | C—H | CF3 | C—H | C—SCF3 | H | H | H | H | 1 |
| 4 | — | 59 | H | C—Cl | C—Cl | C—Cl | C—H | CF3 | C—H | C—SCF3 | H | H | MeCO | H | 1 |
| 4 | — | 60 | H | C—Cl | C—Cl | C—Cl | C—H | CF3 | C—H | C—SCF3 | H | H | EtCO | H | 1 |
| 4 | — | 61 | H | C—Cl | C—Cl | C—Cl | C—H | CF3 | C—H | C—SCF3 | H | H | cyclo-PrCO | H | 1 |
| 4 | — | 62 | H | C—Cl | C—Cl | C—Cl | C—H | CF3 | C—H | C—SCF3 | H | H | cyclo-PrCH2CO | H | 1 |
| 4 | — | 63 | H | C—Cl | C—Cl | C—Cl | C—H | CF3 | C—H | C—SCF3 | H | H | CF3CH2CO | H | 1 |
| 4 | — | 64 | H | C—Cl | C—Cl | C—Cl | C—H | CF3 | C—H | C—SCF3 | H | H | CH3SCH2CO | H | 1 |
| 4 | — | 65 | H | C—Cl | C—Cl | C—Cl | C—H | CF3 | C—H | C—SCF3 | H | H | CH3SO2CH2CO | H | 1 |
| 4 | — | 66 | H | C—Cl | C—Cl | C—Cl | C—H | CF3 | C—H | C—SCF3 | H | H | EtNHCO | H | 1 |
| 4 | — | 67 | H | C—Cl | C—Cl | C—Cl | C—H | CF3 | C—H | C—SOCF3 | H | H | MeCO | H | 1 |
| 4 | — | 68 | H | C—Cl | C—Cl | C—Cl | C—H | CF3 | C—H | C—SOCF3 | H | H | EtCO | H | 1 |
| 4 | — | 69 | H | C—Cl | C—Cl | C—Cl | C—H | CF3 | C—H | C—SOCF3 | H | H | cyclo-PrCO | H | 1 |
| 4 | — | 70 | H | C—Cl | C—Cl | C—Cl | C—H | CF3 | C—H | C—SOCF3 | H | H | cyclo-PrCH2CO | H | 1 |
| 4 | — | 71 | H | C—Cl | C—Cl | C—Cl | C—H | CF3 | C—H | C—SOCF3 | H | H | CF3CH2CO | H | 1 |
| 4 | — | 72 | H | C—Cl | C—Cl | C—Cl | C—H | CF3 | C—H | C—SOCF3 | H | H | CH3SCH2CO | H | 1 |

TABLE 4-1-continued

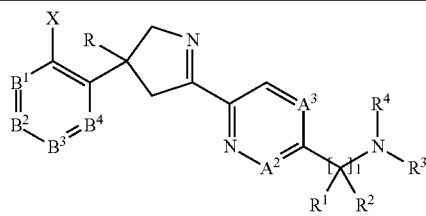

| Example | No. | X | B¹ | B² | B³ | B⁴ | R | A² | A³ | R¹ | R² | R⁴ | R³ | I |
|---|---|---|---|---|---|---|---|---|---|---|---|---|---|---|
| 4 | — | 73 | H | C—Cl | C—Cl | C—Cl | C—H | CF3 | C—H | C—SOCF3 | H | H | CH3SO2CH2CO | H | 1 |
| 4 | — | 74 | H | C—Cl | C—Cl | C—Cl | C—H | CF3 | C—H | C—SOCF3 | H | H | EtNHCO | H | 1 |
| 4 | — | 75 | H | C—Cl | C—Cl | C—Cl | C—H | CF3 | C—H | C—SO2CF3 | H | H | H | H | 1 |
| 4 | — | 76 | H | C—Cl | C—Cl | C—Cl | C—H | CF3 | C—H | C—SO2CF3 | H | H | MeCO | H | 1 |
| 4 | — | 77 | H | C—Cl | C—Cl | C—Cl | C—H | CF3 | C—H | C—SO2CF3 | H | H | EtCO | H | 1 |
| 4 | — | 78 | H | C—Cl | C—Cl | C—Cl | C—H | CF3 | C—H | C—SO2CF3 | H | H | cyclo-PrCO | H | 1 |
| 4 | — | 79 | H | C—Cl | C—Cl | C—Cl | C—H | CF3 | C—H | C—SO2CF3 | H | H | cyclo-PrCH2CO | H | 1 |
| 4 | — | 80 | H | C—Cl | C—Cl | C—Cl | C—H | CF3 | C—H | C—SO2CF3 | H | H | CF3CH2CO | H | 1 |
| 4 | — | 81 | H | C—Cl | C—Cl | C—Cl | C—H | CF3 | C—H | C—SO2CF3 | H | H | CH3SCH2CO | H | 1 |
| 4 | — | 82 | H | C—Cl | C—Cl | C—Cl | C—H | CF3 | C—H | C—SO2CF3 | H | H | CH3SO2CH2CO | H | 1 |
| 4 | — | 83 | H | C—Cl | C—Cl | C—Cl | C—H | CF3 | C—H | C—SO2CF3 | H | H | EtNHCO | H | 1 |
| 4 | — | 84 | H | C—Cl | C—H | C—Cl | C—H | CF3 | C—H | C—CF3 | H | H | H | H | 1 |
| 4 | — | 85 | H | C—Cl | C—H | C—Cl | C—H | CF3 | C—H | C—Cl | H | H | H | H | 1 |
| 4 | — | 86 | H | C—CF3 | C—H | C—CF3 | C—H | CF3 | C—H | C—CF3 | H | H | H | H | 1 |
| 4 | — | 87 | H | C—CF3 | C—H | C—CF3 | C—H | CF3 | C—H | C—CF3 | H | H | CH3OCH2CH2CO | H | 1 |
| 4 | — | 88 | H | C—CF3 | C—H | C—CF3 | C—H | CF3 | C—H | C—CF3 | H | H | CH3OCH(Me)CH2CO | H | 1 |
| 4 | — | 89 | H | C—CF3 | C—H | C—CF3 | C—H | CF3 | C—H | C—CF3 | H | H | cyclo-PrCH2CO | H | 1 |
| 4 | — | 90 | H | C—CF3 | C—H | C—CF3 | C—H | CF3 | C—H | C—Cl | H | H | MeCO | H | 1 |
| 4 | — | 91 | H | C—CF3 | C—H | C—CF3 | C—H | CF3 | C—H | C—Cl | H | H | EtCO | H | 1 |
| 4 | — | 92 | H | C—CF3 | C—H | C—CF3 | C—H | CF3 | C—H | C—Cl | H | H | CF3CH2CO | H | 1 |
| 4 | — | 93 | H | C—CF3 | C—H | C—CF3 | C—H | CF3 | C—H | C—Cl | H | H | cyclo-PrCO | H | 1 |
| 4 | — | 94 | H | C—CF3 | C—H | C—CF3 | C—H | CF3 | C—H | C—Cl | H | H | EtNHCO | H | 1 |
| 4 | — | 95 | H | C—CF3 | C—H | C—CF3 | C—H | CF3 | C—H | C—Cl | H | H | CH3SCH2CO | H | 1 |
| 4 | — | 96 | H | C—CF3 | C—H | C—CF3 | C—H | CF3 | C—H | C—Cl | H | H | CH3SOCH2CO | H | 1 |
| 4 | — | 97 | H | C—CF3 | C—H | C—CF3 | C—H | CF3 | C—H | C—Cl | H | H | CH3SO2CH2CO | H | 1 |
| 4 | — | 98 | H | C—CF3 | C—H | C—CF3 | C—H | CF3 | C—H | C—Cl | H | H | tert-BuOC(=O) | H | 1 |
| 4 | — | 99 | H | C—CF3 | C—H | C—CF3 | C—H | CF3 | C—H | C—Cl | H | H | H | H | 1 |
| 4 | — | 100 | H | C—CF3 | C—H | C—CF3 | C—H | CF3 | C—H | C—Cl | H | H | CH3OCH2CH2CO | H | 1 |
| 4 | — | 101 | H | C—CF3 | C—H | C—CF3 | C—H | CF3 | C—H | C—Cl | H | H | CH3OCH(Me)CH2CO | H | 1 |
| 4 | — | 102 | H | C—CF3 | C—H | C—CF3 | C—H | CF3 | C—H | C—Cl | H | H | cyclo-PrCH2CO | H | 1 |
| 4 | — | 103 | H | C—CF3 | C—H | C—CF3 | C—H | CF3 | C—H | C—Sme | H | H | H | H | 1 |
| 4 | — | 104 | H | C—CF3 | C—H | C—CF3 | C—H | CF3 | C—H | C—Sme | H | H | EtCO | H | 1 |
| 4 | — | 105 | H | C—CF3 | C—H | C—CF3 | C—H | CF3 | C—H | C—Sme | H | H | CF3CH2CO | H | 1 |
| 4 | — | 106 | H | C—CF3 | C—H | C—CF3 | C—H | CF3 | C—H | C—SCF3 | H | H | H | H | 1 |
| 4 | — | 107 | H | C—CF3 | C—H | C—CF3 | C—H | CF3 | C—H | C—SCF3 | H | H | EtCO | H | 1 |
| 4 | — | 108 | H | C—CF3 | C—H | C—CF3 | C—H | CF3 | C—H | C—SCF3 | H | H | CF3CH2CO | H | 1 |
| 4 | — | 109 | H | C—CF3 | C—H | C—CF3 | C—H | CF3 | C—H | C—Me | H | H | H | H | 1 |
| 4 | — | 110 | H | C—CF3 | C—H | C—CF3 | C—H | CF3 | C—H | C—Me | H | H | EtCO | H | 1 |
| 4 | — | 111 | H | C—CF3 | C—H | C—CF3 | C—H | CF3 | C—H | C—Me | H | H | CF3CH2CO | H | 1 |
| 4 | — | 112 | H | C—CF3 | C—H | C—Cl | C—H | CF3 | C—H | C—CF3 | H | H | H | H | 1 |
| 4 | — | 113 | H | C—CF3 | C—H | C—Cl | C—H | CF3 | C—H | C—CF3 | H | H | MeCO | H | 1 |
| 4 | — | 114 | H | C—CF3 | C—H | C—Cl | C—H | CF3 | C—H | C—CF3 | H | H | EtCO | H | 1 |
| 4 | — | 115 | H | C—CF3 | C—H | C—Cl | C—H | CF3 | C—H | C—CF3 | H | H | CF3CH2CO | H | 1 |
| 4 | — | 116 | H | C—CF3 | C—H | C—Cl | C—H | CF3 | C—H | C—CF3 | H | H | cyclo-PrCO | H | 1 |
| 4 | — | 117 | H | C—CF3 | C—H | C—Cl | C—H | CF3 | C—H | C—CF3 | H | H | EtNHCO | H | 1 |
| 4 | — | 118 | H | C—CF3 | C—H | C—Cl | C—H | CF3 | C—H | C—CF3 | H | H | CH3SCH2CO | H | 1 |
| 4 | — | 119 | H | C—CF3 | C—H | C—Cl | C—H | CF3 | C—H | C—CF3 | H | H | CH3SOCH2CO | H | 1 |
| 4 | — | 120 | H | C—CF3 | C—H | C—Cl | C—H | CF3 | C—H | C—CF3 | H | H | CH3SO2CH2CO | H | 1 |
| 4 | — | 121 | H | C—CF3 | C—H | C—Cl | C—H | CF3 | C—H | C—CF3 | H | H | tert-BuOC(=O) | H | 1 |
| 4 | — | 122 | H | C—CF3 | C—H | C—Cl | C—H | CF3 | C—H | C—CF3 | Me | H | EtCO | H | 1 |
| 4 | — | 123 | H | C—CF3 | C—H | C—Cl | C—H | CF3 | C—H | C—CF3 | Me | H | CF3CH2CO | H | 1 |
| 4 | — | 124 | H | C—CF3 | C—H | C—Cl | C—H | CF3 | C—H | C—CF3 | —CH2CH2— | | EtCO | H | 1 |
| 4 | — | 125 | H | C—CF3 | C—H | C—Cl | C—H | CF3 | C—H | C—CF3 | —CH2CH2— | | CF3CH2CO | H | 1 |
| 4 | — | 126 | H | C—CF3 | C—H | C—Cl | C—H | CF3 | C—H | C—Cl | H | H | H | H | 1 |
| 4 | — | 127 | H | C—CF3 | C—H | C—Cl | C—H | CF3 | C—H | C—Cl | H | H | EtCO | H | 1 |
| 4 | — | 128 | H | C—CF3 | C—H | C—Cl | C—H | CF3 | C—H | C—Cl | H | H | CF3CH2CO | H | 1 |
| 4 | — | 129 | H | C—CF3 | C—H | C—Cl | C—H | CF3 | C—H | C—SMe | H | H | H | H | 1 |
| 4 | — | 130 | H | C—CF3 | C—H | C—Cl | C—H | CF3 | C—H | C—Sme | H | H | EtCO | H | 1 |
| 4 | — | 131 | H | C—CF3 | C—H | C—Cl | C—H | CF3 | C—H | C—Sme | H | H | CF3CH2CO | H | 1 |
| 4 | — | 132 | H | C—CF3 | C—H | C—Cl | C—H | CF3 | C—H | C—SCF3 | H | H | H | H | 1 |
| 4 | — | 133 | H | C—CF3 | C—H | C—Cl | C—H | CF3 | C—H | C—SCF3 | H | H | EtCO | H | 1 |
| 4 | — | 134 | H | C—CF3 | C—H | C—Cl | C—H | CF3 | C—H | C—SCF3 | H | H | CF3CH2CO | H | 1 |
| 4 | — | 135 | H | C—CF3 | C—H | C—Cl | C—H | CF3 | C—H | C—Me | H | H | H | H | 1 |
| 4 | — | 136 | H | C—CF3 | C—H | C—Cl | C—H | CF3 | C—H | C—Me | H | H | EtCO | H | 1 |
| 4 | — | 137 | H | C—CF3 | C—H | C—Cl | C—H | CF3 | C—H | C—Me | H | H | CF3CH2CO | H | 1 |
| 4 | — | 138 | H | C—CF3 | C—F | C—H | C—H | CF3 | C—H | C—CF3 | H | H | H | H | 1 |
| 4 | — | 139 | H | C—CF3 | C—F | C—H | C—H | CF3 | C—H | C—CF3 | H | H | MeCO | H | 1 |

TABLE 4-1-continued

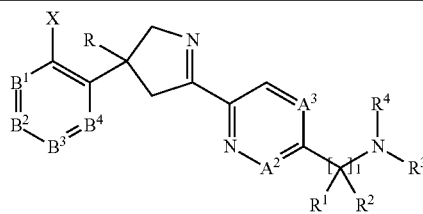

| Example | No. | X | B¹ | B² | B³ | B⁴ | R | A² | A³ | R¹ | R² | R⁴ | R³ | I |
|---|---|---|---|---|---|---|---|---|---|---|---|---|---|---|
| 4 | 140 | H | C—CF3 | C—F | C—H | C—H | CF3 | C—H | C—CF3 | H | H | EtCO | H | 1 |
| 4 | 141 | H | C—CF3 | C—F | C—H | C—H | CF3 | C—H | C—CF3 | H | H | CF3CH2CO | H | 1 |
| 4 | 142 | H | C—CF3 | C—F | C—H | C—H | CF3 | C—H | C—CF3 | H | H | cyclo-PrCO | H | 1 |
| 4 | 143 | H | C—CF3 | C—F | C—H | C—H | CF3 | C—H | C—CF3 | H | H | EtNHCO | H | 1 |
| 4 | 144 | H | C—CF3 | C—F | C—H | C—H | CF3 | C—H | C—CF3 | H | H | CH3SCH2CO | H | 1 |
| 4 | 145 | H | C—CF3 | C—F | C—H | C—H | CF3 | C—H | C—CF3 | H | H | CH3SOCH2CO | H | 1 |
| 4 | 146 | H | C—CF3 | C—F | C—H | C—H | CF3 | C—H | C—CF3 | H | H | CH3SO2CH2CO | H | 1 |
| 4 | 147 | H | C—CF3 | C—F | C—H | C—H | CF3 | C—H | C—CF3 | H | H | tert-BuOC(=O) | H | 1 |
| 4 | 148 | H | C—CF3 | C—F | C—H | C—H | CF3 | C—H | C—CF3 | Me | H | EtCO | H | 1 |
| 4 | 149 | H | C—CF3 | C—F | C—H | C—H | CF3 | C—H | C—CF3 | Me | H | CF3CH2CO | H | 1 |
| 4 | 150 | H | C—CF3 | C—F | C—H | C—H | CF3 | C—H | C—CF3 | —CH2CH2— | | EtCO | H | 1 |
| 4 | 151 | H | C—CF3 | C—F | C—H | C—H | CF3 | C—H | C—CF3 | —CH2CH2— | | CF3CH2CO | H | 1 |
| 4 | 152 | H | C—CF3 | C—F | C—H | C—H | CF3 | C—H | C—Cl | H | H | H | H | 1 |
| 4 | 153 | H | C—CF3 | C—F | C—H | C—H | CF3 | C—H | C—Cl | H | H | EtCO | H | 1 |
| 4 | 154 | H | C—CF3 | C—F | C—H | C—H | CF3 | C—H | C—Cl | H | H | CF3CH2CO | H | 1 |
| 4 | 155 | H | C—CF3 | C—F | C—H | C—H | CF3 | C—H | C—SMe | H | H | H | H | 1 |
| 4 | 156 | H | C—CF3 | C—F | C—H | C—H | CF3 | C—H | C—Sme | H | H | EtCO | H | 1 |
| 4 | 157 | H | C—CF3 | C—F | C—H | C—H | CF3 | C—H | C—Sme | H | H | CF3CH2CO | H | 1 |
| 4 | 158 | H | C—CF3 | C—F | C—H | C—H | CF3 | C—H | C—SCF3 | H | H | H | H | 1 |
| 4 | 159 | H | C—CF3 | C—F | C—H | C—H | CF3 | C—H | C—SCF3 | H | H | EtCO | H | 1 |
| 4 | 160 | H | C—CF3 | C—F | C—H | C—H | CF3 | C—H | C—SCF3 | H | H | CF3CH2CO | H | 1 |
| 4 | 161 | H | C—CF3 | C—F | C—H | C—H | CF3 | C—H | C—Me | H | H | H | H | 1 |
| 4 | 162 | H | C—CF3 | C—F | C—H | C—H | CF3 | C—H | C—Me | H | H | EtCO | H | 1 |
| 4 | 163 | H | C—CF3 | C—F | C—H | C—H | CF3 | C—H | C—Me | H | H | CF3CH2CO | H | 1 |
| 4 | 164 | H | C—CF3 | C—H | C—H | C—H | CF3 | C—H | C—CF3 | H | H | H | H | 1 |
| 4 | 165 | H | C—CF3 | C—H | C—H | C—H | CF3 | C—H | C—CF3 | H | H | MeCO | H | 1 |
| 4 | 166 | H | C—CF3 | C—H | C—H | C—H | CF3 | C—H | C—CF3 | H | H | EtCO | H | 1 |
| 4 | 167 | H | C—CF3 | C—H | C—H | C—H | CF3 | C—H | C—CF3 | H | H | CF3CH2CO | H | 1 |
| 4 | 168 | H | C—CF3 | C—H | C—H | C—H | CF3 | C—H | C—CF3 | H | H | cyclo-PrCO | H | 1 |
| 4 | 169 | H | C—CF3 | C—H | C—H | C—H | CF3 | C—CF3 | C—CF3 | H | H | EtNHCO | H | 1 |
| 4 | 170 | H | C—CF3 | C—H | C—H | C—H | CF3 | C—H | C—CF3 | H | H | CH3SCH2CO | H | 1 |
| 4 | 171 | H | C—CF3 | C—H | C—H | C—H | CF3 | C—H | C—CF3 | H | H | CH3SOCH2CO | H | 1 |
| 4 | 172 | H | C—CF3 | C—H | C—H | C—H | CF3 | C—H | C—CF3 | H | H | CH3SO2CH2CO | H | 1 |
| 4 | 173 | H | C—CF3 | C—H | C—H | C—H | CF3 | C—H | C—CF3 | H | H | tert-BuOC(=O) | H | 1 |
| 4 | 174 | H | C—CF3 | C—H | C—H | C—H | CF3 | C—H | C—CF3 | Me | H | EtCO | H | 1 |
| 4 | 175 | H | C—CF3 | C—H | C—H | C—H | CF3 | C—H | C—CF3 | Me | H | CF3CH2CO | H | 1 |
| 4 | 176 | H | C—CF3 | C—H | C—H | C—H | CF3 | C—H | C—CF3 | —CH2CH2— | | EtCO | H | 1 |
| 4 | 177 | H | C—CF3 | C—H | C—H | C—H | CF3 | C—H | C—CF3 | —CH2CH2— | | CF3CH2CO | H | 1 |
| 4 | 178 | H | C—CF3 | C—H | C—H | C—H | CF3 | C—H | C—Cl | H | H | H | H | 1 |
| 4 | 179 | H | C—CF3 | C—H | C—H | C—H | CF3 | C—H | C—Cl | H | H | EtCO | H | 1 |
| 4 | 180 | H | C—CF3 | C—H | C—H | C—H | CF3 | C—H | C—Cl | H | H | CF3CH2CO | H | 1 |
| 4 | 181 | H | C—CF3 | C—H | C—H | C—H | CF3 | C—H | C—SMe | H | H | H | H | 1 |
| 4 | 182 | H | C—CF3 | C—H | C—H | C—H | CF3 | C—H | C—Sme | H | H | EtCO | H | 1 |
| 4 | 183 | H | C—CF3 | C—H | C—H | C—H | CF3 | C—H | C—Sme | H | H | CF3CH2CO | H | 1 |
| 4 | 184 | H | C—CF3 | C—H | C—H | C—H | CF3 | C—H | C—SCF3 | H | H | H | H | 1 |
| 4 | 185 | H | C—CF3 | C—H | C—H | C—H | CF3 | C—H | C—SCF3 | H | H | EtCO | H | 1 |
| 4 | 186 | H | C—CF3 | C—H | C—H | C—H | CF3 | C—H | C—SCF3 | H | H | CF3CH2CO | H | 1 |
| 4 | 187 | H | C—CF3 | C—H | C—H | C—H | CF3 | C—H | C—Me | H | H | H | H | 1 |
| 4 | 188 | H | C—CF3 | C—H | C—H | C—H | CF3 | C—H | C—Me | H | H | EtCO | H | 1 |
| 4 | 189 | H | C—CF3 | C—H | C—H | C—H | CF3 | C—H | C—Me | H | H | CF3CH2CO | H | 1 |
| 4 | 190 | H | C—Cl | C—F | C—Cl | C—H | CF3 | C—H | C—CF3 | H | H | H | H | 1 |
| 4 | 191 | H | C—Cl | C—F | C—Cl | C—H | CF3 | C—H | C—CF3 | H | H | MeCO | H | 1 |
| 4 | 192 | H | C—Cl | C—F | C—Cl | C—H | CF3 | C—H | C—CF3 | H | H | EtCO | H | 1 |
| 4 | 193 | H | C—Cl | C—F | C—Cl | C—H | CF3 | C—H | C—CF3 | H | H | CF3CH2CO | H | 1 |
| 4 | 194 | H | C—Cl | C—F | C—Cl | C—H | CF3 | C—H | C—CF3 | H | H | cyclo-PrCO | H | 1 |
| 4 | 195 | H | C—Cl | C—F | C—Cl | C—H | CF3 | C—H | C—CF3 | H | H | EtNHCO | H | 1 |
| 4 | 196 | H | C—Cl | C—F | C—Cl | C—H | CF3 | C—H | C—CF3 | H | H | CH3SCH2 | H | 1 |
| 4 | 197 | H | C—Cl | C—F | C—Cl | C—H | CF3 | C—H | C—CF3 | H | H | CH3SOCH2CO | H | 1 |
| 4 | 198 | H | C—Cl | C—F | C—Cl | C—H | CF3 | C—H | C—CF3 | H | H | CH3SO2CH2CO | H | 1 |
| 4 | 199 | H | C—Cl | C—F | C—Cl | C—H | CF3 | C—H | C—CF3 | H | H | tert-BuOC(=O) | H | 1 |
| 4 | 200 | H | C—Cl | C—F | C—Cl | C—H | CF3 | C—H | C—CF3 | Me | H | EtCO | H | 1 |
| 4 | 201 | H | C—Cl | C—F | C—Cl | C—H | CF3 | C—H | C—CF3 | Me | H | CF3CH2CO | H | 1 |
| 4 | 202 | H | C—Cl | C—F | C—Cl | C—H | CF3 | C—H | C—CF3 | —CH2CH2— | | EtCO | H | 1 |
| 4 | 203 | H | C—Cl | C—F | C—Cl | C—H | CF3 | C—H | C—CF3 | —CH2CH2— | | CF3CH2CO | H | 1 |
| 4 | 204 | H | C—Cl | C—F | C—Cl | C—H | CF3 | C—H | C—Cl | H | H | H | H | 1 |
| 4 | 205 | H | C—Cl | C—F | C—Cl | C—H | CF3 | C—H | C—Cl | H | H | EtCO | H | 1 |
| 4 | 206 | H | C—Cl | C—F | C—Cl | C—H | CF3 | C—H | C—Cl | H | H | CF3CH2CO | H | 1 |

TABLE 4-1-continued

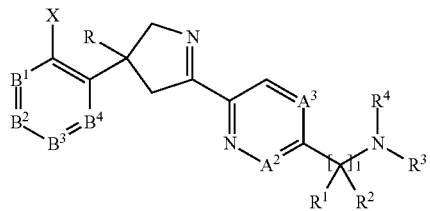

| Example | No. | X | B¹ | B² | B³ | B⁴ | R | A² | A³ | R¹ | R² | R⁴ | R³ | I |
|---|---|---|---|---|---|---|---|---|---|---|---|---|---|---|
| 4 | 207 | H | C—Cl | C—F | C—Cl | C—H | CF3 | C—H | C—SMe | H | H | H | H | 1 |
| 4 | 208 | H | C—Cl | C—F | C—Cl | C—H | CF3 | C—H | C—Sme | H | H | EtCO | H | 1 |
| 4 | 209 | H | C—Cl | C—F | C—Cl | C—H | CF3 | C—H | C—Sme | H | H | CF3CH2CO | H | 1 |
| 4 | 210 | H | C—Cl | C—F | C—Cl | C—H | CF3 | C—H | C—SCF3 | H | H | H | H | 1 |
| 4 | 211 | H | C—Cl | C—F | C—Cl | C—H | CF3 | C—H | C—SCF3 | H | H | EtCO | H | 1 |
| 4 | 212 | H | C—Cl | C—F | C—Cl | C—H | CF3 | C—H | C—SCF3 | H | H | CF3CH2CO | H | 1 |
| 4 | 213 | H | C—Cl | C—F | C—Cl | C—H | CF3 | C—H | C—Me | H | H | H | H | 1 |
| 4 | 214 | H | C—Cl | C—F | C—Cl | C—H | CF3 | C—H | C—Me | H | H | EtCO | H | 1 |
| 4 | 215 | H | C—Cl | C—F | C—Cl | C—H | CF3 | C—H | C—Me | H | H | CF3CH2CO | H | 1 |
| 4 | 294 | F | C—CF3 | C—H | C—H | C—H | CF3 | C—H | C—CF3 | H | H | H | H | 1 |
| 4 | 295 | F | C—CF3 | C—H | C—H | C—H | CF3 | C—H | C—CF3 | H | H | MeCO | H | 1 |
| 4 | 296 | F | C—CF3 | C—H | C—H | C—H | CF3 | C—H | C—CF3 | H | H | EtCO | H | 1 |
| 4 | 297 | F | C—CF3 | C—H | C—H | C—H | CF3 | C—H | C—CF3 | H | H | CF3CH2CO | H | 1 |
| 4 | 298 | F | C—CF3 | C—H | C—H | C—H | CF3 | C—H | C—CF3 | H | H | cyclo-PrCO | H | 1 |
| 4 | 299 | F | C—CF3 | C—H | C—H | C—H | CF3 | C—H | C—CF3 | H | H | EtNHCO | H | 1 |
| 4 | 300 | F | C—CF3 | C—H | C—H | C—H | CF3 | C—H | C—CF3 | H | H | CH3SCH2CO | H | 1 |
| 4 | 301 | F | C—CF3 | C—H | C—H | C—H | CF3 | C—H | C—CF3 | H | H | CH3SOCH2CO | H | 1 |
| 4 | 302 | F | C—CF3 | C—H | C—H | C—H | CF3 | C—H | C—CF3 | H | H | CH3SO2CH2CO | H | 1 |
| 4 | 303 | F | C—CF3 | C—H | C—H | C—H | CF3 | C—H | C—CF3 | H | H | tert-BuOC(=O) | H | 1 |
| 4 | 304 | F | C—CF3 | C—H | C—H | C—H | CF3 | C—H | C—CF3 | Me | H | EtCO | H | 1 |
| 4 | 305 | F | C—CF3 | C—H | C—H | C—H | CF3 | C—H | C—CF3 | Me | H | CF3CH2CO | H | 1 |
| 4 | 306 | F | C—CF3 | C—H | C—H | C—H | CF3 | C—H | C—CF3 | —CH2CH2— | | EtCO | H | 1 |
| 4 | 307 | F | C—CF3 | C—H | C—H | C—H | CF3 | C—H | C—CF3 | —CH2CH2— | | CF3CH2CO | H | 1 |
| 4 | 308 | F | C—CF3 | C—H | C—H | C—H | CF3 | C—H | C—Cl | H | H | H | H | 1 |
| 4 | 309 | F | C—CF3 | C—H | C—H | C—H | CF3 | C—H | C—Cl | H | H | EtCO | H | 1 |
| 4 | 310 | F | C—CF3 | C—H | C—H | C—H | CF3 | C—H | C—Cl | H | H | CF3CH2CO | H | 1 |
| 4 | 311 | F | C—CF3 | C—H | C—H | C—H | CF3 | C—H | C—SMe | H | H | H | H | 1 |
| 4 | 312 | F | C—CF3 | C—H | C—H | C—H | CF3 | C—H | C—Sme | H | H | EtCO | H | 1 |
| 4 | 313 | F | C—CF3 | C—H | C—H | C—H | CF3 | C—H | C—Sme | H | H | CF3CH2CO | H | 1 |
| 4 | 314 | F | C—CF3 | C—H | C—H | C—H | CF3 | C—H | C—SCF3 | H | H | H | H | 1 |
| 4 | 315 | F | C—CF3 | C—H | C—H | C—H | CF3 | C—H | C—SCF3 | H | H | EtCO | H | 1 |
| 4 | 316 | F | C—CF3 | C—H | C—H | C—H | CF3 | C—H | C—SCF3 | H | H | CF3CH2CO | H | 1 |
| 4 | 317 | F | C—CF3 | C—H | C—H | C—H | CF3 | C—H | C—Me | H | H | H | H | 1 |
| 4 | 318 | F | C—CF3 | C—H | C—H | C—H | CF3 | C—H | C—Me | H | H | EtCO | H | 1 |
| 4 | 319 | F | C—CF3 | C—H | C—H | C—H | CF3 | C—H | C—Me | H | H | CF3CH2CO | H | 1 |
| 4 | 335 | H | C—CF3 | C—Cl | C—Cl | C—H | CF3 | C—H | C—CF3 | H | H | H | H | 1 |
| 4 | 336 | H | C—CF3 | C—Cl | C—Cl | C—H | CF3 | C—H | C—CF3 | H | H | EtCO | H | 1 |
| 4 | 337 | H | C—CF3 | C—Cl | C—Cl | C—H | CF3 | C—H | C—CF3 | H | H | CF3CH2CO | H | 1 |
| 4 | 338 | H | C—Cl | C—CF3 | C—Cl | C—H | CF3 | C—H | C—CF3 | H | H | H | H | 1 |
| 4 | 339 | H | C—Cl | C—CF3 | C—Cl | C—H | CF3 | C—H | C—CF3 | H | H | EtCO | H | 1 |
| 4 | 340 | H | C—Cl | C—CF3 | C—Cl | C—H | CF3 | C—H | C—CF3 | H | H | CF3CH2CO | H | 1 |
| 4 | 341 | H | C—Br | C—Cl | C—Br | C—H | CF3 | C—H | C—CF3 | H | H | H | H | 1 |
| 4 | 342 | H | C—Br | C—Cl | C—Br | C—H | CF3 | C—H | C—CF3 | H | H | EtCO | H | 1 |
| 4 | 343 | H | C—Br | C—Cl | C—Br | C—H | CF3 | C—H | C—CF3 | H | H | CF3CH2CO | H | 1 |
| 4 | 344 | H | C—Cl | C—Cl | C—Br | C—H | CF3 | C—H | C—CF3 | H | H | H | H | 1 |
| 4 | 345 | H | C—Cl | C—Cl | C—Br | C—H | CF3 | C—H | C—CF3 | H | H | EtCO | H | 1 |
| 4 | 346 | H | C—Cl | C—Cl | C—Br | C—H | CF3 | C—H | C—CF3 | H | H | CF3CH2CO | H | 1 |
| 4 | 347 | H | C—Cl | C—CF3 | C—H | C—H | CF3 | C—H | C—CF3 | H | H | H | H | 1 |
| 4 | 348 | H | C—Cl | C—CF3 | C—H | C—H | CF3 | C—H | C—CF3 | H | H | EtCO | H | 1 |
| 4 | 349 | H | C—Cl | C—CF3 | C—H | C—H | CF3 | C—H | C—CF3 | H | H | CF3CH2CO | H | 1 |
| 4 | 350 | F | C—Cl | C—F | C—Cl | C—H | CF3 | C—H | C—CF3 | H | H | H | H | 1 |
| 4 | 351 | F | C—Cl | C—F | C—Cl | C—H | CF3 | C—H | C—CF3 | H | H | EtCO | H | 1 |
| 4 | 352 | F | C—Cl | C—F | C—Cl | C—H | CF3 | C—H | C—CF3 | H | H | CF3CH2CO | H | 1 |
| 4 | 353 | H | C—Cl | —OCH2O— | | C—H | CF3 | C—H | C—CF3 | H | H | H | H | 1 |
| 4 | 354 | H | C—Cl | —OCH2O— | | C—H | CF3 | C—H | C—CF3 | H | H | EtCO | H | 1 |
| 4 | 355 | H | C—Cl | —OCH2O— | | C—H | CF3 | C—H | C—CF3 | H | H | CF3CH2CO | H | 1 |
| 4 | 356 | H | C—Cl | —OCF2O— | | C—H | CF3 | C—H | C—CF3 | H | H | H | H | 1 |
| 4 | 357 | H | C—Cl | —OCF2O— | | C—H | CF3 | C—H | C—CF3 | H | H | EtCO | H | 1 |
| 4 | 358 | H | C—Cl | —OCF2O— | | C—H | CF3 | C—H | C—CF3 | H | H | CF3CH2CO | H | 1 |
| 4 | 359 | H | C—Cl | C—Cl | C—Cl | C—H | CF3 | C—H | C—Br | H | H | H | H | 1 |
| 4 | 360 | H | C—Cl | C—Cl | C—Cl | C—H | CF3 | C—H | C—Br | H | H | MeCO | H | 1 |
| 4 | 361 | H | C—Cl | C—Cl | C—Cl | C—H | CF3 | C—H | C—Br | H | H | EtCO | H | 1 |
| 4 | 362 | H | C—Cl | C—Cl | C—Cl | C—H | CF3 | C—H | C—Br | H | H | n-PrCO | H | 1 |
| 4 | 363 | H | C—Cl | C—Cl | C—Cl | C—H | CF3 | C—H | C—Br | H | H | cyclo-PrCO | H | 1 |
| 4 | 364 | H | C—Cl | C—Cl | C—Cl | C—H | CF3 | C—H | C—Br | H | H | cyclo-PrCH2CO | H | 1 |
| 4 | 365 | H | C—Cl | C—Cl | C—Cl | C—H | CF3 | C—H | C—Br | H | H | CF3CH2CO | H | 1 |
| 4 | 366 | H | C—Cl | C—Cl | C—Cl | C—H | CF3 | C—H | C—Br | H | H | CH3SCH2CO | H | 1 |

TABLE 4-1-continued

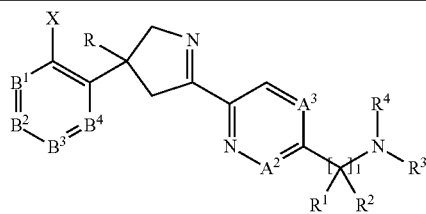

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 4 | — | 367 | H | C—Cl | C—Cl | C—Cl | C—H | CF3 | C—H | C—Br | H | H | CH3SO2CH2CO | H | 1 |
| 4 | — | 368 | H | C—Cl | C—Cl | C—Cl | C—H | CF3 | C—H | C—Br | H | H | CH3OCH2CH2CO | H | 1 |
| 4 | — | 369 | H | C—Cl | C—Cl | C—Cl | C—H | CF3 | C—H | C—Br | H | H | CH3OCH(Me)CH2CO | H | 1 |
| 4 | — | 370 | H | C—Cl | C—Cl | C—Cl | C—H | CF3 | C—H | C—Br | H | H | EtNHCO | H | 1 |
| 4 | — | 371 | H | C—Cl | C—H | C—Cl | C—H | CF3 | C—H | C—Br | H | H | H | H | 1 |
| 4 | — | 372 | H | C—CF3 | C—H | C—CF3 | C—H | CF3 | C—H | C—Br | H | H | MeCO | H | 1 |
| 4 | — | 373 | H | C—CF3 | C—H | C—CF3 | C—H | CF3 | C—H | C—Br | H | H | EtCO | H | 1 |
| 4 | — | 374 | H | C—CF3 | C—H | C—CF3 | C—H | CF3 | C—H | C—Br | H | H | CF3CH2CO | H | 1 |
| 4 | — | 375 | H | C—CF3 | C—H | C—CF3 | C—H | CF3 | C—H | C—Br | H | H | cyclo-PrCO | H | 1 |
| 4 | — | 376 | H | C—CF3 | C—H | C—CF3 | C—H | CF3 | C—H | C—Br | H | H | EtNHCO | H | 1 |
| 4 | — | 377 | H | C—CF3 | C—H | C—CF3 | C—H | CF3 | C—H | C—Br | H | H | CH3SCH2CO | H | 1 |
| 4 | — | 378 | H | C—CF3 | C—H | C—CF3 | C—H | CF3 | C—H | C—Br | H | H | CH3SOCH2CO | H | 1 |
| 4 | — | 379 | H | C—CF3 | C—H | C—CF3 | C—H | CF3 | C—H | C—Br | H | H | CH3SO2CH2CO | H | 1 |
| 4 | — | 380 | H | C—CF3 | C—H | C—CF3 | C—H | CF3 | C—H | C—Br | CN | H | tert-BuOC(=O) | H | 1 |
| 4 | — | 381 | H | C—CF3 | C—H | C—CF3 | C—H | CF3 | C—H | C—Br | H | H | H | H | 1 |
| 4 | — | 382 | H | C—CF3 | C—H | C—CF3 | C—H | CF3 | C—H | C—Br | H | H | cyclo-PrCH2CO | H | 1 |
| 4 | — | 383 | H | C—CF3 | C—H | C—Cl | C—H | CF3 | C—H | C—Br | H | H | H | H | 1 |
| 4 | — | 384 | H | C—CF3 | C—H | C—Cl | C—H | CF3 | C—H | C—Br | H | H | EtCO | H | 1 |
| 4 | — | 385 | H | C—CF3 | C—H | C—Cl | C—H | CF3 | C—H | C—Br | H | H | CF3CH2CO | H | 1 |
| 4 | — | 386 | H | C—CF3 | C—F | C—H | C—H | CF3 | C—H | C—Br | H | H | H | H | 1 |
| 4 | — | 387 | H | C—CF3 | C—F | C—H | C—H | CF3 | C—H | C—Br | H | H | EtCO | H | 1 |
| 4 | — | 388 | H | C—CF3 | C—F | C—H | C—H | CF3 | C—H | C—Br | H | H | CF3CH2CO | H | 1 |
| 4 | — | 389 | H | C—CF3 | C—H | C—H | C—H | CF3 | C—H | C—Br | H | H | H | H | 1 |
| 4 | — | 390 | H | C—CF3 | C—H | C—H | C—H | CF3 | C—H | C—Br | H | H | EtCO | H | 1 |
| 4 | — | 391 | H | C—CF3 | C—H | C—H | C—H | CF3 | C—H | C—Br | H | H | CF3CH2CO | H | 1 |
| 4 | — | 392 | H | C—Cl | C—F | C—Cl | C—H | CF3 | C—H | C—Br | H | H | H | H | 1 |
| 4 | — | 393 | H | C—Cl | C—F | C—Cl | C—H | CF3 | C—H | C—Br | H | H | EtCO | H | 1 |
| 4 | — | 394 | H | C—Cl | C—F | C—Cl | C—H | CF3 | C—H | C—Br | H | H | CF3CH2CO | H | 1 |
| 4 | — | 404 | F | C—CF3 | C—H | C—H | C—H | CF3 | C—H | C—Br | H | H | H | H | 1 |
| 4 | — | 405 | F | C—CF3 | C—H | C—H | C—H | CF3 | C—H | C—Br | H | H | EtCO | H | 1 |
| 4 | — | 406 | F | C—CF3 | C—H | C—H | C—H | CF3 | C—H | C—Br | H | H | CF3CH2CO | H | 1 |

TABLE 4-2

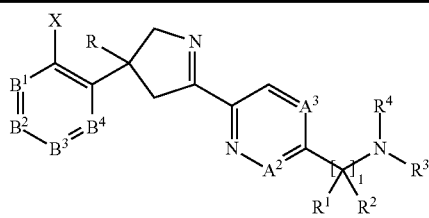

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 4 | — | 216 | H | C—Cl | N | C—Cl | C—H | CF3 | C—H | C—CF3 | H | H | H | H | 1 |
| 4 | — | 217 | H | C—Cl | N | C—Cl | C—H | CF3 | C—H | C—CF3 | H | H | MeCO | H | 1 |
| 4 | — | 218 | H | C—Cl | N | C—Cl | C—H | CF3 | C—H | C—CF3 | H | H | EtCO | H | 1 |
| 4 | — | 219 | H | C—Cl | N | C—Cl | C—H | CF3 | C—H | C—CF3 | H | H | CF3CH2CO | H | 1 |
| 4 | — | 220 | H | C—Cl | N | C—Cl | C—H | CF3 | C—H | C—CF3 | H | H | cyclo-PrCO | H | 1 |
| 4 | — | 221 | H | C—Cl | N | C—Cl | C—H | CF3 | C—H | C—CF3 | H | H | EtNHCO | H | 1 |
| 4 | — | 222 | H | C—Cl | N | C—Cl | C—H | CF3 | C—H | C—CF3 | H | H | CH3SCH2CO | H | 1 |
| 4 | — | 223 | H | C—Cl | N | C—Cl | C—H | CF3 | C—H | C—CF3 | H | H | CH3SOCH2CO | H | 1 |
| 4 | — | 224 | H | C—Cl | N | C—Cl | C—H | CF3 | C—H | C—CF3 | H | H | CH3SO2CH2CO | H | 1 |
| 4 | — | 225 | H | C—Cl | N | C—Cl | C—H | CF3 | C—H | C—CF3 | H | H | tert-BuOC(=O) | H | 1 |
| 4 | — | 226 | H | C—Cl | N | C—Cl | C—H | CF3 | C—H | C—CF3 | Me | H | EtCO | H | 1 |
| 4 | — | 227 | H | C—Cl | N | C—Cl | C—H | CF3 | C—H | C—CF3 | Me | H | CF3CH2CO | H | 1 |
| 4 | — | 228 | H | C—Cl | N | C—Cl | C—H | CF3 | C—H | C—CF3 | —CH2CH2— | | EtCO | H | 1 |
| 4 | — | 229 | H | C—Cl | N | C—Cl | C—H | CF3 | C—H | C—CF3 | —CH2CH2— | | CF3CH2CO | H | 1 |
| 4 | — | 230 | H | C—Cl | N | C—Cl | C—H | CF3 | C—H | C—Cl | H | H | H | H | 1 |
| 4 | — | 231 | H | C—Cl | N | C—Cl | C—H | CF3 | C—H | C—Cl | H | H | EtCO | H | 1 |
| 4 | — | 232 | H | C—Cl | N | C—Cl | C—H | CF3 | C—H | C—Cl | H | H | CF3CH2CO | H | 1 |
| 4 | — | 233 | H | C—Cl | N | C—Cl | C—H | CF3 | C—H | C—SMe | H | H | H | H | 1 |

TABLE 4-2-continued

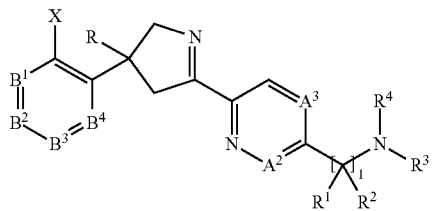

| Example No. | | | X | B¹ | B² | B³ | B⁴ | R | A² | A³ | R¹ | R² | R⁴ | R³ | I |
|---|---|---|---|---|---|---|---|---|---|---|---|---|---|---|---|
| 4 | — | 234 | H | C—Cl | N | C—Cl | C—H | CF3 | C—H | C—Sme | H | H | EtCO | H | 1 |
| 4 | — | 235 | H | C—Cl | N | C—Cl | C—H | CF3 | C—H | C—Sme | H | H | CF3CH2CO | H | 1 |
| 4 | — | 236 | H | C—Cl | N | C—Cl | C—H | CF3 | C—H | C—SCF3 | H | H | H | H | 1 |
| 4 | — | 237 | H | C—Cl | N | C—Cl | C—H | CF3 | C—H | C—SCF3 | H | H | EtCO | H | 1 |
| 4 | — | 238 | H | C—Cl | N | C—Cl | C—H | CF3 | C—H | C—SCF3 | H | H | CF3CH2CO | H | 1 |
| 4 | — | 239 | H | C—Cl | N | C—Cl | C—H | CF3 | C—H | C—Me | H | H | H | H | 1 |
| 4 | — | 240 | H | C—Cl | N | C—Cl | C—H | CF3 | C—H | C—Me | H | H | EtCO | H | 1 |
| 4 | — | 241 | H | C—Cl | N | C—Cl | C—H | CF3 | C—H | C—Me | H | H | CF3CH2CO | H | 1 |
| 4 | — | 242 | H | C—CF3 | N | C—H | C—H | CF3 | C—H | C—CF3 | H | H | H | H | 1 |
| 4 | — | 243 | H | C—CF3 | N | C—H | C—H | CF3 | C—H | C—CF3 | H | H | MeCO | H | 1 |
| 4 | — | 244 | H | C—CF3 | N | C—H | C—H | CF3 | C—H | C—CF3 | H | H | EtCO | H | 1 |
| 4 | — | 245 | H | C—CF3 | N | C—H | C—H | CF3 | C—H | C—CF3 | H | H | CF3CH2CO | H | 1 |
| 4 | — | 246 | H | C—CF3 | N | C—H | C—H | CF3 | C—H | C—CF3 | H | H | cyclo-PrCO | H | 1 |
| 4 | — | 247 | H | C—CF3 | N | C—H | C—H | CF3 | C—H | C—CF3 | H | H | EtNHCO | H | 1 |
| 4 | — | 248 | H | C—CF3 | N | C—H | C—H | CF3 | C—H | C—CF3 | H | H | CH3SCH2CO | H | 1 |
| 4 | — | 249 | H | C—CF3 | N | C—H | C—H | CF3 | C—H | C—CF3 | H | H | CH3SOCH2CO | H | 1 |
| 4 | — | 250 | H | C—CF3 | N | C—H | C—H | CF3 | C—H | C—CF3 | H | H | CH3SO2CH2CO | H | 1 |
| 4 | — | 251 | H | C—CF3 | N | C—H | C—H | CF3 | C—H | C—CF3 | H | H | tert-BuOC(=O) | H | 1 |
| 4 | — | 252 | H | C—CF3 | N | C—H | C—H | CF3 | C—H | C—CF3 | Me | H | EtCO | H | 1 |
| 4 | — | 253 | H | C—CF3 | N | C—H | C—H | CF3 | C—H | C—CF3 | Me | H | CF3CH2CO | H | 1 |
| 4 | — | 254 | H | C—CF3 | N | C—H | C—H | CF3 | C—H | C—CF3 | —CH2CH2— | | EtCO | H | 1 |
| 4 | — | 255 | H | C—CF3 | N | C—H | C—H | CF3 | C—H | C—CF3 | —CH2CH2— | | CF3CH2CO | H | 1 |
| 4 | — | 256 | H | C—CF3 | N | C—H | C—H | CF3 | C—H | C—Cl | H | H | H | H | 1 |
| 4 | — | 257 | H | C—CF3 | N | C—H | C—H | CF3 | C—H | C—Cl | H | H | EtCO | H | 1 |
| 4 | — | 258 | H | C—CF3 | N | C—H | C—H | CF3 | C—H | C—Cl | H | H | CF3CH2CO | H | 1 |
| 4 | — | 259 | H | C—CF3 | N | C—H | C—H | CF3 | C—H | C—SMe | H | H | H | H | 1 |
| 4 | — | 260 | H | C—CF3 | N | C—H | C—H | CF3 | C—H | C—Sme | H | H | EtCO | H | 1 |
| 4 | — | 261 | H | C—CF3 | N | C—H | C—H | CF3 | C—H | C—Sme | H | H | CF3CH2CO | H | 1 |
| 4 | — | 262 | H | C—CF3 | N | C—H | C—H | CF3 | C—H | C—SCF3 | H | H | H | H | 1 |
| 4 | — | 263 | H | C—CF3 | N | C—H | C—H | CF3 | C—H | C—SCF3 | H | H | EtCO | H | 1 |
| 4 | — | 264 | H | C—CF3 | N | C—H | C—H | CF3 | C—H | C—SCF3 | H | H | CF3CH2CO | H | 1 |
| 4 | — | 265 | H | C—CF3 | N | C—H | C—H | CF3 | C—H | C—Me | H | H | H | H | 1 |
| 4 | — | 266 | H | C—CF3 | N | C—H | C—H | CF3 | C—H | C—Me | H | H | EtCO | H | 1 |
| 4 | — | 267 | H | C—CF3 | N | C—H | C—H | CF3 | C—H | C—Me | H | H | CF3CH2CO | H | 1 |
| 4 | — | 268 | H | C—CF3 | N | C—CF3 | C—H | CF3 | C—H | C—CF3 | H | H | MeCO | H | 1 |
| 4 | — | 269 | H | C—CF3 | N | C—CF3 | C—H | CF3 | C—H | C—CF3 | H | H | MeCO | H | 1 |
| 4 | — | 270 | H | C—CF3 | N | C—CF3 | C—H | CF3 | C—H | C—CF3 | H | H | EtCO | H | 1 |
| 4 | — | 271 | H | C—CF3 | N | C—CF3 | C—H | CF3 | C—H | C—CF3 | H | H | CF3CH2CO | H | 1 |
| 4 | — | 272 | H | C—CF3 | N | C—CF3 | C—H | CF3 | C—H | C—CF3 | H | H | cyclo-PrCO | H | 1 |
| 4 | — | 273 | H | C—CF3 | N | C—CF3 | C—H | CF3 | C—H | C—CF3 | H | H | EtNHCO | H | 1 |
| 4 | — | 274 | H | C—CF3 | N | C—CF3 | C—H | CF3 | C—H | C—CF3 | H | H | CH3SCH2CO | H | 1 |
| 4 | — | 275 | H | C—CF3 | N | C—CF3 | C—H | CF3 | C—H | C—CF3 | H | H | CH3SOCH2CO | H | 1 |
| 4 | — | 276 | H | C—CF3 | N | C—CF3 | C—H | CF3 | C—H | C—CF3 | H | H | CH3SO2CH2O | H | 1 |
| 4 | — | 277 | H | C—CF3 | N | C—CF3 | C—H | CF3 | C—H | C—CF3 | H | H | tert-BuOC(=O) | H | 1 |
| 4 | — | 278 | H | C—CF3 | N | C—CF3 | C—H | CF3 | C—H | C—CF3 | Me | H | EtCO | H | 1 |
| 4 | — | 279 | H | C—CF3 | N | C—CF3 | C—H | CF3 | C—H | C—CF3 | Me | H | CF3CH2CO | H | 1 |
| 4 | — | 280 | H | C—CF3 | N | C—CF3 | C—H | CF3 | C—H | C—CF3 | —CH2CH2— | | EtCO | H | 1 |
| 4 | — | 281 | H | C—CF3 | N | C—CF3 | C—H | CF3 | C—H | C—CF3 | —CH2CH2— | | CF3CH2CO | H | 1 |
| 4 | — | 282 | H | C—CF3 | N | C—CF3 | C—H | CF3 | C—H | C—Cl | H | H | H | H | 1 |
| 4 | — | 283 | H | C—CF3 | N | C—CF3 | C—H | CF3 | C—H | C—Cl | H | H | EtCO | H | 1 |
| 4 | — | 284 | H | C—CF3 | N | C—CF3 | C—H | CF3 | C—H | C—Cl | H | H | CF3CH2CO | H | 1 |
| 4 | — | 285 | H | C—CF3 | N | C—CF3 | C—H | CF3 | C—H | C—SMe | H | H | H | H | 1 |
| 4 | — | 286 | H | C—CF3 | N | C—CF3 | C—H | CF3 | C—H | C—SMe | H | H | EtCO | H | 1 |
| 4 | — | 287 | H | C—CF3 | N | C—CF3 | C—H | CF3 | C—H | C—SMe | H | H | CF3CH2CO | H | 1 |
| 4 | — | 288 | H | C—CF3 | N | C—CF3 | C—H | CF3 | C—H | C—SCF3 | H | H | H | H | 1 |
| 4 | — | 289 | H | C—CF3 | N | C—CF3 | C—H | CF3 | C—H | C—SCF3 | H | H | EtCO | H | 1 |
| 4 | — | 290 | H | C—CF3 | N | C—CF3 | C—H | CF3 | C—H | C—SCF3 | H | H | CF3CH2CO | H | 1 |
| 4 | — | 291 | H | C—CF3 | N | C—CF3 | C—H | CF3 | C—H | C—Me | H | H | H | H | 1 |
| 4 | — | 292 | H | C—CF3 | N | C—CF3 | C—H | CF3 | C—H | C—Me | H | H | EtCO | H | 1 |
| 4 | — | 293 | H | C—CF3 | N | C—CF3 | C—H | CF3 | C—H | C—Me | H | H | CF3CH2CO | H | 1 |
| 4 | — | 320 | H | C—CF3 | C—H | C—Cl | N | CF3 | C—H | C—CF3 | H | H | H | H | 1 |
| 4 | — | 321 | H | C—CF3 | C—H | C—Cl | N | CF3 | C—H | C—CF3 | H | H | EtCO | H | 1 |
| 4 | — | 322 | H | C—CF3 | C—H | C—Cl | N | CF3 | C—H | C—CF3 | H | H | CF3CH2CO | H | 1 |
| 4 | — | 323 | H | C—CF3 | C—H | C—Br | N | CF3 | C—H | C—CF3 | H | H | H | H | 1 |
| 4 | — | 324 | H | C—CF3 | C—H | C—Br | N | CF3 | C—H | C—CF3 | H | H | EtCO | H | 1 |
| 4 | — | 325 | H | C—CF3 | C—H | C—Br | N | CF3 | C—H | C—CF3 | H | H | CF3CH2CO | H | 1 |
| 4 | — | 326 | H | C—CF3 | C—H | C—H | N | CF3 | C—H | C—CF3 | H | H | H | H | 1 |

TABLE 4-2-continued

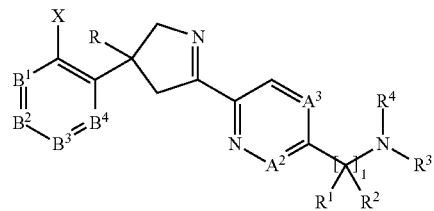

| Example No. | | X | B¹ | B² | B³ | B⁴ | R | A² | A³ | R¹ | R² | R⁴ | R³ | I |
|---|---|---|---|---|---|---|---|---|---|---|---|---|---|---|
| 4 | — | 327 | H | C—CF3 | C—H | C—H | N | CF3 | C—H | C—CF3 | H | H | EtCO | H | 1 |
| 4 | — | 328 | H | C—CF3 | C—H | C—H | N | CF3 | C—H | C—CF3 | H | H | CF3CH2CO | H | 1 |
| 4 | — | 329 | H | C—H | C—H | C—CF3 | N | CF3 | C—H | C—CF3 | H | H | H | H | 1 |
| 4 | — | 330 | H | C—H | C—H | C—CF3 | N | CF3 | C—H | C—CF3 | H | H | EtCO | H | 1 |
| 4 | — | 331 | H | C—H | C—H | C—CF3 | N | CF3 | C—H | C—CF3 | H | H | CF3CH2CO | H | 1 |
| 4 | — | 332 | H | C—CF3 | C—H | C—CF3 | N | CF3 | C—H | C—CF3 | H | H | H | H | 1 |
| 4 | — | 333 | H | C—CF3 | C—H | C—CF3 | N | CF3 | C—H | C—CF3 | H | H | EtCO | H | 1 |
| 4 | — | 334 | H | C—CF3 | C—H | C—CF3 | N | CF3 | C—H | C—CF3 | H | H | CF3CH2CO | H | 1 |
| 4 | — | 395 | H | C—Cl | N | C—Cl | C—H | CF3 | C—H | C—Br | H | H | H | H | 1 |
| 4 | — | 396 | H | C—Cl | N | C—Cl | C—H | CF3 | C—H | C—Br | H | H | EtCO | H | 1 |
| 4 | — | 397 | H | C—Cl | N | C—Cl | C—H | CF3 | C—H | C—Br | H | H | CF3CH2CO | H | 1 |
| 4 | — | 398 | H | C—CF3 | N | C—H | C—H | CF3 | C—H | C—Br | H | H | H | H | 1 |
| 4 | — | 399 | H | C—CF3 | N | C—H | C—H | CF3 | C—H | C—Br | H | H | EtCO | H | 1 |
| 4 | — | 400 | H | C—CF3 | N | C—H | C—H | CF3 | C—H | C—Br | H | H | CF3CH2CO | H | 1 |
| 4 | — | 401 | H | C—CF3 | N | C—CF3 | C—H | CF3 | C—H | C—Br | H | H | H | H | 1 |
| 4 | — | 402 | H | C—CF3 | N | C—CF3 | C—H | CF3 | C—H | C—Br | H | H | EtCO | H | 1 |
| 4 | — | 403 | H | C—CF3 | N | C—CF3 | C—H | CF3 | C—H | C—Br | H | H | CF3CH2CO | H | 1 |

TABLE 5-1

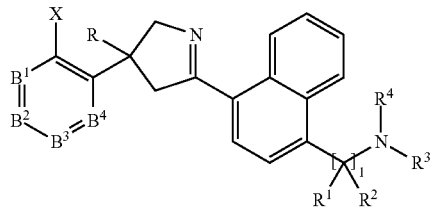

| Example No. | | X | B¹ | B² | B³ | B⁴ | R | R¹ | R² | R⁴ | R³ | I |
|---|---|---|---|---|---|---|---|---|---|---|---|---|
| 5 | — | 60 | H | C—Cl | C—Cl | C—Cl | C—H | CF₃ | H | H | n-PrCO | H | 1 |
| 5 | — | 61 | H | C—Cl | C—Cl | C—Cl | C—H | CF₃ | H | H | cyclo-PrCH2CO | H | 1 |
| 5 | — | 62 | H | C—Cl | C—Cl | C—Cl | C—H | CF₃ | H | H | EtNHCO | H | 1 |
| 5 | — | 63 | H | C—Cl | C—Cl | C—Cl | C—H | CF₃ | H | H | cyclo-PrCH2CO | H | 1 |
| 5 | — | 64 | H | C—Cl | C—Cl | C—Cl | C—H | CF₃ | H | H | CH3SCH2CO | H | 1 |
| 5 | — | 65 | H | C—Cl | C—Cl | C—Cl | C—H | CF₃ | H | H | CH3SOCH2CO | H | 1 |
| 5 | — | 66 | H | C—Cl | C—Cl | C—Cl | C—H | CF₃ | H | H | CH3SO2CH2CO | H | 1 |
| 5 | — | 67 | H | C—Cl | C—Cl | C—Cl | C—H | CF₃ | H | H | CH3OCH2CH2CO | H | 1 |
| 5 | — | 68 | H | C—Cl | C—Cl | C—Cl | C—H | CF₃ | H | H | CH3OCH(Me)CH2CO | H | 1 |
| 5 | — | 69 | H | C—Cl | C—Cl | C—Cl | C—H | CF₃ | H | H | tert-BuO(C=O) | H | 1 |
| 5 | — | 70 | H | C—Cl | C—Cl | C—Cl | C—H | CF₃ | H | H | EtCS | H | 1 |
| 5 | — | 71 | H | C—Cl | C—Cl | C—Cl | C—H | CF₃ | H | H | EtNHCS | H | 1 |
| 5 | — | 72 | H | C—Cl | C—Cl | C—Cl | C—H | CF₃ | Me | H | EtCO | H | 1 |
| 5 | — | 73 | H | C—Cl | C—Cl | C—Cl | C—H | CF₃ | —CH2CH2— | | EtCO | H | 1 |
| 5 | — | 74 | H | C—CF3 | C—H | C—CF3 | C—H | CF₃ | H | H | CH3SCH2CO | H | 1 |
| 5 | — | 75 | H | C—CF3 | C—H | C—CF3 | C—H | CF₃ | H | H | CH3SOCH2CO | H | 1 |
| 5 | — | 76 | H | C—CF3 | C—H | C—CF3 | C—H | CF₃ | H | H | CH3SO2CH2CO | H | 1 |
| 5 | — | 77 | H | C—CF3 | C—H | C—CF3 | C—H | CF₃ | H | H | CH3OCH2CH2CO | H | 1 |
| 5 | — | 78 | H | C—CF3 | C—H | C—CF3 | C—H | CF₃ | H | H | CH3OCH(Me)CH2CO | H | 1 |
| 5 | — | 79 | H | C—CF3 | C—F | C—H | C—H | CF₃ | H | H | H | H | 1 |
| 5 | — | 80 | H | C—CF3 | C—F | C—H | C—H | CF₃ | H | H | MeCO | H | 1 |
| 5 | — | 81 | H | C—CF3 | C—F | C—H | C—H | CF₃ | H | H | EtCO | H | 1 |
| 5 | — | 82 | H | C—CF3 | C—F | C—H | C—H | CF₃ | H | H | CF₃CH₂CO | H | 1 |
| 5 | — | 83 | H | C—CF3 | C—F | C—H | C—H | CF₃ | H | H | CH3SCH2CO | H | 1 |
| 5 | — | 84 | H | C—CF3 | C—F | C—H | C—H | CF₃ | H | H | CH3SO2CH2CO | H | 1 |
| 5 | — | 85 | H | C—CF3 | C—F | C—H | C—H | CF₃ | H | H | CH3OCH2CH2CO | H | 1 |
| 5 | — | 86 | H | C—CF3 | C—F | C—H | C—H | CF₃ | H | H | CH3OCH(Me)CH2CO | H | 1 |
| 5 | — | 87 | H | C—CF3 | C—H | C—F | C—H | CF₃ | H | H | H | H | 1 |
| 5 | — | 88 | H | C—CF3 | C—H | C—F | C—H | CF₃ | H | H | MeCO | H | 1 |
| 5 | — | 89 | H | C—CF3 | C—H | C—F | C—H | CF₃ | H | H | EtCO | H | 1 |
| 5 | — | 90 | H | C—CF3 | C—H | C—F | C—H | CF₃ | H | H | CF₃CH₂CO | H | 1 |
| 5 | — | 91 | H | C—CF3 | C—H | C—F | C—H | CF₃ | H | H | CH3SCH2CO | H | 1 |

TABLE 5-1-continued

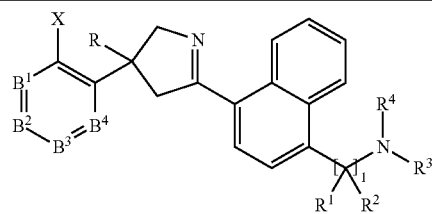

| Example No. | | | X | B¹ | B² | B³ | B⁴ | R | R¹ | R² | R⁴ | R³ | I |
|---|---|---|---|---|---|---|---|---|---|---|---|---|---|
| 5 | — | 92 | H | C—CF3 | C—H | C—F | C—H | CF₃ | H | H | CH3SO2CH2CO | H | 1 |
| 5 | — | 93 | H | C—CF3 | C—H | C—F | C—H | CF₃ | H | H | CH3OCH2CH2CO | H | 1 |
| 5 | — | 94 | H | C—CF3 | C—H | C—F | C—H | CF₃ | H | H | CH3OCH(Me)CH2CO | H | 1 |
| 5 | — | 95 | H | C—CF3 | C—H | C—Cl | C—H | CF₃ | H | H | H | H | 1 |
| 5 | — | 96 | H | C—CF3 | C—H | C—Cl | C—H | CF₃ | H | H | MeCO | H | 1 |
| 5 | — | 97 | H | C—CF3 | C—H | C—Cl | C—H | CF₃ | H | H | EtCO | H | 1 |
| 5 | — | 98 | H | C—CF3 | C—H | C—Cl | C—H | CF₃ | H | H | CF₃CH₂CO | H | 1 |
| 5 | — | 99 | H | C—CF3 | C—H | C—Cl | C—H | CF₃ | H | H | CH3SCH2CO | H | 1 |
| 5 | — | 100 | H | C—CF3 | C—H | C—Cl | C—H | CF₃ | H | H | CH3SO2CH2CO | H | 1 |
| 5 | — | 101 | H | C—CF3 | C—H | C—Cl | C—H | CF₃ | H | H | CH3OCH2CH2CO | H | 1 |
| 5 | — | 102 | H | C—CF3 | C—H | C—Cl | C—H | CF₃ | H | H | CH3OCH(Me)CH2CO | H | 1 |
| 5 | — | 103 | H | C—Cl | C—F | C—Cl | C—H | CF₃ | H | H | H | H | 1 |
| 5 | — | 104 | H | C—Cl | C—F | C—Cl | C—H | CF₃ | H | H | MeCO | H | 1 |
| 5 | — | 105 | H | C—Cl | C—F | C—Cl | C—H | CF₃ | H | H | EtCO | H | 1 |
| 5 | — | 106 | H | C—Cl | C—F | C—Cl | C—H | CF₃ | H | H | CF₃CH₂CO | H | 1 |
| 5 | — | 107 | H | C—Cl | C—F | C—Cl | C—H | CF₃ | H | H | CH3SCH2CO | H | 1 |
| 5 | — | 108 | H | C—Cl | C—F | C—Cl | C—H | CF₃ | H | H | CH3SO2CH2CO | H | 1 |
| 5 | — | 109 | H | C—Cl | C—F | C—Cl | C—H | CF₃ | H | H | CH3OCH2CH2CO | H | 1 |
| 5 | — | 110 | H | C—Cl | C—F | C—Cl | C—H | CF₃ | H | H | CH3OCH(Me)CH2CO | H | 1 |
| 5 | — | 111 | F | C—CF3 | C—H | C—H | C—H | CF₃ | H | H | H | H | 1 |
| 5 | — | 112 | F | C—CF3 | C—H | C—H | C—H | CF₃ | H | H | MeCO | H | 1 |
| 5 | — | 113 | F | C—CF3 | C—H | C—H | C—H | CF₃ | H | H | EtCO | H | 1 |
| 5 | — | 114 | F | C—CF3 | C—H | C—H | C—H | CF₃ | H | H | CF₃CH₂CO | H | 1 |
| 5 | — | 115 | F | C—CF3 | C—H | C—H | C—H | CF₃ | H | H | CH3SCH2CO | H | 1 |
| 5 | — | 116 | F | C—CF3 | C—H | C—H | C—H | CF₃ | H | H | CH3SO2CH2CO | H | 1 |
| 5 | — | 117 | F | C—CF3 | C—H | C—H | C—H | CF₃ | H | H | CH3OCH2CH2CO | H | 1 |
| 5 | — | 118 | F | C—CF3 | C—H | C—H | C—H | CF₃ | H | H | CH3OCH(Me)CH2CO | H | 1 |
| 5 | — | 119 | H | C—Cl | C—Br | C—Cl | C—H | CF₃ | H | H | H | H | 1 |
| 5 | — | 120 | H | C—Cl | C—Br | C—Cl | C—H | CF₃ | H | H | MeCO | H | 1 |
| 5 | — | 121 | H | C—Cl | C—Br | C—Cl | C—H | CF₃ | H | H | EtCO | H | 1 |
| 5 | — | 122 | H | C—Cl | C—Br | C—Cl | C—H | CF₃ | H | H | CF₃CH₂CO | H | 1 |
| 5 | — | 123 | H | C—Cl | C—Br | C—Cl | C—H | CF₃ | H | H | CH3SCH2CO | H | 1 |
| 5 | — | 124 | H | C—Cl | C—Br | C—Cl | C—H | CF₃ | H | H | CH3SO2CH2CO | H | 1 |
| 5 | — | 125 | H | C—Cl | C—Br | C—Cl | C—H | CF₃ | H | H | CH3OCH2CH2CO | H | 1 |
| 5 | — | 126 | H | C—Cl | C—Br | C—Cl | C—H | CF₃ | H | H | CH3OCH(Me)CH2CO | H | 1 |

TABLE 5-2

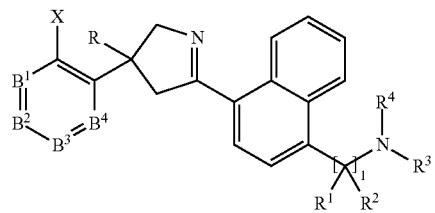

| Example No. | | | X | B¹ | B² | B³ | B⁴ | R | R¹ | R² | R⁴ | R³ | I |
|---|---|---|---|---|---|---|---|---|---|---|---|---|---|
| 5 | — | 1 | H | C—Cl | N | C—Cl | C—H | CF₃ | H | H | H | H | 1 |
| 5 | — | 2 | H | C—Cl | N | C—Cl | C—H | CF₃ | H | H | MeCO | H | 1 |
| 5 | — | 3 | H | C—Cl | N | C—Cl | C—H | CF₃ | H | H | EtCO | H | 1 |
| 5 | — | 4 | H | C—Cl | N | C—Cl | C—H | CF₃ | H | H | cyc-PrCO | H | 1 |
| 5 | — | 5 | H | C—Cl | N | C—Cl | C—H | CF₃ | H | H | CF₃CH₂CO | H | 1 |
| 5 | — | 6 | H | C—Cl | N | C—Cl | C—H | CF₃ | H | H | n-PrCO | H | 1 |
| 5 | — | 7 | H | C—Cl | N | C—Cl | C—H | CF₃ | H | H | cyclo-PrCH2CO | H | 1 |
| 5 | — | 8 | H | C—Cl | N | C—Cl | C—H | CF₃ | H | H | EtNHCO | H | 1 |
| 5 | — | 9 | H | C—Cl | N | C—Cl | C—H | CF₃ | H | H | cyclo-PrCH2CO | H | 1 |
| 5 | — | 10 | H | C—Cl | N | C—Cl | C—H | CF₃ | H | H | CH3SCH2CO | H | 1 |
| 5 | — | 11 | H | C—Cl | N | C—Cl | C—H | CF₃ | H | H | CH3SOCH2CO | H | 1 |
| 5 | — | 12 | H | C—Cl | N | C—Cl | C—H | CF₃ | H | H | CH3SO2CH2CO | H | 1 |
| 5 | — | 13 | H | C—Cl | N | C—Cl | C—H | CF₃ | H | H | CH3OCH2CH2CO | H | 1 |
| 5 | — | 14 | H | C—Cl | N | C—Cl | C—H | CF₃ | H | H | CH3OCH(Me)CH2CO | H | 1 |

TABLE 5-2-continued

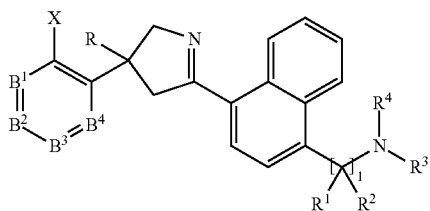

| Example No. | | X | B¹ | B² | B³ | B⁴ | R | R¹ | R² | R⁴ | R³ | I |
|---|---|---|---|---|---|---|---|---|---|---|---|---|
| 5 | — | 15 | H | C—Cl | N | C—Cl | C—H | CF₃ | H | H | tert-BuO(C=O) | H | 1 |
| 5 | — | 16 | H | C—Cl | N | C—Cl | C—H | CF₃ | H | H | EtCS | H | 1 |
| 5 | — | 17 | H | C—Cl | N | C—Cl | C—H | CF₃ | H | H | EtNHCS | | |
| 5 | — | 18 | H | C—Cl | N | C—Cl | C—H | CF₃ | Me | H | EtCO | H | 1 |
| 5 | — | 19 | H | C—Cl | N | C—Cl | C—H | CF₃ | —CH2CH2— | | EtCO | H | 1 |
| 5 | — | 20 | H | C—CF3 | N | C—H | C—H | CF₃ | H | H | H | H | 1 |
| 5 | — | 21 | H | C—CF3 | N | C—H | C—H | CF₃ | H | H | MeCO | H | 1 |
| 5 | — | 22 | H | C—CF3 | N | C—H | C—H | CF₃ | H | H | EtCO | H | 1 |
| 5 | — | 23 | H | C—CF3 | N | C—H | C—H | CF₃ | H | H | CF₃CH₂CO | H | 1 |
| 5 | — | 24 | H | C—CF3 | N | C—H | C—H | CF₃ | H | H | CH3SCH2CO | H | 1 |
| 5 | — | 25 | H | C—CF3 | N | C—H | C—H | CF₃ | H | H | CH3SO2CH2CO | H | 1 |
| 5 | — | 26 | H | C—CF3 | N | C—H | C—H | CF₃ | H | H | CH3OCH2CH2CO | H | 1 |
| 5 | — | 27 | H | C—CF3 | N | C—H | C—H | CF₃ | H | H | CH3OCH(Me)CH2CO | H | 1 |
| 5 | — | 28 | H | C—CF3 | N | C—CF3 | C—H | CF₃ | H | H | H | H | 1 |
| 5 | — | 29 | H | C—CF3 | N | C—CF3 | C—H | CF₃ | H | H | MeCO | H | 1 |
| 5 | — | 30 | H | C—CF3 | N | C—CF3 | C—H | CF₃ | H | H | EtCO | H | 1 |
| 5 | — | 31 | H | C—CF3 | N | C—CF3 | C—H | CF₃ | H | H | CF₃CH₂CO | H | 1 |
| 5 | — | 32 | H | C—CF3 | N | C—CF3 | C—H | CF₃ | H | H | CH3SCH2CO | H | 1 |
| 5 | — | 33 | H | C—CF3 | N | C—CF3 | C—H | CF₃ | H | H | CH3SO2CH2CO | H | 1 |
| 5 | — | 34 | H | C—CF3 | N | C—CF3 | C—H | CF₃ | H | H | CH3OCH2CH2CO | H | 1 |
| 5 | — | 35 | H | C—CF3 | N | C—CF3 | C—H | CF₃ | H | H | CH3OCH(Me)CH2CO | H | 1 |
| 5 | — | 36 | H | C—CF3 | C—H | C—H | N | CF₃ | H | H | H | H | 1 |
| 5 | — | 37 | H | C—CF3 | C—H | C—H | N | CF₃ | H | H | MeCO | H | 1 |
| 5 | — | 38 | H | C—CF3 | C—H | C—H | N | CF₃ | H | H | EtCO | H | 1 |
| 5 | — | 39 | H | C—CF3 | C—H | C—H | N | CF₃ | H | H | CF₃CH₂CO | H | 1 |
| 5 | — | 40 | H | C—CF3 | C—H | C—H | N | CF₃ | H | H | CH3SCH2CO | H | 1 |
| 5 | — | 41 | H | C—CF3 | C—H | C—H | N | CF₃ | H | H | CH3SO2CH2CO | H | 1 |
| 5 | — | 42 | H | C—CF3 | C—H | C—H | N | CF₃ | H | H | CH3OCH2CH2CO | H | 1 |
| 5 | — | 43 | H | C—CF3 | C—H | C—H | N | CF₃ | H | H | CH3OCH(Me)CH2CO | H | 1 |
| 5 | — | 44 | H | C—H | C—H | C—CF3 | N | CF₃ | H | H | H | H | 1 |
| 5 | — | 45 | H | C—H | C—H | C—CF3 | N | CF₃ | H | H | MeCO | H | 1 |
| 5 | — | 46 | H | C—H | C—H | C—CF3 | N | CF₃ | H | H | EtCO | H | 1 |
| 5 | — | 47 | H | C—H | C—H | C—CF3 | N | CF₃ | H | H | CF₃CH₂CO | H | 1 |
| 5 | — | 48 | H | C—H | C—H | C—CF3 | N | CF₃ | H | H | CH3SCH2CO | H | 1 |
| 5 | — | 49 | H | C—H | C—H | C—CF3 | N | CF₃ | H | H | CH3SO2CH2CO | H | 1 |
| 5 | — | 50 | H | C—H | C—H | C—CF3 | N | CF₃ | H | H | CH3OCH2CH2CO | H | 1 |
| 5 | — | 51 | H | C—H | C—H | C—CF3 | N | CF₃ | H | H | CH3OCH(Me)CH2CO | H | 1 |
| 5 | — | 52 | H | C—CF3 | C—H | C—CF3 | N | CF₃ | H | H | H | H | 1 |
| 5 | — | 53 | H | C—CF3 | C—H | C—CF3 | N | CF₃ | H | H | MeCO | H | 1 |
| 5 | — | 54 | H | C—CF3 | C—H | C—CF3 | N | CF₃ | H | H | EtCO | H | 1 |
| 5 | — | 55 | H | C—CF3 | C—H | C—CF3 | N | CF₃ | H | H | CF₃CH₂CO | H | 1 |
| 5 | — | 56 | H | C—CF3 | C—H | C—CF3 | N | CF₃ | H | H | CH3SCH2CO | H | 1 |
| 5 | — | 57 | H | C—CF3 | C—H | C—CF3 | N | CF₃ | H | H | CH3SO2CH2CO | H | 1 |
| 5 | — | 58 | H | C—CF3 | C—H | C—CF3 | N | CF₃ | H | H | CH3OCH2CH2CO | H | 1 |
| 5 | — | 59 | H | C—CF3 | C—H | C—CF3 | N | CF₃ | H | H | CH3OCH(Me)CH2CO | H | 1 |

TABLE 6

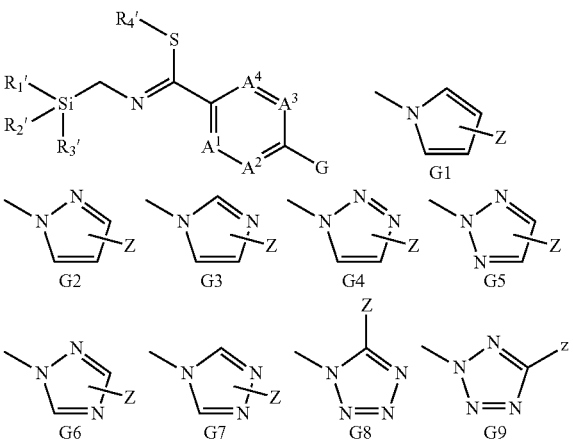

| Example No. | | | $R_1'$ | $R_2'$ | $R_3'$ | $R_4'$ | $A^1$ | $A^2$ | $A^3$ | $A^4$ | G | Z |
|---|---|---|---|---|---|---|---|---|---|---|---|---|
| 6 | — | 1 | Me | Me | Me | H | C—H | C—H | C—H | C—H | G6 | H |
| 6 | — | 2 | Me | Me | Me | H | C—H | C—H | C—F | C—H | G6 | H |
| 6 | — | 3 | Me | Me | Me | H | C—H | C—H | C—Cl | C—H | G6 | H |
| 6 | — | 4 | Me | Me | Me | H | C—H | C—H | C—I | C—H | G6 | H |
| 6 | — | 5 | Me | Me | Me | H | C—H | C—H | C—Me | C—H | G6 | H |
| 6 | — | 6 | Me | Me | Me | H | C—H | C—H | C—CF$_3$ | C—H | G6 | H |
| 6 | — | 7 | Me | Me | Me | H | N | C—H | C—CN | C—H | G6 | H |
| 6 | — | 8 | Me | Me | Me | H | C—H | N | C—CN | C—H | G6 | H |
| 6 | — | 9 | Me | Me | Me | H | C—H | C—H | C—CN | N | G6 | H |
| 6 | — | 10 | Me | Me | Me | H | N | C—H | C—CN | C—H | G2 | H |
| 6 | — | 11 | Me | Me | Me | H | C—H | N | C—CN | C—H | G2 | H |
| 6 | — | 12 | Me | Me | Me | H | C—H | C—H | C—CN | N | G2 | H |
| 6 | — | 13 | Me | Me | Me | H | N | C—H | C—CN | C—H | G2 | 4-CN |
| 6 | — | 14 | Me | Me | Me | H | C—H | N | C—CN | C—H | G2 | 4-CN |
| 6 | — | 15 | Me | Me | Me | H | C—H | C—H | C—CN | N | G2 | 4-CN |
| 6 | — | 16 | Me | Me | Me | H | N | C—H | C—CN | C—H | G2 | 4-NO2 |
| 6 | — | 17 | Me | Me | Me | H | C—H | N | C—CN | C—H | G2 | 4-NO2 |
| 6 | — | 18 | Me | Me | Me | H | C—H | C—H | C—CN | N | G2 | 4-NO2 |
| 6 | — | 19 | Me | Me | Me | H | N | C—H | C—CN | C—H | G8 | H |
| 6 | — | 20 | Me | Me | Me | H | C—H | N | C—CN | C—H | G8 | H |
| 6 | — | 21 | Me | Me | Me | H | C—H | C—H | C—CN | N | G8 | H |
| 6 | — | 22 | Me | Me | Me | H | N | C—H | C—CN | C—H | G9 | H |
| 6 | — | 23 | Me | Me | Me | H | C—H | N | C—CN | C—H | G9 | H |
| 6 | — | 24 | Me | Me | Me | H | C—H | C—H | C—CN | N | G9 | H |
| 6 | — | 25 | Me | Me | Me | Me | N | C—H | C—CN | C—H | G6 | H |
| 6 | — | 26 | Me | Me | Me | Me | C—H | N | C—CN | C—H | G6 | H |
| 6 | — | 27 | Me | Me | Me | Me | C—H | C—H | C—CN | N | G6 | H |
| 6 | — | 28 | Me | Me | Me | Me | N | C—H | C—CN | C—H | G2 | H |
| 6 | — | 29 | Me | Me | Me | Me | C—H | N | C—CN | C—H | G2 | H |
| 6 | — | 30 | Me | Me | Me | Me | C—H | C—H | C—CN | N | G2 | H |
| 6 | — | 31 | Me | Me | Me | Me | N | C—H | C—CN | C—H | G2 | 4-CN |
| 6 | — | 32 | Me | Me | Me | Me | C—H | N | C—CN | C—H | G2 | 4-CN |
| 6 | — | 33 | Me | Me | Me | Me | C—H | C—H | C—CN | N | G2 | 4-CN |
| 6 | — | 34 | Me | Me | Me | Me | N | C—H | C—CN | C—H | G2 | 4-NO2 |
| 6 | — | 35 | Me | Me | Me | Me | C—H | N | C—CN | C—H | G2 | 4-NO2 |
| 6 | — | 36 | Me | Me | Me | Me | C—H | C—H | C—CN | N | G2 | 4-NO2 |
| 6 | — | 37 | Me | Me | Me | Me | N | C—H | C—CN | C—H | G8 | H |
| 6 | — | 38 | Me | Me | Me | Me | C—H | N | C—CN | C—H | G8 | H |
| 6 | — | 39 | Me | Me | Me | Me | C—H | C—H | C—CN | N | G8 | H |
| 6 | — | 40 | Me | Me | Me | Me | N | C—H | C—CN | C—H | G9 | H |
| 6 | — | 41 | Me | Me | Me | Me | C—H | N | C—CN | C—H | G9 | H |
| 6 | — | 42 | Me | Me | Me | Me | C—H | C—H | C—CN | N | G9 | H |
| 6 | — | 43 | Me | Me | Me | H | C—H | C—H | C—CN | C—H | F | H |
| 6 | — | 44 | Me | Me | Me | H | C—H | C—H | C—Br | C—H | F | H |
| 6 | — | 45 | Me | Me | Me | H | N | C—H | C—CN | C—H | F | H |
| 6 | — | 46 | Me | Me | Me | H | N | C—H | C—Br | C—H | F | H |
| 6 | — | 47 | Me | Me | Me | H | C—H | N | C—CN | C—H | F | H |
| 6 | — | 48 | Me | Me | Me | H | C—H | N | C—Br | C—H | F | H |
| 6 | — | 49 | Me | Me | Me | H | C—H | C—H | C—CN | N | F | H |
| 6 | — | 50 | Me | Me | Me | H | C—H | C—H | C—Br | N | F | H |
| 6 | — | 51 | Me | Me | Me | Me | C—H | C—H | C—CN | C—H | F | H |
| 6 | — | 52 | Me | Me | Me | Me | C—H | C—H | C—Br | C—H | F | H |
| 6 | — | 53 | Me | Me | Me | Me | N | C—H | C—CN | C—H | F | H |
| 6 | — | 54 | Me | Me | Me | Me | N | C—H | C—Br | C—H | F | H |

TABLE 6-continued

Example No. | | | R₁' | R₂' | R₃' | R₄' | A¹ | A² | A³ | A⁴ | G | Z
---|---|---|---|---|---|---|---|---|---|---|---|---
6 | — | 55 | Me | Me | Me | Me | C—H | N | C—CN | C—H | F | H
6 | — | 56 | Me | Me | Me | Me | C—H | N | C—Br | C—H | F | H
6 | — | 57 | Me | Me | Me | Me | C—H | C—H | C—CN | N | F | H
6 | — | 58 | Me | Me | Me | Me | C—H | C—H | C—Br | N | F | H

TABLE 7

Example No. | | | R₁' | R₂' | R₃' | R₄' | A¹ | A² | A³ | A⁴ | R¹ | R² | R₅'
---|---|---|---|---|---|---|---|---|---|---|---|---|---
7 | — | 1 | Me | Me | Me | Me | CH | CH | C—H | N | H | H | Me
7 | — | 2 | Me | Me | Me | Me | CH | CH | C—Cl | N | H | H | Me
7 | — | 3 | Me | Me | Me | Me | CH | CH | C—Br | N | H | H | Me
7 | — | 4 | Me | Me | Me | Me | CH | CH | C—F | N | H | H | Me
7 | — | 5 | Me | Me | Me | Me | CH | CH | C—I | N | H | H | Me
7 | — | 6 | Me | Me | Me | Me | CH | CH | C—Me | N | H | H | Me
7 | — | 7 | Me | Me | Me | Me | CH | CH | C—CF3 | N | H | H | Me
7 | — | 8 | Me | Me | Me | Me | CH | CH | C—NO2 | N | H | H | Me
7 | — | 9 | Me | Me | Me | Me | CH | CH | C—SMe | N | H | H | Me
7 | — | 10 | Me | Me | Me | Me | CH | N | C—H | CH | H | H | Me
7 | — | 11 | Me | Me | Me | Me | CH | N | C—Cl | CH | H | H | Me
7 | — | 12 | Me | Me | Me | Me | CH | N | C—Br | CH | H | H | Me
7 | — | 13 | Me | Me | Me | Me | CH | N | C—F | CH | H | H | Me
7 | — | 14 | Me | Me | Me | Me | CH | N | C—I | CH | H | H | Me
7 | — | 15 | Me | Me | Me | Me | CH | N | C—Me | CH | H | H | Me
7 | — | 16 | Me | Me | Me | Me | CH | N | C—CF3 | CH | H | H | Me
7 | — | 17 | Me | Me | Me | Me | CH | N | C—NO2 | CH | H | H | Me
7 | — | 18 | Me | Me | Me | Me | CH | N | C—SMe | CH | H | H | Me
7 | — | 19 | Me | Me | Me | H | CH | CH | C—H | N | H | H | Me
7 | — | 20 | Me | Me | Me | H | CH | CH | C—Cl | N | H | H | Me
7 | — | 21 | Me | Me | Me | H | CH | CH | C—Br | N | H | H | Me
7 | — | 22 | Me | Me | Me | H | CH | CH | C—F | N | H | H | Me
7 | — | 23 | Me | Me | Me | H | CH | CH | C—I | N | H | H | Me
7 | — | 24 | Me | Me | Me | H | CH | CH | C—Me | N | H | H | Me
7 | — | 25 | Me | Me | Me | H | CH | CH | C—CF3 | N | H | H | Me
7 | — | 26 | Me | Me | Me | H | CH | CH | C—NO2 | N | H | H | Me
7 | — | 27 | Me | Me | Me | H | CH | CH | C—SMe | N | H | H | Me
7 | — | 28 | Me | Me | Me | H | CH | N | C—H | CH | H | H | Me
7 | — | 29 | Me | Me | Me | H | CH | N | C—Cl | CH | H | H | Me
7 | — | 30 | Me | Me | Me | H | CH | N | C—Br | CH | H | H | Me
7 | — | 31 | Me | Me | Me | H | CH | N | C—F | CH | H | H | Me
7 | — | 32 | Me | Me | Me | H | CH | N | C—I | CH | H | H | Me
7 | — | 33 | Me | Me | Me | H | CH | N | C—Me | CH | H | H | Me
7 | — | 34 | Me | Me | Me | H | CH | N | C—CF3 | CH | H | H | Me TABLE 7-continued

| Example No. | | | $R_1'$ | $R_2'$ | $R_3'$ | $R_4'$ | $A^1$ | $A^2$ | $A^3$ | $A^4$ | $R^1$ | $R^2$ | $R_5'$ |
|---|---|---|---|---|---|---|---|---|---|---|---|---|---|
| 7 | — | 35 | Me | Me | Me | H | CH | N | C—NO2 | CH | H | H | Me |
| 7 | — | 36 | Me | Me | Me | H | CH | N | C—SMe | CH | H | H | Me |
| 7 | — | 37 | Me | Me | Me | H | N | CH | C—H | CH | H | H | Me |
| 7 | — | 38 | Me | Me | Me | H | N | CH | C—CF3 | CH | H | H | Me |
| 7 | — | 39 | Me | Me | Me | H | N | CH | C—Cl | CH | H | H | Me |
| 7 | — | 40 | Me | Me | Me | Me | N | CH | C—H | CH | H | H | Me |
| 7 | — | 41 | Me | Me | Me | Me | N | CH | C—CF3 | CH | H | H | Me |
| 7 | — | 42 | Me | Me | Me | Me | N | CH | C—Cl | CH | H | H | Me |

TABLE 8

| Example No. | | | $R_1'$ | $R_2'$ | $R_3'$ | $R_4'$ | $A^1$ | $A^2$ | $A^3$ | $A^4$ | $R^1$ | $R^2$ | $R^3$ | $R^4$ |
|---|---|---|---|---|---|---|---|---|---|---|---|---|---|---|
| 8 | — | 1 | Me | Me | Me | Me | C—H | N | C—H | C—H | H | H | H | tert-BuO(C=O) |
| 8 | — | 2 | Me | Me | Me | Me | C—H | N | C—Br | C—H | H | H | H | tert-BuO(C=O) |
| 8 | — | 3 | Me | Me | Me | Me | C—H | N | C—Cl | C—H | H | H | H | tert-BuO(C=O) |
| 8 | — | 4 | Me | Me | Me | Me | C—H | N | C—CF3 | C—H | H | H | H | tert-BuO(C=O) |
| 8 | — | 5 | Me | Me | Me | Me | C—H | N | C—Me | C—H | H | H | H | tert-BuO(C=O) |
| 8 | — | 6 | Me | Me | Me | Me | C—H | N | C—F | C—H | H | H | H | tert-BuO(C=O) |
| 8 | — | 7 | Me | Me | Me | Me | C—H | N | C—I | C—H | H | H | H | tert-BuO(C=O) |
| 8 | — | 8 | Me | Me | Me | Me | C—H | N | C—NO2 | C—H | H | H | H | tert-BuO(C=O) |
| 8 | — | 9 | Me | Me | Me | Me | C—H | N | C—SMe | C—H | H | H | H | tert-BuO(C=O) |
| 8 | — | 10 | Me | Me | Me | H | C—H | C—H | C—H | N | H | H | H | tert-BuO(C=O) |
| 8 | — | 11 | Me | Me | Me | H | C—H | C—H | C—Br | N | H | H | H | tert-BuO(C=O) |
| 8 | — | 12 | Me | Me | Me | H | C—H | C—H | C—Cl | N | H | H | H | tert-BuO(C=O) |
| 8 | — | 13 | Me | Me | Me | H | C—H | C—H | C—CF3 | N | H | H | H | tert-BuO(C=O) |
| 8 | — | 14 | Me | Me | Me | H | C—H | C—H | C—Me | N | H | H | H | tert-BuO(C=O) |
| 8 | — | 15 | Me | Me | Me | H | C—H | C—H | C—F | N | H | H | H | tert-BuO(C=O) |
| 8 | — | 16 | Me | Me | Me | H | C—H | C—H | C—I | N | H | H | H | tert-BuO(C=O) |
| 8 | — | 17 | Me | Me | Me | H | C—H | C—H | C—NO2 | N | H | H | H | tert-BuO(C=O) |
| 8 | — | 18 | Me | Me | Me | H | C—H | C—H | C—SMe | N | H | H | H | tert-BuO(C=O) |
| 8 | — | 19 | Me | Me | Me | Me | C—H | C—H | C—H | C—H | Me | H | H | tert-BuO(C=O) |
| 8 | — | 20 | Me | Me | Me | Me | C—H | C—H | C—Br | C—H | Me | H | H | tert-BuO(C=O) |
| 8 | — | 21 | Me | Me | Me | Me | C—H | C—H | C—Cl | C—H | Me | H | H | tert-BuO(C=O) |
| 8 | — | 22 | Me | Me | Me | Me | C—H | C—H | C—CF3 | C—H | Me | H | H | tert-BuO(C=O) |
| 8 | — | 23 | Me | Me | Me | Me | C—H | C—H | C—Me | C—H | Me | H | H | tert-BuO(C=O) |
| 8 | — | 24 | Me | Me | Me | Me | C—H | C—H | C—F | C—H | Me | H | H | tert-BuO(C=O) |

TABLE 9

| Ex.-No. | 1H-NMR |
|---|---|
| 1-1 | 1H-NMR (CDCl3) δ: 3.47 (1H, d), 3.83 (1H, d), 4.49 (1H, d), 4.96 (1H, d), 7.25 (2H, s), 7.95 (1H, d), 8.23-8.31 (3H, m), 8.91 (1H, s) |
| 1-2 | 1H-NMR (CDCl3) δ: 3.47 (1H, d), 3.84 (1H, d), 4.46 (1H, d), 4.92 (1H, d), 7.29 (2H, s), 7.82 (2H, d), 8.01 (2H, d), 8.14 (1H, s), 8.65 (1H, s) |
| 1-3 | 1H-NMR (CDCl3) δ: 2.90 (6H, s), 3.48 (1H, d), 3.79 (1H, d), 4.50 (1H, d), 4.92 (1H, d), 7.27 (2H, s), 7.92 (1H, d), 8.22-8.35 (3H, m), 8.89 (1H, s) |
| 1-4 | 1H-NMR (CDCl3) δ:3.54 (1H, d), 3.89 (1H, d), 4.54 (1H, d), 5.02 (1H, d), 7.27-7.33 (1H, m), 7.58-7.63 (2H, m), 7.93 (1H, d), 8.21-8.34 (3H, m), 8.90 (1H, s) |
| 1-10 | 1H-NMR (CDCl3) δ: 3.53 (1H, d), 3.88 (1H, d), 4.54 (1H, d), 5.02 (1H, d), 7.52 (1H, s), 7.57 (1H, s), 7.67 (1H, s), 7.94 (1H, d), 8.22 (1H, s), 8.26 (1H, d), 8.34 (1H, s), 8.90 (1H, s) |

TABLE 9-continued

| Ex.-No. | 1H-NMR |
|---|---|
| 1-13 | 1H-NMR (CDCl3) δ: 3.49 (1H, d), 3.83 (1H, d), 4.50 (1H, d), 4.95 (1H, d), 7.35 (2H, d), 7.93 (1H, d), 8.22-8.28 (2H, m), 8.32 (1H, s), 8.90 (1H, s) |
| 1-15 | 1H-NMR (CDCl3) δ: 3.48 (1H, d), 3.82 (1H, d), 4.50 (1H, d), 4.96 (1H, d), 7.40 (2H, s), 7.94 (1H, d), 8.22-8.27 (2H, m), 8.32 (1H, s), 8.90 (1H, s) |
| 1-19 | 1H-NMR (CDCl3) δ: 3.56 (1H, d), 3.94 (1H, d), 4.54 (1H, d), 5.09 (1H, d), 7.36 (1H, t), 7.59 (1H, t), 7.70 (1H, t), 7.93 (1H, d), 8.22 (1H, s), 8.24-8.35 (2H, m), 8.89 (1H, s) |
| 1-20 | 1H-NMR (CDCl3) δ: 3.50 (1H, d), 3.90 (1H, d), 4.47 (1H, d), 5.05 (1H, d), 7.34 (1H, t), 7.93 (1H, d), 8.22 (1H, s), 8.26 (1H, d), 8.33 (1H, s), 8.90 (1H, s) |
| 1-21 | 1H-NMR (CDCl3) δ: 3.54 (1H, d), 3.90 (1H, d), 4.56 (1H, d), 5.04 (1H, d), 7.52-7.69 (2H, m), 7.95 (1H, d), 8.22-8.34 (3H, m), 8.82 (1H, d), 8.91 (1H, s) |
| 1-22 | 1H-NMR (CDCl3) δ: 3.55 (1H, d), 3.96 (1H, d), 4.58 (1H, d), 5.09 (1H, d), 7.87 (2H, s), 7.96 (1H, d), 8.23-8.29 (2H, m), 8.34 (1H, s), 8.91 (1H, s) |
| 1-25 | 1H-NMR (CDCl3) δ: 3.51 (1H, d), 3.84 (1H, d), 4.52 (1H, d), 4.98 (1H, d), 7.12 (3H, m), 7.93 (1H, d), 8.22-8.32 (3H, m), 8.89 (1H, s) |
| 1-27 | 1H-NMR (CDCl3) δ:3.48 (1H, d), 3.83 (1H, d), 4.47 (1H, d), 4.92 (1H, d), 7.42 (2H, s), 7.81 (2H, d), 8.01 (2H, d), 8.14 (1H, s), 8.64 (1H, s) |
| 1-29 | 1H-NMR (CDCl3) δ: 3.46 (1H, d), 3.80 (1H, d), 4.47 (1H, d), 4.92 (1H, d), 7.41 (2H, s), 7.75 (1H, d), 7.86 (1H, d), 8.07 (1H, t), 8.15 (1H, s), 8.77 (1H, s) |
| 1-30 | 1H-NMR (CDCl3) δ: 3.47 (1H, d), 3.81 (1H, d), 4.48 (1H, d), 4.93 (1H, d), 7.41 (2H, s), 7.74 (1H, d), 7.89 (1H, d), 8.09 (1H, s), 8.16 (1H, s), 8.67 (1H, s) |
| 1-31 | 1H-NMR (CDCl3) δ: 3.46 (1H, d), 3.80 (1H, d), 4.48 (1H, d), 4.94 (1H, d), 7.41 (2H, s), 7.64 (1H, d), 7.94 (1H, d), 8.16 (1H, s), 8.26 (1H, s), 8.60 (1H, s) |
| 1-34 | 1H-NMR (CDCl3) δ: 3.52 (1H, d), 3.85 (1H, d), 4.51 (1H, d), 4.96 (1H, d), 7.42 (2H, s), 7.67 (1H, d), 8.17-8.20 (2H, m), 8.34-8.38 (2H, m) |
| 1-35 | 1H-NMR (CDCl3) δ: 3.51 (1H, d), 3.84 (1H, d), 4.51 (1H, d), 4.97 (1H, d), 7.41 (2H, s), 7.71 (1H, d), 8.16 (1H, s), 8.24 (1H, s), 8.46 (2H, m) |
| 1-52 | 1H-NMR (CDCl3) δ: 3.49 (1H, d), 3.82 (1H, d), 4.51 (1H, d), 4.97 (1H, d), 7.41 (2H, s), 8.26 (1H, s), 8.68 (1H, d), 9.08 (1H, d), 9.23 (1H, s) |
| 1-66 | 1H-NMR (CDCl3) δ: 3.49 (1H, d), 3.84 (1H, d), 4.51 (1H, d), 4.99 (1H, d), 7.28 (2H, s), 8.27 (1H, s), 8.68 (1H, d), 9.08 (1H, d), 9.23 (1H, s) |
| 1-70 | 1H-NMR (CDCl3) δ: 3.61 (1H, d), 4.07 (1H, d), 4.54 (1H, d), 5.00 (1H, d), 7.44 (2H, s), 8.26 (1H, s), 8.33 (1H, d), 8.56 (1H, d), 9.03 (1H, s) |
| 1-84 | 1H-NMR (CDCl3) δ: 3.71 (1H, d), 4.10 (1H, d), 4.69 (1H, d), 4.92 (1H, d), 7.60 (1H, s), 7.63 (1H, s), 7.92 (1H, d), 8.22 (1H, s), 8.27 (1H, d), 8.35 (1H, s), 8.89 (1H, s) |
| 1-110 | 1H-NMR (CDCl3) δ: 3.48 (1H, d), 3.83 (1H, d), 4.47 (1H, d), 4.93 (1H, d), 7.42 (2H, s), 8.02 (1H, d), 8.13 (1H, s), 8.39 (1H, dd), 8.87 (1H, d), 9.22 (1H, d). |
| 1-126 | 1H-NMR (CDCl3) δ: 3.68 (1H, d), 4.23 (1H, d), 4.71 (1H, d), 4.92 (1H, d), 7.70-7.74 (2H, m), 7.90-8.01(2H, m), 8.22(1H, s), 8.27 (1H, d), 8.35 (1H, s), 8.89 (1H, s) |
| 1-156 | 1H-NMR (CDCl3) δ: 3.53 (1H, d), 3.91 (1H, d), 4.56 (1H, d), 5.04 (1H, d), 7.53 (1H, d), 7.70 (1H, s), 7.95 (1H, d), 8.22 (1H, s), 8.26 (1H, d), 8.33 (1H, s), 8.85 (1H, d), 8.91 (1H, s) |
| 1-174 | 1H-NMR (CDCl3) δ: 2.64 (3H, s), 3.55 (1H, d), 3.88 (1H, d), 4.56 (1H, d), 5.01 (1H, d), 7.44 (1H, d), 7.54 (1H, d), 7.94 (1H, d), 8.02 (1H, s), 8.22-8.35 (3H, m), 8.90 (1H, s) |
| 1-180 | 1H-NMR (CDCl3) δ: 2.54 (3H, s), 3.58 (1H, d), 3.90 (1H, d), 4.57 (1H, d), 5.04 (1H, d), 7.53 (1H, s), 7.94 (1H, d), 8.08 (2H, m), 8.22 (1H, s), 8.28 (1H, d), 8.35 (1H, s), 8.90 (1H, s) |
| 1-480 | 1H-NMR (CDCl3) δ: 3.54 (1H, d), 3.89 (1H, d), 4.56 (1H, d), 5.02 (1H, d), 7.72 (1H, s), 7.94 (1H, d), 8.22-8.28 (2H, m), 8.33 (1H, s), 8.56 (1H, s), 8.62 (1H, s), 8.90 (1H, s) |
| 1-481 | 1H-NMR (CDCl3) δ: 3.56 (1H, d), 3.94 (1H, d), 4.59 (1H, d), 5.08 (1H, d), 7.94-7.97 (2H, m), 8.23 (1H, s), 8.27 (1H, d), 8.34 (1H, s), 8.87-8.94 (3H, m) |
| 1-482 | 1H-NMR (CDCl3) δ: 3.54 (1H, d), 3.94 (1H, d), 4.52 (1H, d), 5.10 (1H, d), 7.26-7.34 (1H, m), 7.62-7.72 (2H, m), 7.93 (1H, d), 8.22 (1H, s), 8.27 (1H, d), 8.35 (1H, s), 8.89 (1H, s) |
| 1-483 | 1H-NMR (CDCl3) δ: 3.53 (1H, d), 3.84 (1H, d), 4.55 (1H, d), 4.99 (1H, d), 6.55 (1H, t), 7.15-7.26 (3H, m) 7.44 (1H, t), 7.92 (1H, d), 8.22 (1H, s), 8.26 (1H, d), 8.33 (1H, s), 8.89 (1H, s) |
| 1-484 | 1H-NMR (CDCl3) δ: 3.51 (1H, d), 3.85 (1H, d), 4.53 (1H, d), 4.98 (1H, d), 7.25 (1H, s), 7.37 (1H, s), 7.94 (1H, d), 8.22-8.27 (2H, m), 8.33 (1H, s),8.47 (1H, d), 8.90 (1H, s) |
| 1-485 | 1H-NMR (CDCl3) δ: 3.50 (1H, d), 3.83 (1H, d), 4.52 (1H, d), 4.97 (1H, d), 6.56 (2H, t), 6.98-7.03 (3H, m), 7.93 (1H, d), 8.22-8.27 (2H, m), 8.32 (1H, s), 8.89 (1H, s) |
| 1-486 | 1H-NMR (CDCl3) δ: 3.53 (1H, d), 3.92 (1H, d), 4.56 (1H, d), 5.05 (1H, d), 7.54 (1H, d), 7.68 (1H, s), 7.95 (1H, d), 8.22 (1H, s), 8.26 (1H, d), 8.33 (1H, s), 8.86 (1H, d), 8.91 (1H, s) |
| 1-487 | 1H-NMR (CDCl3) δ: 3.58 (1H, d), 3.93 (1H, d), 4.59 (1H, d), 5.06 (1H, d), 7.96 (1H, d), 8.22 (1H, s), 8.27 (1H, d), 8.35 (1H, s), 8.83 (2H, s), 8.91 (1H, s), 9.25 (1H, s) |
| 1-488 | 1H-NMR (CDCl3) δ: 3.65 (1H, d), 3.92 (1H, d), 4.61 (1H, d), 5.09 (1H, d), 7.36 (1H, d), 7.58 (1H, d), 7.93 (1H, d), 8.22-8.34 (3H, m), 8.89 (1H, s) |
| 1-489 | 1H-NMR (CDCl3) δ: 3.50 (1H, d), 3.87 (1H, d), 4.52 (1H, d), 5.00 (1H, d), 7.47 (2H, s), 7.95 (1H, d), 8.22 (1H, s), 8.24-8.27 (1H, m), 8.32 (1H, d), 8.91 (1H, s) |
| 1-490 | 1H-NMR (CDCl3) δ: 3.48 (1H, d), 3.84 (1H, d), 4.50 (1H, d), 4.96 (1H, d), 7.29 (2H, s), 8.21 (1H, s), 8.48 (1H, s), 8.85 (1H, s), 8.91 (1H, s) |
| 1-491 | 1H-NMR (CDCl3) δ: 3.56 (1H, d), 3.94 (1H, d), 4.58 (1H, d), 5.09 (1H, d), 7.83 (2H, s), 7.95 (1H, s), 8.21 (1H, s), 8.50 (1H, d), 8.89 (1H, d), 8.91 (1H, s) |
| 1-492 | 1H-NMR (CDCl3) δ: 3.51 (1H, d), 3.90 (1H, d), 4.54 (1H, d), 5.02 (1H, d), 7.55 (1H, s), 7.59 (1H, s), 7.96 (1H, d), 8.22 (1H, s), 8.26 (1H, dd), 8.33 (1H, d), 8.91 (1H, s) |
| 1-494 | 1H-NMR (CDCl3) δ: 3.57 (1H, d), 3.95 (1H, dd), 4.59 (1H, d), 5.11 (1H, dd), 7.83 (2H, s), 7.95 (1H, d), 8.26 (1H, d), 8.70 (1H, d), 9.11 (1H, d), 9.23 (1H, s) |
| 1-496 | 1H-NMR (CDCl3) δ: 3.55 (1H, d), 3.87 (1H, d), 4.55 (1H, d), 5.02 (1H, d), 7.22 (1H, s), 7.29 (1H, s), 7.93 (1H, d), 8.22-8.34 (3H, m), 8.90 (1H, s) |
| 1-497 | 1H-NMR (CDCl3) δ: 3.53 (1H, d), 3.88 (1H, d), 4.55 (1H, d), 5.02 (1H, d), 6.60 (1H, t), 7.36 (1H, s), 7.44 (1H, s), 7.49 (1H, s), 7.93 (1H, s), 8.22 (1H, s), 8.27 (1H, s), 8.34 (1H, s), 8.90 (1H, s) |

TABLE 9-continued

| Ex.-No. | 1H-NMR |
|---|---|
| 1-506 | 1H-NMR (CDCl3) δ: 3.50 (1H, d), 3.82 (1H, d), 4.51 (1H, d), 4.96 (1H, d), 7.28 (2H, s), 7.41 (1H, s), 7.93 (1H, d), 8.22 (1H, s), 8.25 (1H, d), 8.32 (1H, s), 8.90 (1H, s) |
| 1-724 | 1H-NMR (CDCl3) δ: 3.50 (1H, d), 3.84-3.87 (1H, m), 4.52 (1H, d), 4.97 (1H, d), 6.87 (2H, s), 7.95 (1H, d), 8.21-8.32 (3H, m), 8.91 (1H, s) |
| 2-76 | 1H-NMR (CDCl3) δ: 2.38 (3H, s), 3.42 (1H, d), 3.78-3.90 (m), 4.40-4.44 (m), 4.85 (1H, d), 7.37-7.48 (3H, m), 7.63-7.66 (2H, m) |
| 2-77 | 1H-NMR (CDCl3) δ: 1.47 (9H, s), 2.37 (3H, s), 3.42 (1H, d), 3.78 (1H, dd), 4.36-4.42 (3H, m), 4.83-4.89 (2H, m), 7.33 (1H, d), 7.41 (2H, s), 7.62 (1H, d), 7.68 (1H, s) |
| 2-167 | 1H-NMR (CDCl3) δ: 3.43 (1H, d), 3.79 (1H, d), 3.95 (2H, s), 4.42 (1H, d), 4.86 (1H, d), 7.41-7.45 (4H, m), 7.82 (1H, d) |
| 2-168 | 1H-NMR (CDCl3) δ:2.04 (3H, s), 3.42 (1H, d), 3.77 (1H, d), 4.39-4.48 (3H, m), 4.86 (1H, d), 6.04 (1H, s), 7.34-7.41 (4H, m), 7.80 (2H, d) |
| 2-169 | 1H-NMR (CDCl3) δ: 1.19 (3H, t), 2.27 (2H, q), 3.42 (1H, d), 3.77 (1H, d), 4.39-4.49 (3H, m), 4.86 (1H, d), 5.96 (1H, s), 7.34-7.40 (4H, m), 7.80 (2H, d) |
| 2-170 | 1H-NMR (CDCl3) δ: 3.15 (2H, q), 3.63 (1H, d), 3.81 (1H, d), 4.45 (1H, d), 4.54 (2H, d), 4.89 (1H, d), 6.23 (1H, s), 7.34-7.40 (4H, m), 7.80 (2H, d) |
| 2-547 | 1H-NMR (CDCl3) δ: 2.38 (3H, s), 3.50 (1H, d), 3.88-3.93 (3H, m), 4.45-4.51 (2H, m), 4.98 (1H, d), 7.40-7.42 (1H, m), 7.64-7.69 (2H, m), 7.83 (2H, s), 7.90 (1H, s) |
| 2-548 | 1H-NMR (CDCl3) δ: 1.47 (9H, s), 2.38 (3H, s), 3.49 (1H, d), 3.90 (1H, dd), 4.35 (2H, d), 4.49 (1H, d), 4.79 (1H, br s), 4.98 (1H, d), 7.34 (1H, d), 7.65-7.69 (2H, m), 7.83 (2H, s), 7.90 (1H, s) |
| 2-645 | 1H-NMR (CDCl3) δ: 3.50 (1H, d), 3.88-3.95 (3H, m), 4.47-4.53 (3H, m), 4.99 (1H, d), 7.43 (2H, d), 7.82-7.90 (5H, m) |
| 2-647 | 1H-NMR (CDCl3) δ: 1.20 (3H, t), 2.28 (2H, q), 3.50 (1H, d), 3.90 (1H, d), 4.47-4.52 (3H, m), 4.99 (1H, d), 5.79 (1H, s), 7.38 (2H, d), 7.82-7.91 (5H, m) |
| 2-648 | 1H-NMR (CDCl3) δ: 3.16 (2H, q), 3.53 (1H, d), 3.92 (1H, d), 4.49-4.56 (3H, m), 5.01 (1H, d), 6.22 (1H, s), 7.36 (2H, d), 7.82-7.91 (5H, m) |
| 2-2149 | 1H-NMR (CDCl3) δ: 3.45 (1H, d), 3.82 (1H, dz), 4.09 (s), 4.45 (1H, d), 4.62 (s), 4.90 (1H, d), 7.28 (2H, s), 7.77-7.85 (1H, m), 7.97-8.03 (1H, m), 8.12 (1H, s) |
| 2-2151 | 1H-NMR (CDCl3) δ: 1.17 (3H, t), 2.27 (2H, q), 3.45 (1H, d), 3.81 (1H, dd), 4.45 (1H, d), 4.65 (2H, d), 4.90 (1H, dd), 6.03-6.05 (1H, m), 7.28 (2H, s), 7.67 (1H, d), 7.96 (1H, d), 8.13 (1H, s) |
| 2-2732 | 1H-NMR (CDCl3) δ: 2.17 (3H, s), 3.46 (1H, d), 3.88 (1H, dd), 4.47-4.55 (3H, m), 5.00 (1H, dd), 6.03 (1H, br s), 7.50 (1H, d), 7.74 (1H, dd), 7.85 (2H, s), 8.08 (1H, d) |
| 2-2733 | 1H-NMR (CDCl3) δ: 1.18 (3H, t), 2.27 (2H, q), 3.46 (1H, d), 3.88 (1H, d), 4.47-4.56 (3H, m), 5.00 (1H, d), 5.97 (1H, br s), 7.50 (1H, d), 7.74 (1H, dd), 7.84 (2H, s), 8.08 (1H, d) |
| 2-2737 | 1H-NMR (CDCl3) δ: 2.12 (3H, s), 3.24 (2H, s), 3.48 (1H, d), 3.89 (1H, dd), 4.51 (1H, d), 4.59 (2H, d), 5.01 (1H, dd), 7.43-7.52 (2H, m), 7.75 (1H), 7.85 (2H, s), 8.10 (1H, d) |
| 2-2739 | 1H-NMR (CDCl3) δ: 3.14 (3H, s), 3.93 (1H, d), 4.04-4.12 (3H, m), 4.59 (2H, d), 4.67 (1H, d), 5.07 (1H, dd), 7.60 (1H, d), 7.88 (1H, dd), 8.16 (1H, d), 8.22 (2H, s) |
| 2-2872 | 1H-NMR (CDCl3) δ: 1.16 (3H, t), 2.17-2.27 (5H, m), 3.48 (1H, d), 3.91 (1H, d), 4.49 (1H, d), 4.98 (1H, d), 5.11-5.22 (1H, m), 5.71 (1H, d), 7.41 (2H, d), 7.81-7.85 (4H, m) |
| 6-34 | 1H-NMR (CDCl3) δ: 0.20 (9H, s), 3.55 (2H, d), 7.54 (1H, d), 7.73-7.77 (2H, m), 7.95 (1H, t), 8.14 (1H, s), 8.73 (1H, s) |
| 6-51 | 1H-NMR (CDCl3) δ: 0.11 (9H, s), 2.10 (3H, s), 3.68 (2H, s), 7.22-7.87 (3H, m) |

BIOLOGICAL EXAMPLES

Unless not mentioned otherwise, the test solutions were prepared as follows:

Containing as solvent: Dimethylformamide, 3 parts by weight; and as emulsifier: Polyoxyethylene alkyl phenyl ether, 1 part by weight. To prepare the test solution, 1 part by weight of an active compound is mixed with the above-mentioned amount of solvent containing the above-mentioned amount of emulsifier, and the mixture is diluted with water to the desired concentration.

Biological Test Example 1

Test Against Tobacco Cutworm (*Spodoptera litura*) Larvae

The leaves of sweet potato were immersed in the test solution at the appropriate concentration, and the leaves were dried in air. The leaves were then placed in a petri dish having a diameter of 9 cm, and ten third-instar larvae of tobacco cutworm were released therein. The petri dish was placed in a temperature-controlled chamber at 25° C. After 2 days and 4 days sweet potato leaves were additionally added. After 7 days, the number of dead larvae was counted to calculate the insecticidal activity. An insecticidal activity of 100% means that all larvae were killed, whereas an insecticidal activity of 0% means that no larva was killed. In the current test, the results of two petri dishes for each partition were averaged.

In the Biological Test Example 1, the compounds Nos. 1-1, 1-2, 1-4, 1-10, 1-13, 1-15, 1-19, 1-20, 1-21, 1-22, 1-25, 1-27, 1-29, 1-30, 1-31, 1-34, 1-35, 1-52, 1-66, 1-84, 1-110, 1-126, 1-156, 1-481, 1-482, 1-485, 1-488, 1-489, 1-490, 1-491, 1-492, 1-494, 1-496, 1-497, 1-506, 2-76, 2-168, 2-169, 2-170, 2-547, 2-548, 2-647, 2-648, 2-2151, 2-2732, 2-2733, 2-2737, 2-2739 and 2-2872 showed an insecticidal activity of 100% at an active compound concentration of 100 ppm.

Biological Test Example 2

Test Against Two-Spotted Spider Mite (*Tetranychus urticae*)

50 to 100 adult two-spotted spider mites were inoculated onto the leaves of kidney beans at the two-true leaf stage, which plant had been cultivated in a pot having a diameter of 6 cm. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, whereas an acaricidal activity of 0% means that no mite was killed.

In the Biological Test Example 2, the compound No. 1-1, 1-2, 1-4, 1-10, 1-13, 1-15, 1-19, 1-20, 1-21, 1-22, 1-27, 1-30, 1-31, 1-35, 1-52, 1-84, 1-110, 1-156, 1-174, 1-180, 1-480, 1-482, 1-483, 1-484, 1-485, 1-488, 1-492, 1-496, 1-506, 2-168, 2-169, 2-170, 2-548, 2-647, 2-648, 2-2151 2-2732, 2-2733, 2-2737 and 2-2739 showed an acaricidal activity rate of 100% at a concentration of 100 ppm.

Biological Test Example 3

Test Against Cucurbit Leaf Beetle (*Aulacophora femoralis*)

Cucumber leaves were immersed in the test solution at the appropriate concentration, and the leaves were dried in air. The leaves were then placed in a plastic cup containing sterilized black soil, and five second-instar larvae of cucurbit leaf beetle were released therein. The plastic cup was placed in a temperature-controlled chamber at 25° C. After 7 days, the number of dead larvae was counted, and thus the insecticidal activity was calculated. An insecticidal activity of 100% means that all beetles were killed, whereas an insecticidal activity of 0% means that no beetle was killed.

Compounds Nos. 1-1, 1-2, 1-4, 1-10, 1-13, 1-15, 1-19, 1-20, 1-21, 1-22, 1-25, 1-27, 1-29, 1-30, 1-31, 1-34, 1-35, 1-52, 1-66, 1-84, 1-110, 1-126, 1-156, 1-480, 1-481, 1-482, 1-483, 1-484, 1-485, 1-488, 1-490, 1-491, 1-492, 1-494, 1-496, 1-497, 1-506, 2-168, 2-169, 2-170, 2-548, 2-647, 2-648, 2-2151, 2-2732, 2-2733, 2-2737, 2-2739 showed an insecticidal activity of 100% at an active compound concentration of 100 ppm.

Biological Test Example 4

Test Against Tobacco Cutworm (*Spodoptera litura*) Larvae

Root Systemicity

The roots of seedling of broccoli at 1.2 leaf stage were dipped into the test solution at the appropriate concentration. After 3 days, the leaves were cut and placed in a petri dish having a diameter of 9 cm. And then five second-instar larvae of tobacco cutworm were released therein. The petri dish was placed in a temperature-controlled room at 25° C. After 4 days, the number of dead larvae was counted, to calculate the insecticidal activity. An insecticidal activity of 100% means that all larvae were killed, whereas an insecticidal activity of 0% means that no larva was killed. In the Biological Test Example 4, the compounds Nos. 1-1, 1-2, 1-4, 1-10, 1-13, 1-20, 1-21, 1-22, 1-25, 1-66, 1-84, 1-126, 1-485, 1-492, 1-497, 2-647, 2-648, 2-2872 showed an insecticidal activity of 100% at an active compound concentration of 100 ppm.

Biological Test Example 5

Test Against Tobacco Cutworm (*Spodoptera litura*) Larvae

Systemic Test by Soil Drench 20 ml of the test solution at the appropriate concentration was treated on the soil surface of potted broccoli seedling at 2 to 3 leaf stage. After 7 days, the leaves were cut and placed in a petri dish having a diameter of 9 cm. And then ten third-instar larvae of tobacco cutworm were released therein. The petri dish was placed in a temperature-controlled room at 25° C. After 7 days, the number of dead larvae was counted to calculate the insecticidal activity. An insecticidal activity of 100% means that all larvae were killed, whereas an insecticidal activity of 0% means that no larva was killed. In the Biological Test Example 5, the compounds Nos. 1-1, 1-21 and 1-22 showed an insecticidal activity of 100% at an active compound concentration of 250 ppm. On the other hand, the comparative compound A showed an insecticidal activity of 10% at an active compound concentration of 250 ppm. The comparative compound A is No. 1-72 in WO2009/097992.

Biological Test Example 6

Test Against Rice Leafroller (*Cnaphalocrocis medinalis*) Larvae

Seed Treatment

To prepare the test solution, 1 part by weight of an active compound is mixed with the 8 parts of acetone, and mix with 20 mg of micronized mineral. After that 1 g of dry rice seeds and 50 ul of water are added and mixed well and dried in the air. Sow treated seeds in the pot having a diameter of 12 cm. 28 days after seeding the leaves were cut and placed in a petri dish having a diameter of 9 cm. And then five third-instar larvae of rice leafroller were released therein. The petri dish was placed in a temperature-controlled room at 25° C. After 7 days, the number of dead larvae was counted to calculate the insecticidal activity. An insecticidal activity of 100% means that all larvae were killed, whereas an insecticidal activity of 0% means that no larva was killed. In the Biological Test Example 6, the compounds Nos. 1-1, 1-22 showed an insecticidal activity of 100% at an active compound weight of 8 g/1 kg dry seeds. On the other hand, the comparative compound B showed an insecticidal activity of 0% at an active compound weight of 8 g/1 kg dry seeds. The comparative compound B is No. 1-79 in WO2009/097992.

Biological Test Example 6

*Amblyomma hebraeum*—Test (AMBYHE)

Solvent: dimethyl sulfoxide

To produce a suitable preparation of active compound, 10 mg of active compound are dissolved in 0.5 ml solvent, and the concentrate is diluted with water to the desired concentration. Nymphs of the tick *Amblyomma hebraeum* are placed in perforated plastic beakers and immersed in aqueous compound solution for one minute. Ticks are transferred to a filter paper in a petri dish and incubated in a climate chamber for 42 days.

After 42 days mortality in % is determined. 100% means that all the ticks have been killed; 0% means that none of the ticks have been killed.

In this test for example, the following compounds from the preparation examples showed good activity of 100% at application rate of 100 ppm: 1-10, 1-13, 1-20.

Biological Test Example 7

*Boophilus microplus* (Dip)

Solvent: Dimethylsulfoxid

To produce a suitable preparation of active compound, 10 mg of active compound are dissolved in 0.5 ml solvent, and the concentrate is diluted with water to the desired concentration. Eight to ten adult engorged female *Boophilus*

*microplus* ticks are placed in perforated plastic beakers and immersed in aqueous compound solution for one minute. Ticks are transferred to a filter paper in a plastic tray. Egg deposition of fertile eggs is monitored after. After 7 days mortality in % is determined. 100% means that all the ticks have been killed; 0% means that none of the ticks have been killed.

In this test for example, the following compounds from the preparation examples showed good activity of 80% at application rate of 100 ppm: 1-489.

In this test for example, the following compounds from the preparation examples showed good activity of 90% at application rate of 100 ppm: 1-52, 1-485.

In this test for example, the following compounds from the preparation examples showed good activity of 95% at application rate of 100 ppm: 1-29.

In this test for example, the following compounds from the preparation examples showed good activity of 100% at application rate of 100 ppm: 1-1, 1-3, 1-4, 1-10, 1-13, 1-20, 1-22, 1-27, 1-30, 1-31, 1-34, 1-35, 1-84, 1-482, 1-488, 1-492, 2-168, 2-169, 2-170, 2-647, 2-648, 2-2151.

Biological Test Example 8

*Ctenocephalides felis*—Test (CTECFE)

Solvent: dimethyl sulfoxide

To produce a suitable preparation of active compound, 10 mg of active compound are dissolved in 0.5 ml solvent, and the concentrate is diluted with cattle blood to the desired concentration. Approximately 20 adult unfed (*Ctenocepahlides felis*) are placed in flea chambers. The blood chamber, sealed with parafilm on the bottom, are filled with cattle blood supplied with compound solution and placed on top of the flea chamber, so that the fleas are able to suck the blood. The blood chamber is heated to 37° C. whereas the flea chamber is kept at room temperature. After 2 days mortality in % is determined. 100% means that all the fleas have been killed; 0% means that none of the fleas have been killed.

In this test for example, the following compounds from the preparation examples showed good activity of 90% at application rate of 100 ppm: 1-30, 1-126, 1-480, 1-483

In this test for example, the following compounds from the preparation examples showed good activity of 95% at application rate of 100 ppm: 1-3, 1-19, 1-21, 1-25, 1-110, 1-481, 1-484, 1-489

In this test for example, the following compounds from the preparation examples showed good activity of 100% at application rate of 100 ppm: 1-1, 1-2, 1-4, 1-10, 1-13, 1-20, 1-22, 1-27, 1-29, 1-31, 1-34, 1-35, 1-52, 1-66, 1-84, 1-174, 1-482, 1-485, 1-488, 2-168, 2-169, 2-170, 2-647, 2-648, 2-2151

Biological Test Example 9

*Lucilia cuprina* (48 h)

Species: *Lucilia cuprina* $1^{st}$ instar larvae (age 24 hrs)
Solvent: dimethyl sulfoxide 10 mg active compound are dissolved in 0.5 ml dimethyl sulfoxide. Serial dilutions are made to obtain the desired rates. Approximately 20 *Lucilia cuprina* $1^{st}$ instar larvae are transferred into a test tube containing 1 $cm^3$ of minced horse meat and 0.5 ml aqueous dilution of test compound. After 48 hrs percentage of larval mortality are recorded. 100% efficacy=all larvae are killed, % efficacy=normally developed larvae after 48 hrs.

In this test for example, the following compounds from the preparation examples showed good activity of 90% at application rate of 100 ppm: 1-25

In this test for example, the following compounds from the preparation examples showed good activity of 100% at application rate of 100 ppm: 1-1, 1-2, 1-3, 1-4, 1-10, 1-13, 1-19, 1-20, 1-21, 1-22, 1-27, 1-29, 1-30, 1-31, 1-34, 1-35, 1-52, 1-66, 1-84, 1-110, 1-126, 1-482, 1-484, 1-485, 1-489, 2-168, 2-169, 2-170, 2-647, 2-648, 2-2151.

Biological Test Example 10

*Musca domestica*—Test

Solvent: dimethyl sulfoxide

To produce a suitable preparation of active compound, 10 mg of active compound are dissolved in 0.5 ml solvent, and the concentrate is diluted with water to the desired concentration. Prior to the assay, a piece of kitchen sponge is soaked with a mixture of sugar and compound solution and placed into a container. 10 adults (*Musca domestica*) are placed into the container and closed with a perforated lid. After 2 days mortality in % is determined. 100% means that all the flies have been killed; 0% means that none of the flies have been killed.

In this test for example, the following compounds from the preparation examples showed good activity of 80% at application rate of 100 ppm: 1-21, 1-66, 1-489.

In this test for example, the following compounds from the preparation examples showed good activity of 90% at application rate of 100 ppm: 1-2, 1-19, 1-25, 1-126.

In this test for example, the following compounds from the preparation examples showed good activity of 100% at application rate of 100 ppm: 1-1, 1-41-10, 1-13, 1-20, 1-22, 1-27, 1-29, 1-30, 1-31, 1-34, 1-35, 1-52, 1-84, 1-110, 1-482, 1-485, 2-168, 2-169, 2-170, 2-647, 2-648, 2-2151.

Biological Test Example 11

*Phaedon cochleariae*—Test

PHAECO Spray Application

Solvent: 78.0 parts by weight of acetone
1.5 parts by weight of dimethylformamide
Emulsifier: 0.5 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Chinese cabbage (*Brassica pekinesis*) leaf-disks are sprayed with a preparation of the active ingredient of the desired concentration. Once dry, the leaf disks are infested with mustard beetle larvae (*Phaedon cochleariae*).

After 7 days mortality in % is determined. 100% means that all beetle larvae have been killed and 0% means that none of the beetle larvae have been killed.

In this test for example, the following compounds from the preparation examples showed good activity of 100% at application rate of 100 g/ha: 1-3

Biological Test Example 12

*Spodoptera frugiperda*—Test

SPODFR Spray Application

Solvent: 78.0 parts by weight acetone
1.5 parts by weight dimethylformamide
Emulsifier: 0.5 parts by weight alkylarylpolyglycolether To produce a suitable preparation of the active compound, 1 part by weight of active compound is mixed with the stated amount of solvent and emulsifier, and the concentrate is dilutes with emulsifier-containing water to the desired concentration. Maize (*Zea mais*) leaf sections are sprayed with a preparation of the active ingredient of the desired concentration. Once dry, the leaf sections are infested with fall armyworm larvae (*Spodoptera frugiperda*).

After 7 days mortality in % is determined. 100% means that all caterpillars have been killed and 0% means that none of the caterpillars have been killed.

In this test for example, the following compounds from the preparation examples showed good activity of 83% at application rate of 100 g/ha: 1-3

Biological Test Example 13

*Tetranychus urticae*—Test

OP-Resistant (TETRUR Spray Application)

Solvent: 78.0 parts by weight acetone
1.5 parts by weight dimethylformamide
Emulsifier: 0.5 parts by weight alkylarylpolyglycolether To produce a suitable preparation of active compound, 1 part by weight of active compound is mixed with the stated amount of solvent and emulsifier, and the concentrate is diluted with emulsifier-containing water to the desired concentration. French beans (*Phaseolus vulgaris*) which are heavily infested with all stages of the two spotted spidermite (*Tetranychus urticae*), are sprayed with a preparation of the active ingredient at the desired concentration.

After 6 days mortality in % is determined. 100% means that all spider mites have been killed and 0% means that none of the spider mites have been killed.

In this test for example, the following compounds from the preparation examples showed good activity of 100% at application rate of 100 g/ha: 1-3

Biological Test Example 14

Myzus-Test

Oral (MYZUPE O)

Solvent: 80 parts by weight acetone

To produce a suitable preparation of active compound, 1 part by weight of active compound ist mixed with the stated amount of solvent and emulsifier, and the concentrate is diluted with emulsifier-containing water to the desired concentration. Containers are infested with a mixed population of the green peach aphid (*Myzus persicae*), the aphids suck on a preparation of the active compound at the desired concentration.

After 5 days mortality in % is determined. 100% means that all aphids have been killed; 0% means that none of the aphids have been killed.

In this test for example, the following compounds from the preparation examples showed good activity of 100% at application rate of 100 g/ha: 1-3.

FORMULATION EXAMPLES

Formulation Example 1

Granules

To a mixture of 10 parts of Compound No. 1-1, 30 parts of bentonite (montmorillonite), 58 parts of talc and 2 parts of lignin sulfonate, 25 parts of water is added. The mixture is thoroughly kneaded. The product is fabricated into particles of 10 to 40 mesh by extruding through an extruder type granulating machine, and dried at 40 to 50° C. to obtain a granular preparation.

Formulation Example 2

Granules 95 parts of clay mineral particles having a particle size distribution in the range of 0.2 to 2 mm is introduced into a rotary mixer, and while rotating, 5 parts of Compound No. 1-1 is sprayed together with a liquid diluent to uniformly wet the particles. Then, the particles are dried at 40 to 50° C. to obtain a granular preparation.

Formulation Example 3

Emulsion 30 parts of Compound No. 1-1, 55 parts of xylene, 8 parts of polyoxyethylene alkyl phenyl ether and 7 parts of calcium alkylbenzenesulfonate are mixed and stirred to obtain an emulsion preparation.

Formulation Example 4

Wettable Powder 15 parts of Compound No. 1-1, 80 parts of a mixture of white carbon (finely powdered amorphous hydrous silicon oxide) and clay powder (1:5), 2 parts of sodium alkylbenzenesulfonate and 3 parts of sodium alkylnaphthalenesulfonate-formalin condensate are pulverized and mixed to obtain a wettable powder preparation.

Formulation Example 5

Wettable Granules 20 parts of Compound No. 1-1, 30 parts of sodium ligninsulfonate, 15 parts of bentonite and 35 parts of calcined diatomaceous earth powder are sufficiently mixed, and water is added thereto. The mixture is extruded through a screen of 0.3 mm and dried to obtain a wettable granule preparation.

The novel arylpyrroline derivatives of the present invention have an excellent insecticidal action and can be used as an insecticide as demonstrated through the Examples.

The invention claimed is:
1. Arylpynoline compounds of formula (I) wherein

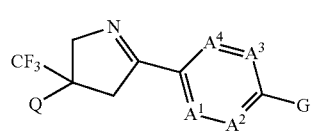

Q stands for a pyridyl or a phenyl group, each group may be substituted with at least one substituent X or $X^1$;
X and $X^1$ each independently stand for fluorine, chlorine, bromine, iodine, $C_{1-12}$haloalkyl, nitro, $C_{1-12}$alkyl, or $C_{1-12}$alkoxyl, cyano, $C_{1-12}$haloalkoxyl, $C_{1-12}$alkylsulfenyl, $C_{1-12}$alkylsulfinyl, $C_{1-12}$alkylsulfonyl, $C_{1-12}$haloalkylsulfenyl, C$_{1-12}$haloalkylsulfinyl, or C$_{1-12}$haloalkylsulfonyl, hydroxyl, thiol, amino, C$_{1-12}$acylamino, C$_{1-12}$alkoxy-carbonylamino, C$_{1-12}$haloalkoxycarbonylamino, C$_{1-12}$alkoxyimino, C$_{1-12}$haloalkoxyimino, or C$_{1-12}$alkylsulfonylamino, or sulfur pentafluoride;

A$^1$, A$^2$, A$^3$ and A$^4$ each independently stand for a carbon atom which may be substituted by a substituent Y, and whereas two adjacent substituents Y together with the carbon atoms to which they are attached may form a 5- or 6-membered aromatic ring, or A$^1$, A$^2$, A$^3$ and A$^4$ each independently stand for a nitrogen atom, under the proviso that only 2 of the chemical groups A$^1$, A$^2$, A$^3$ and A$^4$ stand at the same time for nitrogen;

Y stands for fluorine, chlorine, bromine, iodine, C$_{1-12}$haloalkyl, nitro, C$_{1-12}$alkyl, C$_{3-8}$cycloalkyl, C$_{3-8}$cyclohaloalkyl, cyano, C$_{1-12}$haloalkoxyl, C$_{1-12}$alkylsulfenyl, C$_{1-12}$alkylsulfinyl, C$_{1-12}$alkylsulfonyl, C$_{1-12}$haloalkylsulfenyl, C$_{1-12}$haloalkylsulfinyl, C$_{1-12}$haloalkylsulfonyl, C$_{1-12}$alkylsulfonyloxy, C$_{1-12}$haloalkylsulfonyloxy, C$_{1-12}$alkylaminosulfonyl, C$_{1-12}$haloalkylaminosulfonyl, di(C$_{1-12}$)alkylaminosulfonyl, or di((C$_{1-12}$)haloalkyl)aminosulfonyl, hydroxyl, thiol, amino, C$_{1-12}$alkylamino, di(C$_{1-12}$)alkylamino, C$_{1-12}$acylamino, C$_{1-12}$alkoxycarbonylamino, C$_{1-12}$haloalkoxycarbonylamino, C$_{1-12}$alkylsulfonylamino, C$_{1-12}$haloalkylsulfonylamino, C$_{1-12}$trialkylsilyl, C$_{1-12}$alkoxyimino, C$_{1-12}$haloalkoxyimino, C$_{1-12}$alkoxyiminoalkyl, C$_{1-12}$haloalkoxyimino(C$_{1-12}$)alkyl, C$_{1-12}$alkylsulfinylimino, C$_{1-12}$alkylsulfinylimino(C$_{1-12}$)alkyl, C$_{1-12}$alkylsulfinylimino(C$_{1-12}$)alkylcarbonyl, C$_{1-12}$alkylsulfoxyimino, C$_{1-12}$alkylsulfoxyimino(C$_{1-12}$)alkyl, C$_{1-12}$alkoxycarbonyl, C$_{1-12}$alkylcarbonyl, aminocarbonyl, C$_{1-12}$alkylaminocarbonyl, aminothiocarbonyl, C$_{1-12}$alkylaminothiocarbonyl, di(C$_{1-12}$)alkylaminocarbonyl, or di(C$_{1-12}$)alkylaminothiocarbonyl;

G stands for a heterocyclic group G1 to G9 having the following formula

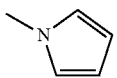
G1

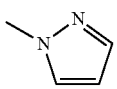
G2

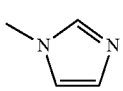
G3

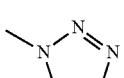
G4

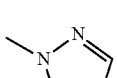
G5

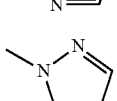
G6

-continued

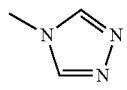
G7

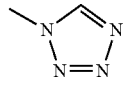
G8

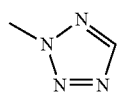
G9 which may be substituted by a substituent Z which is selected among fluorine, chlorine, bromine, iodine, C$_{1-6}$ haloalkyl, nitro, C$_{1-6}$alkoxy, cyano, C$_{1-6}$haloalkoxy, C$_{1-6}$alkylsulfenyl, C$_{1-6}$alkylsulfinyl, C$_{1-6}$alkylsulfonyl, C$_{1-6}$haloalkylsulfenyl, C$_{1-6}$haloalkylsultinyl, C$_{1-6}$haloalkylsulfonyl, hydroxyl and thiol, or represents a chemical group G10 characterized by the following formula:

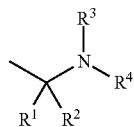
G10 wherein

R$^1$ and R$^2$ each independently stand for hydrogen, C$_{1-12}$alkyl, C$_{3-8}$cycloalkyl, C$_{1-12}$haloalkyl, C$_{3-8}$ cyclohaloalkyl, C$_{2-12}$alkenyl, C$_{2-12}$alkynyl, C$_{2-12}$haloalkenyl, C$_{2-12}$haloalkynyl, cyano, C$_{1-12}$alkoxycarbonyl, or C$_{1-12}$alkoxythiocarbonyl, or R$^1$ and R$^2$, together with the carbon atom to which they are attached, form a 3 to 6-membered carbocyclic ring;

R$^3$ represents hydrogen, amino, hydroxyl, C$_{1-12}$alkoxy, C$_{1-12}$alkylcarbonylamino, C$_{1-12}$alkylimino, C$_{1-12}$alkyl, C$_{3-8}$cycloalkyl, or C$_{1-12}$haloalkyl, cyano, or C$_{2-12}$alkenyl, C$_{2-12}$alkynyl, or C$_{1-12}$alkylcarbonyl, or is selected from the following groups CH$_2$—R$^5$, C(=O)R$^5$, C(=S)R$^5$, R$^4$ represents a chemical group selected among hydrogen, cyano, carbonyl, thiocarbonyl, C$_{1-12}$alkylcarbonyl, C$_{1-12}$alkylthiocarbonyl, C$_{1-12}$haloalkylcarbonyl, C$_{1-12}$haloalkylthiocarbonyl, C$_{1-12}$ alkylaminocarbonyl, C$_{1-12}$alkylaminothiocarbonyl, di(C$_{1-12}$)alkylaminocarbonyl, di(C$_{1-12}$)alkylaminothiocarbonyl, C$_{1-12}$alkoxyaminocarbonyl, C$_{1-12}$alkoxyaminothiocarbonyl, C$_{1-12}$alkoxycarbonyl, C$_{1-12}$alkoxythiocarbonyl, C$_{1-12}$thioalkoxycarbonyl, C$_{1-12}$thioalkoxythiocarbonyl, C$_{1-12}$alkylsulfonyl, C$_{1-12}$haloalkylsulfonyl, C$_{3-8}$cycloalkylcarbonyl, C$_{2-12}$alkenylcarbonyl, C$_{2-12}$alkynylcarbonyl, C$_{3-8}$cycloalkyl-(C$_{1-12}$)alkylcarbonyl, C$_{1-12}$alkylsulfenyl(C$_{1-12}$)alkylcarbonyl, C$_{1-12}$alkylsulfinyl(C$_{1-12}$)alkylcarbonyl, C$_{1-12}$alkylsulfonyl(C$_{1-12}$)alkylcarbonyl, C$_{1-12}$alkylcarbonyl(C$_{1-12}$)alkylcarbonyl, C$_{3-8}$cyclalkylaminocarbonyl, C$_{2-12}$alkenylaminocarbonyl, C$_{2-12}$alkynylaminocarbonyl, C$_{1-12}$alkoxy(C$_{1-12}$)alkyl, or is selected from the groups C(=O)R$^5$ and C(=S)R$^5$, or R$^3$ and R$^4$, together with the nitrogen atom to which they are bound, form a 3- to 6-membered heterocyclic ring which may be substituted with a substituent X or $X^1$, or may be substituted with a keto, thioketo or nitroimino group; and $R^5$ represents optionally substituted phenyl, or an optionally substituted heterocyclic ring.

2. Arylpyrroline compounds according to claim 1, wherein in formula (I) the grouping

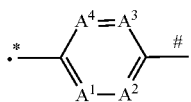

stands for a grouping selected among P1 to P4

 P1

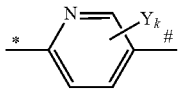 P2

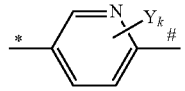 P3

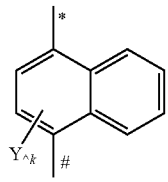 P4 wherein Y is as defined herein, and k stands for 0, 1, 2, 3 or 4.

3. Arylpyrroline compounds according to claim 1, wherein Q stands for a 2-pyridyl group, a 3-pyridyl group, or a 4-pyridyl group which may be substituted by at least one substituent X or $X^1$.

4. A composition, comprising at least one compound according to claim 1 for controlling animal pests.

5. A method for controlling animal pests, characterized in that compounds according to claim 1 are applied to animal pests and/or their habitat.

* * * * *